United States Patent
Sun et al.

(10) Patent No.: US 6,657,054 B1
(45) Date of Patent: Dec. 2, 2003

(54) REGULATED ANGIOGENESIS GENES AND POLYPEPTIDES

(75) Inventors: Zairen Sun, Rockville, MD (US); Xuan Li, Silver Spring, MD (US); Gilbert Jay, North Bethesda, MD (US)

(73) Assignee: Origene Technologies, Inc., Rockville, MD (US)

( * ) Notice: Subject to any disclaimer, the term of this patent is extended or adjusted under 35 U.S.C. 154(b) by 0 days.

(21) Appl. No.: 10/164,595

(22) Filed: Jun. 10, 2002

(51) Int. Cl.⁷ .............................................. C07H 21/04
(52) U.S. Cl. ...................................... 536/23.5
(58) Field of Search ........................ 536/23.5

(56) References Cited

FOREIGN PATENT DOCUMENTS

WO    WO 200253719 A2 * 7/2002

OTHER PUBLICATIONS

Attwood TK. Genomics. The Babel of bioinformatics. Science. 290(5491):471–473, 2000.*
Skolnick et al. From genes to protein structure and function: novel applications of computational approaches in the genomic era. Trends Biotechnol. 18(1):34–9, 2000.*
Ngo J.T, Marks J., Karplus M., Computational complexity, protein structure prediction, and the Levinthal paradox in The Protein Folding Problem, ch. 14, pp. 435–508, Birkhauser, 1994.*
AL133087. NCBI Genbank Record, Feb. 18, 2000.

* cited by examiner

*Primary Examiner*—Christina Chan
*Assistant Examiner*—Maher Haddad
(74) *Attorney, Agent, or Firm*—Millen, White, Zelano & Branigan, P.C.

(57) ABSTRACT

The present invention relates to all facets of novel polynucleotides, the polypeptides they encode, antibodies and specific binding partners thereto, and their applications to research, diagnosis, drug discovery, therapy, clinical medicine, forensic science and medicine, etc. The polynucleotides are modulated during angiogeneis and are therefore useful in variety of ways, including, but not limited to, as molecular markers, as drug targets, and for detecting, diagnosing, staging, monitoring, prognosticating, preventing or treating, determining predisposition to, etc., diseases and conditions, determining predisposition to, etc., diseases and conditions, such as abnormal, insufficient, excessive, etc., angiogenesis, inflammatory diseases, rheumatoid arthritis, osteoarthritis, asthma, pulmonary fibrosis, age-related macular degeneration (ARMD), diabetic retinopathy, macular degeneration, and retinopathy of prematurity (ROP), endometriosis, cancer, Coats' disease, peripheral retinal neovascularization, neovascular glaucoma, psoriasis, retrolental fibroplasias, angiofibroma, inflammation, etc.

3 Claims, 27 Drawing Sheets

```
                    *        20         *        40         *
ANH0009    : MEVKPPPGRPQPDSGRRRRRRGEEGHDPKEPEQLRKLFIGGLSFETTDDS : 50
XM_087061  : MEVKPPPGRPQPDSGRRRRRRGEEGHDPKEPEQLRKLFIGGLSFETTDDS : 50

60         *        80         *        100
ANH0009    : LREHFEKWGTLTDCVVMRDPQTKRSRGFGFVTYSCVEEVDAAMCARPHKV : 100
XM_087061  : LREHFEKWGTLTDCVVMRDPQTKRSRGFGFVTYSCVEEVDAAMCARPHKV : 100

*        120        *        140        *
ANH0009    : DGRVVEPKRAVSREDSVKPGAHLTVKKIFVGGIKEDTEEYNLRDYFEKYG : 150
XM_087061  : DGRVVEPKRAVSREDSVKPGAHLTVKKIFVGGIKEDTEEYNLRDYFEKYG : 150

160        *        180        *        200
ANH0009    : KIETIEVMEDRQSGKKRGFAFVTFDDHDTVDKIVVQKYHTINGHNCEVKK : 200
XM_087061  : KIETIEVMEDRQSGKKRGFAFVTFDDHDTVDKIVVQKYHTINGHNCEVKK : 200

*        220        *        240        *
ANH0009    : ALSKQEMQSAGSQRGRGGGSGNFMGRGGNFGGGGGNFGRGGNFGGRGGYG : 250
XM_087061  : ALSKQEMQSAGSQRGRGGGSGNFMGRGGNFGGGGGNFGRGGNFGGRGRLW : 250

260        *        280        *        300
ANH0009    : GGGGGSRGSYGGGDGGYNGFGGDGGNYGGGPGYSSRGGYGGGGPGYGNQG : 300
XM_087061  : WWRWWQQR----------------------------------------- : 258

*        320        *        340        *
ANH0009    : GGYGGGGGYDGYNEGGNFGGGNYGGGGNYNDFGNYSGQQQSNYGPMKGGS : 350
XM_087061  : ------------------------------------------------- : -

360        *
ANH0009    : EGGRSSGSPYGGGYGSGGGSGGYGSRRF : 378
XM_087061  : ---------------------------- : -
```

FIG. 1

```
               *        20         *        40         *        6
ANH0024A : MTAPEKPVKQEEMAALDVDSGGGGGGGGGHGEYLQQQQQHGNGAVAAAAAAQDTQPSPL :  59
ANH0024B : MTAPEKPVKQEEMAALDVDSGGGGGGGGGHGEYLQQQQQHGNGAVAAAAAAQ------- :  52
ANH0024D : -------------------------LPARGANAPTPPAPPRLARLPPFCARDTQPSPL :  33
ANH0024C : ---------------------------------------------------------- :   -
X68560   : ---------------------------------------------------------- :   -

0         *        80         *        100        *        1
ANH0024A : ALLAATCSKIGPPSPGDDEEEAAAAAGAPAAAGATGDLASAQLGGAPNRWEVLSATPTT : 118
ANH0024B : ---------------------------------TGDLASAQLGGAPNRWEVLSATPTT :  77
ANH0024D : ALLAATCSKIGPPSPGDDEEEAAAAAGAPAAAGATGDLASAQLGGAPNRWEVLSATPTT :  92
ANH0024C : ---------------------------------------------------------- :   -
X68560   : ---------------------------------------------------------- :   -

20        *        140        *        160        *
ANH0024A : IKDEAGNLVQIPSAATSSGQYVLPLQNLQNQQIFSVAPGSDSSNGAVSSVQYQVIPQIQ : 177
ANH0024B : IKDEAGNLVQIPSAATSSGQYVLPLQNLQNQQIFSVAPGSDSSNGAVSSVQYQVIPQIQ : 136
ANH0024D : IKDEAGNLVQIPSAATSSGQYVLPLQNLQNQQIFSVAPGSDSSNGAVSSVQYQVIPQIQ : 151
ANH0024C : ---------------------------------------------------------- :   -
X68560   : ---------------------------------------------------------- :   -

180        *        200        *        220        *
ANH0024A : SADGQQVQIGFTGSSDNGGINQESSQIQIIPGSNQTLLASGTPSANIQNLIPQTGQVQV : 236
ANH0024B : SADGQQVQIGFTGSSDNGGINQESSQIQIIPGSNQTLLASGTPSANIQNLIPQTGQVQV : 195
ANH0024D : SADGQQVQIGFTGSSDNGGINQESSQIQIIPGSNQTLLASGTPSANIQNLIPQTGQVQV : 210
ANH0024C : ---------------------------------------------------------- :   -
X68560   : ---------------------------------------------------------- :   -

240        *        260        *        280        *
ANH0024A : QGVAIGGSSFPGQTQVVANVPLGLPGNITFVPINSVDLDSLGLSGSSQTMTAGINADGH : 295
ANH0024B : QGVAIGGSSFPGQTQVVANVPLGLPGNITFVPINSVDLDSLGLSGSSQTMTAGINADGH : 254
ANH0024D : QGVAIGGSSFPGQTQVVANVPLGLPGNITFVPINSVDLDSLGLSGSSQTMTAGINADGH : 269
ANH0024C : ------------------------------------------------MTAGINADGH :  10
X68560   : ------------------------------------------------MTAGINADGH :  10

300        *        320        *        340        *
ANH0024A : LINTGQAMDSSDNSERTGERVSPDINETNTDTDLFVPTSSSSQLPVTIDSTGILQQNTN : 354
ANH0024B : LINTGQAMDSSDNSERTGERVSPDINETNTDTDLFVPTSSSSQLPVTIDSTGILQQNTN : 313
ANH0024D : LINTGQAMDSSDNSERTGERVSPDINETNTDTDLFVPTSSSSQLPVTIDSTGILQQNTN : 328
ANH0024C : LINTGQAMDSSDNSERTGERVSPDINETNTDTDLFVPTSSSSQLPVTIDSTGILQQNTN :  69
X68560   : LINTGQAMDSSDNSERTGERVSPDINETNTDTDLFVPTSSSSQLPVTIDSTGILQQNTN :  69

360        *        380        *        400        *
ANH0024A : SLTTSSGQVHSSDLQGNYIQSPVSEETQAQNIQVSTAQPVVQHLQLQESQQPTSQAQIV : 413
ANH0024B : SLTTSSGQVHSSDLQGNYIQSPVSEETQAQNIQVSTAQPVVQHLQLQESQQPTSQAQIV : 372
ANH0024D : SLTTSSGQVHSSDLQGNYIQSPVSEETQAQNIQVSTAQPVVQHLQLQESQQPTSQAQIV : 387
ANH0024C : SLTTSSGQVHSSDLQGNYIQSPVSEETQAQNIQVSTAQPVVQHLQLQESQQPTSQAQIV : 128
X68560   : SLTTSSGQVHSSDLQGNYIQSPVSEETQAQNIQVSTAQPVVQHLQLQESQQPTSQAQIV : 128

420        *        440        *        460        *
ANH0024A : QGITPQTIHGVQASGQNISQQALQNLQLQLNPGTFLIQAQTVTPSGQVTWQTFQVQGVQ : 472
ANH0024B : QGITPQTIHGVQASGQNISQQALQNLQLQLNPGTFLIQAQTVTPSGQVTWQTFQVQGVQ : 431
ANH0024D : QGITPQTIHGVQASGQNISQQALQNLQLQLNPGTFLIQAQTVTPSGQVTWQTFQVQGVQ : 446
ANH0024C : QGITPQTIHGVQASGQNISQQALQNLQLQLNPGTFLIQAQTVTPSGQVTWQTFQVQGVQ : 187
X68560   : QGITPQTIHGVQASGQNISQQALQNLQLQLNPGTFLIQAQTVTPSGQVTWQTFQVQGVQ : 187
```

FIG. 2A

```
              480         *         500         *         520         *
ANH0024A :  NLQNLQIQNTAAQQITLTPVQTLTLGQVAAGGAFTSTPVSLSTGQLPNLQTVTVNSIDS  :  531
ANH0024B :  NLQNLQIQNTAAQQITLTPVQTLTLGQVAAGGAFTSTPVSLSTGQLPNLQTVTVNSIDS  :  490
ANH0024D :  NLQNLQIQNTAAQQITLTPVQTLTLGQVAAGGAFTSTPVSLSTGQLPNLQTVTVNSIDS  :  505
ANH0024C :  NLQNLQIQNTAAQQITLTPVQTLTLGQVAAGGAFTSTPVSLSTGQLPNLQTVTVNSIDS  :  246
X68560   :  NLQNLQIQNTAAQQITLTPVQTLTLGQVAAGGAFTSTPVSLSTGQLPNLQTVTVNSIDS  :  246

540         *         560         *         580         *
ANH0024A :  AGIQLHPGENADSPADIRIKEEEPDPEEWQLSGDSTLNTNDLTHLRVQVVDEEGDQQHQ  :  590
ANH0024B :  AGIQLHPGENADSPADIRIKEEEPDPEEWQLSGDSTLNTNDLTHLRVQVVDEEGDQQHQ  :  549
ANH0024D :  AGIQLHPGENADSPADIRIKEEEPDPEEWQLSGDSTLNTNDLTHLRVQVVDEEGDQQHQ  :  564
ANH0024C :  AGIQLHPGENADSPADIRIKEEEPDPEEWQLSGDSTLNTNDLTHLRVQVVDEEGDQQHQ  :  305
X68560   :  AGIQLHPGENADSPADIRIKEEEPDPEEWQLSGDSTLNTNDLTHLRVQVVDEEGDQQHQ  :  305

600         *         620         *         640
ANH0024A :  EGKRLRRVACTCPNCKEGGGRGTNLGKKKQHICHIPGCGKVYGKTSHLRAHLRWHSGER  :  649
ANH0024B :  EGKRLRRVACTCPNCKEGGGRGTNLGKKKQHICHIPGCGKVYGKTSHLRAHLRWHSGER  :  608
ANH0024D :  EGKRLRRVACTCPNCKEGGGRGTNLGKKKQHICHIPGCGKVYGKTSHLRAHLRWHSGER  :  623
ANH0024C :  EGKRLRRVACTCPNCKEGGGRGTNLGKKKQHICHIPGCGKVYGKTSHLRAHLRWHSGER  :  364
X68560   :  EGKRLRRVACTCPNCKEGGGRGTNLGKKKQHICHIPGCGKVYGKTSHLRAHLRWHSGER  :  364

*         660         *         680         *         700
ANH0024A :  PFVCNWMYCGKRFTRSDELQRHRRTHTGEKKFVCPECSKRFMRSDHLAKHIKTHQNKKG  :  708
ANH0024B :  PFVCNWMYCGKRFTRSDELQRHRRTHTGEKKFVCPECSKRFMRSDHLAKHIKTHQNKKG  :  667
ANH0024D :  PFVCNWMYCGKRFTRSDELQRHRRTHTGEKKFVCPECSKRFMRSDHLAKHIKTHQNKKG  :  682
ANH0024C :  PFVCNWMYCGKRFTRSDELQRHRRTHTGEKKFVCPECSKRFMRSDHLAKHIKTHQNKKG  :  423
X68560   :  PFVCNWMYCGKRFTRSDELQRHRRTHTGEKKFVCPECSKRFMRSDHLAKHIKTHQNKKG  :  423

*         720         *         740         *         760
ANH0024A :  IHSSSTVLASVEAARDDTLITAGGTTLILAKIQQGSVSGIGTVNTSATSNQDILTNTEI  :  767
ANH0024B :  IHSSSTVLASVEAARDDTLITAGGTTLILAKIQQGSVSGIGTVNTSATSNQDILTNTEI  :  726
ANH0024D :  IHSSSTVLASVEAARDDTLITAGGTTLILAKIQQGSVSGIGTVNTSATSNQDILTNTEI  :  741
ANH0024C :  IHSSSTVLASVEAARDDTLITAGGTTLILAKIQQGSVSGIGTVNTSATSNQDILTNTEI  :  482
X68560   :  IHSSSTVLASVEAARDDTLITAGGTTLILAKIQQGSVSGIGTVNTSATSNQDILTNTEI  :  482

*         780
ANH0024A :  PLQLVTVSGNETME  :  781
ANH0024B :  PLQLVTVSGNETME  :  740
ANH0024D :  PLQLVTVSGNETME  :  755
ANH0024C :  PLQLVTVSGNETME  :  496
X68560   :  PLQLVTVSGNETME  :  496
```

FIG. 2B

```
              *        20         *         40         *        60
ANH0039    : MDLRQFLMCLSLCTAFALSKPTEKKDRVHHEPQLSDKVHNDAQSFDYDHDAFLGAEEAKT :  60
XM_045848  : MDLRQFLMCLSLCTAFALSKPTEKKDRVHHEPQLSDKVHNDAQSFDYDHDAFLGAEEAKT :  60

*        80         *        100         *        120
ANH0039    : FDQLTPEESKERLGMIVDKIDADKDGFVTEGELKSWIKHAQKKYIYDNVENQWQEFDMNQ : 120
XM_045848  : FDQLTPEESKERLGKIVSKIDGDKDGFVTVDELKDWIKFAQKRWIYEDVERQWKGHDLNE : 120

*       140         *        160         *        180
ANH0039    : DGLISWDEYRNVTYGTYLDDPDPDDGFNYKQMMVRDERRFKMADKDGDLIATKEEFTAFL : 180
XM_045848  : DGLVSWEEYKNATYGYVLDDPDPDDGFNYKQMMVRDERRFKMADKDGDLIATKEEFTAFL : 180

*       200         *        220         *        240
ANH0039    : HPEEYDYMKDIVVQETMEDIDKNADGFIDLEEYIGDMYSHDGNTDEPEWVKTEREQFVEF : 240
XM_045848  : HPEEYDYMKDIVVQETMEDIDKNADGFIDLEEYIGDMYSHDGNTDEPEWVKTEREQFVEF : 240

*       260         *        280         *        300
ANH0039    : RDKNRDGKMDKEETKDWILPSDYDHAEAEARHLVYESDQNKDGKLTKEEIVDKYDLFVGS : 300
XM_045848  : RDKNRDGKMDKEETKDWILPSDYDHAEAEARHLVYESDQNKDGKLTKEEIVDKYDLFVGS : 300

*
ANH0039    : QATDFGEALVRHDEF : 315
XM_045848  : QATDFGEALVRHDEF : 315
```

FIG. 3

```
                  *        20         *        40         *        60
XM_055371 : MRAPSMDRAAVARVGAVASASVCALVAGVVLAQYIFTLKRKTGRKTKI-IEMMPEFQKSS :  59
ANH0068   : ------------------------------------MTNQESAVHVKMMPEFQKSS :  20

*        80         *       100         *       120
XM_055371 : VRIKNPTRVEEIICGLIKGGAAKLQIITDFDMTLSRFSYKGKRCPTCHNIIDNCKLVTDE : 119
ANH0068   : VRIKNPTRVEEIICGLIKGGAAKLQIITDFDMTLSRFSYKGKRCPTCHNIIDNCKLVTDE :  80

*       140         *       160         *       180
XM_055371 : CRKKLLQLKEKYYAIEVDPVLTVEEKYPYMVEWYTKSHGLLVQQALPKAKLKEIVAESDV : 179
ANH0068   : CRKKLLQLKEKYYAIEVDPVLTVEEKYPYMVEWYTKSHGLLVQQALPKAKLKEIVAESDV : 140

*       200         *       220         *       240
XM_055371 : MLKEGYENFFDKLQQHSIPVFIFSAGIGDVLEEVIRQAGVYHPNVKVVSNFMDFDETGVL : 239
ANH0068   : MLKEGYENFFDKLQQHSIPVFIFSAGIGDVLEEVIRQAGVYHPNVKVVSNFMDFDETGVL : 200

*       260         *       280         *       300
XM_055371 : KGFKGELIHVFNKHDGALRNTEYFNQLKDNSNIILLGDSQGDLRMADGVANVEHILKIGY : 299
ANH0068   : KGFKGELIHVFNKHDGALRNTEYFNQLKDNSNIILLGDSQGDLRMADGVANVEHILKIGY : 260

*       320         *
XM_055371 : LNDRVDELLEKYMDSYDIVLVQDESLEVANSILQKIL- : 336
ANH0068   : LNDRVDELLEKYMDSYDIVLVQDESLEVANSILQKIL- : 297
```

FIG. 4

```
                  *        20         *        40         *        60
ANH0114    : MALGLEQAEEQRLYQQTLLQDGLKDMLDHGKFLDCVVRAGEREFPCHRLVLAACSPYFRA :  60
XM_076374  : MALGLEQAEEQRLYQQTLLQDGLKDMLDHGKFLDCVVRAGEREFPCHRLVLAACSPYFRA :  60

*        80         *       100         *       120
ANH0114    : RFLAEPERAGELHLEEVSPDVVAQVLHYLYTSEIALDEASVQDLFAAAHRFQIPSIFTIC : 120
XM_076374  : RFLAEPERAGELHLEEVSPDVVAQVLHYLYTSEIALDEASVQDLFAAAHRFQIPSIFTIC : 120

*       140         *       160         *       180
ANH0114    : VSFLQKRLCLSNCLAVFRLGLLLDCARLAVAARDFICAHFTLVARDADFLGLSADELIAI : 180
XM_076374  : VSFLQKRLCLSNCLAVFRLGLLLDCARLAVAARDFICAHFTLVARDADFLGLSADELIAI : 180

*       200         *       220         *       240
ANH0114    : ISSDGLNVEKEEAVFEAVMRWAGSGDAEAQAERQRALPTVFESVRCRLLPRAFLESRVER : 240
XM_076374  : ISSDGLNVEKEEAVFEAVMRWAGSGDAEAQAERQRALPTVFESVRCRLLPRAFLESRVER : 240

*       260         *       280         *       300
ANH0114    : HPLVRAQPELLRKVQMVKDAHEGRITTLRKKKKGKDGAGAKEADKGTSKAKAEEDEEAER : 300
XM_076374  : HPLVRAQPELLRKVQMVKDAHEGRITTLRKKKKGKDGAGAKEADKGTSKAKAEEDEEAER : 300

*       320         *       340         *       360
ANH0114    : ILPGILNDTLRFGMFLQDLIFMISEEGAVAYDPAANECYCASLSSQVPKNHVSLVTKENQ : 360
XM_076374  : ILPGILNDTLRFGMFLQDLIFMISEEGAVAYDPAANECYCASLSNQVPKNHVSLVTKENQ : 360

*       380         *       400         *       420
ANH0114    : VFVAGGLFYNEDNKEDPMSAYFLQFDHLDSEWLGMPPLPSPRCLFGLGEALNSIYVVGGR : 420
XM_076374  : VFVAGGLFYNEDNKEDPMSAYFLQFDHLDSEWLGMPPLPSPRCLFGLGEALNSIYVVGGR : 420

*       440         *       460         *       480
ANH0114    : EIKDGERCLDSVMCYDRLSFKWGESDPLPYVVYGHTVLSHMDLVYVIGGKGSDRKCLNKM : 480
XM_076374  : EIKDGERCLDSVMCYDRLSFKWCHRHRADQFCRSVQHHRQQVGTLRGLPTGA-------- : 472

*       500         *       520         *       540
ANH0114    : CVYDPKKFEWKELAPMQTARSLFGATVHDGRIIVAAGVTDGLTSSAEVYSITDNKWAPF  : 540
XM_076374  : ------------------------------------------------------------ :   -

*       560         *       580         *       600
ANH0114    : EAFPQERSSLSLVSLVGTLYAIGGFATLETESGELVPTELNDIWRYNEEEKKWEGVLREI : 600
XM_076374  : ------------------------------------------------------------ :   -

*       620
ANH0114    : AYAAGATFLPVRLNVLRLTKM : 621
XM_076374  : --------------------- :   -
```

FIG. 5

```
              *        20         *         40         *         60
ANH0144A  : MAEGRRREDEEEELRERRELGGQRRARGRALSGHSAADRNERNKPEHRSSSQGPLSSIPA  :  60
ANH0144B  : MAEGRRREDEEEELRERRELGGQRRARGRALSGHSAADRNERNKPEHRSSSQGPLSSIRA  :  60
ANH0144C  : MAEGRRREDEEEELRERRELGGQRRARGRALSGHSAADRNERNKPEHRSSSQGPLSSIRA  :  60
AL133047  : ------------------------------------------------------------  :   -

*        80         *        100         *        120
ANH0144A  : VIKRSSRTSIQSELHRDRRRPEITIVAAEPLRPASWFPGTPPPGLGFPTSSAAGSWRPNE  : 120
ANH0144B  : VIKRSSRTSIQSELHRDRRRPEITIVAAEPLRPASWFPGTPPPGLGFPTSSAAGSWRPNE  : 120
ANH0144C  : VIKRSSRTSIQSELHRDRRRPEITIVAAEPLRPASWFPGTPPPGLGFPTSSAAGSWRPNE  : 120
AL133047  : ------------------------------------------------------------  :   -

*       140         *        160         *        180
ANH0144A  : LVPAELPPSYEQVIKEINQVQVNTTNNNNAAATPRHTITSATQTDFSEEIDNDLPC---T  : 177
ANH0144B  : LVPAELPPSYEQVIKEINQVQVNTTNNNNAAATPRHTITSATQTDFSEEIDNDLPC---T  : 177
ANH0144C  : LVPAELPPSYEQVIKEINQVQVNTTNNNNAAATPRHTITSATQTDFSEEIDNDLPQSNAT  : 180
AL133047  : ------------------------------------------------------------  :   -

*       200         *        220         *        240
ANH0144A  : LQAPLKPLQPFSAVSSGNLPTNVAPLIVFDISEEPNCPENPSATRCPVPKPRSKSNLRPI  : 237
ANH0144B  : LQAPLKPLQPFSAVSSGNLPTNVAPLIVFDISEEPNCPENPSATRCPVPKPRSKSNLRPI  : 237
ANH0144C  : LQAPLKPLQPFSAVSSGNLPTNVAPLIVFDISEEPNCPENPSATRCPVPKPRSKSNLRPI  : 240
AL133047  : ------------------------------------------------------------  :   -

*       260         *        280         *        300
ANH0144A  : PRDSHIKEQSQQKISPAAVGEESSPCRPQSLLDNASTSDSQAVMNIMNTEQSQNSIVSRI  : 297
ANH0144B  : PRDSHIKEQSQQKISPAAVGEESSPGRPQSLLDNASTSDSQAVMNIMNTEQSQNSIVSRI  : 297
ANH0144C  : PRDSHIKEQSQQKISPAAVGEESSPGRPQSLLDNASTSDSQAVMNIMNTEQSQNSIVSRI  : 300
AL133047  : ------------------------------------------------------------  :   -

*       320         *        340         *        360
ANH0144A  : KVFEGQTNIETSGLPKKPEITPRSLPPKPTVSSGKPSVAPKPAANRASGEWDSGTENRLK  : 357
ANH0144B  : KVFEGQTNIETSGLPKKPEITPRSLPPKPTVSSGKPSVAPKPAANRASGEWDSGTENRLK  : 357
ANH0144C  : KVFEGQTNIETSGLPKKPEITPRSLPPKPTVSSGKPSVAPKPAANRASGEWDSGTENRLK  : 360
AL133047  : ------------------------------------------------------------  :   -

*       380         *        400         *        420
ANH0144A  : VTSKEGLTPYPPLQEAGSIPVTKPELPKKPNPGLIRSVNPEIPGRGPLAESSDSGKKVPT  : 417
ANH0144B  : VTSKEGLTPYPPLQEAGSIPVTKPELPKKPNPGLIRSVNPEIPGRGPLAESSDSGKKVPT  : 417
ANH0144C  : VTSKEGLTPYPPLQEAGSIPVTKPELPKKPNPGLIRSVNPEIPGRGPLAESSDSGKKVPT  : 420
AL133047  : ------------------------------------------------------------  :   -

*       440         *        460         *        480
ANH0144A  : PAPRPLLLKKSVSSENPTYPSAPLKPVTVPPRLAGASQAKAYKSLGEGPPANPPVPVLQS  : 477
ANH0144B  : PAPRPLLLKKSVSSENPTYPSAPLKPVTVPPRLAGASQAKAYKSLGEGPPANPPVPVLQS  : 477
ANH0144C  : PAPRPLLLKKSVSSENPTYPSAPLKPVTVPPRLAGASQAKAYKSLGEGPPANPPVPVLQS  : 480
AL133047  : ------------------------------------------------------------  :   -

*       500         *        520         *        540
ANH0144A  : KPLVDIDLISFDDDVLPTPSGNLAEESVGSEMVLDPFQLPAKTEPIKERAVQPAPTRKPT  : 537
ANH0144B  : KPLVDIDLISFDDDVLPTPSGNLAEESVGSEMVLDPFQLPAKTEPIKERAVQPAPTRKPT  : 537
ANH0144C  : KPLVDIDLISFDDDVLPTPSGNLAEESVGSEMVLDPFQLPAKTEPIKERAVQPAPTRKPT  : 540
AL133047  : ------------------------------------------------------------  :   -

*       560         *        580         *        600
ANH0144A  : VIRIPAKPGKCLHEDPQSPPPLPAEKPIGNTFSTVSGKLSNVERTRNLESNHPGQTGGFV  : 597
ANH0144B  : VIRIPAKPGKCLHEDPQSPPPLPAEKPIGNTFSTVSGKLSNVERTRNLESNHPGQTGGFV  : 597
ANH0144C  : VIRIPAKPGKCLHEDPQSPPPLPAEKPIGNTFSTVSGKLSNVERTRNLESNHPGQTGGFV  : 600
AL133047  : ------------------------------------------------------------  :   -
```

FIG. 6A

```
                   *         620         *         640         *         660
ANH0144A :  RVPPRLPPRPVNG---------------------------------------------------- :  610
ANH0144B :  RVPPRLPPRPVNGHLIMTTILFMSCSARARMGFTGIVHILRFKLLLESWCWSEAGGSVIE       :  657
ANH0144C :  RVPPRLPPRPVNG---------------------------------------------------- :  613
AL133047 :  ------------------------------------------------------------------ :    -

*         680         *         700         *         720
ANH0144A :  ------------------------------------------------------------      :    -
ANH0144B :  LAEAFARLQIMSSFSSKHGWSFIDWSVRLPVIGWPSQNPLFWMRNGLFCLDMTELYHLET      :  717
ANH0144C :  ------------------------------------------------------------      :    -
AL133047 :  ------------------------------------------------------------      :    -

*         740         *         760         *         780
ANH0144A :  -KTIPTQQPPTKVPPERPPPKLSATRRSNKKLPFNRSSSDMDLQKKQSNLATGLSKAKS       :  669
ANH0144B :  KKTIPTQQPPTKVPPERPPPKLSATRRSNKKLPFNRSSSDMDLQKKQSNLATGLSKAKS       :  777
ANH0144C :  -KTIPTQQPPTKVPPERPPPKLSATRRSNKKLPFNRSSSDMDLQKKQSNLATGLSKAKS       :  672
AL133047 :  ----------------------------------------------------------       :    -

*         800         *         820         *         840
ANH0144A :  QVFKNQDPVLPPRPKPGHPLYSKYMLSVPHGIANEDIVSQNPGELSCKRGDVLVMLKQTE      :  729
ANH0144B :  QVFKNQDPVLPPRPKPGHPLYSKYA-----------------------RGDVLVMLKQTE     :  814
ANH0144C :  QVFKNQDPVLPPRPKPGHPLYSKYMLSVPHGIANEDIVSQNPGELSCKRGDVLVMLKQTE      :  732
AL133047 :  -----------------------MLSVPHGIANEDIVSQNPGELSCKRGDVLVMLKQTE      :   36

*         860         *         880         *         900
ANH0144A :  NNYLECQKGEDTGRVHLSQMKIITPLDEHLRSRPNDPSHAQKPVDSGAPHAVVLHDFPAE     :  789
ANH0144B :  NNYLECQKGEDTGRVHLSQMKIITPLDEHLRSRPNDPSHAQKPVDSGAPHAVVLHDFPAE     :  874
ANH0144C :  NNYLECQKGEDTGRVHLSQMKIITPLDEHLRSRPNDPSHAQKPVDSGAPHAVVLHDFPAE     :  792
AL133047 :  NNYLECQKGEDTGRVHLSQMKIITPLDEHLRSRPNDPSHAQKPVDSGAPHAVVLHDFPAE     :   96

*         920         *         940         *         960
ANH0144A :  QVDDLNLTSGEIVYLLEKIDTDWYRGNCRNQIGIFPANYVKVIIDIPEGGNGKRECVSSH     :  849
ANH0144B :  QVDDLNLTSGEIVYLLEKIDTDWYRGNCRNQIGIFPANYVKVIIDIPEGGNGKRECVSSH     :  934
ANH0144C :  QVDDLNLTSGEIVYLLEKIDTDWYRGNCRNQIGIFPANYVKVIIDIPEGGNGKRECVSSH     :  852
AL133047 :  QVDDLNLTSGEIVYLLEKIDTDWYRGNCRNQIGIFPANYVKVIIDIPEGGNGKRECVSSH     :  156

*         980         *        1000         *        1020
ANH0144A :  CVKGSRCVARFEYIGEQKDELSFSEGEIIILKEYVNEEWARGEVRGRTGIFPLNFVEPVE     :  909
ANH0144B :  CVKGSRCVARFEYIGEQKDELSFSEGEIIILKEYVNEEWARGEVRGRTGIFPLNFVEPVE     :  994
ANH0144C :  CVKGSRCVARFEYIGEQKDELSFSEGEIIILKEYVNEEWARGEVRGRTGIFPLNFVEPVE     :  912
AL133047 :  CVKGSRCVARFEYIGEQKDELSFSEGEIIILKEYVNEEWARGEVRGRTGIFPLNFVEPVE     :  216

*        1040         *        1060         *        1080
ANH0144A :  DYPTSGANVLSTKVPLKTKKEDSGSNSQVNSLPAEWCEALHSFTAETSDDLSFKRGDRIQ     :  969
ANH0144B :  DYPTSCCKCFKHKGTTENQKRRFWLKLSG--------------------------------    : 1023
ANH0144C :  DYPTSGANVLSTKVPLKTKKEDSGSNSQVNSLPAEWCEALHSFTAETSDDLSFKRGDRIQ     :  972
AL133047 :  DYPTSGANVLSTKVPLKTKKEDSGSNSQVNSLPAEWCEALHSFTAETSDDLSFKRGDRIQ     :  276

*        1100         *        1120         *        1140
ANH0144A :  ILERLDSDWCRGRLQDREGIFPAVFVRPCPAEAKSMLAIVPKGRKAKALYDFRGENEDEL    : 1029
ANH0144B :  ------------------------------------------------------------    :    -
ANH0144C :  ILERLDSDWCRGRLQDREGIFPAVFVRPCPAEAKSMLAIVPKGRKAKALYDFRGENEDEL    : 1032
AL133047 :  ILERLDSDWCRGRLQDREGIFPAVFVRPCPAEAKSMLAIVPKGRKAKALYDFRGENEDEL    :  336

*        1160         *        1180
ANH0144A :  SFKAGDIITELESVDDDWMSGELMGKSGIFPKNYIQFLQIS    : 1070
ANH0144B :  -----------------------------------------   :    -
ANH0144C :  SFKAGDIITELESVDDDWMSGELMGKSGIFPKNYIQFLQIS    : 1073
AL133047 :  SFKAGDIITELESVDDDWMSGELMGKSGIFPKNYIQFLQIS    :  377
```

FIG. 6B

```
                    *         20         *         40         *         60
ANH0241    : MDISTRSKDPGSAERTAQKRKFPSPPHSSNGHSPQDTSTSPIKKKKKPGLLNSNNKEQSE :  60
XM_086643  : MDISTRSKDPGSAERTAQKRKFPSPPHSSNGHSPQDTSTSPIKKKKKPGLLNSNNKEQSE :  60

*         80         *        100         *        120
ANH0241    : LRHGPFYYMKQPLTTDPVDVVPQDGRNDFYCWVCHREGQVLCCELCPRVYHAKCLRLTSE : 120
XM_086643  : LRHGPFYYMKQPLTTDPVDVVPQDGRNDFYCWVCHREGQVLCCELCPRVYHAKCLRLTSE : 120

*        140         *        160         *        180
ANH0241    : PEGDWFCPECEKITVAECIETQSKAMTMLTIEQLSYLLKFAIQKMKQPGTDAFQKPVPLE : 180
XM_086643  : PEGDWFCPECEKITVAECIETQSKAMTMLTIEQLSYLLKFAIQKMKQPGTDAFQKPVPLE : 180

*        200         *        220         *        240
ANH0241    : QHPDYAEYIFHPMDLCTLEKNAKKKMYGCTEAFLADAKWILHNCIIYNGGNHKLTQIAKV : 240
XM_086643  : QHPDYAEYIFHPMDLCTLEKNAKKKMYGCTEAFLADAKWILHNCIIYNGGNHKLTQIAKV : 240

*        260         *        280         *        300
ANH0241    : VIKICEHEMNEIEVCPECYLAACQKRDNWFCEPCSNPHPLVWAKLKGFPFWPAKALRDKD : 300
XM_086643  : VIKICEHEMNEIEVCPECYLAACQKRDNWFCEPCSNPHPLVWAKLKGFPFWPAKALRDKD : 300

*        320         *        340         *        360
ANH0241    : GQVDARFFGQHDRAWVPINNCYLMSKEIPFSVKKTKSIFNSAMQEMEVYVENIRRKFGVF : 360
XM_086643  : GQVDARFFGQHDRAWVPINNCYLMSKEIPFSVKKTKSIFNSAMQEMEVYVENIRRKFGVF : 360

*        380         *        400         *        420
ANH0241    : NYSPFRTPYTPNSQYQMLLDPTNPSAGTAKIDKQEKVKLNFDMTASPKILMSKPVLSGGT : 420
XM_086643  : NYSPFRTPYTPNSQYQMLLDPTNPSAGTAKIDKQEKVKLNFDMTASPKILMSKPVLSGGT : 420

*        440         *        460         *        480
ANH0241    : GRRISLSDMPRSPMSTNSSVHTGSDVEQDAEKKATSSHFSASEESMDFLDKSTASPASTK : 480
XM_086643  : GRRISLSDMPRSPMSTNSSVHTGSDVEQDAEKKATSSHFSASEESMDFLDKSTASPASTK : 480

*        500         *        520         *        540
ANH0241    : TGQAGSLSGSPKPFSPQLSAPITTKTDKTSTTGSILNLNLDRSKAEMDLKELSESVQQQS : 540
XM_086643  : TGQAGSLSGSPKPFSPQLSAPITTKTDKTSTTGSILNLNLDRSKAEMDLKELSESVQQQS : 540

*        560         *        580         *        600
ANH0241    : TPVPLISPKRQIRSRFQLNLDKTIESCKAQLGINEISEDVYTAVEHSDSEDSEKSDSSDS : 600
XM_086643  : TPVPLISPKRQIRSRFQLNLDKTIESCKAQLGINEISEDVYTAVEHSDSEDSEKSDSSDS : 600

*        620         *        640         *        660
ANH0241    : EYISDDEQKSKNEPEDTEDKEGCQMDKEPSAVKKKPKPTNPVEIKEELKSTSPASEKADP : 660
XM_086643  : EYISDDEQKSKNEPEDTEDKEGCQMDKEPSAVKKKPKPTNPVEIKEELKSTSPASEKADP : 660
```

FIG. 7A

```
              *         680         *         700         *         720
ANH0241   : GAVKDKASPEPEKDFSEKAKPSPHPIKDKLKGKDETDSPTVHLGLDSDSESELVIDLGED :  720
XM_086643 : GAVKDKASPEPEKDFSEKAKPSPHPIKDKLKGKDETDSPTVHLGLDSDSESELVIDLGED :  720

*         740         *         760         *         780
ANH0241   : HSGREGRKNKKEPKEPSPKQDVVGKTPPSTTVGSHSPPETPVLTRSSAQTSAAGATATTS :  780
XM_086643 : HSGREGRKNKKEPKEPSPKQDVVGKTPPSTTVGSHSPPETPVLTRSSAQTSAAGATATTS :  780

*         800         *         820         *         840
ANH0241   : TSSTVTVTAPAPAATGSPVKKQRPLLPKETAPAVQRVVWNSSSKFQTSSQKWHMQKMQRQ :  840
XM_086643 : TSSTVTVTAPAPAATGSPVKKQRPLLPKETAPAVQRVVWNSSSKFQTSSQKWHMQKMQRQ :  840

*         860         *         880         *         900
ANH0241   : QQQQQQQNQQQQPQSSQGTRYQTRQAVKAVQQKEITQSPSTSTITLVTSTQSSPLVTSSG :  900
XM_086643 : QQQQQQQNQQQQPQSSQGTRYQTRQAVKAVQQKEITQSPSTSTITLVTSTQSSPLVTSSG :  900

*         920         *         940         *         960
ANH0241   : SMSTLVSSVNADLPIATASADVAADIAKYTSKMMDAIKGTMTEIYNDLSKNTTGSTIAEI :  960
XM_086643 : SMSTLVSSVNADLPIATASADVAADIAKYTSKVNGCNKRNNDRNIQRSF----------- :  949

*         980         *        1000         *        1020
ANH0241   : RRLRIEIEKLQWLHQQELSEMKHNLELTMAEMRQSLEQERDRLIAEVKKQLELEKQQAVD : 1020
XM_086643 : ------------------------------------------------------------ :   -

*        1040         *        1060         *        1080
ANH0241   : ETKKKQWCANCKKEAIFYCCWNTSYCDYPCQQAHWPEHMKSCTQSATAPQQEADAEVNTE : 1080
XM_086643 : ------------------------------------------------------------ :   -

*        1100         *        1120         *        1140
ANH0241   : TLNKSSQGSSSSTQSAPSETASASKEKETSAEKSKESGSTLDLSGSRETPSSILLGSNQG : 1140
XM_086643 : ------------------------------------------------------------ :   -

*        1160         *        1180         *        1200
ANH0241   : SVSKRCDKQPAYAPTTTDHQPHPNYPAQKYHSRSNKSSWSSSDEKRGSTRSDHNTSTSTK : 1200
XM_086643 : ------------------------------------------------------------ :   -

*
ANH0241   : SLLPKESRLDTFWD : 1214
XM_086643 : -------------- :   -
```

FIG. 7B

```
              *         20         *         40         *         60
ANH0245   : --------------------MRWKSIAHSVIGYFHDEKWFYEETESSDDVEVLTLKKFK :  39
AK027731  : MDSGCWLFGGBFEDSVFEERPERRSGPPASYCAKLCEPQWFYEETESSDDVEVLTLKKFK :  60

*         80         *        100         *        120
ANH0245   : GDLAYRRQEYQKALQEYSSISEKLSSTNFAMKRDVQEGQARCLAHLGRHMEALEIAANLE :  99
AK027731  : GDLAYRRQEYQKALQEYSSISEKLSSTNFAMKRDVQEGQARCLAHLGRHMEALEIAANLE : 120

*        140         *        160         *        180
ANH0245   : NKATNTDHLTTVLYLQLAICSSLQNLEKTIFCLQKLISLHPFNPWNWGKLAEAYLNLGPA : 159
AK027731  : NKATNTDHLTTVLYLQLAICSSLQNLEKTIFCLQKLISLHPFNPWNWGKLAEAYLNLGPA : 180

*        200         *        220         *        240
ANH0245   : LSAALASSQKQHSFTSSDKTIKSFFPHSGKDCLLCFPETLPESSLFSVEANSSNSQKNEK : 219
AK027731  : LSAALASSQKQHSFTSSDKTIKSFFPHSGKDCLLCFPETLPESSLFSVEANSSNSQKNEK : 240

*        260         *        280         *        300
ANH0245   : ALTNIQNCMAEKRETVLIETQLKACASFIRTRLLLQFTQPQQTSFALERNLRTQQEIEDK : 279
AK027731  : ALTNIQNCMAEKRETVLIETQLKACASFIRTRLLLQFTQPQQTSFALERNLRTQQEIEDK : 300

*        320         *        340         *        360
ANH0245   : MKGFSFKEDTLLLIAEVMGEDIPEKIKDEVHPEVKCVGSVALTALVTVSSEEFEDKWFRK : 339
AK027731  : MKGFSFKEDTLLLIAEVMGEDIPEKIKDEVHPEVKCVGSVALTALVTVSSEEFEDKWFRK : 360

*        380
ANH0245   : IKDHFCPFENQFHTEIQILA : 359
AK027731  : IKDHFCPFENQFHTEIQILA : 380
```

FIG. 8

```
              *        20         *        40         *        60
ANH0296    : MKSRFSTIDLRAVLAELNASLLGMRVNNVYDVDNKTYLIRLQKPDFKATLLLESGIRIHT :  60
NM_004713  : ------------------------------------------------------------ :   -
AK000913   : MKSRFSTIDLRAVLAELNASLLGMRVNNVYDVDNKTYLIRLQKPDFKATLLLESGIRIHT :  60

*        80         *       100         *       120
ANH0296    : TEFEWPKNMMPSSFAMKCRKHLKSRRLVSAKQLGVDRIVDFQFGSDEAAYHLIIELYDRG : 120
NM_004713  : ------------------------------------------------------------ :   -
AK000913   : TEFEWPKNMMPSSFAMKCRKHLKSRRLVSAKQLGVDRIVDFQFGSDEAAYHLIIELYDRG : 120

*       140         *       160         *       180
ANH0296    : NIVLTDYEYVILNILRFRTDEADDVKFAVRERYPLDHARAAEPLLTLERLTEIVASAPKG : 180
NM_004713  : ------------------------------------------------------------ :   -
AK000913   : NIVLTDYEYVILNILRFRTDEADDVKFAVRERYPLDHARAAEPLLTLERLTEIVASAPKG : 180

*       200         *       220         *       240
ANH0296    : ELLKRVLNPLLPYGPALIEHCLLENGFSGNVKVDEKLETKDIEKVLVSLQKAEDYMKTTS : 240
NM_004713  : ------------------------------------------------------------ :   -
AK000913   : ELLKRVLNPLLPYGPALIEHCLLENGFSGNVKVDEKLETKDIEKVLVSLQKAEDYMKTTS : 240

*       260         *       280         *       300
ANH0296    : NFSGKGYIIQKREIKPCLEADKPVEDILTYEEFHPFLESQHSQCPYIEFESFDKAVDEFY : 300
NM_004713  : ------------------------------------------------------------ :   -
AK000913   : NFSGKGYIIQKREIKPCLEADKPVEDILTYEEFHPFLESQHSQCPYIEFESFDKAVDEFY : 300

*       320         *       340         *       360
ANH0296    : SKIEGQKIDLKALQQEKQALKKLDNVRKDHENRLEALQQAQEIDKLKGELIEMNLQIVDR : 360
NM_004713  : ------------------------------------------------------------ :   -
AK000913   : SKIEGQKIDLKALQQEKQALKKLDNVRKDHENRLEALQQAQEIDKLKGELIEMNLQIVDR : 360

*       380         *       400         *       420
ANH0296    : AIQVVRSALANQIDWTEIGLIVKEAQAQGDPVASAIKELKLQTNHVTMLLRNPYLLSEEE : 420
NM_004713  : ------------------------------------------------------------ :   -
AK000913   : AIQVVRSALANQIDWTEIGLIVKEAQAQGDPVASAIKELKLQTNHVTMLLRNPYLLSEEE : 420

*       440         *       460         *       480
ANH0296    : DDDVDGDVNVEKNETEPPKGKKKKQKNKQLQKPQKNKPLLVDVDLSLSAYANAKKYYDHK : 480
NM_004713  : ------------------------------------------------------------ :   -
AK000913   : DDDVDGDVNVEKNETEPPKGKKKKQKNKQLQKPQKNKPLLVDVDLSLSAYANAKKYYDHK : 480

*       500         *       520         *       540
ANH0296    : RYAAKKTQKTVEAAEKAFKSAEKKTKQTLKEVQTVTSIQKARKVYWFEKFLWFISSENYL : 540
NM_004713  : ------------------------------------------------------------ :   -
AK000913   : RYAAKKTQKTVEAAEKAFKSAEKKTKQTLKEVQTVTSI---------------------- : 518

*       560         *       580         *       600
ANH0296    : IIGGRDQQQNEIIVKRYLTPGDIYVHADLHGATSCVIKNPTGEPIPPRTLTEAGTMALCY : 600
NM_004713  : ------------------------------------------------------------ :   -
AK000913   : ------------------------------------------------------------ :   -
```

FIG. 9A

```
                   *         620         *         640         *         660
ANH0296   : SAAWDARVITSAWWVYHHQVSKTAPTGEYLTTGSFMIRGKKNFLPPSYLMMGFSFLFKVD : 660
NM_004713 : ------------------------------------------------------------ : -
AK000913  : ------------------------------------------------------------ : -

*         680         *         700         *         720
ANH0296   : ESCVWRHQGERKVRVQDEDMETLASCTSELISEEMEQLDGGDTSSDEDKEEHETPVEVEL : 720
NM_004713 : ------------------------------------------------------------ : -
AK000913  : ------------------------------------------------------------ : -

*         740         *         760         *         780
ANH0296   : MTQVDQEDITLQSGRDELNEELIQEESSEDEGEYEEVRKDQDSVGEMKDEGEETLNYPDT : 780
NM_004713 : MTQVDQEDITLQSGRDELNEELIQEESSEDEGEYEEVRKDQDSVGEMKDEGEETLNYPDT : 60
AK000913  : ------------------------------------------------------------ : -

*         800         *         820         *         840
ANH0296   : TIDLSHLQPQRSTQKLASKEESSNSSDSKSQSRRHLSAKERREMKKKLPSDSGDLEALE : 840
NM_004713 : TIDLSHLQPQRSTQKLASKEESSNSSDSKSQSRRHLSAKERREMKKKLPSDSGDLEALE : 120
AK000913  : ------------------------------------------------------------ : -

*         860         *         880         *         900
ANH0296   : GKDKEKESTVHIETHQNTSKNVAAVQPMKRGQKSKMKKMKEKYKDQDEEDRELIMKLLGS : 900
NM_004713 : GKDKEKESTVHIETHQNTSKNVAAVQPMKRGQKSKMKKMKEKYKDQDEEDRELIMKLLGS : 180
AK000913  : ------------------------------------------------------------ : -

*         920         *         940         *         960
ANH0296   : AGSNKEEKGKKGKKGKTKDEPVKKQPQKPRGGQRVSDNIKKETPFLEVITHELQDFAVDD : 960
NM_004713 : AGSNKEEKGKKGKKGKTKDEPVKKQPQKPRGGQRVSDNIKKETPFLEVITHELQDFAVDD : 240
AK000913  : ------------------------------------------------------------ : -

*         980         *         1000        *         1020
ANH0296   : PHDDKEEQDLDQQGNEENLFDSLTGQPHPEDVLLFAIPICAPYTTMTNYKYRVKLTPGVQ : 1020
NM_004713 : PHDDKEEQDLDQQGNEENLFDSLTGQPHPEDVLLFAIPICAPYTTMTNYKYRVKLTPGVQ : 300
AK000913  : ------------------------------------------------------------ : -

*         1040        *         1060        *         1080
ANH0296   : KKGKAAKTALNSFMHSKEATAREKDLFRSVKDTDLSRNIPGKVKSVCTQSSERKKEIAEM : 1080
NM_004713 : KKGKAAKTALNSFMHSKEATAREKDLFRSVKDTDLSRNIPGKVKSVCTQSSERKKEIAEM : 360
AK000913  : ------------------------------------------------------------ : -

ANH0296   : KF : 1082
NM_004713 : KF : 362
AK000913  : -- : -
```

FIG. 9B

```
                      *         20         *         40         *         60
ANH0423    : MESGRGSSTPPGPIAALGMPDTGPGSSSLGKLQALPVGPRAHCGDPVSLAAAGDGSPDIG :  60
XM_053487  : MESGRGSSTPPGPIAALGMPDTGPGSSSLGKLQALPVGPRAHCGDPVSLAAAGDGSPDIG :  60

*         80         *        100         *        120
ANH0423    : PTGELSGSLKIPNRDSGIDSPSSSVAGENFPCEEGLEAGPSPTVLGAHAEMALDSQVPKV : 120
XM_053487  : PTGELSGSLKIPNRDSGIDSPSSSVAGENFPCEEGLEAGPSPTVLGAHAEMALDSQVPKV : 120

*        140         *        160         *        180
ANH0423    : TPQEEADSDVGEEPDSENTPQKADKDAGLAQHSGPQKLLHIAQELLHTEETYVKRLHLLD : 180
XM_053487  : TPQEEADSDVGEEPDSENTPQKADKDAGLAQHSGPQKLLHIAQELLHTEETYVKRLHLLD : 180

*        200         *        220         *        240
ANH0423    : QVFCTRLTDAGIPPEVIMGIFSNISSIHRFHGQFLLPELKTRITEEWDTNPRLGDILQKI : 240
XM_053487  : QVFCTRLTDAGIPPEVIMGIFSNISSIHRFHGQFLLPELKTRITEEWDTNPRLGDILQKL : 240

*        260         *        280         *        300
ANH0423    : APFLKMYGEYVKNFDRAVGLVSTWTQRSPLFKDVVHSIQKQEVCGNLTLQHHMLEPVQRV : 300
XM_053487  : APFLKMYGEYVKNFDRAVGLVSTWTQRSPLFKDVVHSIQKQEVCGNLTLQHHMLEPVQRV : 300

*        320         *        340         *        360
ANH0423    : PRYELLLKDYLKRLPQDAPDRKDAERSLELISTAANHSNAAIRKVEKMHKLLEVYEQLGC : 360
XM_053487  : PRYELLLKDYLKRLPQDAPDRKDAERSLELISTAANHSNAAIRKVEKMHKLLEVYEQLGC : 360

*        380         *        400         *        420
ANH0423    : EEDIVNPANELIKEGQIQKLSAKNGTPQDRHLFLFNSMILYCVPKLRLMGQKFSVREKMD : 420
XM_053487  : EEDIVNPANELIKEGQIQKLSAKNGTPQDRHLFLFNSMILYCVPKLRLMGQKFSVREKMD : 420

*        440         *        460         *        480
ANH0423    : ISGLQVQDIVKPNTAHTFIITGRKRSLELQTRTEEEKKEWIQIIQATIEKHKQNSETFKA : 480
XM_053487  : ISGLQVQDIVKPNTAHTFIITGRKRSLELQTRTEEEKKEWIQIIQATIEKHKQNSETFKA : 480

*        500         *        520         *        540
ANH0423    : FGGAFSQDEDPSLSPDMPITSTSPVEPVVTTEGSSGAAGLEPRKLSSKTRRDKEKQSCKS : 540
XM_053487  : FGGAFSQDEDPSLSPDMPITSTSPVEPVVTTEGSSGAAGLEPRKLSSKTRRDKEKQSCKS : 540

*        560         *        580         *        600
ANH0423    : CGETFNSITKRRHHCKLCGAVICGKCSEFKAENSRQSRVCRDCFLTQPVAPESTEKTPTA : 600
XM_053487  : CGETFNSITKRRHHCKLCGAVICGKCSEFKAENSRQSRVCRDCFLTQPVAPESTEVGAPS : 600

*        620         *        640         *        660
ANH0423    : DPQPSLLCGPLRLSESGETWSEVWAAIPMSDPQVLHLQGGSQDGRLPRTIPLPSCKLSVP : 660
XM_053487  : SCSPPGGAAEPPDTCSCAPAAPAASAFGVSLGPG--------------------------- : 634

*        680         *        700         *        720
ANH0423    : DPEERLDSGHVWKLQWAKQSWYLSASSAELQQQWLETLSTAAHGDTAQDSPGALQLQVPM : 720
XM_053487  : ------------------------------------------------------------ :   -

ANH0423    : GAAAP : 725
XM_053487  : ----- :   -
```

FIG. 10

```
                    *         20         *         40         *         60
ANH0459B  : MDAIKKKMQMLKLDKENALDRAEQAEADKKAAEDRSKQLEEDIAAKEKLERVSEDERDRV :  60
ANH0459C  : ------------------------------------MAGSSSLEAVREKLRSLQEQALAA :  24
ANH0459D  : ------------------------------------------------------------ :   -
NM_000366 : MDAIKKKMQMLKLDKENALDRAEQAEADKKAAEDRSKQLEDELVSLQKKLKGTEDELDKY :  60

*         80         *        100         *        120
ANH0459B  : LEELHKAEDSLLAAEEAAAKAEADVASLNRRIQLVEEELDRAQERLATALQKLEEAEKAA : 120
ANH0459C  : EERAGTLQRELDHERKLRETAEADVASLNRRIQLVEEELDRAQERLATALQKLEEAEKAA :  84
ANH0459D  : ------------------------------------------------------------ :   -
NM_000366 : SEALKDAQEKLELAEKKATDAEADVASLNRRIQLVEEELDRAQERLATALQKLEEAEKAA : 120

*        140         *        160         *        180
ANH0459B  : DESERGMKVIESRAQKDEEKMEIQEIQLKEAKHIAEDADRKYEEVARKLVIIESDLERAE : 180
ANH0459C  : DESERGMKVIESRAQKDEEKMEIQEIQLKEAKHIAEDADRKYEEVARKLVIIESDLERAE : 144
ANH0459D  : ------MKVIESRAQKDEEKMEIQEIQLKEAKHIAEDADRKYEEVARKLVIIESDLERAE :  54
NM_000366 : DESERGMKVIESRAQKDEEKMEIQEIQLKEAKHIAEDADRKYEEVARKLVIIESDLERAE : 180

*        200         *        220         *        240
ANH0459B  : ERAELSEGQVRQLEEQLRIMDQTLKALMAAEDKYSQKEDRYEEEIKVLSDKLKEAETRAE : 240
ANH0459C  : ERAELSEGKCAELEEELKTVTNNLKSLEAQAEKYSQKEDRYEEEIKVLSDKLKEAETRAE : 204
ANH0459D  : ERAELSEGQVRQLEEQLRIMDQTLKALMAAEDKYSQKEDRYEEEIKVLSDKLKEAETRAE : 114
NM_000366 : ERAELSEGQVRQLEEQLRIMDQTLKALMAAEDKYSQKEDRYEEEIKVLSDKLKEAETRAE : 240

*        260         *        280
ANH0459B  : FAERSVTKLEKSIDDLEEKVAHAKEENLSMHQMIDQTLLELNNM : 284
ANH0459C  : FAERSVTKLEKSIDDLEDQLYQQLEQN---RRLTNELKLALNED : 245
ANH0459D  : FAERSVTKLEKSIDDLEEKVAHAKEENLSMHQMIDQTLLELNNM : 158
NM_000366 : FAERSVTKLEKSIDDLEEKVAHAKEENLSMHQMIDQTLLELNNM : 284
```

FIG. 11

```
              *        20         *        40         *        60
ANH0769  : MAVLKLTDQPPLVQAIFSGDPEEIRMLIHKTEDVNTLDSEKRTPLHVAAFLGDAEIIELL :  60
AL133087 : ------------------------------------------------------------ :   -

*        80         *       100         *       120
ANH0769  : ILSGARVNAKDNMWLTPLHRAVASRSEEAVQVLIKHSADVNARDKNWQTPLHVAAANKAV : 120
AL133087 : ------------------------------------------------------------ :   -

*       140         *       160         *       180
ANH0769  : KCAEVIIPLLSSVNVSDRGGRTALHHAALNGHVEMVNLLLAKGANINAFDKKDRRALHWA : 180
AL133087 : ------------------------------------------------------------ :   -

*       200         *       220         *       240
ANH0769  : AYMGHLDVVALLINHGAEVTCKDKKGYTPLHAAASNGQINVVKHLLNLGVEIDEINVYGN : 240
AL133087 : ------------------------------------------------------------ :   -

*       260         *       280         *       300
ANH0769  : TALHIACYNGQDAVVNELIDYGANVNQPNNGFTPLHFAAASTHGALCLELLVNNGADVN  : 300
AL133087 : ------------------------------------------------------------ :   -

*       320         *       340         *       360
ANH0769  : IQSKDGKSPLHMTAVHGRFTRSQTLIQNGGEIDCVDKDGNTPLHVAARYGHELLINTLIT : 360
AL133087 : -----------MTAVHGRFTRSQTLIQNGGEIDCVDKDGNTPLHVAARYGHELLINTLIT :  49

*       380         *       400         *       420
ANH0769  : SGADTAKCGIHSMFPLHLAALNAHSDCCRKLLSSGQKYSIVSLFSNEHVLSAGFEIDTPD : 420
AL133087 : SGADTAKCGIHSMFPLHLAALNAHSDCCRKLLSSGQKYSIVSLFSNEHVLSAGFEIDTPD : 109

*       440         *       460         *       480
ANH0769  : KFGRTCLHAAAAGGNVECIKLLQSSGADFHKKDKCGRTPLHYAAANCHFHCIETLVTTGA : 480
AL133087 : KFGRTCLHAAAAGGNVECIKLLQSSGADFHKKDKCGRTPLHYAAANCHFHCIETLVTTGA : 169

*       500         *       520         *       540
ANH0769  : NVNETDDWGRTALHYAAASDMDRNKTILGNAHDNSEELERARELKEKEATLCLEFLLQND : 540
AL133087 : NVNETDDWGRTALHYAAASDMDRNKTILGNAHDNSEELERARELKEKEATLCLEFLLQND : 229

*       560         *       580         *       600
ANH0769  : ANPSIRDKEGYNSIHYAAAYGHRQCLELLLERTNSGFEESDSGATKSPLHLAAYNGHHQA : 600
AL133087 : ANPSIRDKEGYNSIHYAAAYGHRQCLELLLERTNSGFEESDSGATKSPLHLAAYNGHHQA : 289

*       620         *       640         *       660
ANH0769  : LEVLLQSLVDLDIRDEKGRTALDLAAFKGHTECVEALINQGASIFVKDNVTKRTPLHASV : 660
AL133087 : LEVLLQSLVDLDIRDEKGRTALDLAAFKGHTECVEALINQGASIFVKDNVTKRTPLHASV : 349

*       680         *       700         *       720
ANH0769  : INGHTLCLRLLLEIADNPEAVDVKDAKGQTPLMLAVAYGHIDAVSLLLEKEANVDTVDIL : 720
AL133087 : INGHTLCLRLLLEIADNPEAVDVKDAKGQTPLMLAVAYGHIDAVSLLLEKEANVDTVDIL : 409
```

FIG. 12A

```
                    *         740         *         760         *         780
ANH0769   : GCTALHRGIMTGHEECVQMLLEQEVSILCKDSRGRTPLHYAAARGHATWLSELLQMALSE : 780
AL133087  : GCTALHRGIMTGHEECVQMLLEQEVSILCKDSRGRTPLHYAAARGHATWLSELLQMALSE : 469

*         800         *         820         *         840
ANH0769   : EDCCFKDNQGYTPLHWACYNGNENCIEVLLEQKCFRKFIGNPFTPLHCAIINDHGNCASL : 840
AL133087  : EDCCFKDNQGYTPLHWACYNGNENCIEVLLEQKCFRKFIGNPFTPLHCAIINDHGNCASL : 529

*         860         *         880         *         900
ANH0769   : LLGAIDSSIVSCRDDKGRTPLHAAAFADHVECLQLLLRHSAPVNAVDNSGKTALMMAAEN : 900
AL133087  : LLGAIDSSIVSCRDDKGRTPLHAAAFADHVECLQLLLRHSAPVNAVDNSGKTALMMAAEN : 589

*         920         *         940         *         960
ANH0769   : GQAGAVDILVNSAQADLTVKDKDLNTPLHLACSKGHEKCALLILDKIQDESLINEKNNAL : 960
AL133087  : GQAGAVDILVNSAQADLTVKDKDLNTPLHLACSKGHEKCALLILDKIQDESLINEKNNAL : 649

*         980         *
ANH0769   : QTPLHVAARNGLKVVVEELLAKGACVLAVDENGC : 994
AL133087  : QTPLHVAARNGLKVVVEELLAKGACVLAVDENGC : 683
```

FIG. 12B

```
                    *         20         *         40         *
ANH0658    : MSLKLPRNWDFNLKVEAAKIARSRSVMTGEQMAAFHPSSTPNPLERPIKMGWLKKQRS : 58
NM_014882  : MSL-------GQSACLFLSIARSRSVMTGEQMAAFHPSSTPNPLERPIKMGWLKKQRS : 51

60         *         80         *        100         *
ANH0658    : IVKNWQQRYFVLRAQQLYYYKDEEDTKPQGCMYLPGCTIKEIATNPEEAGKFVFEIIP : 116
NM_014882  : IVKNWQQRYFVLRAQQLYYYKDEEDTKPQGCMYLPGCTIKEIATNPEEAGKFVFEIIP : 109

120         *        140         *        160         *
ANH0658    : ASWDQNRMGQDSYVLMASSQAEMEEWVKFLRRVAGTPCGVFGQRLDETVAYEQKFGPH : 174
NM_014882  : ASWDQNRMGQDSYVLMASSQAEMEEWVKFLRRVAGTPCGVFGQRLDETVAYEQKFGPH : 167

180         *        200         *        220         *
ANH0658    : LVPILVEKCAEFILEHGRNEEGIFRLPGQDNLVKQLRDAFDAGERPSFDRDTDVHTVA : 232
NM_014882  : LVPILVEKCAEFILEHGRNEEGIFRLPGQDNLVKQLRDAFDAGERPSFDRDTDVHTVA : 225

240         *        260         *        280         *
ANH0658    : SLLKLYLRDLPEPVVPWSQYEGFLLCGQLTNADEAKAQQELMKQLSILPRDNYSLLSY : 290
NM_014882  : SLLKLYLRDLPEPVVPWSQYEGFLLCGQLTNADEAKAQQELMKQLSILPRDNYSLLSY : 283

300         *        320         *        340
ANH0658    : ICRFLHEIQLNCAVNKMSVDNLATVIGVNLIRSKVEDPAVIMRGTPQIQRVMTMMIRD : 348
NM_014882  : ICRFLHEIQLNCAVNKMSVDNLATVIGVNLIRSKVEDPAVIMRGTPQIQRVMTMMIRD : 341

*        360         *        380         *        400
ANH0658    : HEVLFPKSKDIPLSPPAQKNDPKKAPVARSSVGWDATEDLRISRTDSFSSMTSDSDTT : 406
NM_014882  : HEVLFPKSKDIPLSPPAQKNDPKKAPVARSSVGWDATEDLRISRTDSFSSMTSDSDTT : 399

*        420         *        440         *        460
ANH0658    : SPTGQQPSDAFPEDSSKVPREKPGDWKMQSRKRTQTLPNRKCFLTSAFQGANSSKMEI : 464
NM_014882  : SPTGQQPSDAFPEDSSKVPREKPGDWKMQSRKRTQTLPNRKCFLTSAFQGANSSKMEI : 457

*        480         *        500         *        520
ANH0658    : FKNEFWSPSSEAKAGEGHRRTMSQDLRQLSDSQRTSTYDNVPSLPGSPGEEASALSSQ : 522
NM_014882  : FKNEFWSPSSEAKAGEGHRRTMSQDLRQLSDSQRTSTYDNVPSLPGSPGEEASALSSQ : 515

*        540         *        560         *        580
ANH0658    : ACDSKGDTLASPNSETGPGKKNSGEEEIDSLQRMVQELRKEIETQKQMYEEQIKNLEK : 580
NM_014882  : ACDSKGDTLASPNSETGPGKKNSGEEEIDSLQRMVQELRKEIETQKQMYEEQIKNLEK : 573

*        600         *        620         *        6
ANH0658    : ENYDVWAKVVRLNEELEKEKKKSAALEISLRNMERSREDVEKRNKALEEEVKEFVKSM : 638
NM_014882  : ENYDVWAKVVRLNEELEKEKKKSAALEISLRNMERSREDVEKRNKALEEEVKEFVKSM : 631

40
ANH0658    : KEPKTEA--- : 645
NM_014882  : KEPKTEA--- : 638
```

FIG. 13

```
             *        20         *        40         *
ANH0668   : MHQTYSRHCRPEESTFSAAMTTMQGMEQAMPGAGPGVPQLGNMAVIHSHL :  50
XM_015539 : MHQTYSRHCRPEESTFSAAMTTMQGMEQAMPGAGPGVPQLGNMAVIHSHL :  50

60         *        80         *       100
ANH0668   : WKGLQEKFLKGEPKVLGVVQILTALMSLSMGITMMCMASNTYGSNPISVY : 100
XM_015539 : WKGLQEKFLKGEPKVLGVVQILTALMSLSMGITMMCMASNTYGSNPISVY : 100

*       120         *       140         *
ANH0668   : IGYTIWGSVMFIISGSLSIAAGIRTTKGL--------------------  : 129
XM_015539 : IGYTIWGSVMFIISGSLSIAAGIRTTKGIVRGSLGMNITSSVIAASGILI : 150

160         *       180         *       200
ANH0668   : -----------------------------------GLDGMVLLLSVLEFCIAV : 147
XM_015539 : NTFSLAFYSFHHPYCNYYGNSNNCHGTMSILMGLDGMVLLLSVLEFCIAV : 200

*       220         *
ANH0668   : SLSAFGCKVLCCTPGGVVLILPSHSHMAETASPTPLNEV : 186
XM_015539 : SLSAFGCKVLCCTPGGVVLILPSHSHMAETASPTPLNEV : 239
```

FIG. 14

```
                    *        20         *        40         *        60
ANH0757    : MPQPSVSGMDPPFGDAFRSHTFSEQTLMSTDLLANSSDPDFMYELDREMNYQQNPRDNFL :  60
XM_087631  : ------------------------------------------------------------ :   -

*        80         *       100         *       120
ANH0757    : SLEDCKDIENLESFTDVLDNEGALTSNWEQWDTYCEDLTKYTKLTSCDIWGTKEVDYLGL : 120
XM_087631  : ------------------------------------------------------------ :   -

*       140         *       160         *       180
ANH0757    : DDFSSPYQDEEVISKTPTLAQLNSEDSQSVSDSLYYPDSLFSVKQNPLPSSFPGKKITSR : 180
XM_087631  : ------------------------------------------------------------ :   -

*       200         *       220         *       240
ANH0757    : AAAPVCSSKTLQAEVPLSDCVQKASKPPSSTQIMVKTNMYHNEKVNFHVECKDYVKKAKV : 240
XM_087631  : ------------------------------------------------------------ :   -

*       260         *       280         *       300
ANH0757    : KINPVQQSRPLLSQIHTDAAKENTCYCGAVAKRQEKKGMEPLQGHATPALPFKETQELLL : 300
XM_087631  : ------------------------------------------------------------ :   -

*       320         *       340         *       360
ANH0757    : SPLPQEGPGSLAAGESSSLSASTSVSDSSQKKEEHNYSLFVSDNLGEQPTKCSPEEDEED : 360
XM_087631  : ------------------------------------------------------------ :   -

*       380         *       400         *       420
ANH0757    : EEDVDDEDHDEGFGSEHELSENEEEEEEEDYEDDKDDDISDTFSEPGYENDSVEDLKEV  : 420
XM_087631  : ------------------------------------------------------------ :   -

*       440         *       460         *       480
ANH0757    : TSISSRKRGKRRYFWEYSEQLTPSQQERMLRPSEWNRDTLPSNMYQKNGLHHGKYAVKKS : 480
XM_087631  : ---------------------------MLRPSEWNRDTLPSNMYQKNGLHHGKYAVKKS :  32

*       500         *       520         *       540
ANH0757    : RRTDVEDLTPNPKKLLQIGNELRKLNKVISDLTPVSELPLTARPRSRKEKNKLAFRACRL : 540
XM_087631  : RRTDVEDLTPNPKKLLQIGNELRKLNKVISDLTPVSELPLTARPRSRKEKNSWLPELVG- :  91

*       560         *       580         *       600
ANH0757    : KKKAQYEANKVKLWGLNTEYDNLLFVINSIKQEIVNRVQNPRDERGPNMGQKLEILIKDT : 600
XM_087631  : ------------------------------------------------------------ :   -

*       620         *
ANH0757    : LGLPVAGQTSEFVNQVLEKTAEGNPTGGLVGLRIPTSKV : 639
XM_087631  : --------------------------------------- :   -
```

FIG. 15

```
                    *         20         *         40         *         60
ANH0687A   : MSDTRRRVKVYTLNEDRQWDDRGTGHVSSTYVEELKGMSLLVRAESDGSLLLESKINPNT :  60
ANH0687B   : MSDTRRRVKVYTLNEDRQWDDRGTGHVSSTYVEELKGMSLLVRAESDGSLLLESKINPNT :  60
XM_048092  : MSDTRRRVKVYTLNEDRQWDDRGTGHVSSTYVEELKGMSLLVRAESDGSLLLESKINPNT :  60

*         80         *        100         *        120
ANH0687A   : AYQKQQDTLIVWSEAENYDLALSFQEKAGCDEIWEKICQ--------------------- :  99
ANH0687B   : AYQKQQDTLIVWSEAENYDLALSFQEKAGCDEIWEKICQVQGKDPSVEVTQDLIDESEEE : 120
XM_048092  : AYQKQQDTLIVWSEAENYDLALSFQEKAGCDEIWEKICQVQGKDPSVEVTQDLIDESEEE : 120

*        140         *        160         *        180
ANH0687A   : ------------------------------------------------------------ :   -
ANH0687B   : RFEEMPETSHLIDLPTCELNKLEEIADLVTSVLSSPIRREKLALALENEGYIKKLLQLFQ : 180
XM_048092  : RFEEMPETSHLIDLPTCELNKLEEIADLVTSVLSSPIRREKLALALENEGYIKKLLQLFQ : 180

*        200         *        220         *        240
ANH0687A   : ------------------------------------------------------------ :   -
ANH0687B   : ACENLENTEGLHHLYEIIRGILFLNKATLFEVMFSDECIMDVVGCLEYDPALAQPKRHRE : 240
XM_048092  : ACENLENTEGLHHLYEIIRGILFLNKATLFEVMFSDECIMDVVGCLEYDPALAQPKRHRE : 240

*        260         *        280         *        300
ANH0687A   : ------------------------------------------------------------ :   -
ANH0687B   : FLTKTAKFKEVIPITDSELRQKIHQTYRVQYIQDIILPTPSVFEENFLSTLTSFIFFNKV : 300
XM_048092  : FLTKTAKFKEVIPITDSELRQKIHQTYRVQYIQDIILPTPSVFEENFLSTLTSFIFFNKV : 300

*        320         *        340         *        360
ANH0687A   : -------EDEKFLSEVFAQLTDEATDDDKRRELVNFFKEFCAFSQTLQPQNRDAFFKTLA : 152
ANH0687B   : EIVSMLQEDEKFLSEVFAQLTDEATDDDKRRELVNFFKEFCAFSQTLQPQNRDAFFKTLA : 360
XM_048092  : EIVSMLQEDEKFLSEVFAQLTDEATDDDKRRELVNFFKEFCAFSQTLQPQNRDAFFKTLA : 360

*        380         *        400         *        420
ANH0687A   : KLGILPALEIVMGMDDLQVRSAATDIFSYLVEFSPSMVREFVMQEAQQSDDDILLINVVI : 212
ANH0687B   : KLGILPALEIVMGMDDLQVRSAATDIFSYLVEFSPSMVREFVMQEAQQSDDDILLINVVI : 420
XM_048092  : KLGILPALEIVMGMDDLQVRSAATDIFSYLVEFSPSMVREFVMQEAQQSDDDILLINVVI : 420

*        440         *        460         *        480
ANH0687A   : EQMICDTDPELGGAVQLMGLLRTLIDPENMLATTNKTEKSEFLNFFYNHCMHVLTAPLLT : 272
ANH0687B   : EQMICDTDPELGGAVQLMGLLRTLIDPENMLATTNKTEKSEFLNFFYNHCMHVLTAPLLT : 480
XM_048092  : EQMICDTDPELGGAVQLMGLLRTLIDPENMLATTNKTEKSEFLNFFYNHCMHVLTAPLLT : 480

*        500         *        520         *        540
ANH0687A   : NTSEDKCEKDFFLKHYRYSWSFICTPSHSHSHSTPSSSISQDNIVGSNKNNTICPDNYQT : 332
ANH0687B   : NTSEDKCEKD------------------------------NIVGSNKNNTICPDNYQT : 508
XM_048092  : NTSEDKCEKDFFLKHYRYSWSFICTPSHSHSHSTPSSSISQDNIVGSNKNNTICPDNYQT : 540
```

FIG. 16A

```
              *         560         *         580         *         600
ANH0687A  : AQLLALILELLTFCVEHHTYHIKNYIMNKDLLRRVLVLMNSKHTFLALCALRFMRRIIGL : 392
ANH0687B  : AQLLALILELLTFCVEHHTYHIKNYIMNKDLLRRVLVLMNSKHTFLALCALRFMRRIIGL : 568
XM_048092 : AQLLALILELLTFCVEHHTYHIKNYIMNKDLLRRVLVLMNSKHTFLALCALRFMRRIIGL : 600

*         620         *         640         *         660
ANH0687A  : KDEFYNRYITKGNLFEPVINALLDNGTRYNLLNSAVIELFEFIRVEDIKSLTAHIVENFY : 452
ANH0687B  : KDEFYNRYITKGNLFEPVINALLDNGTRYNLLNSAVIELFEFIRVEDIKSLTAHIVENFY : 628
XM_048092 : KDEFYNRYITKGNLFEPVINALLDNGTRYNLLNSAVIELFEFIRVEDIKSLTAHIVENFY : 660

*         680         *         700         *         720
ANH0687A  : KALESIEYVQTFKGLKTKYEQEKDRQNQKLNSVPSILRSNRFRRDAKALEEDEEMWFNED : 512
ANH0687B  : KALESIEYVQTFKGLKTKYEQEKDRQNQKLNSVPSILRSNRFRRDAKALEEDEEMWFNED : 688
XM_048092 : KALESIEYVQTFKGLKTKYEQEKDRQNQKLNSVPSILRSNRFRRDAKALEEDEEMWFNED : 720

*         740         *         760         *         780
ANH0687A  : EEEEGKAVVAPVEKPKPEDDFPDNYEKFMETKKAKESEDKENLPKRTSPGGFKFTFSHSA : 572
ANH0687B  : EEEEGKAVVAPVEKPKPEDDFPDNYEKFMETKKAKESEDKENLPKRTSPGGFKFTFSHSA : 748
XM_048092 : EEEEGKAVVAPVEKPKPEDDFPDNYEKFMETKKAKESEDKENLPKRTSPGGFKFTFSHSA : 780

*         800         *         820         *         840
ANH0687A  : SAANGTNSKSVVAQIPPATSNGSSSKTTNLPTSVTATKGSLVGLVDYPDDEEEDEEEESS : 632
ANH0687B  : SAANGTNSKSVVAQIPPATSNGSSSKTTNLPTSVTATKGSLVGLVDYPDDEEEDEEEESS : 808
XM_048092 : SAANGTNSKSVVAQIPPATSNGSSSKTTNLPTSVTATKGSLVGLVDYPDDEEEDEEEESS : 840

ANH0687A  : PRKRPRLGS : 641
ANH0687B  : PRKRPRLGS : 817
XM_048092 : PRKRPRLGS : 849
```

FIG. 16B

```
              *         20         *         40         *
ANH0693  : MQREEKQLEASLDALLSQVADLKNSLGSFICKLENEYGRLTWPSVLDSFA :  50
NM_052877 : -------------------------------------------------- :   -

60         *         80         *        100
ANH0693  : LLSGQLNTLNKVLKHEKTPLFRNQVIIPLVLSPDRDEDLMRQTEGRVPVF : 100
NM_052877 : ---------------------------------MSGGQTEGRVPVF :  13

*        120         *        140         *
ANH0693  : SHEVVPDHLRTKPDPEVEEQEKQLTTDAARIGADAAQKQIQSLNKMCSNL : 150
NM_052877 : SHEVVPDHLRTKPDPEVEEQEKQLTTDAARIGADAAQKQIQSLNKMCSNL :  63

160         *        180         *        200
ANH0693  : LEKISKEERESESGGLRPNKQTFNPTDTNALVAAVAFGKGLSNWRPSGSS : 200
NM_052877 : LEKISKEERESESGGLRPNKQTFNPTDTNALVAAVAFGKGLSNWRPSGSS : 113

*        220         *        240         *
ANH0693  : GPGQAGQPGAGTILAGTSGLQQVQMAGAPSQQQPMLSGVQMAQAGQPGKM : 250
NM_052877 : GPGQAGQPGAGTILAGTSGLQQVQMAGAPSQQQPMLSGVQMAQAGQPGKM : 163

260         *        280         *        300
ANH0693  : PSGIKTNIKSASMHPYQR-------------------------------- : 268
NM_052877 : PSGIKTNIKSASMHPYQRPSCLGFILAIPLRRKVKKLLGQEGKKNAHLQL : 213

ANH0693  : -   :   -
NM_052877 : W   : 214
```

FIG. 17

```
                        *         20         *         40         *         60
ANH0122A  : MSFPPHLNRPPMGIPALPPGIPPPQFPGFPPPVPPGTPMIPVPMSIMAPAPTVLVPTVSM :  60
ANH0122B  : MSFPPHLNRPPMGIPALPPGIPPPQFPGFPPPVPPGTPMIPVPMSIMAPAPTVLVPTVSM :  60
AAF19255  : -----------------------------------------------------------M :   1
AAC97961  : ------------------------------------------------------------ :   -

*         80         *        100         *        120
ANH0122A  : VGKHLGARKDHPGLKAKENDENCGPTTTVFVGNISEKASDMLIRQLLAKCGLVLSWKRVQ : 120
ANH0122B  : VGKHLGARKDHPGLKAKENDENCGPTTTVFVGNISEKASDMLIRQLLAKCGLVLSWKRVQ : 120
AAF19255  : VGKHLGARKDHPGLKAKENDENCGPTTTVFVGNISEKASDMLIRQLLAKCGLVLSWKRVQ :  61
AAC97961  : ------------------------------------------------KCGLVLSWKRVQ :  12

*        140         *        160         *        180
ANH0122A  : GASGKLQAFGFCEYKEPESTLRALRLLHDLQIGEKKLLVKVDAKTKAQLDEWKAKKKASN : 180
ANH0122B  : GASGKLQAFGFCEYKEPESTLRALRLLHDLQIGEKKLLVKVDAKTKAQLDEWKAKKKASN : 180
AAF19255  : GASGKLQAFGFCEYKEPESTLRALRLLHDLQIGEKKLLVKVDAKTKAQLDEWKAKKKASN : 121
AAC97961  : GASGKLQAFGFCEYKEPESTLRALRLLHDLQIGEKKLLVKVDAKTKAQLDEWKAKKKASN :  72

*        200         *        220         *        240
ANH0122A  : GNARPETVTNDDEEALDEETKRRDQMIKGAIEVLIREYSSELNAPSQESDSHPRKKKKEK : 240
ANH0122B  : GNARPETVTNDDEEALDEETKRRDQMIKGAIEVLIREYSSELNAPSQESDSHPRKKKKEK : 240
AAF19255  : GNARPETVTNDDEEALDEETKRRDQMIKGAIEVLIREYSSELNAPSQESDSHPRKKKKEK : 181
AAC97961  : GNARPETVTNDDEEALDEETKRRDQMIKGAIEVLIREYSSELNAPSQESDSHPRKKKKEK : 132

*        260         *        280         *        300
ANH0122A  : KEDIFRRFPVAPLIPYPLITKEDINAIEMEEDKRDLISREISKFRDTHKKLEEEKGKKEK : 300
ANH0122B  : KEDIFRRFPVAPLIPYPLITKEDINAIEMEEDKRDLISREISKFRDTHKKLEEEKGKKEK : 300
AAF19255  : KEDIFRRFPVAPLIPYPLITKEDINAIEMEEDKRDLISREISKFRDTHKKLEEEKGKKEK : 241
AAC97961  : KEDIFRRFPVAPLIPYPLITKEDINAIEMEEDKRDLISREISKFRDTHKKLEEEKGKKEK : 192

*        320         *        340         *        360
ANH0122A  : ERQEIEKERRERERERERERERRERERERERERERERERERERERERDRDRDRTKERDRD : 360
ANH0122B  : ERQEIEKERRERERERERERERRERERER------------------------------- : 327
AAF19255  : ERQEIEKERRERERERERERERRERERERERERERERERERERERERDRDRDRTKERDRD : 301
AAC97961  : ERQEIEKERRERERERERERERRERERERERERERERERERERERERDRDRDRTKERDRL : 252

*        380         *        400         *        420
ANH0122A  : RDRERDRDRDRERSSDRNKDRSRSREKSRDRERERERERERERERERERERERERERERE : 420
ANH0122B  : ---------------------------------ERERERERERERERERERERERERERE : 356
AAF19255  : RDRERDRDRDRERSSDRNKDRSRSREKSRDRERERERERERERERERERERERERERERE : 361
AAC97961  : RDRERDRDRDRERSSDRNKDRSRSREKSRDRERERERERERERERERERERERERERERE : 312

*        440         *        460         *        480
ANH0122A  : RERERERKDKKRDREEDEEDAYERRKLERKLREKEAAYQERLKNWEIRERKKTREYEKEAE : 480
ANH0122B  : RERERERKDKKRDREEDEEDAYERRKLERKLREKEAAYQERLKNWEIRERKKTREYEKEAE : 416
AAF19255  : RERERERKDKKRDREEDEEDAYERRKLERKLREKEAAYQERLKNWEIRERKKTREYEKEAE : 421
AAC97961  : RERERERKDKKRDREEDEEDAYERRKLERKLREKEAAYQERLKNWEIRERKKTREYEKEAE : 372
```

FIG. 18A

```
                  *         500         *         520         *         540
ANH0122A  : REEERRREMAKEAKRLKEFLEDYDDDRDDPKYYRGSALQKRLRDREKEMEADERDRKREK :  540
ANH0122B  : REEERRREMAKEAKRLKEFLEDYDDDRDDPKYYRGSALQKRLRDREKEMEADERDRKREK :  476
AAF19255  : REEERRREMAKEAKRLKEFLEDYDDDRDDPKYYRGSALQKRLRDREKEMEADERDRKREK :  481
AAC97961  : REEERRREMAKEAKRLKEFLEDYDDDRDDPKYYRGSALQKRLRDREKEMEADERDRKREK :  432

*         560         *         580         *         600
ANH0122A  : EELEEIRQRLLAEGHPDPDAELQRMEQEAERRRQPQIKQEPESEEEEEEKQEKEEKREEP :  600
ANH0122B  : EELEEIRQRLLAEGHPDPDAELQRMEQEAERRRQPQIKQEPESEEEEEEKQEKEEKREEP :  536
AAF19255  : EELEEIRQRLLAEGHPDPDAELQRMEQEAERRRQPQIKQEPESEEEEEEKQEKEEKREEP :  541
AAC97961  : EELEEIRQRLLAEGHPDPDAELQRMEQEAERRRQPQIKQEPESEEEEEEKQEKEEKREEP :  492

*         620         *         640         *         660
ANH0122A  : MEEEEPEQKPCLKPTLRPISSAPSVSSASGNATPNTPGDESPCGIIIPHENSPDQQQPE :  660
ANH0122B  : MEEEEPEQKPCLKPTLRPISSAPSVSSASGNATPNTPGDESPCGIIIPHENSPDQQQPE :  596
AAF19255  : MEEEEPEQKPCLKPTLRPISSAPSVSSASGNATPNTPGDESPCGIIIPHENSPDQQQPE :  601
AAC97961  : MEEEEPEQKPCLKPTLRPISSAPSVSSASGNATPNTPGDESPCGIIIPHENSPDQQQPE :  552

*         680         *         700         *         720
ANH0122A  : EHRPKIGLSLKLGASNSPGQPNSVKRKKLPVDSVFNKFEDEDSDDVPRKRKLVPLDYGED :  720
ANH0122B  : EHRPKIGLSLKLGASNSPGQPNSVKRKKLPVDSVFNKFEDEDSDDVPRKRKLVPLDYGED :  656
AAF19255  : EHRPKIGLSLKLGASNSPGQPNSVKRKKLPVDSVFNKFEDEDSDDVPRKRKLVPLDYGED :  661
AAC97961  : EHRPKIGLSLKLGASNSPGQPNSVKRKKLPVDSVFNKFEDEDSDDVPRKRKLVPLDYGED :  612

*         740         *         760         *         780
ANH0122A  : DKNATKGTVNTEEKRKHIKSLIEKIPTAKPELFAYPLDWSIVDSILMERRIRPWINKKII :  780
ANH0122B  : DKNATKGTVNTEEKRKHIKSLIEKIPTAKPELFAYPLDWSIVDSILMERRIRPWINKKII :  716
AAF19255  : DKNATKGTVNTEEKRKHIKSLIEKIPTAKPELFAYPLDWSIVDSILMERRIRPWINKKII :  721
AAC97961  : DKNATKGTVNTEEKRKHIKSLIEKIPTAKPELFAYPLDWSIVDSILMERRIRPWINKKII :  672

*         800         *         820         *         840
ANH0122A  : EYIGEEEATLVDFVCSKVMAHSSPQSILDDVAMVLDEEAEVFIVKMWRLLIYETEAKKIG :  840
ANH0122B  : EYIGEEEATLVDFVCSKVMAHSSPQSILDDVAMVLDEEAEVFIVKMWRLLIYETEAKKIG :  776
AAF19255  : EYIGEEEATLVDFVCSKVMAHSSPQSILDDVAMVLDEEAEVFIVKMWRLLIYETEAKKIG :  781
AAC97961  : EYIGEEEATLVDFVCSKVMAHSSPQSILDDVAMVLDEEAEVFIVKMWRLLIYETEAKKIG :  732

ANH0122A  : LVK :  843
ANH0122B  : LVK :  779
AAF19255  : LVK :  784
AAC97961  : LVK :  735
```

FIG. 18B

```
                      *         20         *         40         *         60
ANH0316     : MAWKTLPIYLLLLLSVFVIQQVSSQ------------------------------------  :  25
XM_001738   : MAWKTLPIYLLLLLSVFVIQQVSSQDLSSCAGRCGEGYSRDATCNCDYNCQHYMECCPDF  :  60

*         80         *        100         *        120
ANH0316     : ------ELSCKGRCFESFERGRECDCDAQCKKYDKCCPDYESFCAEVHNPTSPPSSKKAP  :  79
XM_001738   : KRVCTAELSCKGRCFESFERGRECDCDAQCKKYDKCCPDYESFCAEVHNPTSPPSSKKAP  : 120

*        140         *        160         *        180
ANH0316     : PPSGASQTIKSTTKRSPKPPNKKKTKKVIESEEITE------------------------  : 115
XM_001738   : PPSGASQTIKSTTKRSPKPPNKKKTKKVIESEEITEHSVSENQESSSSSSSSSSSSTIR  : 180

*        200         *        220         *        240
ANH0316     : -------------------VKDNKKNRTKKKPTPKPPVVDEAGSGLDNGDFKVTTPDTST  : 156
XM_001738   : KIKSSKNSAANRELQKKLKVKDNKKNRTKKKPTPKPPVVDEAGSGLDNGDFKVTTPDTST  : 240

*        260         *        280         *        300
ANH0316     : TQHNKVSTSPKITTAKPINPRPSLPPNSDTSKETSLTVNKETTVETKETTTTNKQTSTDG  : 216
XM_001738   : TQHNKVSTSPKITTAKPINPRPSLPPNSDTSKETSLTVNKETTVETKETTTTNKQTSTDG  : 300

*        320         *        340         *        360
ANH0316     : KEKTTSAKETQSIEKTSAKDLAPTSKVLAKPTKAETTTKGPALTTPKEPTPTTPKEPAS  : 276
XM_001738   : KEKTTSAKETQSIEKTSAKDLAPTSKVLAKPTKAETTTKGPALTTPKEPTPTTPKEPAS  : 360

*        380         *        400         *        420
ANH0316     : TTPKEPTPTTIKSAPTTPKEPAPTTTKSAPTTPKEPAPTTTKEPAPTTPKEPAPTTTKEP  : 336
XM_001738   : TTPKEPTPTTIKSAPTTPKEPAPTTTKSAPTTPKEPAPTTTKEPAPTTPKEPAPTTTKEP  : 420

*        440         *        460         *        480
ANH0316     : APTTTKSAPTTPKEPAPTTPKKPAPTTPKEPAPTTPKEPTPTTPKEPAPTTKEPAPTTPK  : 396
XM_001738   : APTTTKSAPTTPKEPAPTTPKKPAPTTPKEPAPTTPKEPTPTTPKEPAPTTKEPAPTTPK  : 480

*        500         *        520         *        540
ANH0316     : EPAPTAPKKPAPTTPKEPAPTTPKEPAPTTTKEPSPTTPKEPAPTTTKSAPTTTKEPAPT  : 456
XM_001738   : EPAPTAPKKPAPTTPKEPAPTTPKEPAPTTTKEPSPTTPKEPAPTTTKSAPTTTKEPAPT  : 540

*        560         *        580         *        600
ANH0316     : TTKSAPTTPKEPSPTTTKEPAPTTPKEPAPTTPKKPAPTTPKEPAPTTPKEPAPTTTKKP  : 516
XM_001738   : TTKSAPTTPKEPSPTTTKEPAPTTPKEPAPTTPKKPAPTTPKEPAPTTPKEPAPTTTKKP  : 600

*        620         *        640         *        660
ANH0316     : APTTPKEPAPTTPKETAPTTPKKLTPTTPEKLAPTTPEKPAPTTPEELAPTTPEEPTPTT  : 576
XM_001738   : APTTPKEPAPTTPKETAPTTPKKLTPTTPEKLAPTTPEKPAPTTPEELAPTTPEEPTPTT  : 660

*        680         *        700         *        720
ANH0316     : PEEPAPTTPKAAAPNTPKEPAPTTPKEPAPTTPKEPAPTTPKETAPTTPKGTAPTTLKEP  : 636
XM_001738   : PEEPAPTTPKAAAPNTPKEPAPTTPKEPAPTTPKEPAPTTPKETAPTTPKGTAPTTLKEP  : 720
```

FIG. 19A

```
                      *         740         *         760         *         780
ANH0316    : APTTPKKPAPKELAPTTTKEPTSTTCDKPAPTTPKGTAPTTPKEPAPTTPKEPAPTTPKG :  696
XM_001738  : APTTPKKPAPKELAPTTTKEPTSTTCDKPAPTTPKGTAPTTPKEPAPTTPKEPAPTTPKG :  780

*         800         *         820         *         840
ANH0316    : TAPTTLKEPAPTTPKKPAPKELAPTTTKGPTSTTSDKPAPTTPKETAPTTPKEPAPTTPK :  756
XM_001738  : TAPTTLKEPAPTTPKKPAPKELAPTTTKGPTSTTSDKPAPTTPKETAPTTPKEPAPTTPK :  840

*         860         *         880         *         900
ANH0316    : KPAPTTPETPPPTSEVSTPTTTKEPTTIHKSPDESTPELSAEPTPKALENSPKEPGVPT  :  816
XM_001738  : KPAPTTPETPPPTSEVSTPTTTKEPTTIHKSPDESTPELSAEPTPKALENSPKEPGVPT  :  900

*         920         *         940         *         960
ANH0316    : TKTPAATKPEMTTTAKDKTTERDLRTTPETTTAAPKMTKETATTTEKTTESKITATTTQV :  876
XM_001738  : TKTPAATKPEMTTTAKDKTTERDLRTTPETTTAAPKMTKETATTTEKTTESKITATTTQV :  960

*         980         *        1000         *        1020
ANH0316    : TSTTTQDTTPFKITTLKTTTLAPKVTTTKKTITTTEIMNKPEETAKPKDRATNSKATTPK :  936
XM_001738  : TSTTTQDTTPFKITTLKTTTLAPKVTTTKKTITTTEIMNKPEETAKPKDRATNSKATTPK : 1020

*        1040         *        1060         *        1080
ANH0316    : PQKPTKAPKKPTSTKKPKTMPRVRKPKTTPTPRKMTSTMPELNPTSRIAEAMLQTTTRPN :  996
XM_001738  : PQKPTKAPKKPTSTKKPKTMPRVRKPKTTPTPRKMTSTMPELNPTSRIAEAMLQTTTRPN : 1080

*        1100         *        1120         *        1140
ANH0316    : QTPNSKLVEVNPKSEDAGGAEGETPHMLLRPHVFMPEVTPDMDYLPRVPNQGIIINPMLS : 1056
XM_001738  : QTPNSKLVEVNPKSEDAGGAEGETPHMLLRPHVFMPEVTPDMDYLPRVPNQGIIINPMLS : 1140

*        1160         *        1180         *        1200
ANH0316    : DETNICNGKPVDGLTTLRNGTLVAFRGHYFWMLSPFSPPSPARRITEVWGIPSPIDTVFT : 1116
XM_001738  : DETNICNGKPVDGLTTLRNGTLVAFRGHYFWMLSPFSPPSPARRITEVWGIPSPIDTVFT : 1200

*        1220         *        1240         *        1260
ANH0316    : RCNCEGKTFFFKDSQYWRFTNDIKDAGYPKPIFKGFGGLTGQIVAALSTAKYKNWPESVY : 1176
XM_001738  : RCNCEGKTFFFKDSQYWRFTNDIKDAGYPKPIFKGFGGLTGQIVAALSTAKYKNWPESVY : 1260

*        1280         *        1300         *        1320
ANH0316    : FFKRGGSIQQYIYKQEPVQKCPGRRPALNYPVYGETTQVRRRRFERAIGPSQTHTIRIQY : 1236
XM_001738  : FFKRGGSIQQYIYKQEPVQKCPGRRPALNYPVYGETTQVRRRRFERAIGPSQTHTIRIQY : 1320

*        1340         *        1360         *        1380
ANH0316    : SPARLAYQDKGVLHNEVKVSILWRGLPNVVTSAISLPNIRKPDGYDYYAFSKDQYYNIDV : 1296
XM_001738  : SPARLAYQDKGVLHNEVKVSILWRGLPNVVTSAISLPNIRKPDGYDYYAFSKDQYYNIDV : 1380

*        1400
ANH0316    : PSRTARAITTRSGQTLSKVWYNCP : 1320
XM_001738  : PSRTARAITTRSGQTLSKVWYNCP : 1404
```

FIG. 19B

SEQUENCE LISTING

<160> NUMBER OF SEQ ID NOS: 80

<210> SEQ ID NO 1
<211> LENGTH: 5682
<212> TYPE: DNA
<213> ORGANISM: Homo sapiens
<220> FEATURE:
<221> NAME/KEY: CDS
<222> LOCATION: (62)..(1195)
<223> OTHER INFORMATION:

<400> SEQUENCE: 1

```
ccgcctcttc ctctcggtcc catattgaac tcgagttgga agaggcgagt ccggtctcaa        60
```

| | | | | | | | | | | | | | | |
|---|---|---|---|---|---|---|---|---|---|---|---|---|---|---|
| a atg | gag | gta | aaa | ccg | ccg | ccc | ggt | cgc | ccc | cag | ccc | gac | tcc | ggc cgt  109 |
| Met | Glu | Val | Lys | Pro | Pro | Gly | Arg | Pro | Gln | Pro | Asp | Ser | Gly | Arg |
| 1 | | | 5 | | | | | 10 | | | | | 15 | |

| cgc | cgt | cgc | cgc | cgg | ggg | gag | gag | ggc | cat | gat | cca | aag | gaa | cca gag  157 |
|---|---|---|---|---|---|---|---|---|---|---|---|---|---|---|
| Arg | Arg | Arg | Arg | Arg | Gly | Glu | Glu | Gly | His | Asp | Pro | Lys | Glu | Pro Glu |
| | | | 20 | | | | | 25 | | | | | 30 | |

| cag | ttg | aga | aaa | ctg | ttt | att | ggt | ggt | ctg | agc | ttt | gaa | act | aca gat  205 |
|---|---|---|---|---|---|---|---|---|---|---|---|---|---|---|
| Gln | Leu | Arg | Lys | Leu | Phe | Ile | Gly | Gly | Leu | Ser | Phe | Glu | Thr | Thr Asp |
| | | 35 | | | | | 40 | | | | | 45 | | |

| gat | agt | tta | cga | gaa | cat | ttt | gag | aaa | tgg | ggc | aca | ctc | aca | gat tgt  253 |
|---|---|---|---|---|---|---|---|---|---|---|---|---|---|---|
| Asp | Ser | Leu | Arg | Glu | His | Phe | Glu | Lys | Trp | Gly | Thr | Leu | Thr | Asp Cys |
| 50 | | | | | 55 | | | | | 60 | | | | |

| gtg | gta | atg | aga | gac | ccc | caa | aca | aaa | cgt | tcc | agg | ggc | ttt | ggt ttt  301 |
|---|---|---|---|---|---|---|---|---|---|---|---|---|---|---|
| Val | Val | Met | Arg | Asp | Pro | Gln | Thr | Lys | Arg | Ser | Arg | Gly | Phe | Gly Phe |
| 65 | | | | | 70 | | | | | 75 | | | | 80 |

| gtg | act | tat | tct | tgt | gtt | gaa | gag | gtg | gat | gca | gca | atg | tgt | gct cga  349 |
|---|---|---|---|---|---|---|---|---|---|---|---|---|---|---|
| Val | Thr | Tyr | Ser | Cys | Val | Glu | Glu | Val | Asp | Ala | Ala | Met | Cys | Ala Arg |
| | | | | 85 | | | | | 90 | | | | | 95 |

| cca | cac | aag | gtt | gat | ggg | cgt | gta | gtg | gaa | cca | aag | aga | gct | gtt tct  397 |
|---|---|---|---|---|---|---|---|---|---|---|---|---|---|---|
| Pro | His | Lys | Val | Asp | Gly | Arg | Val | Val | Glu | Pro | Lys | Arg | Ala | Val Ser |
| | | | 100 | | | | | 105 | | | | | 110 | |

| aga | gag | gat | tct | gta | aag | cct | ggt | gcc | cat | cta | aca | gtg | aag | aaa att  445 |
|---|---|---|---|---|---|---|---|---|---|---|---|---|---|---|
| Arg | Glu | Asp | Ser | Val | Lys | Pro | Gly | Ala | His | Leu | Thr | Val | Lys | Lys Ile |
| | | 115 | | | | | 120 | | | | | 125 | | |

| ttt | gtt | ggt | ggt | att | aaa | gaa | gat | aca | gaa | gaa | tat | aat | ttg | aga gac  493 |
|---|---|---|---|---|---|---|---|---|---|---|---|---|---|---|
| Phe | Val | Gly | Gly | Ile | Lys | Glu | Asp | Thr | Glu | Glu | Tyr | Asn | Leu | Arg Asp |
| | 130 | | | | | 135 | | | | | 140 | | | |

| tac | ttt | gaa | aag | tat | ggc | aag | att | gaa | acc | ata | gaa | gtt | atg | gaa gac  541 |
|---|---|---|---|---|---|---|---|---|---|---|---|---|---|---|
| Tyr | Phe | Glu | Lys | Tyr | Gly | Lys | Ile | Glu | Thr | Ile | Glu | Val | Met | Glu Asp |
| 145 | | | | | 150 | | | | | 155 | | | | 160 |

| agg | cag | agt | gga | aaa | aag | aga | gga | ttt | gct | ttt | gta | act | ttt | gat gat  589 |
|---|---|---|---|---|---|---|---|---|---|---|---|---|---|---|
| Arg | Gln | Ser | Gly | Lys | Lys | Arg | Gly | Phe | Ala | Phe | Val | Thr | Phe | Asp Asp |
| | | | | 165 | | | | | 170 | | | | | 175 |

| cat | gat | aca | gtt | gat | aaa | att | gtt | gtt | cag | aaa | tac | cac | act | att aat  637 |
|---|---|---|---|---|---|---|---|---|---|---|---|---|---|---|
| His | Asp | Thr | Val | Asp | Lys | Ile | Val | Val | Gln | Lys | Tyr | His | Thr | Ile Asn |
| | | | 180 | | | | | 185 | | | | | 190 | |

| ggg | cat | aat | tgt | gaa | gtg | aaa | aag | gcc | ctt | tct | aaa | caa | gag | atg cag  685 |
|---|---|---|---|---|---|---|---|---|---|---|---|---|---|---|
| Gly | His | Asn | Cys | Glu | Val | Lys | Lys | Ala | Leu | Ser | Lys | Gln | Glu | Met Gln |
| | | 195 | | | | | 200 | | | | | 205 | | |

| tct | gct | gga | tca | cag | aga | ggt | cgt | gga | ggt | gga | tct | ggc | aat | ttt atg  733 |
|---|---|---|---|---|---|---|---|---|---|---|---|---|---|---|
| Ser | Ala | Gly | Ser | Gln | Arg | Gly | Arg | Gly | Gly | Gly | Ser | Gly | Asn | Phe Met |
| 210 | | | | | 215 | | | | | 220 | | | | |

| ggt | cgc | gga | ggg | aac | ttt | gga | ggt | ggt | gga | ggt | aat | ttt | ggc | cgt ggt  781 |
|---|---|---|---|---|---|---|---|---|---|---|---|---|---|---|
| Gly | Arg | Gly | Gly | Asn | Phe | Gly | Gly | Gly | Gly | Gly | Asn | Phe | Gly | Arg Gly |
| 225 | | | | | 230 | | | | | 235 | | | | 240 |

| gga | aac | ttt | ggt | gga | aga | gga | ggc | tat | ggt | ggt | gga | ggt | ggt | ggc agc  829 |
|---|---|---|---|---|---|---|---|---|---|---|---|---|---|---|
| Gly | Asn | Phe | Gly | Gly | Arg | Gly | Gly | Tyr | Gly | Gly | Gly | Gly | Gly | Gly Ser |
| | | | | 245 | | | | | 250 | | | | | 255 |

| aga | ggt | agt | tat | gga | gga | ggt | gat | ggt | gga | tat | aat | gga | ttt | gga ggt  877 |
|---|---|---|---|---|---|---|---|---|---|---|---|---|---|---|
| Arg | Gly | Ser | Tyr | Gly | Gly | Gly | Asp | Gly | Gly | Tyr | Asn | Gly | Phe | Gly Gly |
| | | | 260 | | | | | 265 | | | | | 270 | |

| gat | ggt | ggc | aac | tat | ggc | ggt | ggt | cct | ggt | tat | agt | agt | aga | ggg ggc  925 |
|---|---|---|---|---|---|---|---|---|---|---|---|---|---|---|
| Asp | Gly | Gly | Asn | Tyr | Gly | Gly | Gly | Pro | Gly | Tyr | Ser | Ser | Arg | Gly Gly |
| | | 275 | | | | | 280 | | | | | 285 | | |

| tat | ggt | ggt | ggt | gga | cca | gga | tat | gga | aac | caa | ggt | ggt | gga | tat ggt  973 |
|---|---|---|---|---|---|---|---|---|---|---|---|---|---|---|
| Tyr | Gly | Gly | Gly | Gly | Pro | Gly | Tyr | Gly | Asn | Gln | Gly | Gly | Gly | Tyr Gly |
| | 290 | | | | | 295 | | | | | 300 | | | |

-continued

| | |
|---|---|
| gga ggt gga gga tat gat ggt tac aat gaa gga gga aat ttt ggc ggt<br>Gly Gly Gly Gly Tyr Asp Gly Tyr Asn Glu Gly Gly Asn Phe Gly Gly<br>305                   310                   315                   320 | 1021 |
| ggt aac tat ggt ggt ggt ggg aac tat aat gat ttt gga aat tat agt<br>Gly Asn Tyr Gly Gly Gly Asn Tyr Asn Asp Phe Gly Asn Tyr Ser<br>                   325                          330                      335 | 1069 |
| gga caa cag caa tca aat tat gga ccc atg aaa ggg ggc agt ttt ggt<br>Gly Gln Gln Gln Ser Asn Tyr Gly Pro Met Lys Gly Gly Ser Phe Gly<br>                    340                      345                      350 | 1117 |
| gga aga agc tcg ggc agt ccc tat ggt ggt ggt tat gga tct ggt ggt<br>Gly Arg Ser Ser Gly Ser Pro Tyr Gly Gly Gly Tyr Gly Ser Gly Gly<br>355                   360                   365 | 1165 |
| gga agt ggt gga tat ggt agc aga agg ttc taaaaacagc agaaagggc<br>Gly Ser Gly Gly Tyr Gly Ser Arg Arg Phe<br>   370                 375 | 1215 |
| tacagttctt agcaggagag agagcgagga gttgtcagga aagctgcagg ttactttgag | 1275 |
| acagtcgtcc caaatgcatt agaggaactg taaaaatctg ccacagaagg aacgatgatc | 1335 |
| catagtcaga aaagttactg cagcttaaac aggaaaccct tcttgttcag gactgtcata | 1395 |
| gccacagttt gcaaaagtg cagctattga ttaatgcaat gtagtgtcaa ttagatgtac | 1455 |
| attcctgagg tcttttatct gttgtagctt tgtcttttc tttttctttt cattacatca | 1515 |
| ggtatattgc cctgtaaatt gtggtagtgg taccaggaat aaaaaattaa ggaattttta | 1575 |
| acttttcaat atttgtgtag ttcagttttt ctacatttta gtacagaaac tttaacaaaa | 1635 |
| tgcagtttcg aaggtgtttc cttgtgagtt aacaagtaaa aagatcatt gttaattact | 1695 |
| attttgtatg aattttgcta aagttaactg taaagaaaca cctgctgact tgcagtttaa | 1755 |
| ggggaatcta ttctccccat ttccaaacca tgatatgaat gggcgctgac atgtggagag | 1815 |
| aatagataat ttgtgtgttt gcaatgtgtg ttttagataa ataggattgg gtatttaaat | 1875 |
| tagcatttgt gaatttaata gcattaagat taccttcaaa tgaaaaaaaa tctcaaaatt | 1935 |
| tctatttggt ttttgtgcat tttcttttaa aatgtaatca tatgatttta gtgtgttaga | 1995 |
| cttgctgagt cctagctgtg tttagaacat ctctattcta catttacctt ggtcaaattt | 2055 |
| gaactgctgc ataggttttt gggtgtaaag aatgtttact gccctccatt taaattctga | 2115 |
| aaagggatgg tggatgtttt ccctctccta cgttagaaac cattcttaaa aacttttgaa | 2175 |
| aatatagaac cattaagcct gctatatctg agcaaattaa tgggtacctt ttttttctta | 2235 |
| tttaaagcac aagaggccca taaatcttga gttactttaa attctttttt ttgatacaag | 2295 |
| ttttcagagc aagagaataa aaatcatgtg ttattaaacc cctaactggc tggcatgctt | 2355 |
| tcctgtttgt attctataca ttttgctgga tgaaaccaag gatagttcag gtataattgt | 2415 |
| ccaaaataac ctaactgcag cagaaatgta gcacagttgc ttagtacagg cttctcactt | 2475 |
| cctacagacc tgaattcaaa tttggatagt ctgagttctt aaattcccaa agaacacact | 2535 |
| gttatttctt gtgtatattt caacataaat catgttgtta ccaatttgtt tggaaggccc | 2595 |
| tggttgagaa gagttttagt taataaggtc atatatacat atattaatat aaaccaatgt | 2655 |
| ctactgtttt gctccagcta gtgcttacag tttcattcga gccctgagta tgtgccctgc | 2715 |
| tgttactctc tttggtagtt gaacgttgaa ttcaagtctt tgttttaag aagtactaag | 2775 |
| caaacaagca ataaaaggg gaatggggtg tgctagtgtt tgaatatgct ctcttgttgc | 2835 |
| tctaattctg tgcctctgtg cattaatatt tggatgcatg caatgccagc atggaaattg | 2895 |
| gtcttcacat atactgcagt tttccagaaa cattcacaaa ccaataaatg taacagacat | 2955 |
| tccatttgtt aatgggcata tatgtgaaaa gcagtgtaga aaataggcta atattagaaa | 3015 |

```
atggttaagt cctaaataac ttcaagtgtg gttatataat ggacactgtc aatgttcata    3075
acttaaacct gggtacctgg tcaaaataat gcttgggaaa cattaaaatt gagctaaatt    3135
gtctcaagtt cttttattca tataaataaa gtttaaagga atgggggaga ttaacatttc    3195
ctgttttatg tttgtgaaat tgtttgacac aaccttgaca gtatccttta atggcatgag    3255
gttaattgta ctgttaacca actttctatg ttctggaact agtattatag tgaaaacatt    3315
tacagtaagt tgatgtttac aacctataag caggtgaaat ctgtgtatgt gacctgttta    3375
taagttgtat tagcttagct cttgtgaaca gtgtggaaaa gtaagccatg aggagagcga    3435
tttaaccacc tttaaaggac ctaagatgtg cttttttaagc acagtgtgga tcacagaaac    3495
tcactaagac aggacttcag cagccttttg tgtttgacaa agtcagcata aataaagaat    3555
gacaaggcag cagcaagagc ttcaactaca gagaagtgaa ggcataagat actatgatga    3615
tagtgagcaa ctttccaaaa gctagttaaa tctgcttatt acaactgaaa tatcgaagaa    3675
agtctagcag gaaggagctc ttcgcctttt ggaacatcaa tgagagatag ttgccacagt    3735
cactaggtct agcatttaga cctgcaagga agggcaataa gcattaggta aggcttgaat    3795 ttgaatttt tcactaatta aagagtaatt ttttgtaaag caaggtaaga gtaatctttt     3855
tgatttgcag gttgaatgag aaccctactt gcctaaatga ggaatgtctt tcctaccatc    3915
taaaatacga aggtttctgg ctgggtaagg tttgtagttg acagtaaaac ctgatgacac    3975
catttgtttc cctgcaagtc tacattacat atttcacaac tttgtccctc tctagtaggc    4035
acattggaaa aattcttcaa ctgaaaacta ccttggtacc atgtcctaca cgttttaaac    4095
cttagtttta aaaattcccc tgcgaaatag ccataagtat tcatatcaag tcagttgtga    4155
ctccttgtgt atacaattca ttttttgtgt cttcagggta aactcaattt ttggtaaagt    4215
ggtttcagct tttgtgaaaa ccgttttttgt gtgtaagcat gacacacaac agactcagta    4275
agctgcccat cctcatacta ggaaaacacc ttcaaaggaa cattaaaagt taccagggcc    4335
aggcacagtg gctcacgcct gtaatcccag cactttggga ggctgaggca gatggatccc    4395
aagtccagga atttgagacg agcctgggca acatagtgag agcctgtcaa caaaaaatag    4455
aaaaattagt tgggcttggt gatacacatc tgtagtccca gctatttggg aggctgcctt    4515
gatatcaggc agtcgaggct gcagtgagct gactgcccca ctgtattcca gcctgggtga    4575
ccccatctca aagaagaaaa gttaccagat gtcatgggta aaggttggtc ttcaagtggc    4635
ctcataagtt gtcttgcatt taaattcagg gaattcattg gaccaatagg ttacattttc    4695
gttccttttt tgttttggtt catctgttaa gcagtggggg cctaattact gctccttttgt   4755 aaaaacacat tttcccaaag aacactgaat taccgttcaa actggttgtt gatgggtaat    4815
aagggctgtt tttgctgccc caaaagggct taacaattta ggcggatagt ttacttaaaa    4875
aaaaaaatcc tttggagaca tactgaaaat gcaaactagt ttctaaatta tcaattccct    4935
acatgaagaa gcagtttgcc agagtttagt ctcagaaaat gactggttgg ctctatttaa    4995
atcagaaccc aatttctacg cgtgttgaat aaggtaacag cctttgatga atttccttca    5055
caacatggtt ttagtgaagc aaacattttt tttttaaggg cattgttctt tctagtttat    5115 ttcttttat gaaataaaat tattttattt aaacagttcc attgtcgttt ctgaaaacta    5175
cagtattctc agaagttgta gcagcagtaa aaaaaaaaaa gttgttatat aagtgattgg    5235
ggcagattta actgattttg ttaaaccaat ttgtaagtta ctgcttctaa tattacactt    5295
ctaaaaagct gaatttatac tcatgtccta aaggagaata tgtggtaata agtatatttt    5355
```

-continued

```
gttaagtaac taattgaaat aggcttggtt ttaagagttc cagtatataa taatcacaaa      5415
ttgaaacctg acagtatctt gggagttcca gtaatgtcac aaattagtga ataagcatgc      5475
cagtgtgcaa gggtaatgta aggattgtta gcctatctaa atattcaaaa ttactttaaa      5535
acttaagtat gttttctgat ttttaagaat tcagaagtgt tctgtaatgg attcagatgt      5595
ttcatttgta gtataatgaa atgtttacag aaagataact ttttcattaa aatatttta       5655 gaaatgtgaa aaaaaaaaaa aaaaaaa                                          5682
```

<210> SEQ ID NO 2
<211> LENGTH: 378
<212> TYPE: PRT
<213> ORGANISM: Homo sapiens

<400> SEQUENCE: 2

```
Met Glu Val Lys Pro Pro Gly Arg Pro Gln Pro Asp Ser Gly Arg
1               5                   10                  15

Arg Arg Arg Arg Gly Glu Glu Gly His Asp Pro Lys Glu Pro Glu
                20                  25                  30

Gln Leu Arg Lys Leu Phe Ile Gly Gly Leu Ser Phe Glu Thr Thr Asp
            35                  40                  45

Asp Ser Leu Arg Glu His Phe Glu Lys Trp Gly Thr Leu Thr Asp Cys
50                  55                  60

Val Val Met Arg Asp Pro Gln Thr Lys Arg Ser Arg Gly Phe Gly Phe
65                  70                  75                  80

Val Thr Tyr Ser Cys Val Glu Val Asp Ala Ala Met Cys Ala Arg
                85                  90                  95

Pro His Lys Val Asp Gly Arg Val Val Glu Pro Lys Arg Ala Val Ser
                100                 105                 110

Arg Glu Asp Ser Val Lys Pro Gly Ala His Leu Thr Val Lys Lys Ile
            115                 120                 125

Phe Val Gly Gly Ile Lys Glu Asp Thr Glu Glu Tyr Asn Leu Arg Asp
    130                 135                 140

Tyr Phe Glu Lys Tyr Gly Lys Ile Glu Thr Ile Glu Val Met Glu Asp
145                 150                 155                 160

Arg Gln Ser Gly Lys Lys Arg Gly Phe Ala Phe Val Thr Phe Asp Asp
                165                 170                 175

His Asp Thr Val Asp Lys Ile Val Val Gln Lys Tyr His Thr Ile Asn
                180                 185                 190

Gly His Asn Cys Glu Val Lys Lys Ala Leu Ser Lys Gln Glu Met Gln
        195                 200                 205

Ser Ala Gly Ser Gln Arg Gly Arg Gly Gly Ser Gly Asn Phe Met
    210                 215                 220

Gly Arg Gly Gly Asn Phe Gly Gly Gly Gly Asn Phe Gly Arg Gly
225                 230                 235                 240

Gly Asn Phe Gly Gly Arg Gly Gly Tyr Gly Gly Gly Gly Ser
                245                 250                 255

Arg Gly Ser Tyr Gly Gly Gly Asp Gly Gly Tyr Asn Gly Phe Gly Gly
            260                 265                 270

Asp Gly Gly Asn Tyr Gly Gly Gly Pro Gly Tyr Ser Ser Arg Gly Gly
        275                 280                 285

Tyr Gly Gly Gly Gly Pro Gly Tyr Gly Asn Gln Gly Gly Gly Tyr Gly
            290                 295                 300

Gly Gly Gly Gly Tyr Asp Gly Tyr Asn Glu Gly Gly Asn Phe Gly Gly
305                 310                 315                 320
```

-continued

```
Gly Asn Tyr Gly Gly Gly Asn Tyr Asn Asp Phe Gly Asn Tyr Ser
            325                 330                 335
Gly Gln Gln Gln Ser Asn Tyr Gly Pro Met Lys Gly Gly Ser Phe Gly
        340                 345                 350
Gly Arg Ser Ser Gly Ser Pro Tyr Gly Gly Gly Tyr Gly Ser Gly Gly
        355                 360                 365
Gly Ser Gly Gly Tyr Gly Ser Arg Arg Phe
        370                 375

<210> SEQ ID NO 3
<211> LENGTH: 3985
<212> TYPE: DNA
<213> ORGANISM: Homo sapiens
<220> FEATURE:
<221> NAME/KEY: CDS
<222> LOCATION: (187)..(2529)
<223> OTHER INFORMATION:

<400> SEQUENCE: 3
cttttgggct ggaggctcca ccttttgtgt ttcccgcaca gtcaatcaaa ataggaaaaa      60
aaaatccccg gaccgctccg gccgtgtccg ccgccgcttc ccgcatcctc tcccgccgcc     120
gccgccttcg ctcctcacca tgtgtaaggc ggcggggagc cccgcctgag gtgccctaaa     180 cacact atg acc gct ccc gaa aag ccc gtg aaa caa gag gaa atg gct         228
       Met Thr Ala Pro Glu Lys Pro Val Lys Gln Glu Glu Met Ala
         1               5                  10 gcc ttg gac gtg gat agc ggc ggc ggc ggt ggc ggc ggc ggc cac            276
Ala Leu Asp Val Asp Ser Gly Gly Gly Gly Gly Gly Gly Gly His
 15                  20                  25                  30 ggc gag tat ctg cag cag cag caa cag cac gga aac ggt gcg gtg gcg       324
Gly Glu Tyr Leu Gln Gln Gln Gln Gln His Gly Asn Gly Ala Val Ala
                 35                  40                  45 gcg gca gcg gcg gcc cag gac act cag ccg tca ccg ctc gct ctg ctg       372
Ala Ala Ala Ala Ala Gln Asp Thr Gln Pro Ser Pro Leu Ala Leu Leu
             50                  55                  60 gcc gct acc tgc agc aag ata ggg ccg cca tcg ccg ggc gac gac gag       420
Ala Ala Thr Cys Ser Lys Ile Gly Pro Pro Ser Pro Gly Asp Asp Glu
         65                  70                  75 gag gag gcg gcc gcc gca gcc ggg gcc ccc gcc gcc gcc gga gcg aca       468
Glu Glu Ala Ala Ala Ala Ala Gly Ala Pro Ala Ala Ala Gly Ala Thr
     80                  85                  90 ggt gat ttg gct tct gca cag tta gga gga gca cca aac cga tgg gag       516
Gly Asp Leu Ala Ser Ala Gln Leu Gly Gly Ala Pro Asn Arg Trp Glu
 95                 100                 105                 110 gtt ttg tca gcc aca cct aca act ata aaa gat gaa gct ggt aat cta       564
Val Leu Ser Ala Thr Pro Thr Thr Ile Lys Asp Glu Ala Gly Asn Leu
                115                 120                 125 gtc cag att cca agt gct gct act tca agt ggg cag tat gtt ctt ccc       612
Val Gln Ile Pro Ser Ala Ala Thr Ser Ser Gly Gln Tyr Val Leu Pro
            130                 135                 140 ctt cag aat ttg cag aat caa caa ata ttt tcc gtt gca cca gga tca       660
Leu Gln Asn Leu Gln Asn Gln Gln Ile Phe Ser Val Ala Pro Gly Ser
        145                 150                 155 gat tca tca aat ggt gca gtg tcc agt gtt caa tat caa gtg ata cca       708
Asp Ser Ser Asn Gly Ala Val Ser Ser Val Gln Tyr Gln Val Ile Pro
    160                 165                 170 cag atc cag tca gca gat ggt cag cag gtt caa att ggt ttc aca ggc       756
Gln Ile Gln Ser Ala Asp Gly Gln Gln Val Gln Ile Gly Phe Thr Gly
175                 180                 185                 190
```

| | | |
|---|---|---|
| tct tca gat aat ggg ggt ata aat caa gaa agc agt caa att cag atc<br>Ser Ser Asp Asn Gly Gly Ile Asn Gln Glu Ser Ser Gln Ile Gln Ile<br>195 200 205 | | 804 |
| att cct ggc tct aat caa acc tta ctt gcc tct gga aca cct tct gct<br>Ile Pro Gly Ser Asn Gln Thr Leu Leu Ala Ser Gly Thr Pro Ser Ala<br>210 215 220 | | 852 |
| aac atc cag aat ctc ata cca cag act ggt caa gtc cag gtt cag gga<br>Asn Ile Gln Asn Leu Ile Pro Gln Thr Gly Gln Val Gln Val Gln Gly<br>225 230 235 | | 900 |
| gtt gca att ggt ggt tca tct ttt cct ggt caa acc caa gta gtt gct<br>Val Ala Ile Gly Gly Ser Ser Phe Pro Gly Gln Thr Gln Val Val Ala<br>240 245 250 | | 948 |
| aat gtg cct ctt ggt ctg cca gga aat att acg ttt gta cca atc aat<br>Asn Val Pro Leu Gly Leu Pro Gly Asn Ile Thr Phe Val Pro Ile Asn<br>255 260 265 270 | | 996 |
| agt gtc gat cta gat tct ttg gga ctc tcg ggc agt tct cag aca atg<br>Ser Val Asp Leu Asp Ser Leu Gly Leu Ser Gly Ser Ser Gln Thr Met<br>275 280 285 | | 1044 |
| act gca ggc att aat gcc gac gga cat ttg ata aac aca gga caa gct<br>Thr Ala Gly Ile Asn Ala Asp Gly His Leu Ile Asn Thr Gly Gln Ala<br>290 295 300 | | 1092 |
| atg gat agt tca gac aat tca gaa agg act ggt gag cgg gtt tct cct<br>Met Asp Ser Ser Asp Asn Ser Glu Arg Thr Gly Glu Arg Val Ser Pro<br>305 310 315 | | 1140 |
| gat att aat gaa act aat act gat aca gat tta ttt gtg cca aca tcc<br>Asp Ile Asn Glu Thr Asn Thr Asp Thr Asp Leu Phe Val Pro Thr Ser<br>320 325 330 | | 1188 |
| tct tca tca cag ttg cct gtt acg ata gat agt aca ggt ata tta caa<br>Ser Ser Ser Gln Leu Pro Val Thr Ile Asp Ser Thr Gly Ile Leu Gln<br>335 340 345 350 | | 1236 |
| caa aac aca aat agc ttg act aca tct agt ggg cag gtt cat tct tca<br>Gln Asn Thr Asn Ser Leu Thr Thr Ser Ser Gly Gln Val His Ser Ser<br>355 360 365 | | 1284 |
| gat ctt cag gga aat tat atc cag tcg cct gtt tct gaa gag aca cag<br>Asp Leu Gln Gly Asn Tyr Ile Gln Ser Pro Val Ser Glu Glu Thr Gln<br>370 375 380 | | 1332 |
| gca cag aat att cag gtt tct aca gca cag cct gtt gta cag cat cta<br>Ala Gln Asn Ile Gln Val Ser Thr Ala Gln Pro Val Val Gln His Leu<br>385 390 395 | | 1380 |
| caa ctt caa gag tct cag cag cca acc agt caa gcc caa att gtg caa<br>Gln Leu Gln Glu Ser Gln Gln Pro Thr Ser Gln Ala Gln Ile Val Gln<br>400 405 410 | | 1428 |
| ggt att aca cca cag aca atc cat ggt gtg caa gcc agt ggt caa aat<br>Gly Ile Thr Pro Gln Thr Ile His Gly Val Gln Ala Ser Gly Gln Asn<br>415 420 425 430 | | 1476 |
| ata tca caa cag gct ttg caa aat ctt cag ttg cag ctg aat cct gga<br>Ile Ser Gln Gln Ala Leu Gln Asn Leu Gln Leu Gln Leu Asn Pro Gly<br>435 440 445 | | 1524 |
| acc ttt tta att cag gca cag aca gtg acc cct tct gga cag gta act<br>Thr Phe Leu Ile Gln Ala Gln Thr Val Thr Pro Ser Gly Gln Val Thr<br>450 455 460 | | 1572 |
| tgg caa acg ttt caa gta caa ggg gtc cag aac ttg cag aat ttg caa<br>Trp Gln Thr Phe Gln Val Gln Gly Val Gln Asn Leu Gln Asn Leu Gln<br>465 470 475 | | 1620 |
| ata cag aat act gct gcc caa caa ata act ctg acg cct gtt caa acc<br>Ile Gln Asn Thr Ala Ala Gln Gln Ile Thr Leu Thr Pro Val Gln Thr<br>480 485 490 | | 1668 |
| ctc aca ctt ggt caa gtt gcg gca ggt gga gcc ttc act tca act cca<br>Leu Thr Leu Gly Gln Val Ala Ala Gly Gly Ala Phe Thr Ser Thr Pro<br>495 500 505 510 | | 1716 |

```
gtt agt cta agc act ggt cag ttg cca aat cta caa aca gtt aca gtg    1764
Val Ser Leu Ser Thr Gly Gln Leu Pro Asn Leu Gln Thr Val Thr Val
                515                 520                 525 aac tct ata gat tct gct ggt ata cag cta cat cca gga gag aat gct    1812
Asn Ser Ile Asp Ser Ala Gly Ile Gln Leu His Pro Gly Glu Asn Ala
            530                 535                 540 gac agt cct gca gat att agg atc aag gaa gaa gaa cct gat cct gaa    1860
Asp Ser Pro Ala Asp Ile Arg Ile Lys Glu Glu Glu Pro Asp Pro Glu
        545                 550                 555 gag tgg cag ctc agt ggt gat tct acc ttg aat acc aat gac cta aca    1908
Glu Trp Gln Leu Ser Gly Asp Ser Thr Leu Asn Thr Asn Asp Leu Thr
    560                 565                 570 cac tta aga gta cag gtg gta gat gaa gaa ggg gac caa caa cat caa    1956
His Leu Arg Val Gln Val Val Asp Glu Glu Gly Asp Gln Gln His Gln
575                 580                 585                 590 gaa gga aaa aga ctt cgg agg gta gct tgc acc tgt ccc aac tgt aaa    2004
Glu Gly Lys Arg Leu Arg Arg Val Ala Cys Thr Cys Pro Asn Cys Lys
                595                 600                 605 gaa ggt ggt gga aga ggt acc aat ctt ggg aaa aag aag caa cac att    2052
Glu Gly Gly Gly Arg Gly Thr Asn Leu Gly Lys Lys Lys Gln His Ile
            610                 615                 620 tgt cat ata cca gga tgt ggt aaa gtc tat ggg aag acc tca cat ctg    2100
Cys His Ile Pro Gly Cys Gly Lys Val Tyr Gly Lys Thr Ser His Leu
        625                 630                 635 aga gct cat ctg cgt tgg cat tct gga gaa cgc cct ttt gtt tgt aac    2148
Arg Ala His Leu Arg Trp His Ser Gly Glu Arg Pro Phe Val Cys Asn
    640                 645                 650 tgg atg tac tgt ggt aaa aga ttt act cga agt gat gaa tta cag agg    2196
Trp Met Tyr Cys Gly Lys Arg Phe Thr Arg Ser Asp Glu Leu Gln Arg
655                 660                 665                 670 cac aga aga aca cat aca ggt gag aag aaa ttt gtt tgt cca gaa tgt    2244
His Arg Arg Thr His Thr Gly Glu Lys Lys Phe Val Cys Pro Glu Cys
                675                 680                 685 tca aaa cgc ttt atg aga agt gac cac ctt gcc aaa cat att aaa aca    2292
Ser Lys Arg Phe Met Arg Ser Asp His Leu Ala Lys His Ile Lys Thr
            690                 695                 700 cac cag aat aaa aaa ggt att cac tct agc agt aca gtg ctg gca tct    2340
His Gln Asn Lys Lys Gly Ile His Ser Ser Ser Thr Val Leu Ala Ser
        705                 710                 715 gtg gaa gct gcg cga gat gat act ttg att act gca gga gga aca acg    2388
Val Glu Ala Ala Arg Asp Asp Thr Leu Ile Thr Ala Gly Gly Thr Thr
    720                 725                 730 ctt atc ctt gca aag att caa caa ggt tct gtt tca ggg ata gga act    2436
Leu Ile Leu Ala Lys Ile Gln Gln Gly Ser Val Ser Gly Ile Gly Thr
735                 740                 745                 750 gtt aat act tcc gcc acc agc aat caa gat atc ctt acc aac act gaa    2484
Val Asn Thr Ser Ala Thr Ser Asn Gln Asp Ile Leu Thr Asn Thr Glu
                755                 760                 765 ata cct tta cag ctt gtc aca gtt tct gga aat gag aca atg gag        2529
Ile Pro Leu Gln Leu Val Thr Val Ser Gly Asn Glu Thr Met Glu
            770                 775                 780 taaatattac acaaatactt attcattgtg gttattttta tacagtagtg agaagaatat  2589
tgttcctaag ttcttagata tctttttatt gatgtgcaaa aattttttgga ttgacagtaa 2649 cttggttata catgacactg aaatgcctta ctttgtatga tattccatag tatattaaaa  2709
atggtaaaat tgcatggggtt ttgtaggtac ttttggaatc tagaagaaat gaaattttac 2769 caagttatat aaagagaaaa ttgaatttaa caatgcgaat ggtagtctaa ccaaatgcat  2829
```

-continued

```
caatcctgtg tggtttagtg taaaaatgag aacatgttgg tatttatcta ttgtaagata    2889
aaaaagctgg tgggtgaaag aaatcatgtt atgataaaaa attttgtaat tttcttgatg    2949
actggaattt ttattatgca taactgacaa atcaagtttc caagcaaatg ttacatagtg    3009
taggctttac ttagcttatc aatttgtcat tttgaagcta attattttaa ttaggttaac    3069
tatgtacaat attttaagca ttactcttgt aagattttga aaactacatt ttaacatgga    3129
actctaggga tagtcacctt ttaaatcctg ttgaaaagcc atgtttaaga tttaatttgc    3189 caaataatg tcttgttaat attctttcaa taacgaagtt gggcaatata accaatgttt     3249 aaaaagttt aaaatgtata agttgaggca tttgggtggt aagagaatgt tatagtgaat     3309
tatccctttt cttgactatt ggaggaccaa aaaataaggt gtattgcgtc ttagcagtga    3369
ttttatccaa tcttgtttcc aaaaaccatg gtctcccagg gccttaaaag ccatcatgta    3429
aattaccagt aaagtgtaac atatgcaaac ataacaaaat cacttccata gtgacgatac    3489
tccaaccata tggatattag tcatagaaga actagaggtt ttatgatatt ttttttaagtc   3549 tttttttttt gtctaggtag tcagtctgca cttaaatatc aatcatttc ctttttgct     3609 tcttcccta aaatttatat gtatccagta catttaattg agaagcgtat gttttttatt    3669
atgctgtatt ttcttttat tttttaatta ttgtttatat tttcaattca aaaatgtaca   3729
aaataaagtt acattgctgg tctgtgtaag agctatacag ttttcctaaa tgtataccctg  3789 taactgcagc agttcaccta tttgcaaaaa tttggaattc tgttcatttg ttattcttaa   3849
gaccacctca aatttaaagg ctaccttatt gtacgtttaa agtgtattat aacagtgtgg   3909
tagttaataa aacactattt ttttttcttt tgaaaaaaaa aaaaaaaaaa aaaaaaaaa    3969 aaaaaaaaaa aaaaaa                                                    3985
```

<210> SEQ ID NO 4
<211> LENGTH: 781
<212> TYPE: PRT
<213> ORGANISM: Homo sapiens

<400> SEQUENCE: 4

```
Met Thr Ala Pro Glu Lys Pro Val Lys Gln Glu Glu Met Ala Ala Leu
1               5                   10                  15

Asp Val Asp Ser Gly Gly Gly Gly Gly Gly Gly Gly His Gly Glu
                20                  25                  30

Tyr Leu Gln Gln Gln Gln His Gly Asn Gly Ala Val Ala Ala Ala
            35                  40                  45

Ala Ala Ala Gln Asp Thr Gln Pro Ser Pro Leu Ala Leu Leu Ala Ala
    50                  55                  60

Thr Cys Ser Lys Ile Gly Pro Pro Ser Pro Gly Asp Asp Glu Glu Glu
65                  70                  75                  80

Ala Ala Ala Ala Ala Gly Ala Pro Ala Ala Gly Ala Thr Gly Asp
                85                  90                  95

Leu Ala Ser Ala Gln Leu Gly Gly Ala Pro Asn Arg Trp Glu Val Leu
            100                 105                 110

Ser Ala Thr Pro Thr Thr Ile Lys Asp Glu Ala Gly Asn Leu Val Gln
        115                 120                 125

Ile Pro Ser Ala Ala Thr Ser Ser Gly Gln Tyr Val Leu Pro Leu Gln
    130                 135                 140

Asn Leu Gln Asn Gln Gln Ile Phe Ser Val Ala Pro Gly Ser Asp Ser
145                 150                 155                 160

Ser Asn Gly Ala Val Ser Ser Val Gln Tyr Gln Val Ile Pro Gln Ile
```

```
                         165                 170                 175
Gln Ser Ala Asp Gly Gln Gln Val Gln Ile Gly Phe Thr Gly Ser Ser
                180                 185                 190
Asp Asn Gly Gly Ile Asn Gln Glu Ser Ser Gln Ile Gln Ile Ile Pro
            195                 200                 205
Gly Ser Asn Gln Thr Leu Leu Ala Ser Gly Thr Pro Ser Ala Asn Ile
        210                 215                 220
Gln Asn Leu Ile Pro Gln Thr Gly Val Gln Val Gln Gly Val Ala
225                 230                 235                 240
Ile Gly Gly Ser Ser Phe Pro Gly Gln Thr Gln Val Val Ala Asn Val
                245                 250                 255
Pro Leu Gly Leu Pro Gly Asn Ile Thr Phe Val Pro Ile Asn Ser Val
            260                 265                 270
Asp Leu Asp Ser Leu Gly Leu Ser Gly Ser Ser Gln Thr Met Thr Ala
        275                 280                 285
Gly Ile Asn Ala Asp Gly His Leu Ile Asn Thr Gly Gln Ala Met Asp
    290                 295                 300
Ser Ser Asp Asn Ser Glu Arg Thr Gly Glu Arg Val Ser Pro Asp Ile
305                 310                 315                 320
Asn Glu Thr Asn Thr Asp Thr Asp Leu Phe Val Pro Thr Ser Ser Ser
                325                 330                 335
Ser Gln Leu Pro Val Thr Ile Asp Ser Thr Gly Ile Leu Gln Gln Asn
            340                 345                 350
Thr Asn Ser Leu Thr Thr Ser Ser Gly Gln Val His Ser Ser Asp Leu
        355                 360                 365
Gln Gly Asn Tyr Ile Gln Ser Pro Val Ser Glu Glu Thr Gln Ala Gln
    370                 375                 380
Asn Ile Gln Val Ser Thr Ala Gln Pro Val Val Gln His Leu Gln Leu
385                 390                 395                 400
Gln Glu Ser Gln Gln Pro Thr Ser Gln Ala Gln Ile Val Gln Gly Ile
                405                 410                 415
Thr Pro Gln Thr Ile His Gly Val Gln Ala Ser Gly Gln Asn Ile Ser
            420                 425                 430
Gln Gln Ala Leu Gln Asn Leu Gln Leu Gln Leu Asn Pro Gly Thr Phe
        435                 440                 445
Leu Ile Gln Ala Gln Thr Val Thr Pro Ser Gly Gln Val Thr Trp Gln
    450                 455                 460
Thr Phe Gln Val Gln Gly Val Gln Asn Leu Gln Asn Leu Gln Ile Gln
465                 470                 475                 480
Asn Thr Ala Ala Gln Gln Ile Thr Leu Thr Pro Val Gln Thr Leu Thr
                485                 490                 495
Leu Gly Gln Val Ala Ala Gly Ala Phe Thr Ser Thr Pro Val Ser
            500                 505                 510
Leu Ser Thr Gly Gln Leu Pro Asn Leu Gln Thr Val Thr Val Asn Ser
        515                 520                 525
Ile Asp Ser Ala Gly Ile Gln Leu His Pro Gly Glu Asn Ala Asp Ser
    530                 535                 540
Pro Ala Asp Ile Arg Ile Lys Glu Glu Glu Pro Asp Pro Glu Glu Trp
545                 550                 555                 560
Gln Leu Ser Gly Asp Ser Thr Leu Asn Thr Asn Asp Leu Thr His Leu
                565                 570                 575
Arg Val Gln Val Val Asp Glu Glu Gly Asp Gln Gln His Gln Glu Gly
            580                 585                 590
```

-continued

```
Lys Arg Leu Arg Arg Val Ala Cys Thr Cys Pro Asn Cys Lys Glu Gly
        595                 600                 605
Gly Gly Arg Gly Thr Asn Leu Gly Lys Lys Lys Gln His Ile Cys His
    610                 615                 620
Ile Pro Gly Cys Gly Lys Val Tyr Gly Lys Thr Ser His Leu Arg Ala
625                 630                 635                 640
His Leu Arg Trp His Ser Gly Glu Arg Pro Phe Val Cys Asn Trp Met
            645                 650                 655
Tyr Cys Gly Lys Arg Phe Thr Arg Ser Asp Glu Leu Gln Arg His Arg
        660                 665                 670
Arg Thr His Thr Gly Glu Lys Lys Phe Val Cys Pro Glu Cys Ser Lys
    675                 680                 685
Arg Phe Met Arg Ser Asp His Leu Ala Lys His Ile Lys Thr His Gln
690                 695                 700
Asn Lys Lys Gly Ile His Ser Ser Ser Thr Val Leu Ala Ser Val Glu
705                 710                 715                 720
Ala Ala Arg Asp Asp Thr Leu Ile Thr Ala Gly Gly Thr Thr Leu Ile
            725                 730                 735
Leu Ala Lys Ile Gln Gln Gly Ser Val Ser Gly Ile Gly Thr Val Asn
        740                 745                 750
Thr Ser Ala Thr Ser Asn Gln Asp Ile Leu Thr Asn Thr Glu Ile Pro
    755                 760                 765
Leu Gln Leu Val Thr Val Ser Gly Asn Glu Thr Met Glu
        770                 775                 780

<210> SEQ ID NO 5
<211> LENGTH: 3862
<212> TYPE: DNA
<213> ORGANISM: Homo sapiens
<220> FEATURE:
<221> NAME/KEY: CDS
<222> LOCATION: (187)..(2406)
<223> OTHER INFORMATION:

<400> SEQUENCE: 5
cttttgggct ggaggctcca cctttttgtgt ttcccgcaca gtcaatcaaa ataggaaaaa      60
aaaatccccg gaccgctccg gccgtgtccg ccgccgcttc ccgcatcctc tcccgccgcc     120
gccgccttcg ctcctcacca tgtgtaaggc ggcggggagc cccgcctgag gtgccctaaa     180 cacact atg acc gct ccc gaa aag ccc gtg aaa caa gag gaa atg gct        228
        Met Thr Ala Pro Glu Lys Pro Val Lys Gln Glu Glu Met Ala
        1               5                   10 gcc ttg gac gtg gat agc ggc ggc ggt ggc ggc ggc ggc ggc cac           276
Ala Leu Asp Val Asp Ser Gly Gly Gly Gly Gly Gly Gly Gly His
15                  20                  25                  30 ggc gag tat ctg cag cag cag caa cag cac gga aac ggt gcg gtg gcg      324
Gly Glu Tyr Leu Gln Gln Gln Gln Gln His Gly Asn Gly Ala Val Ala
                35                  40                  45 gcg gca gcg gcg gcc cag aca ggt gat ttg gct tct gca cag tta gga      372
Ala Ala Ala Ala Ala Gln Thr Gly Asp Leu Ala Ser Ala Gln Leu Gly
            50                  55                  60 gga gca cca aac cga tgg gag gtt ttg tca gcc aca cct aca act ata      420
Gly Ala Pro Asn Arg Trp Glu Val Leu Ser Ala Thr Pro Thr Thr Ile
        65                  70                  75 aaa gat gaa gct ggt aat cta gtc cag att cca agt gct gct act tca      468
Lys Asp Glu Ala Gly Asn Leu Val Gln Ile Pro Ser Ala Ala Thr Ser
80                  85                  90
```

-continued

| | | |
|---|---|---|
| agt ggg cag tat gtt ctt ccc ctt cag aat ttg cag aat caa caa ata<br>Ser Gly Gln Tyr Val Leu Pro Leu Gln Asn Leu Gln Asn Gln Gln Ile<br>95                      100                105                110 | 516 |
| ttt tcc gtt gca cca gga tca gat tca tca aat ggt gca gtg tcc agt<br>Phe Ser Val Ala Pro Gly Ser Asp Ser Ser Asn Gly Ala Val Ser Ser<br>                115                120                125 | 564 |
| gtt caa tat caa gtg ata cca cag atc cag tca gca gat ggt cag cag<br>Val Gln Tyr Gln Val Ile Pro Gln Ile Gln Ser Ala Asp Gly Gln Gln<br>130                      135                140 | 612 |
| gtt caa att ggt ttc aca ggc tct tca gat aat ggg ggt ata aat caa<br>Val Gln Ile Gly Phe Thr Gly Ser Ser Asp Asn Gly Gly Ile Asn Gln<br>                145                150                155 | 660 |
| gaa agc agt caa att cag atc att cct ggc tct aat caa acc tta ctt<br>Glu Ser Ser Gln Ile Gln Ile Ile Pro Gly Ser Asn Gln Thr Leu Leu<br>160                      165                170 | 708 |
| gcc tct gga aca cct tct gct aac atc cag aat ctc ata cca cag act<br>Ala Ser Gly Thr Pro Ser Ala Asn Ile Gln Asn Leu Ile Pro Gln Thr<br>175                      180                185                190 | 756 |
| ggt caa gtc cag gtt cag gga gtt gca att ggt ggt tca tct ttt cct<br>Gly Gln Val Gln Val Gln Gly Val Ala Ile Gly Gly Ser Ser Phe Pro<br>                195                200                205 | 804 |
| ggt caa acc caa gta gtt gct aat gtg cct ctt ggt ctg cca gga aat<br>Gly Gln Thr Gln Val Val Ala Asn Val Pro Leu Gly Leu Pro Gly Asn<br>210                      215                220 | 852 |
| att acg ttt gta cca atc aat agt gtc gat cta gat tct ttg gga ctc<br>Ile Thr Phe Val Pro Ile Asn Ser Val Asp Leu Asp Ser Leu Gly Leu<br>                225                230                235 | 900 |
| tcg ggc agt tct cag aca atg act gca ggc att aat gcc gac gga cat<br>Ser Gly Ser Ser Gln Thr Met Thr Ala Gly Ile Asn Ala Asp Gly His<br>240                      245                250 | 948 |
| ttg ata aac aca gga caa gct atg gat agt tca gac aat tca gaa agg<br>Leu Ile Asn Thr Gly Gln Ala Met Asp Ser Ser Asp Asn Ser Glu Arg<br>255                      260                265                270 | 996 |
| act ggt gag cgg gtt tct cct gat att aat gaa act aat act gat aca<br>Thr Gly Glu Arg Val Ser Pro Asp Ile Asn Glu Thr Asn Thr Asp Thr<br>                275                280                285 | 1044 |
| gat tta ttt gtg cca aca tcc tct tca tca cag ttg cct gtt acg ata<br>Asp Leu Phe Val Pro Thr Ser Ser Ser Ser Gln Leu Pro Val Thr Ile<br>                      290                295                300 | 1092 |
| gat agt aca ggt ata tta caa caa aac aca aat agc ttg act aca tct<br>Asp Ser Thr Gly Ile Leu Gln Gln Asn Thr Asn Ser Leu Thr Thr Ser<br>                305                310                315 | 1140 |
| agt ggg cag gtt cat tct tca gat ctt cag gga aat tat atc cag tcg<br>Ser Gly Gln Val His Ser Ser Asp Leu Gln Gly Asn Tyr Ile Gln Ser<br>320                      325                330 | 1188 |
| cct gtt tct gaa gag aca cag gca cag aat att cag gtt tct aca gca<br>Pro Val Ser Glu Glu Thr Gln Ala Gln Asn Ile Gln Val Ser Thr Ala<br>335                      340                345                350 | 1236 |
| cag cct gtt gta cag cat cta caa ctt caa gag tct cag cag cca acc<br>Gln Pro Val Val Gln His Leu Gln Leu Gln Glu Ser Gln Gln Pro Thr<br>                355                360                365 | 1284 |
| agt caa gcc caa att gtg caa ggt att aca cca cag aca atc cat ggt<br>Ser Gln Ala Gln Ile Val Gln Gly Ile Thr Pro Gln Thr Ile His Gly<br>                      370                375                380 | 1332 |
| gtg caa gcc agt ggt caa aat ata tca caa cag gct ttg caa aat ctt<br>Val Gln Ala Ser Gly Gln Asn Ile Ser Gln Gln Ala Leu Gln Asn Leu<br>385                      390                395 | 1380 |
| cag ttg cag ctg aat cct gga acc ttt tta att cag gca cag aca gtg<br>Gln Leu Gln Leu Asn Pro Gly Thr Phe Leu Ile Gln Ala Gln Thr Val<br>          400                    405                410 | 1428 |

-continued

| | | |
|---|---|---|
| acc cct tct gga cag gta act tgg caa acg ttt caa gta caa ggg gtc<br>Thr Pro Ser Gly Gln Val Thr Trp Gln Thr Phe Gln Val Gln Gly Val<br>415                    420                    425                    430 | | 1476 |
| cag aac ttg cag aat ttg caa ata cag aat act gct gcc caa caa ata<br>Gln Asn Leu Gln Asn Leu Gln Ile Gln Asn Thr Ala Ala Gln Gln Ile<br>                    435                    440                    445 | | 1524 |
| act ctg acg cct gtt caa acc ctc aca ctt ggt caa gtt gcg gca ggt<br>Thr Leu Thr Pro Val Gln Thr Leu Thr Leu Gly Gln Val Ala Ala Gly<br>                    450                    455                    460 | | 1572 |
| gga gcc ttc act tca act cca gtt agt cta agc act ggt cag ttg cca<br>Gly Ala Phe Thr Ser Thr Pro Val Ser Leu Ser Thr Gly Gln Leu Pro<br>                465                    470                    475 | | 1620 |
| aat cta caa aca gtt aca gtg aac tct ata gat tct gct ggt ata cag<br>Asn Leu Gln Thr Val Thr Val Asn Ser Ile Asp Ser Ala Gly Ile Gln<br>480                    485                    490 | | 1668 |
| cta cat cca gga gag aat gct gac agt cct gca gat att agg atc aag<br>Leu His Pro Gly Glu Asn Ala Asp Ser Pro Ala Asp Ile Arg Ile Lys<br>495                    500                    505                    510 | | 1716 |
| gaa gaa gaa cct gat cct gaa gag tgg cag ctc agt ggt gat tct acc<br>Glu Glu Glu Pro Asp Pro Glu Glu Trp Gln Leu Ser Gly Asp Ser Thr<br>                    515                    520                    525 | | 1764 |
| ttg aat acc aat gac cta aca cac tta aga gta cag gtg gta gat gaa<br>Leu Asn Thr Asn Asp Leu Thr His Leu Arg Val Gln Val Val Asp Glu<br>                    530                    535                    540 | | 1812 |
| gaa ggg gac caa caa cat caa gaa gga aaa aga ctt cgg agg gta gct<br>Glu Gly Asp Gln Gln His Gln Glu Gly Lys Arg Leu Arg Arg Val Ala<br>                545                    550                    555 | | 1860 |
| tgc acc tgt ccc aac tgt aaa gaa ggt ggt gga aga ggt acc aat ctt<br>Cys Thr Cys Pro Asn Cys Lys Glu Gly Gly Gly Arg Gly Thr Asn Leu<br>560                    565                    570 | | 1908 |
| ggg aaa aag aag caa cac att tgt cat ata cca gga tgt ggt aaa gtc<br>Gly Lys Lys Lys Gln His Ile Cys His Ile Pro Gly Cys Gly Lys Val<br>575                    580                    585                    590 | | 1956 |
| tat ggg aag acc tca cat ctg aga gct cat ctg cgt tgg cat tct gga<br>Tyr Gly Lys Thr Ser His Leu Arg Ala His Leu Arg Trp His Ser Gly<br>                    595                    600                    605 | | 2004 |
| gaa cgc cct ttt gtt tgt aac tgg atg tac tgt ggt aaa aga ttt act<br>Glu Arg Pro Phe Val Cys Asn Trp Met Tyr Cys Gly Lys Arg Phe Thr<br>                    610                    615                    620 | | 2052 |
| cga agt gat gaa tta cag agg cac aga aga aca cat aca ggt gag aag<br>Arg Ser Asp Glu Leu Gln Arg His Arg Arg Thr His Thr Gly Glu Lys<br>                625 | | 2100 |
| aaa ttt gtt tgt cca gaa tgt tca aaa cgc ttt atg aga agt gac cac<br>Lys Phe Val Cys Pro Glu Cys Ser Lys Arg Phe Met Arg Ser Asp His<br>640                    645                    650 | | 2148 |
| ctt gcc aaa cat att aaa aca cac cag aat aaa aaa ggt att cac tct<br>Leu Ala Lys His Ile Lys Thr His Gln Asn Lys Lys Gly Ile His Ser<br>655                    660                    665                    670 | | 2196 |
| agc agt aca gtg ctg gca tct gtg gaa gct gcg cga gat gat act ttg<br>Ser Ser Thr Val Leu Ala Ser Val Glu Ala Ala Arg Asp Asp Thr Leu<br>                    675                    680                    685 | | 2244 |
| att act gca gga gga aca acg ctt atc ctt gca aag att caa caa ggt<br>Ile Thr Ala Gly Gly Thr Thr Leu Ile Leu Ala Lys Ile Gln Gln Gly<br>                    690                    695                    700 | | 2292 |
| tct gtt tca ggg ata gga act gtt aat act tcc gcc acc agc aat caa<br>Ser Val Ser Gly Ile Gly Thr Val Asn Thr Ser Ala Thr Ser Asn Gln<br>                705                    710                    715 | | 2340 |
| gat atc ctt acc aac act gaa ata cct tta cag ctt gtc aca gtt tct<br>Asp Ile Leu Thr Asn Thr Glu Ile Pro Leu Gln Leu Val Thr Val Ser | | 2388 |

```
              720              725              730
gga aat gag aca atg gag taaatattac acaaatactt attcattgtg        2436
Gly Asn Glu Thr Met Glu
735             740 gttatttta tacagtagtg agaagaatat tgttcctaag ttcttagata tcttttatt  2496 gatgtgcaaa aattttgga ttgacagtaa cttggttata catgcactg aaatgcctta  2556 cttgtatga tattccatag tatattaaaa atggtaaaat tgcatgggtt tgtaggtac  2616 ttttggaatc tagaagaaat gaaattttac caagttatat aaagagaaaa ttgaattaa  2676 caatgcgaat ggtagtctaa ccaaatgcat caatcctgtg tggtttagtg taaaaatgag  2736
aacatgttgg tattatcta ttgtaagata aaaaagctgg tgggtgaaag aaatcatgtt  2796
atgataaaaa attttgtaat tttcttgatg actggaattt ttattatgca taactgacaa  2856
atcaagtttc caagcaaatg ttacatagtg taggctttac ttagcttatc aatttgtcat  2916
tttgaagcta attatttaa ttaggttaac tatgtacaat attttaagca ttactcttgt    2976
aagattttga aaactacatt ttaacatgga actctaggga tagtcacctt ttaaatcctg  3036
ttgaaaagcc atgtttaaga tttaatttgc caaaataatg tcttgttaat attctttcaa  3096
taacgaagtt gggcaatata accaatgttt aaaaagttt aaaatgtata agttgaggca    3156
tttgggtggt aagagaatgt tatagtgaat tatccctttt cttgactatt ggaggaccaa  3216
aaaataaggt gtattgcgtc ttagcagtga ttttatccaa tcttgtttcc aaaaaccatg  3276
gtctcccagg gccttaaaag ccatcatgta aattaccagt aaagtgtaac atatgcaaac  3336
ataacaaaat cacttccata gtgacgatac tccaaccata tggatattag tcatagaaga  3396
actagaggtt ttatgatatt ttttaagtc tttttttttt gtctaggtag tcagtctgca   3456
cttaaatatc aatcattttc cttttttgct tcttcccta aaatttatat gtatccagta   3516
catttaattg agaagcgtat gtttttatt atgctgtatt ttctttttat tttttaatta   3576
ttgtttatat tttcaattca aaatgtaca aataaagtt acattgctgg tctgtgtaag    3636
agctatacag ttttcctaaa tgtatacctg taactgcagc agttcaccta tttgcaaaaa  3696
tttggaattc tgttcatttg ttattcttaa gaccacctca aatttaaagg ctaccttatt  3756
gtacgtttaa agtgtattat aacagtgtgg tagttaataa aacactattt tttttctttt  3816
tgaaaaaaaa aaaaaaaaaa aaaaaaaaaa aaaaaaaaaa aaaaaa               3862
```

<210> SEQ ID NO 6
<211> LENGTH: 740
<212> TYPE: PRT
<213> ORGANISM: Homo sapiens

<400> SEQUENCE: 6

Met Thr Ala Pro Glu Lys Pro Val Lys Gln Glu Glu Met Ala Ala Leu
1               5                   10                  15

Asp Val Asp Ser Gly Gly Gly Gly Gly Gly Gly Gly His Gly Glu
                20                  25                  30

Tyr Leu Gln Gln Gln Gln His Gly Asn Gly Ala Val Ala Ala Ala
            35                  40                  45

Ala Ala Ala Gln Thr Gly Asp Leu Ala Ser Ala Gln Leu Gly Gly Ala
        50                  55                  60

Pro Asn Arg Trp Glu Val Leu Ser Ala Thr Pro Thr Thr Ile Lys Asp
65                  70                  75                  80

Glu Ala Gly Asn Leu Val Gln Ile Pro Ser Ala Ala Thr Ser Ser Gly
                85                  90                  95

-continued

```
Gln Tyr Val Leu Pro Leu Gln Asn Leu Gln Asn Gln Gln Ile Phe Ser
            100                 105                 110
Val Ala Pro Gly Ser Asp Ser Ser Asn Gly Ala Val Ser Ser Val Gln
            115                 120                 125
Tyr Gln Val Ile Pro Gln Ile Gln Ser Ala Asp Gly Gln Gln Val Gln
            130                 135                 140
Ile Gly Phe Thr Gly Ser Ser Asp Asn Gly Gly Ile Asn Gln Glu Ser
145                 150                 155                 160
Ser Gln Ile Gln Ile Ile Pro Gly Ser Asn Gln Thr Leu Leu Ala Ser
                    165                 170                 175
Gly Thr Pro Ser Ala Asn Ile Gln Asn Leu Ile Pro Gln Thr Gly Gln
                    180                 185                 190
Val Gln Val Gln Gly Val Ala Ile Gly Gly Ser Ser Phe Pro Gly Gln
                    195                 200                 205
Thr Gln Val Val Ala Asn Val Pro Leu Gly Leu Pro Gly Asn Ile Thr
                    210                 215                 220
Phe Val Pro Ile Asn Ser Val Asp Leu Asp Ser Leu Gly Leu Ser Gly
225                 230                 235                 240
Ser Ser Gln Thr Met Thr Ala Gly Ile Asn Ala Asp Gly His Leu Ile
                    245                 250                 255
Asn Thr Gly Gln Ala Met Asp Ser Ser Asp Asn Ser Glu Arg Thr Gly
                    260                 265                 270
Glu Arg Val Ser Pro Asp Ile Asn Glu Thr Asn Thr Asp Thr Asp Leu
                    275                 280                 285
Phe Val Pro Thr Ser Ser Ser Gln Leu Pro Val Thr Ile Asp Ser
290                 295                 300
Thr Gly Ile Leu Gln Gln Asn Thr Asn Ser Leu Thr Thr Ser Ser Gly
305                 310                 315                 320
Gln Val His Ser Ser Asp Leu Gln Gly Asn Tyr Ile Gln Ser Pro Val
                    325                 330                 335
Ser Glu Glu Thr Gln Ala Gln Asn Ile Gln Val Ser Thr Ala Gln Pro
                    340                 345                 350
Val Val Gln His Leu Gln Leu Gln Glu Ser Gln Gln Pro Thr Ser Gln
                    355                 360                 365
Ala Gln Ile Val Gln Gly Ile Thr Pro Gln Thr Ile His Gly Val Gln
                    370                 375                 380
Ala Ser Gly Gln Asn Ile Ser Gln Gln Ala Leu Gln Asn Leu Gln Leu
385                 390                 395                 400
Gln Leu Asn Pro Gly Thr Phe Leu Ile Gln Ala Gln Thr Val Thr Pro
                    405                 410                 415
Ser Gly Gln Val Thr Trp Gln Thr Phe Gln Val Gln Gly Val Gln Asn
                    420                 425                 430
Leu Gln Asn Leu Gln Ile Gln Asn Thr Ala Ala Gln Ile Thr Leu
                    435                 440                 445
Thr Pro Val Gln Thr Leu Thr Leu Gly Gln Val Ala Ala Gly Gly Ala
                    450                 455                 460
Phe Thr Ser Thr Pro Val Ser Leu Ser Thr Gly Gln Leu Pro Asn Leu
465                 470                 475                 480
Gln Thr Val Thr Val Asn Ser Ile Asp Ser Ala Gly Ile Gln Leu His
                    485                 490                 495
Pro Gly Glu Asn Ala Asp Ser Pro Ala Asp Ile Arg Ile Lys Glu Glu
                    500                 505                 510
```

-continued

Glu Pro Asp Pro Glu Glu Trp Gln Leu Ser Gly Asp Ser Thr Leu Asn
            515                 520                 525

Thr Asn Asp Leu Thr His Leu Arg Val Gln Val Val Asp Glu Glu Gly
        530                 535                 540

Asp Gln Gln His Gln Glu Gly Lys Arg Leu Arg Arg Val Ala Cys Thr
545                 550                 555                 560

Cys Pro Asn Cys Lys Glu Gly Gly Gly Arg Gly Thr Asn Leu Gly Lys
                565                 570                 575

Lys Lys Gln His Ile Cys His Ile Pro Gly Cys Gly Lys Val Tyr Gly
            580                 585                 590

Lys Thr Ser His Leu Arg Ala His Leu Arg Trp His Ser Gly Glu Arg
        595                 600                 605

Pro Phe Val Cys Asn Trp Met Tyr Cys Gly Lys Arg Phe Thr Arg Ser
    610                 615                 620

Asp Glu Leu Gln Arg His Arg Arg Thr His Thr Gly Glu Lys Lys Phe
625                 630                 635                 640

Val Cys Pro Glu Cys Ser Lys Arg Phe Met Arg Ser Asp His Leu Ala
                645                 650                 655

Lys His Ile Lys Thr His Gln Asn Lys Lys Gly Ile His Ser Ser Ser
            660                 665                 670

Thr Val Leu Ala Ser Val Glu Ala Ala Arg Asp Asp Thr Leu Ile Thr
        675                 680                 685

Ala Gly Gly Thr Thr Leu Ile Leu Ala Lys Ile Gln Gln Gly Ser Val
    690                 695                 700

Ser Gly Ile Gly Thr Val Asn Thr Ser Ala Thr Ser Asn Gln Asp Ile
705                 710                 715                 720

Leu Thr Asn Thr Glu Ile Pro Leu Gln Leu Val Thr Val Ser Gly Asn
                725                 730                 735

Glu Thr Met Glu
            740

<210> SEQ ID NO 7
<211> LENGTH: 3937
<212> TYPE: DNA
<213> ORGANISM: Homo sapiens
<220> FEATURE:
<221> NAME/KEY: CDS
<222> LOCATION: (994)..(2481)
<223> OTHER INFORMATION:

<400> SEQUENCE: 7
ccccagcgtg ccctcccggg ggtgggttcc gggcggaagg cggaggcccg gcgcgcagcc      60
cgccgcccgc ctgcccgcgg accggggagc cggggtgctt ggagcggggg acgccaggcg     120
tgggctggcg gcgggaccag gaggaggagg aggaggagga ggagagcgcg ggctggcgct     180
tgcccgggcg cagtcggcgg ggaccgagtc gtacttcctg tgcgaaaggc ggcccgaccc     240
taaccgccac cccctccccc tgtctccctc tctgaacccg cccattgggg gtaggacact     300
cagccgtcac cgctcgctct gctggccgct acctgcagca agatagggcc gccatcgccg     360
ggcgacgacg aggaggaggc ggccgccgca gccgggcccc cgccgccgc cggagcgaca      420 ggtgatttgg cttctgcaca gttaggagga gcaccaaacc gatgggaggt tttgtcagcc     480
acacctacaa ctataaaaga tgaagctggt aatctagtcc agattccaag tgctgctact     540
tcaagtgggc agtatgttct tcccttcag aatttgcaga atcaacaaat attttccgtt      600
gcaccaggat cagattcatc aaatggtgca gtgtccagtg ttcaatatca agtgatacca     660

```
cagatccagt cagcagatgg tcagcaggtt caaattggtt tcacaggctc ttcagataat        720
gggggtataa atcaagaaag cagtcaaatt cagatcattc ctggctctaa tcaaaccta         780 cttgcctctg gaacacccttc tgctaacatc agaatctca taccacagac tggtcaagtc        840
caggttcagg gagttgcaat tggtggttca tctttctg gtcaaaccca agtagttgct          900
aatgtgcctc ttggtctgcc aggaaatat acgtttgtac caatcaatag tgtcgatcta         960
gattctttgg gactctcggg cagttctcag aca atg act gca ggc att aat gcc       1014
                                   Met Thr Ala Gly Ile Asn Ala
                                    1               5 gac gga cat ttg ata aac aca gga caa gct atg gat agt tca gac aat        1062
Asp Gly His Leu Ile Asn Thr Gly Gln Ala Met Asp Ser Ser Asp Asn
         10                  15                  20 tca gaa agg act ggt gag cgg gtt tct cct gat att aat gaa act aat        1110
Ser Glu Arg Thr Gly Glu Arg Val Ser Pro Asp Ile Asn Glu Thr Asn
 25                  30                  35 act gat aca gat tta ttt gtg cca aca tcc tct tca tca cag ttg cct        1158
Thr Asp Thr Asp Leu Phe Val Pro Thr Ser Ser Ser Ser Gln Leu Pro
 40                  45                  50                  55 gtt acg ata gat agt aca ggt ata tta caa caa aac aca aat agc ttg        1206
Val Thr Ile Asp Ser Thr Gly Ile Leu Gln Gln Asn Thr Asn Ser Leu
                 60                  65                  70 act aca tct agt ggg cag gtt cat tct tca gat ctt cag gga aat tat        1254
Thr Thr Ser Ser Gly Gln Val His Ser Ser Asp Leu Gln Gly Asn Tyr
             75                  80                  85 atc cag tcg cct gtt tct gaa gag aca cag gca cag aat att cag gtt        1302
Ile Gln Ser Pro Val Ser Glu Glu Thr Gln Ala Gln Asn Ile Gln Val
         90                  95                 100 tct aca gca cag cct gtt gta cag cat cta caa ctt caa gag tct cag        1350
Ser Thr Ala Gln Pro Val Val Gln His Leu Gln Leu Gln Glu Ser Gln
105                 110                 115 cag cca acc agt caa gcc caa att gtg caa ggt att aca cca cag aca        1398
Gln Pro Thr Ser Gln Ala Gln Ile Val Gln Gly Ile Thr Pro Gln Thr
120                 125                 130                 135 atc cat ggt gtg caa gcc agt ggt caa aat ata tca caa cag gct ttg        1446
Ile His Gly Val Gln Ala Ser Gly Gln Asn Ile Ser Gln Gln Ala Leu
                140                 145                 150 caa aat ctt cag ttg cag ctg aat cct gga acc ttt tta att cag gca        1494
Gln Asn Leu Gln Leu Gln Leu Asn Pro Gly Thr Phe Leu Ile Gln Ala
            155                 160                 165 cag aca gtg acc cct tct gga cag gta act tgg caa acg ttt caa gta        1542
Gln Thr Val Thr Pro Ser Gly Gln Val Thr Trp Gln Thr Phe Gln Val
        170                 175                 180 caa ggg gtc cag aac ttg cag aat ttg caa ata cag aat act gct gcc        1590
Gln Gly Val Gln Asn Leu Gln Asn Leu Gln Ile Gln Asn Thr Ala Ala
    185                 190                 195 caa caa ata act ttg acg cct gtt caa acc ctc aca ctt ggt caa gtt        1638
Gln Gln Ile Thr Leu Thr Pro Val Gln Thr Leu Thr Leu Gly Gln Val
200                 205                 210                 215 gcg gca ggt gga gcc ttc act tca act cca gtt agt cta agc act ggt        1686
Ala Ala Gly Gly Ala Phe Thr Ser Thr Pro Val Ser Leu Ser Thr Gly
                220                 225                 230 cag ttg cca aat cta caa aca gtt aca gtg aac tct ata gat tct gct        1734
Gln Leu Pro Asn Leu Gln Thr Val Thr Val Asn Ser Ile Asp Ser Ala
            235                 240                 245 ggt ata cag cta cat cca gga gag aat gct gac agt cct gca gat att        1782
Gly Ile Gln Leu His Pro Gly Glu Asn Ala Asp Ser Pro Ala Asp Ile
        250                 255                 260 agg atc aag gaa gaa gaa cct gat cct gaa gag tgg cag ctc agt ggt        1830
```

```
                Arg Ile Lys Glu Glu Pro Asp Pro Glu Trp Gln Leu Ser Gly
                    265                 270                 275 gat tct acc ttg aat acc aat gac cta aca cac tta aga gta cag gtg      1878
Asp Ser Thr Leu Asn Thr Asn Asp Leu Thr His Leu Arg Val Gln Val
280                 285                 290                 295 gta gat gaa gaa ggg gac caa caa cat caa gaa gga aaa aga ctt cgg      1926
Val Asp Glu Glu Gly Asp Gln Gln His Gln Glu Gly Lys Arg Leu Arg
                300                 305                 310 agg gta gct tgc acc tgt ccc aac tgt aaa gaa ggt ggt gga aga ggt      1974
Arg Val Ala Cys Thr Cys Pro Asn Cys Lys Glu Gly Gly Gly Arg Gly
            315                 320                 325 acc aat ctt ggg aaa aag aag caa cac att tgt cat ata cca gga tgt      2022
Thr Asn Leu Gly Lys Lys Lys Gln His Ile Cys His Ile Pro Gly Cys
        330                 335                 340 ggt aaa gtc tat ggg aag acc tca cat ctg aga gct cat ctg cgt tgg      2070
Gly Lys Val Tyr Gly Lys Thr Ser His Leu Arg Ala His Leu Arg Trp
    345                 350                 355 cat tct gga gaa cgc cct ttt gtt tgt aac tgg atg tac tgt ggt aaa      2118
His Ser Gly Glu Arg Pro Phe Val Cys Asn Trp Met Tyr Cys Gly Lys
360                 365                 370                 375 aga ttt act cga agt gat gaa tta cag agg cac aga aga aca cat aca      2166
Arg Phe Thr Arg Ser Asp Glu Leu Gln Arg His Arg Arg Thr His Thr
                380                 385                 390 ggt gag aag aaa ttt gtt tgt cca gaa tgt tca aaa cgc ttt atg aga      2214
Gly Glu Lys Lys Phe Val Cys Pro Glu Cys Ser Lys Arg Phe Met Arg
                395                 400                 405 agt gac cac ctt gcc aaa cat att aaa aca cac cag aat aaa aaa ggt      2262
Ser Asp His Leu Ala Lys His Ile Lys Thr His Gln Asn Lys Lys Gly
            410                 415                 420 att cac tct agc agt aca gtg ctg gca tct gtg gaa gct gcg cga gat      2310
Ile His Ser Ser Ser Thr Val Leu Ala Ser Val Glu Ala Ala Arg Asp
        425                 430                 435 gat act ttg att act gca gga gga aca acg ctt atc ctt gca aag att      2358
Asp Thr Leu Ile Thr Ala Gly Gly Thr Thr Leu Ile Leu Ala Lys Ile
    440                 445                 450                 455 caa caa ggt tct gtt tca ggg ata gga act gtt aat act tcc gcc acc      2406
Gln Gln Gly Ser Val Ser Gly Ile Gly Thr Val Asn Thr Ser Ala Thr
                460                 465                 470 agc aat caa gat atc ctt acc aac act gaa ata cct tta cag ctt gtc      2454
Ser Asn Gln Asp Ile Leu Thr Asn Thr Glu Ile Pro Leu Gln Leu Val
                475                 480                 485 aca gtt tct gga aat gag aca atg gag taaatattac acaaatactt            2501
Thr Val Ser Gly Asn Glu Thr Met Glu
            490                 495 attcattgtg gttatttta tacagtagtg agaagaatat tgttcctaag ttcttagata     2561
tctttttatt gatgtgcaaa aatttttgga ttgacagtaa cttggttata catgacactg    2621
aaatgcctta ctttgtatga tattccatag tatattaaaa atggtaaaat tgcatggtt     2681 ttgtaggtac ttttggaatc tagaagaaat gaaattttac caagttatat aaagagaaaa    2741
ttgaatttaa caatgcgaat ggtagtctaa ccaaatgcat caatcctgtg tggtttagtg    2801
taaaaatgag aacatgttgg tatttatcta ttgtaagata aaaaagctgg tgggtgaaag    2861
aaatcatgtt atgataaaaa attttgtaat tttcttgatg actggaattt ttattatgca    2921
taactgacaa atcaagtttc caagcaaatg ttacatagtg taggctttac ttagcttatc    2981
aatttgtcat tttgaagcta attattttaa ttaggttaac tatgtacaat attttaagca    3041
ttactcttgt aagattttga aaactacatt ttaacatgga actctaggga tagtcacctt    3101
```

-continued

```
ttaaatcctg ttgaaaagcc atgtttaaga tttaatttgc caaataatg tcttgttaat    3161 attctttcaa taacgaagtt gggcaatata accaatgttt aaaaaagttt aaaatgtata    3221
agttgaggca tttgggtggt aagagaatgt tatagtgaat tatcccttt cttgactatt    3281 ggaggaccaa aaaataaggt gtattgcgtc ttagcagtga ttttatccaa tcttgtttcc    3341
aaaaaccatg gtctcccagg gccttaaaag ccatcatgta aattaccagt aaagtgtaac    3401
atatgcaaac ataacaaaat cacttccata gtgacgatac tccaaccata tggatattag    3461
tcatagaaga actagaggtt ttatgatatt tttttaagtc tttttttttt gtctaggtag    3521
tcagtctgca cttaaatatc aatcatttc cttttttgct tcttccctta aaatttatat    3581
gtatccagta catttaattg agaagcgtat gttttttatt atgctgtatt ttcttttat    3641 ttttaatta ttgtttatat tttcaattca aaaatgtaca aaataaagtt acattgctgg    3701
tctgtgtaag agctatacag ttttcctaaa tgtatacctg taactgcagc agttcaccta    3761
tttgcaaaaa tttggaattc tgttcatttg ttattcttaa gaccacctca aatttaaagg    3821
ctaccttatt gtacgtttaa agtgtattat aacagtgtgg tagttaataa aacactattt    3881
tttttctttt tgaaaaaaaa aaaaaaaaaa aaaaaaaaaa aaaaaaaaaa aaaaaa        3937
```

<210> SEQ ID NO 8
<211> LENGTH: 496
<212> TYPE: PRT
<213> ORGANISM: Homo sapiens

<400> SEQUENCE: 8

```
Met Thr Ala Gly Ile Asn Ala Asp Gly His Leu Ile Asn Thr Gly Gln
1               5                   10                  15

Ala Met Asp Ser Ser Asp Asn Ser Glu Arg Thr Gly Glu Arg Val Ser
                20                  25                  30

Pro Asp Ile Asn Glu Thr Asn Thr Asp Thr Asp Leu Phe Val Pro Thr
            35                  40                  45

Ser Ser Ser Ser Gln Leu Pro Val Thr Ile Asp Ser Thr Gly Ile Leu
        50                  55                  60

Gln Gln Asn Thr Asn Ser Leu Thr Thr Ser Ser Gly Gln Val His Ser
65                  70                  75                  80

Ser Asp Leu Gln Gly Asn Tyr Ile Gln Ser Pro Val Ser Glu Glu Thr
                85                  90                  95

Gln Ala Gln Asn Ile Gln Val Ser Thr Ala Gln Pro Val Val Gln His
            100                 105                 110

Leu Gln Leu Gln Glu Ser Gln Gln Pro Thr Ser Gln Ala Gln Ile Val
        115                 120                 125

Gln Gly Ile Thr Pro Gln Thr Ile His Gly Val Gln Ala Ser Gly Gln
    130                 135                 140

Asn Ile Ser Gln Gln Ala Leu Gln Asn Leu Gln Leu Gln Leu Asn Pro
145                 150                 155                 160

Gly Thr Phe Leu Ile Gln Ala Gln Thr Val Thr Pro Ser Gly Gln Val
                165                 170                 175

Thr Trp Gln Thr Phe Gln Val Gln Gly Val Gln Asn Leu Gln Asn Leu
            180                 185                 190

Gln Ile Gln Asn Thr Ala Ala Gln Ile Thr Leu Thr Pro Val Gln
        195                 200                 205

Thr Leu Thr Leu Gly Gln Val Ala Ala Gly Gly Ala Phe Thr Ser Thr
    210                 215                 220

Pro Val Ser Leu Ser Thr Gly Gln Leu Pro Asn Leu Gln Thr Val Thr
```

```
                      225                 230                 235                 240
Val Asn Ser Ile Asp Ser Ala Gly Ile Gln Leu His Pro Gly Glu Asn
                245                 250                 255

Ala Asp Ser Pro Ala Asp Ile Arg Ile Lys Glu Glu Pro Asp Pro
            260                 265                 270

Glu Glu Trp Gln Leu Ser Gly Asp Ser Thr Leu Asn Thr Asn Asp Leu
        275                 280                 285

Thr His Leu Arg Val Gln Val Asp Glu Glu Gly Asp Gln Gln His
    290                 295                 300

Gln Glu Gly Lys Arg Leu Arg Arg Val Ala Cys Thr Cys Pro Asn Cys
305                 310                 315                 320

Lys Glu Gly Gly Gly Arg Gly Thr Asn Leu Gly Lys Lys Lys Gln His
                325                 330                 335

Ile Cys His Ile Pro Gly Cys Gly Lys Val Tyr Gly Lys Thr Ser His
                340                 345                 350

Leu Arg Ala His Leu Arg Trp His Ser Gly Glu Arg Pro Phe Val Cys
            355                 360                 365

Asn Trp Met Tyr Cys Gly Lys Arg Phe Thr Arg Ser Asp Glu Leu Gln
370                 375                 380

Arg His Arg Arg Thr His Thr Gly Glu Lys Lys Phe Val Cys Pro Glu
385                 390                 395                 400

Cys Ser Lys Arg Phe Met Arg Ser Asp His Leu Ala Lys His Ile Lys
                405                 410                 415

Thr His Gln Asn Lys Lys Gly Ile His Ser Ser Ser Thr Val Leu Ala
                420                 425                 430

Ser Val Glu Ala Ala Arg Asp Asp Thr Leu Ile Thr Ala Gly Gly Thr
            435                 440                 445

Thr Leu Ile Leu Ala Lys Ile Gln Gln Gly Ser Val Ser Gly Ile Gly
        450                 455                 460

Thr Val Asn Thr Ser Ala Thr Ser Asn Gln Asp Ile Leu Thr Asn Thr
465                 470                 475                 480

Glu Ile Pro Leu Gln Leu Val Thr Val Ser Gly Asn Glu Thr Met Glu
                485                 490                 495

<210> SEQ ID NO 9
<211> LENGTH: 3722
<212> TYPE: DNA
<213> ORGANISM: Homo sapiens
<220> FEATURE:
<221> NAME/KEY: CDS
<222> LOCATION: (2)..(2266)
<223> OTHER INFORMATION:

<400> SEQUENCE: 9 g ctg ccc gcc cga ggc gcc aac gct ccg acc ccg ccc gcg ccg ccc cgc      49
  Leu Pro Ala Arg Gly Ala Asn Ala Pro Thr Pro Pro Ala Pro Pro Arg
  1               5                  10                  15 ctc gcc cgc ctg ccg cct ttt tgt gcg cgt gac act cag ccg tca ccg       97
Leu Ala Arg Leu Pro Pro Phe Cys Ala Arg Asp Thr Gln Pro Ser Pro
             20                  25                  30 ctc gct ctg ctg gcc gct acc tgc agc aag ata ggg ccg cca tcg ccg      145
Leu Ala Leu Leu Ala Ala Thr Cys Ser Lys Ile Gly Pro Pro Ser Pro
         35                  40                  45 ggc gac gac gag gag gag gcg gcc gcc gca gcc ggg gcc ccc gcc gcc      193
Gly Asp Asp Glu Glu Glu Ala Ala Ala Ala Gly Ala Pro Ala Ala
     50                  55                  60 gcc gga gcg aca ggt gat ttg gct tct gca cag tta gga gga gca cca      241
```

```
Ala Gly Ala Thr Gly Asp Leu Ala Ser Ala Gln Leu Gly Gly Ala Pro
 65                  70                  75                  80 aac cga tgg gag gtt ttg tca gcc aca cct aca act ata aaa gat gaa       289
Asn Arg Trp Glu Val Leu Ser Ala Thr Pro Thr Thr Ile Lys Asp Glu
                 85                  90                  95 gct ggt aat cta gtc cag att cca agt gct gct act tca agt ggg cag       337
Ala Gly Asn Leu Val Gln Ile Pro Ser Ala Ala Thr Ser Ser Gly Gln
            100                 105                 110 tat gtt ctt ccc ctt cag aat ttg cag aat caa caa ata ttt tcc gtt       385
Tyr Val Leu Pro Leu Gln Asn Leu Gln Asn Gln Gln Ile Phe Ser Val
        115                 120                 125 gca cca gga tca gat tca tca aat ggt gca gtg tcc agt gtt caa tat       433
Ala Pro Gly Ser Asp Ser Ser Asn Gly Ala Val Ser Ser Val Gln Tyr
    130                 135                 140 caa gtg ata cca cag atc cag tca gca gat ggt cag cag gtt caa att       481
Gln Val Ile Pro Gln Ile Gln Ser Ala Asp Gly Gln Gln Val Gln Ile
145                 150                 155                 160 ggt ttc aca ggc tct tca gat aat ggg ggt ata aat caa gaa agc agt       529
Gly Phe Thr Gly Ser Ser Asp Asn Gly Gly Ile Asn Gln Glu Ser Ser
                165                 170                 175 caa att cag atc att cct ggc tct aat caa acc tta ctt gcc tct gga       577
Gln Ile Gln Ile Ile Pro Gly Ser Asn Gln Thr Leu Leu Ala Ser Gly
            180                 185                 190 aca cct tct gct aac atc cag aat ctc ata cca cag act ggt caa gtc       625
Thr Pro Ser Ala Asn Ile Gln Asn Leu Ile Pro Gln Thr Gly Gln Val
        195                 200                 205 cag gtt cag gga gtt gca att ggt ggt tca tct ttt cct ggt caa acc       673
Gln Val Gln Gly Val Ala Ile Gly Gly Ser Ser Phe Pro Gly Gln Thr
    210                 215                 220 caa gta gtt gct aat gtg cct ctt ggt ctg cca gga aat att acg ttt       721
Gln Val Val Ala Asn Val Pro Leu Gly Leu Pro Gly Asn Ile Thr Phe
225                 230                 235                 240 gta cca atc aat agt gtc gat cta gat tct ttg gga ctc tcg ggc agt       769
Val Pro Ile Asn Ser Val Asp Leu Asp Ser Leu Gly Leu Ser Gly Ser
                245                 250                 255 tct cag aca atg act gca ggc att aat gcc gac gga cat ttg ata aac       817
Ser Gln Thr Met Thr Ala Gly Ile Asn Ala Asp Gly His Leu Ile Asn
            260                 265                 270 aca gga caa gct atg gat agt tca gac aat tca gaa agg act ggt gag       865
Thr Gly Gln Ala Met Asp Ser Ser Asp Asn Ser Glu Arg Thr Gly Glu
        275                 280                 285 cgg gtt tct cct gat att aat gaa act aat act gat aca gat tta ttt       913
Arg Val Ser Pro Asp Ile Asn Glu Thr Asn Thr Asp Thr Asp Leu Phe
    290                 295                 300 gtg cca aca tcc tct tca tca cag ttg cct gtt acg ata gat agt aca       961
Val Pro Thr Ser Ser Ser Ser Gln Leu Pro Val Thr Ile Asp Ser Thr
305                 310                 315                 320 ggt ata tta caa caa aac aca aat agc ttg act aca tct agt ggg cag      1009
Gly Ile Leu Gln Gln Asn Thr Asn Ser Leu Thr Thr Ser Ser Gly Gln
                325                 330                 335 gtt cat tct tca gat ctt cag gga aat tat atc cag tcg cct gtt tct      1057
Val His Ser Ser Asp Leu Gln Gly Asn Tyr Ile Gln Ser Pro Val Ser
            340                 345                 350 gaa gag aca cag gca cag aat att cag gtt tct aca gca cag cct gtt      1105
Glu Glu Thr Gln Ala Gln Asn Ile Gln Val Ser Thr Ala Gln Pro Val
        355                 360                 365 gta cag cat cta caa ctt caa gag tct cag cag cca acc agt caa gcc      1153
Val Gln His Leu Gln Leu Gln Glu Ser Gln Gln Pro Thr Ser Gln Ala
    370                 375                 380
```

```
caa att gtg caa ggt att aca cca cag aca atc cat ggt gtg caa gcc      1201
Gln Ile Val Gln Gly Ile Thr Pro Gln Thr Ile His Gly Val Gln Ala
385                 390                 395                 400 agt ggt caa aat ata tca caa cag gct ttg caa aat ctt cag ttg cag      1249
Ser Gly Gln Asn Ile Ser Gln Gln Ala Leu Gln Asn Leu Gln Leu Gln
                405                 410                 415 ctg aat cct gga acc ttt tta att cag gca cag aca gtg acc cct tct      1297
Leu Asn Pro Gly Thr Phe Leu Ile Gln Ala Gln Thr Val Thr Pro Ser
            420                 425                 430 gga cag gta act tgg caa acg ttt caa gta caa ggg gtc cag aac ttg      1345
Gly Gln Val Thr Trp Gln Thr Phe Gln Val Gln Gly Val Gln Asn Leu
        435                 440                 445 cag aat ttg caa ata cag aat act gct gcc caa caa ata act ttg acg      1393
Gln Asn Leu Gln Ile Gln Asn Thr Ala Ala Gln Gln Ile Thr Leu Thr
    450                 455                 460 cct gtt caa acc ctc aca ctt ggt caa gtt gcg gca ggt gga gcc ttc      1441
Pro Val Gln Thr Leu Thr Leu Gly Gln Val Ala Ala Gly Gly Ala Phe
465                 470                 475                 480 act tca act cca gtt agt cta agc act ggt cag ttg cca aat cta caa      1489
Thr Ser Thr Pro Val Ser Leu Ser Thr Gly Gln Leu Pro Asn Leu Gln
                485                 490                 495 aca gtt aca gtg aac tct ata gat tct gct ggt ata cag cta cat cca      1537
Thr Val Thr Val Asn Ser Ile Asp Ser Ala Gly Ile Gln Leu His Pro
            500                 505                 510 gga gag aat gct gac agt cct gca gat att agg atc aag gaa gaa gaa      1585
Gly Glu Asn Ala Asp Ser Pro Ala Asp Ile Arg Ile Lys Glu Glu Glu
        515                 520                 525 cct gat cct gaa gag tgg cag ctc agt ggt gat tct acc ttg aat acc      1633
Pro Asp Pro Glu Glu Trp Gln Leu Ser Gly Asp Ser Thr Leu Asn Thr
    530                 535                 540 aat gac cta aca cac tta aga gta cag gtg gta gat gaa gaa ggg gac      1681
Asn Asp Leu Thr His Leu Arg Val Gln Val Val Asp Glu Glu Gly Asp
545                 550                 555                 560 caa caa cat caa gaa gga aaa aga ctt cgg agg gta gct tgc acc tgt      1729
Gln Gln His Gln Glu Gly Lys Arg Leu Arg Arg Val Ala Cys Thr Cys
                565                 570                 575 ccc aac tgt aaa gaa ggt ggt gga aga ggt acc aat ctt ggg aaa aag      1777
Pro Asn Cys Lys Glu Gly Gly Gly Arg Gly Thr Asn Leu Gly Lys Lys
            580                 585                 590 aag caa cac att tgt cat ata cca gga tgt ggt aaa gtc tat ggg aag      1825
Lys Gln His Ile Cys His Ile Pro Gly Cys Gly Lys Val Tyr Gly Lys
        595                 600                 605 acc tca cat ctg aga gct cat ctg cgt tgg cat tct gga gaa cgc cct      1873
Thr Ser His Leu Arg Ala His Leu Arg Trp His Ser Gly Glu Arg Pro
    610                 615                 620 ttt gtt tgt aac tgg atg tac tgt ggt aaa aga ttt act cga agt gat      1921
Phe Val Cys Asn Trp Met Tyr Cys Gly Lys Arg Phe Thr Arg Ser Asp
625                 630                 635                 640 gaa tta cag agg cac aga aga aca cat aca ggt gag aag aaa ttt gtt      1969
Glu Leu Gln Arg His Arg Arg Thr His Thr Gly Glu Lys Lys Phe Val
                645                 650                 655 tgt cca gaa tgt tca aaa cgc ttt atg aga agt gac cac ctt gcc aaa      2017
Cys Pro Glu Cys Ser Lys Arg Phe Met Arg Ser Asp His Leu Ala Lys
            660                 665                 670 cat att aaa aca cac cag aat aaa aaa ggt att cac tct agc agt aca      2065
His Ile Lys Thr His Gln Asn Lys Lys Gly Ile His Ser Ser Ser Thr
        675                 680                 685 gtg ctg gca tct gtg gaa gct gcg cga gat gat act ttg att act gca      2113
Val Leu Ala Ser Val Glu Ala Ala Arg Asp Asp Thr Leu Ile Thr Ala
    690                 695                 700
```

-continued

```
gga gga aca acg ctt atc ctt gca aag att caa caa ggt tct gtt tca    2161
Gly Gly Thr Thr Leu Ile Leu Ala Lys Ile Gln Gln Gly Ser Val Ser
705                 710                 715                 720 ggg ata gga act gtt aat act tcc gcc acc agc aat caa gat atc ctt    2209
Gly Ile Gly Thr Val Asn Thr Ser Ala Thr Ser Asn Gln Asp Ile Leu
                725                 730                 735 acc aac act gaa ata cct tta cag ctt gtc aca gtt tct gga aat gag    2257
Thr Asn Thr Glu Ile Pro Leu Gln Leu Val Thr Val Ser Gly Asn Glu
            740                 745                 750 aca atg gag taaatattac acaaatactt attcattgtg gttattttta            2306
Thr Met Glu
        755 tacagtagtg agaagaatat tgttcctaag ttcttagata tcttttatt gatgtgcaaa    2366 aattttgga ttgacagtaa cttggttata catgacactg aaatgcctta ctttgtatga   2426 tattccatag tatattaaaa atggtaaaat tgcatgggtt ttgtaggtac ttttggaatc   2486 tagaagaaat gaaattttac caagttatat aaagagaaaa ttgaatttaa caatgcgaat   2546 ggtagtctaa ccaaatgcat caatcctgtg tggtttagtg taaaaatgag aacatgttgg   2606 tatttatcta ttgtaagata aaaagctgg tgggtgaaag aaatcatgtt atgataaaaa    2666 attttgtaat tttcttgatg actggaattt ttattatgca taactgacaa atcaagtttc   2726 caagcaaatg ttacatagtg taggctttac ttagcttatc aatttgtcat tttgaagcta   2786 attattttaa ttaggttaac tatgtacaat attttaagca ttactcttgt aagattttga   2846 aaactacatt ttaacatgga actctaggga tagtcacctt ttaaatcctg ttgaaaagcc   2906 atgtttaaga tttaatttgc caaaataatg tcttgttaat attctttcaa taacgaagtt   2966 gggcaatata accaatgttt aaaaagttt aaaatgtata agttgaggca tttgggtggt    3026 aagagaatgt tatagtgaat tatccctttt cttgactatt ggaggaccaa aaaataaggt   3086 gtattgcgtc ttagcagtga ttttatccaa tcttgtttcc aaaaaccatg gtctcccagg   3146 gccttaaaag ccatcatgta aattaccagt aaagtgtaac atatgcaaac ataacaaaat   3206 cacttccata gtgacgatac tccaaccata tggatattag tcatagaaga actagaggtt   3266 ttatgatatt ttttaagtc ttttttttt gtctaggtag tcagtctgca cttaaatatc    3326 aatcattttc ctttttgct tcttcccttta aaatttatat gtatccagta catttaattg   3386 agaagcgtat gttttttatt atgctgtatt ttctttttat tttttaatta ttgtttatat   3446 tttcaattca aaaatgtaca aaataaagtt acattgctgg tctgtgtaag agctatacag   3506 ttttcctaaa tgtatacctg taactgcagc agttcaccta tttgcaaaaa tttggaattc   3566 tgttcatttg ttattcttaa gaccacctca aatttaaagg ctaccttatt gtacgtttaa   3626 agtgtattat aacagtgtgg tagttaataa aacactattt tttttctttt tgaaaaaaaa   3686 aaaaaaaaaa aaaaaaaaaa aaaaaaaaaa aaaaaa                            3722
```

<210> SEQ ID NO 10
<211> LENGTH: 755
<212> TYPE: PRT
<213> ORGANISM: Homo sapiens

<400> SEQUENCE: 10

```
Leu Pro Ala Arg Gly Ala Asn Ala Pro Thr Pro Ala Pro Pro Arg
1               5                   10                  15

Leu Ala Arg Leu Pro Pro Phe Cys Ala Arg Asp Thr Gln Pro Ser Pro
            20                  25                  30
```

-continued

```
Leu Ala Leu Ala Ala Thr Cys Ser Lys Ile Gly Pro Ser Pro
         35                  40                  45

Gly Asp Asp Glu Glu Glu Ala Ala Ala Ala Gly Ala Pro Ala Ala
 50                  55                  60

Ala Gly Ala Thr Gly Asp Leu Ala Ser Ala Gln Leu Gly Gly Ala Pro
 65                  70                  75                  80

Asn Arg Trp Glu Val Leu Ser Ala Thr Pro Thr Thr Ile Lys Asp Glu
                 85                  90                  95

Ala Gly Asn Leu Val Gln Ile Pro Ser Ala Ala Thr Ser Ser Gly Gln
             100                 105                 110

Tyr Val Leu Pro Leu Gln Asn Leu Gln Asn Gln Gln Ile Phe Ser Val
         115                 120                 125

Ala Pro Gly Ser Asp Ser Asn Gly Ala Val Ser Ser Val Gln Tyr
 130                 135                 140

Gln Val Ile Pro Gln Ile Gln Ser Ala Asp Gly Gln Gln Val Gln Ile
145                 150                 155                 160

Gly Phe Thr Gly Ser Ser Asp Asn Gly Gly Ile Asn Gln Glu Ser Ser
                 165                 170                 175

Gln Ile Gln Ile Ile Pro Gly Ser Asn Gln Thr Leu Leu Ala Ser Gly
             180                 185                 190

Thr Pro Ser Ala Asn Ile Gln Asn Leu Ile Pro Gln Thr Gly Gln Val
         195                 200                 205

Gln Val Gln Gly Val Ala Ile Gly Gly Ser Ser Phe Pro Gly Gln Thr
 210                 215                 220

Gln Val Val Ala Asn Val Pro Leu Gly Leu Pro Gly Asn Ile Thr Phe
225                 230                 235                 240

Val Pro Ile Asn Ser Val Asp Leu Asp Ser Leu Gly Leu Ser Gly Ser
                 245                 250                 255

Ser Gln Thr Met Thr Ala Gly Ile Asn Ala Asp Gly His Leu Ile Asn
             260                 265                 270

Thr Gly Gln Ala Met Asp Ser Ser Asp Asn Ser Glu Arg Thr Gly Glu
         275                 280                 285

Arg Val Ser Pro Asp Ile Asn Glu Thr Asn Thr Asp Thr Asp Leu Phe
 290                 295                 300

Val Pro Thr Ser Ser Ser Gln Leu Pro Val Thr Ile Asp Ser Thr
305                 310                 315                 320

Gly Ile Leu Gln Gln Asn Thr Asn Ser Leu Thr Thr Ser Ser Gly Gln
                 325                 330                 335

Val His Ser Ser Asp Leu Gln Gly Asn Tyr Ile Gln Ser Pro Val Ser
             340                 345                 350

Glu Glu Thr Gln Ala Gln Asn Ile Gln Val Ser Thr Ala Gln Pro Val
         355                 360                 365

Val Gln His Leu Gln Leu Gln Glu Ser Gln Gln Pro Thr Ser Gln Ala
 370                 375                 380

Gln Ile Val Gln Gly Ile Thr Pro Gln Thr Ile His Gly Val Gln Ala
385                 390                 395                 400

Ser Gly Gln Asn Ile Ser Gln Gln Ala Leu Gln Asn Leu Gln Leu Gln
                 405                 410                 415

Leu Asn Pro Gly Thr Phe Leu Ile Gln Ala Gln Thr Val Thr Pro Ser
             420                 425                 430

Gly Gln Val Thr Trp Gln Thr Phe Gln Val Gly Val Gln Asn Leu
         435                 440                 445

Gln Asn Leu Gln Ile Gln Asn Thr Ala Ala Gln Gln Ile Thr Leu Thr
```

|     |     |     |     |     |     | 450 |     |     |     |     |     | 455 |     |     |     |     |     | 460 |     |
| --- | --- | --- | --- | --- | --- | --- | --- | --- | --- | --- | --- | --- | --- | --- | --- | --- | --- | --- | --- |

Pro Val Gln Thr Leu Thr Leu Gly Gln Val Ala Ala Gly Gly Ala Phe
465                 470                 475                 480

Thr Ser Thr Pro Val Ser Leu Ser Thr Gly Gln Leu Pro Asn Leu Gln
                485                 490                 495

Thr Val Thr Val Asn Ser Ile Asp Ser Ala Gly Ile Gln Leu His Pro
            500                 505                 510

Gly Glu Asn Ala Asp Ser Pro Ala Asp Ile Arg Ile Lys Glu Glu Glu
        515                 520                 525

Pro Asp Pro Glu Glu Trp Gln Leu Ser Gly Asp Ser Thr Leu Asn Thr
    530                 535                 540

Asn Asp Leu Thr His Leu Arg Val Gln Val Val Asp Glu Glu Gly Asp
545                 550                 555                 560

Gln Gln His Gln Glu Gly Lys Arg Leu Arg Arg Val Ala Cys Thr Cys
                565                 570                 575

Pro Asn Cys Lys Glu Gly Gly Gly Arg Gly Thr Asn Leu Gly Lys Lys
            580                 585                 590

Lys Gln His Ile Cys His Ile Pro Gly Cys Gly Lys Val Tyr Gly Lys
        595                 600                 605

Thr Ser His Leu Arg Ala His Leu Arg Trp His Ser Gly Glu Arg Pro
    610                 615                 620

Phe Val Cys Asn Trp Met Tyr Cys Gly Lys Arg Phe Thr Arg Ser Asp
625                 630                 635                 640

Glu Leu Gln Arg His Arg Arg Thr His Thr Gly Glu Lys Lys Phe Val
                645                 650                 655

Cys Pro Glu Cys Ser Lys Arg Phe Met Arg Ser Asp His Leu Ala Lys
            660                 665                 670

His Ile Lys Thr His Gln Asn Lys Lys Gly Ile His Ser Ser Ser Thr
        675                 680                 685

Val Leu Ala Ser Val Glu Ala Ala Arg Asp Asp Thr Leu Ile Thr Ala
    690                 695                 700

Gly Gly Thr Thr Leu Ile Leu Ala Lys Ile Gln Gly Ser Val Ser
705                 710                 715                 720

Gly Ile Gly Thr Val Asn Thr Ser Ala Thr Ser Asn Gln Asp Ile Leu
                725                 730                 735

Thr Asn Thr Glu Ile Pro Leu Gln Leu Val Thr Val Ser Gly Asn Glu
            740                 745                 750

Thr Met Glu
        755

<210> SEQ ID NO 11
<211> LENGTH: 3311
<212> TYPE: DNA
<213> ORGANISM: Homo sapiens
<220> FEATURE:
<221> NAME/KEY: CDS
<222> LOCATION: (57)..(1001)
<223> OTHER INFORMATION:

<400> SEQUENCE: 11
gagcggcggc cacggcatcc tgtgctgtgg gggctacgag gaaagatcta attatc atg    59
                                                              Met
                                                                1 gac ctg cga cag ttt ctt atg tgc ctg tcc ctg tgc aca gcc ttt gcc    107
Asp Leu Arg Gln Phe Leu Met Cys Leu Ser Leu Cys Thr Ala Phe Ala
        5                   10                  15

```
ttg agc aaa ccc aca gaa aag aag gac cgt gta cat cat gag cct cag    155
Leu Ser Lys Pro Thr Glu Lys Lys Asp Arg Val His His Glu Pro Gln
        20                  25                  30 ctc agt gac aag gtt cac aat gat gct cag agt ttt gat tat gac cat    203
Leu Ser Asp Lys Val His Asn Asp Ala Gln Ser Phe Asp Tyr Asp His
 35                  40                  45 gat gcc ttc ttg ggt gct gaa gaa gca aag acc ttt gat cag ctg aca    251
Asp Ala Phe Leu Gly Ala Glu Glu Ala Lys Thr Phe Asp Gln Leu Thr
 50                  55                  60                  65 cca gaa gag agc aag gaa agg ctt gga atg att gta gat aaa ata gac    299
Pro Glu Glu Ser Lys Glu Arg Leu Gly Met Ile Val Asp Lys Ile Asp
                 70                  75                  80 gcg gat aaa gat ggg ttt gtg acg gag ggg gag ctg aaa tcc tgg att    347
Ala Asp Lys Asp Gly Phe Val Thr Glu Gly Glu Leu Lys Ser Trp Ile
         85                  90                  95 aag cac gcc cag aag aaa tac ata tat gac aat gtt gaa aac caa tgg    395
Lys His Ala Gln Lys Lys Tyr Ile Tyr Asp Asn Val Glu Asn Gln Trp
        100                 105                 110 cag gag ttt gat atg aat caa gac ggc tta atc tcc tgg gat gag tac    443
Gln Glu Phe Asp Met Asn Gln Asp Gly Leu Ile Ser Trp Asp Glu Tyr
115                 120                 125 aga aac gtg act tat ggc act tac ctg gat gat cca gat cct gat gat    491
Arg Asn Val Thr Tyr Gly Thr Tyr Leu Asp Asp Pro Asp Pro Asp Asp
130                 135                 140                 145 gga ttt aac tat aaa cag atg atg gtt aga gat gag cgg agg ttt aaa    539
Gly Phe Asn Tyr Lys Gln Met Met Val Arg Asp Glu Arg Arg Phe Lys
                150                 155                 160 atg gca gac aag gat gga gac ctc att gcc acc aag gag gag ttc aca    587
Met Ala Asp Lys Asp Gly Asp Leu Ile Ala Thr Lys Glu Glu Phe Thr
            165                 170                 175 gct ttc ctg cac cct gag gag tat gac tac atg aaa gat ata gta gta    635
Ala Phe Leu His Pro Glu Glu Tyr Asp Tyr Met Lys Asp Ile Val Val
        180                 185                 190 cag gaa aca atg gaa gat ata gat aag aat gct gat ggt ttc att gat    683
Gln Glu Thr Met Glu Asp Ile Asp Lys Asn Ala Asp Gly Phe Ile Asp
    195                 200                 205 cta gaa gag tat att ggt gac atg tac agc cat gat ggg aat act gat    731
Leu Glu Glu Tyr Ile Gly Asp Met Tyr Ser His Asp Gly Asn Thr Asp
210                 215                 220                 225 gag cca gaa tgg gta aag aca gag cga gag cag ttt gtt gag ttt cgg    779
Glu Pro Glu Trp Val Lys Thr Glu Arg Glu Gln Phe Val Glu Phe Arg
                230                 235                 240 gat aag aac cgt gat ggg aag atg gac aag gaa gag acc aaa gac tgg    827
Asp Lys Asn Arg Asp Gly Lys Met Asp Lys Glu Glu Thr Lys Asp Trp
            245                 250                 255 atc ctt ccc tca gac tat gat cat gca gag gca gaa gcc agg cac ctg    875
Ile Leu Pro Ser Asp Tyr Asp His Ala Glu Ala Glu Ala Arg His Leu
        260                 265                 270 gtc tat gaa tca gac caa aac aag gat ggc aag ctt acc aag gag gag    923
Val Tyr Glu Ser Asp Gln Asn Lys Asp Gly Lys Leu Thr Lys Glu Glu
    275                 280                 285 atc gtt gac aag tat gac tta ttt gtt ggc agc cag gcc aca gat ttt    971
Ile Val Asp Lys Tyr Asp Leu Phe Val Gly Ser Gln Ala Thr Asp Phe
290                 295                 300                 305 ggg gag gcc tta gta cgg cat gat gag ttc tgagctacgg aggaaccctc     1021
Gly Glu Ala Leu Val Arg His Asp Glu Phe
                310                 315 atttcctcaa aagtaattta ttttttacagc ttctggtttc acatgaaatt gtttgcgcta  1081
ctgagactgt tactacaaac tttttaagac atgaaaaggc gtaatgaaaa ccatcccgtc  1141
```

```
cccattcctc ctcctctctg agggactgga gggaagccgt gcttctgagg aacaactcta    1201
attagtacac ttgtgtttgt agatttacac tttgtattat gtattaacat ggcgtgttta    1261
tttttgtatt tttctctggt tgggagtatg atatgaagga tcaagatcct caactcacac    1321
atgtagacaa acattagctc tttactcttt ctcaacccct tttatgattt taataattct    1381
cacttaacta attttgtaag cctgagatca ataagaaatg ttcaggagag aggaaagaaa    1441
aaaaatatat gctccacaat ttatatttag agagagaaca cttagtcttg cctgtcaaaa    1501
agtccaacat ttcataggta gtaggggcca catattacat tcagttgcta taggtccagc    1561
aactgaacct gccattacct gggcaaggaa agatcccttt gctctaggaa agcttggccc    1621
aaattgattt tcttcttttt cccctgtag gactgactg tggctaattt tgtcaagcac      1681
agctgtggtg ggaagagtta gggccagtgt cttgaaaatc aatcaagtag tgaatgtgat    1741
ctctttgcag agctatagat agaaacagct ggaaaactaa aggaaaata caagtgtttt     1801 cggggcatac attttttttc tgggtgtgca tctgttgaaa tgctcaagac ttcattattt    1861
gccttttgaa atcactgtaa atgcccccat ccggttcctc ttcttcccag gtgtgccaag    1921
gaattaatct tggtttcact acaattaaaa ttcactcctt tccaatcatg tcattgaaag    1981
tgcctttaac gaaagaaatg gtcactgaat gggaattctc ttaagaaacc ctgagattaa    2041
aaaaagacta tttggataac ttataggaaa gcctagaacc tcccagtaga gtgggatt     2101 ttttcttctt ccctttctct tttggacaat agttaaatta gcagtattag ttatgagttt    2161
ggttgcagtg ttcttatctt gtgggctgat ttccaaaaac cacatgctgc tgaatttacc    2221
agggatcctc atacctcaca atgcaaacca cttactacca ggccttttc tgtgtccact     2281 ggagagcttg agctcacact caaagatcag aggacctaca gagagggctc tttggtttga    2341
ggaccatggc ttacctttcc tgcctttgac ccatcacacc ccatttcctc ctctttccct    2401
ctccccgctg ccaaaaaaaa aaaaaagga aacgtttatc atgaatcaac agggtttcag    2461
tccttatcaa agagagatgt ggaaagagct aaagaaacca cccttgtc ccaactccac     2521 tttacccata ttttatgcaa cacaaacact gtccttttgg gtcccttct acagatgga     2581 cctcttgaga agaattatcg tattccacgt ttttagccct caggttacca agataaaat    2641 atgtatatat aaccttat attgctatat cttgtggat aatacattca ggtggtgctg     2701 ggtgattat tataatctga acctaggtat atccttggt cttccacagt catgttgagg     2761
tgggctccct ggtatggtaa aaagccaggt ataatgtaac ttcaccccag cctttgtact    2821
aagctcttga tagtggatat actcttttaa gtttagcccc aatatagggt aatgaaatt    2881 tcctgccctc tgggttcccc attttttacta ttaagaagac cagtgataat ttaataatgc   2941
caccaactct ggcttagtta agtgagagtg tgaactgtgt ggcaagagag cctcacacct    3001
cactaggtgc agagagccca ggcttatgt taaaatcatg cacttgaaaa gcaaaccttta    3061 atctgcaaag acagcagcaa gcattatacg gtcatcttga atgatccctt tgaatttt     3121 tttttgtttg tttgtttaaa tcaagcctga ggctggtgaa cagtagctac acacccatat    3181
tgtgtgttct gtgaatgcta gctctcttga atttggatat tggttatttt ttatagagtg    3241
taaaccaagt tttatattct gcaatgcgaa caggtaccta tctgtttcta aataaaactg    3301
tttacattca                                                          3311
```

<210> SEQ ID NO 12
<211> LENGTH: 315
<212> TYPE: PRT

<213> ORGANISM: Homo sapiens

<400> SEQUENCE: 12

```
Met Asp Leu Arg Gln Phe Leu Met Cys Leu Ser Leu Cys Thr Ala Phe
1               5                   10                  15

Ala Leu Ser Lys Pro Thr Glu Lys Lys Asp Arg Val His His Glu Pro
            20                  25                  30

Gln Leu Ser Asp Lys Val His Asn Asp Ala Gln Ser Phe Asp Tyr Asp
        35                  40                  45

His Asp Ala Phe Leu Gly Ala Glu Glu Ala Lys Thr Phe Asp Gln Leu
    50                  55                  60

Thr Pro Glu Glu Ser Lys Glu Arg Leu Gly Met Ile Val Asp Lys Ile
65                  70                  75                  80

Asp Ala Asp Lys Asp Gly Phe Val Thr Glu Gly Glu Leu Lys Ser Trp
                85                  90                  95

Ile Lys His Ala Gln Lys Lys Tyr Ile Tyr Asp Asn Val Glu Asn Gln
            100                 105                 110

Trp Gln Glu Phe Asp Met Asn Gln Asp Gly Leu Ile Ser Trp Asp Glu
        115                 120                 125

Tyr Arg Asn Val Thr Tyr Gly Thr Tyr Leu Asp Asp Pro Asp Pro Asp
130                 135                 140

Asp Gly Phe Asn Tyr Lys Gln Met Met Val Arg Asp Glu Arg Arg Phe
145                 150                 155                 160

Lys Met Ala Asp Lys Asp Gly Asp Leu Ile Ala Thr Lys Glu Glu Phe
                165                 170                 175

Thr Ala Phe Leu His Pro Glu Glu Tyr Asp Tyr Met Lys Asp Ile Val
            180                 185                 190

Val Gln Glu Thr Met Glu Asp Ile Asp Lys Asn Ala Asp Gly Phe Ile
        195                 200                 205

Asp Leu Glu Glu Tyr Ile Gly Asp Met Tyr Ser His Asp Gly Asn Thr
210                 215                 220

Asp Glu Pro Glu Trp Val Lys Thr Glu Arg Glu Gln Phe Val Glu Phe
225                 230                 235                 240

Arg Asp Lys Asn Arg Asp Gly Lys Met Asp Lys Glu Glu Thr Lys Asp
                245                 250                 255

Trp Ile Leu Pro Ser Asp Tyr Asp His Ala Glu Ala Glu Ala Arg His
            260                 265                 270

Leu Val Tyr Glu Ser Asp Gln Asn Lys Asp Gly Lys Leu Thr Lys Glu
        275                 280                 285

Glu Ile Val Asp Lys Tyr Asp Leu Phe Val Gly Ser Gln Ala Thr Asp
290                 295                 300

Phe Gly Glu Ala Leu Val Arg His Asp Glu Phe
305                 310                 315
```

<210> SEQ ID NO 13
<211> LENGTH: 1719
<212> TYPE: DNA
<213> ORGANISM: Homo sapiens
<220> FEATURE:
<221> NAME/KEY: CDS
<222> LOCATION: (239)..(1129)
<223> OTHER INFORMATION:

<400> SEQUENCE: 13
ggcaccaggc gcttccgaga atcgcagtct acgcgagctg cctgtttttt tcctgcttgg      60
acgcgcatga gggccccgtc catggaccgc gcggccgtgg cgagggtggg cgcggtagcg     120

```
agcgccagcg tgtgcgccct ggtggcgggg gtggtgctgg ctcagtacat attcaccttg    180
aagaggaaga cggggcggaa gaccaagatc atcgagatga agattggata accaagaa     238 atg act aat caa gag tct gcc gta cat gtg aaa atg atg cca gaa ttc    286
Met Thr Asn Gln Glu Ser Ala Val His Val Lys Met Met Pro Glu Phe
 1               5                  10                  15 cag aaa agt tca gtt cga atc aag aac cct aca aga gta gaa gaa att    334
Gln Lys Ser Ser Val Arg Ile Lys Asn Pro Thr Arg Val Glu Glu Ile
                 20                  25                  30 atc tgt ggt ctt atc aaa gga gga gct gcc aaa ctt cag ata ata acg    382
Ile Cys Gly Leu Ile Lys Gly Gly Ala Ala Lys Leu Gln Ile Ile Thr
             35                  40                  45 gac ttt gat atg aca ctc agt aga ttt tca tat aaa ggg aaa aga tgc    430
Asp Phe Asp Met Thr Leu Ser Arg Phe Ser Tyr Lys Gly Lys Arg Cys
 50                  55                  60 cca aca tgt cat aat atc att gac aac tgt aag ctg gtt aca gat gaa    478
Pro Thr Cys His Asn Ile Ile Asp Asn Cys Lys Leu Val Thr Asp Glu
 65                  70                  75                  80 tgt aga aaa aag tta ttg caa cta aag gaa aaa tac tac gct att gaa    526
Cys Arg Lys Lys Leu Leu Gln Leu Lys Glu Lys Tyr Tyr Ala Ile Glu
                 85                  90                  95 gtt gat cct gtt ctt act gta gaa gag aag tac cct tat atg gtg gaa    574
Val Asp Pro Val Leu Thr Val Glu Glu Lys Tyr Pro Tyr Met Val Glu
                100                 105                 110 tgg tat act aaa tca cat ggt ttg ctt gtt cag caa gct tta cca aaa    622
Trp Tyr Thr Lys Ser His Gly Leu Leu Val Gln Gln Ala Leu Pro Lys
            115                 120                 125 gct aaa ctt aaa gaa att gtg gca gaa tct gac gtt atg ctc aaa gaa    670
Ala Lys Leu Lys Glu Ile Val Ala Glu Ser Asp Val Met Leu Lys Glu
130                 135                 140 gga tat gag aat ttc ttt gat aag ctc caa caa cat agc atc ccc gtg    718
Gly Tyr Glu Asn Phe Phe Asp Lys Leu Gln Gln His Ser Ile Pro Val
145                 150                 155                 160 ttc ata ttt tcg gct gga atc ggc gat gta cta gag gaa gtt att cgt    766
Phe Ile Phe Ser Ala Gly Ile Gly Asp Val Leu Glu Glu Val Ile Arg
                165                 170                 175 caa gct ggt gtt tat cat ccc aat gtc aaa gtt gtg tcc aat ttt atg    814
Gln Ala Gly Val Tyr His Pro Asn Val Lys Val Val Ser Asn Phe Met
            180                 185                 190 gat ttt gat gaa act ggg gtg ctc aaa gga ttt aaa gga gaa cta att    862
Asp Phe Asp Glu Thr Gly Val Leu Lys Gly Phe Lys Gly Glu Leu Ile
        195                 200                 205 cat gta ttt aac aaa cat gat ggt gcc ttg agg aat aca gaa tat ttc    910
His Val Phe Asn Lys His Asp Gly Ala Leu Arg Asn Thr Glu Tyr Phe
    210                 215                 220 aat caa cta aaa gac aat agt aac ata att ctt ctg gga gac tcc caa    958
Asn Gln Leu Lys Asp Asn Ser Asn Ile Ile Leu Leu Gly Asp Ser Gln
225                 230                 235                 240 gga gac tta aga atg gca gat gga gtg gcc aat gtt gag cac att ctg   1006
Gly Asp Leu Arg Met Ala Asp Gly Val Ala Asn Val Glu His Ile Leu
                245                 250                 255 aaa att gga tat cta aat gat aga gtg gat gag ctt tta gaa aag tac   1054
Lys Ile Gly Tyr Leu Asn Asp Arg Val Asp Glu Leu Leu Glu Lys Tyr
            260                 265                 270 atg gac tct tat gat att gtt tta gta caa gat gaa tca tta gaa gta   1102
Met Asp Ser Tyr Asp Ile Val Leu Val Gln Asp Glu Ser Leu Glu Val
        275                 280                 285 gcc aac tct att tta cag aag att cta taaacaagca ttctccaaga          1149
Ala Asn Ser Ile Leu Gln Lys Ile Leu
    290                 295
```

-continued

```
agacctctct cctgtgggtg caattgaact gttcatccgt tcatcttgct gagagactta    1209
tttataatat atccttactc tcgaagtgtt ccctttgtat aactgaagta ttttcagata    1269
tggtgaatgc attgactgga agctcctttt ctccacctct ctcaacacac tcctcaccgt    1329 atctttaac ccatttaaaa aaaaaaaaaa gctaaaatta gaaaataac tccctactt     1389 tccaaagtga attttgtagt ttaatgttat catgcagctt ttgaggagtc ttttacactg    1449
ggaaagtttg tagaaatttt aaaataagtt ttatgaaatg gtgaaataat atgcatgatt    1509
ttaagtattg ccatttttgt aatttgggtt attatgctga tggtatcacc atctcttgaa    1569
attgtgttag gtttggttat tttgtctggg gaaaaaatat ttactggaaa agactagcag    1629
ttagtgttgg aaaaacctgg tggtgtttac aatgttgcta atcattacaa aacattctat    1689
attgaagcac tgataataaa tatgaaatgc                                    1719
```

<210> SEQ ID NO 14
<211> LENGTH: 297
<212> TYPE: PRT
<213> ORGANISM: Homo sapiens

<400> SEQUENCE: 14

```
Met Thr Asn Gln Glu Ser Ala Val His Val Lys Met Met Pro Glu Phe
1               5                   10                  15

Gln Lys Ser Ser Val Arg Ile Lys Asn Pro Thr Arg Val Glu Glu Ile
                20                  25                  30

Ile Cys Gly Leu Ile Lys Gly Gly Ala Ala Lys Leu Gln Ile Ile Thr
            35                  40                  45

Asp Phe Asp Met Thr Leu Ser Arg Phe Ser Tyr Lys Gly Lys Arg Cys
        50                  55                  60

Pro Thr Cys His Asn Ile Ile Asp Asn Cys Lys Leu Val Thr Asp Glu
65                  70                  75                  80

Cys Arg Lys Lys Leu Leu Gln Leu Lys Glu Lys Tyr Tyr Ala Ile Glu
                85                  90                  95

Val Asp Pro Val Leu Thr Val Glu Glu Lys Tyr Pro Tyr Met Val Glu
                100                 105                 110

Trp Tyr Thr Lys Ser His Gly Leu Leu Val Gln Gln Ala Leu Pro Lys
            115                 120                 125

Ala Lys Leu Lys Glu Ile Val Ala Glu Ser Asp Val Met Leu Lys Glu
        130                 135                 140

Gly Tyr Glu Asn Phe Phe Asp Lys Leu Gln Gln His Ser Ile Pro Val
145                 150                 155                 160

Phe Ile Phe Ser Ala Gly Ile Gly Asp Val Leu Glu Glu Val Ile Arg
                165                 170                 175

Gln Ala Gly Val Tyr His Pro Asn Val Lys Val Val Ser Asn Phe Met
                180                 185                 190

Asp Phe Asp Glu Thr Gly Val Leu Lys Gly Phe Lys Gly Glu Leu Ile
            195                 200                 205

His Val Phe Asn Lys His Asp Gly Ala Leu Arg Asn Thr Glu Tyr Phe
        210                 215                 220

Asn Gln Leu Lys Asp Asn Ser Asn Ile Ile Leu Leu Gly Asp Ser Gln
225                 230                 235                 240

Gly Asp Leu Arg Met Ala Asp Gly Val Ala Asn Val Glu His Ile Leu
                245                 250                 255

Lys Ile Gly Tyr Leu Asn Asp Arg Val Asp Glu Leu Leu Glu Lys Tyr
                260                 265                 270
```

```
Met Asp Ser Tyr Asp Ile Val Leu Val Gln Asp Glu Ser Leu Glu Val
        275                 280                 285

Ala Asn Ser Ile Leu Gln Lys Ile Leu
        290                 295

<210> SEQ ID NO 15
<211> LENGTH: 2371
<212> TYPE: DNA
<213> ORGANISM: Homo sapiens
<220> FEATURE:
<221> NAME/KEY: CDS
<222> LOCATION: (56)..(1918)
<223> OTHER INFORMATION:

<400> SEQUENCE: 15 agggtacag agaggagccc ccttggcacc gccaccgcac cctaggccac ccacc atg      58
                                                            Met
                                                             1 gcg ctg ggc ttg gag cag gcg gag gag cag cgg ttg tac cag cag acg    106
Ala Leu Gly Leu Glu Gln Ala Glu Glu Gln Arg Leu Tyr Gln Gln Thr
        5                   10                  15 ctc ctg caa gac ggg ctc aaa gac atg ctg gac cat ggc aag ttc ctc    154
Leu Leu Gln Asp Gly Leu Lys Asp Met Leu Asp His Gly Lys Phe Leu
         20                  25                  30 gac tgt gtg gtg cgg gcg ggc gag cgc gag ttc ccg tgc cat cgc ctg    202
Asp Cys Val Val Arg Ala Gly Glu Arg Glu Phe Pro Cys His Arg Leu
     35                  40                  45 gtg ctg gcc gcc tgc agc ccc tac ttc cgg gcg cgc ttt cta gcc gag    250
Val Leu Ala Ala Cys Ser Pro Tyr Phe Arg Ala Arg Phe Leu Ala Glu
 50                  55                  60                  65 ccg gag cgc gcg ggc gag ctg cac ctg gag gag gtg tcc ccg gac gtg    298
Pro Glu Arg Ala Gly Glu Leu His Leu Glu Glu Val Ser Pro Asp Val
                 70                  75                  80 gtg gcc cag gtg ctg cac tac ctg tac aca tca gag atc gcg ctg gat    346
Val Ala Gln Val Leu His Tyr Leu Tyr Thr Ser Glu Ile Ala Leu Asp
             85                  90                  95 gag gcg agc gtg cag gat ttg ttc gcc gcg gca cac cgc ttc cag atc    394
Glu Ala Ser Val Gln Asp Leu Phe Ala Ala Ala His Arg Phe Gln Ile
         100                 105                 110 cct tcc atc ttc acc atc tgc gtg tcc ttc ctg cag aag cgc ctg tgc    442
Pro Ser Ile Phe Thr Ile Cys Val Ser Phe Leu Gln Lys Arg Leu Cys
     115                 120                 125 ctc tcc aac tgc ttg gcc gtc ttc cgt ctc ggc ctc ctc gac tgc        490
Leu Ser Asn Cys Leu Ala Val Phe Arg Leu Gly Leu Leu Asp Cys
130                 135                 140                 145 gcg cgt ctc gcc gtg gct gcc cgc gac ttc atc tgc gct cac ttc acg    538
Ala Arg Leu Ala Val Ala Ala Arg Asp Phe Ile Cys Ala His Phe Thr
                 150                 155                 160 ctg gtg gcg cgc gac gct gac ttc ctc gga ctc tcg gcc gac gag ctc    586
Leu Val Ala Arg Asp Ala Asp Phe Leu Gly Leu Ser Ala Asp Glu Leu
             165                 170                 175 atc gcc atc atc tcc agc gac ggc ctt aac gtg gag aag gag gag gca    634
Ile Ala Ile Ile Ser Ser Asp Gly Leu Asn Val Glu Lys Glu Glu Ala
         180                 185                 190 gtg ttc gag gcg gtg atg cgg tgg gcg ggt agc ggc gac gcc gag gcg    682
Val Phe Glu Ala Val Met Arg Trp Ala Gly Ser Gly Asp Ala Glu Ala
     195                 200                 205 cag gct gag cgc cag cgc gcg ctg ccc acc gtc ttc gag agc gtg cgc    730
Gln Ala Glu Arg Gln Arg Ala Leu Pro Thr Val Phe Glu Ser Val Arg
210                 215                 220                 225
```

```
tgc cgc ttg ctg ccg cgc gcc ttt ctg gaa agc cgc gtg gag cgc cac      778
Cys Arg Leu Leu Pro Arg Ala Phe Leu Glu Ser Arg Val Glu Arg His
                230                 235                 240 cct ctc gtg cgt gcc cag ccc gag ttg ctg cgc aag gtg cag atg gtg      826
Pro Leu Val Arg Ala Gln Pro Glu Leu Leu Arg Lys Val Gln Met Val
                245                 250                 255 aag gat gca cac gag ggc cgc atc acc acg ctg cgg aag aaa aag aag      874
Lys Asp Ala His Glu Gly Arg Ile Thr Thr Leu Arg Lys Lys Lys Lys
                260                 265                 270 ggg aag gat gga gcc ggg gcc aag gag gct gat aag ggc aca agc aaa      922
Gly Lys Asp Gly Ala Gly Ala Lys Glu Ala Asp Lys Gly Thr Ser Lys
        275                 280                 285 gcc aaa gca gag gag gat gag gag gcc gaa cgt atc ctt cct ggg atc      970
Ala Lys Ala Glu Glu Asp Glu Glu Ala Glu Arg Ile Leu Pro Gly Ile
290                 295                 300                 305 ctc aat gac acc ctg cgc ttc ggc atg ttc ctg cag gat ctc atc ttc     1018
Leu Asn Asp Thr Leu Arg Phe Gly Met Phe Leu Gln Asp Leu Ile Phe
                310                 315                 320 atg atc agt gag gag ggc gct gtg gcc tac gat cca gca gcc aac gag     1066
Met Ile Ser Glu Glu Gly Ala Val Ala Tyr Asp Pro Ala Ala Asn Glu
                325                 330                 335 tgc tac tgt gct tcc ctc tcc agc cag gtc ccc aag aac cac gtc agc     1114
Cys Tyr Cys Ala Ser Leu Ser Ser Gln Val Pro Lys Asn His Val Ser
                340                 345                 350 ctg gtt acc aag gag aac cag gtc ttc gtg gct gga ggc ctc ttc tac     1162
Leu Val Thr Lys Glu Asn Gln Val Phe Val Ala Gly Gly Leu Phe Tyr
355                 360                 365 aac gaa gac aac aaa gag gac ccc atg agc gca tac ttc ctg cag ttt     1210
Asn Glu Asp Asn Lys Glu Asp Pro Met Ser Ala Tyr Phe Leu Gln Phe
370                 375                 380                 385 gac cat ctg gac tca gag tgg ctg ggg atg cca ccg ctg ccc tcg ccc     1258
Asp His Leu Asp Ser Glu Trp Leu Gly Met Pro Pro Leu Pro Ser Pro
                390                 395                 400 cgc tgc ctc ttt ggc ctg gga gaa gct ctc aac tcc atc tac gtg gtc     1306
Arg Cys Leu Phe Gly Leu Gly Glu Ala Leu Asn Ser Ile Tyr Val Val
                405                 410                 415 ggt ggc aga gag atc aag gac ggc gag cgc tgc ctg gac tcg gtc atg     1354
Gly Gly Arg Glu Ile Lys Asp Gly Glu Arg Cys Leu Asp Ser Val Met
                420                 425                 430 tgc tac gac agg ctg tca ttc aaa tgg ggt gaa tcg gac ccg ctg cct     1402
Cys Tyr Asp Arg Leu Ser Phe Lys Trp Gly Glu Ser Asp Pro Leu Pro
435                 440                 445 tac gtg gtg tat ggc cac aca gtg ctc tcc cac atg gac ctt gtc tac     1450
Tyr Val Val Tyr Gly His Thr Val Leu Ser His Met Asp Leu Val Tyr
450                 455                 460                 465 gta att ggc ggc aaa ggc agt gac agg aag tgc ctg aac aag atg tgc     1498
Val Ile Gly Gly Lys Gly Ser Asp Arg Lys Cys Leu Asn Lys Met Cys
                470                 475                 480 gtc tat gac ccc aag aag ttt gag tgg aag gag ctg gca ccc atg cag     1546
Val Tyr Asp Pro Lys Lys Phe Glu Trp Lys Glu Leu Ala Pro Met Gln
                485                 490                 495 acc gcc cgc tca ctc ttt ggg gcc act gtc cat gat ggc cgc att atc     1594
Thr Ala Arg Ser Leu Phe Gly Ala Thr Val His Asp Gly Arg Ile Ile
                500                 505                 510 gtg gca gct ggg gtc acc gac aca ggg ctg acc agt tct gcc gaa gtg     1642
Val Ala Ala Gly Val Thr Asp Thr Gly Leu Thr Ser Ser Ala Glu Val
        515                 520                 525 tac agc atc aca gac aac aag tgg gca ccc ttc gag gcc ttc cca cag     1690
Tyr Ser Ile Thr Asp Asn Lys Trp Ala Pro Phe Glu Ala Phe Pro Gln
530                 535                 540                 545
```

```
gag cgt agc tca ctc agc ctg gtc agc ctg gtg ggt acc ctc tat gcc    1738
Glu Arg Ser Ser Leu Ser Leu Val Ser Leu Val Gly Thr Leu Tyr Ala
            550                 555                 560 att ggt ggc ttt gcc aca ctg gag acg gag tct gga gag ctg gtt ccc    1786
Ile Gly Gly Phe Ala Thr Leu Glu Thr Glu Ser Gly Glu Leu Val Pro
        565                 570                 575 aca gag ctc aat gac atc tgg agg tat aac gag gag gag aag aaa tgg    1834
Thr Glu Leu Asn Asp Ile Trp Arg Tyr Asn Glu Glu Glu Lys Lys Trp
    580                 585                 590 gag ggt gtc ctg cgg gag atc gcc tat gca gca ggt gcc acc ttc cta    1882
Glu Gly Val Leu Arg Glu Ile Ala Tyr Ala Ala Gly Ala Thr Phe Leu
595                 600                 605 cca gtg cgg ctc aat gtg ctg cgc ctg act aag atg tgaccagctc         1928
Pro Val Arg Leu Asn Val Leu Arg Leu Thr Lys Met
                615                 620 aggcagactg aactaagcac ccctcccatc ctgcgaccct cactggcctg gccttgtggg   1988
ggctccagaa aagaggctag gagaggccag agtctacctg gatccagtta tggtgcctca   2048
ggggctgcgt cagccaagga aagggaagtg ctgcttagtc ctggactttt gggccagggt   2108
gagaaactag aggcttctcc agtgttgcca tatccccta ggttgtcttg atccatgaac    2168
cagaaccaca gggcggtatc ccaggccgtg tgctggccct gccccagcct agctgagtgt   2228
gctggcaaag ttccccacag gactcagcct tctcgtctgt ccgatgggag catccccatc   2288
aagtgcagtg tacagtgcag atatgtctcc ttctttagga agaataaagt gccttctgag   2348
caagcaaaaa aaaaaaaaaa aaa                                          2371

<210> SEQ ID NO 16
<211> LENGTH: 621
<212> TYPE: PRT
<213> ORGANISM: Homo sapiens

<400> SEQUENCE: 16

Met Ala Leu Gly Leu Glu Gln Ala Glu Gln Arg Leu Tyr Gln Gln
1               5                   10                  15

Thr Leu Leu Gln Asp Gly Leu Lys Asp Met Leu Asp His Gly Lys Phe
            20                  25                  30

Leu Asp Cys Val Val Arg Ala Gly Glu Arg Glu Phe Pro Cys His Arg
        35                  40                  45

Leu Val Leu Ala Ala Cys Ser Pro Tyr Phe Arg Ala Arg Phe Leu Ala
    50                  55                  60

Glu Pro Glu Arg Ala Gly Glu Leu His Leu Glu Glu Val Ser Pro Asp
65                  70                  75                  80

Val Val Ala Gln Val Leu His Tyr Leu Tyr Thr Ser Glu Ile Ala Leu
                85                  90                  95

Asp Glu Ala Ser Val Gln Asp Leu Phe Ala Ala His Arg Phe Gln
            100                 105                 110

Ile Pro Ser Ile Phe Thr Ile Cys Val Ser Phe Leu Gln Lys Arg Leu
        115                 120                 125

Cys Leu Ser Asn Cys Leu Ala Val Phe Arg Leu Gly Leu Leu Leu Asp
    130                 135                 140

Cys Ala Arg Leu Ala Val Ala Ala Arg Asp Phe Ile Cys Ala His Phe
145                 150                 155                 160

Thr Leu Val Ala Arg Asp Ala Asp Phe Leu Gly Leu Ser Ala Asp Glu
                165                 170                 175

Leu Ile Ala Ile Ile Ser Ser Asp Gly Leu Asn Val Glu Lys Glu Glu
```

```
                180              185              190
Ala Val Phe Glu Ala Val Met Arg Trp Ala Gly Ser Gly Asp Ala Glu
                195              200              205
Ala Gln Ala Glu Arg Gln Arg Ala Leu Pro Thr Val Phe Glu Ser Val
    210              215              220
Arg Cys Arg Leu Leu Pro Arg Ala Phe Leu Glu Ser Arg Val Glu Arg
225              230              235              240
His Pro Leu Val Arg Ala Gln Pro Glu Leu Leu Arg Lys Val Gln Met
                245              250              255
Val Lys Asp Ala His Glu Gly Arg Ile Thr Thr Leu Arg Lys Lys Lys
            260              265              270
Lys Gly Lys Asp Gly Ala Gly Ala Lys Glu Ala Asp Lys Gly Thr Ser
        275              280              285
Lys Ala Lys Ala Glu Glu Asp Glu Glu Ala Glu Arg Ile Leu Pro Gly
    290              295              300
Ile Leu Asn Asp Thr Leu Arg Phe Gly Met Phe Leu Gln Asp Leu Ile
305              310              315              320
Phe Met Ile Ser Glu Glu Gly Ala Val Ala Tyr Asp Pro Ala Ala Asn
                325              330              335
Glu Cys Tyr Cys Ala Ser Leu Ser Ser Gln Val Pro Lys Asn His Val
            340              345              350
Ser Leu Val Thr Lys Glu Asn Gln Val Phe Val Ala Gly Gly Leu Phe
        355              360              365
Tyr Asn Glu Asp Asn Lys Glu Asp Pro Met Ser Ala Tyr Phe Leu Gln
    370              375              380
Phe Asp His Leu Asp Ser Glu Trp Leu Gly Met Pro Pro Leu Pro Ser
385              390              395              400
Pro Arg Cys Leu Phe Gly Leu Gly Glu Ala Leu Asn Ser Ile Tyr Val
                405              410              415
Val Gly Gly Arg Glu Ile Lys Asp Gly Glu Arg Cys Leu Asp Ser Val
            420              425              430
Met Cys Tyr Asp Arg Leu Ser Phe Lys Trp Gly Glu Ser Asp Pro Leu
        435              440              445
Pro Tyr Val Val Tyr Gly His Thr Val Leu Ser His Met Asp Leu Val
    450              455              460
Tyr Val Ile Gly Gly Lys Gly Ser Asp Arg Lys Cys Leu Asn Lys Met
465              470              475              480
Cys Val Tyr Asp Pro Lys Lys Phe Glu Trp Lys Glu Leu Ala Pro Met
                485              490              495
Gln Thr Ala Arg Ser Leu Phe Gly Ala Thr Val His Asp Gly Arg Ile
            500              505              510
Ile Val Ala Ala Gly Val Thr Asp Thr Gly Leu Thr Ser Ser Ala Glu
        515              520              525
Val Tyr Ser Ile Thr Asp Asn Lys Trp Ala Pro Phe Glu Ala Phe Pro
    530              535              540
Gln Glu Arg Ser Ser Leu Ser Leu Val Ser Leu Val Gly Thr Leu Tyr
545              550              555              560
Ala Ile Gly Gly Phe Ala Thr Leu Glu Thr Glu Ser Gly Glu Leu Val
                565              570              575
Pro Thr Glu Leu Asn Asp Ile Trp Arg Tyr Asn Glu Glu Lys Lys
            580              585              590
Trp Glu Gly Val Leu Arg Glu Ile Ala Tyr Ala Ala Gly Ala Thr Phe
        595              600              605
```

```
Leu Pro Val Arg Leu Asn Val Leu Arg Leu Thr Lys Met
    610             615             620

<210> SEQ ID NO 17
<211> LENGTH: 5325
<212> TYPE: DNA
<213> ORGANISM: Homo sapiens
<220> FEATURE:
<221> NAME/KEY: CDS
<222> LOCATION: (264)..(3473)
<223> OTHER INFORMATION:

<400> SEQUENCE: 17
gggaaaggcc agggattaag aggccgccgg gacgccgcaa ggaggcgggg aatcggctcg      60
gcccgcgccc tgccgctgcc cggccggctg caggtggagt tcgcggaggt ggccatttcc    120
acagccgccg ccgacgcctc ctctccggga gccgccttcc ccccggcccg agggcggtgg    180
cgtggggcgc cgggtgcagg cgttctgggg cgccggggcc gcagctcgct ggccatcccg    240
cggctgcgcc ccgcgcctcg ccc atg gct gag ggc cgg cgg cgg gag gac gag    293
                          Met Ala Glu Gly Arg Arg Arg Glu Asp Glu
                            1               5                  10 gag gaa gag cta cgc gag cgc cgc gaa ctt ggt ggc cag cgc cgc gcc      341
Glu Glu Glu Leu Arg Glu Arg Arg Glu Leu Gly Gly Gln Arg Arg Ala
            15                  20                  25 cgg ggc cgt gcg ctc tcg ggc cac tcg gca gca gat cgc aac gaa cga      389
Arg Gly Arg Ala Leu Ser Gly His Ser Ala Ala Asp Arg Asn Glu Arg
         30                  35                  40 aat aaa cca gaa cat cgt tct tca agc caa gga ccc ttg tca tcc att      437
Asn Lys Pro Glu His Arg Ser Ser Ser Gln Gly Pro Leu Ser Ser Ile
     45                  50                  55 aga gcg gta atc aag aga tct tct cgg act tct att cag agt gaa ctt      485
Arg Ala Val Ile Lys Arg Ser Ser Arg Thr Ser Ile Gln Ser Glu Leu
 60                  65                  70 cat cga gat aga agg cgc cca gag atc acc att gtg gca gct gag cca      533
His Arg Asp Arg Arg Arg Pro Glu Ile Thr Ile Val Ala Ala Glu Pro
 75                  80                  85                  90 ctg agg cca gcc tcg tgg ttt cca gga acc cca ccc cca gga ctg gga      581
Leu Arg Pro Ala Ser Trp Phe Pro Gly Thr Pro Pro Pro Gly Leu Gly
                 95                 100                 105 ttt cct aca tca tct gca gca ggc tct tgg agg cct aat gag ctg gtt      629
Phe Pro Thr Ser Ser Ala Ala Gly Ser Trp Arg Pro Asn Glu Leu Val
            110                 115                 120 cct gct gag ctc cca cca tct tat gaa caa gtt ata aaa gaa atc aac      677
Pro Ala Glu Leu Pro Pro Ser Tyr Glu Gln Val Ile Lys Glu Ile Asn
        125                 130                 135 caa gtt caa gtt aat act aca aat aat aat aat gct gct gct act cca      725
Gln Val Gln Val Asn Thr Thr Asn Asn Asn Asn Ala Ala Ala Thr Pro
    140                 145                 150 agg cac act att act tct gca act cag act gac ttt tca gaa gaa ata      773
Arg His Thr Ile Thr Ser Ala Thr Gln Thr Asp Phe Ser Glu Glu Ile
155                 160                 165                 170 gac aac gat ctg cct caa aca cta cag gca cct ctc aag cct ctt cag      821
Asp Asn Asp Leu Pro Gln Thr Leu Gln Ala Pro Leu Lys Pro Leu Gln
                175                 180                 185 cct ttc tca gca gtc tcg tct ggc aat ctt cca aca aat gtg gca cct      869
Pro Phe Ser Ala Val Ser Ser Gly Asn Leu Pro Thr Asn Val Ala Pro
            190                 195                 200 tta atc gtc ttt gat att tct gaa gaa ccg aat tgt cca gaa aac ccc      917
Leu Ile Val Phe Asp Ile Ser Glu Glu Pro Asn Cys Pro Glu Asn Pro
        205                 210                 215
```

```
agt gct aca aga tgt cca gtg cca aaa cca aga tca aaa agc aac ctc      965
Ser Ala Thr Arg Cys Pro Val Pro Lys Pro Arg Ser Lys Ser Asn Leu
220             225                 230 aga cca ata ccc aga gat tct cac att aaa gag caa agt caa cag aaa     1013
Arg Pro Ile Pro Arg Asp Ser His Ile Lys Glu Gln Ser Gln Gln Lys
235             240                 245                 250 atc agc cca gca gcc gta gga gag gag tca tcc cca ggc cgg ccc cag     1061
Ile Ser Pro Ala Ala Val Gly Glu Glu Ser Ser Pro Gly Arg Pro Gln
                255                 260                 265 tct ctg ctg gac aac gct agc acc tca gac agt cag gca gtg atg aac     1109
Ser Leu Leu Asp Asn Ala Ser Thr Ser Asp Ser Gln Ala Val Met Asn
            270                 275                 280 att atg aac aca gaa caa agc caa aat agt att gtt tcc aga att aaa     1157
Ile Met Asn Thr Glu Gln Ser Gln Asn Ser Ile Val Ser Arg Ile Lys
        285                 290                 295 gtg ttt gag ggt cag aca aac ata gaa acc tca gga ctg ccc aag aaa     1205
Val Phe Glu Gly Gln Thr Asn Ile Glu Thr Ser Gly Leu Pro Lys Lys
    300                 305                 310 cca gaa att act cca cgt tca ctt cct cca aag cct act gtt tcc tca     1253
Pro Glu Ile Thr Pro Arg Ser Leu Pro Pro Lys Pro Thr Val Ser Ser
315                 320                 325                 330 ggg aaa cct tct gta gct ccc aaa cca gct gct aac aga gct tct gga     1301
Gly Lys Pro Ser Val Ala Pro Lys Pro Ala Ala Asn Arg Ala Ser Gly
                335                 340                 345 gag tgg gac tct ggg act gag aac aga ctc aag gtg acc tcc aag gaa     1349
Glu Trp Asp Ser Gly Thr Glu Asn Arg Leu Lys Val Thr Ser Lys Glu
            350                 355                 360 gga ctc acc cca tac cct ccc ctg caa gaa gcg gga agc atc cca gta     1397
Gly Leu Thr Pro Tyr Pro Pro Leu Gln Glu Ala Gly Ser Ile Pro Val
        365                 370                 375 acc aaa cct gaa ttg cca aag aaa cca aac cct ggc ctt ata cga agt     1445
Thr Lys Pro Glu Leu Pro Lys Lys Pro Asn Pro Gly Leu Ile Arg Ser
    380                 385                 390 gtt aat cct gag att ccg gga aga ggg ccc ctg gct gag agc tct gat     1493
Val Asn Pro Glu Ile Pro Gly Arg Gly Pro Leu Ala Glu Ser Ser Asp
395                 400                 405                 410 agt ggg aag aaa gtg cca act cct gcc ccg cgg cct ttg ctg ctg aag     1541
Ser Gly Lys Lys Val Pro Thr Pro Ala Pro Arg Pro Leu Leu Leu Lys
                415                 420                 425 aaa tct gtt tcc tca gaa aac ccc acc tac cct tca gct cca ctg aaa     1589
Lys Ser Val Ser Ser Glu Asn Pro Thr Tyr Pro Ser Ala Pro Leu Lys
            430                 435                 440 cct gtc act gtt cct ccc cga ctc gca ggg gca tca caa gcc aaa gca     1637
Pro Val Thr Val Pro Pro Arg Leu Ala Gly Ala Ser Gln Ala Lys Ala
        445                 450                 455 tac aag tca ctg gga gaa ggg ccc cca gcc aac ccc cca gtt cca gtt     1685
Tyr Lys Ser Leu Gly Glu Gly Pro Pro Ala Asn Pro Pro Val Pro Val
    460                 465                 470 ctg cag agc aag ccc ttg gtg gac atc gat ctc atc agc ttt gat gat     1733
Leu Gln Ser Lys Pro Leu Val Asp Ile Asp Leu Ile Ser Phe Asp Asp
475                 480                 485                 490 gat gtt ttg ccc acc cca tcg ggg aac ctg gct gaa gaa tct gtt ggt     1781
Asp Val Leu Pro Thr Pro Ser Gly Asn Leu Ala Glu Glu Ser Val Gly
                495                 500                 505 tca gag atg gtt cta gat ccc ttt cag ctc cct gca aaa aca gaa cca     1829
Ser Glu Met Val Leu Asp Pro Phe Gln Leu Pro Ala Lys Thr Glu Pro
            510                 515                 520 ata aaa gaa cga gca gtt caa cca gca ccc acc agg aag ccc act gta     1877
Ile Lys Glu Arg Ala Val Gln Pro Ala Pro Thr Arg Lys Pro Thr Val
```

-continued

|  |  |  |  |  |  |  |  |  |  |  |  |  |  |  |  |
|--|--|--|--|--|--|--|--|--|--|--|--|--|--|--|--|
| | 525 | | | | | 530 | | | | | 535 | | | | |

```
att cga att cca gcc aaa cca gga aaa tgt tta cat gag gat cca caa      1925
Ile Arg Ile Pro Ala Lys Pro Gly Lys Cys Leu His Glu Asp Pro Gln
        540                 545                 550 agt cca cct cct ctc cct gct gaa aaa cct att gga aac act ttc agt      1973
Ser Pro Pro Pro Leu Pro Ala Glu Lys Pro Ile Gly Asn Thr Phe Ser
555                 560                 565                 570 aca gta tct gga aag ctc agt aat gtt gag aga act aga aac ttg gaa      2021
Thr Val Ser Gly Lys Leu Ser Asn Val Glu Arg Thr Arg Asn Leu Glu
                575                 580                 585 tcc aac cac cca ggt caa aca gga ggt ttt gtg cga gta ccc cca agg      2069
Ser Asn His Pro Gly Gln Thr Gly Gly Phe Val Arg Val Pro Pro Arg
                590                 595                 600 ttg cca ccg aga cct gtg aat gga aaa acc att cca act caa cag cct      2117
Leu Pro Pro Arg Pro Val Asn Gly Lys Thr Ile Pro Thr Gln Gln Pro
            605                 610                 615 cca acc aag gtg ccc cct gag aga cca cct ccc cca aag ctt tct gca      2165
Pro Thr Lys Val Pro Pro Glu Arg Pro Pro Pro Lys Leu Ser Ala
        620                 625                 630 acc aga aga tct aat aag aaa ctg cct ttt aat cga tcc tct tct gac      2213
Thr Arg Arg Ser Asn Lys Lys Leu Pro Phe Asn Arg Ser Ser Ser Asp
635                 640                 645                 650 atg gat ctt cag aaa aaa caa agt aac ttg gca act gga ctc tca aaa      2261
Met Asp Leu Gln Lys Lys Gln Ser Asn Leu Ala Thr Gly Leu Ser Lys
                655                 660                 665 gcc aag agt caa gtt ttt aaa aat caa gat ccg gtg cta ccc cct cgt      2309
Ala Lys Ser Gln Val Phe Lys Asn Gln Asp Pro Val Leu Pro Pro Arg
                670                 675                 680 ccc aaa cca gga cac cct ctc tac agt aaa tac atg ctg tct gtg cct      2357
Pro Lys Pro Gly His Pro Leu Tyr Ser Lys Tyr Met Leu Ser Val Pro
            685                 690                 695 cat gga att gcc aat gaa gat att gtc tct caa aac ccc gga gaa ctc      2405
His Gly Ile Ala Asn Glu Asp Ile Val Ser Gln Asn Pro Gly Glu Leu
        700                 705                 710 tct tgt aag cgt ggg gat gta ctt gtg atg ctg aag cag acg gaa aat      2453
Ser Cys Lys Arg Gly Asp Val Leu Val Met Leu Lys Gln Thr Glu Asn
715                 720                 725                 730 aat tac ttg gag tgc caa aag gga gaa gac act ggc aga gtt cac ctg      2501
Asn Tyr Leu Glu Cys Gln Lys Gly Glu Asp Thr Gly Arg Val His Leu
                735                 740                 745 tct caa atg aag att atc act cca ctt gat gaa cat ctt aga agc aga      2549
Ser Gln Met Lys Ile Ile Thr Pro Leu Asp Glu His Leu Arg Ser Arg
                750                 755                 760 cca aac gat cca agc cac gct cag aag cct gtt gac agt ggt gct cct      2597
Pro Asn Asp Pro Ser His Ala Gln Lys Pro Val Asp Ser Gly Ala Pro
            765                 770                 775 cat gct gtc gtt ctt cat gat ttc cca gca gag caa gtt gat gat ttg      2645
His Ala Val Val Leu His Asp Phe Pro Ala Glu Gln Val Asp Asp Leu
        780                 785                 790 aac ctc act tct gga gaa att gtt tat ctt ctg gag aag ata gat aca      2693
Asn Leu Thr Ser Gly Glu Ile Val Tyr Leu Leu Glu Lys Ile Asp Thr
795                 800                 805                 810 gat tgg tac aga ggg aac tgt aga aac cag att ggc ata ttt cct gcc      2741
Asp Trp Tyr Arg Gly Asn Cys Arg Asn Gln Ile Gly Ile Phe Pro Ala
                815                 820                 825 aac tat gtc aaa gtg att att gat atc cca gaa gga gga aat ggg aaa      2789
Asn Tyr Val Lys Val Ile Ile Asp Ile Pro Glu Gly Gly Asn Gly Lys
            830                 835                 840 aga gaa tgt gtt tca tct cat tgt gtt aaa ggc tca aga tgt gtt gct      2837
```

-continued

| | |
|---|---|
| Arg Glu Cys Val Ser Ser His Cys Val Lys Gly Ser Arg Cys Val Ala<br>     845               850              855 | |
| cgg ttt gaa tat att gga gag cag aag gat gag ttg agt ttc tca gag<br>Arg Phe Glu Tyr Ile Gly Glu Gln Lys Asp Glu Leu Ser Phe Ser Glu<br>860               865               870 | 2885 |
| gga gaa att att att ctt aaa gag tat gtg aat gag gaa tgg gcc aga<br>Gly Glu Ile Ile Ile Leu Lys Glu Tyr Val Asn Glu Glu Trp Ala Arg<br>875               880              885              890 | 2933 |
| gga gaa gtt cga ggc aga act ggg att ttc ccc ctg aac ttt gtg gag<br>Gly Glu Val Arg Gly Arg Thr Gly Ile Phe Pro Leu Asn Phe Val Glu<br>               895              900              905 | 2981 |
| cct gtt gag gat tat ccc acc tct ggt gca aat gtt tta agc aca aag<br>Pro Val Glu Asp Tyr Pro Thr Ser Gly Ala Asn Val Leu Ser Thr Lys<br>         910               915              920 | 3029 |
| gta cca ctg aaa acc aaa aaa gaa gat tct ggc tca aac tct cag gtt<br>Val Pro Leu Lys Thr Lys Lys Glu Asp Ser Gly Ser Asn Ser Gln Val<br>925               930              935 | 3077 |
| aac agt ctt ccg gca gaa tgg tgt gaa gct ctt cac agt ttt aca gca<br>Asn Ser Leu Pro Ala Glu Trp Cys Glu Ala Leu His Ser Phe Thr Ala<br>940               945              950 | 3125 |
| gag acc agt gat gac tta tca ttc aag agg gga gac cgg atc cag att<br>Glu Thr Ser Asp Asp Leu Ser Phe Lys Arg Gly Asp Arg Ile Gln Ile<br>955               960              965              970 | 3173 |
| ctg gaa cgt ctg gat tct gac tgg tgc agg ggc aga ctg cag gac agg<br>Leu Glu Arg Leu Asp Ser Asp Trp Cys Arg Gly Arg Leu Gln Asp Arg<br>               975              980              985 | 3221 |
| gag ggg atc ttc cca gca gtg ttt gtg agg ccc tgc cca gct gag gca<br>Glu Gly Ile Phe Pro Ala Val Phe Val Arg Pro Cys Pro Ala Glu Ala<br>         990               995             1000 | 3269 |
| aaa agt atg ttg gcc ata gta ccg aag ggg agg aag gcc aaa gcc<br>Lys Ser Met Leu Ala Ile Val Pro Lys Gly Arg Lys Ala Lys Ala<br>1005              1010               1015 | 3314 |
| tta tat gat ttc cga ggg gag aat gaa gat gaa ctt tcc ttc aag<br>Leu Tyr Asp Phe Arg Gly Glu Asn Glu Asp Glu Leu Ser Phe Lys<br>1020              1025               1030 | 3359 |
| gct gga gat ata ata aca gag ctg gaa tct gta gat gat gac tgg<br>Ala Gly Asp Ile Ile Thr Glu Leu Glu Ser Val Asp Asp Asp Trp<br>1035              1040               1045 | 3404 |
| atg agt gga gaa ctt atg gga aaa tct gga ata ttt ccc aaa aac<br>Met Ser Gly Glu Leu Met Gly Lys Ser Gly Ile Phe Pro Lys Asn<br>1050              1055               1060 | 3449 |
| tac ata cag ttt cta cag atc agc tagaggagaa gcttgtctgt<br>Tyr Ile Gln Phe Leu Gln Ile Ser<br>1065              1070 | 3493 |
| gttccttggc acaagaactc acttgaacta tcaccttgac tatcagatat gtttttgcac | 3553 |
| tatttttttt aactgaaaaa gaaatatcta agctgtacat ggtacactag aattttctga | 3613 |
| aagcagaaaa cgttcagatt ttgtagttaa ttttcattac aatagaaaca cgcacatgga | 3673 |
| aacccatgag ctaggattct accgaggaaa acatctagtg ggattagcaa ggtgaaggga | 3733 |
| aagcatctgg tggcatggca gcatggggag gctcacacac agaagttgca cgtggacatc | 3793 |
| tgttttaatc agcacaagtg aattaaccat gcttcttcat ttttttttact ttagttaaaa | 3853 |
| aagaggacat ttaatattct acatgctgta actatcagga catggttagc aatctcaatt | 3913 |
| tcatttttga tattcaaatt aattcttaca gcttgagcat atcagcctta ttaccagagc | 3973 |
| aaatccttcc ttcagatggg atagtttact gactagttgg agcatttgta agcacatggt | 4033 |
| gaaatcagcc cctgcccacc aaaataatct ttatgttacc aagtgattcc catttgtcta | 4093 |

-continued

```
aggatttgaa gggggtctaa attggatgta tcttagtcta aagaaccaaa accatccctg    4153
aaatgccttg ctaatacaac taatccttcc atatatgtgc catacttatt tttttcctca    4213
gtgtatactt tatgttaaca gggttattac aaagcacatt ttctgaatct gcaatcattc    4273
ctttgacaat tactggaccc aaaggaaaat tcattttctt tgcattattc cagtaatata    4333
taaaaactgt gtcttgttat agtagtacat tatgaatcac atataaaatc ttacaataca    4393
gaacaactgt taagatggaa aacagtgcca aacctccaca gctcatttct ttgtaatata    4453
atcagaatga aaaataattt aagaggacag aagactggta cttttttgtt ttattttttc    4513
tctagcttat ccctgcacaa ttattagagt gaatgaaaaa ccactttcct gctttccatt    4573
gttataaatt ctaagcttaa gataaaagtg gttctttaca tgactgaatc aattacaatt    4633
tatgggctag agccaaatag gttgaagaca atcatccaaa cagatcaatg gaatagaatt    4693
tcattggaaa tgtaaaacac tttcccaaca atggtcatga ctttcttctg tttttgagaa    4753
gagtttcata tgctggacca cattttagct tttattgttt ttttttttccc attgtccaaa    4813 aagttaagca acaagtggcc acacttttac gtgactacaa cctggagttc tgcaaagaag    4873
gtaatattta cttggtcttt gactaaagtt atctccccat tctatggtta cattttattt    4933
tggactatgg ggacttctaa tacgttttgg taaagaagag agtataaaga aaattcttgt    4993
caaatttcac tcaaaagtaa tttcatgaga aatcaatgat ttaaagcatt atccaaatta    5053
aattatcatt tgcagcaaac tgtacaacag caggaaggat atggaatgga acatgagta    5113 tatatctttg cctttataat tttaacatct tatattgaag attctgaaaa cctatctta    5173 ttagaggaaa atctcaatct tcagttttgg ccttctgtca ccagaatgat aagtgcaata    5233
gttgtaaatc tacttgacac tgtaataaac tgaactgaac tttcaaaaaa aaaaaaaaaa    5293
aaaaaaaaaa aaaaaaaaaa aaaaaaaaaa aa                                 5325
```

```
<210> SEQ ID NO 18
<211> LENGTH: 1070
<212> TYPE: PRT
<213> ORGANISM: Homo sapiens

<400> SEQUENCE: 18

Met Ala Glu Gly Arg Arg Arg Glu Asp Glu Glu Glu Leu Arg Glu
1               5                   10                  15

Arg Arg Glu Leu Gly Gly Gln Arg Arg Ala Arg Gly Arg Ala Leu Ser
            20                  25                  30

Gly His Ser Ala Ala Asp Arg Asn Glu Arg Asn Lys Pro Glu His Arg
        35                  40                  45

Ser Ser Ser Gln Gly Pro Leu Ser Ser Ile Arg Ala Val Ile Lys Arg
    50                  55                  60

Ser Ser Arg Thr Ser Ile Gln Ser Glu Leu His Arg Asp Arg Arg
65                  70                  75                  80

Pro Glu Ile Thr Ile Val Ala Ala Glu Pro Leu Arg Pro Ala Ser Trp
                85                  90                  95

Phe Pro Gly Thr Pro Pro Gly Leu Gly Phe Pro Thr Ser Ser Ala
            100                 105                 110

Ala Gly Ser Trp Arg Pro Asn Glu Leu Val Pro Ala Glu Leu Pro Pro
        115                 120                 125

Ser Tyr Glu Gln Val Ile Lys Glu Ile Asn Gln Val Gln Val Asn Thr
    130                 135                 140

Thr Asn Asn Asn Asn Ala Ala Ala Thr Pro Arg His Thr Ile Thr Ser
145                 150                 155                 160
```

-continued

```
Ala Thr Gln Thr Asp Phe Ser Glu Glu Ile Asp Asn Asp Leu Pro Gln
                165                 170                 175
Thr Leu Gln Ala Pro Leu Lys Pro Leu Gln Pro Phe Ser Ala Val Ser
            180                 185                 190
Ser Gly Asn Leu Pro Thr Asn Val Ala Pro Leu Ile Val Phe Asp Ile
        195                 200                 205
Ser Glu Glu Pro Asn Cys Pro Glu Asn Pro Ser Ala Thr Arg Cys Pro
    210                 215                 220
Val Pro Lys Pro Arg Ser Lys Ser Asn Leu Arg Pro Ile Pro Arg Asp
225                 230                 235                 240
Ser His Ile Lys Glu Gln Ser Gln Gln Lys Ile Ser Pro Ala Ala Val
            245                 250                 255
Gly Glu Glu Ser Ser Pro Gly Arg Pro Gln Ser Leu Leu Asp Asn Ala
            260                 265                 270
Ser Thr Ser Asp Ser Gln Ala Val Met Asn Ile Met Asn Thr Glu Gln
        275                 280                 285
Ser Gln Asn Ser Ile Val Ser Arg Ile Lys Val Phe Glu Gly Gln Thr
        290                 295                 300
Asn Ile Glu Thr Ser Gly Leu Pro Lys Lys Pro Glu Ile Thr Pro Arg
305                 310                 315                 320
Ser Leu Pro Pro Lys Pro Thr Val Ser Ser Gly Lys Pro Ser Val Ala
                325                 330                 335
Pro Lys Pro Ala Ala Asn Arg Ala Ser Gly Glu Trp Asp Ser Gly Thr
            340                 345                 350
Glu Asn Arg Leu Lys Val Thr Ser Lys Glu Gly Leu Thr Pro Tyr Pro
            355                 360                 365
Pro Leu Gln Glu Ala Gly Ser Ile Pro Val Thr Lys Pro Glu Leu Pro
    370                 375                 380
Lys Lys Pro Asn Pro Gly Leu Ile Arg Ser Val Asn Pro Glu Ile Pro
385                 390                 395                 400
Gly Arg Gly Pro Leu Ala Glu Ser Ser Asp Ser Gly Lys Lys Val Pro
                405                 410                 415
Thr Pro Ala Pro Arg Pro Leu Leu Lys Lys Ser Val Ser Ser Glu
            420                 425                 430
Asn Pro Thr Tyr Pro Ser Ala Pro Leu Lys Pro Val Thr Val Pro Pro
        435                 440                 445
Arg Leu Ala Gly Ala Ser Gln Ala Lys Ala Tyr Lys Ser Leu Gly Glu
    450                 455                 460
Gly Pro Pro Ala Asn Pro Pro Val Pro Val Leu Gln Ser Lys Pro Leu
465                 470                 475                 480
Val Asp Ile Asp Leu Ile Ser Phe Asp Asp Val Leu Pro Thr Pro
            485                 490                 495
Ser Gly Asn Leu Ala Glu Glu Ser Val Gly Ser Glu Met Val Leu Asp
        500                 505                 510
Pro Phe Gln Leu Pro Ala Lys Thr Glu Pro Ile Lys Glu Arg Ala Val
    515                 520                 525
Gln Pro Ala Pro Thr Arg Lys Pro Thr Val Ile Arg Ile Pro Ala Lys
    530                 535                 540
Pro Gly Lys Cys Leu His Glu Asp Pro Gln Ser Pro Pro Leu Pro
545                 550                 555                 560
Ala Glu Lys Pro Ile Gly Asn Thr Phe Ser Thr Val Ser Gly Lys Leu
                565                 570                 575
```

-continued

```
Ser Asn Val Glu Arg Thr Arg Asn Leu Glu Ser Asn His Pro Gly Gln
            580                 585                 590

Thr Gly Gly Phe Val Arg Val Pro Pro Arg Leu Pro Arg Pro Val
        595                 600                 605

Asn Gly Lys Thr Ile Pro Thr Gln Gln Pro Pro Thr Lys Val Pro Pro
            610                 615                 620

Glu Arg Pro Pro Pro Lys Leu Ser Ala Thr Arg Arg Ser Asn Lys
625                 630                 635                 640

Lys Leu Pro Phe Asn Arg Ser Ser Asp Met Asp Leu Gln Lys Lys
                645                 650                 655

Gln Ser Asn Leu Ala Thr Gly Leu Ser Lys Ala Lys Ser Gln Val Phe
            660                 665                 670

Lys Asn Gln Asp Pro Val Leu Pro Pro Arg Pro Lys Pro Gly His Pro
            675                 680                 685

Leu Tyr Ser Lys Tyr Met Leu Ser Val Pro His Gly Ile Ala Asn Glu
            690                 695                 700

Asp Ile Val Ser Gln Asn Pro Gly Glu Leu Ser Cys Lys Arg Gly Asp
705                 710                 715                 720

Val Leu Val Met Leu Lys Gln Thr Glu Asn Asn Tyr Leu Glu Cys Gln
                725                 730                 735

Lys Gly Glu Asp Thr Gly Arg Val His Leu Ser Gln Met Lys Ile Ile
            740                 745                 750

Thr Pro Leu Asp Glu His Leu Arg Ser Arg Pro Asn Asp Pro Ser His
            755                 760                 765

Ala Gln Lys Pro Val Asp Ser Gly Ala Pro His Ala Val Leu His
            770                 775                 780

Asp Phe Pro Ala Glu Gln Val Asp Asp Leu Asn Leu Thr Ser Gly Glu
785                 790                 795                 800

Ile Val Tyr Leu Leu Glu Lys Ile Asp Thr Asp Trp Tyr Arg Gly Asn
                805                 810                 815

Cys Arg Asn Gln Ile Gly Ile Phe Pro Ala Asn Tyr Val Lys Val Ile
            820                 825                 830

Ile Asp Ile Pro Glu Gly Gly Asn Gly Lys Arg Glu Cys Val Ser Ser
            835                 840                 845

His Cys Val Lys Gly Ser Arg Cys Val Ala Arg Phe Glu Tyr Ile Gly
            850                 855                 860

Glu Gln Lys Asp Glu Leu Ser Phe Ser Glu Gly Glu Ile Ile Ile Leu
865                 870                 875                 880

Lys Glu Tyr Val Asn Glu Glu Trp Ala Arg Gly Glu Val Arg Gly Arg
                885                 890                 895

Thr Gly Ile Phe Pro Leu Asn Phe Val Glu Pro Val Glu Asp Tyr Pro
            900                 905                 910

Thr Ser Gly Ala Asn Val Leu Ser Thr Lys Val Pro Leu Lys Thr Lys
            915                 920                 925

Lys Glu Asp Ser Gly Ser Asn Ser Gln Val Asn Ser Leu Pro Ala Glu
            930                 935                 940

Trp Cys Glu Ala Leu His Ser Phe Thr Ala Glu Thr Ser Asp Asp Leu
945                 950                 955                 960

Ser Phe Lys Arg Gly Asp Arg Ile Gln Ile Leu Glu Arg Leu Asp Ser
                965                 970                 975

Asp Trp Cys Arg Gly Arg Leu Gln Asp Arg Glu Gly Ile Phe Pro Ala
            980                 985                 990

Val Phe Val Arg Pro Cys Pro Ala  Glu Ala Lys Ser Met  Leu Ala Ile
```

```
                    995                  1000                 1005
Val Pro Lys Gly Arg Lys Ala Lys Ala Leu Tyr Asp Phe Arg Gly
    1010                1015                1020

Glu Asn Glu Asp Glu Leu Ser Phe Lys Ala Gly Asp Ile Ile Thr
    1025                1030                1035

Glu Leu Glu Ser Val Asp Asp Asp Trp Met Ser Gly Glu Leu Met
    1040                1045                1050

Gly Lys Ser Gly Ile Phe Pro Lys Asn Tyr Ile Gln Phe Leu Gln
    1055                1060                1065
Ile Ser
    1070

<210> SEQ ID NO 19
<211> LENGTH: 5581
<212> TYPE: DNA
<213> ORGANISM: Homo sapiens
<220> FEATURE:
<221> NAME/KEY: CDS
<222> LOCATION: (264)..(3332)
<223> OTHER INFORMATION:

<400> SEQUENCE: 19
gggaaaggcc agggattaag aggccgccgg gacgccgcaa ggaggcgggg aatcggctcg      60
gcccgcgccc tgccgctgcc cggccggctg caggtggagt tcgcggaggt ggccatttcc    120
acagccgccg ccgacgcctc ctctccggga gccgccttcc cccggcccg agggcggtgg     180 cgtggggcgc cgggtgcagg cgttctgggg cgccggggcc gcagctcgct ggccatcccg    240
cggctgcgcc ccgcgcctcg ccc atg gct gag ggc cgg cgg cgg gag gac gag    293
                          Met Ala Glu Gly Arg Arg Arg Glu Asp Glu
                            1               5                  10 gag gaa gag cta cgc gag cgc cgc gaa ctt ggt ggc cag cgc cgc gcc     341
Glu Glu Glu Leu Arg Glu Arg Arg Glu Leu Gly Gly Gln Arg Arg Ala
            15                  20                  25 cgg ggc cgt gcg ctc tcg ggc cac tcg gcc gca gat cgc aac gaa cga    389
Arg Gly Arg Ala Leu Ser Gly His Ser Ala Ala Asp Arg Asn Glu Arg
        30                  35                  40 aat aaa cca gaa cat cgt tct tca agc caa gga ccc ttg tca tcc att    437
Asn Lys Pro Glu His Arg Ser Ser Ser Gln Gly Pro Leu Ser Ser Ile
    45                  50                  55 aga gcg gta atc aag aga tct tct cgg act tct att cag agt gaa ctt    485
Arg Ala Val Ile Lys Arg Ser Ser Arg Thr Ser Ile Gln Ser Glu Leu
60                  65                  70 cat cga gat aga agg cgc cca gag atc acc att gtg gca gct gag cca    533
His Arg Asp Arg Arg Arg Pro Glu Ile Thr Ile Val Ala Ala Glu Pro
75                  80                  85                  90 ctg agg cca gcc tcg tgg ttt cca gga acc cca ccc cca gga ctg gga    581
Leu Arg Pro Ala Ser Trp Phe Pro Gly Thr Pro Pro Pro Gly Leu Gly
                95                  100                 105 ttt cct aca tca tct gca gca ggc tct tgg agg cct aat gag ctg gtt    629
Phe Pro Thr Ser Ser Ala Ala Gly Ser Trp Arg Pro Asn Glu Leu Val
            110                 115                 120 cct gct gag ctc cca cca tct tat gaa caa gtt ata aaa gaa atc aac    677
Pro Ala Glu Leu Pro Pro Ser Tyr Glu Gln Val Ile Lys Glu Ile Asn
        125                 130                 135 caa gtt caa gtt aat act aca aat aat aat aat gct gct gct act cca    725
Gln Val Gln Val Asn Thr Thr Asn Asn Asn Asn Ala Ala Ala Thr Pro
    140                 145                 150 agg cac act att act tct gca act cag act gac ttt tca gaa gaa ata    773
Arg His Thr Ile Thr Ser Ala Thr Gln Thr Asp Phe Ser Glu Glu Ile
155                 160                 165                 170
```

```
gac aac gat ctg cct caa aca cta cag gca cct ctc aag cct ctt cag      821
Asp Asn Asp Leu Pro Gln Thr Leu Gln Ala Pro Leu Lys Pro Leu Gln
                175                 180                 185 cct ttc tca gca gtc tcg tct ggc aat ctt cca aca aat gtg gca cct      869
Pro Phe Ser Ala Val Ser Ser Gly Asn Leu Pro Thr Asn Val Ala Pro
                190                 195                 200 tta atc gtc ttt gat att tct gaa gaa ccg aat tgt cca gaa aac ccc      917
Leu Ile Val Phe Asp Ile Ser Glu Glu Pro Asn Cys Pro Glu Asn Pro
                205                 210                 215 agt gct aca aga tgt cca gtg cca aaa cca aga tca aaa agc aac ctc      965
Ser Ala Thr Arg Cys Pro Val Pro Lys Pro Arg Ser Lys Ser Asn Leu
        220                 225                 230 aga cca ata ccc aga gat tct cac att aaa gag caa agt caa cag aaa      1013
Arg Pro Ile Pro Arg Asp Ser His Ile Lys Glu Gln Ser Gln Gln Lys
235                 240                 245                 250 atc agc cca gca gcc gta gga gag gag tca tcc cca ggc cgg ccc cag      1061
Ile Ser Pro Ala Ala Val Gly Glu Glu Ser Ser Pro Gly Arg Pro Gln
                255                 260                 265 tct ctg ctg gac aac gct agc acc tca gac agt cag gca gtg atg aac      1109
Ser Leu Leu Asp Asn Ala Ser Thr Ser Asp Ser Gln Ala Val Met Asn
                270                 275                 280 att atg aac aca gaa caa agc caa aat agt att gtt tcc aga att aaa      1157
Ile Met Asn Thr Glu Gln Ser Gln Asn Ser Ile Val Ser Arg Ile Lys
            285                 290                 295 gtg ttt gag ggt cag aca aac ata gaa acc tca gga ctg ccc aag aaa      1205
Val Phe Glu Gly Gln Thr Asn Ile Glu Thr Ser Gly Leu Pro Lys Lys
    300                 305                 310 cca gaa att act cca cgt tca ctt cct cca aag cct act gtt tcc tca      1253
Pro Glu Ile Thr Pro Arg Ser Leu Pro Pro Lys Pro Thr Val Ser Ser
315                 320                 325                 330 ggg aaa cct tct gta gct ccc aaa cca gct gct aac aga gct tct gga      1301
Gly Lys Pro Ser Val Ala Pro Lys Pro Ala Ala Asn Arg Ala Ser Gly
                335                 340                 345 gag tgg gac tct ggg act gag aac aga ctc aag gtg acc tcc aag gaa      1349
Glu Trp Asp Ser Gly Thr Glu Asn Arg Leu Lys Val Thr Ser Lys Glu
                350                 355                 360 gga ctc acc cca tac cct ccc ctg caa gaa gcg gga agc atc cca gta      1397
Gly Leu Thr Pro Tyr Pro Pro Leu Gln Glu Ala Gly Ser Ile Pro Val
            365                 370                 375 acc aaa cct gaa ttg cca aag aaa cca aac cct ggc ctt ata cga agt      1445
Thr Lys Pro Glu Leu Pro Lys Lys Pro Asn Pro Gly Leu Ile Arg Ser
    380                 385                 390 gtt aat cct gag att ccg gga aga ggg ccc ctg gct gag agc tct gat      1493
Val Asn Pro Glu Ile Pro Gly Arg Gly Pro Leu Ala Glu Ser Ser Asp
395                 400                 405                 410 agt ggg aag aaa gtg cca act cct gcc ccg cgg cct ttg ctg ctg aag      1541
Ser Gly Lys Lys Val Pro Thr Pro Ala Pro Arg Pro Leu Leu Leu Lys
                415                 420                 425 aaa tct gtt tcc tca gaa aac ccc acc tac cct tca gct cca ctg aaa      1589
Lys Ser Val Ser Ser Glu Asn Pro Thr Tyr Pro Ser Ala Pro Leu Lys
                430                 435                 440 cct gtc act gtt cct ccc cga ctc gca ggg gca tca caa gcc aaa gca      1637
Pro Val Thr Val Pro Pro Arg Leu Ala Gly Ala Ser Gln Ala Lys Ala
            445                 450                 455 tac aag tca ctg gga gaa ggg ccc cca gcc aac ccc cca gtt cca gtt      1685
Tyr Lys Ser Leu Gly Glu Gly Pro Pro Ala Asn Pro Pro Val Pro Val
    460                 465                 470 ctg cag agc aag ccc ttg gtg gac atc gat ctc atc agc ttt gat gat      1733
Leu Gln Ser Lys Pro Leu Val Asp Ile Asp Leu Ile Ser Phe Asp Asp
```

```
475                 480                 485                 490
gat gtt ttg ccc acc cca tcg ggg aac ctg gct gaa gaa tct gtt ggt    1781
Asp Val Leu Pro Thr Pro Ser Gly Asn Leu Ala Glu Glu Ser Val Gly
                    495                 500                 505 tca gag atg gtt cta gat ccc ttt cag ctc cct gca aaa aca gaa cca    1829
Ser Glu Met Val Leu Asp Pro Phe Gln Leu Pro Ala Lys Thr Glu Pro
        510                 515                 520 ata aaa gaa cga gca gtt caa cca gca ccc acc agg aag ccc act gta    1877
Ile Lys Glu Arg Ala Val Gln Pro Ala Pro Thr Arg Lys Pro Thr Val
                525                 530                 535 att cga att cca gcc aaa cca gga aaa tgt tta cat gag gat cca caa    1925
Ile Arg Ile Pro Ala Lys Pro Gly Lys Cys Leu His Glu Asp Pro Gln
        540                 545                 550 agt cca cct cct ctc cct gct gaa aaa cct att gga aac act ttc agt    1973
Ser Pro Pro Pro Leu Pro Ala Glu Lys Pro Ile Gly Asn Thr Phe Ser
555                 560                 565                 570 aca gta tct gga aag ctc agt aat gtt gag aga act aga aac ttg gaa    2021
Thr Val Ser Gly Lys Leu Ser Asn Val Glu Arg Thr Arg Asn Leu Glu
                575                 580                 585 tcc aac cac cca ggt caa aca gga ggt ttt gtg cga gta ccc cca agg    2069
Ser Asn His Pro Gly Gln Thr Gly Gly Phe Val Arg Val Pro Pro Arg
        590                 595                 600 ttg cca ccg aga cct gtg aat ggt cat cta att atg aca aca ata ctc    2117
Leu Pro Pro Arg Pro Val Asn Gly His Leu Ile Met Thr Thr Ile Leu
        605                 610                 615 ttc atg tcg tgc tct gcc cga gcc cgg atg ggt ttc act ggt att gta    2165
Phe Met Ser Cys Ser Ala Arg Ala Arg Met Gly Phe Thr Gly Ile Val
    620                 625                 630 cac att cta cga ttc aag ctt ctt ctc gag tcg tgg tgc tgg agc gag    2213
His Ile Leu Arg Phe Lys Leu Leu Leu Glu Ser Trp Cys Trp Ser Glu
635                 640                 645                 650 gct ggt ggc tca gtg ata gag ctg gca gag gca ttc gct cgt cta cag    2261
Ala Gly Gly Ser Val Ile Glu Leu Ala Glu Ala Phe Ala Arg Leu Gln
                655                 660                 665 ata atg tct tcg ttc tcc tcc aaa cat gga tgg tcc ttc ata gac tgg    2309
Ile Met Ser Ser Phe Ser Ser Lys His Gly Trp Ser Phe Ile Asp Trp
        670                 675                 680 tcg gtc aga ctt ccg gtc ata gga tgg cct agt caa aac ccc ctc ttc    2357
Ser Val Arg Leu Pro Val Ile Gly Trp Pro Ser Gln Asn Pro Leu Phe
        685                 690                 695 tgg atg agg aat ggt ctt ttt tgt ctc gat atg act gag ctc tat cat    2405
Trp Met Arg Asn Gly Leu Phe Cys Leu Asp Met Thr Glu Leu Tyr His
    700                 705                 710 ctc gag aca aaa aaa acc att cca act caa cag cct cca acc aag gtg    2453
Leu Glu Thr Lys Lys Thr Ile Pro Thr Gln Gln Pro Pro Thr Lys Val
715                 720                 725                 730 ccc cct gag aga cca cct ccc cca aag ctt tct gca acc aga aga tct    2501
Pro Pro Glu Arg Pro Pro Pro Lys Leu Ser Ala Thr Arg Arg Ser
                735                 740                 745 aat aag aaa ctg cct ttt aat cga tcc tct tct gac atg gat ctt cag    2549
Asn Lys Lys Leu Pro Phe Asn Arg Ser Ser Ser Asp Met Asp Leu Gln
                750                 755                 760 aaa aaa caa agt aac ttg gca act gga ctc tca aaa gcc aag agt caa    2597
Lys Lys Gln Ser Asn Leu Ala Thr Gly Leu Ser Lys Ala Lys Ser Gln
            765                 770                 775 gtt ttt aaa aat caa gat ccg gtg cta ccc cct cgt ccc aaa cca gga    2645
Val Phe Lys Asn Gln Asp Pro Val Leu Pro Pro Arg Pro Lys Pro Gly
        780                 785                 790 cac cct ctc tac agt aaa tac atg cgt ggg gat gta ctt gtg atg ctg    2693
```

```
                                                                      -continued His Pro Leu Tyr Ser Lys Tyr Met Arg Gly Asp Val Leu Val Met Leu
795                 800                 805                 810 aag cag acg gaa aat aat tac ttg gag tgc caa aag gga gaa gac act       2741
Lys Gln Thr Glu Asn Asn Tyr Leu Glu Cys Gln Lys Gly Glu Asp Thr
                        815                 820                 825 ggc aga gtt cac ctg tct caa atg aag att atc act cca ctt gat gaa      2789
Gly Arg Val His Leu Ser Gln Met Lys Ile Ile Thr Pro Leu Asp Glu
                830                 835                 840 cat ctt aga agc aga cca aac gat cca agc cac gct cag aag cct gtt      2837
His Leu Arg Ser Arg Pro Asn Asp Pro Ser His Ala Gln Lys Pro Val
            845                 850                 855 gac agt ggt gct cct cat gct gtc gtt ctt cat gat ttc cca gca gag      2885
Asp Ser Gly Ala Pro His Ala Val Val Leu His Asp Phe Pro Ala Glu
860                 865                 870 caa gtt gat gat ttg aac ctc act tct gga gaa att gtt tat ctt ctg      2933
Gln Val Asp Asp Leu Asn Leu Thr Ser Gly Glu Ile Val Tyr Leu Leu
875                 880                 885                 890 gag aag ata gat aca gat tgg tac aga ggg aac tgt aga aac cag att      2981
Glu Lys Ile Asp Thr Asp Trp Tyr Arg Gly Asn Cys Arg Asn Gln Ile
                        895                 900                 905 ggc ata ttt cct gcc aac tat gtc aaa gtg att att gat atc cca gaa      3029
Gly Ile Phe Pro Ala Asn Tyr Val Lys Val Ile Ile Asp Ile Pro Glu
                910                 915                 920 gga gga aat ggg aaa aga gaa tgt gtt tca tct cat tgt gtt aaa ggc      3077
Gly Gly Asn Gly Lys Arg Glu Cys Val Ser Ser His Cys Val Lys Gly
            925                 930                 935 tca aga tgt gtt gct cgg ttt gaa tat att gga gag cag aag gat gag      3125
Ser Arg Cys Val Ala Arg Phe Glu Tyr Ile Gly Glu Gln Lys Asp Glu
940                 945                 950 ttg agt ttc tca gag gga gaa att att att ctt aaa gag tat gtg aat      3173
Leu Ser Phe Ser Glu Gly Glu Ile Ile Ile Leu Lys Glu Tyr Val Asn
955                 960                 965                 970 gag gaa tgg gcc aga gga gaa gtt cga ggc aga act ggg att ttc ccc      3221
Glu Glu Trp Ala Arg Gly Glu Val Arg Gly Arg Thr Gly Ile Phe Pro
                        975                 980                 985 ctg aac ttt gtg gag cct gtt gag gat tat ccc acc tct ggg  tgc aaa     3269
Leu Asn Phe Val Glu Pro Val Glu Asp Tyr Pro Thr Ser Gly  Cys Lys
                990                 995                 1000 tgt ttt aag  cac aaa ggt acc act  gaa aac caa aaa aga  aga ttc       3314
Cys Phe Lys  His Lys Gly Thr Thr  Glu Asn Gln Lys Arg  Arg Phe
     1005                 1010                 1015 tgg ctc aaa  ctc tca ggt taacagtctt ccggcagaat ggtgtgaagc             3362
Trp Leu Lys  Leu Ser Gly
             1020 tcttcacagt tttacagcag agaccagtga tgacttatca ttcaagaggg gagaccggat     3422 ccagattctg gaacgtctgg attctgactg gtgcaggggc agactgcagg acagggaggg     3482 gatcttccca gcagtgtttg tgaggccctg cccagctgag gcaaaaagta tgttggccat     3542 agtaccgaag gggaggaagg ccaaagcctt atatgatttc gaggggagaa atgaagatga     3602 actttccttc aaggctggag atataataac agagctggaa tctgtagatg atgactggat     3662 gagtggagaa cttatgggaa aatctggaat atttcccaaa aactacatac agtttctaca     3722 gatcagctag aggagaagct tgtctgtgtt ccttggcaca agaactcact tgaactatca     3782 ccttgactat cagatatgtt tttgcactat ttttttttaac tgaaaagaa atatctaagc     3842 tgtacatggt acactagaat tttctgaaag cagaaaacgt tcagattttg tagttaattt     3902 tcattacaat agaaacacgc acatggaaac ccatgagcta ggattctacc gaggaaaaca     3962
```

-continued

```
tctagtggga ttagcaaggt gaagggaaag catctggtgg catggcagca tggggaggct   4022
cacacacaga agttgcacgt ggacatctgt tttaatcagc acaagtgaat taaccatgct   4082
tcttcatttt ttttacttta gttaaaaaag aggacattta atattctaca tgctgtaact   4142
atcaggacat ggttagcaat ctcaatttca tttttgatat tcaaattaat tcttacagct   4202
tgagcatatc agccttatta ccagagcaaa tccttccttc agatgggata gtttactgac   4262
tagttggagc atttgtaagc acatggtgaa atcagcccct gcccaccaaa ataatcttta   4322
tgttaccaag tgattcccat ttgtctaagg atttgaaggg ggtctaaatt ggatgtatct   4382
tagtctaaag aaccaaaacc atccctgaaa tgccttgcta atacaactaa tccttccata   4442
tatgtgccat acttattttt ttcctcagtg tatactttat gttaacaggg ttattacaaa   4502
gcacattttc tgaatctgca atcattcctt tgacaattac tggacccaaa ggaaaattca   4562
ttttctttgc attattccag taatatataa aaactgtgtc ttgttatagt agtacattat   4622
gaatcacata taaaatctta caatacagaa caactgttaa gatggaaaac agtgccaaac   4682
ctccacagct catttctttg taatataatc agaatgaaaa ataatttaag aggacagaag   4742
actggtactt ttttgtttta ttttttctct agcttatccc tgcacaatta ttagagtgaa   4802
tgaaaaacca ctttcctgct ttccattgtt ataaattcta agcttaagat aaaagtggtt   4862
ctttacatga ctgaatcaat tacaatttat gggctagagc caaataggtt gaagacaatc   4922
atccaaacag atcaatggaa tagaatttca ttggaaatgt aaaacacttt cccaacaatg   4982
gtcatgactt tcttctgttt tgagaagag tttcatatgc tggaccacat tttagctttt   5042 attgttttt ttttcccatt gtccaaaaag ttaagcaaca agtggccaca cttttacgtg   5102
actacaacct ggagttctgc aaagaaggta atatttactt ggtctttgac taaagttatc   5162
tccccattct atggttacat tttatttttgg actatgggga cttctaatac gttttggtaa   5222
agaagagagt ataagaaaa ttcttgtcaa atttcactca aaagtaattt catgagaaat   5282
caatgattta aagcattatc caaattaaat tatcatttgc agcaaactgt acaacagcag   5342
gaaggatatg gaatggaaca tgaggtatat atctttgcct ttataatttt aacatcttat   5402
attgaagatt ctgaaaacct atctttatta gaggaaaatc tcaatcttca gttttggcct   5462
tctgtcacca gaatgataag tgcaatagtt gtaaatctac ttgacactgt aataaactga   5522
actgaacttt caaaaaaaaa aaaaaaaaa aaaaaaaaa aaaaaaaaa aaaaaaaa      5581
```

<210> SEQ ID NO 20
<211> LENGTH: 1023
<212> TYPE: PRT
<213> ORGANISM: Homo sapiens

<400> SEQUENCE: 20

```
Met Ala Glu Gly Arg Arg Glu Asp Glu Glu Glu Leu Arg Glu
1               5                   10                  15

Arg Arg Glu Leu Gly Gly Gln Arg Arg Ala Arg Gly Arg Ala Leu Ser
                20                  25                  30

Gly His Ser Ala Ala Asp Arg Asn Glu Arg Asn Lys Pro Glu His Arg
            35                  40                  45

Ser Ser Ser Gln Gly Pro Leu Ser Ser Ile Arg Ala Val Ile Lys Arg
        50                  55                  60

Ser Ser Arg Thr Ser Ile Gln Ser Glu Leu His Arg Asp Arg Arg
65                  70                  75                  80

Pro Glu Ile Thr Ile Val Ala Ala Glu Pro Leu Arg Pro Ala Ser Trp
                85                  90                  95
```

```
Phe Pro Gly Thr Pro Pro Gly Leu Gly Phe Pro Thr Ser Ser Ala
            100                 105                 110
Ala Gly Ser Trp Arg Pro Asn Glu Leu Val Pro Ala Glu Leu Pro Pro
        115                 120                 125
Ser Tyr Glu Gln Val Ile Lys Glu Ile Asn Gln Val Gln Val Asn Thr
    130                 135                 140
Thr Asn Asn Asn Asn Ala Ala Ala Thr Pro Arg His Thr Ile Thr Ser
145                 150                 155                 160
Ala Thr Gln Thr Asp Phe Ser Glu Glu Ile Asp Asn Asp Leu Pro Gln
                165                 170                 175
Thr Leu Gln Ala Pro Leu Lys Pro Leu Gln Pro Phe Ser Ala Val Ser
            180                 185                 190
Ser Gly Asn Leu Pro Thr Asn Val Ala Pro Leu Ile Val Phe Asp Ile
        195                 200                 205
Ser Glu Glu Pro Asn Cys Pro Glu Asn Pro Ser Ala Thr Arg Cys Pro
    210                 215                 220
Val Pro Lys Pro Arg Ser Lys Ser Asn Leu Arg Pro Ile Pro Arg Asp
225                 230                 235                 240
Ser His Ile Lys Glu Gln Ser Gln Gln Lys Ile Ser Pro Ala Ala Val
                245                 250                 255
Gly Glu Glu Ser Ser Pro Gly Arg Pro Gln Ser Leu Leu Asp Asn Ala
            260                 265                 270
Ser Thr Ser Asp Ser Gln Ala Val Met Asn Ile Met Asn Thr Glu Gln
        275                 280                 285
Ser Gln Asn Ser Ile Val Ser Arg Ile Lys Val Phe Glu Gly Gln Thr
    290                 295                 300
Asn Ile Glu Thr Ser Gly Leu Pro Lys Lys Pro Glu Ile Thr Pro Arg
305                 310                 315                 320
Ser Leu Pro Pro Lys Pro Thr Val Ser Ser Gly Lys Pro Ser Val Ala
                325                 330                 335
Pro Lys Pro Ala Ala Asn Arg Ala Ser Gly Glu Trp Asp Ser Gly Thr
            340                 345                 350
Glu Asn Arg Leu Lys Val Thr Ser Lys Glu Gly Leu Thr Pro Tyr Pro
        355                 360                 365
Pro Leu Gln Glu Ala Gly Ser Ile Pro Val Thr Lys Pro Glu Leu Pro
    370                 375                 380
Lys Lys Pro Asn Pro Gly Leu Ile Arg Ser Val Asn Pro Glu Ile Pro
385                 390                 395                 400
Gly Arg Gly Pro Leu Ala Glu Ser Ser Asp Ser Gly Lys Lys Val Pro
                405                 410                 415
Thr Pro Ala Pro Arg Pro Leu Leu Lys Lys Ser Val Ser Ser Glu
            420                 425                 430
Asn Pro Thr Tyr Pro Ser Ala Pro Leu Lys Pro Val Thr Val Pro Pro
        435                 440                 445
Arg Leu Ala Gly Ala Ser Gln Ala Lys Ala Tyr Lys Ser Leu Gly Glu
    450                 455                 460
Gly Pro Pro Ala Asn Pro Pro Val Pro Val Leu Gln Ser Lys Pro Leu
465                 470                 475                 480
Val Asp Ile Asp Leu Ile Ser Phe Asp Asp Val Leu Pro Thr Pro
                485                 490                 495
Ser Gly Asn Leu Ala Glu Glu Ser Val Gly Ser Glu Met Val Leu Asp
            500                 505                 510
```

```
Pro Phe Gln Leu Pro Ala Lys Thr Glu Pro Ile Lys Glu Arg Ala Val
        515                 520                 525

Gln Pro Ala Pro Thr Arg Lys Pro Thr Val Ile Arg Ile Pro Ala Lys
    530                 535                 540

Pro Gly Lys Cys Leu His Glu Asp Pro Gln Ser Pro Pro Leu Pro
545                 550                 555                 560

Ala Glu Lys Pro Ile Gly Asn Thr Phe Ser Thr Val Ser Gly Lys Leu
                565                 570                 575

Ser Asn Val Glu Arg Thr Arg Asn Leu Glu Ser Asn His Pro Gly Gln
            580                 585                 590

Thr Gly Gly Phe Val Arg Val Pro Pro Arg Leu Pro Pro Arg Pro Val
        595                 600                 605

Asn Gly His Leu Ile Met Thr Thr Ile Leu Phe Met Ser Cys Ser Ala
    610                 615                 620

Arg Ala Arg Met Gly Phe Thr Gly Ile Val His Ile Leu Arg Phe Lys
625                 630                 635                 640

Leu Leu Leu Glu Ser Trp Cys Trp Ser Glu Ala Gly Gly Ser Val Ile
                645                 650                 655

Glu Leu Ala Glu Ala Phe Ala Arg Leu Gln Ile Met Ser Ser Phe Ser
            660                 665                 670

Ser Lys His Gly Trp Ser Phe Ile Asp Trp Ser Val Arg Leu Pro Val
        675                 680                 685

Ile Gly Trp Pro Ser Gln Asn Pro Leu Phe Trp Met Arg Asn Gly Leu
    690                 695                 700

Phe Cys Leu Asp Met Thr Glu Leu Tyr His Leu Glu Thr Lys Lys Thr
705                 710                 715                 720

Ile Pro Thr Gln Gln Pro Pro Thr Lys Val Pro Pro Glu Arg Pro Pro
                725                 730                 735

Pro Pro Lys Leu Ser Ala Thr Arg Arg Ser Asn Lys Lys Leu Pro Phe
            740                 745                 750

Asn Arg Ser Ser Ser Asp Met Asp Leu Gln Lys Lys Gln Ser Asn Leu
        755                 760                 765

Ala Thr Gly Leu Ser Lys Ala Lys Ser Gln Val Phe Lys Asn Gln Asp
    770                 775                 780

Pro Val Leu Pro Pro Arg Pro Lys Pro Gly His Pro Leu Tyr Ser Lys
785                 790                 795                 800

Tyr Met Arg Gly Asp Val Leu Val Met Leu Lys Gln Thr Glu Asn Asn
                805                 810                 815

Tyr Leu Glu Cys Gln Lys Gly Glu Asp Thr Gly Arg Val His Leu Ser
            820                 825                 830

Gln Met Lys Ile Ile Thr Pro Leu Asp Glu His Leu Arg Ser Arg Pro
        835                 840                 845

Asn Asp Pro Ser His Ala Gln Lys Pro Val Asp Ser Gly Ala Pro His
850                 855                 860

Ala Val Val Leu His Asp Phe Pro Ala Glu Gln Val Asp Asp Leu Asn
865                 870                 875                 880

Leu Thr Ser Gly Glu Ile Val Tyr Leu Leu Glu Lys Ile Asp Thr Asp
                885                 890                 895

Trp Tyr Arg Gly Asn Cys Arg Asn Gln Ile Gly Ile Phe Pro Ala Asn
            900                 905                 910

Tyr Val Lys Val Ile Ile Asp Ile Pro Glu Gly Gly Asn Gly Lys Arg
        915                 920                 925

Glu Cys Val Ser Ser His Cys Val Lys Gly Ser Arg Cys Val Ala Arg
```

```
             930              935             940
Phe Glu Tyr Ile Gly Glu Gln Lys Asp Glu Leu Ser Phe Ser Glu Gly
945                 950                 955                 960

Glu Ile Ile Ile Leu Lys Glu Tyr Val Asn Glu Trp Ala Arg Gly
                965                 970                 975

Glu Val Arg Gly Arg Thr Gly Ile Phe Pro Leu Asn Phe Val Glu Pro
            980                 985                 990

Val Glu Asp Tyr Pro Thr Ser Gly  Cys Lys Cys Phe Lys  His Lys Gly
        995                 1000                1005

Thr Thr  Glu Asn Gln Lys Arg  Arg Phe Trp Leu Lys  Leu Ser Gly
    1010                1015                1020

<210> SEQ ID NO 21
<211> LENGTH: 5334
<212> TYPE: DNA
<213> ORGANISM: Homo sapiens
<220> FEATURE:
<221> NAME/KEY: CDS
<222> LOCATION: (264)..(3482)
<223> OTHER INFORMATION:

<400> SEQUENCE: 21
gggaaaggcc agggattaag aggccgccgg gacgccgcaa ggaggcgggg aatcggctcg      60
gcccgcgccc tgccgctgcc cggccggctg caggtggagt tcgcggaggt ggccatttcc    120
acagccgccg ccgacgcctc ctctccggga gccgccttcc ccccgccccg agggcggtgg    180
cgtggggcgc cgggtgcagg cgttctgggg cgccggggcc gcagctcgct ggccatcccg    240
cggctgcgcc ccgcgcctcg ccc atg gct gag ggc cgg cgg cgg gag gac gag   293
              Met Ala Glu Gly Arg Arg Arg Glu Asp Glu
                1               5                  10 gag gaa gag cta cgc gag cgc cgc gaa ctt ggt ggc cag cgc cgc gcc     341
Glu Glu Glu Leu Arg Glu Arg Arg Glu Leu Gly Gly Gln Arg Arg Ala
            15                  20                  25 cgg ggc cgt gcg ctc tcg ggc cac tcg gcc gca gat cgc aac gaa cga     389
Arg Gly Arg Ala Leu Ser Gly His Ser Ala Ala Asp Arg Asn Glu Arg
        30                  35                  40 aat aaa cca gaa cat cgt tct tca agc caa gga ccc ttg tca tcc att     437
Asn Lys Pro Glu His Arg Ser Ser Ser Gln Gly Pro Leu Ser Ser Ile
    45                  50                  55 aga gcg gta atc aag aga tct tct cgg act tct att cag agt gaa ctt     485
Arg Ala Val Ile Lys Arg Ser Ser Arg Thr Ser Ile Gln Ser Glu Leu
60                  65                  70 cat cga gat aga agg cgc cca gag atc acc att gtg gca gct gag cca     533
His Arg Asp Arg Arg Arg Pro Glu Ile Thr Ile Val Ala Ala Glu Pro
75                  80                  85                  90 ctg agg cca gcc tcg tgg ttt cca gga acc cca ccc cca gga ctg gga     581
Leu Arg Pro Ala Ser Trp Phe Pro Gly Thr Pro Pro Pro Gly Leu Gly
                95                  100                 105 ttt cct aca tca tct gca gca ggc tct tgg agg cct aat gag ctg gtt     629
Phe Pro Thr Ser Ser Ala Ala Gly Ser Trp Arg Pro Asn Glu Leu Val
            110                 115                 120 cct gct gag ctc cca cca tct tat gaa caa gtt ata aaa gaa atc aac     677
Pro Ala Glu Leu Pro Pro Ser Tyr Glu Gln Val Ile Lys Glu Ile Asn
        125                 130                 135 caa gtt caa gtt aat act aca aat aat aat aat gct gct gct act cca     725
Gln Val Gln Val Asn Thr Thr Asn Asn Asn Asn Ala Ala Ala Thr Pro
    140                 145                 150 agg cac act att act tct gca act cag act gac ttt tca gaa gaa ata     773
Arg His Thr Ile Thr Ser Ala Thr Gln Thr Asp Phe Ser Glu Glu Ile
```

```
                155                 160                 165                 170
gac aac gat ctg cct caa agt aat gca aca cta cag gca cct ctc aag       821
Asp Asn Asp Leu Pro Gln Ser Asn Ala Thr Leu Gln Ala Pro Leu Lys
                    175                 180                 185 cct ctt cag cct ttc tca gca gtc tcg tct ggc aat ctt cca aca aat       869
Pro Leu Gln Pro Phe Ser Ala Val Ser Ser Gly Asn Leu Pro Thr Asn
                190                 195                 200 gtg gca cct tta atc gtc ttt gat att tct gaa gaa ccg aat tgt cca       917
Val Ala Pro Leu Ile Val Phe Asp Ile Ser Glu Glu Pro Asn Cys Pro
            205                 210                 215 gaa aac ccc agt gct aca aga tgt cca gtg cca aaa cca aga tca aaa       965
Glu Asn Pro Ser Ala Thr Arg Cys Pro Val Pro Lys Pro Arg Ser Lys
        220                 225                 230 agc aac ctc aga cca ata ccc aga gat tct cac att aaa gag caa agt      1013
Ser Asn Leu Arg Pro Ile Pro Arg Asp Ser His Ile Lys Glu Gln Ser
235                 240                 245                 250 caa cag aaa atc agc cca gca gcc gta gga gag gag tca tcc cca ggc      1061
Gln Gln Lys Ile Ser Pro Ala Ala Val Gly Glu Glu Ser Ser Pro Gly
                255                 260                 265 cgg ccc cag tct ctg ctg gac aac gct agc acc tca gac agt cag gca      1109
Arg Pro Gln Ser Leu Leu Asp Asn Ala Ser Thr Ser Asp Ser Gln Ala
            270                 275                 280 gtg atg aac att atg aac aca gaa caa agc caa aat agt att gtt tcc      1157
Val Met Asn Ile Met Asn Thr Glu Gln Ser Gln Asn Ser Ile Val Ser
        285                 290                 295 aga att aaa gtg ttt gag ggt cag aca aac ata gaa acc tca gga ctg      1205
Arg Ile Lys Val Phe Glu Gly Gln Thr Asn Ile Glu Thr Ser Gly Leu
    300                 305                 310 ccc aag aaa cca gaa att act cca cgt tca ctt cct cca aag cct act      1253
Pro Lys Lys Pro Glu Ile Thr Pro Arg Ser Leu Pro Pro Lys Pro Thr
315                 320                 325                 330 gtt tcc tca ggg aaa cct tct gta gct ccc aaa cca gct gct aac aga      1301
Val Ser Ser Gly Lys Pro Ser Val Ala Pro Lys Pro Ala Ala Asn Arg
                335                 340                 345 gct tct gga gag tgg gac tct ggg act gag aac aga ctc aag gtg acc      1349
Ala Ser Gly Glu Trp Asp Ser Gly Thr Glu Asn Arg Leu Lys Val Thr
            350                 355                 360 tcc aag gaa gga ctc acc cca tac cct ccc ctg caa gaa gcg gga agc      1397
Ser Lys Glu Gly Leu Thr Pro Tyr Pro Pro Leu Gln Glu Ala Gly Ser
        365                 370                 375 atc cca gta acc aaa cct gaa ttg cca aag aaa cca aac cct ggc ctt      1445
Ile Pro Val Thr Lys Pro Glu Leu Pro Lys Lys Pro Asn Pro Gly Leu
    380                 385                 390 ata cga agt gtt aat cct gag att ccg gga aga ggg ccc ctg gct gag      1493
Ile Arg Ser Val Asn Pro Glu Ile Pro Gly Arg Gly Pro Leu Ala Glu
395                 400                 405                 410 agc tct gat agt ggg aag aaa gtg cca act cct gcc ccg cgg cct ttg      1541
Ser Ser Asp Ser Gly Lys Lys Val Pro Thr Pro Ala Pro Arg Pro Leu
                415                 420                 425 ctg ctg aag aaa tct gtt tcc tca gaa aac ccc acc tac cct tca gct      1589
Leu Leu Lys Lys Ser Val Ser Ser Glu Asn Pro Thr Tyr Pro Ser Ala
            430                 435                 440 cca ctg aaa cct gtc act gtt cct ccc cga ctc gca ggg gca tca caa      1637
Pro Leu Lys Pro Val Thr Val Pro Pro Arg Leu Ala Gly Ala Ser Gln
        445                 450                 455 gcc aaa gca tac aag tca ctg gga gaa ggg ccc cca gcc aac ccc cca      1685
Ala Lys Ala Tyr Lys Ser Leu Gly Glu Gly Pro Pro Ala Asn Pro
    460                 465                 470 gtt cca gtt ctg cag agc aag ccc ttg gtg gac atc gat ctc atc agc      1733
Val Pro Val Leu Gln Ser Lys Pro Leu Val Asp Ile Asp Leu Ile Ser
```

```
Val Pro Val Leu Gln Ser Lys Pro Leu Val Asp Ile Asp Leu Ile Ser
475                 480                 485                 490 ttt gat gat gat gtt ttg ccc acc cca tcg ggg aac ctg gct gaa gaa    1781
Phe Asp Asp Asp Val Leu Pro Thr Pro Ser Gly Asn Leu Ala Glu Glu
                495                 500                 505 tct gtt ggt tca gag atg gtt cta gat ccc ttt cag ctc cct gca aaa    1829
Ser Val Gly Ser Glu Met Val Leu Asp Pro Phe Gln Leu Pro Ala Lys
                510                 515                 520 aca gaa cca ata aaa gaa cga gca gtt caa cca gca ccc acc agg aag    1877
Thr Glu Pro Ile Lys Glu Arg Ala Val Gln Pro Ala Pro Thr Arg Lys
                525                 530                 535 ccc act gta att cga att cca gcc aaa cca gga aaa tgt tta cat gag    1925
Pro Thr Val Ile Arg Ile Pro Ala Lys Pro Gly Lys Cys Leu His Glu
            540                 545                 550 gat cca caa agt cca cct cct ctc cct gct gaa aaa cct att gga aac    1973
Asp Pro Gln Ser Pro Pro Pro Leu Pro Ala Glu Lys Pro Ile Gly Asn
555                 560                 565                 570 act ttc agt aca gta tct gga aag ctc agt aat gtt gag aga act aga    2021
Thr Phe Ser Thr Val Ser Gly Lys Leu Ser Asn Val Glu Arg Thr Arg
                575                 580                 585 aac ttg gaa tcc aac cac cca ggt caa aca gga ggt ttt gtg cga gta    2069
Asn Leu Glu Ser Asn His Pro Gly Gln Thr Gly Gly Phe Val Arg Val
                590                 595                 600 ccc cca agg ttg cca ccg aga cct gtg aat gga aaa acc att cca act    2117
Pro Pro Arg Leu Pro Pro Arg Pro Val Asn Gly Lys Thr Ile Pro Thr
            605                 610                 615 caa cag cct cca acc aag gtg ccc cct gag aga cca cct ccc cca aag    2165
Gln Gln Pro Pro Thr Lys Val Pro Pro Glu Arg Pro Pro Pro Pro Lys
        620                 625                 630 ctt tct gca acc aga aga tct aat aag aaa ctg cct ttt aat cga tcc    2213
Leu Ser Ala Thr Arg Arg Ser Asn Lys Lys Leu Pro Phe Asn Arg Ser
635                 640                 645                 650 tct tct gac atg gat ctt cag aaa aaa caa agt aac ttg gca act gga    2261
Ser Ser Asp Met Asp Leu Gln Lys Lys Gln Ser Asn Leu Ala Thr Gly
                655                 660                 665 ctc tca aaa gcc aag agt caa gtt ttt aaa aat caa gat ccg gtg cta    2309
Leu Ser Lys Ala Lys Ser Gln Val Phe Lys Asn Gln Asp Pro Val Leu
            670                 675                 680 ccc cct cgt ccc aaa cca gga cac cct ctc tac agt aaa tac atg ctg    2357
Pro Pro Arg Pro Lys Pro Gly His Pro Leu Tyr Ser Lys Tyr Met Leu
        685                 690                 695 tct gtg cct cat gga att gcc aat gaa gat att gtc tct caa aac ccc    2405
Ser Val Pro His Gly Ile Ala Asn Glu Asp Ile Val Ser Gln Asn Pro
    700                 705                 710 gga gaa ctc tct tgt aag cgt ggg gat gta ctt gtg atg ctg aag cag    2453
Gly Glu Leu Ser Cys Lys Arg Gly Asp Val Leu Val Met Leu Lys Gln
715                 720                 725                 730 acg gaa aat aat tac ttg gag tgc caa aag gga gaa gac act ggc aga    2501
Thr Glu Asn Asn Tyr Leu Glu Cys Gln Lys Gly Glu Asp Thr Gly Arg
                735                 740                 745 gtt cac ctg tct caa atg aag att atc act cca ctt gat gaa cat ctt    2549
Val His Leu Ser Gln Met Lys Ile Ile Thr Pro Leu Asp Glu His Leu
            750                 755                 760 aga agc aga cca aac gat cca agc cac gct cag aag cct gtt gac agt    2597
Arg Ser Arg Pro Asn Asp Pro Ser His Ala Gln Lys Pro Val Asp Ser
        765                 770                 775 ggt gct cct cat gct gtc gtt ctt cat gat ttc cca gca gag caa gtt    2645
Gly Ala Pro His Ala Val Val Leu His Asp Phe Pro Ala Glu Gln Val
    780                 785                 790
```

-continued

| | |
|---|---|
| gat gat ttg aac ctc act tct gga gaa att gtt tat ctt ctg gag aag<br>Asp Asp Leu Asn Leu Thr Ser Gly Glu Ile Val Tyr Leu Leu Glu Lys<br>795                            800                         805                     810 | 2693 |
| ata gat aca gat tgg tac aga ggg aac tgt aga aac cag att ggc ata<br>Ile Asp Thr Asp Trp Tyr Arg Gly Asn Cys Arg Asn Gln Ile Gly Ile<br>                       815                       820                     825 | 2741 |
| ttt cct gcc aac tat gtc aaa gtg att att gat atc cca gaa gga gga<br>Phe Pro Ala Asn Tyr Val Lys Val Ile Ile Asp Ile Pro Glu Gly Gly<br>           830                       835                       840 | 2789 |
| aat ggg aaa aga gaa tgt gtt tca tct cat tgt gtt aaa ggc tca aga<br>Asn Gly Lys Arg Glu Cys Val Ser Ser His Cys Val Lys Gly Ser Arg<br>               845                       850                     855 | 2837 |
| tgt gtt gct cgg ttt gaa tat att gga gag cag aag gat gag ttg agt<br>Cys Val Ala Arg Phe Glu Tyr Ile Gly Glu Gln Lys Asp Glu Leu Ser<br>860                          865                       870 | 2885 |
| ttc tca gag gga gaa att att att ctt aaa gag tat gtg aat gag gaa<br>Phe Ser Glu Gly Glu Ile Ile Ile Leu Lys Glu Tyr Val Asn Glu Glu<br>875                            880                       885                     890 | 2933 |
| tgg gcc aga gga gaa gtt cga ggc aga act ggg att ttc ccc ctg aac<br>Trp Ala Arg Gly Glu Val Arg Gly Arg Thr Gly Ile Phe Pro Leu Asn<br>                       895                       900                     905 | 2981 |
| ttt gtg gag cct gtt gag gat tat ccc acc tct ggt gca aat gtt tta<br>Phe Val Glu Pro Val Glu Asp Tyr Pro Thr Ser Gly Ala Asn Val Leu<br>           910                       915                       920 | 3029 |
| agc aca aag gta cca ctg aaa acc aaa aaa gaa gat tct ggc tca aac<br>Ser Thr Lys Val Pro Leu Lys Thr Lys Lys Glu Asp Ser Gly Ser Asn<br>               925                       930                     935 | 3077 |
| tct cag gtt aac agt ctt ccg gca gaa tgg tgt gaa gct ctt cac agt<br>Ser Gln Val Asn Ser Leu Pro Ala Glu Trp Cys Glu Ala Leu His Ser<br>940                          945                       950 | 3125 |
| ttt aca gca gag acc agt gat gac tta tca ttc aag agg gga gac cgg<br>Phe Thr Ala Glu Thr Ser Asp Asp Leu Ser Phe Lys Arg Gly Asp Arg<br>955                          960                       965                     970 | 3173 |
| atc cag att ctg gaa cgt ctg gat tct gac tgg tgc agg ggc aga ctg<br>Ile Gln Ile Leu Glu Arg Leu Asp Ser Asp Trp Cys Arg Gly Arg Leu<br>               975                       980                     985 | 3221 |
| cag gac agg gag ggg atc ttc cca gca gtg ttt gtg agg ccc tgc cca<br>Gln Asp Arg Glu Gly Ile Phe Pro Ala Val Phe Val Arg Pro Cys Pro<br>           990                       995                    1000 | 3269 |
| gct gag gca aaa agt atg ttg gcc ata gta ccg aag ggg agg aag<br>Ala Glu Ala Lys Ser Met Leu Ala Ile Val Pro Lys Gly Arg Lys<br>          1005                     1010                  1015 | 3314 |
| gcc aaa gcc tta tat gat ttc cga ggg gag aat gaa gat gaa ctt<br>Ala Lys Ala Leu Tyr Asp Phe Arg Gly Glu Asn Glu Asp Glu Leu<br>          1020                     1025                  1030 | 3359 |
| tcc ttc aag gct gga gat ata ata aca gag ctg gaa tct gta gat<br>Ser Phe Lys Ala Gly Asp Ile Ile Thr Glu Leu Glu Ser Val Asp<br>          1035                     1040                  1045 | 3404 |
| gat gac tgg atg agt gga gaa ctt atg gga aaa tct gga ata ttt<br>Asp Asp Trp Met Ser Gly Glu Leu Met Gly Lys Ser Gly Ile Phe<br>          1050                     1055                  1060 | 3449 |
| ccc aaa aac tac ata cag ttt cta cag atc agc tagaggagaa<br>Pro Lys Asn Tyr Ile Gln Phe Leu Gln Ile Ser<br>          1065                     1070 | 3492 |
| gcttgtctgt gttccttggc acaagaactc acttgaacta tcaccttgac tatcagatat | 3552 |
| gttttttgcac tattttttttt aactgaaaaa gaaatatcta agctgtacat ggtacactag | 3612 |
| aattttctga agcagaaaaa cgttcagatt ttgtagttaa ttttcattac aatagaaaca | 3672 |
| cgcacatgga aacccatgag ctaggattct accgaggaaa acatctagtg ggattagcaa | 3732 |

```
ggtgaaggga aagcatctgg tggcatggca gcatggggag gctcacacac agaagttgca    3792
cgtggacatc tgttttaatc agcacaagtg aattaaccat gcttcttcat tttttttact    3852
ttagttaaaa aagaggacat ttaatattct acatgctgta actatcagga catggttagc    3912
aatctcaatt tcattttga tattcaaatt aattcttaca gcttgagcat atcagcctta     3972
ttaccagagc aaatccttcc ttcagatggg atagtttact gactagttgg agcatttgta    4032
agcacatggt gaaatcagcc cctgcccacc aaaataatct ttatgttacc aagtgattcc    4092
catttgtcta aggatttgaa gggggtctaa attggatgta tcttagtcta aagaaccaaa    4152
accatccctg aaatgccttg ctaatacaac taatccttcc atatatgtgc catacttatt    4212
tttttcctca gtgtatactt tatgttaaca gggttattac aaagcacatt ttctgaatct    4272
gcaatcattc ctttgacaat tactggaccc aaaggaaaat tcattttctt tgcattattc    4332
cagtaatata taaaaactgt gtcttgttat agtagtacat tatgaatcac atataaaatc    4392
ttacaataca gaacaactgt taagatggaa acagtgccaa acctccaca gctcatttct     4452 ttgtaatata atcagaatga aaataattt aagaggacag aagactggta cttttttgtt     4512
ttattttttc tctagcttat ccctgcacaa ttattagagt gaatgaaaaa ccactttcct    4572
gctttccatt gttataaatt ctaagcttaa gataaaagtg gttctttaca tgactgaatc    4632
aattacaatt tatgggctag agccaaatag gttgaagaca atcatccaaa cagatcaatg    4692
gaatagaatt tcattggaaa tgtaaaacac tttcccaaca atggtcatga ctttcttctg    4752
tttttgagaa gagtttcata tgctggacca cattttagct tttattgttt ttttttttccc    4812 attgtccaaa aagttaagca acaagtggcc acactttac gtgactacaa cctggagttc      4872
tgcaaagaag gtaatattta cttggtcttt gactaaagtt atctccccat tctatggtta    4932
cattttattt tggactatgg ggacttctaa tacgttttgg taaagaagag agtataaaga    4992
aaattcttgt caaatttcac tcaaaagtaa tttcatgaga aatcaatgat ttaaagcatt    5052
atccaaatta aattatcatt tgcagcaaac tgtacaacag caggaaggat atggaatgga    5112
acatgaggta tatatctttg cctttataat tttaacatct tatattgaag attctgaaaa    5172
cctatcttta ttagaggaaa atctcaatct tcagttttgg ccttctgtca ccagaatgat    5232
aagtgcaata gttgtaaatc tacttgacac tgtaataaac tgaactgaac tttcaaaaaa    5292
aaaaaaaaaa aaaaaaaaa aaaaaaaaa aaaaaaaaa aa                          5334
```

<210> SEQ ID NO 22
<211> LENGTH: 1073
<212> TYPE: PRT
<213> ORGANISM: Homo sapiens

<400> SEQUENCE: 22

Met Ala Glu Gly Arg Arg Arg Glu Asp Glu Glu Glu Leu Arg Glu
1               5                   10                  15

Arg Arg Glu Leu Gly Gly Gln Arg Arg Ala Arg Gly Arg Ala Leu Ser
            20                  25                  30

Gly His Ser Ala Ala Asp Arg Asn Glu Arg Asn Lys Pro Glu His Arg
        35                  40                  45

Ser Ser Ser Gln Gly Pro Leu Ser Ser Ile Arg Ala Val Ile Lys Arg
    50                  55                  60

Ser Ser Arg Thr Ser Ile Gln Ser Glu Leu His Arg Asp Arg Arg
65                  70                  75                  80

Pro Glu Ile Thr Ile Val Ala Ala Glu Pro Leu Arg Pro Ala Ser Trp

```
                    85                  90                      95
Phe Pro Gly Thr Pro Pro Gly Leu Gly Phe Pro Thr Ser Ser Ala
                100             105             110
Ala Gly Ser Trp Arg Pro Asn Glu Leu Val Pro Ala Glu Leu Pro Pro
            115                 120             125
Ser Tyr Glu Gln Val Ile Lys Glu Ile Asn Gln Val Gln Val Asn Thr
    130                 135             140
Thr Asn Asn Asn Asn Ala Ala Ala Thr Pro Arg His Thr Ile Thr Ser
145                 150             155                 160
Ala Thr Gln Thr Asp Phe Ser Glu Glu Ile Asp Asn Asp Leu Pro Gln
                165             170             175
Ser Asn Ala Thr Leu Gln Ala Pro Leu Lys Pro Leu Gln Pro Phe Ser
            180             185             190
Ala Val Ser Ser Gly Asn Leu Pro Thr Asn Val Ala Pro Leu Ile Val
        195             200             205
Phe Asp Ile Ser Glu Glu Pro Asn Cys Pro Glu Asn Pro Ser Ala Thr
    210             215             220
Arg Cys Pro Val Pro Lys Pro Arg Ser Lys Ser Asn Leu Arg Pro Ile
225             230             235                 240
Pro Arg Asp Ser His Ile Lys Glu Gln Ser Gln Gln Lys Ile Ser Pro
                245             250             255
Ala Ala Val Gly Glu Glu Ser Ser Pro Gly Arg Pro Gln Ser Leu Leu
            260             265             270
Asp Asn Ala Ser Thr Ser Asp Ser Gln Ala Val Met Asn Ile Met Asn
            275             280             285
Thr Glu Gln Ser Gln Asn Ser Ile Val Ser Arg Ile Lys Val Phe Glu
    290             295             300
Gly Gln Thr Asn Ile Glu Thr Ser Gly Leu Pro Lys Lys Pro Glu Ile
305             310             315                 320
Thr Pro Arg Ser Leu Pro Pro Lys Pro Thr Val Ser Ser Gly Lys Pro
                325             330             335
Ser Val Ala Pro Lys Pro Ala Ala Asn Arg Ala Ser Gly Glu Trp Asp
            340             345             350
Ser Gly Thr Glu Asn Arg Leu Lys Val Thr Ser Lys Glu Gly Leu Thr
            355             360             365
Pro Tyr Pro Pro Leu Gln Glu Ala Gly Ser Ile Pro Val Thr Lys Pro
370                 375             380
Glu Leu Pro Lys Lys Pro Asn Pro Gly Leu Ile Arg Ser Val Asn Pro
385             390             395                 400
Glu Ile Pro Gly Arg Gly Pro Leu Ala Glu Ser Ser Asp Ser Gly Lys
                405             410             415
Lys Val Pro Thr Pro Ala Pro Arg Pro Leu Leu Leu Lys Lys Ser Val
            420             425             430
Ser Ser Glu Asn Pro Thr Tyr Pro Ser Ala Pro Leu Lys Pro Val Thr
            435             440             445
Val Pro Pro Arg Leu Ala Gly Ala Ser Gln Ala Lys Ala Tyr Lys Ser
        450             455             460
Leu Gly Glu Gly Pro Pro Ala Asn Pro Val Pro Val Leu Gln Ser
465             470             475             480
Lys Pro Leu Val Asp Ile Asp Leu Ile Ser Phe Asp Asp Val Leu
            485             490             495
Pro Thr Pro Ser Gly Asn Leu Ala Glu Glu Ser Val Gly Ser Glu Met
            500             505             510
```

```
Val Leu Asp Pro Phe Gln Leu Pro Ala Lys Thr Glu Pro Ile Lys Glu
            515                 520                 525

Arg Ala Val Gln Pro Ala Pro Thr Arg Lys Pro Thr Val Ile Arg Ile
530                 535                 540

Pro Ala Lys Pro Gly Lys Cys Leu His Glu Asp Pro Gln Ser Pro Pro
545                 550                 555                 560

Pro Leu Pro Ala Glu Lys Pro Ile Gly Asn Thr Phe Ser Thr Val Ser
            565                 570                 575

Gly Lys Leu Ser Asn Val Glu Arg Thr Arg Asn Leu Glu Ser Asn His
            580                 585                 590

Pro Gly Gln Thr Gly Gly Phe Val Arg Val Pro Pro Arg Leu Pro Pro
            595                 600                 605

Arg Pro Val Asn Gly Lys Thr Ile Pro Thr Gln Gln Pro Pro Thr Lys
            610                 615                 620

Val Pro Pro Glu Arg Pro Pro Pro Lys Leu Ser Ala Thr Arg Arg
625                 630                 635                 640

Ser Asn Lys Lys Leu Pro Phe Asn Arg Ser Ser Asp Met Asp Leu
            645                 650                 655

Gln Lys Lys Gln Ser Asn Leu Ala Thr Gly Leu Ser Lys Ala Lys Ser
            660                 665                 670

Gln Val Phe Lys Asn Gln Asp Pro Val Leu Pro Pro Arg Pro Lys Pro
            675                 680                 685

Gly His Pro Leu Tyr Ser Lys Tyr Met Leu Ser Val Pro His Gly Ile
            690                 695                 700

Ala Asn Glu Asp Ile Val Ser Gln Asn Pro Gly Glu Leu Ser Cys Lys
705                 710                 715                 720

Arg Gly Asp Val Leu Val Met Leu Lys Gln Thr Glu Asn Asn Tyr Leu
            725                 730                 735

Glu Cys Gln Lys Gly Glu Asp Thr Gly Arg Val His Leu Ser Gln Met
            740                 745                 750

Lys Ile Ile Thr Pro Leu Asp Glu His Leu Arg Ser Arg Pro Asn Asp
            755                 760                 765

Pro Ser His Ala Gln Lys Pro Val Asp Ser Gly Ala Pro His Ala Val
770                 775                 780

Val Leu His Asp Phe Pro Ala Glu Gln Val Asp Asp Leu Asn Leu Thr
785                 790                 795                 800

Ser Gly Glu Ile Val Tyr Leu Leu Glu Lys Ile Asp Thr Asp Trp Tyr
            805                 810                 815

Arg Gly Asn Cys Arg Asn Gln Ile Gly Ile Phe Pro Ala Asn Tyr Val
            820                 825                 830

Lys Val Ile Ile Asp Ile Pro Glu Gly Gly Asn Gly Lys Arg Glu Cys
            835                 840                 845

Val Ser Ser His Cys Val Lys Gly Ser Arg Cys Val Ala Arg Phe Glu
850                 855                 860

Tyr Ile Gly Glu Gln Lys Asp Glu Leu Ser Phe Ser Glu Gly Glu Ile
865                 870                 875                 880

Ile Ile Leu Lys Glu Tyr Val Asn Glu Glu Trp Ala Arg Gly Glu Val
            885                 890                 895

Arg Gly Arg Thr Gly Ile Phe Pro Leu Asn Phe Val Glu Pro Val Glu
            900                 905                 910

Asp Tyr Pro Thr Ser Gly Ala Asn Val Leu Ser Thr Lys Val Pro Leu
            915                 920                 925
```

```
Lys Thr Lys Lys Glu Asp Ser Gly Ser Asn Ser Gln Val Asn Ser Leu
    930                 935                 940

Pro Ala Glu Trp Cys Glu Ala Leu His Ser Phe Thr Ala Glu Thr Ser
945                 950                 955                 960

Asp Asp Leu Ser Phe Lys Arg Gly Asp Arg Ile Gln Ile Leu Glu Arg
                965                 970                 975

Leu Asp Ser Asp Trp Cys Arg Gly Arg Leu Gln Asp Arg Glu Gly Ile
            980                 985                 990

Phe Pro Ala Val Phe Val Arg Pro  Cys Pro Ala Glu Ala  Lys Ser Met
        995                1000                1005

Leu Ala  Ile Val Pro Lys Gly  Arg Lys Ala Lys Ala  Leu Tyr Asp
    1010                1015                1020

Phe Arg  Gly Glu Asn Glu Asp  Glu Leu Ser Phe Lys  Ala Gly Asp
    1025                1030                1035

Ile Ile  Thr Glu Leu Glu Ser  Val Asp Asp Trp  Met Ser Gly
    1040                1045                1050

Glu Leu  Met Gly Lys Ser Gly  Ile Phe Pro Lys Asn  Tyr Ile Gln
    1055                1060                1065

Phe Leu  Gln Ile Ser
    1070

<210> SEQ ID NO 23
<211> LENGTH: 5228
<212> TYPE: DNA
<213> ORGANISM: Homo sapiens
<220> FEATURE:
<221> NAME/KEY: CDS
<222> LOCATION: (336)..(3977)
<223> OTHER INFORMATION:

<400> SEQUENCE: 23
gcacgagggt taccttttat ccttgttttc attttcctgt cccttttata cattgtatcc        60
tcctctcttc tcctgtgtca tggagtgtag aggaaataaa atcatgtctg tggctcatga       120
cagcattcca tattcagttg ttgggttgtg ttgttgttgt tgtgtgtgtt tttaataata       180
ccatgtaact gtttaaaaaa atttcctttt tgatcaagtc ccaaatctgc cagcctgttc       240
tctcttccta actgtggaaa aatgagacgg ttgcttgaac atttgttggc ttggctgaag       300
aggaaataaa aacagaacag gaggtggtag agggc atg gat atc tct act cgc         353
                                    Met Asp Ile Ser Thr Arg
                                      1               5 tcc aaa gat cct ggc tct gca gag aga aca gcc cag aaa aga aag ttc        401
Ser Lys Asp Pro Gly Ser Ala Glu Arg Thr Ala Gln Lys Arg Lys Phe
            10                  15                  20 ccc agc cct cca cat tct tcc aat ggc cac tcg ccg cag gac aca tca        449
Pro Ser Pro Pro His Ser Ser Asn Gly His Ser Pro Gln Asp Thr Ser
        25                  30                  35 aca agc ccc att aaa aag aaa aag aaa cct ggc tta ctg aac agt aac        497
Thr Ser Pro Ile Lys Lys Lys Lys Lys Pro Gly Leu Leu Asn Ser Asn
    40                  45                  50 aat aag gag cag tca gaa cta aga cat ggt ccg ttt tac tat atg aag        545
Asn Lys Glu Gln Ser Glu Leu Arg His Gly Pro Phe Tyr Tyr Met Lys
55                  60                  65                  70 cag cca ctc acc aca gac cct gtt gat gtt gta ccg cag gat gga cgg        593
Gln Pro Leu Thr Thr Asp Pro Val Asp Val Val Pro Gln Asp Gly Arg
                75                  80                  85 aat gat ttc tac tgc tgg gtt tgt cac cgg gaa ggc caa gtc ctt tgc        641
Asn Asp Phe Tyr Cys Trp Val Cys His Arg Glu Gly Gln Val Leu Cys
            90                  95                 100
```

-continued

| | |
|---|---|
| tgt gag ctc tgt ccc cgg gtt tat cac gct aag tgt ctg aga ctg aca<br>Cys Glu Leu Cys Pro Arg Val Tyr His Ala Lys Cys Leu Arg Leu Thr<br>105            110            115 | 689 |
| tcg gaa cca gag ggg gac tgg ttt tgt cct gaa tgt gag aaa att aca<br>Ser Glu Pro Glu Gly Asp Trp Phe Cys Pro Glu Cys Glu Lys Ile Thr<br>120            125            130 | 737 |
| gta gca gaa tgc atc gag acc cag agt aaa gcc atg aca atg ctc acc<br>Val Ala Glu Cys Ile Glu Thr Gln Ser Lys Ala Met Thr Met Leu Thr<br>135            140            145            150 | 785 |
| att gaa cag tta tcc tac ctg ctc aag ttt gcc att cag aaa atg aaa<br>Ile Glu Gln Leu Ser Tyr Leu Leu Lys Phe Ala Ile Gln Lys Met Lys<br>           155            160            165 | 833 |
| cag cca ggg aca gat gca ttc cag aag ccc gtt cca ttg gaa cag cac<br>Gln Pro Gly Thr Asp Ala Phe Gln Lys Pro Val Pro Leu Glu Gln His<br>170            175            180 | 881 |
| cct gac tat gcg gaa tac atc ttc cat cca atg gac ctt tgt aca ttg<br>Pro Asp Tyr Ala Glu Tyr Ile Phe His Pro Met Asp Leu Cys Thr Leu<br>185            190            195 | 929 |
| gaa aag aat gcg aaa aag aaa atg tat ggc tgc aca gaa gcc ttc ctg<br>Glu Lys Asn Ala Lys Lys Lys Met Tyr Gly Cys Thr Glu Ala Phe Leu<br>200            205            210 | 977 |
| gct gat gca aag tgg att ttg cac aac tgc atc att tat aat ggg gga<br>Ala Asp Ala Lys Trp Ile Leu His Asn Cys Ile Ile Tyr Asn Gly Gly<br>215            220            225            230 | 1025 |
| aat cac aaa ttg acg caa ata gcg aaa gta gtc atc aaa atc tgt gaa<br>Asn His Lys Leu Thr Gln Ile Ala Lys Val Val Ile Lys Ile Cys Glu<br>           235            240            245 | 1073 |
| cat gag atg aat gaa atc gaa gta tgt cca gaa tgt tat cta gct gct<br>His Glu Met Asn Glu Ile Glu Val Cys Pro Glu Cys Tyr Leu Ala Ala<br>250            255            260 | 1121 |
| tgc caa aaa cga gat aac tgg ttt tgt gag cct tgt agc aat cca cat<br>Cys Gln Lys Arg Asp Asn Trp Phe Cys Glu Pro Cys Ser Asn Pro His<br>265            270            275 | 1169 |
| cct ttg gtc tgg gcc aaa ctg aag ggg ttt cca ttc tgg cct gca aaa<br>Pro Leu Val Trp Ala Lys Leu Lys Gly Phe Pro Phe Trp Pro Ala Lys<br>280            285            290 | 1217 |
| gct cta agg gat aaa gac ggg cag gtc gat gcc cga ttc ttt gga caa<br>Ala Leu Arg Asp Lys Asp Gly Gln Val Asp Ala Arg Phe Phe Gly Gln<br>295            300            305            310 | 1265 |
| cat gac agg gcc tgg gtt cca ata aat aat tgc tac ctc atg tct aaa<br>His Asp Arg Ala Trp Val Pro Ile Asn Asn Cys Tyr Leu Met Ser Lys<br>           315            320            325 | 1313 |
| gaa att cct ttt tct gtg aaa aag act aag agc atc ttc aac agt gcc<br>Glu Ile Pro Phe Ser Val Lys Lys Thr Lys Ser Ile Phe Asn Ser Ala<br>330            335            340 | 1361 |
| atg caa gag atg gag gtt tac gtg gag aac atc cgc agg aag ttt ggg<br>Met Gln Glu Met Glu Val Tyr Val Glu Asn Ile Arg Arg Lys Phe Gly<br>345            350            355 | 1409 |
| gtt ttt aat tac tct cca ttt agg aca ccc tac aca ccc aac agc cag<br>Val Phe Asn Tyr Ser Pro Phe Arg Thr Pro Tyr Thr Pro Asn Ser Gln<br>360            365            370 | 1457 |
| tat caa atg ctg ctc gat ccc acc aac ccc agc gcc ggc act gcc aag<br>Tyr Gln Met Leu Leu Asp Pro Thr Asn Pro Ser Ala Gly Thr Ala Lys<br>375            380            385            390 | 1505 |
| ata gac aag cag gag aag gtc aag ctc aac ttt gac atg acg gca tcc<br>Ile Asp Lys Gln Glu Lys Val Lys Leu Asn Phe Asp Met Thr Ala Ser<br>           395            400            405 | 1553 |
| ccc aag atc ctg atg agc aag cct gtg ctg agt ggg ggc aca ggc cgc<br>Pro Lys Ile Leu Met Ser Lys Pro Val Leu Ser Gly Gly Thr Gly Arg | 1601 |

```
                     410                    415                    420
cgg att tcc ttg tcg gat atg ccg cgc tcc ccc atg agc aca aac tct        1649
Arg Ile Ser Leu Ser Asp Met Pro Arg Ser Pro Met Ser Thr Asn Ser
        425                    430                    435 tct gtg cac acg ggc tcc gac gtg gag cag gat gct gag aag aag gcc        1697
Ser Val His Thr Gly Ser Asp Val Glu Gln Asp Ala Glu Lys Lys Ala
        440                    445                    450 acg tcg agc cac ttc agt gcg agc gag gag tcc atg gac ttc ctg gat        1745
Thr Ser Ser His Phe Ser Ala Ser Glu Glu Ser Met Asp Phe Leu Asp
455                    460                    465                    470 aag agc aca gct tca cca gcc tcc acc aag acg gga caa gca ggg agt        1793
Lys Ser Thr Ala Ser Pro Ala Ser Thr Lys Thr Gly Gln Ala Gly Ser
                475                    480                    485 tta tcc ggc agc cca aag ccc ttc tct cct caa ctg tca gct cct atc        1841
Leu Ser Gly Ser Pro Lys Pro Phe Ser Pro Gln Leu Ser Ala Pro Ile
            490                    495                    500 acg acg aaa acg gac aaa acc tcc acc acc ggc agc atc ctg aat ctt        1889
Thr Thr Lys Thr Asp Lys Thr Ser Thr Thr Gly Ser Ile Leu Asn Leu
        505                    510                    515 aac ctg gat cga agc aaa gct gag atg gat ttg aag gag ctg agc gag        1937
Asn Leu Asp Arg Ser Lys Ala Glu Met Asp Leu Lys Glu Leu Ser Glu
        520                    525                    530 tcg gtc cag caa cag tcc acc cct gtt cct ctc atc tct ccc aag cgc        1985
Ser Val Gln Gln Gln Ser Thr Pro Val Pro Leu Ile Ser Pro Lys Arg
535                    540                    545                    550 cag att cgt agc agg ttc cag ctg aat ctt gac aag acc ata gag agt        2033
Gln Ile Arg Ser Arg Phe Gln Leu Asn Leu Asp Lys Thr Ile Glu Ser
                555                    560                    565 tgc aaa gca caa tta ggc ata aat gaa atc tcg gaa gat gtc tat acg        2081
Cys Lys Ala Gln Leu Gly Ile Asn Glu Ile Ser Glu Asp Val Tyr Thr
            570                    575                    580 gcc gta gag cac agc gat tcg gag gat tct gag aag tca gat agt agc        2129
Ala Val Glu His Ser Asp Ser Glu Asp Ser Glu Lys Ser Asp Ser Ser
        585                    590                    595 gat agt gag tat atc agt gat gat gag cag aag tct aag aac gag cca        2177
Asp Ser Glu Tyr Ile Ser Asp Asp Glu Gln Lys Ser Lys Asn Glu Pro
        600                    605                    610 gaa gac aca gag gac aaa gaa ggt tgt cag atg gac aaa gag cca tct        2225
Glu Asp Thr Glu Asp Lys Glu Gly Cys Gln Met Asp Lys Glu Pro Ser
615                    620                    625                    630 gct gtt aaa aaa aag ccc aag cct aca aac cca gtg gag att aaa gag        2273
Ala Val Lys Lys Lys Pro Lys Pro Thr Asn Pro Val Glu Ile Lys Glu
                635                    640                    645 gag ctg aaa agc acg tca cca gcc agc gag aag gca gac cct gga gca        2321
Glu Leu Lys Ser Thr Ser Pro Ala Ser Glu Lys Ala Asp Pro Gly Ala
            650                    655                    660 gtc aag gac aag gcc agc cct gag cct gag aag gac ttt tcc gaa aag        2369
Val Lys Asp Lys Ala Ser Pro Glu Pro Glu Lys Asp Phe Ser Glu Lys
        665                    670                    675 gca aaa cct tca cct cac ccc ata aag gat aaa ctg aag gga aaa gat        2417
Ala Lys Pro Ser Pro His Pro Ile Lys Asp Lys Leu Lys Gly Lys Asp
        680                    685                    690 gag acg gat tcc cca aca gtc cat ttg ggc ctg gac tct gat tca gag        2465
Glu Thr Asp Ser Pro Thr Val His Leu Gly Leu Asp Ser Asp Ser Glu
695                    700                    705                    710 agc gaa ctt gtc ata gat tta gga gaa gac cat tct ggg cgg gag ggt        2513
Ser Glu Leu Val Ile Asp Leu Gly Glu Asp His Ser Gly Arg Glu Gly
                715                    720                    725 cga aaa aat aag aag gaa ccc aaa gaa cca tct ccc aaa cag gat gtt        2561
```

```
                    Arg Lys Asn Lys Lys Glu Pro Lys Glu Pro Ser Pro Lys Gln Asp Val
                            730                 735                 740 gta ggt aaa act cca cca tcc acg acg gtg ggc agc cat tct ccc ccg          2609
Val Gly Lys Thr Pro Pro Ser Thr Thr Val Gly Ser His Ser Pro Pro
            745                 750                 755 gaa aca ccg gtg ctc acc cgc tct tcc gcc caa act tcc gcg gct ggc          2657
Glu Thr Pro Val Leu Thr Arg Ser Ser Ala Gln Thr Ser Ala Ala Gly
760                 765                 770 gcc aca gcc acc acc agc acg tcc tcc acg gtc acc gtc acg gcc ccg          2705
Ala Thr Ala Thr Thr Ser Thr Ser Ser Thr Val Thr Val Thr Ala Pro
775                 780                 785                 790 gcc ccc gcc gcc aca gga agc cca gtg aaa aag cag agg ccg ctt tta          2753
Ala Pro Ala Ala Thr Gly Ser Pro Val Lys Lys Gln Arg Pro Leu Leu
                795                 800                 805 ccg aag gag act gcc ccg gcc gtg cag cgg gtc gtg tgg aac tca tca          2801
Pro Lys Glu Thr Ala Pro Ala Val Gln Arg Val Val Trp Asn Ser Ser
            810                 815                 820 agt aag ttt caa acg tcc tcc caa aag tgg cac atg cag aag atg cag          2849
Ser Lys Phe Gln Thr Ser Ser Gln Lys Trp His Met Gln Lys Met Gln
                825                 830                 835 cgt cag cag cag cag cag cag caa aac cag cag cag cag cct cag              2897
Arg Gln Gln Gln Gln Gln Gln Gln Asn Gln Gln Gln Gln Pro Gln
840                 845                 850 tct tcc cag ggg acg aga tat cag acc aga cag gct gtg aaa gct gtc          2945
Ser Ser Gln Gly Thr Arg Tyr Gln Thr Arg Gln Ala Val Lys Ala Val
855                 860                 865                 870 cag cag aag gag atc aca cag agc cca tcc acg tcc acc atc acc ctg          2993
Gln Gln Lys Glu Ile Thr Gln Ser Pro Ser Thr Ser Thr Ile Thr Leu
                875                 880                 885 gtg acc agc aca cag tca tcg ccc ctg gtc acc agc tcg ggg tcc atg          3041
Val Thr Ser Thr Gln Ser Ser Pro Leu Val Thr Ser Ser Gly Ser Met
                890                 895                 900 agc acc ctt gtg tcc tca gtc aac gct gac ctg ccc atc gcc act gcc          3089
Ser Thr Leu Val Ser Ser Val Asn Ala Asp Leu Pro Ile Ala Thr Ala
                905                 910                 915 tca gct gat gtc gcc gct gat att gcc aag tac act agc aaa atg atg          3137
Ser Ala Asp Val Ala Ala Asp Ile Ala Lys Tyr Thr Ser Lys Met Met
    920                 925                 930 gat gca ata aaa gga aca atg aca gaa ata tac aac gat ctt tct aaa          3185
Asp Ala Ile Lys Gly Thr Met Thr Glu Ile Tyr Asn Asp Leu Ser Lys
935                 940                 945                 950 aac act act gga agc aca ata gct gag att cgc agg ctg agg atc gag          3233
Asn Thr Thr Gly Ser Thr Ile Ala Glu Ile Arg Arg Leu Arg Ile Glu
                955                 960                 965 ata gag aag ctc cag tgg ctg cac cag caa gag ctc tcc gaa atg aaa          3281
Ile Glu Lys Leu Gln Trp Leu His Gln Gln Glu Leu Ser Glu Met Lys
                970                 975                 980 cac aac tta gag ctg acc atg gcg gag atg cgg cag agc ctg gag cag          3329
His Asn Leu Glu Leu Thr Met Ala Glu Met Arg Gln Ser Leu Glu Gln
            985                 990                 995 gag cgg gac cgg ctc atc gcc  gag gtg aag aag cag  ctg gag ttg            3374
Glu Arg Asp Arg Leu Ile Ala  Glu Val Lys Lys Gln  Leu Glu Leu
            1000                1005                1010 gag aag cag cag gcg gtg gat  gag acc aag aag aag  cag tgg tgc            3419
Glu Lys Gln Gln Ala Val Asp  Glu Thr Lys Lys Lys  Gln Trp Cys
        1015                1020                1025 gcc aac tgc aag aag gag gcc  atc ttt tac tgc tgt  tgg aac acc            3464
Ala Asn Cys Lys Lys Glu Ala  Ile Phe Tyr Cys Cys  Trp Asn Thr
        1030                1035                1040
```

-continued

| | | |
|---|---|---|
| agc tac tgt gac tac ccc tgc cag caa gcc cac tgg cct gag cac<br>Ser Tyr Cys Asp Tyr Pro Cys Gln Gln Ala His Trp Pro Glu His<br>1045                  1050                  1055 | 3509 |
| atg aag tcc tgc acc cag tca gct act gct cct cag cag gaa gcg<br>Met Lys Ser Cys Thr Gln Ser Ala Thr Ala Pro Gln Gln Glu Ala<br>1060                    1065                  1070 | 3554 |
| gat gct gag gtg aac aca gaa aca cta aat aag tcc tcc cag ggg<br>Asp Ala Glu Val Asn Thr Glu Thr Leu Asn Lys Ser Ser Gln Gly<br>1075                    1080                  1085 | 3599 |
| agc tcc tcg agc aca caa tca gca cct tca gaa acg gcc agc gcc<br>Ser Ser Ser Ser Thr Gln Ser Ala Pro Ser Glu Thr Ala Ser Ala<br>1090                    1095                  1100 | 3644 |
| tcc aaa gag aag gag acg tca gct gag aaa agc aag gag agt ggc<br>Ser Lys Glu Lys Glu Thr Ser Ala Glu Lys Ser Lys Glu Ser Gly<br>1105                    1110                  1115 | 3689 |
| tcg acc ctt gac ctt tct ggc tcc aga gag acg ccc tcc tcc att<br>Ser Thr Leu Asp Leu Ser Gly Ser Arg Glu Thr Pro Ser Ser Ile<br>1120                    1125                  1130 | 3734 |
| ctc tta ggc tcc aac caa ggc tct gtt agc aaa agg tgt gac aag<br>Leu Leu Gly Ser Asn Gln Gly Ser Val Ser Lys Arg Cys Asp Lys<br>1135                    1140                  1145 | 3779 |
| caa cct gcc tat gcc cca acc acc aca gac cac cag ccg cac ccc<br>Gln Pro Ala Tyr Ala Pro Thr Thr Thr Asp His Gln Pro His Pro<br>1150                    1155                  1160 | 3824 |
| aac tac ccc gcc cag aag tac cat tcc cgg agt aat aaa tcc agt<br>Asn Tyr Pro Ala Gln Lys Tyr His Ser Arg Ser Asn Lys Ser Ser<br>1165                    1170                  1175 | 3869 |
| tgg agc agc agt gat gag aag agg gga tcg aca cgt tcc gat cac<br>Trp Ser Ser Ser Asp Glu Lys Arg Gly Ser Thr Arg Ser Asp His<br>1180                    1185                  1190 | 3914 |
| aac acc agt acc agc acg aag agc ctc ctc ccg aaa gag tct cgg<br>Asn Thr Ser Thr Ser Thr Lys Ser Leu Leu Pro Lys Glu Ser Arg<br>1195                    1200                  1205 | 3959 |
| ctg gac acc ttc tgg gac tagcagtgaa tcgggacaca aaccacccac<br>Leu Asp Thr Phe Trp Asp<br>1210 | 4007 |

```
cccattggga gaaaaccca gacgccagga aagaagaaa caacaaaggc aggagaacag      4067
ccactttcag acttgaaaat gacaaaaccc tcagttgagc ctgagccccc ggcgcggggg      4127
ctgctacact acaggacacc cagcatcggc tttgactgca gactgttcac ccacacgagc      4187
cctgtgcttt tggtgtaaat aatgtacaat ttgtggatgt cattgaatct agaggacttt      4247
ccccttttta tatttgtatt aactttaact tattaaaaa aaaaaagaa aagaaaaac       4307 gatttaaaaa aaaaaaaaaa aagcaaccaa ccccaacaac aaaaagaat gttttggtat      4367 tggagaaggg atggtcagtt agcctgtctg tcacacgacg gaatggatac tgggcccggg      4427
gaccactttc atactcacgt cctcatcctt ggatacccag ggagggcga accgttttcg      4487 ctcgtgtgtc tgtacgcagc atgttgggat cgggagtttc ggcacagact atcccatcaa      4547
gccgttggct cctttcagct actacgttac acgttccta aaacgcaagc tctccggacc      4607
agacggacac agggagaagc tagtttcttt catgtgattg aaatgatgac tctactccta      4667
aaagggaaaa aacaatatcc ttgtttacag aagagaaaca aacaagcccc actcagctca      4727
gtcacaggag agaacacaga aagtcttagg atcatgaact ctgaaaaaaa gagaaaccett      4787 atctttgctt tgtggttcct ttaaacacac tcacacacac ttggtcagag atgctgtgct      4847
tcttggaagc aaggactcaa aggcaaggtg cacgcagagg acgtttgagt ctgggatgaa      4907
gcatgtacgt attatttata tgatggaatt tcacgttttt atgtaagcat gaaacacagg      4967
```

```
cagtatgaga gaaagcaagg cccgtcatgc tgtccgtaca ctacgtatgc ttgtagagcc    5027
attttgtatg ttgtgtaaaa caaaaagcat tgatgaaaaa gcaaaggtg atgtatgtat    5087 atgagaaaat taattgtacg atatcattcc agtacgtttt gttgtacatt ttagtcttgt    5147
ttactttctc ttcattgtta agaggatgcg aactgtacag tttccagcta gttacccata    5207
ttagagaaga aataagagag t                                               5228
```

<210> SEQ ID NO 24
<211> LENGTH: 1214
<212> TYPE: PRT
<213> ORGANISM: Homo sapiens

<400> SEQUENCE: 24

```
Met Asp Ile Ser Thr Arg Ser Lys Asp Pro Gly Ser Ala Glu Arg Thr
1               5                   10                  15

Ala Gln Lys Arg Lys Phe Pro Ser Pro His Ser Ser Asn Gly His
            20                  25                  30

Ser Pro Gln Asp Thr Ser Thr Ser Pro Ile Lys Lys Lys Lys Pro
        35                  40                  45

Gly Leu Leu Asn Ser Asn Asn Lys Glu Gln Ser Glu Leu Arg His Gly
 50                  55                  60

Pro Phe Tyr Tyr Met Lys Gln Pro Leu Thr Thr Asp Pro Val Asp Val
65                  70                  75                  80

Val Pro Gln Asp Gly Arg Asn Asp Phe Tyr Cys Trp Val Cys His Arg
                85                  90                  95

Glu Gly Gln Val Leu Cys Cys Glu Leu Cys Pro Arg Val Tyr His Ala
            100                 105                 110

Lys Cys Leu Arg Leu Thr Ser Glu Pro Glu Gly Asp Trp Phe Cys Pro
        115                 120                 125

Glu Cys Glu Lys Ile Thr Val Ala Glu Cys Ile Glu Thr Gln Ser Lys
130                 135                 140

Ala Met Thr Met Leu Thr Ile Glu Gln Leu Ser Tyr Leu Leu Lys Phe
145                 150                 155                 160

Ala Ile Gln Lys Met Lys Gln Pro Gly Thr Asp Ala Phe Gln Lys Pro
                165                 170                 175

Val Pro Leu Glu Gln His Pro Asp Tyr Ala Glu Tyr Ile Phe His Pro
            180                 185                 190

Met Asp Leu Cys Thr Leu Glu Lys Asn Ala Lys Lys Met Tyr Gly
        195                 200                 205

Cys Thr Glu Ala Phe Leu Ala Asp Ala Lys Trp Ile Leu His Asn Cys
210                 215                 220

Ile Ile Tyr Asn Gly Gly Asn His Lys Leu Thr Gln Ile Ala Lys Val
225                 230                 235                 240

Val Ile Lys Ile Cys Glu His Glu Met Asn Glu Ile Glu Val Cys Pro
                245                 250                 255

Glu Cys Tyr Leu Ala Ala Cys Gln Lys Arg Asp Asn Trp Phe Cys Glu
            260                 265                 270

Pro Cys Ser Asn Pro His Pro Leu Val Trp Ala Lys Leu Lys Gly Phe
        275                 280                 285

Pro Phe Trp Pro Ala Lys Ala Leu Arg Asp Lys Asp Gly Gln Val Asp
290                 295                 300

Ala Arg Phe Phe Gly Gln His Asp Arg Ala Trp Val Pro Ile Asn Asn
305                 310                 315                 320
```

-continued

```
Cys Tyr Leu Met Ser Lys Glu Ile Pro Phe Ser Val Lys Lys Thr Lys
                325                 330                 335

Ser Ile Phe Asn Ser Ala Met Gln Glu Met Glu Val Tyr Val Glu Asn
            340                 345                 350

Ile Arg Arg Lys Phe Gly Val Phe Asn Tyr Ser Pro Phe Arg Thr Pro
        355                 360                 365

Tyr Thr Pro Asn Ser Gln Tyr Gln Met Leu Leu Asp Pro Thr Asn Pro
    370                 375                 380

Ser Ala Gly Thr Ala Lys Ile Asp Lys Gln Glu Lys Val Lys Leu Asn
385                 390                 395                 400

Phe Asp Met Thr Ala Ser Pro Lys Ile Leu Met Ser Lys Pro Val Leu
                405                 410                 415

Ser Gly Gly Thr Gly Arg Arg Ile Ser Leu Ser Asp Met Pro Arg Ser
            420                 425                 430

Pro Met Ser Thr Asn Ser Ser Val His Thr Gly Ser Asp Val Glu Gln
        435                 440                 445

Asp Ala Glu Lys Lys Ala Thr Ser Ser His Phe Ser Ala Ser Glu Glu
    450                 455                 460

Ser Met Asp Phe Leu Asp Lys Ser Thr Ala Ser Pro Ala Ser Thr Lys
465                 470                 475                 480

Thr Gly Gln Ala Gly Ser Leu Ser Gly Ser Pro Lys Pro Phe Ser Pro
                485                 490                 495

Gln Leu Ser Ala Pro Ile Thr Thr Lys Thr Asp Lys Thr Ser Thr Thr
            500                 505                 510

Gly Ser Ile Leu Asn Leu Asn Leu Asp Arg Ser Lys Ala Glu Met Asp
        515                 520                 525

Leu Lys Glu Leu Ser Glu Ser Val Gln Gln Gln Ser Thr Pro Val Pro
    530                 535                 540

Leu Ile Ser Pro Lys Arg Gln Ile Arg Ser Arg Phe Gln Leu Asn Leu
545                 550                 555                 560

Asp Lys Thr Ile Glu Ser Cys Lys Ala Gln Leu Gly Ile Asn Glu Ile
                565                 570                 575

Ser Glu Asp Val Tyr Thr Ala Val Glu His Ser Asp Ser Glu Asp Ser
            580                 585                 590

Glu Lys Ser Asp Ser Ser Asp Ser Glu Tyr Ile Ser Asp Asp Glu Gln
        595                 600                 605

Lys Ser Lys Asn Glu Pro Glu Asp Thr Glu Asp Lys Glu Gly Cys Gln
    610                 615                 620

Met Asp Lys Glu Pro Ser Ala Val Lys Lys Pro Lys Pro Thr Asn
625                 630                 635                 640

Pro Val Glu Ile Lys Glu Glu Leu Lys Ser Thr Ser Pro Ala Ser Glu
                645                 650                 655

Lys Ala Asp Pro Gly Ala Val Lys Asp Lys Ala Ser Pro Glu Pro Glu
            660                 665                 670

Lys Asp Phe Ser Glu Lys Ala Lys Pro Ser Pro His Pro Ile Lys Asp
        675                 680                 685

Lys Leu Lys Gly Lys Asp Glu Thr Asp Ser Pro Thr Val His Leu Gly
    690                 695                 700

Leu Asp Ser Asp Ser Glu Ser Glu Leu Val Ile Asp Leu Gly Glu Asp
705                 710                 715                 720

His Ser Gly Arg Glu Gly Arg Lys Asn Lys Glu Pro Lys Glu Pro
                725                 730                 735

Ser Pro Lys Gln Asp Val Val Gly Lys Thr Pro Pro Ser Thr Thr Val
```

-continued

```
            740                 745                 750
Gly Ser His Ser Pro Pro Glu Thr Pro Val Leu Thr Arg Ser Ser Ala
            755                 760                 765
Gln Thr Ser Ala Ala Gly Ala Thr Ala Thr Thr Ser Thr Ser Ser Thr
            770                 775                 780
Val Thr Val Thr Ala Pro Ala Pro Ala Ala Thr Gly Ser Pro Val Lys
785                 790                 795                 800
Lys Gln Arg Pro Leu Leu Pro Lys Glu Thr Ala Pro Ala Val Gln Arg
                    805                 810                 815
Val Val Trp Asn Ser Ser Lys Phe Gln Thr Ser Ser Gln Lys Trp
                    820                 825                 830
His Met Gln Lys Met Gln Arg Gln Gln Gln Gln Gln Gln Gln Asn
                    835                 840                 845
Gln Gln Gln Gln Pro Gln Ser Ser Gln Gly Thr Arg Tyr Gln Thr Arg
            850                 855                 860
Gln Ala Val Lys Ala Val Gln Gln Lys Glu Ile Thr Gln Ser Pro Ser
865                 870                 875                 880
Thr Ser Thr Ile Thr Leu Val Ser Thr Gln Ser Ser Pro Leu Val
                    885                 890                 895
Thr Ser Ser Gly Ser Met Ser Thr Leu Val Ser Ser Val Asn Ala Asp
                    900                 905                 910
Leu Pro Ile Ala Thr Ala Ser Ala Asp Val Ala Ala Asp Ile Ala Lys
                    915                 920                 925
Tyr Thr Ser Lys Met Met Asp Ala Ile Lys Gly Thr Met Thr Glu Ile
            930                 935                 940
Tyr Asn Asp Leu Ser Lys Asn Thr Thr Gly Ser Thr Ile Ala Glu Ile
945                 950                 955                 960
Arg Arg Leu Arg Ile Glu Ile Glu Lys Leu Gln Trp Leu His Gln Gln
                    965                 970                 975
Glu Leu Ser Glu Met Lys His Asn Leu Glu Leu Thr Met Ala Glu Met
                    980                 985                 990
Arg Gln Ser Leu Glu Gln Glu Arg Asp Arg Leu Ile Ala Glu Val Lys
            995                 1000                1005
Lys Gln Leu Glu Leu Glu Lys Gln Gln Ala Val Asp Glu Thr Lys
            1010                1015                1020
Lys Lys Gln Trp Cys Ala Asn Cys Lys Lys Glu Ala Ile Phe Tyr
            1025                1030                1035
Cys Cys Trp Asn Thr Ser Tyr Cys Asp Tyr Pro Cys Gln Gln Ala
            1040                1045                1050
His Trp Pro Glu His Met Lys Ser Cys Thr Gln Ser Ala Thr Ala
            1055                1060                1065
Pro Gln Gln Glu Ala Asp Ala Glu Val Asn Thr Glu Thr Leu Asn
            1070                1075                1080
Lys Ser Ser Gln Gly Ser Ser Ser Ser Thr Gln Ser Ala Pro Ser
            1085                1090                1095
Glu Thr Ala Ser Ala Ser Lys Glu Lys Glu Thr Ser Ala Glu Lys
            1100                1105                1110
Ser Lys Glu Ser Gly Ser Thr Leu Asp Leu Ser Gly Ser Arg Glu
            1115                1120                1125
Thr Pro Ser Ser Ile Leu Leu Gly Ser Asn Gln Gly Ser Val Ser
            1130                1135                1140
Lys Arg Cys Asp Lys Gln Pro Ala Tyr Ala Pro Thr Thr Thr Asp
            1145                1150                1155
```

-continued

```
His Gln Pro His Pro Asn Tyr Pro Ala Gln Lys Tyr His Ser Arg
    1160                1165                1170
Ser Asn Lys Ser Ser Trp Ser Ser Asp Glu Lys Arg Gly Ser
    1175                1180                1185
Thr Arg Ser Asp His Asn Thr Ser Thr Ser Thr Lys Ser Leu Leu
    1190                1195                1200
Pro Lys Glu Ser Arg Leu Asp Thr Phe Trp Asp
    1205                1210
```

<210> SEQ ID NO 25
<211> LENGTH: 1251
<212> TYPE: DNA
<213> ORGANISM: Homo sapiens
<220> FEATURE:
<221> NAME/KEY: CDS
<222> LOCATION: (60)..(1136)
<223> OTHER INFORMATION:

<400> SEQUENCE: 25

```
cttgaagaag tctttttttg acgtttaatc aattatatta tgggaaattg cttctgaat         59 atg agg tgg aaa agc ata gct cac tct gta ata ggc tat ttt cat gat        107
Met Arg Trp Lys Ser Ile Ala His Ser Val Ile Gly Tyr Phe His Asp
1               5                   10                  15 ttc aag tgg ttt tat gaa gaa aca gaa agc agt gat gat gtt gaa gtg        155
Phe Lys Trp Phe Tyr Glu Glu Thr Glu Ser Ser Asp Asp Val Glu Val
                20                  25                  30 ctg act ctc aag aaa ttc aaa gga gac ctg gcc tac aga cga caa gag        203
Leu Thr Leu Lys Lys Phe Lys Gly Asp Leu Ala Tyr Arg Arg Gln Glu
            35                  40                  45 tat cag aaa gca ctg cag gag tat tcc agt atc tct gaa aaa ttg tca        251
Tyr Gln Lys Ala Leu Gln Glu Tyr Ser Ser Ile Ser Glu Lys Leu Ser
        50                  55                  60 tca acc aat ttt gcc atg aaa agg gat gtc cag gaa ggt cag gct cgg        299
Ser Thr Asn Phe Ala Met Lys Arg Asp Val Gln Glu Gly Gln Ala Arg
65                  70                  75                  80 tgt ctg gct cac ctg ggt agg cat atg gag gcg ctg gag att gct gca        347
Cys Leu Ala His Leu Gly Arg His Met Glu Ala Leu Glu Ile Ala Ala
                85                  90                  95 aac ttg gaa aat aaa gca acc aac aca gac cat tta acc acg gta ctc        395
Asn Leu Glu Asn Lys Ala Thr Asn Thr Asp His Leu Thr Thr Val Leu
            100                 105                 110 tac ctc cag ctt gct att tgt tca agt ttg cag aac ttg gag aaa aca        443
Tyr Leu Gln Leu Ala Ile Cys Ser Ser Leu Gln Asn Leu Glu Lys Thr
        115                 120                 125 att ttc tgc ctg cag aaa ctg att tct ttg cat cct ttt aat cct tgg        491
Ile Phe Cys Leu Gln Lys Leu Ile Ser Leu His Pro Phe Asn Pro Trp
130                 135                 140 aac tgg ggc aaa ttg gca gag gct tac ctg aat ctg ggg cca gct ctt        539
Asn Trp Gly Lys Leu Ala Glu Ala Tyr Leu Asn Leu Gly Pro Ala Leu
145                 150                 155                 160 tca gca gca ctt gcg tca tct cag aaa cag cac agt ttc acc tca agt        587
Ser Ala Ala Leu Ala Ser Ser Gln Lys Gln His Ser Phe Thr Ser Ser
                165                 170                 175 gac aaa act atc aaa tcc ttc ttt cca cac tca gga aaa gac tgt ctt        635
Asp Lys Thr Ile Lys Ser Phe Phe Pro His Ser Gly Lys Asp Cys Leu
            180                 185                 190 ttg tgt ttt cct gaa acc ttg cct gag agc tct tta ttt tct gtg gaa        683
Leu Cys Phe Pro Glu Thr Leu Pro Glu Ser Ser Leu Phe Ser Val Glu
        195                 200                 205
```

```
gcg aat agc agt aat agc cag aaa aat gag aaa gct ctg aca aat atc       731
Ala Asn Ser Ser Asn Ser Gln Lys Asn Glu Lys Ala Leu Thr Asn Ile
    210                 215                 220 caa aac tgt atg gca gaa aag aga gaa aca gtg ttg ata gag act cag       779
Gln Asn Cys Met Ala Glu Lys Arg Glu Thr Val Leu Ile Glu Thr Gln
225                 230                 235                 240 ctg aaa gca tgt gcc tct ttt ata cga acc agg ctt ctg ctt cag ttt       827
Leu Lys Ala Cys Ala Ser Phe Ile Arg Thr Arg Leu Leu Leu Gln Phe
                245                 250                 255 acc caa cct cag caa aca tcg ttt gct ttg gag agg aac tta agg act       875
Thr Gln Pro Gln Gln Thr Ser Phe Ala Leu Glu Arg Asn Leu Arg Thr
            260                 265                 270 cag cag gaa att gaa gat aaa atg aaa ggg ttc agc ttc aaa gaa gac       923
Gln Gln Glu Ile Glu Asp Lys Met Lys Gly Phe Ser Phe Lys Glu Asp
        275                 280                 285 act ttg ctg ttg ata gct gag gtt atg gga gaa gat atc cca gaa aaa       971
Thr Leu Leu Leu Ile Ala Glu Val Met Gly Glu Asp Ile Pro Glu Lys
    290                 295                 300 ata aaa gat gaa gtt cac cca gag gtg aag tgt gtt ggc tcc gta gcc      1019
Ile Lys Asp Glu Val His Pro Glu Val Lys Cys Val Gly Ser Val Ala
305                 310                 315                 320 ctg act gcc ttg gtg act gta tcc tca gaa gaa ttt gaa gac aag tgg      1067
Leu Thr Ala Leu Val Thr Val Ser Ser Glu Glu Phe Glu Asp Lys Trp
                325                 330                 335 ttc aga aag atc aaa gac cat ttc tgt cca ttt gaa aat cag ttc cat      1115
Phe Arg Lys Ile Lys Asp His Phe Cys Pro Phe Glu Asn Gln Phe His
                340                 345                 350 aca gag ata caa atc ttg gct tagtgggtta taaaaaacaa aaccacaaat         1166
Thr Glu Ile Gln Ile Leu Ala
            355 atcttgtact gtattaattg tccttgttta cttcagacag gatccattgc taatcatgga    1226 gtataaatga ttatttatgt tttat                                          1251

<210> SEQ ID NO 26
<211> LENGTH: 359
<212> TYPE: PRT
<213> ORGANISM: Homo sapiens

<400> SEQUENCE: 26

Met Arg Trp Lys Ser Ile Ala His Ser Val Ile Gly Tyr Phe His Asp
1               5                   10                  15

Phe Lys Trp Phe Tyr Glu Glu Thr Glu Ser Ser Asp Asp Val Glu Val
                20                  25                  30

Leu Thr Leu Lys Lys Phe Lys Gly Asp Leu Ala Tyr Arg Arg Gln Glu
            35                  40                  45

Tyr Gln Lys Ala Leu Gln Glu Tyr Ser Ser Ile Ser Glu Lys Leu Ser
        50                  55                  60

Ser Thr Asn Phe Ala Met Lys Arg Asp Val Gln Glu Gly Gln Ala Arg
65                  70                  75                  80

Cys Leu Ala His Leu Gly Arg His Met Glu Ala Leu Glu Ile Ala Ala
                85                  90                  95

Asn Leu Glu Asn Lys Ala Thr Asn Thr Asp His Leu Thr Thr Val Leu
            100                 105                 110

Tyr Leu Gln Leu Ala Ile Cys Ser Ser Leu Gln Asn Leu Glu Lys Thr
        115                 120                 125

Ile Phe Cys Leu Gln Lys Leu Ile Ser Leu His Pro Phe Asn Pro Trp
    130                 135                 140
```

```
Asn Trp Gly Lys Leu Ala Glu Ala Tyr Leu Asn Leu Gly Pro Ala Leu
145                 150                 155                 160

Ser Ala Leu Ala Ser Ser Gln Lys Gln His Ser Phe Thr Ser Ser
                165                 170                 175

Asp Lys Thr Ile Lys Ser Phe Pro His Ser Gly Lys Asp Cys Leu
            180                 185                 190

Leu Cys Phe Pro Glu Thr Leu Pro Glu Ser Ser Leu Phe Ser Val Glu
        195                 200                 205

Ala Asn Ser Ser Asn Ser Gln Lys Asn Glu Lys Ala Leu Thr Asn Ile
    210                 215                 220

Gln Asn Cys Met Ala Glu Lys Arg Glu Thr Val Leu Ile Glu Thr Gln
225                 230                 235                 240

Leu Lys Ala Cys Ala Ser Phe Ile Arg Thr Arg Leu Leu Leu Gln Phe
                245                 250                 255

Thr Gln Pro Gln Gln Thr Ser Phe Ala Leu Glu Arg Asn Leu Arg Thr
            260                 265                 270

Gln Gln Glu Ile Glu Asp Lys Met Lys Gly Phe Ser Phe Lys Glu Asp
        275                 280                 285

Thr Leu Leu Ile Ala Glu Val Met Gly Glu Asp Ile Pro Glu Lys
290                 295                 300

Ile Lys Asp Glu Val His Pro Glu Val Lys Cys Val Gly Ser Val Ala
305                 310                 315                 320

Leu Thr Ala Leu Val Thr Val Ser Ser Glu Glu Phe Glu Asp Lys Trp
                325                 330                 335

Phe Arg Lys Ile Lys Asp His Phe Cys Pro Phe Glu Asn Gln Phe His
            340                 345                 350

Thr Glu Ile Gln Ile Leu Ala
        355

<210> SEQ ID NO 27
<211> LENGTH: 4079
<212> TYPE: DNA
<213> ORGANISM: Homo sapiens
<220> FEATURE:
<221> NAME/KEY: CDS
<222> LOCATION: (24)..(3269)
<223> OTHER INFORMATION:

<400> SEQUENCE: 27
ggtagtgacc ctcgggcctc gcc atg aag agc cgc ttt agc acc att gac ctc     53
                         Met Lys Ser Arg Phe Ser Thr Ile Asp Leu
                           1               5                  10 cgc gcc gta ctc gcg gag ctg aat gct agc ttg cta gga atg aga gta      101
Arg Ala Val Leu Ala Glu Leu Asn Ala Ser Leu Leu Gly Met Arg Val
                15                  20                  25 aac aat gtt tat gat gtg gat aat aag aca tac ctt att cgt ctt caa      149
Asn Asn Val Tyr Asp Val Asp Asn Lys Thr Tyr Leu Ile Arg Leu Gln
            30                  35                  40 aaa ccg gac ttt aaa gct aca ctt tta ctt gaa tct ggc ata cga att      197
Lys Pro Asp Phe Lys Ala Thr Leu Leu Leu Glu Ser Gly Ile Arg Ile
        45                  50                  55 cat aca aca gaa ttt gag tgg cct aag aat atg atg ccg tct agt ttt      245
His Thr Thr Glu Phe Glu Trp Pro Lys Asn Met Met Pro Ser Ser Phe
    60                  65                  70 gcc atg aag tgc cga aaa cat ttg aag agt cgg aga tta gtc agt gca      293
Ala Met Lys Cys Arg Lys His Leu Lys Ser Arg Arg Leu Val Ser Ala
75                  80                  85                  90 aaa cag ctt ggt gtg gat aga att gta gat ttt caa ttt gga agt gat      341
```

-continued

| | | | | | | | | | | | | | | |
|---|---|---|---|---|---|---|---|---|---|---|---|---|---|---|
| Lys | Gln | Leu | Gly | Val | Asp | Arg | Ile | Val | Asp | Phe | Gln | Phe | Gly | Ser | Asp |
| | | | 95 | | | | | 100 | | | | | 105 | | |

```
gaa gct gct tac cat tta atc att gag ctc tat gat agg ggg aac att      389
Glu Ala Ala Tyr His Leu Ile Ile Glu Leu Tyr Asp Arg Gly Asn Ile
            110                 115                 120 gtt ctt aca gat tat gag tac gta att tta aat att cta agg ttt cga      437
Val Leu Thr Asp Tyr Glu Tyr Val Ile Leu Asn Ile Leu Arg Phe Arg
        125                 130                 135 act gat gag gca gat gat gtt aaa ttt gct gtt cgt gaa cgc tat cca      485
Thr Asp Glu Ala Asp Asp Val Lys Phe Ala Val Arg Glu Arg Tyr Pro
    140                 145                 150 ctt gat cat gct aga gct gct gaa cct ttg ctt act ttg gaa agg ttg      533
Leu Asp His Ala Arg Ala Ala Glu Pro Leu Leu Thr Leu Glu Arg Leu
155                 160                 165                 170 act gaa ata gta gcc agc gca cct aag ggt gaa cta ctg aag agg gtg      581
Thr Glu Ile Val Ala Ser Ala Pro Lys Gly Glu Leu Leu Lys Arg Val
                175                 180                 185 ctt aac cca tta ctt ccc tat gga cca gct ctc att gaa cac tgt ctt      629
Leu Asn Pro Leu Leu Pro Tyr Gly Pro Ala Leu Ile Glu His Cys Leu
            190                 195                 200 tta gaa aat gga ttc tcg ggt aat gtc aaa gtg gat gaa aaa ctt gaa      677
Leu Glu Asn Gly Phe Ser Gly Asn Val Lys Val Asp Glu Lys Leu Glu
        205                 210                 215 act aaa gat att gaa aaa gta ctt gtt tct ctg cag aaa gca gaa gac      725
Thr Lys Asp Ile Glu Lys Val Leu Val Ser Leu Gln Lys Ala Glu Asp
    220                 225                 230 tat atg aaa aca aca tcc aac ttc agt ggg aag gga tat atc att cag      773
Tyr Met Lys Thr Thr Ser Asn Phe Ser Gly Lys Gly Tyr Ile Ile Gln
235                 240                 245                 250 aaa aga gaa ata aaa cca tgc ttg gaa gca gat aaa cca gtt gaa gac      821
Lys Arg Glu Ile Lys Pro Cys Leu Glu Ala Asp Lys Pro Val Glu Asp
                255                 260                 265 ata ctg acg tat gag gaa ttt cat cct ttc ttg ttt tct caa cat tca      869
Ile Leu Thr Tyr Glu Glu Phe His Pro Phe Leu Phe Ser Gln His Ser
            270                 275                 280 caa tgt cca tat ata gaa ttt gaa tca ttt gac aag gcg gtg gat gaa      917
Gln Cys Pro Tyr Ile Glu Phe Glu Ser Phe Asp Lys Ala Val Asp Glu
        285                 290                 295 ttt tat tcc aag ata gaa ggc cag aaa att gac tta aaa gct tta caa      965
Phe Tyr Ser Lys Ile Glu Gly Gln Lys Ile Asp Leu Lys Ala Leu Gln
    300                 305                 310 cag gaa aag caa gca ttg aag aaa tta gat aat gtt cga aag gat cac     1013
Gln Glu Lys Gln Ala Leu Lys Lys Leu Asp Asn Val Arg Lys Asp His
315                 320                 325                 330 gaa aac aga ttg gaa gct ctt cag cag gct cag gaa ata gac aaa ctg     1061
Glu Asn Arg Leu Glu Ala Leu Gln Gln Ala Gln Glu Ile Asp Lys Leu
                335                 340                 345 aaa gga gag ctc ata gaa atg aac cta caa ata gtt gac aga gcc att     1109
Lys Gly Glu Leu Ile Glu Met Asn Leu Gln Ile Val Asp Arg Ala Ile
            350                 355                 360 cag gta gtt cga agt gct tta gct aac cag ata gat tgg aca gaa att     1157
Gln Val Val Arg Ser Ala Leu Ala Asn Gln Ile Asp Trp Thr Glu Ile
        365                 370                 375 ggg tta att gtg aaa gaa gcc cag gct caa gga gac cct gtt gca agt     1205
Gly Leu Ile Val Lys Glu Ala Gln Ala Gln Gly Asp Pro Val Ala Ser
    380                 385                 390 gca atc aaa gaa tta aaa cta caa aca aac cat gtt aca atg ctg cta     1253
Ala Ile Lys Glu Leu Lys Leu Gln Thr Asn His Val Thr Met Leu Leu
395                 400                 405                 410
```

-continued

| | | |
|---|---|---|
| aga aat cca tac ttg tta tca gag gag gaa gat gat gat gtt gat ggt<br>Arg Asn Pro Tyr Leu Leu Ser Glu Glu Glu Asp Asp Asp Val Asp Gly<br>                  415                  420                  425 | 1301 |
| gac gtc aat gtt gag aaa aat gaa act gaa cca cca aaa gga aaa aag<br>Asp Val Asn Val Glu Lys Asn Glu Thr Glu Pro Pro Lys Gly Lys Lys<br>                  430                  435                  440 | 1349 |
| aaa aaa caa aag aat aaa cag ctg cag aag cct cag aaa aat aag ccc<br>Lys Lys Gln Lys Asn Lys Gln Leu Gln Lys Pro Gln Lys Asn Lys Pro<br>                  445                  450                  455 | 1397 |
| tta ctt gta gat gtt gat ctc agc ttg tca gca tat gcc aat gcc aaa<br>Leu Leu Val Asp Val Asp Leu Ser Leu Ser Ala Tyr Ala Asn Ala Lys<br>460                      465                  470 | 1445 |
| aag tat tat gat cac aag aga tat gct gct aag aaa aca caa aag act<br>Lys Tyr Tyr Asp His Lys Arg Tyr Ala Ala Lys Lys Thr Gln Lys Thr<br>475                      480                  485                  490 | 1493 |
| gtt gaa gct gct gag aag gca ttc aag tca gca gaa aag aaa aca aag<br>Val Glu Ala Ala Glu Lys Ala Phe Lys Ser Ala Glu Lys Lys Thr Lys<br>                  495                  500                  505 | 1541 |
| caa aca tta aaa gaa gtt cag act gtt acc tct att caa aaa gca aga<br>Gln Thr Leu Lys Glu Val Gln Thr Val Thr Ser Ile Gln Lys Ala Arg<br>                  510                  515                  520 | 1589 |
| aaa gta tat tgg ttt gag aaa ttt ctg tgg ttc att agc tca gag aac<br>Lys Val Tyr Trp Phe Glu Lys Phe Leu Trp Phe Ile Ser Ser Glu Asn<br>                  525                  530                  535 | 1637 |
| tat cta att ata ggt gga cga gat cag caa cag aat gaa ata att gtg<br>Tyr Leu Ile Ile Gly Gly Arg Asp Gln Gln Gln Asn Glu Ile Ile Val<br>540                      545                  550 | 1685 |
| aaa aga tac ttg aca cca gga gac att tat gta cat gct gat ctt cat<br>Lys Arg Tyr Leu Thr Pro Gly Asp Ile Tyr Val His Ala Asp Leu His<br>555                      560                  565                  570 | 1733 |
| gga gct act agc tgt gta att aag aat cca aca gga gaa ccc atc ccc<br>Gly Ala Thr Ser Cys Val Ile Lys Asn Pro Thr Gly Glu Pro Ile Pro<br>                  575                  580                  585 | 1781 |
| cca cgg acc ttg act gaa gct ggc aca atg gca ctt tgc tac agt gct<br>Pro Arg Thr Leu Thr Glu Ala Gly Thr Met Ala Leu Cys Tyr Ser Ala<br>                  590                  595                  600 | 1829 |
| gct tgg gat gca cga gtt atc act agt gct tgg tgg gtg tac cat cat<br>Ala Trp Asp Ala Arg Val Ile Thr Ser Ala Trp Trp Val Tyr His His<br>                  605                  610                  615 | 1877 |
| cag gta tct aaa aca gca cca act gga gaa tat ttg aca aca gga agc<br>Gln Val Ser Lys Thr Ala Pro Thr Gly Glu Tyr Leu Thr Thr Gly Ser<br>                  620                  625                  630 | 1925 |
| ttc atg ata aga gga aaa aag aat ttt ctt cct ccc tca tat cta atg<br>Phe Met Ile Arg Gly Lys Lys Asn Phe Leu Pro Pro Ser Tyr Leu Met<br>635                      640                  645                  650 | 1973 |
| atg ggg ttt agc ttc ctt ttt aag gta gat gag tct tgt gtt tgg aga<br>Met Gly Phe Ser Phe Leu Phe Lys Val Asp Glu Ser Cys Val Trp Arg<br>                  655                  660                  665 | 2021 |
| cat cag ggt gaa cga aaa gtc aga gta cag gat gaa gac atg gag aca<br>His Gln Gly Glu Arg Lys Val Arg Val Gln Asp Glu Asp Met Glu Thr<br>                  670                  675                  680 | 2069 |
| ctg gca agt tgt aca agt gaa ctc ata tca gaa gaa atg gaa caa tta<br>Leu Ala Ser Cys Thr Ser Glu Leu Ile Ser Glu Glu Met Glu Gln Leu<br>                  685                  690                  695 | 2117 |
| gat gga ggt gac acg agc agt gat gag gat aaa gaa gaa cat gaa act<br>Asp Gly Gly Asp Thr Ser Ser Asp Glu Asp Lys Glu Glu His Glu Thr<br>700                      705                  710 | 2165 |
| cct gtg gaa gta gaa ctc atg act cag gtt gac caa gag gat atc act<br>Pro Val Glu Val Glu Leu Met Thr Gln Val Asp Gln Glu Asp Ile Thr<br>715                      720                  725                  730 | 2213 |

```
ctt cag agt ggc aga gat gaa cta aat gag gag ctc att cag gaa gaa        2261
Leu Gln Ser Gly Arg Asp Glu Leu Asn Glu Glu Leu Ile Gln Glu Glu
            735                 740                 745 agc tct gaa gac gaa gga gaa tat gaa gag gtt aga aaa gat cag gat        2309
Ser Ser Glu Asp Glu Gly Glu Tyr Glu Glu Val Arg Lys Asp Gln Asp
            750                 755                 760 tct gtt ggt gaa atg aag gat gaa ggg gaa gag aca tta aat tat cct        2357
Ser Val Gly Glu Met Lys Asp Glu Gly Glu Glu Thr Leu Asn Tyr Pro
            765                 770                 775 gat act acc att gac ttg tct cac ctt caa ccc caa agg tcc atc cag        2405
Asp Thr Thr Ile Asp Leu Ser His Leu Gln Pro Gln Arg Ser Ile Gln
            780                 785                 790 aaa ttg gct tca aaa gag gaa tct tct aat tct agt gac agt aaa tca        2453
Lys Leu Ala Ser Lys Glu Glu Ser Ser Asn Ser Ser Asp Ser Lys Ser
795                 800                 805                 810 cag agc cgg aga cat ttg tca gcc aag gaa aga agg gaa atg aaa aag        2501
Gln Ser Arg Arg His Leu Ser Ala Lys Glu Arg Arg Glu Met Lys Lys
                815                 820                 825 aaa aaa ctt cca agt gac tca gga gat tta gaa gcg tta gag gga aag        2549
Lys Lys Leu Pro Ser Asp Ser Gly Asp Leu Glu Ala Leu Glu Gly Lys
            830                 835                 840 gat aaa gaa aaa gaa agt act gta cac att gaa act cat cag aac aca        2597
Asp Lys Glu Lys Glu Ser Thr Val His Ile Glu Thr His Gln Asn Thr
            845                 850                 855 agc aaa aat gtt gcg gct gtg cag cca atg aaa cga gga caa aag agt        2645
Ser Lys Asn Val Ala Ala Val Gln Pro Met Lys Arg Gly Gln Lys Ser
            860                 865                 870 aaa atg aaa aaa atg aaa gaa aaa tac aaa gac cag gat gaa gaa gac        2693
Lys Met Lys Lys Met Lys Glu Lys Tyr Lys Asp Gln Asp Glu Glu Asp
875                 880                 885                 890 cgt gaa ctt atc atg aag ttg ctg ggg tct gca ggt tca aac aaa gaa        2741
Arg Glu Leu Ile Met Lys Leu Leu Gly Ser Ala Gly Ser Asn Lys Glu
                895                 900                 905 gaa aaa ggg aag aag ggg aag aaa gga aaa aca aag gac gaa cct gtg        2789
Glu Lys Gly Lys Lys Gly Lys Lys Gly Lys Thr Lys Asp Glu Pro Val
            910                 915                 920 aag aaa cag ccc cag aaa cct aga ggt gga cag agg gtc tct gac aac        2837
Lys Lys Gln Pro Gln Lys Pro Arg Gly Gly Gln Arg Val Ser Asp Asn
            925                 930                 935 att aag aaa gaa act ccg ttc ctt gag gtt ata act cat gag tta caa        2885
Ile Lys Lys Glu Thr Pro Phe Leu Glu Val Ile Thr His Glu Leu Gln
            940                 945                 950 gac ttt gct gta gat gat cca cat gat gac aag gaa gag caa gat ctg        2933
Asp Phe Ala Val Asp Asp Pro His Asp Asp Lys Glu Glu Gln Asp Leu
955                 960                 965                 970 gat caa cag gga aat gag gaa aac cta ttt gat tct ttg aca ggc cag        2981
Asp Gln Gln Gly Asn Glu Glu Asn Leu Phe Asp Ser Leu Thr Gly Gln
                975                 980                 985 cca cat cct gaa gat gta cta ctg ttt gcc att cca ata tgt gcc cct        3029
Pro His Pro Glu Asp Val Leu Leu Phe Ala Ile Pro Ile Cys Ala Pro
            990                 995                 1000 tac acc acc atg aca aac tac aaa tat aaa gtg aaa ctt act cct           3074
Tyr Thr Thr Met Thr Asn Tyr Lys Tyr Lys Val Lys Leu Thr Pro
            1005                1010                1015 gga gtg cag aaa aag gga aaa gct gca aaa aca gcc ttg aat agt           3119
Gly Val Gln Lys Lys Gly Lys Ala Ala Lys Thr Ala Leu Asn Ser
            1020                1025                1030 ttc atg cat tcc aaa gaa gca aca gca aga gaa aaa gac tta ttc           3164
Phe Met His Ser Lys Glu Ala Thr Ala Arg Glu Lys Asp Leu Phe
```

-continued

```
                        1035                  1040                  1045
cgc agc gta aag gac aca gat tta tca aga aac att cct ggc aaa           3209
Arg Ser Val Lys Asp Thr Asp Leu Ser Arg Asn Ile Pro Gly Lys
        1050                1055                1060 gtg aaa agt gtc tgc acc caa tct tct gaa cgt aaa aag gaa ata           3254
Val Lys Ser Val Cys Thr Gln Ser Ser Glu Arg Lys Lys Glu Ile
        1065                1070                1075 gct gaa atg aaa ttc taaaatattt gagaagagcc aattttatag cctttggaa        3309
Ala Glu Met Lys Phe
        1080 gttcaaagat gaaagcacca tgtatcagga tttccgcatt ataaaatga actaaacatt      3369
gccttgctat attcaccaaa aggacttaat tcttgttttt ttcccagttt tatatagagg     3429
aaacactgtc tatgatagga tttccaaaag tatttgtgga cagttaaatg ctaattatat     3489
acatctgtag ttattctaca ttttcttgaa atttgggagg ttaataccaa gtattcattt     3549
catgatgtaa agaaactgaa cagtgaagtg gcttgattgc ttaaactatt gacttggtaa     3609
gtctactgta taacatct aatatatata ttacaggcca aatgaactaa acattgcctt       3669
gctatattca ccaaaaggac ttaattcttg tttttttccc agttttatat agaggaaaca     3729
ctatgatagg atttcctaaa gtatttgtgg acagttaaat gctaattata tacatctgta     3789
gttattctac attttcttga aatttgagag gttaatacca gtattcatt tcatgatgta      3849
aagaaactga acagtgaagt ggcttgattg cttaaactat tgacttggta agtctactgt     3909
atataacatc taatatatat atattatagg ccagctacaa ggggtttaaa tatttaggat     3969
tgtgtcttga aaactaagta ttggagtgga ttttcttctg ctttcattga tacttgtcag     4029
aaaaaaatat tagaccaaaa tgtaaaatat aagtaataat tctcatgaaa                4079
```

<210> SEQ ID NO 28
<211> LENGTH: 1082
<212> TYPE: PRT
<213> ORGANISM: Homo sapiens

<400> SEQUENCE: 28

Met Lys Ser Arg Phe Ser Thr Ile Asp Leu Arg Ala Val Leu Ala Glu
1               5                   10                  15

Leu Asn Ala Ser Leu Leu Gly Met Arg Val Asn Asn Val Tyr Asp Val
            20                  25                  30

Asp Asn Lys Thr Tyr Leu Ile Arg Leu Gln Lys Pro Asp Phe Lys Ala
        35                  40                  45

Thr Leu Leu Leu Glu Ser Gly Ile Arg Ile His Thr Thr Glu Phe Glu
    50                  55                  60

Trp Pro Lys Asn Met Met Pro Ser Ser Phe Ala Met Lys Cys Arg Lys
65                  70                  75                  80

His Leu Lys Ser Arg Arg Leu Val Ser Ala Lys Gln Leu Gly Val Asp
                85                  90                  95

Arg Ile Val Asp Phe Gln Phe Gly Ser Asp Glu Ala Ala Tyr His Leu
            100                 105                 110

Ile Ile Glu Leu Tyr Asp Arg Gly Asn Ile Val Leu Thr Asp Tyr Glu
        115                 120                 125

Tyr Val Ile Leu Asn Ile Leu Arg Phe Arg Thr Asp Glu Ala Asp Asp
    130                 135                 140

Val Lys Phe Ala Val Arg Glu Arg Tyr Pro Leu Asp His Ala Arg Ala
145                 150                 155                 160

Ala Glu Pro Leu Leu Thr Leu Glu Arg Leu Thr Glu Ile Val Ala Ser

```
                165                 170                 175
Ala Pro Lys Gly Glu Leu Leu Lys Arg Val Leu Asn Pro Leu Leu Pro
                180                 185                 190

Tyr Gly Pro Ala Leu Ile Glu His Cys Leu Leu Glu Asn Gly Phe Ser
            195                 200                 205

Gly Asn Val Lys Val Asp Glu Lys Leu Glu Thr Lys Asp Ile Glu Lys
        210                 215                 220

Val Leu Val Ser Leu Gln Lys Ala Glu Asp Tyr Met Lys Thr Thr Ser
225                 230                 235                 240

Asn Phe Ser Gly Lys Gly Tyr Ile Ile Gln Lys Arg Glu Ile Lys Pro
                245                 250                 255

Cys Leu Glu Ala Asp Lys Pro Val Glu Asp Ile Leu Thr Tyr Glu Glu
            260                 265                 270

Phe His Pro Phe Leu Phe Ser Gln His Ser Gln Cys Pro Tyr Ile Glu
        275                 280                 285

Phe Glu Ser Phe Asp Lys Ala Val Asp Glu Phe Tyr Ser Lys Ile Glu
        290                 295                 300

Gly Gln Lys Ile Asp Leu Lys Ala Leu Gln Gln Glu Lys Gln Ala Leu
305                 310                 315                 320

Lys Lys Leu Asp Asn Val Arg Lys Asp His Glu Asn Arg Leu Glu Ala
                325                 330                 335

Leu Gln Gln Ala Gln Glu Ile Asp Lys Leu Lys Gly Glu Leu Ile Glu
            340                 345                 350

Met Asn Leu Gln Ile Val Asp Arg Ala Ile Gln Val Val Arg Ser Ala
        355                 360                 365

Leu Ala Asn Gln Ile Asp Trp Thr Glu Ile Gly Leu Ile Val Lys Glu
        370                 375                 380

Ala Gln Ala Gln Gly Asp Pro Val Ala Ser Ala Ile Lys Glu Leu Lys
385                 390                 395                 400

Leu Gln Thr Asn His Val Thr Met Leu Leu Arg Asn Pro Tyr Leu Leu
                405                 410                 415

Ser Glu Glu Asp Asp Asp Val Asp Gly Asp Val Asn Val Glu Lys
            420                 425                 430

Asn Glu Thr Glu Pro Pro Lys Gly Lys Lys Lys Gln Lys Asn Lys
        435                 440                 445

Gln Leu Gln Lys Pro Gln Lys Asn Lys Pro Leu Leu Val Asp Val Asp
450                 455                 460

Leu Ser Leu Ser Ala Tyr Ala Asn Ala Lys Lys Tyr Tyr Asp His Lys
465                 470                 475                 480

Arg Tyr Ala Ala Lys Thr Gln Lys Thr Val Glu Ala Ala Glu Lys
            485                 490                 495

Ala Phe Lys Ser Ala Glu Lys Lys Thr Lys Gln Thr Leu Lys Glu Val
        500                 505                 510

Gln Thr Val Thr Ser Ile Gln Lys Ala Arg Lys Val Tyr Trp Phe Glu
        515                 520                 525

Lys Phe Leu Trp Phe Ile Ser Ser Glu Asn Tyr Leu Ile Ile Gly Gly
        530                 535                 540

Arg Asp Gln Gln Gln Asn Glu Ile Ile Val Lys Arg Tyr Leu Thr Pro
545                 550                 555                 560

Gly Asp Ile Tyr Val His Ala Asp Leu His Gly Ala Thr Ser Cys Val
                565                 570                 575

Ile Lys Asn Pro Thr Gly Glu Pro Ile Pro Pro Arg Thr Leu Thr Glu
            580                 585                 590
```

-continued

```
Ala Gly Thr Met Ala Leu Cys Tyr Ser Ala Ala Trp Asp Ala Arg Val
        595                 600                 605
Ile Thr Ser Ala Trp Trp Val Tyr His His Gln Val Ser Lys Thr Ala
        610                 615                 620
Pro Thr Gly Glu Tyr Leu Thr Thr Gly Ser Phe Met Ile Arg Gly Lys
625                 630                 635                 640
Lys Asn Phe Leu Pro Pro Ser Tyr Leu Met Met Gly Phe Ser Phe Leu
                645                 650                 655
Phe Lys Val Asp Glu Ser Cys Val Trp Arg His Gln Gly Glu Arg Lys
                    660                 665                 670
Val Arg Val Gln Asp Glu Asp Met Glu Thr Leu Ala Ser Cys Thr Ser
            675                 680                 685
Glu Leu Ile Ser Glu Glu Met Glu Gln Leu Asp Gly Asp Thr Ser
        690                 695                 700
Ser Asp Glu Asp Lys Glu His Glu Thr Pro Val Glu Val Glu Leu
705                 710                 715                 720
Met Thr Gln Val Asp Gln Glu Asp Ile Thr Leu Gln Ser Gly Arg Asp
                    725                 730                 735
Glu Leu Asn Glu Glu Leu Ile Gln Glu Ser Ser Glu Asp Glu Gly
            740                 745                 750
Glu Tyr Glu Glu Val Arg Lys Asp Gln Asp Ser Val Gly Glu Met Lys
        755                 760                 765
Asp Glu Gly Glu Glu Thr Leu Asn Tyr Pro Asp Thr Thr Ile Asp Leu
770                 775                 780
Ser His Leu Gln Pro Gln Arg Ser Ile Gln Lys Leu Ala Ser Lys Glu
785                 790                 795                 800
Glu Ser Ser Asn Ser Ser Asp Ser Lys Ser Gln Ser Arg Arg His Leu
                805                 810                 815
Ser Ala Lys Glu Arg Arg Glu Met Lys Lys Lys Leu Pro Ser Asp
                    820                 825                 830
Ser Gly Asp Leu Glu Ala Leu Glu Gly Lys Asp Lys Glu Lys Glu Ser
            835                 840                 845
Thr Val His Ile Glu Thr His Gln Asn Thr Ser Lys Asn Val Ala Ala
        850                 855                 860
Val Gln Pro Met Lys Arg Gly Gln Lys Ser Lys Met Lys Lys Met Lys
865                 870                 875                 880
Glu Lys Tyr Lys Asp Gln Asp Glu Asp Arg Glu Leu Ile Met Lys
                    885                 890                 895
Leu Leu Gly Ser Ala Gly Ser Asn Lys Glu Lys Gly Lys Lys Gly
            900                 905                 910
Lys Lys Gly Lys Thr Lys Asp Glu Pro Val Lys Lys Gln Pro Gln Lys
        915                 920                 925
Pro Arg Gly Gly Gln Arg Val Ser Asp Asn Ile Lys Lys Glu Thr Pro
930                 935                 940
Phe Leu Glu Val Ile Thr His Glu Leu Gln Asp Phe Ala Val Asp Asp
945                 950                 955                 960
Pro His Asp Asp Lys Glu Glu Gln Asp Leu Asp Gln Gln Gly Asn Glu
                965                 970                 975
Glu Asn Leu Phe Asp Ser Leu Thr Gly Gln Pro His Pro Glu Asp Val
                980                 985                 990
Leu Leu Phe Ala Ile Pro Ile Cys  Ala Pro Tyr Thr Thr  Met Thr Asn
            995                 1000                1005
```

```
Tyr Lys Tyr Lys Val Lys Leu Thr Pro Gly Val Gln Lys Lys Gly
    1010            1015               1020

Lys Ala Ala Lys Thr Ala Leu Asn Ser Phe Met His Ser Lys Glu
    1025            1030               1035

Ala Thr Ala Arg Glu Lys Asp Leu Phe Arg Ser Val Lys Asp Thr
    1040            1045               1050

Asp Leu Ser Arg Asn Ile Pro Gly Lys Val Lys Ser Val Cys Thr
    1055            1060               1065

Gln Ser Ser Glu Arg Lys Lys Glu Ile Ala Glu Met Lys Phe
    1070            1075               1080

<210> SEQ ID NO 29
<211> LENGTH: 3438
<212> TYPE: DNA
<213> ORGANISM: Homo sapiens
<220> FEATURE:
<221> NAME/KEY: CDS
<222> LOCATION: (527)..(2701)
<223> OTHER INFORMATION:

<400> SEQUENCE: 29
ggttgtgggt cctctgtgag cagccctgtt aacctttaaa ccagcacggc cgccgcagct      60
gtgagcctag cacctgatca gtggagagct gtggattgca tgtttgtttg ccattgcccc    120
cgccaccctg caagttgcac cttctagaat cagcaagcca agctcctctc acccagcgta    180
atgatgcgga aatgcaaatg caccatcatg ttgtgaccca tattgcgaaa attagaaaaa    240
aggaagttgt gtttcgctat tgcacgaagt tcagcccaga ggagaaactc gctcgccttc    300
agaagacagt acctcctaaa tggctctact ttgaacctgc tgggcaagga agagattttc    360
aaggaaacca tctaccgtgt gcaagctcct gccggccaac cccagacccc agcacggagc    420
caggcgcctg tgcccgccaa ccctcagcat cctcctcaga aaggctggtg gcatcaggaa    480
gcccctggcc agcctccacc tgagcccagt gagctcagct ttaagg atg gag tca      535
                                                 Met Glu Ser
                                                   1 ggc agg ggg tcc tca acc cct cca gga ccc att gct gcc cta ggg atg     583
Gly Arg Gly Ser Ser Thr Pro Pro Gly Pro Ile Ala Ala Leu Gly Met
  5               10                  15 cca gac act ggg cct ggc agt tcc tcc cta ggg aag ctt cag gcg ctc     631
Pro Asp Thr Gly Pro Gly Ser Ser Ser Leu Gly Lys Leu Gln Ala Leu
 20               25                  30                  35 cct gtt ggg ccc aga gcc cac tgt ggg gac cct gtc agc ctg gct gca     679
Pro Val Gly Pro Arg Ala His Cys Gly Asp Pro Val Ser Leu Ala Ala
             40                  45                  50 gca ggg gac ggc tct cca gac ata ggc ccc acg gga gag ctg agt ggt     727
Ala Gly Asp Gly Ser Pro Asp Ile Gly Pro Thr Gly Glu Leu Ser Gly
         55                  60                  65 agc tta aag atc ccc aac cgg gac agc ggg atc gac agt cca tcc tcc     775
Ser Leu Lys Ile Pro Asn Arg Asp Ser Gly Ile Asp Ser Pro Ser Ser
     70                  75                  80 agt gtg gct gga gag aac ttt ccc tgc gag gag ggc ttg gag gct ggc     823
Ser Val Ala Gly Glu Asn Phe Pro Cys Glu Glu Gly Leu Glu Ala Gly
 85                  90                  95 cca agc ccc act gta ctg ggg gcg cac gca gag atg gcc ctg gac agc     871
Pro Ser Pro Thr Val Leu Gly Ala His Ala Glu Met Ala Leu Asp Ser
100                 105                 110                 115 cag gtc ccg aag gtc acc ccc cag gag gag gcg gac agc gac gtg ggt     919
Gln Val Pro Lys Val Thr Pro Gln Glu Glu Ala Asp Ser Asp Val Gly
            120                 125                 130
```

```
gag gaa cct gac tct gag aac acc ccc cag aag gct gac aag gat gcc      967
Glu Glu Pro Asp Ser Glu Asn Thr Pro Gln Lys Ala Asp Lys Asp Ala
        135                 140                 145 ggc ctg gcc cag cac tct ggc ccc cag aag ctt ctc cac att gcc cag     1015
Gly Leu Ala Gln His Ser Gly Pro Gln Lys Leu Leu His Ile Ala Gln
150                 155                 160 gag ctc ctg cac acc gag gag acc tat gtg aag cgg ctg cac ctg ctg     1063
Glu Leu Leu His Thr Glu Glu Thr Tyr Val Lys Arg Leu His Leu Leu
        165                 170                 175 gac cag gtt ttc tgc acc agg ctg acg gat gcg ggg atc cct cca gaa     1111
Asp Gln Val Phe Cys Thr Arg Leu Thr Asp Ala Gly Ile Pro Pro Glu
180                 185                 190                 195 gtc atc atg ggc ata ttc tct aac atc tcc tcc atc cac cgc ttc cac     1159
Val Ile Met Gly Ile Phe Ser Asn Ile Ser Ser Ile His Arg Phe His
        200                 205                 210 ggg cag ttc ctg ctg ccg gag ctg aag acg cgg atc acg gag gag tgg     1207
Gly Gln Phe Leu Leu Pro Glu Leu Lys Thr Arg Ile Thr Glu Glu Trp
        215                 220                 225 gac aca aac cca cgg ctc ggg gac atc ctg cag aag ctg gcc cca ttc     1255
Asp Thr Asn Pro Arg Leu Gly Asp Ile Leu Gln Lys Leu Ala Pro Phe
        230                 235                 240 ctg aag atg tac ggc gag tat gtc aag aac ttt gac cga gcc gta ggg     1303
Leu Lys Met Tyr Gly Glu Tyr Val Lys Asn Phe Asp Arg Ala Val Gly
245                 250                 255 ctg gtg agc acg tgg acc cag cgc tcc cca ctg ttt aaa gac gtc gtc     1351
Leu Val Ser Thr Trp Thr Gln Arg Ser Pro Leu Phe Lys Asp Val Val
260                 265                 270                 275 cac agc atc cag aag cag gag gta tgc ggg aac ctg acg ctg cag cac     1399
His Ser Ile Gln Lys Gln Glu Val Cys Gly Asn Leu Thr Leu Gln His
        280                 285                 290 cac atg ctg gag ccc gtg cag agg gtc ccc cgg tac gag ctg ctg ctc     1447
His Met Leu Glu Pro Val Gln Arg Val Pro Arg Tyr Glu Leu Leu Leu
        295                 300                 305 aag gac tat ctg aag agg ctc ccg cag gac gcc cca gac cgg aag gat     1495
Lys Asp Tyr Leu Lys Arg Leu Pro Gln Asp Ala Pro Asp Arg Lys Asp
        310                 315                 320 gcg gag agg tcc ttg gag ctc atc tcc aca gcc gcc aac cac tcc aat     1543
Ala Glu Arg Ser Leu Glu Leu Ile Ser Thr Ala Ala Asn His Ser Asn
325                 330                 335 gct gcc att cgg aaa gtg gag aaa atg cac aag ctc ttg gag gtg tac     1591
Ala Ala Ile Arg Lys Val Glu Lys Met His Lys Leu Leu Glu Val Tyr
340                 345                 350                 355 gag cag ctg ggt ggg gaa gaa gac att gtc aac ccg gcc aat gaa ctg     1639
Glu Gln Leu Gly Gly Glu Glu Asp Ile Val Asn Pro Ala Asn Glu Leu
                360                 365                 370 atc aag gag ggc caa atc cag aaa ctg tca gcc aag aac ggc acc ccc     1687
Ile Lys Glu Gly Gln Ile Gln Lys Leu Ser Ala Lys Asn Gly Thr Pro
        375                 380                 385 cag gac cgc cac ctc ttc ctg ttc aac agc atg atc ctt tac tgt gtg     1735
Gln Asp Arg His Leu Phe Leu Phe Asn Ser Met Ile Leu Tyr Cys Val
        390                 395                 400 ccc aag ctg cgg ctc atg ggc cag aag ttc agc gtc cgg gag aag atg     1783
Pro Lys Leu Arg Leu Met Gly Gln Lys Phe Ser Val Arg Glu Lys Met
405                 410                 415 gac atc tca ggc ctc cag gtg cag gat atc gtc aag cca aac aca gca     1831
Asp Ile Ser Gly Leu Gln Val Gln Asp Ile Val Lys Pro Asn Thr Ala
420                 425                 430                 435 cat aca ttc atc ata acg gga aga aaa agg tcc ctg gag ctg cag acg     1879
His Thr Phe Ile Ile Thr Gly Arg Lys Arg Ser Leu Glu Leu Gln Thr
                440                 445                 450
```

-continued

```
cgg aca gag gaa gag aag aaa gaa tgg att cag atc atc cag gcc acc      1927
Arg Thr Glu Glu Glu Lys Lys Glu Trp Ile Gln Ile Ile Gln Ala Thr
            455                 460                 465 atc gag aag cac aaa cag aac agc gaa acc ttc aag gct ttt ggt ggc      1975
Ile Glu Lys His Lys Gln Asn Ser Glu Thr Phe Lys Ala Phe Gly Gly
        470                 475                 480 gcc ttc agc cag gat gag gac ccc agc ctc tct cca gac atg cct atc      2023
Ala Phe Ser Gln Asp Glu Asp Pro Ser Leu Ser Pro Asp Met Pro Ile
    485                 490                 495 acg agc acc agc cct gtg gag cct gtg gtg acc acc gaa ggc agt tcg      2071
Thr Ser Thr Ser Pro Val Glu Pro Val Val Thr Thr Glu Gly Ser Ser
500                 505                 510                 515 ggt gca gca ggg ctc gag ccc aga aaa cta tcc tct aag acc aga cgt      2119
Gly Ala Ala Gly Leu Glu Pro Arg Lys Leu Ser Ser Lys Thr Arg Arg
                520                 525                 530 gac aag gag aag cag agc tgt aag agc tgt ggt gag acc ttc aac tcc      2167
Asp Lys Glu Lys Gln Ser Cys Lys Ser Cys Gly Glu Thr Phe Asn Ser
            535                 540                 545 atc acc aag agg agg cat cac tgc aag ctg tgt ggg gcg gtc atc tgt      2215
Ile Thr Lys Arg Arg His His Cys Lys Leu Cys Gly Ala Val Ile Cys
        550                 555                 560 ggg aag tgc tcc gag ttc aag gcc gag aac agc cgg cag agc cgt gtc      2263
Gly Lys Cys Ser Glu Phe Lys Ala Glu Asn Ser Arg Gln Ser Arg Val
    565                 570                 575 tgc aga gat tgt ttc ctg aca cag cca gtg gcc cct gag agc aca gag      2311
Cys Arg Asp Cys Phe Leu Thr Gln Pro Val Ala Pro Glu Ser Thr Glu
580                 585                 590                 595 aag aca ccc act gca gac ccc cag ccc agc ctc ctc tgc ggc ccc ctg      2359
Lys Thr Pro Thr Ala Asp Pro Gln Pro Ser Leu Leu Cys Gly Pro Leu
                600                 605                 610 cgg ctg tca gag agc ggt gag acc tgg agc gag gtg tgg gcc gcc atc      2407
Arg Leu Ser Glu Ser Gly Glu Thr Trp Ser Glu Val Trp Ala Ala Ile
            615                 620                 625 ccc atg tca gat ccc cag gtg ctg cac ctg cag gga ggc agc cag gac      2455
Pro Met Ser Asp Pro Gln Val Leu His Leu Gln Gly Gly Ser Gln Asp
        630                 635                 640 ggc cgg ctg ccc cgc acc atc cct ctc ccc agc tgc aaa ctg agt gtg      2503
Gly Arg Leu Pro Arg Thr Ile Pro Leu Pro Ser Cys Lys Leu Ser Val
    645                 650                 655 ccg gac cct gag gag agg ctg gac tcg ggg cat gtg tgg aag ctg cag      2551
Pro Asp Pro Glu Glu Arg Leu Asp Ser Gly His Val Trp Lys Leu Gln
660                 665                 670                 675 tgg gcc aag cag tcc tgg tac ctg agc gcc tcc tcc gca gag ctg cag      2599
Trp Ala Lys Gln Ser Trp Tyr Leu Ser Ala Ser Ser Ala Glu Leu Gln
                680                 685                 690 cag cag tgg ctg gaa acc tta agc act gct gcc cat ggg gac acg gcc      2647
Gln Gln Trp Leu Glu Thr Leu Ser Thr Ala Ala His Gly Asp Thr Ala
            695                 700                 705 cag gac agc ccg ggg gcc ctg cag ctt cag gtc cct atg ggc gca gct      2695
Gln Asp Ser Pro Gly Ala Leu Gln Leu Gln Val Pro Met Gly Ala Ala
        710                 715                 720 gct ccg tgagctgagt ctcccactgc cctgcacacc accacattgg acctgtgctg      2751
Ala Pro
    725 tcctgggagg tggtgttgga ggccccatga agagcgccct ggactgctga gggtgggcca   2811 acagcccaga gctcaggaca cttggctttg gggggaagga aactgaggcc cagagagggg   2871 caaccactgg ccaagggtca cccagcaagt tttggctaag agcctggcct ccagccccag   2931
```

-continued

```
cagtgtggcc cagagcaggg gccgactgcc aaagtaacca tcatccatat gggccgtgtg      2991
gtgatgctgg cccggaaggc agaaagaggc agcatgggca ctgccaggga cagccacatc      3051
ctgctggtct gcagcgtggt ccaccccgcc tctgcccagc ctgtctacac cgtgtgagct      3111
gaatcgtgac ttgcttccca cctcctttct ctgtcctctc ctgaggttct gcctgcagcc      3171
cccaggaggt gggcctgccc catcctagct ggactcatgg ttcctaaata accacgctca      3231
gaagctctgc taggacttac cccagccact gagtggcagg cgcatgagat ttgtggctgt      3291
tcctgatgct agtggcacac agtgcttatc tgcataaata aacactggcc accagcaaaa      3351
aaaaaaaaaa aaaaaaaaaa aaaaaaaaaa aaaaaaaaaa aaaaaaaaaa aaaaaaaaaa      3411
aaaaaaaaaa aaaaaaaaaa aaaaaaa                                          3438
```

<210> SEQ ID NO 30
<211> LENGTH: 725
<212> TYPE: PRT
<213> ORGANISM: Homo sapiens

<400> SEQUENCE: 30

```
Met Glu Ser Gly Arg Gly Ser Ser Thr Pro Pro Gly Pro Ile Ala Ala
1               5                   10                  15

Leu Gly Met Pro Asp Thr Gly Pro Gly Ser Ser Ser Leu Gly Lys Leu
            20                  25                  30

Gln Ala Leu Pro Val Gly Pro Arg Ala His Cys Gly Asp Pro Val Ser
        35                  40                  45

Leu Ala Ala Ala Gly Asp Gly Ser Pro Asp Ile Gly Pro Thr Gly Glu
    50                  55                  60

Leu Ser Gly Ser Leu Lys Ile Pro Asn Arg Asp Ser Gly Ile Asp Ser
65                  70                  75                  80

Pro Ser Ser Ser Val Ala Gly Glu Asn Phe Pro Cys Glu Glu Gly Leu
                85                  90                  95

Glu Ala Gly Pro Ser Pro Thr Val Leu Gly Ala His Ala Glu Met Ala
            100                 105                 110

Leu Asp Ser Gln Val Pro Lys Val Thr Pro Gln Glu Glu Ala Asp Ser
        115                 120                 125

Asp Val Gly Glu Glu Pro Asp Ser Glu Asn Thr Pro Gln Lys Ala Asp
    130                 135                 140

Lys Asp Ala Gly Leu Ala Gln His Ser Gly Pro Gln Lys Leu Leu His
145                 150                 155                 160

Ile Ala Gln Glu Leu Leu His Thr Glu Glu Thr Tyr Val Lys Arg Leu
                165                 170                 175

His Leu Leu Asp Gln Val Phe Cys Thr Arg Leu Thr Asp Ala Gly Ile
            180                 185                 190

Pro Pro Glu Val Ile Met Gly Ile Phe Ser Asn Ile Ser Ser Ile His
        195                 200                 205

Arg Phe His Gly Gln Phe Leu Leu Pro Glu Leu Lys Thr Arg Ile Thr
    210                 215                 220

Glu Glu Trp Asp Thr Asn Pro Arg Leu Gly Asp Ile Leu Gln Lys Leu
225                 230                 235                 240

Ala Pro Phe Leu Lys Met Tyr Gly Glu Tyr Val Lys Asn Phe Asp Arg
                245                 250                 255

Ala Val Gly Leu Val Ser Thr Trp Thr Gln Arg Ser Pro Leu Phe Lys
            260                 265                 270

Asp Val Val His Ser Ile Gln Lys Gln Glu Val Cys Gly Asn Leu Thr
        275                 280                 285
```

```
Leu Gln His His Met Leu Glu Pro Val Gln Arg Val Pro Arg Tyr Glu
    290                 295                 300
Leu Leu Leu Lys Asp Tyr Leu Lys Arg Leu Pro Gln Asp Ala Pro Asp
305                 310                 315                 320
Arg Lys Asp Ala Glu Arg Ser Leu Glu Leu Ile Ser Thr Ala Ala Asn
                325                 330                 335
His Ser Asn Ala Ala Ile Arg Lys Val Glu Lys Met His Lys Leu Leu
                340                 345                 350
Glu Val Tyr Glu Gln Leu Gly Gly Glu Glu Asp Ile Val Asn Pro Ala
            355                 360                 365
Asn Glu Leu Ile Lys Glu Gly Gln Ile Gln Lys Leu Ser Ala Lys Asn
    370                 375                 380
Gly Thr Pro Gln Asp Arg His Leu Phe Leu Phe Asn Ser Met Ile Leu
385                 390                 395                 400
Tyr Cys Val Pro Lys Leu Arg Leu Met Gly Gln Lys Phe Ser Val Arg
                405                 410                 415
Glu Lys Met Asp Ile Ser Gly Leu Gln Val Gln Asp Ile Val Lys Pro
                420                 425                 430
Asn Thr Ala His Thr Phe Ile Ile Thr Gly Arg Lys Arg Ser Leu Glu
            435                 440                 445
Leu Gln Thr Arg Thr Glu Glu Lys Lys Glu Trp Ile Gln Ile Ile
    450                 455                 460
Gln Ala Thr Ile Glu Lys His Lys Gln Asn Ser Glu Thr Phe Lys Ala
465                 470                 475                 480
Phe Gly Gly Ala Phe Ser Gln Asp Glu Asp Pro Ser Leu Ser Pro Asp
                485                 490                 495
Met Pro Ile Thr Ser Thr Ser Pro Val Glu Pro Val Val Thr Thr Glu
                500                 505                 510
Gly Ser Ser Gly Ala Ala Gly Leu Glu Pro Arg Lys Leu Ser Ser Lys
            515                 520                 525
Thr Arg Arg Asp Lys Glu Lys Gln Ser Cys Lys Ser Cys Gly Glu Thr
    530                 535                 540
Phe Asn Ser Ile Thr Lys Arg Arg His His Cys Lys Leu Cys Gly Ala
545                 550                 555                 560
Val Ile Cys Gly Lys Cys Ser Glu Phe Lys Ala Glu Asn Ser Arg Gln
                565                 570                 575
Ser Arg Val Cys Arg Asp Cys Phe Leu Thr Gln Pro Val Ala Pro Glu
                580                 585                 590
Ser Thr Glu Lys Thr Pro Thr Ala Asp Pro Gln Pro Ser Leu Leu Cys
            595                 600                 605
Gly Pro Leu Arg Leu Ser Glu Ser Gly Glu Thr Trp Ser Glu Val Trp
    610                 615                 620
Ala Ala Ile Pro Met Ser Asp Pro Gln Val Leu His Leu Gln Gly Gly
625                 630                 635                 640
Ser Gln Asp Gly Arg Leu Pro Arg Thr Ile Pro Leu Pro Ser Cys Lys
                645                 650                 655
Leu Ser Val Pro Asp Pro Glu Glu Arg Leu Asp Ser Gly His Val Trp
                660                 665                 670
Lys Leu Gln Trp Ala Lys Gln Ser Trp Tyr Leu Ser Ala Ser Ser Ala
            675                 680                 685
Glu Leu Gln Gln Gln Trp Leu Glu Thr Leu Ser Thr Ala Ala His Gly
    690                 695                 700
```

Asp Thr Ala Gln Asp Ser Pro Gly Ala Leu Gln Leu Gln Val Pro Met
705                 710                 715                 720

Gly Ala Ala Ala Pro
            725

<210> SEQ ID NO 31
<211> LENGTH: 1738
<212> TYPE: DNA
<213> ORGANISM: Homo sapiens
<220> FEATURE:
<221> NAME/KEY: CDS
<222> LOCATION: (121)..(972)
<223> OTHER INFORMATION:

<400> SEQUENCE: 31
gggaaagtac atatctggga gaagcaggcg gctccgcgct cgcactcccg ctcctccgcc     60
cgaccgcgcg ctcgccccgc cgctcctgct gcagccccag ggcccctcgc cgccgccacc    120 atg gac gcc atc aag aag aag atg cag atg ctg aag ctc gac aag gag     168
Met Asp Ala Ile Lys Lys Lys Met Gln Met Leu Lys Leu Asp Lys Glu
1               5                   10                  15 aac gcc ttg gat cga gct gag cag gcg gag gcc gac aag aag gcg gcg     216
Asn Ala Leu Asp Arg Ala Glu Gln Ala Glu Ala Asp Lys Lys Ala Ala
                20                  25                  30 gaa gac agg agc aag cag ctc gag gag gac atc gcg gcc aag gag aag     264
Glu Asp Arg Ser Lys Gln Leu Glu Glu Asp Ile Ala Ala Lys Glu Lys
            35                  40                  45 ttg ctg cgg gtg tcg gag gac gag cgg gac cgg gtg ctg gag gag ctg     312
Leu Leu Arg Val Ser Glu Asp Glu Arg Asp Arg Val Leu Glu Glu Leu
        50                  55                  60 cac aag gcg gag gac agc ctc ctg gcc gcc gaa gag gcc gcc gcc aag     360
His Lys Ala Glu Asp Ser Leu Leu Ala Ala Glu Glu Ala Ala Ala Lys
65                  70                  75                  80 gct gaa gcc gac gta gct tct ctg aac aga cgc atc cag ctg gtt gag     408
Ala Glu Ala Asp Val Ala Ser Leu Asn Arg Arg Ile Gln Leu Val Glu
                85                  90                  95 gaa gag ttg gat cgt gcc cag gag cgt ctg gca aca gct ttg cag aag     456
Glu Glu Leu Asp Arg Ala Gln Glu Arg Leu Ala Thr Ala Leu Gln Lys
                100                 105                 110 ctg gag gaa gct gag aag gca gca gat gag agt gag aga ggc atg aaa     504
Leu Glu Glu Ala Glu Lys Ala Ala Asp Glu Ser Glu Arg Gly Met Lys
            115                 120                 125 gtc att gag agt cga gcc caa aaa gat gaa gaa aaa atg gaa att cag     552
Val Ile Glu Ser Arg Ala Gln Lys Asp Glu Glu Lys Met Glu Ile Gln
        130                 135                 140 gag atc caa ctg aaa gag gca aag cac att gct gaa gat gcc gac cgc     600
Glu Ile Gln Leu Lys Glu Ala Lys His Ile Ala Glu Asp Ala Asp Arg
145                 150                 155                 160 aaa tat gaa gag gtg gcc cgt aag ctg gtc atc att gag agc gac ctg     648
Lys Tyr Glu Glu Val Ala Arg Lys Leu Val Ile Ile Glu Ser Asp Leu
                165                 170                 175 gaa cgt gca gag gag cgg gct gag ctc tca gaa ggc caa gtc cga cag     696
Glu Arg Ala Glu Glu Arg Ala Glu Leu Ser Glu Gly Gln Val Arg Gln
                180                 185                 190 ctg gaa gaa caa tta aga ata atg gat cag acc ttg aaa gca tta atg     744
Leu Glu Glu Gln Leu Arg Ile Met Asp Gln Thr Leu Lys Ala Leu Met
            195                 200                 205 gct gca gag gat aag tac tcg cag aag gaa gac aga tat gag gaa gag     792
Ala Ala Glu Asp Lys Tyr Ser Gln Lys Glu Asp Arg Tyr Glu Glu Glu
        210                 215                 220 atc aag gtc ctt tcc gac aag ctg aag gag gct gag act cgg gct gag     840

```
Ile Lys Val Leu Ser Asp Lys Leu Lys Glu Ala Glu Thr Arg Ala Glu
225                 230                 235                 240 ttt gcg gag agg tca gta act aaa ttg gag aaa agc att gat gac tta    888
Phe Ala Glu Arg Ser Val Thr Lys Leu Glu Lys Ser Ile Asp Asp Leu
                245                 250                 255 gaa gag aaa gtg gct cat gcc aaa gaa gaa aac ctt agt atg cat cag    936
Glu Glu Lys Val Ala His Ala Lys Glu Glu Asn Leu Ser Met His Gln
        260                 265                 270 atg ctg gat cag act tta ctg gag tta aac aac atg tgaaaacctc         982
Met Leu Asp Gln Thr Leu Leu Glu Leu Asn Asn Met
            275                 280 cttagctgcg accacattct ttcattttgt tttgttttgt tttgttttta aacacctgct  1042
taccccttaa atgcaattta tttacttttta ccactgtcac agaaacatcc acaagatacc 1102 agctaggtca gggggtgggg aaaacacata caaaaaggca agcccatgtc agggcgatcc  1162
tggttcaaat gtgccatttc ccgggttgat gctgccacac tttgtagaga gtttagcaac  1222
acagtgtgct tagtcagcgt aggaatcctc actaaagcag gagaagttcc attcaaagtg  1282
ccaatgatag agtcaacagg aaggttaatg ttggaaacac aatcaggtgt ggattggtgc  1342
tactttgaac aaaaggtccc cctgtggtct tttgttcaac attgtacaat gtagaactct  1402
gtccaacact aatttatttt gtcttgagtt ttactacaag atgagactat ggatcccgca  1462
tgcctgaatt cactaaagcc aagggtctgt aagccacgct gctcttctga gacttccatt  1522
cctttctgat tggcacacgt gcagctcatg acaatctgta ggataacaat cagtgtggat  1582
ttccactctt ttcagtcctt catgttaaag atttagacac cacatacaac tggtaaagga  1642
cgttttcttg agagttttaa ctatatgtaa acattgtata atgatatgga ataaaatgca  1702
cattgtagga cattttctaa aaaaaaaaaa aaaaaa                            1738

<210> SEQ ID NO 32
<211> LENGTH: 284
<212> TYPE: PRT
<213> ORGANISM: Homo sapiens

<400> SEQUENCE: 32

Met Asp Ala Ile Lys Lys Met Gln Met Leu Lys Leu Asp Lys Glu
1               5                   10                  15

Asn Ala Leu Asp Arg Ala Glu Gln Ala Glu Ala Asp Lys Lys Ala Ala
                20                  25                  30

Glu Asp Arg Ser Lys Gln Leu Glu Glu Asp Ile Ala Ala Lys Glu Lys
            35                  40                  45

Leu Leu Arg Val Ser Glu Asp Glu Arg Asp Arg Val Leu Glu Glu Leu
        50                  55                  60

His Lys Ala Glu Asp Ser Leu Leu Ala Ala Glu Ala Ala Lys
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Ser Arg Ala Gln Lys Asp Glu Glu Lys Met Glu Ile Gln
    130                 135                 140

Glu Ile Gln Leu Lys Glu Ala Lys His Ile Ala Glu Asp Ala Asp Arg
145                 150                 155                 160
```

```
Lys Tyr Glu Glu Val Ala Arg Lys Leu Val Ile Ile Glu Ser Asp Leu
                165                 170                 175

Glu Arg Ala Glu Glu Arg Ala Glu Leu Ser Glu Gly Gln Val Arg Gln
            180                 185                 190

Leu Glu Glu Gln Leu Arg Ile Met Asp Gln Thr Leu Lys Ala Leu Met
        195                 200                 205

Ala Ala Glu Asp Lys Tyr Ser Gln Lys Glu Asp Arg Tyr Glu Glu
    210                 215                 220

Ile Lys Val Leu Ser Asp Lys Leu Lys Glu Ala Glu Thr Arg Ala Glu
225                 230                 235                 240

Phe Ala Glu Arg Ser Val Thr Lys Leu Glu Lys Ser Ile Asp Asp Leu
                245                 250                 255

Glu Glu Lys Val Ala His Ala Lys Glu Glu Asn Leu Ser Met His Gln
            260                 265                 270

Met Leu Asp Gln Thr Leu Leu Glu Leu Asn Asn Met
        275                 280

<210> SEQ ID NO 33
<211> LENGTH: 1138
<212> TYPE: DNA
<213> ORGANISM: Homo sapiens
<220> FEATURE:
<221> NAME/KEY: CDS
<222> LOCATION: (231)..(965)
<223> OTHER INFORMATION:

<400> SEQUENCE: 33
cggcgcgcgc ccctcccagc cgcgcgcgcc cgcctgcggt ttgtctgcgc agccctggag      60
gctgcgactt ccggactgct cctggccgca ggggcgccg ccgtcgcaca gagaggcctg     120
ggcggggcgg accggcgctg ggcagccagg acagccgcgg cagccgggtc cgcagggcag     180
cagccggcct ctcccactgc agccctcccg ccgcctacc gtccggcgcg atg gcg       236
                                                       Met Ala
                                                         1 ggg agt agc tcg ctg gag gcg gtg cgc agg aag atc cgg agc ctg cag       284
Gly Ser Ser Ser Leu Glu Ala Val Arg Arg Lys Ile Arg Ser Leu Gln
          5                  10                  15 gag cag gcg gac gcc gct gag gag cgc gcg ggc acc ctg cag cgc gag       332
Glu Gln Ala Asp Ala Ala Glu Glu Arg Ala Gly Thr Leu Gln Arg Glu
     20                  25                  30 ctg gac cac gag agg aag ctg agg gag acc gct gaa gcc gac gta gct       380
Leu Asp His Glu Arg Lys Leu Arg Glu Thr Ala Glu Ala Asp Val Ala
 35                  40                  45                  50 tct ctg aac aga cgc atc cag ctg gtt gag gaa gag ttg gat cgt gcc       428
Ser Leu Asn Arg Arg Ile Gln Leu Val Glu Glu Glu Leu Asp Arg Ala
                 55                  60                  65 cag gag cgt ctg gca aca gct ttg cag aag ctg gag gaa gct gag aag       476
Gln Glu Arg Leu Ala Thr Ala Leu Gln Lys Leu Glu Glu Ala Glu Lys
             70                  75                  80 gca gca gat gag agt gag aga ggc atg aaa gtc att gag agt cga gcc       524
Ala Ala Asp Glu Ser Glu Arg Gly Met Lys Val Ile Glu Ser Arg Ala
         85                  90                  95 caa aaa gat gaa gaa aaa atg gaa att cag gag atc caa ctg aaa gag       572
Gln Lys Asp Glu Glu Lys Met Glu Ile Gln Glu Ile Gln Leu Lys Glu
    100                 105                 110 gca aag cac att gct gaa gat gcc gac cgc aaa tat gaa gag gtg gcc       620
Ala Lys His Ile Ala Glu Asp Ala Asp Arg Lys Tyr Glu Glu Val Ala
115                 120                 125                 130 cgt aag ctg gtc atc att gag agc gac ctg gaa cgt gca gag gag cgg       668
```

-continued

```
Arg Lys Leu Val Ile Ile Glu Ser Asp Leu Glu Arg Ala Glu Arg
                135                 140                 145 gct gag ctc tca gaa ggc aaa tgt gcc gag ctt gaa gaa gaa ttg aaa       716
Ala Glu Leu Ser Glu Gly Lys Cys Ala Glu Leu Glu Glu Glu Leu Lys
                150                 155                 160 act gtg acg aac aac ttg aag tca ctg gag gct cag gct gag aag tac       764
Thr Val Thr Asn Asn Leu Lys Ser Leu Glu Ala Gln Ala Glu Lys Tyr
            165                 170                 175 tcg cag aag gaa gac aga tat gag gaa gag atc aag gtc ctt tcc gac       812
Ser Gln Lys Glu Asp Arg Tyr Glu Glu Glu Ile Lys Val Leu Ser Asp
        180                 185                 190 aag ctg aag gag gct gag act cgg gct gag ttt gcg gag agg tca gta       860
Lys Leu Lys Glu Ala Glu Thr Arg Ala Glu Phe Ala Glu Arg Ser Val
195                 200                 205                 210 act aaa ttg gag aaa agc att gat gac tta gaa gat caa ctc tac cag       908
Thr Lys Leu Glu Lys Ser Ile Asp Asp Leu Glu Asp Gln Leu Tyr Gln
                215                 220                 225 caa ctt gag caa aat cgc cgc ctc act aat gaa cta aag ctg gcc ctg       956
Gln Leu Glu Gln Asn Arg Arg Leu Thr Asn Glu Leu Lys Leu Ala Leu
                230                 235                 240 aat gag gat taaacttaag agtgaaaaaa cttgggctga attctaggcg              1005
Asn Glu Asp
        245 tggagcccat gtgcagaaaa tctaagactg tcctacccct caactaatag agttgaaaac    1065 agttgctttc tgcagaaatg caaatgcaag gaattggctg aaaggctggc cttgcctgct    1125 tgtttctcta tat                                                       1138

<210> SEQ ID NO 34
<211> LENGTH: 245
<212> TYPE: PRT
<213> ORGANISM: Homo sapiens

<400> SEQUENCE: 34

Met Ala Gly Ser Ser Leu Glu Ala Val Arg Arg Lys Ile Arg Ser
1               5                   10                  15

Leu Gln Glu Gln Ala Asp Ala Ala Glu Glu Arg Ala Gly Thr Leu Gln
                20                  25                  30

Arg Glu Leu Asp His Glu Arg Lys Leu Arg Glu Thr Ala Glu Ala Asp
            35                  40                  45

Val Ala Ser Leu Asn Arg Arg Ile Gln Leu Val Glu Glu Glu Leu Asp
        50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Ser
                85                  90                  95

Arg Ala Gln Lys Asp Glu Glu Lys Met Glu Ile Gln Glu Ile Gln Leu
                100                 105                 110

Lys Glu Ala Lys His Ile Ala Glu Asp Ala Asp Arg Lys Tyr Glu Glu
            115                 120                 125

Val Ala Arg Lys Leu Val Ile Ile Glu Ser Asp Leu Glu Arg Ala Glu
        130                 135                 140

Glu Arg Ala Glu Leu Ser Glu Gly Lys Cys Ala Glu Leu Glu Glu Glu
145                 150                 155                 160

Leu Lys Thr Val Thr Asn Asn Leu Lys Ser Leu Glu Ala Gln Ala Glu
                165                 170                 175

Lys Tyr Ser Gln Lys Glu Asp Arg Tyr Glu Glu Glu Ile Lys Val Leu
```

```
                    180                 185                 190
Ser Asp Lys Leu Lys Glu Ala Glu Thr Arg Ala Glu Phe Ala Glu Arg
            195                 200                 205

Ser Val Thr Lys Leu Glu Lys Ser Ile Asp Asp Leu Glu Asp Gln Leu
        210                 215                 220

Tyr Gln Gln Leu Glu Gln Asn Arg Arg Leu Thr Asn Glu Leu Lys Leu
225                 230                 235                 240

Ala Leu Asn Glu Asp
                245

<210> SEQ ID NO 35
<211> LENGTH: 1496
<212> TYPE: DNA
<213> ORGANISM: Homo sapiens
<220> FEATURE:
<221> NAME/KEY: CDS
<222> LOCATION: (257)..(730)
<223> OTHER INFORMATION:

<400> SEQUENCE: 35
ctcgctggag gcggtgcgca ggaagatccg gagcctgcag gagcaggcgg acgccgctga      60
ggagcgcgcg ggcaccctgc agcgcgagct ggaccacgag aggaagctga gggagaccgc     120
tgaagccgac gtagcttctc tgaacagacg catccagctg gttgaggaag agttggatcg     180
tgcccaggag cgtctggcaa cagctttgca gaagctggag gaagctgaga aggcagcaga     240
tgagagtgag agaggc atg aaa gtc att gag agt cga gcc caa aaa gat gaa    292
                 Met Lys Val Ile Glu Ser Arg Ala Gln Lys Asp Glu
                   1               5                  10 gaa aaa atg gaa att cag gag atc caa ctg aaa gag gca aag cac att      340
Glu Lys Met Glu Ile Gln Glu Ile Gln Leu Lys Glu Ala Lys His Ile
             15                  20                  25 gct gaa gat gcc gac cgc aaa tat gaa gag gtg gcc cgt aag ctg gtc      388
Ala Glu Asp Ala Asp Arg Lys Tyr Glu Glu Val Ala Arg Lys Leu Val
         30                  35                  40 atc att gag agc gac ctg gaa cgt gca gag gag cgg gct gag ctc tca      436
Ile Ile Glu Ser Asp Leu Glu Arg Ala Glu Glu Arg Ala Glu Leu Ser
 45                  50                  55                  60 gaa ggc caa gtc cga cag ctg gaa gaa caa tta aga ata atg gat cag      484
Glu Gly Gln Val Arg Gln Leu Glu Glu Gln Leu Arg Ile Met Asp Gln
                 65                  70                  75 acc ttg aaa gca tta atg gct gca gag gat aag tac tcg cag aag gaa      532
Thr Leu Lys Ala Leu Met Ala Ala Glu Asp Lys Tyr Ser Gln Lys Glu
             80                  85                  90 gac aga tat gag gaa gag atc aag gtc ctt tcc gac aag ctg aag gag      580
Asp Arg Tyr Glu Glu Glu Ile Lys Val Leu Ser Asp Lys Leu Lys Glu
         95                 100                 105 gct gag act cgg gct gag ttt gcg gag agg tca gta act aaa ttg gag      628
Ala Glu Thr Arg Ala Glu Phe Ala Glu Arg Ser Val Thr Lys Leu Glu
        110                 115                 120 aaa agc att gat gac tta gaa gag aaa gtg gct cat gcc aaa gaa gaa      676
Lys Ser Ile Asp Asp Leu Glu Glu Lys Val Ala His Ala Lys Glu Glu
125                 130                 135                 140 aac ctt agt atg cat cag atg ctg gat cag act tta ctg gag tta aac      724
Asn Leu Ser Met His Gln Met Leu Asp Gln Thr Leu Leu Glu Leu Asn
                145                 150                 155 aac atg tgaaaacctc cttagctgcg accacattct ttcattttgt tttgttttgt     780
Asn Met tttgttttta aacacctgct taccccttaa atgcaattta tttactttta ccactgtcac     840
```

-continued

```
agaaacatcc acaagatacc agctaggtca gggggtgggg aaaacacata caaaaggca    900 agcccatgtc agggcgatcc tggttcaaat gtgccatttc ccggttgat gctgccacac    960 tttgtagaga gtttagcaac acagtgtgct tagtcagcgt aggaatcctc actaaagcag   1020
gagaagttcc attcaaagtg ccaatgatag agtcaacagg aaggttaatg ttggaaacac   1080
aatcaggtgt ggattggtgc tactttgaac aaaaggtccc cctgtggtct tttgttcaac   1140
attgtacaat gtagaactct gtccaacact aatttatttt gtcttgagtt ttactacaag   1200
atgagactat ggatcccgca tgcctgaatt cactaaagcc aagggtctgt aagccacgct   1260
gctcttctga gacttccatt cctttctgat tggcacacgt gcagctcatg acaatctgta   1320
ggataacaat cagtgtggat ttccactctt ttcagtcctt catgttaaag atttagacac   1380
cacatacaac tggtaaagga cgttttcttg agagttttaa ctatatgtaa acattgtata   1440
atgatatgga ataaaatgca cattgtagga cattttctaa aaaaaaaaaa aaaaaa       1496
```

<210> SEQ ID NO 36
<211> LENGTH: 158
<212> TYPE: PRT
<213> ORGANISM: Homo sapiens

<400> SEQUENCE: 36

```
Met Lys Val Ile Glu Ser Arg Ala Gln Lys Asp Glu Lys Met Glu
1               5                   10                  15

Ile Gln Glu Ile Gln Leu Lys Glu Ala Lys His Ile Ala Glu Asp Ala
            20                  25                  30

Asp Arg Lys Tyr Glu Glu Val Ala Arg Lys Leu Val Ile Ile Glu Ser
        35                  40                  45

Asp Leu Glu Arg Ala Glu Glu Arg Ala Glu Leu Ser Glu Gly Gln Val
    50                  55                  60

Arg Gln Leu Glu Glu Gln Leu Arg Ile Met Asp Gln Thr Leu Lys Ala
65                  70                  75                  80

Leu Met Ala Ala Glu Asp Lys Tyr Ser Gln Lys Glu Asp Arg Tyr Glu
                85                  90                  95

Glu Glu Ile Lys Val Leu Ser Asp Lys Leu Lys Glu Ala Glu Thr Arg
            100                 105                 110

Ala Glu Phe Ala Glu Arg Ser Val Thr Lys Leu Glu Lys Ser Ile Asp
        115                 120                 125

Asp Leu Glu Glu Lys Val Ala His Ala Lys Glu Glu Asn Leu Ser Met
    130                 135                 140

His Gln Met Leu Asp Gln Thr Leu Leu Glu Leu Asn Asn Met
145                 150                 155
```

<210> SEQ ID NO 37
<211> LENGTH: 3606
<212> TYPE: DNA
<213> ORGANISM: Homo sapiens
<220> FEATURE:
<221> NAME/KEY: CDS
<222> LOCATION: (174)..(3155)
<223> OTHER INFORMATION:

<400> SEQUENCE: 37

```
gcacgaggct cggcgggagg aggcggcggc ggaggaggag caggggagg gctgtcaaat    60 tcgggagcca gattttttcc cttctcctgg caatcccttc cgcttccccg gctcccggcg   120
tgacatctgc gggccgggga cctgcatgtg tgtgcgcgcg aaggagcgga aga atg     176
                                                               Met
                                                               1
```

```
gca gtg ctc aaa ctc acc gac cag cca cca ttg gtt cag gca atc ttc    224
Ala Val Leu Lys Leu Thr Asp Gln Pro Pro Leu Val Gln Ala Ile Phe
         5              10              15 agc ggt gat cca gag gag atc cgg atg ctc atc cat aaa act gaa gat    272
Ser Gly Asp Pro Glu Glu Ile Arg Met Leu Ile His Lys Thr Glu Asp
         20              25              30 gtg aat act ctg gat tct gag aaa cga acc cct ctt cat gtg gcc gca    320
Val Asn Thr Leu Asp Ser Glu Lys Arg Thr Pro Leu His Val Ala Ala
         35              40              45 ttt ctg gga gat gca gag atc att gaa ctc ctg att ttg tca gga gct    368
Phe Leu Gly Asp Ala Glu Ile Ile Glu Leu Leu Ile Leu Ser Gly Ala
50              55              60              65 cgt gta aat gcc aag gac aac atg tgg ctg act cca ctg cac cgg gct    416
Arg Val Asn Ala Lys Asp Asn Met Trp Leu Thr Pro Leu His Arg Ala
             70              75              80 gtt gct tcc aga agc gaa gaa gca gta cag gtt ttg att aag cac tca    464
Val Ala Ser Arg Ser Glu Glu Ala Val Gln Val Leu Ile Lys His Ser
             85              90              95 gct gat gtc aat gca agg gac aag aac tgg cag acc cct ctt cat gtg    512
Ala Asp Val Asn Ala Arg Asp Lys Asn Trp Gln Thr Pro Leu His Val
             100             105             110 gca gca gcc aac aag gct gtc aaa tgt gca gaa gtg atc att ccc ctg    560
Ala Ala Ala Asn Lys Ala Val Lys Cys Ala Glu Val Ile Ile Pro Leu
             115             120             125 ctg agc agt gtc aat gtc tcc gac cga ggg ggg cgc aca gcc ttg cac    608
Leu Ser Ser Val Asn Val Ser Asp Arg Gly Gly Arg Thr Ala Leu His
130             135             140             145 cat gcg gct ctg aac ggc cac gtg gag atg gtc aat tta ctc ttg gcc    656
His Ala Ala Leu Asn Gly His Val Glu Met Val Asn Leu Leu Leu Ala
             150             155             160 aaa ggg gca aat atc aat gca ttt gac aag aag gac cgg cgt gct ctg    704
Lys Gly Ala Asn Ile Asn Ala Phe Asp Lys Lys Asp Arg Arg Ala Leu
             165             170             175 cac tgg gca gca tac atg ggc cac ttg gat gtt gta gca ttg ctc att    752
His Trp Ala Ala Tyr Met Gly His Leu Asp Val Val Ala Leu Leu Ile
             180             185             190 aac cat ggc gca gaa gtg acc tgt aag gat aag aag ggt tat acc cct    800
Asn His Gly Ala Glu Val Thr Cys Lys Asp Lys Lys Gly Tyr Thr Pro
             195             200             205 ctg cat gct gca gcc tcc aat gga cag att aat gtt gtc aag cat ctc    848
Leu His Ala Ala Ala Ser Asn Gly Gln Ile Asn Val Val Lys His Leu
210             215             220             225 ctg aac ctg ggg gtg gag att gat gaa atc aat gtc tat gga aat aca    896
Leu Asn Leu Gly Val Glu Ile Asp Glu Ile Asn Val Tyr Gly Asn Thr
             230             235             240 gcg ctt cac atc gcc tgc tac aat gga cag gat gct gtg gtt aac gag    944
Ala Leu His Ile Ala Cys Tyr Asn Gly Gln Asp Ala Val Val Asn Glu
             245             250             255 ttg att gac tac ggt gct aac gtg aac cag cca aac aat aat ggg ttc    992
Leu Ile Asp Tyr Gly Ala Asn Val Asn Gln Pro Asn Asn Asn Gly Phe
             260             265             270 acc cct ttg cat ttt gct gct gcc tcc act cat ggt gct ttg tgt ctt   1040
Thr Pro Leu His Phe Ala Ala Ala Ser Thr His Gly Ala Leu Cys Leu
             275             280             285 gaa ttg tta gta aac aac ggg gca gat gtt aac att cag agt aaa gat   1088
Glu Leu Leu Val Asn Asn Gly Ala Asp Val Asn Ile Gln Ser Lys Asp
290             295             300             305 ggc aaa agt cca ctg cac atg aca gct gtc cat gga agg ttc aca cgg   1136
Gly Lys Ser Pro Leu His Met Thr Ala Val His Gly Arg Phe Thr Arg
```

```
                        310                 315                 320
tca cag acc ctc att cag aat gga ggt gaa att gac tgt gtg gat aag    1184
Ser Gln Thr Leu Ile Gln Asn Gly Gly Glu Ile Asp Cys Val Asp Lys
            325                 330                 335 gac ggc aac act cct ctc cat gtg gct gca aga tac ggt cat gag ctt    1232
Asp Gly Asn Thr Pro Leu His Val Ala Ala Arg Tyr Gly His Glu Leu
        340                 345                 350 ttg att aac acc tta ata acc agc gga gct gac aca gcc aag tgt gga    1280
Leu Ile Asn Thr Leu Ile Thr Ser Gly Ala Asp Thr Ala Lys Cys Gly
    355                 360                 365 atc cat agc atg ttc cct tta cat tta gct gcc cta aat gct cac tct    1328
Ile His Ser Met Phe Pro Leu His Leu Ala Ala Leu Asn Ala His Ser
370                 375                 380                 385 gac tgc tgc aga aag ttg tta tca tcg gga caa aag tat agc ata gta    1376
Asp Cys Cys Arg Lys Leu Leu Ser Ser Gly Gln Lys Tyr Ser Ile Val
            390                 395                 400 tcc ttg ttt agt aat gag cac gtg ctg tct gca ggc ttt gaa ata gac    1424
Ser Leu Phe Ser Asn Glu His Val Leu Ser Ala Gly Phe Glu Ile Asp
        405                 410                 415 acc cca gat aaa ttt gga aga acg tgc ctt cat gct gct gct gca gga    1472
Thr Pro Asp Lys Phe Gly Arg Thr Cys Leu His Ala Ala Ala Ala Gly
    420                 425                 430 ggt aat gtg gaa tgt ata aaa ctc ttg cag agc agc gga gca gat ttc    1520
Gly Asn Val Glu Cys Ile Lys Leu Leu Gln Ser Ser Gly Ala Asp Phe
435                 440                 445 cat aaa aag gac aag tgt ggg agg acc cct ttg cac tat gca gct gcg    1568
His Lys Lys Asp Lys Cys Gly Arg Thr Pro Leu His Tyr Ala Ala Ala
450                 455                 460                 465 aat tgt cat ttc cac tgt att gag aca tta gtg acc aca ggg gcc aac    1616
Asn Cys His Phe His Cys Ile Glu Thr Leu Val Thr Thr Gly Ala Asn
            470                 475                 480 gtt aat gaa aca gat gac tgg gga cgc aca gct ttg cat tac gcc gct    1664
Val Asn Glu Thr Asp Asp Trp Gly Arg Thr Ala Leu His Tyr Ala Ala
        485                 490                 495 gca tca gac atg gat aga aat aag act atc tta gga aat gcc cat gat    1712
Ala Ser Asp Met Asp Arg Asn Lys Thr Ile Leu Gly Asn Ala His Asp
    500                 505                 510 aat tca gaa gaa ctt gaa aga gcc agg gag ctg aag gaa aag gaa gcc    1760
Asn Ser Glu Glu Leu Glu Arg Ala Arg Glu Leu Lys Glu Lys Glu Ala
515                 520                 525 aca cta tgt cta gag ttt ctg ctt caa aat gat gca aat cca tct atc    1808
Thr Leu Cys Leu Glu Phe Leu Leu Gln Asn Asp Ala Asn Pro Ser Ile
530                 535                 540                 545 cgg gac aag gaa ggt tac aat agc ata cat tat gct gcc gcc tat ggg    1856
Arg Asp Lys Glu Gly Tyr Asn Ser Ile His Tyr Ala Ala Ala Tyr Gly
            550                 555                 560 cac agg cag tgt ctg gaa ttg ctt ttg gaa aga aca aac agt gga ttt    1904
His Arg Gln Cys Leu Glu Leu Leu Leu Glu Arg Thr Asn Ser Gly Phe
        565                 570                 575 gaa gaa tca gat tct ggt gct act aag agt cca ctc cac tta gct gcc    1952
Glu Glu Ser Asp Ser Gly Ala Thr Lys Ser Pro Leu His Leu Ala Ala
    580                 585                 590 tac aat ggg cac cat caa gcc ttg gaa gtc ctt ctg cag tcg ttg gtg    2000
Tyr Asn Gly His His Gln Ala Leu Glu Val Leu Leu Gln Ser Leu Val
595                 600                 605 gac ctg gac atc agg gat gag aaa ggc cgc act gct ctg gat ctg gct    2048
Asp Leu Asp Ile Arg Asp Glu Lys Gly Arg Thr Ala Leu Asp Leu Ala
610                 615                 620                 625 gcc ttt aaa gga cac aca gaa tgt gtg gaa gcg ctt atc aat cag ggc    2096
```

```
                                                                -continued

Ala Phe Lys Gly His Thr Glu Cys Val Glu Ala Leu Ile Asn Gln Gly
                630                 635                 640 gca tcc atc ttt gtg aaa gac aat gta acc aaa aga acc cca ctt cat    2144
Ala Ser Ile Phe Val Lys Asp Asn Val Thr Lys Arg Thr Pro Leu His
            645                 650                 655 gcc tca gta att aat ggt cac aca ctg tgt tta cgg ctg ttg cta gaa    2192
Ala Ser Val Ile Asn Gly His Thr Leu Cys Leu Arg Leu Leu Leu Glu
        660                 665                 670 att gca gac aac ccg gag gcg gtc gat gtg aaa gat gcc aaa gga caa    2240
Ile Ala Asp Asn Pro Glu Ala Val Asp Val Lys Asp Ala Lys Gly Gln
    675                 680                 685 aca cca ctg atg ctt gca gta gca tat gga cat att gac gct gtt tca    2288
Thr Pro Leu Met Leu Ala Val Ala Tyr Gly His Ile Asp Ala Val Ser
690                 695                 700                 705 ttg tta ctt gaa aag gaa gcc aac gta gac act gtt gac atc cta gga    2336
Leu Leu Leu Glu Lys Glu Ala Asn Val Asp Thr Val Asp Ile Leu Gly
                710                 715                 720 tgc aca gct tta cac aga ggg att atg aca gga cac gag gaa tgt gtg    2384
Cys Thr Ala Leu His Arg Gly Ile Met Thr Gly His Glu Glu Cys Val
            725                 730                 735 caa atg ctg ctg gaa caa gaa gtg tca att ctc tgt aaa gat tcc aga    2432
Gln Met Leu Leu Glu Gln Glu Val Ser Ile Leu Cys Lys Asp Ser Arg
        740                 745                 750 ggg agg acg ccc ttg cac tat gca gct gct cgt ggc cac gcc acg tgg    2480
Gly Arg Thr Pro Leu His Tyr Ala Ala Ala Arg Gly His Ala Thr Trp
    755                 760                 765 ctg agc gag ctg ctc caa atg gct ctt tct gag gag gac tgt tgt ttc    2528
Leu Ser Glu Leu Leu Gln Met Ala Leu Ser Glu Glu Asp Cys Cys Phe
770                 775                 780                 785 aaa gat aac caa ggc tac acg ccg ctg cac tgg gct tgt tac aat ggt    2576
Lys Asp Asn Gln Gly Tyr Thr Pro Leu His Trp Ala Cys Tyr Asn Gly
                790                 795                 800 aat gaa aac tgt ata gag gta ctt ttg gag caa aaa tgt ttt cgc aaa    2624
Asn Glu Asn Cys Ile Glu Val Leu Leu Glu Gln Lys Cys Phe Arg Lys
            805                 810                 815 ttt atc ggt aat ccc ttt act cca ctg cac tgt gca ata atc aat gat    2672
Phe Ile Gly Asn Pro Phe Thr Pro Leu His Cys Ala Ile Ile Asn Asp
        820                 825                 830 cat ggg aat tgt gca tca ttg ctg ctt ggg gcc ata gat tcc agt atc    2720
His Gly Asn Cys Ala Ser Leu Leu Leu Gly Ala Ile Asp Ser Ser Ile
    835                 840                 845 gtc agt tgt aga gat gac aaa ggc agg aca ccc ctt cat gcg gca gca    2768
Val Ser Cys Arg Asp Asp Lys Gly Arg Thr Pro Leu His Ala Ala Ala
850                 855                 860                 865 ttt gct gat cat gtg gag tgc ttg cag ctt ctt ctg aga cac agt gct    2816
Phe Ala Asp His Val Glu Cys Leu Gln Leu Leu Leu Arg His Ser Ala
                870                 875                 880 cca gtg aac gca gta gat aat tca ggg aaa aca gca ctg atg atg gct    2864
Pro Val Asn Ala Val Asp Asn Ser Gly Lys Thr Ala Leu Met Met Ala
            885                 890                 895 gct gag aat ggg cag gca ggc gct gtg gat att ttg gtg aac agt gcc    2912
Ala Glu Asn Gly Gln Ala Gly Ala Val Asp Ile Leu Val Asn Ser Ala
        900                 905                 910 cag gct gat ctg act gta aag gat aag gac ttg aat aca ccc tta cat    2960
Gln Ala Asp Leu Thr Val Lys Asp Lys Asp Leu Asn Thr Pro Leu His
    915                 920                 925 ttg gct tgt agt aaa ggt cat gaa aaa tgt gcc ttg tta ata ctt gac    3008
Leu Ala Cys Ser Lys Gly His Glu Lys Cys Ala Leu Leu Ile Leu Asp
930                 935                 940                 945
```

```
aag ata caa gac gag agc ctt att aat gaa aaa aat aat gca ctg cag    3056
Lys Ile Gln Asp Glu Ser Leu Ile Asn Glu Lys Asn Asn Ala Leu Gln
            950                 955                 960 aca ccc ctc cac gtc gct gcg cgc aat ggc tta aag gtg gta gtt gag    3104
Thr Pro Leu His Val Ala Ala Arg Asn Gly Leu Lys Val Val Val Glu
        965                 970                 975 gag ttg ctg gcc aaa ggg gcc tgt gta ctt gct gta gat gaa aat ggc    3152
Glu Leu Leu Ala Lys Gly Ala Cys Val Leu Ala Val Asp Glu Asn Gly
    980                 985                 990 tgt taaccattca agatccaaga acatcggttg gctgcaaaac aggcaccctg         3205
Cys agggaccaat tatgaatcag aatgcacttt atcccagcca cagaacgcaa agggttacac   3265
tctgcaggag ctgcggttgg ggaagggaaa gggagtaacc ggattcgcct tgcctgtctg   3325
tgattgggaa gcacgcaccc tttatttttcc aactgggaac aagatactgg aaattcctct   3385
ttcccttaga aaacagaagg caagggtgtt ggctgtggaa attagaactg ggtaatagtt   3445
ctagagcact ttgaaattct ttcaggataa gtgttatacg aacacaaatg atttctttca   3505
ttgttaaatt gtgttcctat cattggtaac gccccaagta aagcctttt aattaaaaat    3565 ctctggatgc tataaaaaaa aaaaaaaaaa aaaaaaaaa a                       3606
```

<210> SEQ ID NO 38
<211> LENGTH: 994
<212> TYPE: PRT
<213> ORGANISM: Homo sapiens

<400> SEQUENCE: 38

```
Met Ala Val Leu Lys Leu Thr Asp Gln Pro Pro Leu Val Gln Ala Ile
1               5                   10                  15

Phe Ser Gly Asp Pro Glu Glu Ile Arg Met Leu Ile His Lys Thr Glu
                20                  25                  30

Asp Val Asn Thr Leu Asp Ser Glu Lys Arg Thr Pro Leu His Val Ala
            35                  40                  45

Ala Phe Leu Gly Asp Ala Glu Ile Ile Glu Leu Leu Ile Leu Ser Gly
        50                  55                  60

Ala Arg Val Asn Ala Lys Asp Asn Met Trp Leu Thr Pro Leu His Arg
65                  70                  75                  80

Ala Val Ala Ser Arg Ser Glu Glu Ala Val Gln Val Leu Ile Lys His
                85                  90                  95

Ser Ala Asp Val Asn Ala Arg Asp Lys Asn Trp Gln Thr Pro Leu His
            100                 105                 110

Val Ala Ala Asn Lys Ala Val Lys Cys Ala Glu Val Ile Ile Pro
        115                 120                 125

Leu Leu Ser Ser Val Asn Val Ser Asp Arg Gly Gly Arg Thr Ala Leu
    130                 135                 140

His His Ala Ala Leu Asn Gly His Val Glu Met Val Asn Leu Leu Leu
145                 150                 155                 160

Ala Lys Gly Ala Asn Ile Asn Ala Phe Asp Lys Lys Asp Arg Arg Ala
                165                 170                 175

Leu His Trp Ala Ala Tyr Met Gly His Leu Asp Val Val Ala Leu Leu
            180                 185                 190

Ile Asn His Gly Ala Glu Val Thr Cys Lys Asp Lys Lys Gly Tyr Thr
        195                 200                 205

Pro Leu His Ala Ala Ala Ser Asn Gly Gln Ile Asn Val Val Lys His
    210                 215                 220
```

-continued

```
Leu Leu Asn Leu Gly Val Glu Ile Asp Glu Ile Asn Val Tyr Gly Asn
225                 230                 235                 240

Thr Ala Leu His Ile Ala Cys Tyr Asn Gly Gln Asp Ala Val Val Asn
            245                 250                 255

Glu Leu Ile Asp Tyr Gly Ala Asn Val Asn Gln Pro Asn Asn Asn Gly
            260                 265                 270

Phe Thr Pro Leu His Phe Ala Ala Ser Thr His Gly Ala Leu Cys
            275                 280                 285

Leu Glu Leu Leu Val Asn Asn Gly Ala Asp Val Asn Ile Gln Ser Lys
290                 295                 300

Asp Gly Lys Ser Pro Leu His Met Thr Ala Val His Gly Arg Phe Thr
305                 310                 315                 320

Arg Ser Gln Thr Leu Ile Gln Asn Gly Gly Glu Ile Asp Cys Val Asp
            325                 330                 335

Lys Asp Gly Asn Thr Pro Leu His Val Ala Ala Arg Tyr Gly His Glu
            340                 345                 350

Leu Leu Ile Asn Thr Leu Ile Thr Ser Gly Ala Asp Thr Ala Lys Cys
            355                 360                 365

Gly Ile His Ser Met Phe Pro Leu His Leu Ala Ala Leu Asn Ala His
370                 375                 380

Ser Asp Cys Cys Arg Lys Leu Leu Ser Ser Gly Gln Lys Tyr Ser Ile
385                 390                 395                 400

Val Ser Leu Phe Ser Asn Glu His Val Leu Ser Ala Gly Phe Glu Ile
            405                 410                 415

Asp Thr Pro Asp Lys Phe Gly Arg Thr Cys Leu His Ala Ala Ala Ala
            420                 425                 430

Gly Gly Asn Val Glu Cys Ile Lys Leu Leu Gln Ser Ser Gly Ala Asp
            435                 440                 445

Phe His Lys Lys Asp Lys Cys Gly Arg Thr Pro Leu His Tyr Ala Ala
            450                 455                 460

Ala Asn Cys His Phe His Cys Ile Glu Thr Leu Val Thr Thr Gly Ala
465                 470                 475                 480

Asn Val Asn Glu Thr Asp Asp Trp Gly Arg Thr Ala Leu His Tyr Ala
            485                 490                 495

Ala Ala Ser Asp Met Asp Arg Asn Lys Thr Ile Leu Gly Asn Ala His
            500                 505                 510

Asp Asn Ser Glu Glu Leu Glu Arg Ala Arg Glu Leu Lys Glu Lys Glu
            515                 520                 525

Ala Thr Leu Cys Leu Glu Phe Leu Leu Gln Asn Asp Ala Asn Pro Ser
530                 535                 540

Ile Arg Asp Lys Glu Gly Tyr Asn Ser Ile His Tyr Ala Ala Ala Tyr
545                 550                 555                 560

Gly His Arg Gln Cys Leu Glu Leu Leu Glu Arg Thr Asn Ser Gly
            565                 570                 575

Phe Glu Glu Ser Asp Ser Gly Ala Thr Lys Ser Pro Leu His Leu Ala
            580                 585                 590

Ala Tyr Asn Gly His His Gln Ala Leu Glu Val Leu Leu Gln Ser Leu
            595                 600                 605

Val Asp Leu Asp Ile Arg Asp Glu Lys Gly Arg Thr Ala Leu Asp Leu
            610                 615                 620

Ala Ala Phe Lys Gly His Thr Glu Cys Val Glu Ala Leu Ile Asn Gln
625                 630                 635                 640

Gly Ala Ser Ile Phe Val Lys Asp Asn Val Thr Lys Arg Thr Pro Leu
```

645                 650                 655
His Ala Ser Val Ile Asn Gly His Thr Leu Cys Leu Arg Leu Leu Leu
                660                 665                 670

Glu Ile Ala Asp Asn Pro Glu Ala Val Asp Val Lys Asp Ala Lys Gly
            675                 680                 685

Gln Thr Pro Leu Met Leu Ala Val Ala Tyr Gly His Ile Asp Ala Val
        690                 695                 700

Ser Leu Leu Leu Glu Lys Glu Ala Asn Val Asp Thr Val Asp Ile Leu
705                 710                 715                 720

Gly Cys Thr Ala Leu His Arg Gly Ile Met Thr Gly His Glu Glu Cys
                725                 730                 735

Val Gln Met Leu Leu Glu Gln Glu Val Ser Ile Leu Cys Lys Asp Ser
                740                 745                 750

Arg Gly Arg Thr Pro Leu His Tyr Ala Ala Arg Gly His Ala Thr
                755                 760                 765

Trp Leu Ser Glu Leu Leu Gln Met Ala Leu Ser Glu Glu Asp Cys Cys
                770                 775                 780

Phe Lys Asp Asn Gln Gly Tyr Thr Pro Leu His Trp Ala Cys Tyr Asn
785                 790                 795                 800

Gly Asn Glu Asn Cys Ile Glu Val Leu Leu Glu Gln Lys Cys Phe Arg
                805                 810                 815

Lys Phe Ile Gly Asn Pro Phe Thr Pro Leu His Cys Ala Ile Ile Asn
                820                 825                 830

Asp His Gly Asn Cys Ala Ser Leu Leu Leu Gly Ala Ile Asp Ser Ser
                835                 840                 845

Ile Val Ser Cys Arg Asp Asp Lys Gly Arg Thr Pro Leu His Ala Ala
850                 855                 860

Ala Phe Ala Asp His Val Glu Cys Leu Gln Leu Leu Arg His Ser
865                 870                 875                 880

Ala Pro Val Asn Ala Val Asp Asn Ser Gly Lys Thr Ala Leu Met Met
                885                 890                 895

Ala Ala Glu Asn Gly Gln Ala Gly Ala Val Asp Ile Leu Val Asn Ser
                900                 905                 910

Ala Gln Ala Asp Leu Thr Val Lys Asp Lys Asp Leu Asn Thr Pro Leu
            915                 920                 925

His Leu Ala Cys Ser Lys Gly His Glu Lys Cys Ala Leu Leu Ile Leu
            930                 935                 940

Asp Lys Ile Gln Asp Glu Ser Leu Ile Asn Glu Lys Asn Asn Ala Leu
945                 950                 955                 960

Gln Thr Pro Leu His Val Ala Ala Arg Asn Gly Leu Lys Val Val Val
                965                 970                 975

Glu Glu Leu Leu Ala Lys Gly Ala Cys Val Leu Ala Val Asp Glu Asn
                980                 985                 990

Gly Cys

<210> SEQ ID NO 39
<211> LENGTH: 2885
<212> TYPE: DNA
<213> ORGANISM: Homo sapiens
<220> FEATURE:
<221> NAME/KEY: CDS
<222> LOCATION: (319)..(2253)
<223> OTHER INFORMATION:

<400> SEQUENCE: 39

```
cgcagaggga agtgtcaact gggatatttc tggtaaaact gaaagcagaa agcagggtgc      60
tagcccctgt gggactgagg gtggaggctg ggggagtttg ggtgccatcc tccagtgaca     120
gatggatgga cctttcatct aagagaaagg aggagacacg ttggcaaatc agcctcaagc     180
ctaagattgc ttgtgaagca atcataagga ggaacaaaaa cagacacaaa aacagaggga     240
aagagtgaaa agacaagaag ggcgcaaact gtgacagact caccgcttca ctaactactc     300
```

| acttaaactg gaagcaaa atg tcc cta aaa ttg cca agg aac tgg gat ttc<br>                            Met Ser Leu Lys Leu Pro Arg Asn Trp Asp Phe<br>                             1            5                  10 | 351 |
|---|---|
| aac ctg aaa gtg gag gct gcg aaa ata gct cgg tca agg agt gtg atg<br>Asn Leu Lys Val Glu Ala Ala Lys Ile Ala Arg Ser Arg Ser Val Met<br>                15                  20                  25 | 399 |
| act ggc gag cag atg gct gcc ttc cat cca tcg tcc acc ccc aac ccg<br>Thr Gly Glu Gln Met Ala Ala Phe His Pro Ser Ser Thr Pro Asn Pro<br>        30                  35                  40 | 447 |
| ctg gag agg ccc atc aag atg ggc tgg ctg aag aag cag agg tcc atc<br>Leu Glu Arg Pro Ile Lys Met Gly Trp Leu Lys Lys Gln Arg Ser Ile<br>        45                  50                  55 | 495 |
| gtg aag aac tgg cag cag agg tac ttt gtg ctg agg gcg cag cag ctc<br>Val Lys Asn Trp Gln Gln Arg Tyr Phe Val Leu Arg Ala Gln Gln Leu<br>60                  65                  70                  75 | 543 |
| tac tac tac aag gat gaa gag gac acg aag ccc cag ggc tgc atg tat<br>Tyr Tyr Tyr Lys Asp Glu Glu Asp Thr Lys Pro Gln Gly Cys Met Tyr<br>                80                  85                  90 | 591 |
| cta cca gga tgt aca atc aag gag atc gcc aca aac cca gaa gaa gct<br>Leu Pro Gly Cys Thr Ile Lys Glu Ile Ala Thr Asn Pro Glu Glu Ala<br>        95                  100               105 | 639 |
| ggg aag ttt gtc ttt gaa atc att cca gcc tca tgg gac cag aat cgc<br>Gly Lys Phe Val Phe Glu Ile Ile Pro Ala Ser Trp Asp Gln Asn Arg<br>          110               115               120 | 687 |
| atg gga cag gac tcc tat gtc ctc atg gcc agc tct cag gcg gag atg<br>Met Gly Gln Asp Ser Tyr Val Leu Met Ala Ser Ser Gln Ala Glu Met<br>        125               130               135 | 735 |
| gag gag tgg gtt aaa ttc ctc agg aga gtt gct ggc aca ccc tgt gga<br>Glu Glu Trp Val Lys Phe Leu Arg Arg Val Ala Gly Thr Pro Cys Gly<br>140                 145               150               155 | 783 |
| gtg ttt ggc cag cgc ttg gat gag act gtg gcc tat gaa cag aaa ttc<br>Val Phe Gly Gln Arg Leu Asp Glu Thr Val Ala Tyr Glu Gln Lys Phe<br>          160               165               170 | 831 |
| ggc ccc cat ctg gtg ccc atc ctg gtg gag aaa tgt gca gag ttc atc<br>Gly Pro His Leu Val Pro Ile Leu Val Glu Lys Cys Ala Glu Phe Ile<br>        175               180               185 | 879 |
| ctg gag cac ggc cgg aat gaa gag ggc atc ttc cgt ctg cct ggg cag<br>Leu Glu His Gly Arg Asn Glu Glu Gly Ile Phe Arg Leu Pro Gly Gln<br>        190               195               200 | 927 |
| gac aac ctg gtg aag cag ctg aga gac gct ttt gat gct ggg gag cgg<br>Asp Asn Leu Val Lys Gln Leu Arg Asp Ala Phe Asp Ala Gly Glu Arg<br>        205               210               215 | 975 |
| ccc tcc ttt gac aga gac aca gat gtg cac act gtg gct tcc ctg tta<br>Pro Ser Phe Asp Arg Asp Thr Asp Val His Thr Val Ala Ser Leu Leu<br>220                 225               230               235 | 1023 |
| aag ctc tac ctc cga gac ctc cca gag ccc gtg gtt ccc tgg agc cag<br>Lys Leu Tyr Leu Arg Asp Leu Pro Glu Pro Val Val Pro Trp Ser Gln<br>          240               245               250 | 1071 |
| tac gaa ggg ttc ctg ctc tgt ggg cag ctc acg aat gcg gat gag gca<br>Tyr Glu Gly Phe Leu Leu Cys Gly Gln Leu Thr Asn Ala Asp Glu Ala<br>        255               260               265 | 1119 |
| aag gct cag cag gag ttg atg aag cag ctc tcc atc ctt cct cgt gac | 1167 |

-continued

```
                Lys Ala Gln Gln Glu Leu Met Lys Gln Leu Ser Ile Leu Pro Arg Asp
                            270                 275                 280 aac tat agt ctc ctg agc tac atc tgc agg ttc cta cat gaa ata cag       1215
Asn Tyr Ser Leu Leu Ser Tyr Ile Cys Arg Phe Leu His Glu Ile Gln
            285                 290                 295 ctg aac tgt gct gtt aac aag atg agt gtg gac aac ctg gct act gtg       1263
Leu Asn Cys Ala Val Asn Lys Met Ser Val Asp Asn Leu Ala Thr Val
300                 305                 310                 315 att ggt gtg aat ctc atc agg tcg aag gtc gaa gac cct gcc gtg atc       1311
Ile Gly Val Asn Leu Ile Arg Ser Lys Val Glu Asp Pro Ala Val Ile
                320                 325                 330 atg aga ggg act cct cag atc caa aga gtg atg act atg atc aga            1359
Met Arg Gly Thr Pro Gln Ile Gln Arg Val Met Thr Met Met Ile Arg
            335                 340                 345 gac cat gaa gtc ctc ttc ccc aag tcc aag gat ata ccc ctg tca ccc       1407
Asp His Glu Val Leu Phe Pro Lys Ser Lys Asp Ile Pro Leu Ser Pro
            350                 355                 360 cct gcc cag aaa aat gac ccc aag aaa gct cca gtg gcc cga agc tct       1455
Pro Ala Gln Lys Asn Asp Pro Lys Lys Ala Pro Val Ala Arg Ser Ser
365                 370                 375 gta ggc tgg gat gcc act gaa gac ctc cga att tct agg aca gac agc       1503
Val Gly Trp Asp Ala Thr Glu Asp Leu Arg Ile Ser Arg Thr Asp Ser
380                 385                 390                 395 ttc agt agc atg aca agc gac tct gat aca acc agc ccc acc gga cag       1551
Phe Ser Ser Met Thr Ser Asp Ser Asp Thr Thr Ser Pro Thr Gly Gln
                400                 405                 410 cag ccg agc gat gcg ttt ccg gag gac agc agc aaa gta ccc agg gaa       1599
Gln Pro Ser Asp Ala Phe Pro Glu Asp Ser Ser Lys Val Pro Arg Glu
            415                 420                 425 aag cca gga gac tgg aaa atg caa tct cgt aaa agg act caa aca ctc       1647
Lys Pro Gly Asp Trp Lys Met Gln Ser Arg Lys Arg Thr Gln Thr Leu
            430                 435                 440 cct aac cgg aaa tgt ttc ttg aca tca gct ttt cag ggt gcc aac agc       1695
Pro Asn Arg Lys Cys Phe Leu Thr Ser Ala Phe Gln Gly Ala Asn Ser
445                 450                 455 agc aaa atg gag atc ttt aaa aat gaa ttc tgg tcg cct tcc tca gag       1743
Ser Lys Met Glu Ile Phe Lys Asn Glu Phe Trp Ser Pro Ser Ser Glu
460                 465                 470                 475 gct aag gca ggg gaa ggg cac agg aga acg atg tct caa gac ttg cgc       1791
Ala Lys Ala Gly Glu Gly His Arg Arg Thr Met Ser Gln Asp Leu Arg
                480                 485                 490 caa ctt tct gac tcc caa cgg act tcc acc tac gat aac gtc cct tcc       1839
Gln Leu Ser Asp Ser Gln Arg Thr Ser Thr Tyr Asp Asn Val Pro Ser
            495                 500                 505 ctg cca ggg tcc cct ggg gag gaa gcc agt gca ctc tct tcc caa gcc       1887
Leu Pro Gly Ser Pro Gly Glu Glu Ala Ser Ala Leu Ser Ser Gln Ala
            510                 515                 520 tgt gac tcc aag gga gat act ctt gcc agt cca aac tct gaa act ggg       1935
Cys Asp Ser Lys Gly Asp Thr Leu Ala Ser Pro Asn Ser Glu Thr Gly
525                 530                 535 cct gga aaa aag aac tct gga gaa gag gaa att gat tct ttg cag agg       1983
Pro Gly Lys Lys Asn Ser Gly Glu Glu Ile Asp Ser Leu Gln Arg
540                 545                 550                 555 atg gtc caa gag cta cga aag gaa ata gaa aca cag aag caa atg tat       2031
Met Val Gln Glu Leu Arg Lys Glu Ile Glu Thr Gln Lys Gln Met Tyr
                560                 565                 570 gag gaa cag att aaa aac ctt gag aag gaa aat tat gac gtt tgg gct       2079
Glu Glu Gln Ile Lys Asn Leu Glu Lys Glu Asn Tyr Asp Val Trp Ala
            575                 580                 585
```

-continued

```
aaa gtg gtg agg ctc aat gaa gaa ctg gag aag gaa aag aag aag tct    2127
Lys Val Val Arg Leu Asn Glu Glu Leu Glu Lys Glu Lys Lys Lys Ser
        590                 595                 600 gca gcc cta gag atc agc ctc cgc aac atg gag cgc tcc cgg gag gat    2175
Ala Ala Leu Glu Ile Ser Leu Arg Asn Met Glu Arg Ser Arg Glu Asp
        605                 610                 615 gtt gag aag agg aac aag gcc ttg gaa gaa gaa gtc aag gaa ttt gtc    2223
Val Glu Lys Arg Asn Lys Ala Leu Glu Glu Glu Val Lys Glu Phe Val
620                 625                 630                 635 aaa tcc atg aag gaa ccc aag acc gag gct taagggtccc aggagtactg      2273
Lys Ser Met Lys Glu Pro Lys Thr Glu Ala
                640                 645 cagggacagc cccagagagg cccaactctg gccccttttct cagtgctatc tgatgacggg  2333
gaaacaaaat tattctctga gagggaaagg acatttgagg gaaacatcaa atttccccat   2393
aaataaatga atggagtttg caggaaggtg agggtgagca gagatgtgtg tggacatctc   2453
tgaccatcca tcgctgtatt caaatggatt gttctattcc attctggtct caggcatgac   2513
cacgtccagt gaagacattt gaggcagcac atctcaggac ccaggcaata gactggcccc   2573
aactcaggct ggactaaggt gtgattaatt ctttgttttt tgtgtggaac agctcacctt   2633
gtcagacagc ctcagggcat ctctgagaca caggggcaga aaatgacatt catcttttga   2693
gtcctcatcc atggagtgct gtgtttgggg ggctgcatct gctgaagcga aaccccatt   2753 ctgccacccc accaggatgc ccattctcca ggacttctcc aacttactat tagactaaac   2813
cagaacaagc aacaaactgt atttatgcaa gcaaattga tgagaaaatt atattcaaat    2873
aaagcaaaat tt                                                       2885
```

<210> SEQ ID NO 40
<211> LENGTH: 645
<212> TYPE: PRT
<213> ORGANISM: Homo sapiens

<400> SEQUENCE: 40

```
Met Ser Leu Lys Leu Pro Arg Asn Trp Asp Phe Asn Leu Lys Val Glu
1               5                   10                  15

Ala Ala Lys Ile Ala Arg Ser Arg Ser Val Met Thr Gly Glu Gln Met
            20                  25                  30

Ala Ala Phe His Pro Ser Ser Thr Pro Asn Pro Leu Glu Arg Pro Ile
        35                  40                  45

Lys Met Gly Trp Leu Lys Lys Gln Arg Ser Ile Val Lys Asn Trp Gln
    50                  55                  60

Gln Arg Tyr Phe Val Leu Arg Ala Gln Gln Leu Tyr Tyr Lys Asp
65                  70                  75                  80

Glu Glu Asp Thr Lys Pro Gln Gly Cys Met Tyr Leu Pro Gly Cys Thr
                85                  90                  95

Ile Lys Glu Ile Ala Thr Asn Pro Glu Glu Ala Gly Lys Phe Val Phe
            100                 105                 110

Glu Ile Ile Pro Ala Ser Trp Asp Gln Asn Arg Met Gly Gln Asp Ser
        115                 120                 125

Tyr Val Leu Met Ala Ser Ser Gln Ala Glu Met Glu Glu Trp Val Lys
    130                 135                 140

Phe Leu Arg Arg Val Ala Gly Thr Pro Cys Gly Val Phe Gly Gln Arg
145                 150                 155                 160

Leu Asp Glu Thr Val Ala Tyr Glu Gln Lys Phe Gly Pro His Leu Val
                165                 170                 175
```

```
Pro Ile Leu Val Glu Lys Cys Ala Glu Phe Ile Leu Glu His Gly Arg
            180                 185                 190

Asn Glu Glu Gly Ile Phe Arg Leu Pro Gly Gln Asp Asn Leu Val Lys
            195                 200                 205

Gln Leu Arg Asp Ala Phe Asp Ala Gly Glu Arg Pro Ser Phe Asp Arg
        210                 215                 220

Asp Thr Asp Val His Thr Val Ala Ser Leu Leu Lys Leu Tyr Leu Arg
225                 230                 235                 240

Asp Leu Pro Glu Pro Val Val Pro Trp Ser Gln Tyr Glu Gly Phe Leu
                245                 250                 255

Leu Cys Gly Gln Leu Thr Asn Ala Asp Glu Ala Lys Ala Gln Gln Glu
            260                 265                 270

Leu Met Lys Gln Leu Ser Ile Leu Pro Arg Asp Asn Tyr Ser Leu Leu
        275                 280                 285

Ser Tyr Ile Cys Arg Phe Leu His Glu Ile Gln Leu Asn Cys Ala Val
        290                 295                 300

Asn Lys Met Ser Val Asp Asn Leu Ala Thr Val Ile Gly Val Asn Leu
305                 310                 315                 320

Ile Arg Ser Lys Val Glu Asp Pro Ala Val Ile Met Arg Gly Thr Pro
                325                 330                 335

Gln Ile Gln Arg Val Met Thr Met Met Ile Arg Asp His Glu Val Leu
            340                 345                 350

Phe Pro Lys Ser Lys Asp Ile Pro Leu Ser Pro Pro Ala Gln Lys Asn
        355                 360                 365

Asp Pro Lys Lys Ala Pro Val Ala Arg Ser Ser Val Gly Trp Asp Ala
        370                 375                 380

Thr Glu Asp Leu Arg Ile Ser Arg Thr Asp Ser Phe Ser Ser Met Thr
385                 390                 395                 400

Ser Asp Ser Asp Thr Thr Ser Pro Thr Gly Gln Gln Pro Ser Asp Ala
                405                 410                 415

Phe Pro Glu Asp Ser Ser Lys Val Pro Arg Glu Lys Pro Gly Asp Trp
            420                 425                 430

Lys Met Gln Ser Arg Lys Arg Thr Gln Thr Leu Pro Asn Arg Lys Cys
        435                 440                 445

Phe Leu Thr Ser Ala Phe Gln Gly Ala Asn Ser Ser Lys Met Glu Ile
        450                 455                 460

Phe Lys Asn Glu Phe Trp Ser Pro Ser Ser Glu Ala Lys Ala Gly Glu
465                 470                 475                 480

Gly His Arg Arg Thr Met Ser Gln Asp Leu Arg Gln Leu Ser Asp Ser
                485                 490                 495

Gln Arg Thr Ser Thr Tyr Asp Asn Val Pro Ser Leu Pro Gly Ser Pro
            500                 505                 510

Gly Glu Glu Ala Ser Ala Leu Ser Ser Gln Ala Cys Asp Ser Lys Gly
        515                 520                 525

Asp Thr Leu Ala Ser Pro Asn Ser Glu Thr Gly Pro Gly Lys Lys Asn
        530                 535                 540

Ser Gly Glu Glu Glu Ile Asp Ser Leu Gln Arg Met Val Gln Glu Leu
545                 550                 555                 560

Arg Lys Glu Ile Glu Thr Gln Lys Gln Met Tyr Glu Glu Gln Ile Lys
                565                 570                 575

Asn Leu Glu Lys Glu Asn Tyr Asp Val Trp Ala Lys Val Val Arg Leu
            580                 585                 590

Asn Glu Glu Leu Glu Lys Glu Lys Lys Ser Ala Ala Leu Glu Ile
```

| | | | | 595 | | | | | 600 | | | | | 605 | | |
|---|---|---|---|---|---|---|---|---|---|---|---|---|---|---|---|---|
| Ser | Leu | Arg | Asn | Met | Glu | Arg | Ser | Arg | Glu | Asp | Val | Glu | Lys | Arg | Asn |
| | | | | 610 | | | | | 615 | | | | | 620 | | |
| Lys | Ala | Leu | Glu | Glu | Val | Lys | Glu | Phe | Val | Lys | Ser | Met | Lys | Glu | |
| 625 | | | | | 630 | | | | | 635 | | | | | 640 | |
| Pro | Lys | Thr | Glu | Ala | | | | | | | | | | | | |
| | | | | 645 | | | | | | | | | | | | |

<210> SEQ ID NO 41
<211> LENGTH: 1417
<212> TYPE: DNA
<213> ORGANISM: Homo sapiens
<220> FEATURE:
<221> NAME/KEY: CDS
<222> LOCATION: (67)..(624)
<223> OTHER INFORMATION:

<400> SEQUENCE: 41

```
tgtggagtgg gggaagttga ttgggtctag accaaagaac tttgaggaac ttgcccagag    60 ccctgc atg cat cag acc tac agc aga cat tgc agg cct gaa gaa agc     108
       Met His Gln Thr Tyr Ser Arg His Cys Arg Pro Glu Glu Ser
        1               5                  10 acc ttt tct gct gcc atg aca acc atg caa gga atg gaa cag gcc atg   156
Thr Phe Ser Ala Ala Met Thr Thr Met Gln Gly Met Glu Gln Ala Met
 15                  20                  25                  30 cca ggg gct ggc cct ggt gtg ccc cag ctg gga aac atg gct gtc ata   204
Pro Gly Ala Gly Pro Gly Val Pro Gln Leu Gly Asn Met Ala Val Ile
                 35                  40                  45 cat tca cat ctg tgg aaa gga ttg caa gag aag ttc ttg aag gga gaa   252
His Ser His Leu Trp Lys Gly Leu Gln Glu Lys Phe Leu Lys Gly Glu
             50                  55                  60 ccc aaa gtc ctt ggg gtt gtg cag att ctg act gcc ctg atg agc ctt   300
Pro Lys Val Leu Gly Val Val Gln Ile Leu Thr Ala Leu Met Ser Leu
         65                  70                  75 agc atg gga ata aca atg atg tgt atg gca tct aat act tat gga agt   348
Ser Met Gly Ile Thr Met Met Cys Met Ala Ser Asn Thr Tyr Gly Ser
 80                  85                  90 aac cct att tcc gtg tat atc ggg tac aca att tgg ggg tca gta atg   396
Asn Pro Ile Ser Val Tyr Ile Gly Tyr Thr Ile Trp Gly Ser Val Met
 95                 100                 105                 110 ttt att att tca gga tcc ttg tca att gca gca gga att aga act aca   444
Phe Ile Ile Ser Gly Ser Leu Ser Ile Ala Ala Gly Ile Arg Thr Thr
                115                 120                 125 aaa ggc ctg ggt ctg gat ggc atg gtg ctc ctc tta agt gtg ctg gaa   492
Lys Gly Leu Gly Leu Asp Gly Met Val Leu Leu Leu Ser Val Leu Glu
            130                 135                 140 ttc tgc att gct gtg tcc ctc tct gcc ttt gga tgt aaa gtg ctc tgt   540
Phe Cys Ile Ala Val Ser Leu Ser Ala Phe Gly Cys Lys Val Leu Cys
        145                 150                 155 tgt acc cct ggt ggg gtt gtg tta att ctg cca tca cat tct cac atg   588
Cys Thr Pro Gly Gly Val Val Leu Ile Leu Pro Ser His Ser His Met
    160                 165                 170 gca gaa aca gca tct ccc aca cca ctt aat gag gtt tgaggccacc         634
Ala Glu Thr Ala Ser Pro Thr Pro Leu Asn Glu Val
175                 180                 185 aaaagatcaa cagacaaatg ctccagaaat ctatgctgac tgtgacacaa gagcctcaca   694
tgagaaatta ccagtatcca acttcgatac tgatagactt gttgatatta ttattatatg   754
taatccaatt atgaactgtg tgtgtataga gagataataa attcaaaatt atgttctcat   814
```

-continued

```
ttttttccct ggaactcaat aactcatttc actggctctt tatcgagagt actagaagtt    874
aaattaataa ataatgcatt taatgaggca acagcacttg aaagttttc attcatcata     934 agaactttat ataaaggcat tacattggca ataaggttt ggaagcagaa gagcaaaaaa     994
aagatattgt taaaatgagg cctccatgca aaacacatac ttccctccca tttatttaac   1054 ttttttttc tcctacctat ggggaccaaa gtgcttttc cttcaggaag tggagatgca    1114
tggccatctc cccctccctt tttccttctc ctgcttttct ttccccatag aaagtacctt   1174
gaagtagcac agcccgtcct tgcatgtgca cgagctatca tttgagtaaa agtatacatg   1234
gagtaaaaat catattaagc atcagattca acttatattt tctatttcat cttcttcctt   1294
tcccttctcc caccttctac tgggcataat tatatcttaa tcatatatgg aaatgtgcaa   1354
catatggtat ttgttaaata cgtttgtttt tattgcagag caaaaataaa tcaaattaga   1414
agc                                                                1417
```

<210> SEQ ID NO 42
<211> LENGTH: 186
<212> TYPE: PRT
<213> ORGANISM: Homo sapiens

<400> SEQUENCE: 42

```
Met His Gln Thr Tyr Ser Arg His Cys Arg Pro Glu Glu Ser Thr Phe
1               5                   10                  15

Ser Ala Ala Met Thr Thr Met Gln Gly Met Glu Gln Ala Met Pro Gly
            20                  25                  30

Ala Gly Pro Gly Val Pro Gln Leu Gly Asn Met Ala Val Ile His Ser
        35                  40                  45

His Leu Trp Lys Gly Leu Gln Glu Lys Phe Leu Lys Gly Glu Pro Lys
    50                  55                  60

Val Leu Gly Val Val Gln Ile Leu Thr Ala Leu Met Ser Leu Ser Met
65                  70                  75                  80

Gly Ile Thr Met Met Cys Met Ala Ser Asn Thr Tyr Gly Ser Asn Pro
                85                  90                  95

Ile Ser Val Tyr Ile Gly Tyr Thr Ile Trp Gly Ser Val Met Phe Ile
            100                 105                 110

Ile Ser Gly Ser Leu Ser Ile Ala Ala Gly Ile Arg Thr Thr Lys Gly
        115                 120                 125

Leu Gly Leu Asp Gly Met Val Leu Leu Ser Val Leu Glu Phe Cys
    130                 135                 140

Ile Ala Val Ser Leu Ser Ala Phe Gly Cys Lys Val Leu Cys Cys Thr
145                 150                 155                 160

Pro Gly Gly Val Val Leu Ile Leu Pro Ser His Ser Met Ala Glu
                165                 170                 175

Thr Ala Ser Pro Thr Pro Leu Asn Glu Val
            180                 185
```

<210> SEQ ID NO 43
<211> LENGTH: 5479
<212> TYPE: DNA
<213> ORGANISM: Homo sapiens
<220> FEATURE:
<221> NAME/KEY: CDS
<222> LOCATION: (329)..(2245)
<223> OTHER INFORMATION:

<400> SEQUENCE: 43

```
tggaccggtc cggattcccg ggatcgggaa cccgtcagga aggacataaa caaaacaaac    60
```

```
ccgaggcagc atggagaggg gccgtggccc ctgcagcgga accggaccca gtccctgagc      120
cgcccctaca cccacagaca gcatcgcaca gaattatttt aaaaaaaagc agtgatccaa      180
gcaattgaat tggaagcact ctggggaaac ctgctgttta ttgtggaaat catcttcgat      240
cttggaattg aaagtaaagc tggaaaggaa tttacaaaca agaaaaaaaa gaagtttgga      300
atcggattca caggatctgg gcttggaa atg cct cag cct agt gta agc gga         352
                                Met Pro Gln Pro Ser Val Ser Gly
                                  1               5
```

| | | | | | | | | | | | | | | | | |
|---|---|---|---|---|---|---|---|---|---|---|---|---|---|---|---|---|
| atg | gat | ccg | cct | ttc | ggg | gat | gcc | ttt | cga | agc | cac | acc | ttt | tcg | gaa | 400 |
| Met | Asp | Pro | Pro | Phe | Gly | Asp | Ala | Phe | Arg | Ser | His | Thr | Phe | Ser | Glu | |
| | 10 | | | | 15 | | | | | 20 | | | | | | |
| caa | act | ctg | atg | agc | aca | gat | ctc | tta | gca | aac | agt | tcg | gat | cca | gat | 448 |
| Gln | Thr | Leu | Met | Ser | Thr | Asp | Leu | Leu | Ala | Asn | Ser | Ser | Asp | Pro | Asp | |
| 25 | | | | | 30 | | | | | 35 | | | | | 40 | |
| ttc | atg | tat | gaa | ctg | gat | aga | gag | atg | aac | tac | caa | cag | aat | cct | aga | 496 |
| Phe | Met | Tyr | Glu | Leu | Asp | Arg | Glu | Met | Asn | Tyr | Gln | Gln | Asn | Pro | Arg | |
| | | | | 45 | | | | | 50 | | | | | 55 | | |
| gac | aac | ttt | ctt | tct | ttg | gag | gac | tgc | aaa | gac | att | gaa | aat | ctg | gag | 544 |
| Asp | Asn | Phe | Leu | Ser | Leu | Glu | Asp | Cys | Lys | Asp | Ile | Glu | Asn | Leu | Glu | |
| | | | 60 | | | | | 65 | | | | | 70 | | | |
| tct | ttc | aca | gat | gtc | ctg | gat | aat | gag | ggt | gct | tta | acc | tca | aac | tgg | 592 |
| Ser | Phe | Thr | Asp | Val | Leu | Asp | Asn | Glu | Gly | Ala | Leu | Thr | Ser | Asn | Trp | |
| | | 75 | | | | | 80 | | | | | 85 | | | | |
| gaa | cag | tgg | gat | aca | tac | tgt | gaa | gac | cta | acg | aaa | tat | acc | aaa | cta | 640 |
| Glu | Gln | Trp | Asp | Thr | Tyr | Cys | Glu | Asp | Leu | Thr | Lys | Tyr | Thr | Lys | Leu | |
| | 90 | | | | | 95 | | | | | 100 | | | | | |
| acc | agc | tgt | gac | atc | tgg | gga | aca | aaa | gaa | gtg | gat | tac | ttg | ggt | ctt | 688 |
| Thr | Ser | Cys | Asp | Ile | Trp | Gly | Thr | Lys | Glu | Val | Asp | Tyr | Leu | Gly | Leu | |
| 105 | | | | | 110 | | | | | 115 | | | | | 120 | |
| gat | gac | ttt | tct | agt | cct | tac | caa | gat | gaa | gag | gtt | ata | agt | aaa | act | 736 |
| Asp | Asp | Phe | Ser | Ser | Pro | Tyr | Gln | Asp | Glu | Glu | Val | Ile | Ser | Lys | Thr | |
| | | | | 125 | | | | | 130 | | | | | 135 | | |
| cca | act | tta | gct | caa | ctt | aat | agt | gag | gac | tca | cag | tct | gtt | tct | gat | 784 |
| Pro | Thr | Leu | Ala | Gln | Leu | Asn | Ser | Glu | Asp | Ser | Gln | Ser | Val | Ser | Asp | |
| | | 140 | | | | | 145 | | | | | 150 | | | | |
| tcc | ctt | tat | tac | ccc | gat | tca | ctt | ttc | agt | gtc | aaa | caa | aat | ccc | tta | 832 |
| Ser | Leu | Tyr | Tyr | Pro | Asp | Ser | Leu | Phe | Ser | Val | Lys | Gln | Asn | Pro | Leu | |
| | 155 | | | | | 160 | | | | | 165 | | | | | |
| ccc | tct | tca | ttc | cct | ggt | aaa | aag | atc | aca | agc | aga | gca | gct | gct | cct | 880 |
| Pro | Ser | Ser | Phe | Pro | Gly | Lys | Lys | Ile | Thr | Ser | Arg | Ala | Ala | Ala | Pro | |
| 170 | | | | | 175 | | | | | 180 | | | | | | |
| gtg | tgt | tct | tct | aag | act | ctg | cag | gct | gag | gtc | cct | ttg | tca | gac | tgt | 928 |
| Val | Cys | Ser | Ser | Lys | Thr | Leu | Gln | Ala | Glu | Val | Pro | Leu | Ser | Asp | Cys | |
| 185 | | | | | 190 | | | | | 195 | | | | | 200 | |
| gtc | caa | aaa | gca | agt | aaa | ccc | cct | tca | agc | aca | caa | atc | atg | gtg | aag | 976 |
| Val | Gln | Lys | Ala | Ser | Lys | Pro | Pro | Ser | Ser | Thr | Gln | Ile | Met | Val | Lys | |
| | | | | 205 | | | | | 210 | | | | | 215 | | |
| acc | aac | atg | tat | cat | aat | gaa | aag | gtg | aac | ttt | cat | gtt | gaa | tgt | aaa | 1024 |
| Thr | Asn | Met | Tyr | His | Asn | Glu | Lys | Val | Asn | Phe | His | Val | Glu | Cys | Lys | |
| | | | | 220 | | | | | 225 | | | | | 230 | | |
| gac | tat | gta | aaa | aag | gca | aag | gta | aag | atc | aac | cca | gtg | caa | cag | agc | 1072 |
| Asp | Tyr | Val | Lys | Lys | Ala | Lys | Val | Lys | Ile | Asn | Pro | Val | Gln | Gln | Ser | |
| | | 235 | | | | | 240 | | | | | 245 | | | | |
| cgg | ccc | ttg | ttg | agc | cag | att | cac | aca | gat | gca | gca | aag | gag | aac | acc | 1120 |
| Arg | Pro | Leu | Leu | Ser | Gln | Ile | His | Thr | Asp | Ala | Ala | Lys | Glu | Asn | Thr | |
| | 250 | | | | | 255 | | | | | 260 | | | | | |
| tgc | tac | tgt | ggt | gca | gtg | gca | aag | aga | caa | gag | aaa | aaa | ggg | atg | gag | 1168 |
| Cys | Tyr | Cys | Gly | Ala | Val | Ala | Lys | Arg | Gln | Glu | Lys | Lys | Gly | Met | Glu | |

```
                                          -continued
265                     270                     275                     280
cct ctt caa ggt cat gcc act ccc gct ttg cct ttt aaa gaa acc cag        1216
Pro Leu Gln Gly His Ala Thr Pro Ala Leu Pro Phe Lys Glu Thr Gln
                        285                     290                     295 gaa cta tta cta agt ccc ctg ccc cag gaa ggt cct ggg tca ctt gca        1264
Glu Leu Leu Leu Ser Pro Leu Pro Gln Glu Gly Pro Gly Ser Leu Ala
                300                     305                     310 gca gga gag agc agc agt ctt tct gcc agt aca tca gtc tca gat tca        1312
Ala Gly Glu Ser Ser Ser Leu Ser Ala Ser Thr Ser Val Ser Asp Ser
            315                     320                     325 tcc cag aaa aaa gaa gag cac aat tat tct ctt ttt gtc tcc gac aac        1360
Ser Gln Lys Lys Glu Glu His Asn Tyr Ser Leu Phe Val Ser Asp Asn
        330                     335                     340 ttg ggt gaa cag cca act aaa tgc agt cct gaa gaa gat gag gag gac        1408
Leu Gly Glu Gln Pro Thr Lys Cys Ser Pro Glu Glu Asp Glu Glu Asp
345                     350                     355                     360 gag gag gat gtt gat gat gag gac cat gat gaa gga ttc ggc agt gag        1456
Glu Glu Asp Val Asp Asp Glu Asp His Asp Glu Gly Phe Gly Ser Glu
                    365                     370                     375 cat gaa ctg tct gaa aat gag gag gag gaa gaa gag gaa gag gat tat        1504
His Glu Leu Ser Glu Asn Glu Glu Glu Glu Glu Glu Glu Glu Asp Tyr
                380                     385                     390 gaa gat gac aag gat gat gat att agt gat act ttc tct gaa cca ggc        1552
Glu Asp Asp Lys Asp Asp Asp Ile Ser Asp Thr Phe Ser Glu Pro Gly
            395                     400                     405 tat gaa aat gat tct gta gaa gac ctg aag gag gtg act tca ata tct        1600
Tyr Glu Asn Asp Ser Val Glu Asp Leu Lys Glu Val Thr Ser Ile Ser
        410                     415                     420 tca cgg aag aga ggt aaa aga aga tac ttc tgg gag tat agt gaa caa        1648
Ser Arg Lys Arg Gly Lys Arg Arg Tyr Phe Trp Glu Tyr Ser Glu Gln
425                     430                     435                     440 ctt aca cca tca cag caa gag agg atg ctg aga cca tct gag tgg aac        1696
Leu Thr Pro Ser Gln Gln Glu Arg Met Leu Arg Pro Ser Glu Trp Asn
                    445                     450                     455 cga gat act ttg cca agt aat atg tat cag aaa aat ggc tta cat cat        1744
Arg Asp Thr Leu Pro Ser Asn Met Tyr Gln Lys Asn Gly Leu His His
                460                     465                     470 gga aaa tat gca gta aag aag tca cgg aga act gat gta gaa gac ctg        1792
Gly Lys Tyr Ala Val Lys Lys Ser Arg Arg Thr Asp Val Glu Asp Leu
            475                     480                     485 act cca aat cct aaa aaa ctc ctc cag ata ggc aat gaa ctt cgg aaa        1840
Thr Pro Asn Pro Lys Lys Leu Leu Gln Ile Gly Asn Glu Leu Arg Lys
        490                     495                     500 ctg aat aag gtg att agt gac ctg act cca gtc agt gag ctt ccc tta        1888
Leu Asn Lys Val Ile Ser Asp Leu Thr Pro Val Ser Glu Leu Pro Leu
505                     510                     515                     520 aca gcc cga cca agg tca agg aag gaa aaa aat aag ctg gct ttc aga        1936
Thr Ala Arg Pro Arg Ser Arg Lys Glu Lys Asn Lys Leu Ala Phe Arg
                    525                     530                     535 gct tgt cgg tta aag aag aaa gcc cag tat gaa gct aat aaa gtg aaa        1984
Ala Cys Arg Leu Lys Lys Lys Ala Gln Tyr Glu Ala Asn Lys Val Lys
                540                     545                     550 tta tgg ggc ctc aac aca gaa tat gat aat tta ttg ttt gta atc aac        2032
Leu Trp Gly Leu Asn Thr Glu Tyr Asp Asn Leu Leu Phe Val Ile Asn
            555                     560                     565 tcc atc aag caa gag att gta aac cgg gta cag aat cca aga gat gag        2080
Ser Ile Lys Gln Glu Ile Val Asn Arg Val Gln Asn Pro Arg Asp Glu
        570                     575                     580 aga gga ccc aac atg ggg cag aag ctt gaa atc ctc att aaa gat act        2128
```

-continued

| | | | | | | | | | | | | | |
|---|---|---|---|---|---|---|---|---|---|---|---|---|---|
| Arg | Gly | Pro | Asn | Met | Gly | Gln | Lys | Leu | Glu | Ile | Leu | Lys | Asp | Thr |
| 585 | | | | 590 | | | | | 595 | | | | 600 | |

```
ctc ggt cta cca gtt gct ggg caa acc tca gaa ttt gtt aac caa gtg     2176
Leu Gly Leu Pro Val Ala Gly Gln Thr Ser Glu Phe Val Asn Gln Val
            605                 610                 615 tta gag aag act gca gaa ggg aat ccc act gga ggc ctt gta gga tta     2224
Leu Glu Lys Thr Ala Glu Gly Asn Pro Thr Gly Gly Leu Val Gly Leu
        620                 625                 630 agg ata cca aca tca aag gtg taatcagcct cattggacca ctggtcagaa        2275
Arg Ile Pro Thr Ser Lys Val
            635 atgtctgcgt tttgtcacgt tatccattgt aaattttcat tctgttttgc atgtcagtta   2335
gcattatgta aacatttaca attaggttac attgttttaa gaactaagta gcataagtga   2395
agcatgatcc aaaatacttg attattgcat tttcagagca taaaccatga ttaaaactgc   2455
tactggcatc agaattgaaa atcatatgtt taagtaaatg ttaggtacag attacaaaaa   2515
tctgttaaag caaaacattt tggaggagtg aaatagtaaa atgccaagta ttgtggcaga   2575
tttatgctct gaaccacaca aaaaaattga ggaagcattt ttttaaacag tcggtttaaa   2635
ttgttttttag aattattgct ttttgttcta attttccaca accattaatc tcacttgtat  2695
atggcacacc cagcacttgt gcctgtgggc catattagat gttcattgtc agagctcaag   2755
atgatatata aaatatata tatatatata tatatataca cacacacaca caaatgtctg    2815
tgcaagtaag aaaaaaaaag catattcttt gtgccttgta ttttggggaa actctaaaac   2875
tggtaatatt ttgtatgatg aaaaccctaa tgagaaaaaa caagatatat agatggaaaa   2935
attatggggt ttaaatgttt ttttgttcca actcttttttc agattttttg aatgtatata  2995
ggactatgtt gaaatgtaga tatatgccac agagtctgtg tattgtataa aaaacaaaac   3055
aaaaaacaac aaaaaaaaga tggctctaga aaactcatat ttcggtactt gaccggaaga   3115
agacaaatac ttgcacatta ttgcgattgt tttatttttt gtaccaaaga caaatgcaac   3175
tgatatggca aactgccagt ctaagtaaag ttttgcacag cttacatgat actgtatgaa   3235
tgtatgaaaa aaaaggagaa aaaaaagaaa aaaaaaggtc agggttaggg atcttactga   3295
actgtgaatt ttatttctgt ttgggtccaa ttatctacag aaggagcatc catacataca   3355
aatattattt tgctgttcct ctagttcgct tccatagtag ataagttggt ggccatttag   3415
atgtctttta tttctgcact tattgtagga aattttaata tatttcattt tagtaagcta   3475
ttgataaaat agttttttgac tttgaaaatt aaaatgttta tttagcttat tgtagtatac  3535
ttccaccaga caacaaaata gattattttt attgtattat gtatatatat atatgtaaag   3595
aaagaaaaaa gctaaaaata tctaattctt tagttgccac ttttccgatt gatgtattat   3655
tgtgcatgta atattttcaa agatcaacac aggctaaaac aaaaacaatt tatagatttt   3715
tatattttttg tacaggtatt ttcaaactag cttcttcaaa cttaacatgt gacttattct  3775
tctatagttt ctagaattga gaaacattaa cacatttagt ttttaggtgc tcttttttgc   3835
tcatataaaa cagcttcatt agtcagtgtt ttaactgtgt tcaagcttta cctcttgatg   3895
agaaatttct tatgtcaagg cagcattata aaccttcccc cacagatttt tccatcctgt   3955
ctctacttac tgttttattc tcaaatcttg tgctttgaac tctgaaaact ggtggcttaa   4015
aaactaaaaa aagaaaaaaa gcatatttag caaggaaaaa aataccaaaa tttcaggcat   4075
agctgctgga aaaattatct atttctccat tacccactgt aggatttctt ttttaattat   4135
actttgacta taaagtgtca agtataatt tgttctttttc ttttacttttg ttaccccatt  4195
```

```
tgtaagctat agcatatgaa gctatatata tagcttgtga aggtttgatc tagaacaccc    4255
agtaacaaat gaacaatgtt gcttacctgc ttctttgaca tcttaaaaaa gaaatccaag    4315
gaggattgta aggattgtct taccaccttg gctgaactgt gatgcacaag attttctat    4375 gtgtttggtg gaaatgtacc tggtttgtac attcacgcta aacagatgat aagctcaagt    4435
ctgatggttt aatagaatgt aagttcatcg tttaaagctt ttccttttta ggttggagaa    4495
ggcaaaacac aggcttgcaa gttggaagta tatgaagtct tgacagagtg tgtctggtaa    4555
attgaaaagt gtttcaaact atggcagttt tgcaatcagg tgaaaatcac ctcatgatat    4615
tcagctgata aggtttataa aattgccct tctagctgc tctgttagga attctggttt    4675
ttgatacttt tttcctgtct gcaaaccaga atttgatttt ttggtcttgc atttcaaaaa    4735
aaaaaagact ttgaatctgt ttagtagatt ccatatcttt gagtttcagt gttttatatg    4795
tactacttaa gttaaatagt taaaagcttt taaatagttg agctttttaa tgttgacact    4855
ttattttgta cctatttata tatgtatgta tatcttagaa aagcactttg ttaaaaaaaa    4915 attgcattt atatgattcc tgccatttgc tgctaaatct gggctggtca gaatgctgca    4975
gcgatacttg atctatataa aaacctggca gtaaaatgta gagtgaaagt taaatcctct    5035
tgctgtttta actttatcat aaagatgaca taggcaagct gtgcagcttt acatttaac     5095 cagggactc tgtggcattt aaaaccgtct agaaatggtt gtactttaat gccagtaata    5155
atctgcttcc tctattgtca ttaaaatata tacgtttagt gtatcacaca aaccaatctt    5215
ataagggtaa tgtaaaaacc ccaacaattg tacatgttct gttttgaaa attgtggcat    5275 gtatttttgg gtgaagatca ttagagaaga gttctctaaa ggttttctgt gttcatacat    5335
ggtatacaga tagctcataa tgaagtccag aatcttactt ttaagtgaag gcattgtgaa    5395
ttcacctcaa gtaaacccat tgttccaaag caattataaa ctttgactct agtactacta    5455
tgatttaaaa aaaaaaaaaa aaaa                                           5479

<210> SEQ ID NO 44
<211> LENGTH: 639
<212> TYPE: PRT
<213> ORGANISM: Homo sapiens

<400> SEQUENCE: 44

Met Pro Gln Pro Ser Val Ser Gly Met Asp Pro Pro Phe Gly Asp Ala
1               5                   10                  15

Phe Arg Ser His Thr Phe Ser Glu Gln Thr Leu Met Ser Thr Asp Leu
            20                  25                  30

Leu Ala Asn Ser Ser Asp Pro Asp Phe Met Tyr Glu Leu Asp Arg Glu
        35                  40                  45

Met Asn Tyr Gln Gln Asn Pro Arg Asp Asn Phe Leu Ser Leu Glu Asp
    50                  55                  60

Cys Lys Asp Ile Glu Asn Leu Glu Ser Phe Thr Asp Val Leu Asp Asn
65                  70                  75                  80

Glu Gly Ala Leu Thr Ser Asn Trp Glu Gln Trp Asp Thr Tyr Cys Glu
                85                  90                  95

Asp Leu Thr Lys Tyr Thr Lys Leu Thr Ser Cys Asp Ile Trp Gly Thr
            100                 105                 110

Lys Glu Val Asp Tyr Leu Gly Leu Asp Asp Phe Ser Ser Pro Tyr Gln
        115                 120                 125

Asp Glu Glu Val Ile Ser Lys Thr Pro Thr Leu Ala Gln Leu Asn Ser
    130                 135                 140
```

```
Glu Asp Ser Gln Ser Val Ser Asp Ser Leu Tyr Tyr Pro Asp Ser Leu
145                 150                 155                 160

Phe Ser Val Lys Gln Asn Pro Leu Pro Ser Ser Phe Pro Gly Lys Lys
            165                 170                 175

Ile Thr Ser Arg Ala Ala Pro Val Cys Ser Ser Lys Thr Leu Gln
            180                 185                 190

Ala Glu Val Pro Leu Ser Asp Cys Val Gln Lys Ala Ser Lys Pro Pro
        195                 200                 205

Ser Ser Thr Gln Ile Met Val Lys Thr Asn Met Tyr His Asn Glu Lys
    210                 215                 220

Val Asn Phe His Val Glu Cys Lys Asp Tyr Val Lys Ala Lys Val
225                 230                 235                 240

Lys Ile Asn Pro Val Gln Gln Ser Arg Pro Leu Leu Ser Gln Ile His
            245                 250                 255

Thr Asp Ala Ala Lys Glu Asn Thr Cys Tyr Cys Gly Ala Val Ala Lys
            260                 265                 270

Arg Gln Glu Lys Lys Gly Met Glu Pro Leu Gln Gly His Ala Thr Pro
        275                 280                 285

Ala Leu Pro Phe Lys Glu Thr Gln Glu Leu Leu Ser Pro Leu Pro
290                 295                 300

Gln Glu Gly Pro Gly Ser Leu Ala Ala Gly Glu Ser Ser Ser Leu Ser
305                 310                 315                 320

Ala Ser Thr Ser Val Ser Asp Ser Ser Gln Lys Lys Glu Glu His Asn
            325                 330                 335

Tyr Ser Leu Phe Val Ser Asp Asn Leu Gly Glu Gln Pro Thr Lys Cys
            340                 345                 350

Ser Pro Glu Glu Asp Glu Glu Asp Glu Glu Asp Val Asp Asp Glu Asp
        355                 360                 365

His Asp Glu Gly Phe Gly Ser Glu His Glu Leu Ser Glu Asn Glu Glu
        370                 375                 380

Glu Glu Glu Glu Glu Asp Tyr Glu Asp Asp Lys Asp Asp Ile
385                 390                 395                 400

Ser Asp Thr Phe Ser Glu Pro Gly Tyr Glu Asn Asp Ser Val Glu Asp
            405                 410                 415

Leu Lys Glu Val Thr Ser Ile Ser Ser Arg Lys Arg Gly Lys Arg Arg
            420                 425                 430

Tyr Phe Trp Glu Tyr Ser Glu Gln Leu Thr Pro Ser Gln Gln Glu Arg
        435                 440                 445

Met Leu Arg Pro Ser Glu Trp Asn Arg Asp Thr Leu Pro Ser Asn Met
    450                 455                 460

Tyr Gln Lys Asn Gly Leu His His Gly Lys Tyr Ala Val Lys Lys Ser
465                 470                 475                 480

Arg Arg Thr Asp Val Glu Asp Leu Thr Pro Asn Pro Lys Lys Leu Leu
            485                 490                 495

Gln Ile Gly Asn Glu Leu Arg Lys Leu Asn Lys Val Ile Ser Asp Leu
        500                 505                 510

Thr Pro Val Ser Glu Leu Pro Leu Thr Ala Arg Pro Arg Ser Arg Lys
        515                 520                 525

Glu Lys Asn Lys Leu Ala Phe Arg Ala Cys Arg Leu Lys Lys Lys Ala
    530                 535                 540

Gln Tyr Glu Ala Asn Lys Val Lys Leu Trp Gly Leu Asn Thr Glu Tyr
545                 550                 555                 560

Asp Asn Leu Leu Phe Val Ile Asn Ser Ile Lys Gln Glu Ile Val Asn
```

```
                        565                 570                 575
Arg Val Gln Asn Pro Arg Asp Glu Arg Gly Pro Asn Met Gly Gln Lys
                580                 585                 590
Leu Glu Ile Leu Ile Lys Asp Thr Leu Gly Leu Pro Val Ala Gly Gln
        595                 600                 605
Thr Ser Glu Phe Val Asn Gln Val Leu Glu Lys Thr Ala Glu Gly Asn
    610                 615                 620
Pro Thr Gly Gly Leu Val Gly Leu Arg Ile Pro Thr Ser Lys Val
625                 630                 635

<210> SEQ ID NO 45
<211> LENGTH: 3938
<212> TYPE: DNA
<213> ORGANISM: Homo sapiens
<220> FEATURE:
<221> NAME/KEY: CDS
<222> LOCATION: (481)..(2403)
<223> OTHER INFORMATION:

<400> SEQUENCE: 45
ccgccccagt cgggtacccc tcctcgcgag agcgccgagc attccggcct gggaagcgcg    60
tgcagaagcg gaggtgctgc tcatgggact tgtcggccgc cgtagcccct gctaggacag   120
cccgtgcgag cctgctggag gaggaagaga aaggcagaga gagtcgggtt acaagatggc   180
ggatctgtag tagttaccgc ggcggcggga gagcaagcga gccctggggg caaagagac   240 gggagagtgg gtgtatgcgc gggtgaagtg agaggtaacg gggcctccgg gcggagaggc   300
ctcagtggct cttgtcaccc cttctcgcgg ctgaaccttt ggagccatgg tgaattcggg   360
cctctccgaa gccgccgccg ccgccaccgc cactactgcc tttaccgtct cctaagagtg   420
aggagcgcgg acgaggtaag cgaggaggcg gcggctagag cggtggagac agcagccacc   480 atg tcg gat acg cgg cgg cga gtg aag gtc tat acc ctg aac gaa gac   528
Met Ser Asp Thr Arg Arg Arg Val Lys Val Tyr Thr Leu Asn Glu Asp
1               5                   10                  15 cgg caa tgg gac gac cga ggc acc ggg cac gtc tcc tcc act tac gtg   576
Arg Gln Trp Asp Asp Arg Gly Thr Gly His Val Ser Ser Thr Tyr Val
            20                  25                  30 gag gag ctc aag ggg atg tcg ctg ctg gtt cgg gca gag tcc gac gga   624
Glu Glu Leu Lys Gly Met Ser Leu Leu Val Arg Ala Glu Ser Asp Gly
        35                  40                  45 tca cta ctc ttg gaa tca aag ata aat cca aat act gca tat cag aaa   672
Ser Leu Leu Leu Glu Ser Lys Ile Asn Pro Asn Thr Ala Tyr Gln Lys
    50                  55                  60 caa cag gat aca tta att gtt tgg tca gaa gca gag aac tat gat ttg   720
Gln Gln Asp Thr Leu Ile Val Trp Ser Glu Ala Glu Asn Tyr Asp Leu
65                  70                  75                  80 gct ctg agt ttt cag gag aaa gct ggc tgt gat gag atc tgg gaa aaa   768
Ala Leu Ser Phe Gln Glu Lys Ala Gly Cys Asp Glu Ile Trp Glu Lys
                85                  90                  95 att tgt cag gaa gat gag aag ttt ttg tct gaa gtt ttt gca caa tta   816
Ile Cys Gln Glu Asp Glu Lys Phe Leu Ser Glu Val Phe Ala Gln Leu
            100                 105                 110 aca gat gag gct aca gat gat gat aaa cgg cgt gaa ttg gtt aat ttt   864
Thr Asp Glu Ala Thr Asp Asp Asp Lys Arg Arg Glu Leu Val Asn Phe
        115                 120                 125 ttc aag gag ttt tgt gca ttt tct cag aca tta caa cct caa aac agg   912
Phe Lys Glu Phe Cys Ala Phe Ser Gln Thr Leu Gln Pro Gln Asn Arg
    130                 135                 140 gat gca ttt ttc aaa aca ttg gca aaa ttg gga att ctt cct gct ctt   960
```

```
Asp Ala Phe Phe Lys Thr Leu Ala Lys Leu Gly Ile Leu Pro Ala Leu
145                 150                 155                 160 gaa awt gta atg ggc atg gat gat ttg caa gtc aga tca gct gct aca      1008
Glu Xaa Val Met Gly Met Asp Asp Leu Gln Val Arg Ser Ala Ala Thr
                165                 170                 175 gat ata ttt tct tat cta gta gaa ttt agt cca tct atg gtc cga gag      1056
Asp Ile Phe Ser Tyr Leu Val Glu Phe Ser Pro Ser Met Val Arg Glu
            180                 185                 190 ttt gta atg caa gaa gct cag cag agt gat gac gat att ctt ctt att      1104
Phe Val Met Gln Glu Ala Gln Gln Ser Asp Asp Asp Ile Leu Leu Ile
        195                 200                 205 aat gtg gta att gaa caa atg atc tgt gat act gat cct gag cta gga      1152
Asn Val Val Ile Glu Gln Met Ile Cys Asp Thr Asp Pro Glu Leu Gly
    210                 215                 220 ggc gct gtt cag tta atg gga ctt ctt cgt act cta att gat cca gag      1200
Gly Ala Val Gln Leu Met Gly Leu Leu Arg Thr Leu Ile Asp Pro Glu
225                 230                 235                 240 aac atg ctg gct aca act aat aaa acc gaa aaa agt gaa ttt cta aat      1248
Asn Met Leu Ala Thr Thr Asn Lys Thr Glu Lys Ser Glu Phe Leu Asn
                245                 250                 255 ttt ttc tac aac cat tgt atg cat gtt ctc aca gca cca ctt ttg acc      1296
Phe Phe Tyr Asn His Cys Met His Val Leu Thr Ala Pro Leu Leu Thr
            260                 265                 270 aat act tca gaa gac aaa tgt gaa aag gat ttt ttt tta aaa cat tac      1344
Asn Thr Ser Glu Asp Lys Cys Glu Lys Asp Phe Phe Leu Lys His Tyr
        275                 280                 285 aga tat agt tgg agt ttc ata tgt acc cct tca cat tcc cat tcc cat      1392
Arg Tyr Ser Trp Ser Phe Ile Cys Thr Pro Ser His Ser His Ser His
    290                 295                 300 tct acc ccc tct tcc tcc atc tct caa gat aat ata gtt gga tca aac      1440
Ser Thr Pro Ser Ser Ser Ile Ser Gln Asp Asn Ile Val Gly Ser Asn
305                 310                 315                 320 aaa aac aac aca att tgt ccc gat aat tat caa aca gca cag cta ctt      1488
Lys Asn Asn Thr Ile Cys Pro Asp Asn Tyr Gln Thr Ala Gln Leu Leu
                325                 330                 335 gcc tta att tta gag tta ctc aca ttt tgt gtg gaa cat cac aca tat      1536
Ala Leu Ile Leu Glu Leu Leu Thr Phe Cys Val Glu His His Thr Tyr
            340                 345                 350 cac ata aaa aac tat att atg aac aag gac ttg cta aga aga gtc ttg      1584
His Ile Lys Asn Tyr Ile Met Asn Lys Asp Leu Leu Arg Arg Val Leu
        355                 360                 365 gtc ttg atg aat tca aag cac act ttt ctg gcc ttg tgt gcc ctt cgc      1632
Val Leu Met Asn Ser Lys His Thr Phe Leu Ala Leu Cys Ala Leu Arg
    370                 375                 380 ttt atg agg cgg ata att gga ctt aaa gat gaa ttt tat aat cgt tac      1680
Phe Met Arg Arg Ile Ile Gly Leu Lys Asp Glu Phe Tyr Asn Arg Tyr
385                 390                 395                 400 atc acc aag gga aat ctt ttt gag cca gtt ata aat gca ctt ctg gat      1728
Ile Thr Lys Gly Asn Leu Phe Glu Pro Val Ile Asn Ala Leu Leu Asp
                405                 410                 415 aat gga act cgg tat aat ctg ttg aat tca gct gtt att gag ttg ttt      1776
Asn Gly Thr Arg Tyr Asn Leu Leu Asn Ser Ala Val Ile Glu Leu Phe
            420                 425                 430 gaa ttt ata aga gtg gaa gat atc aag tct ctt act gcc cat ata gtt      1824
Glu Phe Ile Arg Val Glu Asp Ile Lys Ser Leu Thr Ala His Ile Val
        435                 440                 445 gaa aac ttt tat aaa gca ctt gaa tcg att gaa tat gtt cag aca ttc      1872
Glu Asn Phe Tyr Lys Ala Leu Glu Ser Ile Glu Tyr Val Gln Thr Phe
    450                 455                 460
```

```
aaa gga ttg aag act aaa tat gag caa gaa aaa gac aga caa aat cag    1920
Lys Gly Leu Lys Thr Lys Tyr Glu Gln Glu Lys Asp Arg Gln Asn Gln
465                 470                 475                 480 aaa ctg aac agt gta cca tct ata ttg cgt agt aac aga ttt cgc aga    1968
Lys Leu Asn Ser Val Pro Ser Ile Leu Arg Ser Asn Arg Phe Arg Arg
                485                 490                 495 gat gca aaa gcc ttg gaa gag gat gaa gaa atg tgg ttt aat gaa gat    2016
Asp Ala Lys Ala Leu Glu Glu Asp Glu Glu Met Trp Phe Asn Glu Asp
            500                 505                 510 gaa gaa gag gaa gga aaa gca gtt gtg gca cca gtg gaa aaa cct aag    2064
Glu Glu Glu Glu Gly Lys Ala Val Val Ala Pro Val Glu Lys Pro Lys
        515                 520                 525 cca gaa gat gat ttt cca gat aat tat gaa aag ttt atg gag act aaa    2112
Pro Glu Asp Asp Phe Pro Asp Asn Tyr Glu Lys Phe Met Glu Thr Lys
    530                 535                 540 aaa gca aaa gaa agt gaa gac aag gaa aac ctt ccc aaa agg aca tct    2160
Lys Ala Lys Glu Ser Glu Asp Lys Glu Asn Leu Pro Lys Arg Thr Ser
545                 550                 555                 560 cct ggt ggc ttc aaa ttt act ttc tcc cac tct gcc agt gct gct aat    2208
Pro Gly Gly Phe Lys Phe Thr Phe Ser His Ser Ala Ser Ala Ala Asn
                565                 570                 575 gga aca aac agt aaa tct gta gtg gct cag ata cca cca gca act tct    2256
Gly Thr Asn Ser Lys Ser Val Val Ala Gln Ile Pro Pro Ala Thr Ser
            580                 585                 590 aat gga tcc tct tcc aaa acc aca aac ttg cct acg tca gta aca gcc    2304
Asn Gly Ser Ser Ser Lys Thr Thr Asn Leu Pro Thr Ser Val Thr Ala
        595                 600                 605 acc aag gga agt ttg gtt ggc tta gtg gat tat cca gat gat gaa gag    2352
Thr Lys Gly Ser Leu Val Gly Leu Val Asp Tyr Pro Asp Asp Glu Glu
    610                 615                 620 gaa gat gaa gaa gaa gaa tcg tcc ccc agg aaa aga cct cgt ctt ggc    2400
Glu Asp Glu Glu Glu Glu Ser Ser Pro Arg Lys Arg Pro Arg Leu Gly
625                 630                 635                 640 tca  taaaatattt attaggggac cctcaacatg tggtcttaca atgctgcaac         2453
Ser tgttcagtga gctgaaaatc tgaatcagaa agctttctca attgaactta taaaatatac   2513
aaggagtagc aaaagacagt atatcagcta agagagttta gttctaataa aaatcaggct   2573
tcccaggaac ttgattgctt gctagtaatt aaggggtttg ccttttaggc tgtcaaaaca   2633
aacattagta accagaacct gggagacagc ttctcagcaa ggaaaagtca caggtttggg   2693
gacggtttag gggaggggaa aaggttgata taataatgca gggttgctcc tcggggtgtc   2753
gatctagaaa caattttaca gaacttcagt tgtaaactca ataacattac ttgtataatg   2813
gtgctggcca tgttgttgtt ttaatcagtt gcctcttttt aaaagaaatt tttatggaaa   2873
acacactcaa ctatcattaa aaaaatgaag ttaagctgtt gggaccattt ctttaagatt   2933
taacaaaagt tcagcctttt aggtagttga agggaagtac accccgtatt cagcacatgt   2993
tgagttttct acaccaggaa ttttcaatat gtatattgat gaaaacaagc tcaattcaaa   3053
ctggacagtt ttaagataat gttaaaatca gcacttttag agacaacgaa ggccaagaat   3113
cagtacagta gtattccaaa atgatttttct ctagaaattt gaaagtagat cgaacagaat  3173
gttgtcaacc gcctaccagt acaatctttt gtggaagata ctttgaaatc actttctact   3233
ttgttagtaa agttctgtct ttccagagct gcaagtttta aagtgttact tatacagacc   3293
aaccaagaat agtgctgaat taagtggcat ttagtatcta gaagccattt tgatccaaga   3353
agctacttaa gtgtcaaagt cagcatgcag cacatgtagc ttttctgtaa acaagggtgt   3413
```

-continued

```
gatatgaaag ctgctttttt aagaagagta aaagcacatt ccatatacgt aagtgaattt    3473
taaaaataaa ttgaggcaaa cagttaagtt ttatttttag agcaacaagt taactgtaaa    3533
tattttaatg ttagtttgct catctatgat ctgagatcat gccgaagtga gaaaaatctc    3593
cccaaaatac aatttaatgc attgggaaaa aaaaacttta acagtaattc cagccacaat    3653
ctttagatca cccttgtaat gtgttacggg tccattttc  ctggaatcgt ttaatctaaa    3713
gcagtttccc ctgttttgga gattttgtag ttaatttaa  ttttggctat tgtttggaaa    3773
agatgagctg tctgtgtaga tatgaagtat agttttttcc ataaaacaga tgtttatttt    3833
gtattaaaaa ataccactgt acttgtttta caccatttgt atacatgtgg tgatattaat    3893
gctaaactgt aaaattcagg aattaaaatg tgaccctgta attcc                    3938
```

<210> SEQ ID NO 46
<211> LENGTH: 641
<212> TYPE: PRT
<213> ORGANISM: Homo sapiens
<220> FEATURE:
<221> NAME/KEY: misc_feature
<222> LOCATION: (162)..(162)
<223> OTHER INFORMATION: The 'Xaa' at location 162 stands for Asn, or
      Ile.

<400> SEQUENCE: 46

```
Met Ser Asp Thr Arg Arg Val Lys Val Tyr Thr Leu Asn Glu Asp
1               5                   10                  15

Arg Gln Trp Asp Asp Arg Gly Thr Gly His Val Ser Ser Thr Tyr Val
            20                  25                  30

Glu Glu Leu Lys Gly Met Ser Leu Leu Val Arg Ala Glu Ser Asp Gly
        35                  40                  45

Ser Leu Leu Leu Glu Ser Lys Ile Asn Pro Asn Thr Ala Tyr Gln Lys
    50                  55                  60

Gln Gln Asp Thr Leu Ile Val Trp Ser Glu Glu Asn Tyr Asp Leu
65                  70                  75                  80

Ala Leu Ser Phe Gln Glu Lys Ala Gly Cys Asp Glu Ile Trp Glu Lys
                85                  90                  95

Ile Cys Gln Glu Asp Glu Lys Phe Leu Ser Glu Val Phe Ala Gln Leu
            100                 105                 110

Thr Asp Glu Ala Thr Asp Asp Lys Arg Arg Glu Leu Val Asn Phe
            115                 120                 125

Phe Lys Glu Phe Cys Ala Phe Ser Gln Thr Leu Gln Pro Gln Asn Arg
        130                 135                 140

Asp Ala Phe Phe Lys Thr Leu Ala Lys Leu Gly Ile Leu Pro Ala Leu
145                 150                 155                 160

Glu Xaa Val Met Gly Met Asp Asp Leu Gln Val Arg Ser Ala Ala Thr
                165                 170                 175

Asp Ile Phe Ser Tyr Leu Val Glu Phe Ser Pro Ser Met Val Arg Glu
            180                 185                 190

Phe Val Met Gln Glu Ala Gln Gln Ser Asp Asp Ile Leu Leu Ile
        195                 200                 205

Asn Val Val Ile Glu Gln Met Ile Cys Asp Thr Asp Pro Glu Leu Gly
    210                 215                 220

Gly Ala Val Gln Leu Met Gly Leu Leu Arg Thr Leu Ile Asp Pro Glu
225                 230                 235                 240

Asn Met Leu Ala Thr Thr Asn Lys Thr Glu Lys Ser Glu Phe Leu Asn
                245                 250                 255
```

```
Phe Phe Tyr Asn His Cys Met His Val Leu Thr Ala Pro Leu Leu Thr
            260                 265                 270
Asn Thr Ser Glu Asp Lys Cys Glu Lys Asp Phe Phe Leu Lys His Tyr
        275                 280                 285
Arg Tyr Ser Trp Ser Phe Ile Cys Thr Pro Ser His Ser His Ser His
        290                 295                 300
Ser Thr Pro Ser Ser Ile Ser Gln Asp Asn Ile Val Gly Ser Asn
305                 310                 315                 320
Lys Asn Asn Thr Ile Cys Pro Asp Asn Tyr Gln Thr Ala Gln Leu Leu
                325                 330                 335
Ala Leu Ile Leu Glu Leu Leu Thr Phe Cys Val Glu His His Thr Tyr
            340                 345                 350
His Ile Lys Asn Tyr Ile Met Asn Lys Asp Leu Leu Arg Arg Val Leu
        355                 360                 365
Val Leu Met Asn Ser Lys His Thr Phe Leu Ala Leu Cys Ala Leu Arg
    370                 375                 380
Phe Met Arg Arg Ile Ile Gly Leu Lys Asp Glu Phe Tyr Asn Arg Tyr
385                 390                 395                 400
Ile Thr Lys Gly Asn Leu Phe Glu Pro Val Ile Asn Ala Leu Leu Asp
                405                 410                 415
Asn Gly Thr Arg Tyr Asn Leu Leu Asn Ser Ala Val Ile Glu Leu Phe
            420                 425                 430
Glu Phe Ile Arg Val Glu Asp Ile Lys Ser Leu Thr Ala His Ile Val
        435                 440                 445
Glu Asn Phe Tyr Lys Ala Leu Glu Ser Ile Glu Tyr Val Gln Thr Phe
    450                 455                 460
Lys Gly Leu Lys Thr Lys Tyr Glu Gln Glu Lys Asp Arg Gln Asn Gln
465                 470                 475                 480
Lys Leu Asn Ser Val Pro Ser Ile Leu Arg Ser Asn Arg Phe Arg Arg
                485                 490                 495
Asp Ala Lys Ala Leu Glu Glu Asp Glu Glu Met Trp Phe Asn Glu Asp
            500                 505                 510
Glu Glu Glu Glu Gly Lys Ala Val Val Ala Pro Val Glu Lys Pro Lys
        515                 520                 525
Pro Glu Asp Asp Phe Pro Asp Asn Tyr Glu Lys Phe Met Glu Thr Lys
    530                 535                 540
Lys Ala Lys Glu Ser Glu Asp Lys Glu Asn Leu Pro Lys Arg Thr Ser
545                 550                 555                 560
Pro Gly Gly Phe Lys Phe Thr Phe Ser His Ser Ala Ser Ala Ala Asn
                565                 570                 575
Gly Thr Asn Ser Lys Ser Val Val Ala Gln Ile Pro Pro Ala Thr Ser
            580                 585                 590
Asn Gly Ser Ser Ser Lys Thr Thr Asn Leu Pro Thr Ser Val Thr Ala
        595                 600                 605
Thr Lys Gly Ser Leu Val Gly Leu Val Asp Tyr Pro Asp Asp Glu Glu
    610                 615                 620
Glu Asp Glu Glu Glu Glu Ser Ser Pro Arg Lys Arg Pro Arg Leu Gly
625                 630                 635                 640
Ser

<210> SEQ ID NO 47
<211> LENGTH: 4378
<212> TYPE: DNA
<213> ORGANISM: Homo sapiens
```

-continued

```
<220> FEATURE:
<221> NAME/KEY: CDS
<222> LOCATION: (393)..(2843)
<223> OTHER INFORMATION:

<400> SEQUENCE: 47
```

| | |
|---|---:|
| cttgtcggcc gccgtagccc ctgctaggac agcccgtgcg agcctgctgg aggaggaaga | 60 |
| gaaaggcaga gagagtcggg ttacaagatg gcggatctgt agtagttacc gcggcggcgg | 120 |
| gagagcaagc gagccctggg gggcaaagag acgggagagt gggtgtatgc gcgggtgaag | 180 |
| tgagaggtaa cggggcctcc gggcggagag gcctcagtgg ctcttgtcac cccttctcgc | 240 |
| ggctgaacct ttggagccat ggtgaattcg ggcctctccg aagccgccgc cgccgccacc | 300 |
| gccactactg cctttaccgt ctcctaagag tgaggagcgc ggacgaggta agcgaggagg | 360 |

| | | | | | | | | |
|---|---|---|---|---|---|---|---|---:|
| cggcggctag agcggtggag acagcagcca cc | atg | tcg | gat | acg | cgg | cgg | cga | 413 |
| | Met | Ser | Asp | Thr | Arg | Arg | Arg | |
| | 1 | | | | 5 | | | |

| | | | | | | | | | | | | | | | | |
|---|---|---|---|---|---|---|---|---|---|---|---|---|---|---|---|---:|
| gtg | aag | gtc | tat | acc | ctg | aac | gaa | gac | cgg | caa | tgg | gac | gac | cga | ggc | 461 |
| Val | Lys | Val | Tyr | Thr | Leu | Asn | Glu | Asp | Arg | Gln | Trp | Asp | Asp | Arg | Gly | |
| | 10 | | | | 15 | | | | | 20 | | | | | | |

| | | | | | | | | | | | | | | | | |
|---|---|---|---|---|---|---|---|---|---|---|---|---|---|---|---|---:|
| acc | ggg | cac | gtc | tcc | tcc | act | tac | gtg | gag | gag | ctc | aag | ggg | atg | tcg | 509 |
| Thr | Gly | His | Val | Ser | Ser | Thr | Tyr | Val | Glu | Glu | Leu | Lys | Gly | Met | Ser | |
| | 25 | | | | 30 | | | | | 35 | | | | | | |

| | | | | | | | | | | | | | | | | |
|---|---|---|---|---|---|---|---|---|---|---|---|---|---|---|---|---:|
| ctg | ctg | gtt | cgg | gca | gag | tcc | gac | gga | tca | cta | ctc | ttg | gaa | tca | aag | 557 |
| Leu | Leu | Val | Arg | Ala | Glu | Ser | Asp | Gly | Ser | Leu | Leu | Leu | Glu | Ser | Lys | |
| 40 | | | | | 45 | | | | | 50 | | | | | 55 | |

| | | | | | | | | | | | | | | | | |
|---|---|---|---|---|---|---|---|---|---|---|---|---|---|---|---|---:|
| ata | aat | cca | aat | act | gca | tat | cag | aaa | caa | cag | gat | aca | tta | att | gtt | 605 |
| Ile | Asn | Pro | Asn | Thr | Ala | Tyr | Gln | Lys | Gln | Gln | Asp | Thr | Leu | Ile | Val | |
| | | | | 60 | | | | | 65 | | | | | 70 | | |

| | | | | | | | | | | | | | | | | |
|---|---|---|---|---|---|---|---|---|---|---|---|---|---|---|---|---:|
| tgg | tca | gaa | gca | gag | aac | tat | gat | ttg | gct | ctg | agt | ttt | cag | gag | aaa | 653 |
| Trp | Ser | Glu | Ala | Glu | Asn | Tyr | Asp | Leu | Ala | Leu | Ser | Phe | Gln | Glu | Lys | |
| | | 75 | | | | | 80 | | | | | 85 | | | | |

| | | | | | | | | | | | | | | | | |
|---|---|---|---|---|---|---|---|---|---|---|---|---|---|---|---|---:|
| gct | ggc | tgt | gat | gag | atc | tgg | gaa | aaa | att | tgt | cag | gtt | caa | ggt | aaa | 701 |
| Ala | Gly | Cys | Asp | Glu | Ile | Trp | Glu | Lys | Ile | Cys | Gln | Val | Gln | Gly | Lys | |
| | | 90 | | | | | 95 | | | | | 100 | | | | |

| | | | | | | | | | | | | | | | | |
|---|---|---|---|---|---|---|---|---|---|---|---|---|---|---|---|---:|
| gac | cca | tca | gtg | gaa | gtc | aca | cag | gac | ctc | att | gat | gaa | tct | gaa | gaa | 749 |
| Asp | Pro | Ser | Val | Glu | Val | Thr | Gln | Asp | Leu | Ile | Asp | Glu | Ser | Glu | Glu | |
| | 105 | | | | | 110 | | | | | 115 | | | | | |

| | | | | | | | | | | | | | | | | |
|---|---|---|---|---|---|---|---|---|---|---|---|---|---|---|---|---:|
| gaa | cga | ttt | gaa | gaa | atg | cct | gaa | act | agt | cat | ctg | att | gac | ctg | ccc | 797 |
| Glu | Arg | Phe | Glu | Glu | Met | Pro | Glu | Thr | Ser | His | Leu | Ile | Asp | Leu | Pro | |
| 120 | | | | | 125 | | | | | 130 | | | | | 135 | |

| | | | | | | | | | | | | | | | | |
|---|---|---|---|---|---|---|---|---|---|---|---|---|---|---|---|---:|
| aca | tgt | gaa | ctc | aat | aaa | ctt | gaa | gag | att | gct | gac | tta | gtt | acc | tca | 845 |
| Thr | Cys | Glu | Leu | Asn | Lys | Leu | Glu | Glu | Ile | Ala | Asp | Leu | Val | Thr | Ser | |
| | | | | 140 | | | | | 145 | | | | | 150 | | |

| | | | | | | | | | | | | | | | | |
|---|---|---|---|---|---|---|---|---|---|---|---|---|---|---|---|---:|
| gtg | ctc | tcc | tca | cct | atc | cgt | agg | gaa | aag | ctg | gct | ctc | gcc | ttg | gaa | 893 |
| Val | Leu | Ser | Ser | Pro | Ile | Arg | Arg | Glu | Lys | Leu | Ala | Leu | Ala | Leu | Glu | |
| | | 155 | | | | | 160 | | | | | 165 | | | | |

| | | | | | | | | | | | | | | | | |
|---|---|---|---|---|---|---|---|---|---|---|---|---|---|---|---|---:|
| aat | gaa | ggc | tat | att | aaa | aaa | cta | ttg | cag | ctg | ttc | caa | gct | tgc | gag | 941 |
| Asn | Glu | Gly | Tyr | Ile | Lys | Lys | Leu | Leu | Gln | Leu | Phe | Gln | Ala | Cys | Glu | |
| | | 170 | | | | | 175 | | | | | 180 | | | | |

| | | | | | | | | | | | | | | | | |
|---|---|---|---|---|---|---|---|---|---|---|---|---|---|---|---|---:|
| aac | cta | gaa | aac | act | gaa | ggc | tta | cac | cat | ttg | tat | gaa | att | att | aga | 989 |
| Asn | Leu | Glu | Asn | Thr | Glu | Gly | Leu | His | His | Leu | Tyr | Glu | Ile | Ile | Arg | |
| | 185 | | | | | 190 | | | | | 195 | | | | | |

| | | | | | | | | | | | | | | | | |
|---|---|---|---|---|---|---|---|---|---|---|---|---|---|---|---|---:|
| gga | atc | tta | ttc | cta | aat | aag | gca | act | ctt | ttt | gag | gta | atg | ttt | tct | 1037 |
| Gly | Ile | Leu | Phe | Leu | Asn | Lys | Ala | Thr | Leu | Phe | Glu | Val | Met | Phe | Ser | |
| 200 | | | | | 205 | | | | | 210 | | | | | 215 | |

| | | | | | | | | | | | | | | | | |
|---|---|---|---|---|---|---|---|---|---|---|---|---|---|---|---|---:|
| gat | gag | tgt | atc | atg | gat | gtc | gtg | gga | tgc | ctt | gaa | tat | gac | cct | gct | 1085 |
| Asp | Glu | Cys | Ile | Met | Asp | Val | Val | Gly | Cys | Leu | Glu | Tyr | Asp | Pro | Ala | |
| | | | | 220 | | | | | 225 | | | | | 230 | | |

```
ttg gct cag cca aaa aga cat aga gaa ttc ttg acc aaa act gca aag      1133
Leu Ala Gln Pro Lys Arg His Arg Glu Phe Leu Thr Lys Thr Ala Lys
            235                 240                 245 ttc aag gaa gtt ata cca ata aca gac tct gaa cta agg caa aaa ata      1181
Phe Lys Glu Val Ile Pro Ile Thr Asp Ser Glu Leu Arg Gln Lys Ile
        250                 255                 260 cat cag act tac agg gta cag tac att cag gac atc att ttg ccc aca      1229
His Gln Thr Tyr Arg Val Gln Tyr Ile Gln Asp Ile Ile Leu Pro Thr
    265                 270                 275 cca tct gtt ttt gaa gag aat ttt ctt tct act ctt acg tct ttt att      1277
Pro Ser Val Phe Glu Glu Asn Phe Leu Ser Thr Leu Thr Ser Phe Ile
280                 285                 290                 295 ttc ttc aac aaa gtt gag ata gtc agc atg ttg cag gaa gat gag aag      1325
Phe Phe Asn Lys Val Glu Ile Val Ser Met Leu Gln Glu Asp Glu Lys
            300                 305                 310 ttt ttg tct gaa gtt ttt gca caa tta aca gat gag gct aca gat gat      1373
Phe Leu Ser Glu Val Phe Ala Gln Leu Thr Asp Glu Ala Thr Asp Asp
        315                 320                 325 gat aaa cgg cgt gaa ttg gtt aat ttt ttc aag gag ttt tgt gca ttt      1421
Asp Lys Arg Arg Glu Leu Val Asn Phe Phe Lys Glu Phe Cys Ala Phe
    330                 335                 340 tct cag aca tta caa cct caa aac agg gat gca ttt ttc aaa aca ttg      1469
Ser Gln Thr Leu Gln Pro Gln Asn Arg Asp Ala Phe Phe Lys Thr Leu
345                 350                 355 gca aaa ttg gga att ctt cct gct ctt gaa att gta atg ggc atg gat      1517
Ala Lys Leu Gly Ile Leu Pro Ala Leu Glu Ile Val Met Gly Met Asp
360                 365                 370                 375 gat ttg caa gtc aga tca gct gct aca gat ata ttt tct tat cta gta      1565
Asp Leu Gln Val Arg Ser Ala Ala Thr Asp Ile Phe Ser Tyr Leu Val
            380                 385                 390 gaa ttt agt cca tct atg gtc cga gag ttt gta atg caa gaa gct cag      1613
Glu Phe Ser Pro Ser Met Val Arg Glu Phe Val Met Gln Glu Ala Gln
        395                 400                 405 cag agt gat gac gat att ctt ctt att aat gtg gta att gaa caa atg      1661
Gln Ser Asp Asp Asp Ile Leu Leu Ile Asn Val Val Ile Glu Gln Met
    410                 415                 420 atc tgt gat act gat cct gag cta gga ggc gct gtt cag tta atg gga      1709
Ile Cys Asp Thr Asp Pro Glu Leu Gly Gly Ala Val Gln Leu Met Gly
425                 430                 435 ctt ctt cgt act cta att gat cca gag aac atg ctg gct aca act aat      1757
Leu Leu Arg Thr Leu Ile Asp Pro Glu Asn Met Leu Ala Thr Thr Asn
440                 445                 450                 455 aaa acc gaa aaa agt gaa ttt cta aat ttt ttc tac aac cat tgt atg      1805
Lys Thr Glu Lys Ser Glu Phe Leu Asn Phe Phe Tyr Asn His Cys Met
            460                 465                 470 cat gtt ctc aca gca cca ctt ttg acc aat act tca gaa gac aaa tgt      1853
His Val Leu Thr Ala Pro Leu Leu Thr Asn Thr Ser Glu Asp Lys Cys
        475                 480                 485 gaa aag gat aat ata gtt gga tca aac aaa aac aac aca att tgt ccc      1901
Glu Lys Asp Asn Ile Val Gly Ser Asn Lys Asn Asn Thr Ile Cys Pro
    490                 495                 500 gat aat tat caa aca gca cag cta ctt gcc tta att tta gag tta ctc      1949
Asp Asn Tyr Gln Thr Ala Gln Leu Leu Ala Leu Ile Leu Glu Leu Leu
505                 510                 515 aca ttt tgt gtg gaa cat cac aca tat cac ata aaa aac tat att atg      1997
Thr Phe Cys Val Glu His His Thr Tyr His Ile Lys Asn Tyr Ile Met
520                 525                 530                 535 aac aag gac ttg cta aga aga gtc ttg gtc ttg atg aat tca aag cac      2045
Asn Lys Asp Leu Leu Arg Arg Val Leu Val Leu Met Asn Ser Lys His
            540                 545                 550
```

```
act ttt ctg gcc ttg tgt gcc ctt cgc ttt atg agg cgg ata att gga       2093
Thr Phe Leu Ala Leu Cys Ala Leu Arg Phe Met Arg Arg Ile Ile Gly
            555                 560                 565 ctt aaa gat gaa ttt tat aat cgt tac atc acc aag gga aat ctt ttt       2141
Leu Lys Asp Glu Phe Tyr Asn Arg Tyr Ile Thr Lys Gly Asn Leu Phe
            570                 575                 580 gag cca gtt ata aat gca ctt ctg gat aat gga act cgg tat aat ctg       2189
Glu Pro Val Ile Asn Ala Leu Leu Asp Asn Gly Thr Arg Tyr Asn Leu
585                 590                 595 ttg aat tca gct gtt att gag ttg ttt gaa ttt ata aga gtg gaa gat       2237
Leu Asn Ser Ala Val Ile Glu Leu Phe Glu Phe Ile Arg Val Glu Asp
600                 605                 610                 615 atc aag tct ctt act gcc cat ata gtt gaa aac ttt tat aaa gca ctt       2285
Ile Lys Ser Leu Thr Ala His Ile Val Glu Asn Phe Tyr Lys Ala Leu
                620                 625                 630 gaa tcg att gaa tat gtt cag aca ttc aaa gga ttg aag act aaa tat       2333
Glu Ser Ile Glu Tyr Val Gln Thr Phe Lys Gly Leu Lys Thr Lys Tyr
                635                 640                 645 gag caa gaa aaa gac aga caa aat cag aaa ctg aac agt gta cca tct       2381
Glu Gln Glu Lys Asp Arg Gln Asn Gln Lys Leu Asn Ser Val Pro Ser
            650                 655                 660 ata ttg cgt agt aac aga ttt cgc aga gat gca aaa gcc ttg gaa gag       2429
Ile Leu Arg Ser Asn Arg Phe Arg Arg Asp Ala Lys Ala Leu Glu Glu
665                 670                 675 gat gaa gaa atg tgg ttt aat gaa gat gaa gaa gag gaa gga aaa gca       2477
Asp Glu Glu Met Trp Phe Asn Glu Asp Glu Glu Glu Glu Gly Lys Ala
680                 685                 690                 695 gtt gtg gca cca gtg gaa aaa cct aag cca gaa gat gat ttt cca gat       2525
Val Val Ala Pro Val Glu Lys Pro Lys Pro Glu Asp Asp Phe Pro Asp
                700                 705                 710 aat tat gaa aag ttt atg gag act aaa aaa gca aaa gaa agt gaa gac       2573
Asn Tyr Glu Lys Phe Met Glu Thr Lys Lys Ala Lys Glu Ser Glu Asp
                715                 720                 725 aag gaa aac ctt ccc aaa agg aca tct cct ggt ggc ttc aaa ttt act       2621
Lys Glu Asn Leu Pro Lys Arg Thr Ser Pro Gly Gly Phe Lys Phe Thr
            730                 735                 740 ttc tcc cac tct gcc agt gct gct aat gga aca aac agt aaa tct gta       2669
Phe Ser His Ser Ala Ser Ala Ala Asn Gly Thr Asn Ser Lys Ser Val
745                 750                 755 gtg gct cag ata cca cca gca act tct aat gga tcc tct tcc aaa acc       2717
Val Ala Gln Ile Pro Pro Ala Thr Ser Asn Gly Ser Ser Ser Lys Thr
760                 765                 770                 775 aca aac ttg cct acg tca gta aca gcc acc aag gga agt ttg gtt ggc       2765
Thr Asn Leu Pro Thr Ser Val Thr Ala Thr Lys Gly Ser Leu Val Gly
                780                 785                 790 tta gtg gat tat cca gat gat gaa gag gaa gat gaa gaa gaa gaa tcg       2813
Leu Val Asp Tyr Pro Asp Asp Glu Glu Glu Asp Glu Glu Glu Glu Ser
                795                 800                 805 tcc ccc agg aaa aga cct cgt ctt ggc tca taaaatattt attaggggac         2863
Ser Pro Arg Lys Arg Pro Arg Leu Gly Ser
            810                 815 cctcaacatg tggtcttaca atgctgcaac tgttcagtga gctgaaaatc tgaatcagaa     2923
agctttctca attgaactta taaaatatac aaggagtagc aaaagacagt atatcagcta    2983
agagagttta gttctaataa aaatcaggct tcccaggaac ttgattgctt gctagtaatt    3043
aaggggtttg ccttttaggc tgtcaaaaca acattagta accagaacct gggagayagc    3103
ttctcagcaa ggaaaagtca caggtttggg gacggtttag gggagggaa aaggttgata   3163
```

```
taataatgca gggttgctcc tcggggtgtc gatctagaaa caattttaca gaacttcagt    3223
tgtaaactca ataacattac ttgtataatg gtgctggcca tgttgttgtt ttaatcagtt    3283
gcctcttttt aaaagaaatt tttatggaaa acacattcaa ctatcattaa aaaaatgaag    3343
ttaagctgtt gggaccattt ctttaagatt taacaaaagt tcagcctttt aggtagttga    3403
agggaagtac accccgtatt cagcacatgt tgagttttct acaccaggaa ttttcaatat    3463
gtatattgat gaaaacaagc tcaattcaaa ctggacagtt ttaagataat gttaaaatca    3523
gcacttttag agacaacgaa ggccaagaat cagtacagta gtattccaaa atgattttct    3583
ctagaaattt gaaagtagat cgaacagaat gttgtcaacc gcctaccagt acaatctttt    3643
gtggaagata ctttgaaatc actttctact ttgttagtaa agttctgtct ttccagagct    3703
gcaagtttta aagtgttact tatacagacc aaccaagaat agtgctgaat taagtggcat    3763
ttagtatcta gaagccattt tgatccaaga agctacttaa gtgtcaaagt cagcatgcag    3823
cacatgtagc ttttctgtaa acaagggtgt gatatgaaag ctgctttttt aagaagagta    3883
aaagcacatt ccatatacgt aagtgaattt taaaaataaa ttgaggcaaa cagttaagtt    3943
ttatttttag agcaacaagt taactgtaaa tatttttaatg ttagtttgct catctatgat    4003
ctgagatcat gccgaagtga gaaaaatctc cccaaaatac aatttaatgc attgggaaaa    4063
aaaaacttta acagtaattc cagccacaat ctttagatca cccttgtaat gtgttacggg    4123 tccattttc ctggaatcgt ttaatctaaa gcagtttccc ctgttttgga gattttgtag    4183
ttaattttaa ttttggctat tgtttggaaa agatgagctg tctgtgtaga tatgaagtat    4243 agtttttcc ataaaacaga tgtttatttt gtattaaaaa ataccactgt acttgttta    4303 caccatttgt atacatgtgg tgatattaat gctaaactgt aaaattcagg aattaaaatg    4363
tgaccctgta attcc                                                   4378
```

<210> SEQ ID NO 48
<211> LENGTH: 817
<212> TYPE: PRT
<213> ORGANISM: Homo sapiens

<400> SEQUENCE: 48

```
Met Ser Asp Thr Arg Arg Val Lys Val Tyr Thr Leu Asn Glu Asp
1               5                   10                  15

Arg Gln Trp Asp Asp Arg Gly Thr Gly His Val Ser Ser Thr Tyr Val
            20                  25                  30

Glu Glu Leu Lys Gly Met Ser Leu Leu Val Arg Ala Glu Ser Asp Gly
        35                  40                  45

Ser Leu Leu Leu Glu Ser Lys Ile Asn Pro Asn Thr Ala Tyr Gln Lys
    50                  55                  60

Gln Gln Asp Thr Leu Ile Val Trp Ser Glu Ala Glu Asn Tyr Asp Leu
65                  70                  75                  80

Ala Leu Ser Phe Gln Glu Lys Ala Gly Cys Asp Glu Ile Trp Glu Lys
                85                  90                  95

Ile Cys Gln Val Gln Gly Lys Asp Pro Ser Val Glu Val Thr Gln Asp
            100                 105                 110

Leu Ile Asp Glu Ser Glu Glu Arg Phe Glu Glu Met Pro Glu Thr
            115                 120                 125

Ser His Leu Ile Asp Leu Pro Thr Cys Glu Leu Asn Lys Leu Glu Glu
    130                 135                 140

Ile Ala Asp Leu Val Thr Ser Val Leu Ser Ser Pro Ile Arg Arg Glu
145                 150                 155                 160
```

```
         Lys Leu Ala Leu Ala Leu Glu Asn Glu Gly Tyr Ile Lys Lys Leu Leu
                         165                 170                 175

Gln Leu Phe Gln Ala Cys Glu Asn Leu Glu Asn Thr Glu Gly Leu His
                         180                 185                 190

His Leu Tyr Glu Ile Ile Arg Gly Ile Leu Phe Leu Asn Lys Ala Thr
                         195                 200                 205

Leu Phe Glu Val Met Phe Ser Asp Glu Cys Ile Met Asp Val Val Gly
                 210                 215                 220

Cys Leu Glu Tyr Asp Pro Ala Leu Ala Gln Pro Lys Arg His Arg Glu
         225                 230                 235                 240

Phe Leu Thr Lys Thr Ala Lys Phe Lys Glu Val Ile Pro Ile Thr Asp
                         245                 250                 255

Ser Glu Leu Arg Gln Lys Ile His Gln Thr Tyr Arg Val Gln Tyr Ile
                         260                 265                 270

Gln Asp Ile Ile Leu Pro Thr Pro Ser Val Phe Glu Glu Asn Phe Leu
                         275                 280                 285

Ser Thr Leu Thr Ser Phe Ile Phe Phe Asn Lys Val Glu Ile Val Ser
                 290                 295                 300

Met Leu Gln Glu Asp Glu Lys Phe Leu Ser Glu Val Phe Ala Gln Leu
         305                 310                 315                 320

Thr Asp Glu Ala Thr Asp Asp Lys Arg Arg Glu Leu Val Asn Phe
                         325                 330                 335

Phe Lys Glu Phe Cys Ala Phe Ser Gln Thr Leu Gln Pro Gln Asn Arg
                         340                 345                 350

Asp Ala Phe Phe Lys Thr Leu Ala Lys Leu Gly Ile Leu Pro Ala Leu
                         355                 360                 365

Glu Ile Val Met Gly Met Asp Asp Leu Gln Val Arg Ser Ala Ala Thr
                 370                 375                 380

Asp Ile Phe Ser Tyr Leu Val Glu Phe Ser Pro Ser Met Val Arg Glu
         385                 390                 395                 400

Phe Val Met Gln Glu Ala Gln Gln Ser Asp Asp Asp Ile Leu Leu Ile
                         405                 410                 415

Asn Val Val Ile Glu Gln Met Ile Cys Asp Thr Asp Pro Glu Leu Gly
                         420                 425                 430

Gly Ala Val Gln Leu Met Gly Leu Leu Arg Thr Leu Ile Asp Pro Glu
                         435                 440                 445

Asn Met Leu Ala Thr Thr Asn Lys Thr Glu Lys Ser Glu Phe Leu Asn
                 450                 455                 460

Phe Phe Tyr Asn His Cys Met His Val Leu Thr Ala Pro Leu Leu Thr
         465                 470                 475                 480

Asn Thr Ser Glu Asp Lys Cys Glu Lys Asp Asn Ile Val Gly Ser Asn
                         485                 490                 495

Lys Asn Asn Thr Ile Cys Pro Asp Asn Tyr Gln Thr Ala Gln Leu Leu
                         500                 505                 510

Ala Leu Ile Leu Glu Leu Leu Thr Phe Cys Val Glu His His Thr Tyr
                         515                 520                 525

His Ile Lys Asn Tyr Ile Met Asn Lys Asp Leu Leu Arg Arg Val Leu
                 530                 535                 540

Val Leu Met Asn Ser Lys His Thr Phe Leu Ala Leu Cys Ala Leu Arg
         545                 550                 555                 560

Phe Met Arg Arg Ile Ile Gly Leu Lys Asp Glu Phe Tyr Asn Arg Tyr
                         565                 570                 575
```

```
Ile Thr Lys Gly Asn Leu Phe Glu Pro Val Ile Asn Ala Leu Leu Asp
            580                 585                 590

Asn Gly Thr Arg Tyr Asn Leu Leu Asn Ser Ala Val Ile Glu Leu Phe
            595                 600                 605

Glu Phe Ile Arg Val Glu Asp Ile Lys Ser Leu Thr Ala His Ile Val
            610                 615                 620

Glu Asn Phe Tyr Lys Ala Leu Glu Ser Ile Glu Tyr Val Gln Thr Phe
625                 630                 635                 640

Lys Gly Leu Lys Thr Lys Tyr Glu Gln Glu Lys Asp Arg Gln Asn Gln
                645                 650                 655

Lys Leu Asn Ser Val Pro Ser Ile Leu Arg Ser Asn Arg Phe Arg Arg
                660                 665                 670

Asp Ala Lys Ala Leu Glu Glu Asp Glu Glu Met Trp Phe Asn Glu Asp
                675                 680                 685

Glu Glu Glu Glu Gly Lys Ala Val Val Ala Pro Val Glu Lys Pro Lys
            690                 695                 700

Pro Glu Asp Asp Phe Pro Asp Asn Tyr Glu Lys Phe Met Glu Thr Lys
705                 710                 715                 720

Lys Ala Lys Glu Ser Glu Asp Lys Glu Asn Leu Pro Lys Arg Thr Ser
                725                 730                 735

Pro Gly Gly Phe Lys Phe Thr Phe Ser His Ser Ala Ser Ala Ala Asn
                740                 745                 750

Gly Thr Asn Ser Lys Ser Val Val Ala Gln Ile Pro Pro Ala Thr Ser
                755                 760                 765

Asn Gly Ser Ser Ser Lys Thr Thr Asn Leu Pro Thr Ser Val Thr Ala
            770                 775                 780

Thr Lys Gly Ser Leu Val Gly Leu Val Asp Tyr Pro Asp Asp Glu Glu
785                 790                 795                 800

Glu Asp Glu Glu Glu Glu Ser Ser Pro Arg Lys Arg Pro Arg Leu Gly
                805                 810                 815

Ser

<210> SEQ ID NO 49
<211> LENGTH: 1174
<212> TYPE: DNA
<213> ORGANISM: Homo sapiens
<220> FEATURE:
<221> NAME/KEY: CDS
<222> LOCATION: (30)..(833)
<223> OTHER INFORMATION:

<400> SEQUENCE: 49
ggcacgaggc agccgcctcg gccgccgca atg cag aga gag gag aag cag ctt      53
                                Met Gln Arg Glu Glu Lys Gln Leu
                                 1               5 gag gca tca tta gat gca ctg ctg agt caa gtg gct gat ctg aag aac     101
Glu Ala Ser Leu Asp Ala Leu Leu Ser Gln Val Ala Asp Leu Lys Asn
         10                  15                  20 tct ctg ggg agt ttc att tgc aag ttg gag aac gag tat ggc cgg ctg     149
Ser Leu Gly Ser Phe Ile Cys Lys Leu Glu Asn Glu Tyr Gly Arg Leu
 25                  30                  35                  40 acc tgg cca tct gtc ctg gac agc ttt gcc ttg ctt tct gga cag ctg     197
Thr Trp Pro Ser Val Leu Asp Ser Phe Ala Leu Leu Ser Gly Gln Leu
                 45                  50                  55 aac act ctg aac aag gtc ttg aag cat gaa aaa aca ccg ctg ttc cgt     245
Asn Thr Leu Asn Lys Val Leu Lys His Glu Lys Thr Pro Leu Phe Arg
             60                  65                  70
```

```
aac cag gtc atc att cct ctg gtg ttg tct cca gac cga gat gaa gat    293
Asn Gln Val Ile Ile Pro Leu Val Leu Ser Pro Asp Arg Asp Glu Asp
         75                  80                  85 ctc atg cgg cag act gaa gga cgg gtg cct gtt ttc agc cat gag gta    341
Leu Met Arg Gln Thr Glu Gly Arg Val Pro Val Phe Ser His Glu Val
     90                  95                 100 gtc cct gac cat ctg aga acc aag cct gac cct gaa gtg gaa gaa cag    389
Val Pro Asp His Leu Arg Thr Lys Pro Asp Pro Glu Val Glu Glu Gln
105                 110                 115                 120 gag aag caa ctg acg aca gat gct gcc cgc att ggt gca gat gca gcc    437
Glu Lys Gln Leu Thr Thr Asp Ala Ala Arg Ile Gly Ala Asp Ala Ala
                125                 130                 135 cag aag cag atc cag agc ttg aat aaa atg tgt tca aac ctt ctg gag    485
Gln Lys Gln Ile Gln Ser Leu Asn Lys Met Cys Ser Asn Leu Leu Glu
            140                 145                 150 aaa atc agc aaa gag gag cga gaa tca gag agt gga ggt ctc cgg ccg    533
Lys Ile Ser Lys Glu Glu Arg Glu Ser Glu Ser Gly Gly Leu Arg Pro
155                 160                 165 aac aag cag acc ttt aac cct aca gac act aat gcc ttg gtg gca gct    581
Asn Lys Gln Thr Phe Asn Pro Thr Asp Thr Asn Ala Leu Val Ala Ala
    170                 175                 180 gtt gcc ttt ggg aaa gga cta tct aat tgg aga cct tca ggc agc agt    629
Val Ala Phe Gly Lys Gly Leu Ser Asn Trp Arg Pro Ser Gly Ser Ser
185                 190                 195                 200 ggt cct ggc cag gca ggc cag cca gga gct ggg acg atc ctt gca gga    677
Gly Pro Gly Gln Ala Gly Gln Pro Gly Ala Gly Thr Ile Leu Ala Gly
                205                 210                 215 acc tca gga tta cag cag gtg cag atg gca gga gct cca agc cag cag    725
Thr Ser Gly Leu Gln Gln Val Gln Met Ala Gly Ala Pro Ser Gln Gln
            220                 225                 230 cag cca atg ctc agt ggg gta caa atg gct cag gca ggt caa cca ggg    773
Gln Pro Met Leu Ser Gly Val Gln Met Ala Gln Ala Gly Gln Pro Gly
        235                 240                 245 aaa atg cca agt gga ata aaa acc aac atc aag tcg gct tcc atg cat    821
Lys Met Pro Ser Gly Ile Lys Thr Asn Ile Lys Ser Ala Ser Met His
250                 255                 260 ccc tac cag cgg tgagtgtggc tggcaacctc gactccctgg tgctctttgc        873
Pro Tyr Gln Arg
265 agagttgggc agtgaaatta cctttgctc aaggctcacc tagatgggta caataaaaag    933 aacatgggct ttcagcagca gacaaatccc acttccacca ctgactagct gtgtgacctt    993 ggacaagtga cctaattttt ctgagcctgt ttctcatttg taaatggtga taatacctac   1053 ctcatagggt tgttgtgagg attaaaatga ggaaatgaat gtaaagcact tagtacagta   1113 tatgaaataa tgggtattca ataaatgata gtttctacaa aaaaaaaaaa aaaaaaaaa    1173 a                                                                   1174

<210> SEQ ID NO 50
<211> LENGTH: 268
<212> TYPE: PRT
<213> ORGANISM: Homo sapiens

<400> SEQUENCE: 50

Met Gln Arg Glu Glu Lys Gln Leu Glu Ala Ser Leu Asp Ala Leu Leu
1               5                   10                  15

Ser Gln Val Ala Asp Leu Lys Asn Ser Leu Gly Ser Phe Ile Cys Lys
            20                  25                  30

Leu Glu Asn Glu Tyr Gly Arg Leu Thr Trp Pro Ser Val Leu Asp Ser
```

```
                    35                  40                  45
Phe Ala Leu Leu Ser Gly Gln Leu Asn Thr Leu Asn Lys Val Leu Lys
 50                  55                  60

His Glu Lys Thr Pro Leu Phe Arg Asn Gln Val Ile Ile Pro Leu Val
 65                  70                  75                  80

Leu Ser Pro Asp Arg Asp Glu Asp Leu Met Arg Gln Thr Glu Gly Arg
                 85                  90                  95

Val Pro Val Phe Ser His Glu Val Val Pro Asp His Leu Arg Thr Lys
                100                 105                 110

Pro Asp Pro Glu Val Glu Gln Glu Lys Gln Leu Thr Thr Asp Ala
                115                 120                 125

Ala Arg Ile Gly Ala Asp Ala Ala Gln Lys Gln Ile Gln Ser Leu Asn
130                 135                 140

Lys Met Cys Ser Asn Leu Leu Glu Lys Ile Ser Lys Glu Glu Arg Glu
145                 150                 155                 160

Ser Glu Ser Gly Gly Leu Arg Pro Asn Lys Gln Thr Phe Asn Pro Thr
                165                 170                 175

Asp Thr Asn Ala Leu Val Ala Ala Val Ala Phe Gly Lys Gly Leu Ser
                180                 185                 190

Asn Trp Arg Pro Ser Gly Ser Ser Gly Pro Gly Gln Ala Gly Gln Pro
                195                 200                 205

Gly Ala Gly Thr Ile Leu Ala Gly Thr Ser Gly Leu Gln Gln Val Gln
210                 215                 220

Met Ala Gly Ala Pro Ser Gln Gln Pro Met Leu Ser Gly Val Gln
225                 230                 235                 240

Met Ala Gln Ala Gly Gln Pro Gly Lys Met Pro Ser Gly Ile Lys Thr
                245                 250                 255

Asn Ile Lys Ser Ala Ser Met His Pro Tyr Gln Arg
                260                 265
```

<210> SEQ ID NO 51
<211> LENGTH: 3311
<212> TYPE: DNA
<213> ORGANISM: Homo sapiens
<220> FEATURE:
<221> NAME/KEY: CDS
<222> LOCATION: (518)..(712)
<223> OTHER INFORMATION:

<400> SEQUENCE: 51

```
aagagaccct ccccaatccc ggcctgccac cacctggctc gcgcgcagcc ccggcccaga    60
atgccttaac ctgcgccgat tgctgccgcc gaggtgcccc tccctgtag ggaccccgac   120 gccgccagcc ccttcctcct ttcccgcagg tgcgcactgc tgtgcttgcg gccgggtggg   180
cgccccgccg ctgcggtcgc ggtcgccgct ggtcctcccg ccgagccccg gcgcggggca   240
tgaggagccc ccgggtgccg cccagagacc agcaggctgc gcgcacacct agccagcggc   300
agacggggac atgagcagcg cgcacggggt cccgcgcccg gcggccagcc ctatccggcg   360
gcggccagcg ggtcaacgct gcccgggaga atgaggcagg agccggcggc agcctccttt   420
ttttccttct cctcgccttc ctgcggctcc ggcgctccgg gtccgggccg ggctgcggct   480
ctgctgcgtg ccccgcgcgc ccctcaaccg cctccgg atg cgc ttc tcg gtt agc   535
                                         Met Arg Phe Ser Val Ser
                                           1               5 ctg gca agg aag ata aag aca ttt gca acc aag atg gta atc act agt   583
Leu Ala Arg Lys Ile Lys Thr Phe Ala Thr Lys Met Val Ile Thr Ser
         10                  15                  20
```

```
gaa aat gat gaa gac aga gga ggt caa gaa aaa gaa agt aaa gag gag    631
Glu Asn Asp Glu Asp Arg Gly Gly Gln Glu Lys Glu Ser Lys Glu Glu
            25                  30                  35 agt gtc ttg gca atg ctg ggg att atc ggg acc att ctg aac ctg att    679
Ser Val Leu Ala Met Leu Gly Ile Ile Gly Thr Ile Leu Asn Leu Ile
    40                  45                  50 gtg atc ata ttt gtc tac ata tac acc acc ctg tgaatggccc agagcgtcct  732
Val Ile Ile Phe Val Tyr Ile Tyr Thr Thr Leu
55                  60                  65 cagaggcctc agaatggcca aagacggaag tcctgcgtgt cggcgcatca ctgaccagac  792
cctgcgagaa caagcaggct tgacccgcac ataccaccca atcaaatgca ccttcaaact  852
ttacaaaagg tcacacaaat agaccgatcc tgctgcaggg agcagacact aaagcacaat  912
gattccaaca aaactcattc acagcactag gaactcaacg tctttggcag ggggcccaga  972
agaatgcttg gaagaccagc ctctgacacc atcagtgagc ggatgggtgc agaaattcat 1032 tattccagat cgctgacaga tatcacatat ttgaaaagat gaatagggcg gacatggctc 1092 agatgtgtgt ctcccaggac aagtgtttca tcttcacttg acgagctatt tagtggaaaa 1152 accacaggcg cagccctttg acaggcatcc cattcatcaa aagtgtctaa ctatttgata 1212 ctggggagat aacttatttt tcttttttca ttggcttgac atgtgtatct gttcatgtca 1272 aggtttataa atatatattt ttaataaatg tgctctattt tttagcatga accaaatact 1332 tggagaggca ctcccagatc catagagctt tccttagttt tatctgcttt gtccctcct  1392 cccccaacta cagatgttct gttgtggagc cattctagtc cttttgtctc atcttgagtc 1452 ttttaccttg cgcttttgtt ctctctctct cctctctctc tgcctctttg gtctgaagga 1512 cattttccca tactgtcagc catggttttg ggtgcatgtt ttaagattgt ccattgagtg 1572 gctttttgtt gttatctcgg agatataaaa tgattgtggg catgcagacc ttagatgcac 1632 cctatcttta ctgagaatta tgcatgaata agggctgagt gatagatcag cttaaaatta 1692 aaaggactac ctttgaggaa gagagcgtg gctatatttg cagatgaact tttgaacaga 1752 atattcagct tcttaccggc agcgttattg tttcattctt gtgaccattc gtttatcaga 1812 ttttgatttt agcggtcatg taccgcgaga gttgggaaga acaaggggga aagctcggga 1872 ttaggtgcat tactccttcc tttgcaagat acctgggatc ctcctcaaaa gcgggtgggg 1932 tataaatgac acaagaactc ccccaggaga tctcatggtg attcaggctg tgaggacagc 1992 cctgtgacag gtgactttc agggacatga ggagggggatt taatgattgc cctaaaggac 2052 ttctgtattt ttaaagcccc tggtttacac ccacatgaag ctatttcctc tctggcaggg 2112 atggttgcat aaaaacaaat tagctccctt ctggctccct gaaatgggcc cttgcctggc 2172 tacagtggca tggccttaaa gagagggtta gtattccttc tgccattgcc agctgtatta 2232 gtctgttttc acactgctga aaaagacatc cccaagactg gcaatttac aaagaaagag  2292 gtttattgga cttacagttc cacgtggctg aggaggcctc acaattacgg tggaaggtga 2352 aaggcacgtc tcacatggtg gcagacaaga gaagtgaaca tgtgcaagga gactcccatt 2412 tttaaaacag atctcgtgag acttttcac tatcatgcaa acagcatggg aaacctgccc  2472
ccgtgattca gttacctccc accgggtccc tccacaacaa catgggtatt caagatgaga 2532 tttgggtggg gttacagcca aactctatca ccagccttgc ccctgggcag aagcagcagc 2592 agtctgcctg gctggattca aatgattctg aggcttctat agtctatgcc tgcagatctc 2652 tccctcaccc atgctatagt gtctgaaatt ccaccattag agagtcattt cttgggctct 2712
```

```
gttaaatgga ccaggctctt ttataaagaa aatgccctg agcagctggc tctggcattg    2772
atttatgata tcttctcttc cctgccagaa ggaaggaagc taaggtgcat gtagggcgta    2832
ctgtgtgccc aggcactgtg ccagatgctt tggatacttg gagtcattga attcttgtag    2892
taaccctgtg agagagggag tctttttctcc acattgtaga agaaggaaaa agggctcaga    2952
gaggtcaaga aatgtccctg agatcacatg gcttctagtg gagtcaagat ccaaacccaa    3012
tgtgtctgat tccttagccc ttgggggtcc ggaggctgct gaacaagaaa ggaggtggag    3072
aggagagaaa gctgcaggca taccaccgca caccttctc cctcccctgt aaaaacaacc     3132
ctgggaactc cctggacact agcagaatat catacactaa ggataaggga tgagaggagg    3192
ctggttagaa ataaagcagt gtcaggggga aggagctact cagtaggctc tgtgtgattc    3252
tagaaagact gtatgaaaat tctgaacagt gaacagaata aacaataaag gtgcaatgg     3311
```

<210> SEQ ID NO 52
<211> LENGTH: 65
<212> TYPE: PRT
<213> ORGANISM: Homo sapiens

<400> SEQUENCE: 52

```
Met Arg Phe Ser Val Ser Leu Ala Arg Lys Ile Lys Thr Phe Ala Thr
1               5                   10                  15

Lys Met Val Ile Thr Ser Glu Asn Asp Glu Asp Arg Gly Gly Gln Glu
            20                  25                  30

Lys Glu Ser Lys Glu Glu Ser Val Leu Ala Met Leu Gly Ile Ile Gly
        35                  40                  45

Thr Ile Leu Asn Leu Ile Val Ile Ile Phe Val Tyr Ile Tyr Thr Thr
    50                  55                  60

Leu
65
```

<210> SEQ ID NO 53
<211> LENGTH: 4248
<212> TYPE: DNA
<213> ORGANISM: Homo sapiens
<220> FEATURE:
<221> NAME/KEY: CDS
<222> LOCATION: (189)..(2720)
<223> OTHER INFORMATION:

<400> SEQUENCE: 53

```
aagacctcca tcagctcgcc gcgcagcgcg gctgtatttg cggcctgtgc gagtaggcgc    60
ttgggcactc agtctccctg gcgagcgacg ggcagaaatc tcgaaccagt ggagcgcact   120
cgtaacctgg atcccagaag gtcgcgaagg cagtaccgtt tcctcagcgg cggactgctg   180 cagtaaga atg tct ttt cca cct cat ttg aat cgc cct ccc atg gga atc    230
         Met Ser Phe Pro Pro His Leu Asn Arg Pro Pro Met Gly Ile
          1               5                   10 cca gca ctc cca cca ggg atc cca ccc ccg cag ttt cca gga ttt cct    278
Pro Ala Leu Pro Pro Gly Ile Pro Pro Pro Gln Phe Pro Gly Phe Pro
15                  20                  25                  30 cca cct gta cct cca ggg acc cca atg att cct gta cca atg agc att    326
Pro Pro Val Pro Pro Gly Thr Pro Met Ile Pro Val Pro Met Ser Ile
                35                  40                  45 atg gct cct gct cca act gtc tta gta ccc act gtg tct atg gtt gga    374
Met Ala Pro Ala Pro Thr Val Leu Val Pro Thr Val Ser Met Val Gly
            50                  55                  60 aag cat ttg ggc gca aga aag gat cat cca ggc tta aag gct aaa gaa    422
Lys His Leu Gly Ala Arg Lys Asp His Pro Gly Leu Lys Ala Lys Glu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 65  |     |     |     |     | 70  |     |     |     |     | 75  |     |      |
| aat | gat | gaa | aat | tgt | ggt | cct | act | acc | act | gtt | ttt | gtt | ggc | aac | att | 470  |
| Asn | Asp | Glu | Asn | Cys | Gly | Pro | Thr | Thr | Thr | Val | Phe | Val | Gly | Asn | Ile |      |
|     |     |     | 80  |     |     |     |     | 85  |     |     |     |     | 90  |     |     |      |
| tcc | gag | aaa | gct | tca | gac | atg | ctt | ata | aga | caa | ctc | tta | gct | aaa | tgt | 518  |
| Ser | Glu | Lys | Ala | Ser | Asp | Met | Leu | Ile | Arg | Gln | Leu | Leu | Ala | Lys | Cys |      |
| 95  |     |     |     |     | 100 |     |     |     |     | 105 |     |     |     |     | 110 |      |
| ggt | ttg | gtt | ttg | agc | tgg | aag | aga | gta | caa | ggt | gct | tcc | gga | aag | ctt | 566  |
| Gly | Leu | Val | Leu | Ser | Trp | Lys | Arg | Val | Gln | Gly | Ala | Ser | Gly | Lys | Leu |      |
|     |     |     |     | 115 |     |     |     |     | 120 |     |     |     |     | 125 |     |      |
| caa | gcc | ttc | gga | ttc | tgt | gag | tac | aag | gag | cca | gaa | tct | acc | ctc | cgt | 614  |
| Gln | Ala | Phe | Gly | Phe | Cys | Glu | Tyr | Lys | Glu | Pro | Glu | Ser | Thr | Leu | Arg |      |
|     |     |     | 130 |     |     |     |     | 135 |     |     |     |     | 140 |     |     |      |
| gca | ctc | aga | tta | tta | cat | gac | ctg | caa | att | gga | gag | aaa | aag | cta | ctc | 662  |
| Ala | Leu | Arg | Leu | Leu | His | Asp | Leu | Gln | Ile | Gly | Glu | Lys | Lys | Leu | Leu |      |
|     |     | 145 |     |     |     |     | 150 |     |     |     |     | 155 |     |     |     |      |
| gtt | aaa | gtt | gat | gca | aag | aca | aag | gca | cag | ctg | gat | gaa | tgg | aaa | gca | 710  |
| Val | Lys | Val | Asp | Ala | Lys | Thr | Lys | Ala | Gln | Leu | Asp | Glu | Trp | Lys | Ala |      |
|     | 160 |     |     |     |     | 165 |     |     |     |     | 170 |     |     |     |     |      |
| aag | aag | aaa | gct | tct | aat | ggg | aat | gca | agg | cca | gaa | act | gtc | act | aat | 758  |
| Lys | Lys | Lys | Ala | Ser | Asn | Gly | Asn | Ala | Arg | Pro | Glu | Thr | Val | Thr | Asn |      |
| 175 |     |     |     |     | 180 |     |     |     |     | 185 |     |     |     |     | 190 |      |
| gac | gat | gaa | gaa | gcc | ttg | gat | gaa | gaa | aca | aag | agg | aga | gat | cag | atg | 806  |
| Asp | Asp | Glu | Glu | Ala | Leu | Asp | Glu | Glu | Thr | Lys | Arg | Arg | Asp | Gln | Met |      |
|     |     |     |     | 195 |     |     |     |     | 200 |     |     |     |     | 205 |     |      |
| att | aaa | ggg | gct | att | gaa | gtt | tta | att | cgt | gaa | tac | tcc | agt | gag | cta | 854  |
| Ile | Lys | Gly | Ala | Ile | Glu | Val | Leu | Ile | Arg | Glu | Tyr | Ser | Ser | Glu | Leu |      |
|     |     |     | 210 |     |     |     |     | 215 |     |     |     |     | 220 |     |     |      |
| aat | gcc | ccc | tca | cag | gaa | tct | gat | tct | cac | ccc | agg | aag | aag | aag | aag | 902  |
| Asn | Ala | Pro | Ser | Gln | Glu | Ser | Asp | Ser | His | Pro | Arg | Lys | Lys | Lys | Lys |      |
|     |     | 225 |     |     |     |     | 230 |     |     |     |     | 235 |     |     |     |      |
| gaa | aag | aag | gag | gac | att | ttc | cgc | aga | ttt | cca | gtg | gcc | cca | ctg | atc | 950  |
| Glu | Lys | Lys | Glu | Asp | Ile | Phe | Arg | Arg | Phe | Pro | Val | Ala | Pro | Leu | Ile |      |
|     | 240 |     |     |     |     | 245 |     |     |     |     | 250 |     |     |     |     |      |
| cct | tat | cca | ctc | atc | act | aag | gag | gat | ata | aat | gct | ata | gaa | atg | gaa | 998  |
| Pro | Tyr | Pro | Leu | Ile | Thr | Lys | Glu | Asp | Ile | Asn | Ala | Ile | Glu | Met | Glu |      |
| 255 |     |     |     |     | 260 |     |     |     |     | 265 |     |     |     |     | 270 |      |
| gaa | gac | aaa | aga | gac | ctg | ata | tct | cga | gag | atc | agc | aaa | ttc | aga | gac | 1046 |
| Glu | Asp | Lys | Arg | Asp | Leu | Ile | Ser | Arg | Glu | Ile | Ser | Lys | Phe | Arg | Asp |      |
|     |     |     |     | 275 |     |     |     |     | 280 |     |     |     |     | 285 |     |      |
| aca | cat | aag | aaa | ctg | gaa | gaa | gag | aaa | ggc | aaa | aag | gaa | aaa | gaa | aga | 1094 |
| Thr | His | Lys | Lys | Leu | Glu | Glu | Glu | Lys | Gly | Lys | Lys | Glu | Lys | Glu | Arg |      |
|     |     |     | 290 |     |     |     |     | 295 |     |     |     |     | 300 |     |     |      |
| cag | gaa | att | gag | aaa | gaa | cgg | aga | gaa | aga | gag | agg | gag | cgt | gaa | agg | 1142 |
| Gln | Glu | Ile | Glu | Lys | Glu | Arg | Arg | Glu | Arg | Glu | Arg | Glu | Arg | Glu | Arg |      |
|     |     | 305 |     |     |     |     | 310 |     |     |     |     | 315 |     |     |     |      |
| gaa | cga | gaa | agg | cga | gaa | cgg | gaa | cga | gaa | agg | gaa | aga | gaa | cgt | gaa | 1190 |
| Glu | Arg | Glu | Arg | Arg | Glu | Arg | Glu | Arg | Glu | Arg | Glu | Arg | Glu | Arg | Glu |      |
|     | 320 |     |     |     |     | 325 |     |     |     |     | 330 |     |     |     |     |      |
| cga | gaa | aag | gag | aaa | gaa | cgg | gag | cgg | gaa | cga | gaa | cgg | gat | agg | gac | 1238 |
| Arg | Glu | Lys | Glu | Lys | Glu | Arg | Glu | Arg | Glu | Arg | Glu | Arg | Asp | Arg | Asp |      |
| 335 |     |     |     |     | 340 |     |     |     |     | 345 |     |     |     |     | 350 |      |
| cgt | gac | cgg | aca | aaa | gag | aga | gac | cga | gat | cgg | gat | cga | gag | aga | gat | 1286 |
| Arg | Asp | Arg | Thr | Lys | Glu | Arg | Asp | Arg | Asp | Arg | Asp | Arg | Glu | Arg | Asp |      |
|     |     |     |     | 355 |     |     |     |     | 360 |     |     |     |     | 365 |     |      |
| cgt | gac | cgg | gat | aga | gaa | agg | agc | tca | gat | cgt | aat | aag | gat | cgc | agt | 1334 |
| Arg | Asp | Arg | Asp | Arg | Glu | Arg | Ser | Ser | Asp | Arg | Asn | Lys | Asp | Arg | Ser |      |
|     |     |     | 370 |     |     |     |     | 375 |     |     |     |     | 380 |     |     |      |
| cga | tca | aga | gaa | aaa | agc | aga | gat | cgt | gaa | agg | gaa | cga | gag | cgg | gaa | 1382 |

```
                                           -continued

Arg Ser Arg Glu Lys Ser Arg Asp Arg Glu Arg Glu Arg Glu
    385                 390                 395 aga gag aga gag aga gaa cga gag cga gaa cga gaa cgg gag cga gag        1430
Arg Glu Arg Glu Arg Glu Arg Glu Arg Glu Arg Glu Arg Glu Arg Glu
400                 405                 410 aga gag cga gag agg gaa cgg gag cga gaa aga gaa aaa gac aaa aaa        1478
Arg Glu Arg Glu Arg Glu Arg Glu Arg Glu Arg Glu Lys Asp Lys Lys
415                 420                 425                 430 cgg gac cga gaa gaa gat gaa gaa gat gca tac gaa cga aga aaa ctt        1526
Arg Asp Arg Glu Glu Asp Glu Glu Asp Ala Tyr Glu Arg Arg Lys Leu
                435                 440                 445 gaa aga aaa ctc cga gag aaa gaa gct gct tat caa gag cgc ctt aag        1574
Glu Arg Lys Leu Arg Glu Lys Glu Ala Ala Tyr Gln Glu Arg Leu Lys
            450                 455                 460 aat tgg gaa atc aga gaa cga aag aaa acc cgg gaa tat gag aaa gaa        1622
Asn Trp Glu Ile Arg Glu Arg Lys Lys Thr Arg Glu Tyr Glu Lys Glu
        465                 470                 475 gct gaa aga gaa gaa gaa aga aga aga gaa atg gcc aaa gaa gct aaa        1670
Ala Glu Arg Glu Glu Glu Arg Arg Arg Glu Met Ala Lys Glu Ala Lys
    480                 485                 490 cga cta aaa gaa ttc tta gaa gac tat gat gat gat aga gat gac ccc        1718
Arg Leu Lys Glu Phe Leu Glu Asp Tyr Asp Asp Asp Arg Asp Asp Pro
495                 500                 505                 510 aaa tat tac aga gga agt gct ctt cag aaa agg ttg cgt gat aga gaa        1766
Lys Tyr Tyr Arg Gly Ser Ala Leu Gln Lys Arg Leu Arg Asp Arg Glu
                515                 520                 525 aag gaa atg gaa gca gat gaa cga gat agg aag aga gag aag gag gag        1814
Lys Glu Met Glu Ala Asp Glu Arg Asp Arg Lys Arg Glu Lys Glu Glu
            530                 535                 540 ctt gag gaa atc agg cag cgc ctt ctg gca gaa ggg cat cca gat cca        1862
Leu Glu Glu Ile Arg Gln Arg Leu Leu Ala Glu Gly His Pro Asp Pro
        545                 550                 555 gat gca gag ctc cag agg atg gaa caa gag gct gag agg cgc agg cag        1910
Asp Ala Glu Leu Gln Arg Met Glu Gln Glu Ala Glu Arg Arg Arg Gln
    560                 565                 570 cca caa ata aag caa gag cca gaa tca gaa gag gag gaa gaa aag        1958
Pro Gln Ile Lys Gln Glu Pro Glu Ser Glu Glu Glu Glu Glu Lys
575                 580                 585                 590 caa gaa aaa gaa gaa aaa cga gaa gaa ccc atg gaa gag gaa gag gag        2006
Gln Glu Lys Glu Glu Lys Arg Glu Glu Pro Met Glu Glu Glu Glu
                595                 600                 605 cca gag caa aag cct tgt ctg aaa cct act ctg agg ccc atc agc tct        2054
Pro Glu Gln Lys Pro Cys Leu Lys Pro Thr Leu Arg Pro Ile Ser Ser
            610                 615                 620 gct cca tct gtt tcc tct gcc agt ggc aat gca aca cct aac act cct        2102
Ala Pro Ser Val Ser Ser Ala Ser Gly Asn Ala Thr Pro Asn Thr Pro
        625                 630                 635 ggg gat gag tct ccc tgt ggt att att att cct cat gaa aac tca cca        2150
Gly Asp Glu Ser Pro Cys Gly Ile Ile Ile Pro His Glu Asn Ser Pro
    640                 645                 650 gat caa cag caa cct gag gag cat agg cca aaa ata gga cta agt ctt        2198
Asp Gln Gln Gln Pro Glu Glu His Arg Pro Lys Ile Gly Leu Ser Leu
655                 660                 665                 670 aaa ctg ggt gct tcc aat agt cct ggt cag cct aat tct gtg aag aga        2246
Lys Leu Gly Ala Ser Asn Ser Pro Gly Gln Pro Asn Ser Val Lys Arg
                675                 680                 685 aag aaa cta cct gta gat agt gtc ttt aac aaa ttt gag gat gaa gac        2294
Lys Lys Leu Pro Val Asp Ser Val Phe Asn Lys Phe Glu Asp Glu Asp
            690                 695                 700
```

```
                                                      -continued agt gat gac gta ccc cga aaa agg aaa ctg gtt ccc ttg gat tat ggt    2342
Ser Asp Asp Val Pro Arg Lys Arg Lys Leu Val Pro Leu Asp Tyr Gly
        705                 710                 715 gaa gat gat aaa aat gca acc aaa ggc act gta aac act gaa gaa aag    2390
Glu Asp Asp Lys Asn Ala Thr Lys Gly Thr Val Asn Thr Glu Glu Lys
    720                 725                 730 cgt aaa cac att aag agt ctc att gag aaa atc cct aca gcc aaa cct    2438
Arg Lys His Ile Lys Ser Leu Ile Glu Lys Ile Pro Thr Ala Lys Pro
735                 740                 745                 750 gag ctc ttc gct tat ccc ctg gat tgg tct att gtg gat tct ata ctg    2486
Glu Leu Phe Ala Tyr Pro Leu Asp Trp Ser Ile Val Asp Ser Ile Leu
                755                 760                 765 atg gaa cgt cga att aga cca tgg att aat aag aaa atc ata gaa tat    2534
Met Glu Arg Arg Ile Arg Pro Trp Ile Asn Lys Lys Ile Ile Glu Tyr
            770                 775                 780 ata ggt gaa gaa gaa gct aca tta gtt gat ttt gtt tgt tct aag gtt    2582
Ile Gly Glu Glu Glu Ala Thr Leu Val Asp Phe Val Cys Ser Lys Val
785                 790                 795 atg gct cat agt tca ccc cag agc att tta gat gat gtt gcc atg gta    2630
Met Ala His Ser Ser Pro Gln Ser Ile Leu Asp Asp Val Ala Met Val
    800                 805                 810 ctt gat gaa gaa gca gaa gtt ttt ata gtc aaa atg tgg aga tta ttg    2678
Leu Asp Glu Glu Ala Glu Val Phe Ile Val Lys Met Trp Arg Leu Leu
815                 820                 825                 830 ata tat gaa aca gaa gcc aag aaa att ggt ctt gtg aag taa            2720
Ile Tyr Glu Thr Glu Ala Lys Lys Ile Gly Leu Val Lys
                835                 840 aacttttat atttagagtt ccatttcaga tttcttcttt gccacccttt taaggacttt   2780
gaattttcct ttgtctttga agacattgtg agatctgtaa ttttttttt ttgtagaaaa   2840
tgtgaatttt ttggtcctct aatttgttgt tgccctgtgt actcccttgg ttgtaaagtc  2900
atctgaatcc ttggttctct ttatactcac caggtacaaa ttactggtat gttttataag  2960
ccgcagctac tgtacacagc ctatctgata taatcttgtt ctgctgattt gtttcttgta  3020
aatattaaaa cgactcccca attattttgc agaattgcac ttaatattga aatgtactgt  3080
ataggaacca acatgaacaa ttttaattga aaacaccagt cataaactat taccaccccc  3140
actctctttt gatcagaaat ggcaagccct tgtgaaggca tggagtttaa aattggaatg  3200
caaaaattag cagacaatcc attcctactg tatttctgta tgaatgtgtt tgtgaatgta  3260
tgtgtaaaag tctttctttt ccctaatttg ctttggtggg gtccttaaaa catttcccaa  3320
ctaaagaata gaattgtaaa ggaaagtgg tactgttcca acctgaaatg tctgttataa   3380
ttaggttatt agtttcccag agcatggtgt tctcgtgtcg tgagcaatgt ggtttgctaa  3440
ctggatgggg ttttcttatt aataagatgg ctgcttcagc ttctctttta aaggaatgtg  3500
gatcatagtg attttttcctt ttaattttat tgctcagaaa tgaggcatat cctaaaaatc  3560
ctggagagct gtatttaatg cattttttgca ctaattggtc cttagtttaa ttctattgta 3620
tctgtttatt taacaaaaaa ttcatcatac caaaaagtgt aagtgaaaac ccccttaaa   3680
acaaaacaaa aaaatgaaat aaaattaggc aaattgacag acagtgagag ttttacaaac  3740
atgataggta ttctgctcgg caatttgtaa gtttacatgt tatttaagga taaggtaaa   3800
tcattcaagg cagttaccaa ccactaacta tttgttttca ttttttgtctt gtagaaggtt 3860
tatatcttgt tttaccttgg ctcattagtg tttaaaaatg tactgatgat gtgcttagag  3920
aaattcctgg ggctttcttc gttgtagatc agaatttcac cagggagtaa aattacctga  3980
aaacgtaaga agttttaaac agcttttcac acaaattaga tgcaactgtt cccatgtctg  4040
```

```
agtacttatt taaaagaaag gtaaagattg gcctgttaga aaaagcataa tgtgagcttt    4100
ggattactgg attttttttt tttttaaaca cacctggaga ggacatttga aaacactgtt    4160
cttaccctcg aaccctgatg tggttccatt atgtaaatat ttcaaatatt aaaaatgtat    4220
atatttgaaa aaaaaaaaaa aaaaaaaa                                       4248
```

<210> SEQ ID NO 54
<211> LENGTH: 843
<212> TYPE: PRT
<213> ORGANISM: Homo sapiens

<400> SEQUENCE: 54

```
Met Ser Phe Pro Pro His Leu Asn Arg Pro Met Gly Ile Pro Ala
1               5                   10                  15

Leu Pro Pro Gly Ile Pro Pro Gln Phe Pro Gly Phe Pro Pro Pro
                20                  25                  30

Val Pro Pro Gly Thr Pro Met Ile Pro Val Pro Met Ser Ile Met Ala
                35                  40                  45

Pro Ala Pro Thr Val Leu Val Pro Thr Val Ser Met Val Gly Lys His
    50                  55                  60

Leu Gly Ala Arg Lys Asp His Pro Gly Leu Lys Ala Lys Glu Asn Asp
65                  70                  75                  80

Glu Asn Cys Gly Pro Thr Thr Val Phe Val Gly Asn Ile Ser Glu
                85                  90                  95

Lys Ala Ser Asp Met Leu Ile Arg Gln Leu Leu Ala Lys Cys Gly Leu
                100                 105                 110

Val Leu Ser Trp Lys Arg Val Gln Gly Ala Ser Gly Lys Leu Gln Ala
                115                 120                 125

Phe Gly Phe Cys Glu Tyr Lys Glu Pro Glu Ser Thr Leu Arg Ala Leu
    130                 135                 140

Arg Leu Leu His Asp Leu Gln Ile Gly Glu Lys Lys Leu Leu Val Lys
145                 150                 155                 160

Val Asp Ala Lys Thr Lys Ala Gln Leu Asp Glu Trp Lys Ala Lys Lys
                165                 170                 175

Lys Ala Ser Asn Gly Asn Ala Arg Pro Glu Thr Val Thr Asn Asp Asp
                180                 185                 190

Glu Glu Ala Leu Asp Glu Glu Thr Lys Arg Arg Asp Gln Met Ile Lys
                195                 200                 205

Gly Ala Ile Glu Val Leu Ile Arg Glu Tyr Ser Ser Glu Leu Asn Ala
    210                 215                 220

Pro Ser Gln Glu Ser Asp Ser His Pro Arg Lys Lys Lys Glu Lys
225                 230                 235                 240

Lys Glu Asp Ile Phe Arg Arg Phe Pro Val Ala Pro Leu Ile Pro Tyr
                245                 250                 255

Pro Leu Ile Thr Lys Glu Asp Ile Asn Ala Ile Glu Met Glu Glu Asp
                260                 265                 270

Lys Arg Asp Leu Ile Ser Arg Glu Ile Ser Lys Phe Arg Asp Thr His
                275                 280                 285

Lys Lys Leu Glu Glu Glu Lys Gly Lys Lys Glu Lys Glu Arg Gln Glu
    290                 295                 300

Ile Glu Lys Glu Arg Arg Glu Arg Glu Arg Glu Arg Glu Arg Glu Arg
305                 310                 315                 320

Glu Arg Arg Glu Arg Glu Arg Glu Arg Glu Arg Glu Arg Glu Arg Glu
                325                 330                 335
```

-continued

```
Lys Glu Lys Glu Arg Glu Arg Glu Arg Asp Arg Asp Arg Asp
            340                 345                 350
Arg Thr Lys Glu Arg Asp Arg Asp Arg Asp Arg Glu Arg Asp Arg Asp
            355                 360                 365
Arg Asp Arg Glu Arg Ser Ser Asp Arg Asn Lys Asp Arg Ser Arg Ser
            370                 375                 380
Arg Glu Lys Ser Arg Asp Arg Glu Arg Glu Arg Glu Arg Glu Arg Glu
385                 390                 395                 400
Arg Glu Arg Glu Arg Glu Arg Glu Arg Glu Arg Glu Arg Glu Arg Glu
            405                 410                 415
Arg Glu Arg Glu Arg Glu Arg Glu Arg Glu Lys Asp Lys Lys Arg Asp
            420                 425                 430
Arg Glu Glu Asp Glu Glu Asp Ala Tyr Glu Arg Arg Lys Leu Glu Arg
            435                 440                 445
Lys Leu Arg Glu Lys Glu Ala Ala Tyr Gln Glu Arg Leu Lys Asn Trp
            450                 455                 460
Glu Ile Arg Glu Arg Lys Lys Thr Arg Glu Tyr Glu Lys Glu Ala Glu
465                 470                 475                 480
Arg Glu Glu Glu Arg Arg Arg Glu Met Ala Lys Glu Ala Lys Arg Leu
            485                 490                 495
Lys Glu Phe Leu Glu Asp Tyr Asp Asp Arg Asp Asp Pro Lys Tyr
            500                 505                 510
Tyr Arg Gly Ser Ala Leu Gln Lys Arg Leu Arg Asp Arg Glu Lys Glu
            515                 520                 525
Met Glu Ala Asp Glu Arg Asp Arg Lys Arg Glu Lys Glu Glu Leu Glu
            530                 535                 540
Glu Ile Arg Gln Arg Leu Leu Ala Glu Gly His Pro Asp Pro Asp Ala
545                 550                 555                 560
Glu Leu Gln Arg Met Glu Gln Glu Ala Glu Arg Arg Gln Pro Gln
            565                 570                 575
Ile Lys Gln Glu Pro Glu Ser Glu Glu Glu Glu Glu Lys Gln Glu
            580                 585                 590
Lys Glu Glu Lys Arg Glu Glu Pro Met Glu Glu Glu Glu Pro Glu
            595                 600                 605
Gln Lys Pro Cys Leu Lys Pro Thr Leu Arg Pro Ile Ser Ser Ala Pro
            610                 615                 620
Ser Val Ser Ser Ala Ser Gly Asn Ala Thr Pro Asn Thr Pro Gly Asp
625                 630                 635                 640
Glu Ser Pro Cys Gly Ile Ile Ile Pro His Glu Asn Ser Pro Asp Gln
            645                 650                 655
Gln Gln Pro Glu Glu His Arg Pro Lys Ile Gly Leu Ser Leu Lys Leu
            660                 665                 670
Gly Ala Ser Asn Ser Pro Gly Gln Pro Asn Ser Val Lys Arg Lys Lys
            675                 680                 685
Leu Pro Val Asp Ser Val Phe Asn Lys Phe Glu Asp Glu Asp Ser Asp
            690                 695                 700
Asp Val Pro Arg Lys Arg Lys Leu Val Pro Leu Asp Tyr Gly Glu Asp
705                 710                 715                 720
Asp Lys Asn Ala Thr Lys Gly Thr Val Asn Thr Glu Lys Arg Lys
            725                 730                 735
His Ile Lys Ser Leu Ile Glu Lys Ile Pro Thr Ala Lys Pro Glu Leu
            740                 745                 750
```

-continued

```
Phe Ala Tyr Pro Leu Asp Trp Ser Ile Val Asp Ser Ile Leu Met Glu
        755                 760                 765
Arg Arg Ile Arg Pro Trp Ile Asn Lys Lys Ile Ile Glu Tyr Ile Gly
    770                 775                 780
Glu Glu Glu Ala Thr Leu Val Asp Phe Val Cys Ser Lys Val Met Ala
785                 790                 795                 800
His Ser Ser Pro Gln Ser Ile Leu Asp Asp Val Ala Met Val Leu Asp
                805                 810                 815
Glu Glu Ala Glu Val Phe Ile Val Lys Met Trp Arg Leu Leu Ile Tyr
            820                 825                 830
Glu Thr Glu Ala Lys Lys Ile Gly Leu Val Lys
        835                 840
```

<210> SEQ ID NO 55
<211> LENGTH: 4056
<212> TYPE: DNA
<213> ORGANISM: Homo sapiens
<220> FEATURE:
<221> NAME/KEY: CDS
<222> LOCATION: (189)..(2528)
<223> OTHER INFORMATION:

<400> SEQUENCE: 55

```
aagacctcca tcagctcgcc gcgcagcgcg gctgtatttg cggcctgtgc gagtaggcgc        60
ttgggcactc agtctccctg gcgagcgacg ggcagaaatc tcgaaccagt ggagcgcact       120
cgtaacctgg atcccagaag gtcgcgaagg cagtaccgtt tcctcagcgg cggactgctg       180 cagtaaga atg tct ttt cca cct cat ttg aat cgc cct ccc atg gga atc       230
         Met Ser Phe Pro Pro His Leu Asn Arg Pro Pro Met Gly Ile
           1               5                  10 cca gca ctc cca cca ggg atc cca ccc ccg cag ttt cca gga ttt cct       278
Pro Ala Leu Pro Pro Gly Ile Pro Pro Pro Gln Phe Pro Gly Phe Pro
15                  20                  25                  30 cca cct gta cct cca ggg acc cca atg att cct gta cca atg agc att       326
Pro Pro Val Pro Pro Gly Thr Pro Met Ile Pro Val Pro Met Ser Ile
                35                  40                  45 atg gct cct gct cca act gtc tta gta ccc act gtg tct atg gtt gga       374
Met Ala Pro Ala Pro Thr Val Leu Val Pro Thr Val Ser Met Val Gly
            50                  55                  60 aag cat ttg ggc gca aga aag gat cat cca ggc tta aag gct aaa gaa       422
Lys His Leu Gly Ala Arg Lys Asp His Pro Gly Leu Lys Ala Lys Glu
        65                  70                  75 aat gat gaa aat tgt ggt cct act acc act gtt ttt gtt ggc aac att       470
Asn Asp Glu Asn Cys Gly Pro Thr Thr Thr Val Phe Val Gly Asn Ile
80                  85                  90 tcc gag aaa gct tca gac atg ctt ata aga caa ctc tta gct aaa tgt       518
Ser Glu Lys Ala Ser Asp Met Leu Ile Arg Gln Leu Leu Ala Lys Cys
95                  100                 105                 110 ggt ttg gtt ttg agc tgg aag aga gta caa ggt gct tcc gga aag ctt       566
Gly Leu Val Leu Ser Trp Lys Arg Val Gln Gly Ala Ser Gly Lys Leu
                115                 120                 125 caa gcc ttc gga ttc tgt gag tac aag gag cca gaa tct acc ctc cgt       614
Gln Ala Phe Gly Phe Cys Glu Tyr Lys Glu Pro Glu Ser Thr Leu Arg
            130                 135                 140 gca ctc aga tta tta cat gac ctg caa att gga gag aaa aag cta ctc       662
Ala Leu Arg Leu Leu His Asp Leu Gln Ile Gly Glu Lys Lys Leu Leu
        145                 150                 155 gtt aaa gtt gat gca aag aca aag gca cag ctg gat gaa tgg aaa gca       710
Val Lys Val Asp Ala Lys Thr Lys Ala Gln Leu Asp Glu Trp Lys Ala
    160                 165                 170
```

```
aag aag aaa gct tct aat ggg aat gca agg cca gaa act gtc act aat      758
Lys Lys Lys Ala Ser Asn Gly Asn Ala Arg Pro Glu Thr Val Thr Asn
175             180                 185                 190 gac gat gaa gaa gcc ttg gat gaa gaa aca aag agg aga gat cag atg      806
Asp Asp Glu Glu Ala Leu Asp Glu Glu Thr Lys Arg Arg Asp Gln Met
                195                 200                 205 att aaa ggg gct att gaa gtt tta att cgt gaa tac tcc agt gag cta      854
Ile Lys Gly Ala Ile Glu Val Leu Ile Arg Glu Tyr Ser Ser Glu Leu
210                 215                 220 aat gcc ccc tca cag gaa tct gat tct cac ccc agg aag aag aag aag      902
Asn Ala Pro Ser Gln Glu Ser Asp Ser His Pro Arg Lys Lys Lys Lys
        225                 230                 235 gaa aag aag gag gac att ttc cgc aga ttt cca gtg gcc cca ctg atc      950
Glu Lys Lys Glu Asp Ile Phe Arg Arg Phe Pro Val Ala Pro Leu Ile
    240                 245                 250 cct tat cca ctc atc act aag gag gat ata aat gct ata gaa atg gaa      998
Pro Tyr Pro Leu Ile Thr Lys Glu Asp Ile Asn Ala Ile Glu Met Glu
255                 260                 265                 270 gaa gac aaa aga gac ctg ata tct cga gag atc agc aaa ttc aga gac     1046
Glu Asp Lys Arg Asp Leu Ile Ser Arg Glu Ile Ser Lys Phe Arg Asp
                275                 280                 285 aca cat aag aaa ctg gaa gaa gag aaa ggc aaa aag gaa aaa gaa aga     1094
Thr His Lys Lys Leu Glu Glu Glu Lys Gly Lys Lys Glu Lys Glu Arg
        290                 295                 300 cag gaa att gag aaa gaa cgg aga gaa aga gag agg gag cgt gaa agg     1142
Gln Glu Ile Glu Lys Glu Arg Arg Glu Arg Glu Arg Glu Arg Glu Arg
    305                 310                 315 gaa cga gaa agg cga gaa cgg gaa cga gaa agg gaa cga gag cgg gaa     1190
Glu Arg Glu Arg Arg Glu Arg Glu Arg Glu Arg Glu Arg Glu Arg Glu
320                 325                 330 aga gag aga gag aga gaa cga gag cga gaa cga gaa cgg gag cga gag     1238
Arg Glu Arg Glu Arg Glu Arg Glu Arg Glu Arg Glu Arg Glu Arg Glu
335                 340                 345                 350 aga gag cga gag agg gaa cgg gag cga gaa aga gaa aaa gac aaa aaa     1286
Arg Glu Arg Glu Arg Glu Arg Glu Arg Glu Arg Glu Lys Asp Lys Lys
                355                 360                 365 cgg gac cga gaa gaa gat gaa gaa gat gca tac gaa cga aga aaa ctt     1334
Arg Asp Arg Glu Glu Asp Glu Glu Asp Ala Tyr Glu Arg Arg Lys Leu
        370                 375                 380 gaa aga aaa ctc cga gag aaa gaa gct gct tat caa gag cgc ctt aag     1382
Glu Arg Lys Leu Arg Glu Lys Glu Ala Ala Tyr Gln Glu Arg Leu Lys
    385                 390                 395 aat tgg gaa atc aga gaa cga aag aaa acc cgg gaa tat gag aaa gaa     1430
Asn Trp Glu Ile Arg Glu Arg Lys Lys Thr Arg Glu Tyr Glu Lys Glu
400                 405                 410 gct gaa aga gaa gaa gaa aga aga aga gaa atg gcc aaa gaa gct aaa     1478
Ala Glu Arg Glu Glu Glu Arg Arg Arg Glu Met Ala Lys Glu Ala Lys
415                 420                 425                 430 cga cta aaa gaa ttc tta gaa gac tat gat gat gat aga gat gac ccc     1526
Arg Leu Lys Glu Phe Leu Glu Asp Tyr Asp Asp Asp Arg Asp Asp Pro
                435                 440                 445 aaa tat tac aga gga agt gct ctt cag aaa agg ttg cgt gat aga gaa     1574
Lys Tyr Tyr Arg Gly Ser Ala Leu Gln Lys Arg Leu Arg Asp Arg Glu
        450                 455                 460 aag gaa atg gaa gca gat gaa cga gat agg aag aga gag aag gag gag     1622
Lys Glu Met Glu Ala Asp Glu Arg Asp Arg Lys Arg Glu Lys Glu Glu
    465                 470                 475 ctt gag gaa atc agg cag cgc ctt ctg gca gaa ggg cat cca gat cca     1670
Leu Glu Glu Ile Arg Gln Arg Leu Leu Ala Glu Gly His Pro Asp Pro
```

```
                480                 485                 490
gat gca gag ctc cag agg atg gaa caa gag gct gag agg cgc agg cag    1718
Asp Ala Glu Leu Gln Arg Met Glu Gln Glu Ala Glu Arg Arg Arg Gln
495                 500                 505                 510 cca caa ata aag caa gag cca gaa tca gaa gag gag gaa gaa aag        1766
Pro Gln Ile Lys Gln Glu Pro Glu Ser Glu Glu Glu Glu Glu Lys
                515                 520                 525 caa gaa aaa gaa gaa aaa cga gaa gaa ccc atg gaa gag gaa gag gag    1814
Gln Glu Lys Glu Glu Lys Arg Glu Glu Pro Met Glu Glu Glu Glu Glu
                530                 535                 540 cca gag caa aag cct tgt ctg aaa cct act ctg agg ccc atc agc tct    1862
Pro Glu Gln Lys Pro Cys Leu Lys Pro Thr Leu Arg Pro Ile Ser Ser
                545                 550                 555 gct cca tct gtt tcc tct gcc agt ggc aat gca aca cct aac act cct    1910
Ala Pro Ser Val Ser Ser Ala Ser Gly Asn Ala Thr Pro Asn Thr Pro
560                 565                 570 ggg gat gag tct ccc tgt ggt att att att cct cat gaa aac tca cca    1958
Gly Asp Glu Ser Pro Cys Gly Ile Ile Ile Pro His Glu Asn Ser Pro
575                 580                 585                 590 gat caa cag caa cct gag gag cat agg cca aaa ata gga cta agt ctt    2006
Asp Gln Gln Gln Pro Glu Glu His Arg Pro Lys Ile Gly Leu Ser Leu
                595                 600                 605 aaa ctg ggt gct tcc aat agt cct ggt cag cct aat tct gtg aag aga    2054
Lys Leu Gly Ala Ser Asn Ser Pro Gly Gln Pro Asn Ser Val Lys Arg
                610                 615                 620 aag aaa cta cct gta gat agt gtc ttt aac aaa ttt gag gat gaa gac    2102
Lys Lys Leu Pro Val Asp Ser Val Phe Asn Lys Phe Glu Asp Glu Asp
                625                 630                 635 agt gat gac gta ccc cga aaa agg aaa ctg gtt ccc ttg gat tat ggt    2150
Ser Asp Asp Val Pro Arg Lys Arg Lys Leu Val Pro Leu Asp Tyr Gly
640                 645                 650 gaa gat gat aaa aat gca acc aaa ggc act gta aac act gaa gaa aag    2198
Glu Asp Asp Lys Asn Ala Thr Lys Gly Thr Val Asn Thr Glu Glu Lys
655                 660                 665                 670 cgt aaa cac att aag agt ctc att gag aaa atc cct aca gcc aaa cct    2246
Arg Lys His Ile Lys Ser Leu Ile Glu Lys Ile Pro Thr Ala Lys Pro
                675                 680                 685 gag ctc ttc gct tat ccc ctg gat tgg tct att gtg gat tct ata ctg    2294
Glu Leu Phe Ala Tyr Pro Leu Asp Trp Ser Ile Val Asp Ser Ile Leu
                690                 695                 700 atg gaa cgt cga att aga cca tgg att aat aag aaa atc ata gaa tat    2342
Met Glu Arg Arg Ile Arg Pro Trp Ile Asn Lys Lys Ile Ile Glu Tyr
                705                 710                 715 ata ggt gaa gaa gaa gct aca tta gtt gat ttt gtt tgt tct aag gtt    2390
Ile Gly Glu Glu Glu Ala Thr Leu Val Asp Phe Val Cys Ser Lys Val
720                 725                 730 atg gct cat agt tca ccc cag agc att tta gat gat gtt gcc atg gta    2438
Met Ala His Ser Ser Pro Gln Ser Ile Leu Asp Asp Val Ala Met Val
735                 740                 745                 750 ctt gat gaa gaa gca gaa gtt ttt ata gtc aaa atg tgg aga tta ttg    2486
Leu Asp Glu Glu Ala Glu Val Phe Ile Val Lys Met Trp Arg Leu Leu
                755                 760                 765 ata tat gaa aca gaa gcc aag aaa att ggt ctt gtg aag taa            2528
Ile Tyr Glu Thr Glu Ala Lys Lys Ile Gly Leu Val Lys
                770                 775 aacttttat  atttagagtt  ccatttcaga  tttcttcttt  gccaccctt  taaggacttt    2588 gaattttct  ttgtctttga  agacattgtg  agatctgtaa  ttttttttt  ttgtagaaaa    2648 tgtgaatttt  ttggtcctct  aatttgttgt  tgccctgtgt  actccctggg ttgtaaagtc    2708
```

```
atctgaatcc ttggttctct ttatactcac caggtacaaa ttactggtat gttttataag    2768
ccgcagctac tgtacacagc ctatctgata taatcttgtt ctgctgattt gtttcttgta    2828
aatattaaaa cgactcccca attattttgc agaattgcac ttaatattga aatgtactgt    2888
ataggaacca acatgaacaa ttttaattga aaacaccagt cataaactat taccacccc     2948 actctctttt gatcagaaat ggcaagccct tgtgaaggca tggagtttaa aattggaatg    3008
caaaaattag cagacaatcc attcctactg tatttctgta tgaatgtgtt tgtgaatgta    3068
tgtgtaaaag tctttctttt ccctaatttg ctttggtggg gtccttaaaa catttcccaa    3128
ctaaagaata gaattgtaaa ggaaaagtgg tactgttcca acctgaaatg tctgttataa    3188
ttaggttatt agtttcccag agcatggtgt tctcgtgtcg tgagcaatgt ggtttgctaa    3248
ctggatgggg ttttcttatt aataagatgg ctgcttcagc ttctctttta aaggaatgtg    3308
gatcatagtg attttccctt ttaatttat tgctcagaaa tgaggcatat cctaaaaatc      3368
ctggagagct gtatttaatg cattttgca ctaattggtc cttagtttaa ttctattgta     3428
tctgtttatt taacaaaaaa ttcatcatac caaaagtgt aagtgaaaac ccccttaaa       3488 acaaaacaaa aaaatgaaat aaaattaggc aaattgacag acagtgagag ttttacaaac    3548
atgataggta ttctgctcgg caatttgtaa gtttacatgt tatttaagga taaggtaaa     3608 tcattcaagg cagttaccaa ccactaacta tttgttttca tttttgtctt gtagaaggtt    3668
tatatcttgt tttaccttgg ctcattagtg tttaaaaatg tactgatgat gtgcttagag    3728
aaattcctgg ggctttcttc gttgtagatc agaatttcac cagggagtaa aattacctga    3788
aaacgtaaga agttttaaac agcttttcac acaaattaga tgcaactgtt cccatgtctg    3848
agtacttatt taaagaaag gtaaagattg gcctgttaga aaaagcataa tgtgagcttt     3908
ggattactgg attttttttt tttttaaaca cacctggaga ggacatttga aaacactgtt    3968
cttaccctcg aaccctgatg tggttccatt atgtaaatat ttcaaatatt aaaaatgtat    4028
atatttgaaa aaaaaaaaaa aaaaaaaa                                       4056
```

<210> SEQ ID NO 56
<211> LENGTH: 779
<212> TYPE: PRT
<213> ORGANISM: Homo sapiens

<400> SEQUENCE: 56

```
Met Ser Phe Pro Pro His Leu Asn Arg Pro Pro Met Gly Ile Pro Ala
1               5                   10                  15

Leu Pro Pro Gly Ile Pro Pro Pro Gln Phe Pro Gly Phe Pro Pro Pro
            20                  25                  30

Val Pro Pro Gly Thr Pro Met Ile Pro Val Pro Met Ser Ile Met Ala
        35                  40                  45

Pro Ala Pro Thr Val Leu Val Pro Thr Val Ser Met Val Gly Lys His
    50                  55                  60

Leu Gly Ala Arg Lys Asp His Pro Gly Leu Lys Ala Lys Glu Asn Asp
65                  70                  75                  80

Glu Asn Cys Gly Pro Thr Thr Thr Val Phe Val Gly Asn Ile Ser Glu
                85                  90                  95

Lys Ala Ser Asp Met Leu Ile Arg Gln Leu Leu Ala Lys Cys Gly Leu
            100                 105                 110

Val Leu Ser Trp Lys Arg Val Gln Gly Ala Ser Gly Lys Leu Gln Ala
        115                 120                 125
```

-continued

```
Phe Gly Phe Cys Glu Tyr Lys Glu Pro Glu Ser Thr Leu Arg Ala Leu
            130                 135                 140

Arg Leu Leu His Asp Leu Gln Ile Gly Glu Lys Lys Leu Leu Val Lys
145                 150                 155                 160

Val Asp Ala Lys Thr Lys Ala Gln Leu Asp Glu Trp Lys Ala Lys Lys
                165                 170                 175

Lys Ala Ser Asn Gly Asn Ala Arg Pro Glu Thr Val Thr Asn Asp Asp
            180                 185                 190

Glu Glu Ala Leu Asp Glu Glu Thr Lys Arg Arg Asp Gln Met Ile Lys
            195                 200                 205

Gly Ala Ile Glu Val Leu Ile Arg Glu Tyr Ser Ser Glu Leu Asn Ala
            210                 215                 220

Pro Ser Gln Glu Ser Asp Ser His Pro Arg Lys Lys Lys Glu Lys
225                 230                 235                 240

Lys Glu Asp Ile Phe Arg Arg Phe Pro Val Ala Pro Leu Ile Pro Tyr
                245                 250                 255

Pro Leu Ile Thr Lys Glu Asp Ile Asn Ala Ile Glu Met Glu Glu Asp
                260                 265                 270

Lys Arg Asp Leu Ile Ser Arg Glu Ile Ser Lys Phe Arg Asp Thr His
            275                 280                 285

Lys Lys Leu Glu Glu Glu Lys Gly Lys Lys Glu Lys Glu Arg Gln Glu
            290                 295                 300

Ile Glu Lys Glu Arg Arg Glu Arg Glu Arg Glu Arg Glu Arg Glu Arg
305                 310                 315                 320

Glu Arg Arg Glu Arg Glu Arg Glu Arg Glu Arg Glu Arg Glu Arg Glu
                325                 330                 335

Arg Glu Arg Glu Arg Glu Arg Glu Arg Glu Arg Glu Arg Glu Arg Glu
            340                 345                 350

Arg Glu Arg Glu Arg Glu Arg Glu Arg Glu Lys Asp Lys Lys Arg Asp
            355                 360                 365

Arg Glu Glu Asp Glu Glu Asp Ala Tyr Glu Arg Arg Lys Leu Glu Arg
            370                 375                 380

Lys Leu Arg Glu Lys Glu Ala Ala Tyr Gln Glu Arg Leu Lys Asn Trp
385                 390                 395                 400

Glu Ile Arg Glu Arg Lys Lys Thr Arg Glu Tyr Glu Lys Glu Ala Glu
                405                 410                 415

Arg Glu Glu Glu Arg Arg Arg Glu Met Ala Lys Glu Ala Lys Arg Leu
                420                 425                 430

Lys Glu Phe Leu Glu Asp Tyr Asp Asp Arg Asp Asp Pro Lys Tyr
            435                 440                 445

Tyr Arg Gly Ser Ala Leu Gln Lys Arg Leu Arg Asp Arg Glu Lys Glu
            450                 455                 460

Met Glu Ala Asp Glu Arg Asp Arg Lys Arg Glu Lys Glu Glu Leu Glu
465                 470                 475                 480

Glu Ile Arg Gln Arg Leu Leu Ala Glu Gly His Pro Asp Pro Asp Ala
                485                 490                 495

Glu Leu Gln Arg Met Glu Gln Glu Ala Glu Arg Arg Gln Pro Gln
            500                 505                 510

Ile Lys Gln Glu Pro Glu Ser Glu Glu Glu Glu Lys Gln Glu
            515                 520                 525

Lys Glu Glu Lys Arg Glu Glu Pro Met Glu Glu Glu Glu Pro Glu
            530                 535                 540

Gln Lys Pro Cys Leu Lys Pro Thr Leu Arg Pro Ile Ser Ser Ala Pro
```

```
                545                 550                 555                 560
Ser Val Ser Ser Ala Ser Gly Asn Ala Thr Pro Asn Thr Pro Gly Asp
                    565                 570                 575

Glu Ser Pro Cys Gly Ile Ile Ile Pro His Glu Asn Ser Pro Asp Gln
            580                 585                 590

Gln Gln Pro Glu Glu His Arg Pro Lys Ile Gly Leu Ser Leu Lys Leu
        595                 600                 605

Gly Ala Ser Asn Ser Pro Gly Gln Pro Asn Ser Val Lys Arg Lys Lys
    610                 615                 620

Leu Pro Val Asp Ser Val Phe Asn Lys Phe Glu Asp Glu Ser Asp
625                 630                 635                 640

Asp Val Pro Arg Lys Arg Lys Leu Val Pro Leu Asp Tyr Gly Glu Asp
                    645                 650                 655

Asp Lys Asn Ala Thr Lys Gly Thr Val Asn Thr Glu Lys Arg Lys
                660                 665                 670

His Ile Lys Ser Leu Ile Glu Lys Ile Pro Thr Ala Lys Pro Glu Leu
            675                 680                 685

Phe Ala Tyr Pro Leu Asp Trp Ser Ile Val Asp Ser Ile Leu Met Glu
        690                 695                 700

Arg Arg Ile Arg Pro Trp Ile Asn Lys Lys Ile Ile Glu Tyr Ile Gly
705                 710                 715                 720

Glu Glu Glu Ala Thr Leu Val Asp Phe Val Cys Ser Lys Val Met Ala
                    725                 730                 735

His Ser Ser Pro Gln Ser Ile Leu Asp Asp Val Ala Met Val Leu Asp
                740                 745                 750

Glu Glu Ala Glu Val Phe Ile Val Lys Met Trp Arg Leu Leu Ile Tyr
            755                 760                 765

Glu Thr Glu Ala Lys Lys Ile Gly Leu Val Lys
        770                 775

<210> SEQ ID NO 57
<211> LENGTH: 4847
<212> TYPE: DNA
<213> ORGANISM: Homo sapiens
<220> FEATURE:
<221> NAME/KEY: CDS
<222> LOCATION: (109)..(4068)
<223> OTHER INFORMATION:

<400> SEQUENCE: 57
ctctaatacg actcactata gggaaagctg gtacgcctgc aggtaccggt ccggaattcc     60
cgggtcgacc cacgcgtccg aggtaccta cggtacctga aaacaacg atg gc
                                                      Met Ala Trp
                                                        1 aaa aca ctt ccc att tac ctg ttg ctg ctg tct gtt ttc gtg att         165
Lys Thr Leu Pro Ile Tyr Leu Leu Leu Leu Ser Val Phe Val Ile
 5                  10                  15 cag caa gtt tca tct caa gag ctt tcc tgt aaa ggc cgc tgc ttt gag     213
Gln Gln Val Ser Ser Gln Glu Leu Ser Cys Lys Gly Arg Cys Phe Glu
 20                  25                  30                  35 tcc ttc gag aga ggg agg gag tgt gac tgc gac gcc caa tgt aag aag    261
Ser Phe Glu Arg Gly Arg Glu Cys Asp Cys Asp Ala Gln Cys Lys Lys
                 40                  45                  50 tat gac aag tgc tgt ccc gat tat gag agt ttc tgt gca gaa gtg cat    309
Tyr Asp Lys Cys Cys Pro Asp Tyr Glu Ser Phe Cys Ala Glu Val His
             55                  60                  65 aat ccc aca tca cca cca tct tca aag aaa gca cct cca cct tca gga    357
```

```
Asn Pro Thr Ser Pro Pro Ser Ser Lys Lys Ala Pro Pro Ser Gly
            70                  75                  80 gca tct caa acc atc aaa tca aca acc aaa cgt tca ccc aaa cca cca         405
Ala Ser Gln Thr Ile Lys Ser Thr Thr Lys Arg Ser Pro Lys Pro Pro
    85                  90                  95 aac aag aag aag act aag aaa gtt ata gaa tca gag gaa ata aca gaa         453
Asn Lys Lys Lys Thr Lys Lys Val Ile Glu Ser Glu Glu Ile Thr Glu
100                 105                 110                 115 gta aaa gat aac aag aag aac aga act aaa aag aaa cct acc ccc aaa         501
Val Lys Asp Asn Lys Lys Asn Arg Thr Lys Lys Lys Pro Thr Pro Lys
                120                 125                 130 cca cca gtt gta gat gaa gct gga agt gga ttg gac aat ggt gac ttc         549
Pro Pro Val Val Asp Glu Ala Gly Ser Gly Leu Asp Asn Gly Asp Phe
                135                 140                 145 aag gtc aca act cct gac acg tct acc acc caa cac aat aaa gtc agc         597
Lys Val Thr Thr Pro Asp Thr Ser Thr Thr Gln His Asn Lys Val Ser
            150                 155                 160 aca tct ccc aag atc aca aca gca aaa cca ata aat ccc aga ccc agt         645
Thr Ser Pro Lys Ile Thr Thr Ala Lys Pro Ile Asn Pro Arg Pro Ser
    165                 170                 175 ctt cca cct aat tct gat aca tct aaa gag acg tct ttg aca gtg aat         693
Leu Pro Pro Asn Ser Asp Thr Ser Lys Glu Thr Ser Leu Thr Val Asn
180                 185                 190                 195 aaa gag aca aca gtt gaa act aaa gaa act act aca aca aat aaa cag         741
Lys Glu Thr Thr Val Glu Thr Lys Glu Thr Thr Thr Thr Asn Lys Gln
                200                 205                 210 act tca act gat gga aaa gag aag act act tcc gct aaa gag aca caa         789
Thr Ser Thr Asp Gly Lys Glu Lys Thr Thr Ser Ala Lys Glu Thr Gln
                215                 220                 225 agt ata gag aaa aca tct gct aaa gat tta gca ccc aca tct aaa gtg         837
Ser Ile Glu Lys Thr Ser Ala Lys Asp Leu Ala Pro Thr Ser Lys Val
            230                 235                 240 ctg gct aaa cct aca ccc aaa gct gaa act aca acc aaa ggc cct gct         885
Leu Ala Lys Pro Thr Pro Lys Ala Glu Thr Thr Thr Lys Gly Pro Ala
    245                 250                 255 ctc acc act ccc aag gag ccc acg ccc acc act ccc aag gag cct gca         933
Leu Thr Thr Pro Lys Glu Pro Thr Pro Thr Thr Pro Lys Glu Pro Ala
260                 265                 270                 275 tct acc aca ccc aaa gag ccc aca cct acc acc atc aag tct gca ccc         981
Ser Thr Thr Pro Lys Glu Pro Thr Pro Thr Thr Ile Lys Ser Ala Pro
                280                 285                 290 acc acc ccc aag gag cct gca ccc acc acc acc aag tct gca ccc acc         1029
Thr Thr Pro Lys Glu Pro Ala Pro Thr Thr Thr Lys Ser Ala Pro Thr
                295                 300                 305 act ccc aag gag cct gca ccc acc acc acc aag gag cct gca ccc acc         1077
Thr Pro Lys Glu Pro Ala Pro Thr Thr Thr Lys Glu Pro Ala Pro Thr
            310                 315                 320 act ccc aag gag cct gca ccc acc acc acc aag gag cct gca ccc acc         1125
Thr Pro Lys Glu Pro Ala Pro Thr Thr Thr Lys Glu Pro Ala Pro Thr
    325                 330                 335 acc acc aag tct gca ccc acc act ccc aag gag cct gca ccc acc acc         1173
Thr Thr Lys Ser Ala Pro Thr Thr Pro Lys Glu Pro Ala Pro Thr Thr
340                 345                 350                 355 ccc aag aag cct gcc cca act acc ccc aag gag cct gca ccc acc act         1221
Pro Lys Lys Pro Ala Pro Thr Thr Pro Lys Glu Pro Ala Pro Thr Thr
                360                 365                 370 ccc aag gag cct aca ccc acc act ccc aag gag cct gca ccc acc acc         1269
Pro Lys Glu Pro Thr Pro Thr Thr Pro Lys Glu Pro Ala Pro Thr Thr
                375                 380                 385
```

```
aag gag cct gca ccc acc act ccc aaa gag cct gca ccc act gcc ccc    1317
Lys Glu Pro Ala Pro Thr Thr Pro Lys Glu Pro Ala Pro Thr Ala Pro
        390                 395                 400 aag aag cct gcc cca act acc ccc aag gag cct gca ccc acc act ccc    1365
Lys Lys Pro Ala Pro Thr Thr Pro Lys Glu Pro Ala Pro Thr Thr Pro
    405                 410                 415 aag gag cct gca ccc acc acc acc aag gag cct tca ccc acc act ccc    1413
Lys Glu Pro Ala Pro Thr Thr Thr Lys Glu Pro Ser Pro Thr Thr Pro
420                 425                 430                 435 aag gag cct gca ccc acc acc acc aag tct gca ccc acc act acc aag    1461
Lys Glu Pro Ala Pro Thr Thr Thr Lys Ser Ala Pro Thr Thr Thr Lys
                440                 445                 450 gag cct gca ccc acc act acc aag tct gca ccc acc act ccc aag gag    1509
Glu Pro Ala Pro Thr Thr Thr Lys Ser Ala Pro Thr Thr Pro Lys Glu
            455                 460                 465 cct tca ccc acc acc acc aag gag cct gca ccc acc act ccc aag gag    1557
Pro Ser Pro Thr Thr Thr Lys Glu Pro Ala Pro Thr Thr Pro Lys Glu
        470                 475                 480 cct gca ccc acc acc ccc aag aag cct gcc cca act acc ccc aag gag    1605
Pro Ala Pro Thr Thr Pro Lys Lys Pro Ala Pro Thr Thr Pro Lys Glu
    485                 490                 495 cct gca ccc acc act ccc aag gaa cct gca ccc acc acc acc aag aag    1653
Pro Ala Pro Thr Thr Pro Lys Glu Pro Ala Pro Thr Thr Thr Lys Lys
500                 505                 510                 515 cct gca ccc acc act ccc aaa gag cct gcc cca act acc ccc aag gag    1701
Pro Ala Pro Thr Thr Pro Lys Glu Pro Ala Pro Thr Thr Pro Lys Glu
                520                 525                 530 act gca ccc acc acc ccc aag aag ctc acg ccc acc acc ccc gag aag    1749
Thr Ala Pro Thr Thr Pro Lys Lys Leu Thr Pro Thr Thr Pro Glu Lys
            535                 540                 545 ctc gca ccc acc acc cct gag aag ccc gca ccc acc acc cct gag gag    1797
Leu Ala Pro Thr Thr Pro Glu Lys Pro Ala Pro Thr Thr Pro Glu Glu
        550                 555                 560 ctc gca ccc acc acc cct gag gag ccc aca ccc acc acc cct gag gag    1845
Leu Ala Pro Thr Thr Pro Glu Glu Pro Thr Pro Thr Thr Pro Glu Glu
    565                 570                 575 cct gct ccc acc act ccc aag gca gcg gct ccc aac acc cct aag gag    1893
Pro Ala Pro Thr Thr Pro Lys Ala Ala Ala Pro Asn Thr Pro Lys Glu
580                 585                 590                 595 cct gct cca act acc cct aag gag cct gct cca act acc cct aag gag    1941
Pro Ala Pro Thr Thr Pro Lys Glu Pro Ala Pro Thr Thr Pro Lys Glu
                600                 605                 610 cct gct cca act acc cct aag gag act gct cca act acc cct aaa ggg    1989
Pro Ala Pro Thr Thr Pro Lys Glu Thr Ala Pro Thr Thr Pro Lys Gly
            615                 620                 625 act gct cca act acc ctc aag gaa cct gca ccc act act ccc aag aag    2037
Thr Ala Pro Thr Thr Leu Lys Glu Pro Ala Pro Thr Thr Pro Lys Lys
        630                 635                 640 cct gcc ccc aag gag ctt gca ccc acc acc aag gag ccc aca tcc        2085
Pro Ala Pro Lys Glu Leu Ala Pro Thr Thr Thr Lys Glu Pro Thr Ser
    645                 650                 655 acc acc tgt gac aag ccc gct cca act acc cct aag ggg act gct cca    2133
Thr Thr Cys Asp Lys Pro Ala Pro Thr Thr Pro Lys Gly Thr Ala Pro
660                 665                 670                 675 act acc cct aag gag cct gct cca act acc cct aag gag cct gct cca    2181
Thr Thr Pro Lys Glu Pro Ala Pro Thr Thr Pro Lys Glu Pro Ala Pro
                680                 685                 690 act acc cct aag ggg act gct cca act acc ctc aag gaa cct gca ccc    2229
Thr Thr Pro Lys Gly Thr Ala Pro Thr Thr Leu Lys Glu Pro Ala Pro
            695                 700                 705
```

```
act act ccc aag aag cct gcc ccc aag gag ctt gca ccc acc acc acc     2277
Thr Thr Pro Lys Lys Pro Ala Pro Lys Glu Leu Ala Pro Thr Thr Thr
        710             715                 720 aag ggg ccc aca tcc acc acc tct gac aag cct gct cca act aca cct     2325
Lys Gly Pro Thr Ser Thr Thr Ser Asp Lys Pro Ala Pro Thr Thr Pro
        725             730                 735 aag gag act gct cca act acc ccc aag gag cct gca ccc act acc ccc     2373
Lys Glu Thr Ala Pro Thr Thr Pro Lys Glu Pro Ala Pro Thr Thr Pro
740             745                 750                 755 aag aag cct gct cca act act cct gag aca cct cct cca acc act tca     2421
Lys Lys Pro Ala Pro Thr Thr Pro Glu Thr Pro Pro Thr Thr Ser
            760                 765                 770 gag gtc tct act cca act acc acc aag gag cct acc act atc cac aaa     2469
Glu Val Ser Thr Pro Thr Thr Thr Lys Glu Pro Thr Thr Ile His Lys
            775                 780                 785 agc cct gat gaa tca act cct gag ctt tct gca gaa ccc aca cca aaa     2517
Ser Pro Asp Glu Ser Thr Pro Glu Leu Ser Ala Glu Pro Thr Pro Lys
        790             795                 800 gct ctt gaa aac agt ccc aag gaa cct ggt gta cct aca act aag act     2565
Ala Leu Glu Asn Ser Pro Lys Glu Pro Gly Val Pro Thr Thr Lys Thr
        805             810                 815 cct gca gcg act aaa cct gaa atg act aca aca gct aaa gac aag aca     2613
Pro Ala Ala Thr Lys Pro Glu Met Thr Thr Thr Ala Lys Asp Lys Thr
820             825                 830                 835 aca gaa aga gac tta cgt act aca cct gaa act aca act gct gca cct     2661
Thr Glu Arg Asp Leu Arg Thr Thr Pro Glu Thr Thr Thr Ala Ala Pro
            840                 845                 850 aag atg aca aaa gag aca gca act aca aca gaa aaa act acc gaa tcc     2709
Lys Met Thr Lys Glu Thr Ala Thr Thr Thr Glu Lys Thr Thr Glu Ser
            855                 860                 865 aaa ata aca gct aca acc aca caa gta aca tct acc aca act caa gat     2757
Lys Ile Thr Ala Thr Thr Thr Gln Val Thr Ser Thr Thr Thr Gln Asp
            870                 875                 880 acc aca cca ttc aaa att act act ctt aaa aca act act ctt gca ccc     2805
Thr Thr Pro Phe Lys Ile Thr Thr Leu Lys Thr Thr Thr Leu Ala Pro
        885                 890                 895 aaa gta act aca aca aaa aag aca att act acc act gag att atg aac     2853
Lys Val Thr Thr Thr Lys Lys Thr Ile Thr Thr Thr Glu Ile Met Asn
900             905                 910                 915 aaa cct gaa gaa aca gct aaa cca aaa gac aga gct act aat tct aaa     2901
Lys Pro Glu Glu Thr Ala Lys Pro Lys Asp Arg Ala Thr Asn Ser Lys
            920                 925                 930 gcg aca act cct aaa cct caa aag cca acc aaa gca ccc aaa aaa ccc     2949
Ala Thr Thr Pro Lys Pro Gln Lys Pro Thr Lys Ala Pro Lys Lys Pro
            935                 940                 945 act tct acc aaa aag cca aaa aca atg cct aga gtg aga aaa cca aag     2997
Thr Ser Thr Lys Lys Pro Lys Thr Met Pro Arg Val Arg Lys Pro Lys
        950             955                 960 acg aca cca act ccc cgc aag atg aca tca aca atg cca gaa ttg aac     3045
Thr Thr Pro Thr Pro Arg Lys Met Thr Ser Thr Met Pro Glu Leu Asn
        965             970                 975 cct acc tca aga ata gca gaa gcc atg ctc caa acc acc acc aga cct     3093
Pro Thr Ser Arg Ile Ala Glu Ala Met Leu Gln Thr Thr Thr Arg Pro
980             985                 990                 995 aac caa act cca aac  tcc aaa cta gtt gaa  gta aat cca aag agt       3138
Asn Gln Thr Pro Asn  Ser Lys Leu Val Glu  Val Asn Pro Lys Ser
            1000                1005                1010 gaa gat gca ggt ggt  gct gaa gga gaa aca  cct cat atg ctt ctc       3183
Glu Asp Ala Gly Gly  Ala Glu Gly Glu Thr  Pro His Met Leu Leu
```

```
                              1015                     1020                     1025
agg   ccc   cat   gtg   ttc   atg   cct   gaa   gtt   act   ccc   gac   atg   gat   tac        3228
Arg   Pro   His   Val   Phe   Met   Pro   Glu   Val   Thr   Pro   Asp   Met   Asp   Tyr
                              1030                     1035                     1040 tta   ccg   aga   gta   ccc   aat   caa   ggc   att   atc   atc   aat   ccc   atg   ctt        3273
Leu   Pro   Arg   Val   Pro   Asn   Gln   Gly   Ile   Ile   Ile   Asn   Pro   Met   Leu
                              1045                     1050                     1055 tcc   gat   gag   acc   aat   ata   tgc   aat   ggt   aag   cca   gta   gat   gga   ctg        3318
Ser   Asp   Glu   Thr   Asn   Ile   Cys   Asn   Gly   Lys   Pro   Val   Asp   Gly   Leu
                              1060                     1065                     1070 act   act   ttg   cgc   aat   ggg   aca   tta   gtt   gca   ttc   cga   ggt   cat   tat        3363
Thr   Thr   Leu   Arg   Asn   Gly   Thr   Leu   Val   Ala   Phe   Arg   Gly   His   Tyr
                              1075                     1080                     1085 ttc   tgg   atg   cta   agt   cca   ttc   agt   cca   cca   tct   cca   gct   cgc   aga        3408
Phe   Trp   Met   Leu   Ser   Pro   Phe   Ser   Pro   Pro   Ser   Pro   Ala   Arg   Arg
                              1090                     1095                     1100 att   act   gaa   gtt   tgg   ggt   att   cct   tcc   ccc   att   gat   act   gtt   ttt        3453
Ile   Thr   Glu   Val   Trp   Gly   Ile   Pro   Ser   Pro   Ile   Asp   Thr   Val   Phe
                              1105                     1110                     1115 act   agg   tgc   aac   tgt   gaa   gga   aaa   act   ttc   ttc   ttt   aag   gat   tct        3498
Thr   Arg   Cys   Asn   Cys   Glu   Gly   Lys   Thr   Phe   Phe   Phe   Lys   Asp   Ser
                              1120                     1125                     1130 cag   tac   tgg   cgt   ttt   acc   aat   gat   ata   aaa   gat   gca   ggg   tac   ccc        3543
Gln   Tyr   Trp   Arg   Phe   Thr   Asn   Asp   Ile   Lys   Asp   Ala   Gly   Tyr   Pro
                              1135                     1140                     1145 aaa   cca   att   ttc   aaa   gga   ttt   gga   gga   cta   act   gga   caa   ata   gtg        3588
Lys   Pro   Ile   Phe   Lys   Gly   Phe   Gly   Gly   Leu   Thr   Gly   Gln   Ile   Val
                              1150                     1155                     1160 gca   gcg   ctt   tca   aca   gct   aaa   tat   aag   aac   tgg   cct   gaa   tct   gtg        3633
Ala   Ala   Leu   Ser   Thr   Ala   Lys   Tyr   Lys   Asn   Trp   Pro   Glu   Ser   Val
                              1165                     1170                     1175 tat   ttt   ttc   aag   aga   ggt   ggc   agc   att   cag   cag   tat   att   tat   aaa        3678
Tyr   Phe   Phe   Lys   Arg   Gly   Gly   Ser   Ile   Gln   Gln   Tyr   Ile   Tyr   Lys
                              1180                     1185                     1190 cag   gaa   cct   gta   cag   aag   tgc   cct   gga   aga   agg   cct   gct   cta   aat        3723
Gln   Glu   Pro   Val   Gln   Lys   Cys   Pro   Gly   Arg   Arg   Pro   Ala   Leu   Asn
                              1195                     1200                     1205 tat   cca   gtg   tat   gga   gaa   acg   aca   cag   gtt   agg   aga   cgt   cgc   ttt        3768
Tyr   Pro   Val   Tyr   Gly   Glu   Thr   Thr   Gln   Val   Arg   Arg   Arg   Arg   Phe
                              1210                     1215                     1220 gaa   cgt   gct   ata   gga   cct   tct   caa   aca   cac   acc   atc   aga   att   caa        3813
Glu   Arg   Ala   Ile   Gly   Pro   Ser   Gln   Thr   His   Thr   Ile   Arg   Ile   Gln
                              1225                     1230                     1235 tat   tca   cct   gcc   aga   ctg   gct   tat   caa   gac   aaa   ggt   gtc   ctt   cat        3858
Tyr   Ser   Pro   Ala   Arg   Leu   Ala   Tyr   Gln   Asp   Lys   Gly   Val   Leu   His
                              1240                     1245                     1250 aat   gaa   gtt   aaa   gtg   agt   ata   ctg   tgg   aga   gga   ctt   cca   aat   gtg        3903
Asn   Glu   Val   Lys   Val   Ser   Ile   Leu   Trp   Arg   Gly   Leu   Pro   Asn   Val
                              1255                     1260                     1265 gtt   acc   tca   gct   ata   tca   ctg   ccc   aac   atc   aga   aaa   cct   gac   ggc        3948
Val   Thr   Ser   Ala   Ile   Ser   Leu   Pro   Asn   Ile   Arg   Lys   Pro   Asp   Gly
                              1270                     1275                     1280 tat   gat   tac   tat   gcc   ttt   tct   aaa   gat   caa   tac   tat   aac   att   gat        3993
Tyr   Asp   Tyr   Tyr   Ala   Phe   Ser   Lys   Asp   Gln   Tyr   Tyr   Asn   Ile   Asp
                              1285                     1290                     1295 gtg   cct   agt   aga   aca   gca   aga   gca   att   act   act   cgt   tct   ggg   cag        4038
Val   Pro   Ser   Arg   Thr   Ala   Arg   Ala   Ile   Thr   Thr   Arg   Ser   Gly   Gln
                              1300                     1305                     1310 acc   tta   tcc   aaa   gtc   tgg   tac   aac   tgt   cct   tagactgatg   agcaaaggag          4088
```

```
Thr Leu Ser Lys Val   Trp Tyr Asn Cys Pro
            1315                1320 gagtcaacta atgaagaaat gaataataaa ttttgacact gaaaacatt ttattaataa    4148 agaatattga catgagtata ccagtttata tataaaaatg ttttttaaact tgacaatcat   4208 tacactaaaa cagatttgat aatcttattc acagttgtta ttgtttacag accatttaat   4268
taatatttcc tctgtttatt cctcctctcc ctcccattgc atggctcaca cctgtaaaag   4328
aaaaaagaat caaattgaat atatctttta agaattcaaa actagtgtat tcacttaccc   4388
tagttcatta taaaaatat ctaggcattg tggatataaa actgttgggt attctacaac    4448
ttcaatggaa attattacaa gcagattaat ccctcttttt gtgacacaag tacaatctaa   4508
aagttatatt ggaaaacatg gaaatattaa aattttacac ttttactagc taaaacataa   4568
tcacaaagct ttatcgtgtt gtataaaaaa attaacaata taatggcaat aggtagagat   4628
acaacaaatg aatataacac tataacactt catattttcc aaatcttaat ttggatttaa   4688
ggaagaaatc aataaatata aaatataagc acatatttat tatatatcta aggtatacaa   4748
atctgtctac atgaagttta cagattggta aatatcaccct gctcaacatg taattattta   4808
ataaaacttt ggaacattaa aaaaataaat tggaggctt                          4847

<210> SEQ ID NO 58
<211> LENGTH: 1320
<212> TYPE: PRT
<213> ORGANISM: Homo sapiens

<400> SEQUENCE: 58

Met Ala Trp Lys Thr Leu Pro Ile Tyr Leu Leu Leu Leu Leu Ser Val
1               5                   10                  15

Phe Val Ile Gln Gln Val Ser Ser Gln Glu Leu Ser Cys Lys Gly Arg
                20                  25                  30

Cys Phe Glu Ser Phe Glu Arg Gly Arg Glu Cys Asp Cys Asp Ala Gln
            35                  40                  45

Cys Lys Lys Tyr Asp Lys Cys Cys Pro Asp Tyr Glu Ser Phe Cys Ala
        50                  55                  60

Glu Val His Asn Pro Thr Ser Pro Ser Ser Lys Lys Ala Pro Pro
65                  70                  75                  80

Pro Ser Gly Ala Ser Gln Thr Ile Lys Ser Thr Lys Arg Ser Pro
                85                  90                  95

Lys Pro Asn Lys Lys Thr Lys Val Ile Glu Ser Glu Glu
                100                 105                 110

Ile Thr Glu Val Lys Asp Asn Lys Asn Arg Thr Lys Lys Pro
        115                 120                 125

Thr Pro Lys Pro Pro Val Val Asp Glu Ala Gly Ser Gly Leu Asp Asn
    130                 135                 140

Gly Asp Phe Lys Val Thr Thr Pro Asp Thr Ser Thr Gln His Asn
145                 150                 155                 160

Lys Val Ser Thr Ser Pro Lys Ile Thr Thr Ala Lys Pro Ile Asn Pro
                165                 170                 175

Arg Pro Ser Leu Pro Pro Asn Ser Asp Thr Ser Lys Glu Thr Ser Leu
            180                 185                 190

Thr Val Asn Lys Glu Thr Thr Val Glu Thr Lys Glu Thr Thr Thr
        195                 200                 205

Asn Lys Gln Thr Ser Thr Asp Gly Lys Glu Lys Thr Thr Ser Ala Lys
    210                 215                 220
```

-continued

```
Glu Thr Gln Ser Ile Glu Lys Thr Ser Ala Lys Asp Leu Ala Pro Thr
225                 230                 235                 240

Ser Lys Val Leu Ala Lys Pro Thr Pro Lys Ala Glu Thr Thr Thr Lys
            245                 250                 255

Gly Pro Ala Leu Thr Thr Pro Lys Glu Pro Thr Pro Thr Thr Pro Lys
            260                 265                 270

Glu Pro Ala Ser Thr Thr Pro Lys Glu Pro Thr Pro Thr Thr Ile Lys
            275                 280                 285

Ser Ala Pro Thr Thr Pro Lys Glu Pro Ala Pro Thr Thr Thr Lys Ser
290                 295                 300

Ala Pro Thr Thr Pro Lys Glu Pro Ala Pro Thr Thr Thr Lys Glu Pro
305                 310                 315                 320

Ala Pro Thr Thr Pro Lys Glu Pro Ala Pro Thr Thr Thr Lys Glu Pro
            325                 330                 335

Ala Pro Thr Thr Thr Lys Ser Ala Pro Thr Thr Pro Lys Glu Pro Ala
            340                 345                 350

Pro Thr Thr Pro Lys Lys Pro Ala Pro Thr Thr Pro Lys Glu Pro Ala
            355                 360                 365

Pro Thr Thr Pro Lys Glu Pro Thr Pro Thr Thr Pro Lys Glu Pro Ala
            370                 375                 380

Pro Thr Thr Lys Glu Pro Ala Pro Thr Thr Pro Lys Glu Pro Ala Pro
385                 390                 395                 400

Thr Ala Pro Lys Lys Pro Ala Pro Thr Thr Pro Lys Glu Pro Ala Pro
            405                 410                 415

Thr Thr Pro Lys Glu Pro Ala Pro Thr Thr Lys Glu Pro Ser Pro
            420                 425                 430

Thr Thr Pro Lys Glu Pro Ala Pro Thr Thr Lys Ser Ala Pro Thr
            435                 440                 445

Thr Thr Lys Glu Pro Ala Pro Thr Thr Lys Ser Ala Pro Thr Thr
    450                 455                 460

Pro Lys Glu Pro Ser Pro Thr Thr Thr Lys Glu Pro Ala Pro Thr Thr
465                 470                 475                 480

Pro Lys Glu Pro Ala Pro Thr Pro Lys Lys Pro Ala Pro Thr Thr
            485                 490                 495

Pro Lys Glu Pro Ala Pro Thr Thr Pro Lys Glu Pro Ala Pro Thr Thr
            500                 505                 510

Thr Lys Lys Pro Ala Pro Thr Thr Pro Lys Glu Pro Ala Pro Thr Thr
            515                 520                 525

Pro Lys Glu Thr Ala Pro Thr Thr Pro Lys Lys Leu Thr Pro Thr Thr
            530                 535                 540

Pro Glu Lys Leu Ala Pro Thr Thr Pro Glu Lys Pro Ala Pro Thr Thr
545                 550                 555                 560

Pro Glu Glu Leu Ala Pro Thr Thr Pro Glu Glu Pro Thr Pro Thr Thr
            565                 570                 575

Pro Glu Glu Pro Ala Pro Thr Thr Pro Lys Ala Ala Ala Pro Asn Thr
            580                 585                 590

Pro Lys Glu Pro Ala Pro Thr Thr Pro Lys Glu Pro Ala Pro Thr Thr
            595                 600                 605

Pro Lys Glu Pro Ala Pro Thr Pro Lys Glu Thr Ala Pro Thr Thr
            610                 615                 620

Pro Lys Gly Thr Ala Pro Thr Thr Leu Lys Glu Pro Ala Pro Thr Thr
625                 630                 635                 640

Pro Lys Lys Pro Ala Pro Lys Glu Leu Ala Pro Thr Thr Thr Lys Glu
```

-continued

```
                    645                 650                 655
Pro Thr Ser Thr Thr Cys Asp Lys Pro Ala Pro Thr Thr Pro Lys Gly
                660                 665                 670
Thr Ala Pro Thr Thr Pro Lys Glu Pro Ala Pro Thr Thr Pro Lys Glu
                675                 680                 685
Pro Ala Pro Thr Thr Pro Lys Gly Thr Ala Pro Thr Thr Leu Lys Glu
                690                 695                 700
Pro Ala Pro Thr Thr Pro Lys Lys Pro Ala Pro Lys Glu Leu Ala Pro
705                 710                 715                 720
Thr Thr Thr Lys Gly Pro Thr Ser Thr Ser Asp Lys Pro Ala Pro
                725                 730                 735
Thr Thr Pro Lys Glu Thr Ala Pro Thr Thr Pro Lys Glu Pro Ala Pro
                740                 745                 750
Thr Thr Pro Lys Lys Pro Ala Pro Thr Thr Pro Glu Thr Pro Pro
                755                 760                 765
Thr Thr Ser Glu Val Ser Thr Pro Thr Thr Thr Lys Glu Pro Thr Thr
                770                 775                 780
Ile His Lys Ser Pro Asp Glu Ser Thr Pro Glu Leu Ser Ala Glu Pro
785                 790                 795                 800
Thr Pro Lys Ala Leu Glu Asn Ser Pro Lys Glu Pro Gly Val Pro Thr
                805                 810                 815
Thr Lys Thr Pro Ala Ala Thr Lys Pro Glu Met Thr Thr Thr Ala Lys
                820                 825                 830
Asp Lys Thr Thr Glu Arg Asp Leu Arg Thr Thr Pro Glu Thr Thr Thr
                835                 840                 845
Ala Ala Pro Lys Met Thr Lys Glu Thr Ala Thr Thr Glu Lys Thr
                850                 855                 860
Thr Glu Ser Lys Ile Thr Ala Thr Thr Thr Gln Val Thr Ser Thr Thr
865                 870                 875                 880
Thr Gln Asp Thr Thr Pro Phe Lys Ile Thr Thr Leu Lys Thr Thr Thr
                885                 890                 895
Leu Ala Pro Lys Val Thr Thr Thr Lys Lys Thr Ile Thr Thr Thr Glu
                900                 905                 910
Ile Met Asn Lys Pro Glu Glu Thr Ala Lys Pro Lys Asp Arg Ala Thr
                915                 920                 925
Asn Ser Lys Ala Thr Thr Pro Lys Pro Gln Lys Pro Thr Lys Ala Pro
930                 935                 940
Lys Lys Pro Thr Ser Thr Lys Lys Pro Lys Thr Met Pro Arg Val Arg
945                 950                 955                 960
Lys Pro Lys Thr Thr Pro Thr Pro Arg Lys Met Thr Ser Thr Met Pro
                965                 970                 975
Glu Leu Asn Pro Thr Ser Arg Ile Ala Glu Ala Met Leu Gln Thr Thr
                980                 985                 990
Thr Arg Pro Asn Gln Thr Pro Asn Ser Lys Leu Val Glu Val Asn Pro
                995                 1000                1005
Lys Ser Glu Asp Ala Gly Gly Ala Glu Gly Glu Thr Pro His Met
                1010                1015                1020
Leu Leu Arg Pro His Val Phe Met Pro Glu Val Thr Pro Asp Met
                1025                1030                1035
Asp Tyr Leu Pro Arg Val Pro Asn Gln Gly Ile Ile Ile Asn Pro
                1040                1045                1050
Met Leu Ser Asp Glu Thr Asn Ile Cys Asn Gly Lys Pro Val Asp
                1055                1060                1065
```

-continued

Gly Leu Thr Thr Leu Arg Asn Gly Thr Leu Val Ala Phe Arg Gly
    1070                1075                1080

His Tyr Phe Trp Met Leu Ser Pro Phe Ser Pro Ser Pro Ala
    1085                1090                1095

Arg Arg Ile Thr Glu Val Trp Gly Ile Pro Ser Pro Ile Asp Thr
    1100                1105                1110

Val Phe Thr Arg Cys Asn Cys Glu Gly Lys Thr Phe Phe Lys
    1115                1120                1125

Asp Ser Gln Tyr Trp Arg Phe Thr Asn Asp Ile Lys Asp Ala Gly
    1130                1135                1140

Tyr Pro Lys Pro Ile Phe Lys Gly Phe Gly Leu Thr Gly Gln
    1145                1150                1155

Ile Val Ala Ala Leu Ser Thr Ala Lys Tyr Lys Asn Trp Pro Glu
    1160                1165                1170

Ser Val Tyr Phe Phe Lys Arg Gly Gly Ser Ile Gln Gln Tyr Ile
    1175                1180                1185

Tyr Lys Gln Glu Pro Val Gln Lys Cys Pro Gly Arg Arg Pro Ala
    1190                1195                1200

Leu Asn Tyr Pro Val Tyr Gly Glu Thr Thr Gln Val Arg Arg Arg
    1205                1210                1215

Arg Phe Glu Arg Ala Ile Gly Pro Ser Gln Thr His Thr Ile Arg
    1220                1225                1230

Ile Gln Tyr Ser Pro Ala Arg Leu Ala Tyr Gln Asp Lys Gly Val
    1235                1240                1245

Leu His Asn Glu Val Lys Val Ser Ile Leu Trp Arg Gly Leu Pro
    1250                1255                1260

Asn Val Val Thr Ser Ala Ile Ser Leu Pro Asn Ile Arg Lys Pro
    1265                1270                1275

Asp Gly Tyr Asp Tyr Tyr Ala Phe Ser Lys Asp Gln Tyr Tyr Asn
    1280                1285                1290

Ile Asp Val Pro Ser Arg Thr Ala Arg Ala Ile Thr Thr Arg Ser
    1295                1300                1305

Gly Gln Thr Leu Ser Lys Val Trp Tyr Asn Cys Pro
    1310                1315                1320

<210> SEQ ID NO 59
<211> LENGTH: 258
<212> TYPE: PRT
<213> ORGANISM: Homo sapiens

<400> SEQUENCE: 59

Met Glu Val Lys Pro Pro Gly Arg Pro Gln Pro Asp Ser Gly Arg
1               5                   10                  15

Arg Arg Arg Arg Arg Gly Glu Glu Gly His Asp Pro Lys Glu Pro Glu
                20                  25                  30

Gln Leu Arg Lys Leu Phe Ile Gly Gly Leu Ser Phe Glu Thr Thr Asp
            35                  40                  45

Asp Ser Leu Arg Glu His Phe Glu Lys Trp Gly Thr Leu Thr Asp Cys
        50                  55                  60

Val Val Met Arg Asp Pro Gln Thr Lys Arg Ser Arg Gly Phe Gly Phe
65                  70                  75                  80

Val Thr Tyr Ser Cys Val Glu Glu Val Asp Ala Ala Met Cys Ala Arg
                85                  90                  95

Pro His Lys Val Asp Gly Arg Val Val Glu Pro Lys Arg Ala Val Ser

-continued

```
            100                 105                 110
Arg Glu Asp Ser Val Lys Pro Gly Ala His Leu Thr Val Lys Lys Ile
            115                 120                 125

Phe Val Gly Gly Ile Lys Glu Asp Thr Glu Tyr Asn Leu Arg Asp
    130                 135                 140

Tyr Phe Glu Lys Tyr Gly Lys Ile Glu Thr Ile Glu Val Met Glu Asp
145                 150                 155                 160

Arg Gln Ser Gly Lys Lys Arg Gly Phe Ala Phe Val Thr Phe Asp Asp
                165                 170                 175

His Asp Thr Val Asp Lys Ile Val Val Gln Lys Tyr His Thr Ile Asn
                180                 185                 190

Gly His Asn Cys Glu Val Lys Lys Ala Leu Ser Lys Gln Glu Met Gln
            195                 200                 205

Ser Ala Gly Ser Gln Arg Gly Arg Gly Gly Ser Gly Asn Phe Met
    210                 215                 220

Gly Arg Gly Gly Asn Phe Gly Gly Gly Gly Asn Phe Gly Arg Gly
225                 230                 235                 240

Gly Asn Phe Gly Gly Arg Gly Arg Leu Trp Trp Trp Arg Trp Trp Gln
                245                 250                 255

Gln Arg

<210> SEQ ID NO 60
<211> LENGTH: 496
<212> TYPE: PRT
<213> ORGANISM: Homo sapiens

<400> SEQUENCE: 60

Met Thr Ala Gly Ile Asn Ala Asp Gly His Leu Ile Asn Thr Gly Gln
1               5                   10                  15

Ala Met Asp Ser Ser Asp Asn Ser Glu Arg Thr Gly Glu Arg Val Ser
                20                  25                  30

Pro Asp Ile Asn Glu Thr Asn Thr Asp Thr Asp Leu Phe Val Pro Thr
            35                  40                  45

Ser Ser Ser Ser Gln Leu Pro Val Thr Ile Asp Ser Thr Gly Ile Leu
    50                  55                  60

Gln Gln Asn Thr Asn Ser Leu Thr Thr Ser Ser Gly Gln Val His Ser
65                  70                  75                  80

Ser Asp Leu Gln Gly Asn Tyr Ile Gln Ser Pro Val Ser Glu Glu Thr
                85                  90                  95

Gln Ala Gln Asn Ile Gln Val Ser Thr Ala Gln Pro Val Val Gln His
                100                 105                 110

Leu Gln Leu Gln Glu Ser Gln Gln Pro Thr Ser Gln Ala Gln Ile Val
            115                 120                 125

Gln Gly Ile Thr Pro Gln Thr Ile His Gly Val Gln Ala Ser Gly Gln
    130                 135                 140

Asn Ile Ser Gln Gln Ala Leu Gln Asn Leu Gln Leu Gln Leu Asn Pro
145                 150                 155                 160

Gly Thr Phe Leu Ile Gln Ala Gln Thr Val Thr Pro Ser Gly Gln Val
                165                 170                 175

Thr Trp Gln Thr Phe Gln Val Gln Gly Val Gln Asn Leu Gln Asn Leu
                180                 185                 190

Gln Ile Gln Asn Thr Ala Ala Gln Gln Ile Thr Leu Thr Pro Val Gln
            195                 200                 205

Thr Leu Thr Leu Gly Gln Val Ala Ala Gly Gly Ala Phe Thr Ser Thr
```

```
            210                 215                 220
Pro Val Ser Leu Ser Thr Gly Gln Leu Pro Asn Leu Gln Thr Val Thr
225                 230                 235                 240

Val Asn Ser Ile Asp Ser Ala Gly Ile Gln Leu His Pro Gly Glu Asn
                245                 250                 255

Ala Asp Ser Pro Ala Asp Ile Arg Ile Lys Glu Glu Pro Asp Pro
            260                 265                 270

Glu Glu Trp Gln Leu Ser Gly Asp Ser Thr Leu Asn Thr Asn Asp Leu
                275                 280                 285

Thr His Leu Arg Val Gln Val Val Asp Glu Glu Gly Asp Gln Gln His
            290                 295                 300

Gln Glu Gly Lys Arg Leu Arg Arg Val Ala Cys Thr Cys Pro Asn Cys
305                 310                 315                 320

Lys Glu Gly Gly Gly Arg Gly Thr Asn Leu Gly Lys Lys Lys Gln His
                325                 330                 335

Ile Cys His Ile Pro Gly Cys Gly Lys Val Tyr Gly Lys Thr Ser His
                340                 345                 350

Leu Arg Ala His Leu Arg Trp His Ser Gly Glu Arg Pro Phe Val Cys
            355                 360                 365

Asn Trp Met Tyr Cys Gly Lys Arg Phe Thr Arg Ser Asp Glu Leu Gln
370                 375                 380

Arg His Arg Arg Thr His Thr Gly Glu Lys Lys Phe Val Cys Pro Glu
385                 390                 395                 400

Cys Ser Lys Arg Phe Met Arg Ser Asp His Leu Ala Lys His Ile Lys
                405                 410                 415

Thr His Gln Asn Lys Lys Gly Ile His Ser Ser Ser Thr Val Leu Ala
                420                 425                 430

Ser Val Glu Ala Ala Arg Asp Asp Thr Leu Ile Thr Ala Gly Gly Thr
            435                 440                 445

Thr Leu Ile Leu Ala Lys Ile Gln Gln Gly Ser Val Ser Gly Ile Gly
            450                 455                 460

Thr Val Asn Thr Ser Ala Thr Ser Asn Gln Asp Ile Leu Thr Asn Thr
465                 470                 475                 480

Glu Ile Pro Leu Gln Leu Val Thr Val Ser Gly Asn Glu Thr Met Glu
                485                 490                 495

<210> SEQ ID NO 61
<211> LENGTH: 315
<212> TYPE: PRT
<213> ORGANISM: Homo sapiens

<400> SEQUENCE: 61

Met Asp Leu Arg Gln Phe Leu Met Cys Leu Ser Leu Cys Thr Ala Phe
1               5                   10                  15

Ala Leu Ser Lys Pro Thr Glu Lys Lys Asp Arg Val His His Glu Pro
                20                  25                  30

Gln Leu Ser Asp Lys Val His Asn Asp Ala Gln Ser Phe Asp Tyr Asp
            35                  40                  45

His Asp Ala Phe Leu Gly Ala Glu Ala Lys Thr Phe Asp Gln Leu
        50                  55                  60

Thr Pro Glu Glu Ser Lys Glu Arg Leu Gly Lys Ile Val Ser Lys Ile
65                  70                  75                  80

Asp Gly Asp Lys Asp Gly Phe Val Thr Val Asp Glu Leu Lys Asp Trp
                85                  90                  95
```

-continued

```
Ile Lys Phe Ala Gln Lys Arg Trp Ile Tyr Glu Asp Val Glu Arg Gln
            100                 105                 110
Trp Lys Gly His Asp Leu Asn Glu Asp Gly Leu Val Ser Trp Glu Glu
        115                 120                 125
Tyr Lys Asn Ala Thr Tyr Gly Tyr Val Leu Asp Asp Pro Asp Pro Asp
    130                 135                 140
Asp Gly Phe Asn Tyr Lys Gln Met Met Val Arg Asp Glu Arg Arg Phe
145                 150                 155                 160
Lys Met Ala Asp Lys Asp Gly Asp Leu Ile Ala Thr Lys Glu Glu Phe
                165                 170                 175
Thr Ala Phe Leu His Pro Glu Glu Tyr Asp Tyr Met Lys Asp Ile Val
            180                 185                 190
Val Gln Glu Thr Met Glu Asp Ile Asp Lys Asn Ala Asp Gly Phe Ile
        195                 200                 205
Asp Leu Glu Glu Tyr Ile Gly Asp Met Tyr Ser His Asp Gly Asn Thr
    210                 215                 220
Asp Glu Pro Glu Trp Val Lys Thr Glu Arg Glu Gln Phe Val Glu Phe
225                 230                 235                 240
Arg Asp Lys Asn Arg Asp Gly Lys Met Asp Lys Glu Glu Thr Lys Asp
                245                 250                 255
Trp Ile Leu Pro Ser Asp Tyr Asp His Ala Glu Ala Glu Ala Arg His
            260                 265                 270
Leu Val Tyr Glu Ser Asp Gln Asn Lys Asp Gly Lys Leu Thr Lys Glu
        275                 280                 285
Glu Ile Val Asp Lys Tyr Asp Leu Phe Val Gly Ser Gln Ala Thr Asp
    290                 295                 300
Phe Gly Glu Ala Leu Val Arg His Asp Glu Phe
305                 310                 315

<210> SEQ ID NO 62
<211> LENGTH: 336
<212> TYPE: PRT
<213> ORGANISM: Homo sapiens
<400> SEQUENCE: 62

Met Arg Ala Pro Ser Met Asp Arg Ala Ala Val Ala Arg Val Gly Ala
1               5                   10                  15
Val Ala Ser Ala Ser Val Cys Ala Leu Val Ala Gly Val Val Leu Ala
            20                  25                  30
Gln Tyr Ile Phe Thr Leu Lys Arg Lys Thr Gly Arg Lys Thr Lys Ile
        35                  40                  45
Ile Glu Met Met Pro Glu Phe Gln Lys Ser Ser Val Arg Ile Lys Asn
    50                  55                  60
Pro Thr Arg Val Glu Glu Ile Ile Cys Gly Leu Ile Lys Gly Gly Ala
65                  70                  75                  80
Ala Lys Leu Gln Ile Ile Thr Asp Phe Asp Met Thr Leu Ser Arg Phe
                85                  90                  95
Ser Tyr Lys Gly Lys Arg Cys Pro Thr Cys His Asn Ile Ile Asp Asn
            100                 105                 110
Cys Lys Leu Val Thr Asp Glu Cys Arg Lys Lys Leu Leu Gln Leu Lys
        115                 120                 125
Glu Lys Tyr Tyr Ala Ile Glu Val Asp Pro Val Leu Thr Val Glu Glu
    130                 135                 140
Lys Tyr Pro Tyr Met Val Glu Trp Tyr Thr Lys Ser His Gly Leu Leu
145                 150                 155                 160
```

```
Val Gln Gln Ala Leu Pro Lys Ala Lys Leu Lys Glu Ile Val Ala Glu
                165                 170                 175

Ser Asp Val Met Leu Lys Glu Gly Tyr Glu Asn Phe Asp Lys Leu
            180                 185                 190

Gln Gln His Ser Ile Pro Val Phe Ile Phe Ser Ala Gly Ile Gly Asp
            195                 200                 205

Val Leu Glu Glu Val Ile Arg Gln Ala Gly Val Tyr His Pro Asn Val
    210                 215                 220

Lys Val Val Ser Asn Phe Met Asp Phe Asp Glu Thr Gly Val Leu Lys
225                 230                 235                 240

Gly Phe Lys Gly Glu Leu Ile His Val Phe Asn Lys His Asp Gly Ala
                245                 250                 255

Leu Arg Asn Thr Glu Tyr Phe Asn Gln Leu Lys Asp Asn Ser Asn Ile
            260                 265                 270

Ile Leu Leu Gly Asp Ser Gln Gly Asp Leu Arg Met Ala Asp Gly Val
            275                 280                 285

Ala Asn Val Glu His Ile Leu Lys Ile Gly Tyr Leu Asn Asp Arg Val
    290                 295                 300

Asp Glu Leu Leu Glu Lys Tyr Met Asp Ser Tyr Asp Ile Val Leu Val
305                 310                 315                 320

Gln Asp Glu Ser Leu Glu Val Ala Asn Ser Ile Leu Gln Lys Ile Leu
                325                 330                 335

<210> SEQ ID NO 63
<211> LENGTH: 472
<212> TYPE: PRT
<213> ORGANISM: Homo sapiens

<400> SEQUENCE: 63

Met Ala Leu Gly Leu Glu Gln Ala Glu Glu Arg Leu Tyr Gln Gln
1               5                   10                  15

Thr Leu Leu Gln Asp Gly Leu Lys Asp Met Leu Asp His Gly Lys Phe
            20                  25                  30

Leu Asp Cys Val Val Arg Ala Gly Glu Arg Glu Phe Pro Cys His Arg
        35                  40                  45

Leu Val Leu Ala Ala Cys Ser Pro Tyr Phe Arg Ala Arg Phe Leu Ala
    50                  55                  60

Glu Pro Glu Arg Ala Gly Glu Leu His Leu Glu Glu Val Ser Pro Asp
65                  70                  75                  80

Val Val Ala Gln Val Leu His Tyr Leu Tyr Thr Ser Glu Ile Ala Leu
                85                  90                  95

Asp Glu Ala Ser Val Gln Asp Leu Phe Ala Ala His Arg Phe Gln
            100                 105                 110

Ile Pro Ser Ile Phe Thr Ile Cys Val Ser Phe Leu Gln Lys Arg Leu
        115                 120                 125

Cys Leu Ser Asn Cys Leu Ala Val Phe Arg Leu Gly Leu Leu Leu Asp
    130                 135                 140

Cys Ala Arg Leu Ala Val Ala Ala Arg Asp Phe Ile Cys Ala His Phe
145                 150                 155                 160

Thr Leu Val Ala Arg Asp Ala Asp Phe Leu Gly Leu Ser Ala Asp Glu
                165                 170                 175

Leu Ile Ala Ile Ile Ser Ser Asp Gly Leu Asn Val Glu Lys Glu Glu
            180                 185                 190

Ala Val Phe Glu Ala Val Met Arg Trp Ala Gly Ser Gly Asp Ala Glu
        195                 200                 205
```

```
Ala Gln Ala Glu Arg Gln Arg Ala Leu Pro Thr Val Phe Glu Ser Val
    210                 215                 220

Arg Cys Arg Leu Leu Pro Arg Ala Phe Leu Glu Ser Arg Val Glu Arg
225                 230                 235                 240

His Pro Leu Val Arg Ala Gln Pro Glu Leu Leu Arg Lys Val Gln Met
                245                 250                 255

Val Lys Asp Ala His Glu Gly Arg Ile Thr Thr Leu Arg Lys Lys Lys
            260                 265                 270

Lys Gly Lys Asp Gly Ala Gly Ala Lys Glu Ala Asp Lys Gly Thr Ser
        275                 280                 285

Lys Ala Lys Ala Glu Glu Asp Glu Glu Ala Glu Arg Ile Leu Pro Gly
    290                 295                 300

Ile Leu Asn Asp Thr Leu Arg Phe Gly Met Phe Leu Gln Asp Leu Ile
305                 310                 315                 320

Phe Met Ile Ser Glu Glu Gly Ala Val Ala Tyr Asp Pro Ala Ala Asn
                325                 330                 335

Glu Cys Tyr Cys Ala Ser Leu Ser Asn Gln Val Pro Lys Asn His Val
            340                 345                 350

Ser Leu Val Thr Lys Glu Asn Gln Val Phe Val Ala Gly Gly Leu Phe
        355                 360                 365

Tyr Asn Glu Asp Asn Lys Glu Asp Pro Met Ser Ala Tyr Phe Leu Gln
    370                 375                 380

Phe Asp His Leu Asp Ser Glu Trp Leu Gly Met Pro Pro Leu Pro Ser
385                 390                 395                 400

Pro Arg Cys Leu Phe Gly Leu Gly Glu Ala Leu Asn Ser Ile Tyr Val
                405                 410                 415

Val Gly Gly Arg Glu Ile Lys Asp Gly Glu Arg Cys Leu Asp Ser Val
            420                 425                 430

Met Cys Tyr Asp Arg Leu Ser Phe Lys Trp Gly His Arg His Arg Ala
        435                 440                 445

Asp Gln Phe Cys Arg Ser Val Gln His Arg Gln Val Gly Thr
    450                 455                 460

Leu Arg Gly Leu Pro Thr Gly Ala
465                 470

<210> SEQ ID NO 64
<211> LENGTH: 377
<212> TYPE: PRT
<213> ORGANISM: Homo sapiens

<400> SEQUENCE: 64

Met Leu Ser Val Pro His Gly Ile Ala Asn Glu Asp Ile Val Ser Gln
1               5                   10                  15

Asn Pro Gly Glu Leu Ser Cys Lys Arg Gly Asp Val Leu Val Met Leu
            20                  25                  30

Lys Gln Thr Glu Asn Asn Tyr Leu Glu Cys Gln Lys Gly Glu Asp Thr
        35                  40                  45

Gly Arg Val His Leu Ser Gln Met Lys Ile Ile Thr Pro Leu Asp Glu
    50                  55                  60

His Leu Arg Ser Arg Pro Asn Asp Pro Ser His Ala Gln Lys Pro Val
65                  70                  75                  80

Asp Ser Gly Ala Pro His Ala Val Val Leu His Asp Phe Pro Ala Glu
                85                  90                  95

Gln Val Asp Asp Leu Asn Leu Thr Ser Gly Glu Ile Val Tyr Leu Leu
```

-continued

```
                    100                 105                 110
Glu Lys Ile Asp Thr Asp Trp Tyr Arg Gly Asn Cys Arg Asn Gln Ile
                115                 120                 125

Gly Ile Phe Pro Ala Asn Tyr Val Lys Val Ile Asp Ile Pro Glu
        130                 135                 140

Gly Gly Asn Gly Lys Arg Glu Cys Val Ser Ser His Cys Val Lys Gly
145                 150                 155                 160

Ser Arg Cys Val Ala Arg Phe Glu Tyr Ile Gly Glu Gln Lys Asp Glu
                165                 170                 175

Leu Ser Phe Ser Glu Gly Glu Ile Ile Ile Leu Lys Glu Tyr Val Asn
                180                 185                 190

Glu Glu Trp Ala Arg Gly Glu Val Arg Gly Arg Thr Gly Ile Phe Pro
                195                 200                 205

Leu Asn Phe Val Glu Pro Val Glu Asp Tyr Pro Thr Ser Gly Ala Asn
        210                 215                 220

Val Leu Ser Thr Lys Val Pro Leu Lys Thr Lys Lys Glu Asp Ser Gly
225                 230                 235                 240

Ser Asn Ser Gln Val Asn Ser Leu Pro Ala Glu Trp Cys Glu Ala Leu
                245                 250                 255

His Ser Phe Thr Ala Glu Thr Ser Asp Asp Leu Ser Phe Lys Arg Gly
                260                 265                 270

Asp Arg Ile Gln Ile Leu Glu Arg Leu Asp Ser Asp Trp Cys Arg Gly
                275                 280                 285

Arg Leu Gln Asp Arg Glu Gly Ile Phe Pro Ala Val Phe Val Arg Pro
        290                 295                 300

Cys Pro Ala Glu Ala Lys Ser Met Leu Ala Ile Val Pro Lys Gly Arg
305                 310                 315                 320

Lys Ala Lys Ala Leu Tyr Asp Phe Arg Gly Glu Asn Glu Asp Glu Leu
                325                 330                 335

Ser Phe Lys Ala Gly Asp Ile Ile Thr Glu Leu Glu Ser Val Asp Asp
                340                 345                 350

Asp Trp Met Ser Gly Glu Leu Met Gly Lys Ser Gly Ile Phe Pro Lys
                355                 360                 365

Asn Tyr Ile Gln Phe Leu Gln Ile Ser
        370                 375

<210> SEQ ID NO 65
<211> LENGTH: 949
<212> TYPE: PRT
<213> ORGANISM: Homo sapiens

<400> SEQUENCE: 65

Met Asp Ile Ser Thr Arg Ser Lys Asp Pro Gly Ser Ala Glu Arg Thr
1               5                   10                  15

Ala Gln Lys Arg Lys Phe Pro Ser Pro His Ser Ser Asn Gly His
                20                  25                  30

Ser Pro Gln Asp Thr Ser Thr Ser Pro Ile Lys Lys Lys Lys Pro
            35                  40                  45

Gly Leu Leu Asn Ser Asn Asn Lys Glu Gln Ser Glu Leu Arg His Gly
    50                  55                  60

Pro Phe Tyr Tyr Met Lys Gln Pro Leu Thr Thr Asp Pro Val Asp Val
65                  70                  75                  80

Val Pro Gln Asp Gly Arg Asn Asp Phe Tyr Cys Trp Val Cys His Arg
                85                  90                  95
```

-continued

```
Glu Gly Gln Val Leu Cys Cys Glu Leu Cys Pro Arg Val Tyr His Ala
            100                 105                 110
Lys Cys Leu Arg Leu Thr Ser Glu Pro Glu Gly Asp Trp Phe Cys Pro
        115                 120                 125
Glu Cys Glu Lys Ile Thr Val Ala Glu Cys Ile Glu Thr Gln Ser Lys
    130                 135                 140
Ala Met Thr Met Leu Thr Ile Glu Gln Leu Ser Tyr Leu Leu Lys Phe
145                 150                 155                 160
Ala Ile Gln Lys Met Lys Gln Pro Gly Thr Asp Ala Phe Gln Lys Pro
                165                 170                 175
Val Pro Leu Glu Gln His Pro Asp Tyr Ala Glu Tyr Ile Phe His Pro
            180                 185                 190
Met Asp Leu Cys Thr Leu Glu Lys Asn Ala Lys Lys Met Tyr Gly
        195                 200                 205
Cys Thr Glu Ala Phe Leu Ala Asp Ala Lys Trp Ile Leu His Asn Cys
    210                 215                 220
Ile Ile Tyr Asn Gly Gly Asn His Lys Leu Thr Gln Ile Ala Lys Val
225                 230                 235                 240
Val Ile Lys Ile Cys Glu His Glu Met Asn Glu Ile Glu Val Cys Pro
                245                 250                 255
Glu Cys Tyr Leu Ala Ala Cys Gln Lys Arg Asp Asn Trp Phe Cys Glu
            260                 265                 270
Pro Cys Ser Asn Pro His Pro Leu Val Trp Ala Lys Leu Lys Gly Phe
        275                 280                 285
Pro Phe Trp Pro Ala Lys Ala Leu Arg Asp Lys Asp Gly Gln Val Asp
    290                 295                 300
Ala Arg Phe Phe Gly Gln His Asp Arg Ala Trp Val Pro Ile Asn Asn
305                 310                 315                 320
Cys Tyr Leu Met Ser Lys Glu Ile Pro Phe Ser Val Lys Lys Thr Lys
                325                 330                 335
Ser Ile Phe Asn Ser Ala Met Gln Glu Met Glu Val Tyr Val Glu Asn
            340                 345                 350
Ile Arg Arg Lys Phe Gly Val Phe Asn Tyr Ser Pro Phe Arg Thr Pro
        355                 360                 365
Tyr Thr Pro Asn Ser Gln Tyr Gln Met Leu Leu Asp Pro Thr Asn Pro
    370                 375                 380
Ser Ala Gly Thr Ala Lys Ile Asp Lys Gln Glu Lys Val Lys Leu Asn
385                 390                 395                 400
Phe Asp Met Thr Ala Ser Pro Lys Ile Leu Met Ser Lys Pro Val Leu
                405                 410                 415
Ser Gly Gly Thr Gly Arg Arg Ile Ser Leu Ser Asp Met Pro Arg Ser
            420                 425                 430
Pro Met Ser Thr Asn Ser Ser Val His Thr Gly Ser Asp Val Glu Gln
        435                 440                 445
Asp Ala Glu Lys Lys Ala Thr Ser Ser His Phe Ser Ala Ser Glu Glu
    450                 455                 460
Ser Met Asp Phe Leu Asp Lys Ser Thr Ala Ser Pro Ala Ser Thr Lys
465                 470                 475                 480
Thr Gly Gln Ala Gly Ser Leu Ser Gly Ser Pro Lys Pro Phe Ser Pro
                485                 490                 495
Gln Leu Ser Ala Pro Ile Thr Thr Lys Thr Asp Lys Thr Ser Thr Thr
            500                 505                 510
Gly Ser Ile Leu Asn Leu Asn Leu Asp Arg Ser Lys Ala Glu Met Asp
```

-continued

```
                515                 520                 525
Leu Lys Glu Leu Ser Glu Ser Val Gln Gln Ser Thr Pro Val Pro
    530                 535                 540

Leu Ile Ser Pro Lys Arg Gln Ile Arg Ser Arg Phe Gln Leu Asn Leu
                550                 555                 560

Asp Lys Thr Ile Glu Ser Cys Lys Ala Gln Leu Gly Ile Asn Glu Ile
                565                 570                 575

Ser Glu Asp Val Tyr Thr Ala Val Glu His Ser Asp Ser Glu Asp Ser
                580                 585                 590

Glu Lys Ser Asp Ser Ser Asp Ser Glu Tyr Ile Ser Asp Asp Glu Gln
        595                 600                 605

Lys Ser Lys Asn Glu Pro Glu Asp Thr Glu Asp Lys Glu Gly Cys Gln
        610                 615                 620

Met Asp Lys Glu Pro Ser Ala Val Lys Lys Pro Lys Pro Thr Asn
        625                 630                 635                 640

Pro Val Glu Ile Lys Glu Glu Leu Lys Ser Thr Ser Pro Ala Ser Glu
                645                 650                 655

Lys Ala Asp Pro Gly Ala Val Lys Asp Lys Ala Ser Pro Glu Pro Glu
                660                 665                 670

Lys Asp Phe Ser Glu Lys Ala Lys Pro Ser Pro His Pro Ile Lys Asp
        675                 680                 685

Lys Leu Lys Gly Lys Asp Glu Thr Asp Ser Pro Thr Val His Leu Gly
    690                 695                 700

Leu Asp Ser Asp Ser Glu Ser Glu Leu Val Ile Asp Leu Gly Glu Asp
705                 710                 715                 720

His Ser Gly Arg Glu Gly Arg Lys Asn Lys Lys Glu Pro Lys Glu Pro
                725                 730                 735

Ser Pro Lys Gln Asp Val Val Gly Lys Thr Pro Pro Ser Thr Thr Val
                740                 745                 750

Gly Ser His Ser Pro Pro Glu Thr Pro Val Leu Thr Arg Ser Ser Ala
        755                 760                 765

Gln Thr Ser Ala Ala Gly Ala Thr Ala Thr Thr Ser Thr Ser Ser Thr
    770                 775                 780

Val Thr Val Thr Ala Pro Ala Pro Ala Ala Thr Gly Ser Pro Val Lys
785                 790                 795                 800

Lys Gln Arg Pro Leu Leu Pro Lys Glu Thr Ala Pro Ala Val Gln Arg
                805                 810                 815

Val Val Trp Asn Ser Ser Lys Phe Gln Thr Ser Ser Gln Lys Trp
                820                 825                 830

His Met Gln Lys Met Gln Arg Gln Gln Gln Gln Gln Gln Gln Asn
    835                 840                 845

Gln Gln Gln Gln Pro Gln Ser Ser Gln Gly Thr Arg Tyr Gln Thr Arg
    850                 855                 860

Gln Ala Val Lys Ala Val Gln Gln Lys Glu Ile Thr Gln Ser Pro Ser
865                 870                 875                 880

Thr Ser Thr Ile Thr Leu Val Thr Ser Thr Gln Ser Ser Pro Leu Val
                885                 890                 895

Thr Ser Ser Gly Ser Met Ser Thr Leu Val Ser Ser Val Asn Ala Asp
        900                 905                 910

Leu Pro Ile Ala Thr Ala Ser Ala Asp Val Ala Ala Asp Ile Ala Lys
        915                 920                 925

Tyr Thr Ser Lys Val Asn Gly Cys Asn Lys Arg Asn Asn Asp Arg Asn
    930                 935                 940
```

Ile Gln Arg Ser Phe
945

<210> SEQ ID NO 66
<211> LENGTH: 380
<212> TYPE: PRT
<213> ORGANISM: Homo sapiens

<400> SEQUENCE: 66

Met Asp Ser Gly Cys Trp Leu Phe Gly Gly Glu Phe Glu Asp Ser Val
1               5                   10                  15

Phe Glu Glu Arg Pro Glu Arg Arg Ser Gly Pro Pro Ala Ser Tyr Cys
                20                  25                  30

Ala Lys Leu Cys Glu Pro Gln Trp Phe Tyr Glu Glu Thr Glu Ser Ser
            35                  40                  45

Asp Asp Val Glu Val Leu Thr Leu Lys Lys Phe Lys Gly Asp Leu Ala
        50                  55                  60

Tyr Arg Arg Gln Glu Tyr Gln Lys Ala Leu Gln Glu Tyr Ser Ser Ile
65                  70                  75                  80

Ser Glu Lys Leu Ser Ser Thr Asn Phe Ala Met Lys Arg Asp Val Gln
                85                  90                  95

Glu Gly Gln Ala Arg Cys Leu Ala His Leu Gly Arg His Met Glu Ala
                100                 105                 110

Leu Glu Ile Ala Ala Asn Leu Glu Asn Lys Ala Thr Asn Thr Asp His
            115                 120                 125

Leu Thr Thr Val Leu Tyr Leu Gln Leu Ala Ile Cys Ser Ser Leu Gln
        130                 135                 140

Asn Leu Glu Lys Thr Ile Phe Cys Leu Gln Lys Leu Ile Ser Leu His
145                 150                 155                 160

Pro Phe Asn Pro Trp Asn Trp Gly Lys Leu Ala Glu Ala Tyr Leu Asn
                165                 170                 175

Leu Gly Pro Ala Leu Ser Ala Ala Leu Ala Ser Ser Gln Lys Gln His
                180                 185                 190

Ser Phe Thr Ser Ser Asp Lys Thr Ile Lys Ser Phe Phe Pro His Ser
            195                 200                 205

Gly Lys Asp Cys Leu Leu Cys Phe Pro Glu Thr Leu Pro Glu Ser Ser
        210                 215                 220

Leu Phe Ser Val Glu Ala Asn Ser Ser Asn Ser Gln Lys Asn Glu Lys
225                 230                 235                 240

Ala Leu Thr Asn Ile Gln Asn Cys Met Ala Glu Lys Arg Glu Thr Val
                245                 250                 255

Leu Ile Glu Thr Gln Leu Lys Ala Cys Ala Ser Phe Ile Arg Thr Arg
                260                 265                 270

Leu Leu Leu Gln Phe Thr Gln Pro Gln Gln Thr Ser Phe Ala Leu Glu
            275                 280                 285

Arg Asn Leu Arg Thr Gln Gln Glu Ile Glu Asp Lys Met Lys Gly Phe
        290                 295                 300

Ser Phe Lys Glu Asp Thr Leu Leu Ile Ala Glu Val Met Gly Glu
305                 310                 315                 320

Asp Ile Pro Glu Lys Ile Lys Asp Glu Val His Pro Glu Val Lys Cys
                325                 330                 335

Val Gly Ser Val Ala Leu Thr Ala Leu Val Thr Val Ser Ser Glu Glu
                340                 345                 350

Phe Glu Asp Lys Trp Phe Arg Lys Ile Lys Asp His Phe Cys Pro Phe

```
                355                  360                   365
Glu Asn Gln Phe His Thr Glu Ile Gln Ile Leu Ala
            370                 375                 380
```

<210> SEQ ID NO 67
<211> LENGTH: 518
<212> TYPE: PRT
<213> ORGANISM: Homo sapiens

<400> SEQUENCE: 67

```
Met Lys Ser Arg Phe Ser Thr Ile Asp Leu Arg Ala Val Leu Ala Glu
 1               5                  10                  15

Leu Asn Ala Ser Leu Leu Gly Met Arg Val Asn Asn Val Tyr Asp Val
            20                  25                  30

Asp Asn Lys Thr Tyr Leu Ile Arg Leu Gln Lys Pro Asp Phe Lys Ala
        35                  40                  45

Thr Leu Leu Leu Glu Ser Gly Ile Arg Ile His Thr Thr Glu Phe Glu
    50                  55                  60

Trp Pro Lys Asn Met Met Pro Ser Ser Phe Ala Met Lys Cys Arg Lys
65                  70                  75                  80

His Leu Lys Ser Arg Arg Leu Val Ser Ala Lys Gln Leu Gly Val Asp
                85                  90                  95

Arg Ile Val Asp Phe Gln Phe Gly Ser Asp Glu Ala Ala Tyr His Leu
            100                 105                 110

Ile Ile Glu Leu Tyr Asp Arg Gly Asn Ile Val Leu Thr Asp Tyr Glu
        115                 120                 125

Tyr Val Ile Leu Asn Ile Leu Arg Phe Arg Thr Asp Glu Ala Asp Asp
    130                 135                 140

Val Lys Phe Ala Val Arg Glu Arg Tyr Pro Leu Asp His Ala Arg Ala
145                 150                 155                 160

Ala Glu Pro Leu Leu Thr Leu Glu Arg Leu Thr Glu Ile Val Ala Ser
                165                 170                 175

Ala Pro Lys Gly Glu Leu Leu Lys Arg Val Leu Asn Pro Leu Leu Pro
            180                 185                 190

Tyr Gly Pro Ala Leu Ile Glu His Cys Leu Leu Glu Asn Gly Phe Ser
        195                 200                 205

Gly Asn Val Lys Val Asp Glu Lys Leu Glu Thr Lys Asp Ile Glu Lys
    210                 215                 220

Val Leu Val Ser Leu Gln Lys Ala Glu Asp Tyr Met Lys Thr Thr Ser
225                 230                 235                 240

Asn Phe Ser Gly Lys Gly Tyr Ile Ile Gln Lys Arg Glu Ile Lys Pro
                245                 250                 255

Cys Leu Glu Ala Asp Lys Pro Val Glu Asp Ile Leu Thr Tyr Glu Glu
            260                 265                 270

Phe His Pro Phe Leu Phe Ser Gln His Ser Gln Cys Pro Tyr Ile Glu
        275                 280                 285

Phe Glu Ser Phe Asp Lys Ala Val Asp Glu Phe Tyr Ser Lys Ile Glu
    290                 295                 300

Gly Gln Lys Ile Asp Leu Lys Ala Leu Gln Gln Glu Lys Gln Ala Leu
305                 310                 315                 320

Lys Lys Leu Asp Asn Val Arg Lys Asp His Glu Asn Arg Leu Glu Ala
                325                 330                 335

Leu Gln Gln Ala Gln Glu Ile Asp Lys Leu Lys Gly Glu Leu Ile Glu
            340                 345                 350
```

```
Met Asn Leu Gln Ile Val Asp Arg Ala Ile Gln Val Val Arg Ser Ala
        355                 360                 365

Leu Ala Asn Gln Ile Asp Trp Thr Glu Ile Gly Leu Ile Val Lys Glu
    370                 375                 380

Ala Gln Ala Gln Gly Asp Pro Val Ala Ser Ala Ile Lys Glu Leu Lys
385                 390                 395                 400

Leu Gln Thr Asn His Val Thr Met Leu Leu Arg Asn Pro Tyr Leu Leu
                405                 410                 415

Ser Glu Glu Asp Asp Asp Val Asp Gly Asp Val Asn Val Glu Lys
            420                 425                 430

Asn Glu Thr Glu Pro Pro Lys Gly Lys Lys Lys Gln Lys Asn Lys
        435                 440                 445

Gln Leu Gln Lys Pro Gln Lys Asn Lys Pro Leu Leu Val Asp Val Asp
    450                 455                 460

Leu Ser Leu Ser Ala Tyr Ala Asn Ala Lys Lys Tyr Tyr Asp His Lys
465                 470                 475                 480

Arg Tyr Ala Ala Lys Lys Thr Gln Lys Thr Val Glu Ala Ala Glu Lys
                485                 490                 495

Ala Phe Lys Ser Ala Glu Lys Lys Thr Lys Gln Thr Leu Lys Glu Val
            500                 505                 510

Gln Thr Val Thr Ser Ile
            515

<210> SEQ ID NO 68
<211> LENGTH: 362
<212> TYPE: PRT
<213> ORGANISM: Homo sapiens

<400> SEQUENCE: 68

Met Thr Gln Val Asp Gln Glu Asp Ile Thr Leu Gln Ser Gly Arg Asp
1               5                   10                  15

Glu Leu Asn Glu Glu Leu Ile Gln Glu Glu Ser Ser Glu Asp Glu Gly
            20                  25                  30

Glu Tyr Glu Glu Val Arg Lys Asp Gln Asp Ser Val Gly Glu Met Lys
        35                  40                  45

Asp Glu Gly Glu Glu Thr Leu Asn Tyr Pro Asp Thr Thr Ile Asp Leu
    50                  55                  60

Ser His Leu Gln Pro Gln Arg Ser Ile Gln Lys Leu Ala Ser Lys Glu
65                  70                  75                  80

Glu Ser Ser Asn Ser Ser Asp Ser Lys Ser Gln Ser Arg Arg His Leu
                85                  90                  95

Ser Ala Lys Glu Arg Arg Glu Met Lys Lys Lys Leu Pro Ser Asp
            100                 105                 110

Ser Gly Asp Leu Glu Ala Leu Glu Gly Lys Asp Lys Glu Lys Glu Ser
        115                 120                 125

Thr Val His Ile Glu Thr His Gln Asn Thr Ser Lys Asn Val Ala Ala
    130                 135                 140

Val Gln Pro Met Lys Arg Gly Gln Lys Ser Lys Met Lys Lys Met Lys
145                 150                 155                 160

Glu Lys Tyr Lys Asp Gln Asp Glu Glu Asp Arg Glu Leu Ile Met Lys
                165                 170                 175

Leu Leu Gly Ser Ala Gly Ser Asn Lys Glu Glu Lys Gly Lys Lys Gly
            180                 185                 190

Lys Lys Gly Lys Thr Lys Asp Glu Pro Val Lys Lys Gln Pro Gln Lys
        195                 200                 205
```

```
Pro Arg Gly Gly Gln Arg Val Ser Asp Asn Ile Lys Lys Glu Thr Pro
    210                 215                 220
Phe Leu Glu Val Ile Thr His Glu Leu Gln Asp Phe Ala Val Asp Asp
225                 230                 235                 240
Pro His Asp Asp Lys Glu Gln Asp Leu Asp Gln Gln Gly Asn Glu
            245                 250                 255
Glu Asn Leu Phe Asp Ser Leu Thr Gly Gln Pro His Pro Glu Asp Val
            260                 265                 270
Leu Leu Phe Ala Ile Pro Ile Cys Ala Pro Tyr Thr Thr Met Thr Asn
            275                 280                 285
Tyr Lys Tyr Lys Val Lys Leu Thr Pro Gly Val Gln Lys Gly Lys
    290                 295                 300
Ala Ala Lys Thr Ala Leu Asn Ser Phe Met His Ser Lys Glu Ala Thr
305                 310                 315                 320
Ala Arg Glu Lys Asp Leu Phe Arg Ser Val Lys Asp Thr Asp Leu Ser
                325                 330                 335
Arg Asn Ile Pro Gly Lys Val Lys Ser Val Cys Thr Gln Ser Ser Glu
            340                 345                 350
Arg Lys Lys Glu Ile Ala Glu Met Lys Phe
    355                 360

<210> SEQ ID NO 69
<211> LENGTH: 634
<212> TYPE: PRT
<213> ORGANISM: Homo sapiens

<400> SEQUENCE: 69

Met Glu Ser Gly Arg Gly Ser Ser Thr Pro Gly Pro Ile Ala Ala
                5                  10                  15
Leu GLy Met Pro Asp Thr Gly Pro Gly Ser Ser Ser Leu Gly Lys Leu
            20                  25                  30
Gln Ala Leu Pro Val Gly Pro Arg Ala His Cys Gly Asp Pro Val Ser
        35                  40                  45
Leu Ala Ala Gly Asp Gly Ser Pro Asp Ile Gly Pro Thr Gly Glu
50                  55                  60
Leu Ser Gly Ser Leu Lys Ile Pro Asn Arg Asp Ser Gly Ile Asp Ser
65                  70                  75                  80
Pro Ser Ser Ser Val Ala Gly Glu Asn Phe Pro Cys Glu Glu Gly Leu
                85                  90                  95
Glu Ala Gly Pro Ser Pro Thr Val Leu Gly Ala His Ala Glu Met Ala
            100                 105                 110
Leu Asp Ser Gln Val Pro Lys Val Thr Pro Gln Glu Glu Ala Asp Ser
        115                 120                 125
Asp Val Gly Glu Glu Pro Asp Ser Glu Asn Thr Pro Gln Lys Ala Asp
    130                 135                 140
Lys Asp Ala Gly Leu Ala Gln His Ser Gly Pro Gln Lys Leu Leu His
145                 150                 155                 160
Ile Ala Gln Glu Leu Leu His Thr Glu Glu Thr Tyr Val Lys Arg Leu
                165                 170                 175
His Leu Leu Asp Gln Val Phe Cys Thr Arg Leu Thr Asp Ala Gly Ile
            180                 185                 190
Pro Pro Glu Val Ile Met Gly Ile Phe Ser Asn Ile Ser Ser Ile His
        195                 200                 205
Arg Phe His Gly Gln Phe Leu Leu Pro Glu Leu Lys Thr Arg Ile Thr
```

-continued

```
            210                 215                 220
Glu Glu Trp Asp Thr Asn Pro Arg Leu Gly Asp Ile Leu Gln Lys Leu
225                 230                 235                 240

Ala Pro Phe Leu Lys Met Tyr Gly Glu Tyr Val Lys Asn Phe Asp Arg
                245                 250                 255

Ala Val Gly Leu Val Ser Thr Trp Thr Gln Arg Ser Pro Leu Phe Lys
                260                 265                 270

Asp Val Val His Ser Ile Gln Lys Gln Glu Val Cys Gly Asn Leu Thr
                275                 280                 285

Leu Gln His His Met Leu Glu Pro Val Gln Arg Val Pro Arg Tyr Glu
            290                 295                 300

Leu Leu Leu Lys Asp Tyr Leu Lys Arg Leu Pro Gln Asp Ala Pro Asp
305                 310                 315                 320

Arg Lys Asp Ala Glu Arg Ser Leu Glu Leu Ile Ser Thr Ala Ala Asn
                325                 330                 335

His Ser Asn Ala Ala Ile Arg Lys Val Glu Lys Met His Lys Leu Leu
                340                 345                 350

Glu Val Tyr Glu Gln Leu Gly Gly Glu Asp Ile Val Asn Pro Ala
                355                 360                 365

Asn Glu Leu Ile Lys Glu Gly Gln Ile Gln Lys Leu Ser Ala Lys Asn
370                 375                 380

Gly Thr Pro Gln Asp Arg His Leu Phe Leu Phe Asn Ser Met Ile Leu
385                 390                 395                 400

Tyr Cys Val Pro Lys Leu Arg Leu Met Gly Gln Lys Phe Ser Val Arg
                405                 410                 415

Glu Lys Met Asp Ile Ser Gly Leu Gln Val Gln Asp Ile Val Lys Pro
                420                 425                 430

Asn Thr Ala His Thr Phe Ile Ile Thr Gly Arg Lys Arg Ser Leu Glu
                435                 440                 445

Leu Gln Thr Arg Thr Glu Glu Lys Lys Glu Trp Ile Gln Ile Ile
            450                 455                 460

Gln Ala Thr Ile Glu Lys His Lys Gln Asn Ser Glu Thr Phe Lys Ala
465                 470                 475                 480

Phe Gly Gly Ala Phe Ser Gln Asp Glu Asp Pro Ser Leu Ser Pro Asp
                485                 490                 495

Met Pro Ile Thr Ser Thr Ser Pro Val Glu Pro Val Val Thr Thr Glu
                500                 505                 510

Gly Ser Ser Gly Ala Ala Gly Leu Glu Pro Arg Lys Leu Ser Ser Lys
                515                 520                 525

Thr Arg Arg Asp Lys Glu Lys Gln Ser Cys Lys Ser Cys Gly Glu Thr
                530                 535                 540

Phe Asn Ser Ile Thr Lys Arg Arg His His Cys Lys Leu Cys Gly Ala
545                 550                 555                 560

Val Ile Cys Gly Lys Cys Ser Glu Phe Lys Ala Glu Asn Ser Arg Gln
                565                 570                 575

Ser Arg Val Cys Arg Asp Cys Phe Leu Thr Gln Pro Val Ala Pro Glu
                580                 585                 590

Ser Thr Glu Val Gly Ala Pro Ser Ser Cys Ser Pro Gly Gly Ala
                595                 600                 605

Ala Glu Pro Pro Asp Thr Cys Ser Cys Ala Pro Ala Pro Ala Ala
            610                 615                 620

Ser Ala Phe Gly Val Ser Leu Gly Pro Gly
625                 630
```

<210> SEQ ID NO 70
<211> LENGTH: 284
<212> TYPE: PRT
<213> ORGANISM: Homo sapiens

<400> SEQUENCE: 70

```
Met Asp Ala Ile Lys Lys Met Gln Met Leu Lys Leu Asp Lys Glu
1               5                   10                  15

Asn Ala Leu Asp Arg Ala Glu Gln Ala Glu Ala Asp Lys Lys Ala Ala
            20                  25                  30

Glu Asp Arg Ser Lys Gln Leu Glu Asp Glu Leu Val Ser Leu Gln Lys
        35                  40                  45

Lys Leu Lys Gly Thr Glu Asp Glu Leu Asp Lys Tyr Ser Glu Ala Leu
    50                  55                  60

Lys Asp Ala Gln Glu Lys Leu Glu Leu Ala Glu Lys Ala Thr Asp
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Ser Arg Ala Gln Lys Asp Glu Glu Lys Met Glu Ile Gln
130                 135                 140

Glu Ile Gln Leu Lys Glu Ala Lys His Ile Ala Glu Asp Ala Asp Arg
145                 150                 155                 160

Lys Tyr Glu Glu Val Ala Arg Lys Leu Val Ile Ile Glu Ser Asp Leu
                165                 170                 175

Glu Arg Ala Glu Glu Arg Ala Glu Leu Ser Glu Gly Gln Val Arg Gln
            180                 185                 190

Leu Glu Glu Gln Leu Arg Ile Met Asp Gln Thr Leu Lys Ala Leu Met
        195                 200                 205

Ala Ala Glu Asp Lys Tyr Ser Gln Lys Glu Asp Arg Tyr Glu Glu Glu
    210                 215                 220

Ile Lys Val Leu Ser Asp Lys Leu Lys Glu Ala Glu Thr Arg Ala Glu
225                 230                 235                 240

Phe Ala Glu Arg Ser Val Thr Lys Leu Glu Lys Ser Ile Asp Asp Leu
                245                 250                 255

Glu Glu Lys Val Ala His Ala Lys Glu Glu Asn Leu Ser Met His Gln
            260                 265                 270

Met Leu Asp Gln Thr Leu Leu Glu Leu Asn Asn Met
        275                 280
```

<210> SEQ ID NO 71
<211> LENGTH: 683
<212> TYPE: PRT
<213> ORGANISM: Homo sapiens

<400> SEQUENCE: 71

```
Met Thr Ala Val His Gly Arg Phe Thr Arg Ser Gln Thr Leu Ile Gln
1               5                   10                  15

Asn Gly Gly Glu Ile Asp Cys Val Asp Lys Asp Gly Asn Thr Pro Leu
            20                  25                  30

His Val Ala Ala Arg Tyr Gly His Glu Leu Leu Ile Asn Thr Leu Ile
        35                  40                  45
```

-continued

```
Thr Ser Gly Ala Asp Thr Ala Lys Cys Gly Ile His Ser Met Phe Pro
    50                  55                  60
Leu His Leu Ala Ala Leu Asn Ala His Ser Asp Cys Cys Arg Lys Leu
65                  70                  75                  80
Leu Ser Ser Gly Gln Lys Tyr Ser Ile Val Ser Leu Phe Ser Asn Glu
                85                  90                  95
His Val Leu Ser Ala Gly Phe Glu Ile Asp Thr Pro Asp Lys Phe Gly
                100                 105                 110
Arg Thr Cys Leu His Ala Ala Ala Gly Gly Asn Val Glu Cys Ile
                115                 120                 125
Lys Leu Leu Gln Ser Ser Gly Ala Asp Phe His Lys Lys Asp Lys Cys
    130                 135                 140
Gly Arg Thr Pro Leu His Tyr Ala Ala Ala Asn Cys His Phe His Cys
145                 150                 155                 160
Ile Glu Thr Leu Val Thr Thr Gly Ala Asn Val Asn Glu Thr Asp Asp
                165                 170                 175
Trp Gly Arg Thr Ala Leu His Tyr Ala Ala Ser Asp Met Asp Arg
                180                 185                 190
Asn Lys Thr Ile Leu Gly Asn Ala His Asp Asn Ser Glu Glu Leu Glu
                195                 200                 205
Arg Ala Arg Glu Leu Lys Glu Lys Glu Ala Thr Leu Cys Leu Glu Phe
    210                 215                 220
Leu Leu Gln Asn Asp Ala Asn Pro Ser Ile Arg Asp Lys Glu Gly Tyr
225                 230                 235                 240
Asn Ser Ile His Tyr Ala Ala Ala Tyr Gly His Arg Gln Cys Leu Glu
                245                 250                 255
Leu Leu Leu Glu Arg Thr Asn Ser Gly Phe Glu Glu Ser Asp Ser Gly
                260                 265                 270
Ala Thr Lys Ser Pro Leu His Leu Ala Ala Tyr Asn Gly His His Gln
    275                 280                 285
Ala Leu Glu Val Leu Leu Gln Ser Leu Val Asp Leu Asp Ile Arg Asp
    290                 295                 300
Glu Lys Gly Arg Thr Ala Leu Asp Leu Ala Ala Phe Lys Gly His Thr
305                 310                 315                 320
Glu Cys Val Glu Ala Leu Ile Asn Gln Gly Ala Ser Ile Phe Val Lys
                325                 330                 335
Asp Asn Val Thr Lys Arg Thr Pro Leu His Ala Ser Val Ile Asn Gly
                340                 345                 350
His Thr Leu Cys Leu Arg Leu Leu Glu Ile Ala Asp Asn Pro Glu
                355                 360                 365
Ala Val Asp Val Lys Asp Ala Lys Gly Gln Thr Pro Leu Met Leu Ala
    370                 375                 380
Val Ala Tyr Gly His Ile Asp Ala Val Ser Leu Leu Glu Lys Glu
385                 390                 395                 400
Ala Asn Val Asp Thr Val Asp Ile Leu Gly Cys Thr Ala Leu His Arg
                405                 410                 415
Gly Ile Met Thr Gly His Glu Glu Cys Val Gln Met Leu Leu Glu Gln
                420                 425                 430
Glu Val Ser Ile Leu Cys Lys Asp Ser Arg Gly Arg Thr Pro Leu His
    435                 440                 445
Tyr Ala Ala Ala Arg Gly His Ala Thr Trp Leu Ser Glu Leu Leu Gln
450                 455                 460
```

```
Met Ala Leu Ser Glu Glu Asp Cys Cys Phe Lys Asp Asn Gln Gly Tyr
465                 470                 475                 480

Thr Pro Leu His Trp Ala Cys Tyr Asn Gly Asn Glu Asn Cys Ile Glu
                485                 490                 495

Val Leu Leu Glu Gln Lys Cys Phe Arg Lys Phe Ile Gly Asn Pro Phe
            500                 505                 510

Thr Pro Leu His Cys Ala Ile Ile Asn Asp His Gly Asn Cys Ala Ser
        515                 520                 525

Leu Leu Leu Gly Ala Ile Asp Ser Ser Ile Val Ser Cys Arg Asp Asp
    530                 535                 540

Lys Gly Arg Thr Pro Leu His Ala Ala Ala Phe Ala Asp His Val Glu
545                 550                 555                 560

Cys Leu Gln Leu Leu Arg His Ser Ala Pro Val Asn Ala Val Asp
                565                 570                 575

Asn Ser Gly Lys Thr Ala Leu Met Met Ala Ala Glu Asn Gly Gln Ala
            580                 585                 590

Gly Ala Val Asp Ile Leu Val Asn Ser Ala Gln Ala Asp Leu Thr Val
                595                 600                 605

Lys Asp Lys Asp Leu Asn Thr Pro Leu His Leu Ala Cys Ser Lys Gly
610                 615                 620

His Glu Lys Cys Ala Leu Leu Ile Leu Asp Lys Ile Gln Asp Glu Ser
625                 630                 635                 640

Leu Ile Asn Glu Lys Asn Asn Ala Leu Gln Thr Pro Leu His Val Ala
                645                 650                 655

Ala Arg Asn Gly Leu Lys Val Val Glu Glu Leu Leu Ala Lys Gly
                660                 665                 670

Ala Cys Val Leu Ala Val Asp Glu Asn Gly Cys
            675                 680
```

```
<210> SEQ ID NO 72
<211> LENGTH: 547
<212> TYPE: PRT
<213> ORGANISM: Homo sapiens

<400> SEQUENCE: 72

Met Ala Ala Val Ser Leu Arg Leu Gly Asp Leu Val Trp Gly Lys Leu
1               5                   10                  15

Gly Arg Tyr Pro Pro Trp Pro Gly Lys Ile Val Asn Pro Pro Lys Asp
            20                  25                  30

Leu Lys Lys Pro Arg Gly Lys Lys Cys Phe Phe Val Lys Phe Phe Gly
            35                  40                  45

Thr Glu Asp His Ala Trp Ile Lys Val Glu Gln Leu Lys Pro Tyr His
    50                  55                  60

Ala His Lys Glu Glu Met Ile Lys Ile Asn Lys Gly Lys Arg Phe Gln
65                  70                  75                  80

Gln Ala Val Asp Ala Val Glu Glu Phe Leu Arg Arg Ala Lys Gly Lys
                85                  90                  95

Asp Gln Thr Ser Ser His Asn Ser Asp Asp Lys Asn Arg Arg Asn
            100                 105                 110

Ser Ser Glu Glu Arg Ser Arg Pro Asn Ser Gly Asp Glu Lys Arg Lys
        115                 120                 125

Leu Ser Leu Ser Glu Gly Lys Val Lys Asn Met Gly Glu Gly Lys
    130                 135                 140

Lys Arg Val Ser Ser Gly Ser Ser Glu Arg Gly Ser Lys Ser Pro Leu
145                 150                 155                 160
```

```
Lys Arg Ala Gln Glu Gln Ser Pro Arg Lys Arg Gly Arg Pro Pro Lys
                165                 170                 175

Asp Glu Lys Asp Leu Thr Ile Pro Glu Ser Ser Thr Val Lys Gly Met
            180                 185                 190

Met Ala Gly Pro Met Ala Ala Phe Lys Trp Gln Pro Thr Ala Ser Glu
        195                 200                 205

Pro Val Lys Asp Ala Asp Pro His Phe His His Phe Leu Leu Ser Gln
    210                 215                 220

Thr Glu Lys Pro Ala Val Cys Tyr Gln Ala Ile Thr Lys Lys Leu Lys
225                 230                 235                 240

Ile Cys Glu Glu Thr Gly Ser Thr Ser Ile Gln Ala Ala Asp Ser
                245                 250                 255

Thr Ala Val Asn Gly Ser Ile Thr Pro Thr Asp Lys Lys Ile Gly Phe
            260                 265                 270

Leu Gly Leu Gly Leu Met Gly Ser Gly Ile Val Ser Asn Leu Leu Lys
                275                 280                 285

Met Gly His Thr Val Thr Val Trp Asn Arg Thr Ala Glu Lys Glu Gly
        290                 295                 300

Ala Arg Leu Gly Arg Thr Pro Ala Glu Val Val Ser Thr Cys Asp Ile
305                 310                 315                 320

Thr Phe Ala Cys Val Ser Asp Pro Lys Ala Ala Lys Asp Leu Val Leu
                325                 330                 335

Gly Pro Ser Gly Val Leu Gln Gly Ile Arg Pro Gly Lys Cys Tyr Val
            340                 345                 350

Asp Met Ser Thr Val Asp Ala Asp Thr Val Thr Glu Leu Ala Gln Val
        355                 360                 365

Ile Val Ser Arg Gly Gly Arg Phe Leu Glu Ala Pro Val Ser Gly Asn
    370                 375                 380

Gln Gln Leu Ser Asn Asp Gly Met Leu Val Ile Leu Ala Ala Gly Asp
385                 390                 395                 400

Arg Gly Leu Tyr Glu Asp Cys Ser Ser Cys Phe Gln Ala Met Gly Lys
                405                 410                 415

Thr Ser Phe Phe Leu Gly Glu Val Gly Asn Ala Ala Lys Met Met Leu
            420                 425                 430

Ile Val Asn Met Val Gln Gly Ser Phe Met Ala Thr Ile Ala Glu Gly
        435                 440                 445

Leu Thr Leu Ala Gln Val Thr Gly Gln Ser Gln Thr Leu Leu Asp
    450                 455                 460

Ile Leu Asn Gln Gly Gln Leu Ala Ser Ile Phe Leu Asp Gln Lys Cys
465                 470                 475                 480

Gln Asn Ile Leu Gln Gly Asn Phe Lys Pro Asp Phe Tyr Leu Lys Tyr
                485                 490                 495

Ile Gln Lys Asp Leu Arg Leu Ala Ile Ala Leu Gly Asp Ala Val Asn
            500                 505                 510

His Pro Thr Pro Met Ala Ala Ala Asn Glu Val Tyr Lys Arg Ala
        515                 520                 525

Lys Ala Leu Asp Gln Ser Asp Asn Asp Met Ser Ala Val Tyr Arg Ala
530                 535                 540

Tyr Ile His
545

<210> SEQ ID NO 73
<211> LENGTH: 638
```

-continued

```
<212> TYPE: PRT
<213> ORGANISM: Homo sapiens

<400> SEQUENCE: 73

Met Ser Leu Gly Gln Ser Ala Cys Leu Phe Leu Ser Ile Ala Arg Ser
1               5                   10                  15

Arg Ser Val Met Thr Gly Glu Gln Met Ala Ala Phe His Pro Ser Ser
            20                  25                  30

Thr Pro Asn Pro Leu Glu Arg Pro Ile Lys Met Gly Trp Leu Lys Lys
        35                  40                  45

Gln Arg Ser Ile Val Lys Asn Trp Gln Gln Arg Tyr Phe Val Leu Arg
    50                  55                  60

Ala Gln Gln Leu Tyr Tyr Tyr Lys Asp Glu Glu Asp Thr Lys Pro Gln
65                  70                  75                  80

Gly Cys Met Tyr Leu Pro Gly Cys Thr Ile Lys Glu Ile Ala Thr Asn
                85                  90                  95

Pro Glu Glu Ala Gly Lys Phe Val Phe Glu Ile Ile Pro Ala Ser Trp
            100                 105                 110

Asp Gln Asn Arg Met Gly Gln Asp Ser Tyr Val Leu Met Ala Ser Ser
        115                 120                 125

Gln Ala Glu Met Glu Glu Trp Val Lys Phe Leu Arg Arg Val Ala Gly
    130                 135                 140

Thr Pro Cys Gly Val Phe Gly Gln Arg Leu Asp Glu Thr Val Ala Tyr
145                 150                 155                 160

Glu Gln Lys Phe Gly Pro His Leu Val Pro Ile Leu Val Glu Lys Cys
                165                 170                 175

Ala Glu Phe Ile Leu Glu His Gly Arg Asn Glu Glu Gly Ile Phe Arg
            180                 185                 190

Leu Pro Gly Gln Asp Asn Leu Val Lys Gln Leu Arg Asp Ala Phe Asp
        195                 200                 205

Ala Gly Glu Arg Pro Ser Phe Asp Arg Asp Thr Asp Val His Thr Val
    210                 215                 220

Ala Ser Leu Leu Lys Leu Tyr Leu Arg Asp Leu Pro Glu Pro Val Val
225                 230                 235                 240

Pro Trp Ser Gln Tyr Glu Gly Phe Leu Leu Cys Gly Gln Leu Thr Asn
                245                 250                 255

Ala Asp Glu Ala Lys Ala Gln Gln Glu Leu Met Lys Gln Leu Ser Ile
            260                 265                 270

Leu Pro Arg Asp Asn Tyr Ser Leu Leu Ser Tyr Ile Cys Arg Phe Leu
        275                 280                 285

His Glu Ile Gln Leu Asn Cys Ala Val Asn Lys Met Ser Val Asp Asn
    290                 295                 300

Leu Ala Thr Val Ile Gly Val Asn Leu Ile Arg Ser Lys Val Glu Asp
305                 310                 315                 320

Pro Ala Val Ile Met Arg Gly Thr Pro Gln Ile Gln Arg Val Met Thr
                325                 330                 335

Met Met Ile Arg Asp His Glu Val Leu Phe Pro Lys Ser Lys Asp Ile
            340                 345                 350

Pro Leu Ser Pro Pro Ala Gln Lys Asn Asp Pro Lys Lys Ala Pro Val
        355                 360                 365

Ala Arg Ser Ser Val Gly Trp Asp Ala Thr Glu Asp Leu Arg Ile Ser
    370                 375                 380

Arg Thr Asp Ser Phe Ser Ser Met Thr Ser Asp Ser Asp Thr Thr Ser
385                 390                 395                 400
```

```
Pro Thr Gly Gln Gln Pro Ser Asp Ala Phe Pro Glu Asp Ser Ser Lys
                405                 410                 415
Val Pro Arg Glu Lys Pro Gly Asp Trp Lys Met Gln Ser Arg Lys Arg
            420                 425                 430
Thr Gln Thr Leu Pro Asn Arg Lys Cys Phe Leu Thr Ser Ala Phe Gln
        435                 440                 445
Gly Ala Asn Ser Ser Lys Met Glu Ile Phe Lys Asn Glu Phe Trp Ser
    450                 455                 460
Pro Ser Ser Glu Ala Lys Ala Gly Glu Gly His Arg Arg Thr Met Ser
465                 470                 475                 480
Gln Asp Leu Arg Gln Leu Ser Asp Ser Gln Arg Thr Ser Thr Tyr Asp
                485                 490                 495
Asn Val Pro Ser Leu Pro Gly Ser Pro Gly Glu Glu Ala Ser Ala Leu
                500                 505                 510
Ser Ser Gln Ala Cys Asp Ser Lys Gly Asp Thr Leu Ala Ser Pro Asn
            515                 520                 525
Ser Glu Thr Gly Pro Gly Lys Lys Asn Ser Gly Glu Glu Glu Ile Asp
        530                 535                 540
Ser Leu Gln Arg Met Val Gln Glu Leu Arg Lys Glu Ile Glu Thr Gln
545                 550                 555                 560
Lys Gln Met Tyr Glu Glu Gln Ile Lys Asn Leu Glu Lys Glu Asn Tyr
                565                 570                 575
Asp Val Trp Ala Lys Val Val Arg Leu Asn Glu Leu Glu Lys Glu
                580                 585                 590
Lys Lys Lys Ser Ala Ala Leu Glu Ile Ser Leu Arg Asn Met Glu Arg
            595                 600                 605
Ser Arg Glu Asp Val Glu Lys Arg Asn Lys Ala Leu Glu Glu Glu Val
        610                 615                 620
Lys Glu Phe Val Lys Ser Met Lys Glu Pro Lys Thr Glu Ala
625                 630                 635

<210> SEQ ID NO 74
<211> LENGTH: 239
<212> TYPE: PRT
<213> ORGANISM: Homo sapiens

<400> SEQUENCE: 74

Met His Gln Thr Tyr Ser Arg His Cys Arg Pro Glu Glu Ser Thr Phe
1               5                   10                  15
Ser Ala Ala Met Thr Thr Met Gln Gly Met Glu Gln Ala Met Pro Gly
            20                  25                  30
Ala Gly Pro Gly Val Pro Gln Leu Gly Asn Met Ala Val Ile His Ser
        35                  40                  45
His Leu Trp Lys Gly Leu Gln Glu Lys Phe Leu Lys Gly Glu Pro Lys
    50                  55                  60
Val Leu Gly Val Val Gln Ile Leu Thr Ala Leu Met Ser Leu Ser Met
65                  70                  75                  80
Gly Ile Thr Met Met Cys Met Ala Ser Asn Thr Tyr Gly Ser Asn Pro
                85                  90                  95
Ile Ser Val Tyr Ile Gly Tyr Thr Ile Trp Gly Ser Val Met Phe Ile
                100                 105                 110
Ile Ser Gly Ser Leu Ser Ile Ala Ala Gly Ile Arg Thr Thr Lys Gly
            115                 120                 125
Leu Val Arg Gly Ser Leu Gly Met Asn Ile Thr Ser Ser Val Leu Ala
```

```
            130                 135                 140
Ala Ser Gly Ile Leu Ile Asn Thr Phe Ser Leu Ala Phe Tyr Ser Phe
145                 150                 155                 160

His His Pro Tyr Cys Asn Tyr Tyr Gly Asn Ser Asn Asn Cys His Gly
                165                 170                 175

Thr Met Ser Ile Leu Met Gly Leu Asp Gly Met Val Leu Leu Leu Ser
            180                 185                 190

Val Leu Glu Phe Cys Ile Ala Val Ser Leu Ser Ala Phe Gly Cys Lys
        195                 200                 205

Val Leu Cys Cys Thr Pro Gly Val Val Leu Ile Leu Pro Ser His
    210                 215                 220

Ser His Met Ala Glu Thr Ala Ser Pro Thr Pro Leu Asn Glu Val
225                 230                 235

<210> SEQ ID NO 75
<211> LENGTH: 91
<212> TYPE: PRT
<213> ORGANISM: Homo sapiens

<400> SEQUENCE: 75

Met Leu Arg Pro Ser Glu Trp Asn Arg Asp Thr Leu Pro Ser Asn Met
1               5                   10                  15

Tyr Gln Lys Asn Gly Leu His His Gly Lys Tyr Ala Val Lys Lys Ser
            20                  25                  30

Arg Arg Thr Asp Val Glu Asp Leu Thr Pro Asn Pro Lys Lys Leu Leu
        35                  40                  45

Gln Ile Gly Asn Glu Leu Arg Lys Leu Asn Lys Val Ile Ser Asp Leu
    50                  55                  60

Thr Pro Val Ser Glu Leu Pro Leu Thr Ala Arg Pro Arg Ser Arg Lys
65                  70                  75                  80

Glu Lys Asn Ser Trp Leu Pro Glu Leu Val Gly
                85                  90

<210> SEQ ID NO 76
<211> LENGTH: 849
<212> TYPE: PRT
<213> ORGANISM: Homo sapiens

<400> SEQUENCE: 76

Met Ser Asp Thr Arg Arg Val Lys Val Tyr Thr Leu Asn Glu Asp
1               5                   10                  15

Arg Gln Trp Asp Asp Arg Gly Thr Gly His Val Ser Ser Thr Tyr Val
            20                  25                  30

Glu Glu Leu Lys Gly Met Ser Leu Leu Val Arg Ala Glu Ser Asp Gly
        35                  40                  45

Ser Leu Leu Leu Glu Ser Lys Ile Asn Pro Asn Thr Ala Tyr Gln Lys
    50                  55                  60

Gln Gln Asp Thr Leu Ile Val Trp Ser Glu Ala Glu Asn Tyr Asp Leu
65                  70                  75                  80

Ala Leu Ser Phe Gln Glu Lys Ala Gly Cys Asp Glu Ile Trp Glu Lys
                85                  90                  95

ILe Cys Gln Val Gln Gly Lys Asp Pro Ser Val Glu Val Thr Gln Asp
            100                 105                 110

Leu Ile Asp Glu Ser Glu Glu Glu Arg Phe Glu Glu Met Pro Glu Thr
        115                 120                 125

Ser His Leu Ile Asp Leu Pro Thr Cys Glu Leu Asn Lys Leu Glu Glu
```

```
                130                 135                 140
Ile Ala Asp Leu Val Thr Ser Val Leu Ser Ser Pro Ile Arg Arg Glu
145                 150                 155                 160
Lys Leu Ala Leu Ala Leu Glu Asn Glu Gly Tyr Ile Lys Lys Leu Leu
                165                 170                 175
Gln Leu Phe Gln Ala Cys Glu Asn Leu Glu Asn Thr Glu Gly Leu His
            180                 185                 190
His Leu Tyr Glu Ile Ile Arg Gly Ile Leu Phe Leu Asn Lys Ala Thr
            195                 200                 205
Leu Phe Glu Val Met Phe Ser Asp Glu Cys Ile Met Asp Val Val Gly
    210                 215                 220
Cys Leu Glu Tyr Asp Pro Ala Leu Ala Gln Pro Lys Arg His Arg Glu
225                 230                 235                 240
Phe Leu Thr Lys Thr Ala Lys Phe Lys Glu Val Ile Pro Ile Thr Asp
                245                 250                 255
Ser Glu Leu Arg Gln Lys Ile His Gln Thr Tyr Arg Val Gln Tyr Ile
            260                 265                 270
Gln Asp Ile Ile Leu Pro Thr Pro Ser Val Phe Glu Glu Asn Phe Leu
        275                 280                 285
Ser Thr Leu Thr Ser Phe Ile Phe Phe Asn Lys Val Glu Ile Val Ser
    290                 295                 300
Met Leu Gln Glu Asp Glu Lys Phe Leu Ser Glu Val Phe Ala Gln Leu
305                 310                 315                 320
Thr Asp Glu Ala Thr Asp Asp Lys Arg Arg Glu Leu Val Asn Phe
                325                 330                 335
Phe Lys Glu Phe Cys Ala Phe Ser Gln Thr Leu Gln Pro Gln Asn Arg
            340                 345                 350
Asp Ala Phe Phe Lys Thr Leu Ala Lys Leu Gly Ile Leu Pro Ala Leu
            355                 360                 365
Glu Ile Val Met Gly Met Asp Asp Leu Gln Val Arg Ser Ala Ala Thr
    370                 375                 380
Asp Ile Phe Ser Tyr Leu Val Glu Phe Ser Pro Ser Met Val Arg Glu
385                 390                 395                 400
Phe Val Met Gln Glu Ala Gln Gln Ser Asp Asp Ile Leu Leu Ile
                405                 410                 415
Asn Val Val Ile Glu Gln Met Ile Cys Asp Thr Asp Pro Glu Leu Gly
            420                 425                 430
Gly Ala Val Gln Leu Met Gly Leu Leu Arg Thr Leu Ile Asp Pro Glu
            435                 440                 445
Asn Met Leu Ala Thr Thr Asn Lys Thr Glu Lys Ser Glu Phe Leu Asn
    450                 455                 460
Phe Phe Tyr Asn His Cys Met His Val Leu Thr Ala Pro Leu Leu Thr
465                 470                 475                 480
Asn Thr Ser Glu Asp Lys Cys Glu Lys Asp Phe Phe Leu Lys His Tyr
                485                 490                 495
Arg Tyr Ser Trp Ser Phe Ile Cys Thr Pro Ser His Ser His Ser His
            500                 505                 510
Ser Thr Pro Ser Ser Ser Ile Ser Gln Asp Asn Ile Val Gly Ser Asn
    515                 520                 525
Lys Asn Asn Thr Ile Cys Pro Asp Asn Tyr Gln Thr Ala Gln Leu Leu
    530                 535                 540
Ala Leu Ile Leu Glu Leu Leu Thr Phe Cys Val Glu His Thr Tyr
545                 550                 555                 560
```

-continued

```
His Ile Lys Asn Tyr Ile Met Asn Lys Asp Leu Leu Arg Arg Val Leu
                565                 570                 575

Val Leu Met Asn Ser Lys His Thr Phe Leu Ala Leu Cys Ala Leu Arg
            580                 585                 590

Phe Met Arg Arg Ile Ile Gly Leu Lys Asp Glu Phe Tyr Asn Arg Tyr
        595                 600                 605

Ile Thr Lys Gly Asn Leu Phe Glu Pro Val Ile Asn Ala Leu Leu Asp
    610                 615                 620

Asn Gly Thr Arg Tyr Asn Leu Leu Asn Ser Ala Val Ile Glu Leu Phe
625                 630                 635                 640

Glu Phe Ile Arg Val Glu Asp Ile Lys Ser Leu Thr Ala His Ile Val
                645                 650                 655

Glu Asn Phe Tyr Lys Ala Leu Glu Ser Ile Glu Tyr Val Gln Thr Phe
            660                 665                 670

Lys Gly Leu Lys Thr Lys Tyr Glu Gln Glu Lys Asp Arg Gln Asn Gln
        675                 680                 685

Lys Leu Asn Ser Val Pro Ser Ile Leu Arg Ser Asn Arg Phe Arg Arg
    690                 695                 700

Asp Ala Lys Ala Leu Glu Glu Asp Glu Glu Met Trp Phe Asn Glu Asp
705                 710                 715                 720

Glu Glu Glu Glu Gly Lys Ala Val Val Ala Pro Val Glu Lys Pro Lys
                725                 730                 735

Pro Glu Asp Asp Phe Pro Asp Asn Tyr Glu Lys Phe Met Glu Thr Lys
            740                 745                 750

Lys Ala Lys Glu Ser Glu Asp Lys Glu Asn Leu Pro Lys Arg Thr Ser
        755                 760                 765

Pro Gly Gly Phe Lys Phe Thr Phe Ser His Ser Ala Ser Ala Ala Asn
    770                 775                 780

Gly Thr Asn Ser Lys Ser Val Val Ala Gln Ile Pro Pro Ala Thr Ser
785                 790                 795                 800

Asn Gly Ser Ser Ser Lys Thr Thr Asn Leu Pro Thr Ser Val Thr Ala
                805                 810                 815

Thr Lys Gly Ser Leu Val Gly Leu Val Asp Tyr Pro Asp Asp Glu Glu
            820                 825                 830

Glu Asp Glu Glu Glu Glu Ser Ser Pro Arg Lys Arg Pro Arg Leu Gly
        835                 840                 845

Ser
```

<210> SEQ ID NO 77
<211> LENGTH: 214
<212> TYPE: PRT
<213> ORGANISM: Homo sapiens

<400> SEQUENCE: 77

```
Met Ser Gly Gly Gln Thr Glu Gly Arg Val Pro Val Phe Ser His Glu
1               5                   10                  15

Val Val Pro Asp His Leu Arg Thr Lys Pro Asp Pro Glu Val Glu Glu
                20                  25                  30

Gln Glu Lys Gln Leu Thr Thr Asp Ala Ala Arg Ile Gly Ala Asp Ala
            35                  40                  45

Ala Gln Lys Gln Ile Gln Ser Leu Asn Lys Met Cys Ser Asn Leu Leu
        50                  55                  60

Glu Lys Ile Ser Lys Glu Glu Arg Glu Ser Glu Ser Gly Gly Leu Arg
65                  70                  75                  80
```

-continued

```
Pro Asn Lys Gln Thr Phe Asn Pro Thr Asp Thr Asn Ala Leu Val Ala
                 85                  90                  95

Ala Val Ala Phe Gly Lys Gly Leu Ser Asn Trp Arg Pro Ser Gly Ser
            100                 105                 110

Ser Gly Pro Gly Gln Ala Gly Gln Pro Gly Ala Gly Thr Ile Leu Ala
        115                 120                 125

Gly Thr Ser Gly Leu Gln Gln Val Gln Met Ala Gly Ala Pro Ser Gln
    130                 135                 140

Gln Gln Pro Met Leu Ser Gly Val Gln Met Ala Gln Ala Gly Gln Pro
145                 150                 155                 160

Gly Lys Met Pro Ser Gly Ile Lys Thr Asn Ile Lys Ser Ala Ser Met
                165                 170                 175

His Pro Tyr Gln Arg Pro Ser Cys Leu Gly Phe Ile Leu Ala Ile Pro
            180                 185                 190

Leu Arg Arg Lys Val Lys Lys Leu Leu Gly Gln Glu Gly Lys Lys Asn
        195                 200                 205

Ala His Leu Gln Leu Trp
    210
```

<210> SEQ ID NO 78
<211> LENGTH: 1404
<212> TYPE: PRT
<213> ORGANISM: Homo sapiens

<400> SEQUENCE: 78

```
Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
                20                  25                  30

Arg Cys Gly Glu Gly Tyr Ser Arg Asp Ala Thr Cys Asn Cys Asp Tyr
            35                  40                  45

Asn Cys Gln His Tyr Met Glu Cys Cys Pro Asp Phe Lys Arg Val Cys
        50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Asn Lys Lys Lys
    130                 135                 140

Thr Lys Lys Val Ile Glu Ser Glu Ile Thr Glu His Ser Val
145                 150                 155                 160

Ser Glu Asn Gln Glu Ser Ser Ser Ser Ser Ser Ser Ser Ser Ser
                165                 170                 175

Ser Thr Ile Arg Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
```

-continued

```
                225                 230                 235                 240
            Thr Gln His Asn Lys Val Ser Thr Ser Pro Lys Ile Thr Thr Ala Lys
                            245                 250                 255

Pro Ile Asn Pro Arg Pro Ser Leu Pro Pro Asn Ser Asp Thr Ser Lys
                            260                 265                 270

Glu Thr Ser Leu Thr Val Asn Lys Glu Thr Val Glu Thr Lys Glu
                    275                 280                 285

Thr Thr Thr Asn Lys Gln Thr Ser Thr Asp Gly Lys Glu Lys Thr
                    290                 295                 300

Thr Ser Ala Lys Glu Thr Gln Ser Ile Glu Lys Thr Ser Ala Lys Asp
            305                 310                 315                 320

Leu Ala Pro Thr Ser Lys Val Leu Ala Lys Pro Thr Pro Lys Ala Glu
                            325                 330                 335

Thr Thr Thr Lys Gly Pro Ala Leu Thr Thr Pro Lys Glu Pro Thr Pro
                            340                 345                 350

Thr Thr Pro Lys Glu Pro Ala Ser Thr Thr Pro Lys Glu Pro Thr Pro
                            355                 360                 365

Thr Thr Ile Lys Ser Ala Pro Thr Thr Pro Lys Glu Pro Ala Pro Thr
                    370                 375                 380

Thr Thr Lys Ser Ala Pro Thr Thr Pro Lys Glu Pro Ala Pro Thr Thr
            385                 390                 395                 400

Thr Lys Glu Pro Ala Pro Thr Thr Pro Lys Glu Pro Ala Pro Thr Thr
                            405                 410                 415

Thr Lys Glu Pro Ala Pro Thr Thr Lys Ser Ala Pro Thr Thr Pro
                            420                 425                 430

Lys Glu Pro Ala Pro Thr Thr Pro Lys Lys Pro Ala Pro Thr Thr Pro
                            435                 440                 445

Lys Glu Pro Ala Pro Thr Thr Pro Lys Glu Pro Thr Pro Thr Thr Pro
                            450                 455                 460

Lys Glu Pro Ala Pro Thr Thr Lys Glu Pro Ala Pro Thr Thr Pro Lys
            465                 470                 475                 480

Glu Pro Ala Pro Thr Ala Pro Lys Lys Pro Ala Pro Thr Thr Pro Lys
                            485                 490                 495

Glu Pro Ala Pro Thr Thr Pro Lys Glu Pro Ala Pro Thr Thr Thr Lys
                            500                 505                 510

Glu Pro Ser Pro Thr Thr Pro Lys Glu Pro Ala Pro Thr Thr Thr Lys
                            515                 520                 525

Ser Ala Pro Thr Thr Thr Lys Glu Pro Ala Pro Thr Thr Lys Ser
            530                 535                 540

Ala Pro Thr Thr Pro Lys Glu Pro Ser Pro Thr Thr Lys Glu Pro
            545                 550                 555                 560

Ala Pro Thr Thr Pro Lys Glu Pro Ala Pro Thr Thr Pro Lys Lys Pro
                            565                 570                 575

Ala Pro Thr Thr Pro Lys Glu Pro Ala Pro Thr Thr Pro Lys Glu Pro
                            580                 585                 590

Ala Pro Thr Thr Lys Lys Pro Ala Pro Thr Thr Pro Lys Glu Pro
                    595                 600                 605

Ala Pro Thr Thr Pro Lys Glu Thr Ala Pro Thr Thr Pro Lys Lys Leu
                    610                 615                 620

Thr Pro Thr Thr Pro Glu Lys Leu Ala Pro Thr Thr Pro Glu Lys Pro
            625                 630                 635                 640

Ala Pro Thr Thr Pro Glu Glu Leu Ala Pro Thr Thr Pro Glu Glu Pro
                            645                 650                 655
```

-continued

```
Thr Pro Thr Thr Pro Glu Glu Pro Ala Pro Thr Pro Lys Ala Ala
            660                 665                 670
Ala Pro Asn Thr Pro Lys Glu Pro Ala Pro Thr Pro Lys Glu Pro
        675                 680                 685
Ala Pro Thr Thr Pro Lys Glu Pro Ala Pro Thr Thr Pro Lys Glu Thr
    690                 695                 700
Ala Pro Thr Thr Pro Lys Gly Thr Ala Pro Thr Thr Leu Lys Glu Pro
705                 710                 715                 720
Ala Pro Thr Thr Pro Lys Lys Pro Ala Pro Lys Glu Leu Ala Pro Thr
                725                 730                 735
Thr Thr Lys Glu Pro Thr Ser Thr Thr Cys Asp Lys Pro Ala Pro Thr
            740                 745                 750
Thr Pro Lys Gly Thr Ala Pro Thr Thr Pro Lys Glu Pro Ala Pro Thr
        755                 760                 765
Thr Pro Lys Glu Pro Ala Pro Thr Thr Pro Lys Gly Thr Ala Pro Thr
    770                 775                 780
Thr Leu Lys Glu Pro Ala Pro Thr Thr Pro Lys Lys Pro Ala Pro Lys
785                 790                 795                 800
Glu Leu Ala Pro Thr Thr Thr Lys Gly Pro Thr Ser Thr Thr Ser Asp
                805                 810                 815
Lys Pro Ala Pro Thr Thr Pro Lys Glu Thr Ala Pro Thr Thr Pro Lys
            820                 825                 830
Glu Pro Ala Pro Thr Thr Pro Lys Lys Pro Ala Pro Thr Thr Pro Glu
        835                 840                 845
Thr Pro Pro Pro Thr Thr Ser Glu Val Ser Thr Pro Thr Thr Thr Lys
    850                 855                 860
Glu Pro Thr Thr Ile His Lys Ser Pro Asp Glu Ser Thr Pro Glu Leu
865                 870                 875                 880
Ser Ala Glu Pro Thr Pro Lys Ala Leu Glu Asn Ser Pro Lys Glu Pro
                885                 890                 895
Gly Val Pro Thr Thr Lys Thr Pro Ala Ala Thr Lys Pro Glu Met Thr
            900                 905                 910
Thr Thr Ala Lys Asp Lys Thr Thr Glu Arg Asp Leu Arg Thr Thr Pro
        915                 920                 925
Glu Thr Thr Thr Ala Ala Pro Lys Met Thr Lys Glu Thr Ala Thr Thr
    930                 935                 940
Thr Glu Lys Thr Thr Glu Ser Lys Ile Thr Ala Thr Thr Gln Val
945                 950                 955                 960
Thr Ser Thr Thr Thr Gln Asp Thr Thr Pro Phe Lys Ile Thr Thr Leu
                965                 970                 975
Lys Thr Thr Thr Leu Ala Pro Lys Val Thr Thr Thr Lys Lys Thr Ile
            980                 985                 990
Thr Thr Thr Glu Ile Met Asn Lys  Pro Glu Glu Thr Ala  Lys Pro Lys
        995                1000                1005
Asp Arg  Ala Thr Asn Ser Lys  Ala Thr Thr Pro Lys  Pro Gln Lys
    1010                1015                1020
Pro Thr  Lys Ala Pro Lys Lys  Pro Thr Ser Thr Lys  Lys Pro Lys
    1025                1030                1035
Thr Met  Pro Arg Val Arg Lys  Pro Lys Thr Thr Pro  Thr Pro Arg
    1040                1045                1050
Lys Met  Thr Ser Thr Met Pro  Glu Leu Asn Pro Thr  Ser Arg Ile
    1055                1060                1065
```

-continued

```
Ala Glu Ala Met Leu Gln Thr Thr Thr Arg Pro Asn Gln Thr Pro
    1070                1075                1080

Asn Ser Lys Leu Val Glu Val Asn Pro Lys Ser Glu Asp Ala Gly
    1085                1090                1095

Gly Ala Glu Gly Glu Thr Pro His Met Leu Leu Arg Pro His Val
    1100                1105                1110

Phe Met Pro Glu Val Thr Pro Asp Met Asp Tyr Leu Pro Arg Val
    1115                1120                1125

Pro Asn Gln Gly Ile Ile Ile Asn Pro Met Leu Ser Asp Glu Thr
    1130                1135                1140

Asn Ile Cys Asn Gly Lys Pro Val Asp Gly Leu Thr Thr Leu Arg
    1145                1150                1155

Asn Gly Thr Leu Val Ala Phe Arg Gly His Tyr Phe Trp Met Leu
    1160                1165                1170

Ser Pro Phe Ser Pro Pro Ser Pro Ala Arg Arg Ile Thr Glu Val
    1175                1180                1185

Trp Gly Ile Pro Ser Pro Ile Asp Thr Val Phe Thr Arg Cys Asn
    1190                1195                1200

Cys Glu Gly Lys Thr Phe Phe Phe Lys Asp Ser Gln Tyr Trp Arg
    1205                1210                1215

Phe Thr Asn Asp Ile Lys Asp Ala Gly Tyr Pro Lys Pro Ile Phe
    1220                1225                1230

Lys Gly Phe Gly Gly Leu Thr Gly Gln Ile Val Ala Ala Leu Ser
    1235                1240                1245

Thr Ala Lys Tyr Lys Asn Trp Pro Glu Ser Val Tyr Phe Phe Lys
    1250                1255                1260

Arg Gly Gly Ser Ile Gln Gln Tyr Ile Tyr Lys Gln Glu Pro Val
    1265                1270                1275

Gln Lys Cys Pro Gly Arg Arg Pro Ala Leu Asn Tyr Pro Val Tyr
    1280                1285                1290

Gly Glu Thr Thr Gln Val Arg Arg Arg Phe Glu Arg Ala Ile
    1295                1300                1305

Gly Pro Ser Gln Thr His Thr Ile Arg Ile Gln Tyr Ser Pro Ala
    1310                1315                1320

Arg Leu Ala Tyr Gln Asp Lys Gly Val Leu His Asn Glu Val Lys
    1325                1330                1335

Val Ser Ile Leu Trp Arg Gly Leu Pro Asn Val Thr Ser Ala
    1340                1345                1350

Ile Ser Leu Pro Asn Ile Arg Lys Pro Asp Gly Tyr Asp Tyr Tyr
    1355                1360                1365

Ala Phe Ser Lys Asp Gln Tyr Tyr Asn Ile Asp Val Pro Ser Arg
    1370                1375                1380

Thr Ala Arg Ala Ile Thr Thr Arg Ser Gly Gln Thr Leu Ser Lys
    1385                1390                1395

Val Trp Tyr Asn Cys Pro
    1400

<210> SEQ ID NO 79
<211> LENGTH: 784
<212> TYPE: PRT
<213> ORGANISM: Homo sapiens

<400> SEQUENCE: 79

Met Val Gly Lys His Leu Gly Ala Arg Lys Asp His Pro Gly Leu Lys
1               5                   10                  15
```

-continued

```
Ala Lys Glu Asn Asp Glu Asn Cys Gly Pro Thr Thr Thr Val Phe Val
             20                  25                  30
Gly Asn Ile Ser Glu Lys Ala Ser Asp Met Leu Ile Arg Gln Leu Leu
             35                  40                  45
Ala Lys Cys Gly Leu Val Leu Ser Trp Lys Arg Val Gln Gly Ala Ser
 50                  55                  60
Gly Lys Leu Gln Ala Phe Gly Phe Cys Glu Tyr Lys Glu Pro Glu Ser
 65                  70                  75                  80
Thr Leu Arg Ala Leu Arg Leu Leu His Asp Leu Gln Ile Gly Glu Lys
                 85                  90                  95
Lys Leu Leu Val Lys Val Asp Ala Lys Thr Lys Ala Gln Leu Asp Glu
                100                 105                 110
Trp Lys Ala Lys Lys Ala Ser Asn Gly Asn Ala Arg Pro Glu Thr
                115                 120                 125
Val Thr Asn Asp Asp Glu Glu Ala Leu Asp Glu Thr Lys Arg Arg
                130                 135                 140
Asp Gln Met Ile Lys Gly Ala Ile Glu Val Leu Ile Arg Glu Tyr Ser
145                 150                 155                 160
Ser Glu Leu Asn Ala Pro Ser Gln Glu Ser Asp Ser His Pro Arg Lys
                165                 170                 175
Lys Lys Lys Glu Lys Lys Glu Asp Ile Phe Arg Arg Phe Pro Val Ala
                180                 185                 190
Pro Leu Ile Pro Tyr Pro Leu Ile Thr Lys Glu Asp Ile Asn Ala Ile
                195                 200                 205
Glu Met Glu Glu Asp Lys Arg Asp Leu Ile Ser Arg Glu Ile Ser Lys
210                 215                 220
Phe Arg Asp Thr His Lys Lys Leu Glu Glu Glu Lys Gly Lys Lys Glu
225                 230                 235                 240
Lys Glu Arg Gln Glu Ile Glu Lys Glu Arg Arg Glu Arg Glu Arg Glu
                245                 250                 255
Arg Glu Arg Glu Arg Glu Arg Arg Glu Arg Glu Arg Glu Arg Glu Arg
                260                 265                 270
Glu Arg Glu Arg Glu Lys Glu Lys Glu Arg Glu Arg Glu Arg Glu Arg
                275                 280                 285
Asp Arg Asp Arg Asp Arg Thr Lys Glu Arg Asp Arg Asp Arg Asp Arg
                290                 295                 300
Glu Arg Asp Arg Asp Arg Asp Arg Glu Ser Ser Asp Arg Asn Lys
305                 310                 315                 320
Asp Arg Ser Arg Ser Arg Glu Lys Ser Arg Asp Arg Glu Arg Glu Arg
                325                 330                 335
Glu Arg Glu Arg Glu Arg Glu Arg Glu Arg Glu Arg Glu Arg Glu Arg
                340                 345                 350
Glu Arg Glu Arg Glu Arg Glu Arg Glu Arg Glu Arg Glu Arg Glu Lys
                355                 360                 365
Asp Lys Lys Arg Asp Arg Glu Glu Asp Glu Glu Asp Ala Tyr Glu Arg
370                 375                 380
Arg Lys Leu Glu Arg Lys Leu Arg Glu Lys Glu Ala Ala Tyr Gln Glu
385                 390                 395                 400
Arg Leu Lys Asn Trp Glu Ile Arg Glu Arg Lys Lys Thr Arg Glu Tyr
                405                 410                 415
Glu Lys Glu Ala Glu Arg Glu Glu Arg Arg Arg Glu Met Ala Lys
                420                 425                 430
```

```
Glu Ala Lys Arg Leu Lys Glu Phe Leu Glu Asp Tyr Asp Asp Arg
            435                 440                 445

Asp Asp Pro Lys Tyr Tyr Arg Gly Ser Ala Leu Gln Lys Arg Leu Arg
            450                 455                 460

Asp Arg Glu Lys Glu Met Glu Ala Asp Glu Arg Asp Arg Lys Arg Glu
465                 470                 475                 480

Lys Glu Glu Leu Glu Glu Ile Arg Gln Arg Leu Leu Ala Glu Gly His
                485                 490                 495

Pro Asp Pro Asp Ala Glu Leu Gln Arg Met Glu Gln Glu Ala Glu Arg
            500                 505                 510

Arg Arg Gln Pro Gln Ile Lys Gln Glu Pro Glu Ser Glu Glu Glu Glu
            515                 520                 525

Glu Glu Lys Gln Glu Lys Glu Glu Lys Arg Glu Glu Pro Met Glu Glu
            530                 535                 540

Glu Glu Glu Pro Glu Gln Lys Pro Cys Leu Lys Pro Thr Leu Arg Pro
545                 550                 555                 560

Ile Ser Ser Ala Pro Ser Val Ser Ser Ala Ser Gly Asn Ala Thr Pro
                565                 570                 575

Asn Thr Pro Gly Asp Glu Ser Pro Cys Gly Ile Ile Pro His Glu
            580                 585                 590

Asn Ser Pro Asp Gln Gln Pro Glu Glu His Arg Pro Lys Ile Gly
            595                 600                 605

Leu Ser Leu Lys Leu Gly Ala Ser Asn Ser Pro Gly Gln Pro Asn Ser
            610                 615                 620

Val Lys Arg Lys Lys Leu Pro Val Asp Ser Val Phe Asn Lys Phe Glu
625                 630                 635                 640

Asp Glu Asp Ser Asp Val Pro Arg Lys Arg Lys Leu Val Pro Leu
            645                 650                 655

Asp Tyr Gly Glu Asp Asp Lys Asn Ala Thr Lys Gly Thr Val Asn Thr
            660                 665                 670

Glu Glu Lys Arg Lys His Ile Lys Ser Leu Ile Glu Lys Ile Pro Thr
            675                 680                 685

Ala Lys Pro Glu Leu Phe Ala Tyr Pro Leu Asp Trp Ser Ile Val Asp
            690                 695                 700

Ser Ile Leu Met Glu Arg Arg Ile Arg Pro Trp Ile Asn Lys Lys Ile
705                 710                 715                 720

Ile Glu Tyr Ile Gly Glu Glu Ala Thr Leu Val Asp Phe Val Cys
                725                 730                 735

Ser Lys Val Met Ala His Ser Ser Pro Gln Ser Ile Leu Asp Asp Val
            740                 745                 750

Ala Met Val Leu Asp Glu Glu Ala Glu Val Phe Ile Val Lys Met Trp
            755                 760                 765

Arg Leu Leu Ile Tyr Glu Thr Glu Ala Lys Lys Ile Gly Leu Val Lys
            770                 775                 780

<210> SEQ ID NO 80
<211> LENGTH: 735
<212> TYPE: PRT
<213> ORGANISM: Homo sapiens

<400> SEQUENCE: 80

Lys Cys Gly Leu Val Leu Ser Trp Lys Arg Val Gln Gly Ala Ser Gly
1               5                   10                  15

Lys Leu Gln Ala Phe Gly Phe Cys Glu Tyr Lys Glu Pro Glu Ser Thr
            20                  25                  30
```

```
Leu Arg Ala Leu Arg Leu Leu His Asp Leu Gln Ile Gly Glu Lys Lys
            35                  40                  45

Leu Leu Val Lys Val Asp Ala Lys Thr Lys Ala Gln Leu Asp Glu Trp
 50                  55                  60

Lys Ala Lys Lys Ala Ser Asn Gly Asn Ala Arg Pro Glu Thr Val
 65                  70                  75                  80

Thr Asn Asp Asp Glu Ala Leu Asp Glu Thr Lys Arg Arg Asp
                85                  90                  95

Gln Met Ile Lys Gly Ala Ile Glu Val Leu Ile Arg Glu Tyr Ser Ser
            100                 105                 110

Glu Leu Asn Ala Pro Ser Gln Glu Ser Asp Ser His Pro Arg Lys Lys
            115                 120                 125

Lys Lys Glu Lys Lys Glu Asp Ile Phe Arg Arg Phe Pro Val Ala Pro
130                 135                 140

Leu Ile Pro Tyr Pro Leu Ile Thr Lys Glu Asp Ile Asn Ala Ile Glu
145                 150                 155                 160

Met Glu Glu Asp Lys Arg Asp Leu Ile Ser Arg Glu Ile Ser Lys Phe
                165                 170                 175

Arg Asp Thr His Lys Lys Leu Glu Glu Glu Lys Gly Lys Lys Glu Lys
            180                 185                 190

Glu Arg Gln Glu Ile Glu Lys Glu Arg Arg Glu Arg Glu Arg
            195                 200                 205

Glu Arg Glu Arg Glu Arg Arg Glu Arg Glu Arg Glu Arg Glu Arg Glu
    210                 215                 220

Arg Glu Arg Glu Lys Glu Lys Glu Arg Glu Arg Glu Arg Glu Arg Asp
225                 230                 235                 240

Arg Asp Arg Asp Arg Thr Lys Glu Arg Asp Arg Asp Arg Asp Arg Glu
                245                 250                 255

Arg Asp Arg Asp Arg Asp Arg Glu Arg Ser Ser Asp Arg Asn Lys Asp
            260                 265                 270

Arg Ser Arg Ser Arg Glu Lys Ser Arg Asp Arg Glu Arg Glu Arg Glu
            275                 280                 285

Arg Glu Arg Glu Arg Glu Arg Glu Arg Glu Arg Glu Arg Glu Arg Glu
    290                 295                 300

Arg Glu Arg Glu Arg Glu Arg Glu Arg Glu Arg Glu Arg Glu Lys Asp
305                 310                 315                 320

Lys Lys Arg Asp Arg Glu Glu Asp Glu Glu Asp Ala Tyr Glu Arg Arg
                325                 330                 335

Lys Leu Glu Arg Lys Leu Arg Glu Lys Glu Ala Ala Tyr Gln Glu Arg
            340                 345                 350

Leu Lys Asn Trp Glu Ile Arg Glu Arg Lys Lys Thr Arg Glu Tyr Glu
            355                 360                 365

Lys Glu Ala Glu Arg Glu Glu Glu Arg Arg Arg Glu Met Ala Lys Glu
            370                 375                 380

Ala Lys Arg Leu Lys Glu Phe Leu Glu Asp Tyr Asp Asp Arg Asp
385                 390                 395                 400

Asp Pro Lys Tyr Tyr Arg Gly Ser Ala Leu Gln Lys Arg Leu Arg Asp
                405                 410                 415

Arg Glu Lys Glu Met Glu Ala Asp Glu Arg Asp Arg Lys Arg Glu Lys
            420                 425                 430

Glu Glu Leu Glu Glu Ile Arg Gln Arg Leu Leu Ala Glu Gly His Pro
            435                 440                 445
```

-continued

```
Asp Pro Asp Ala Glu Leu Gln Arg Met Glu Gln Glu Ala Glu Arg Arg
    450                 455                 460
Arg Gln Pro Gln Ile Lys Gln Glu Pro Glu Ser Glu Glu Glu Glu Glu
465                 470                 475                 480
Glu Lys Gln Glu Lys Glu Glu Lys Arg Glu Glu Pro Met Glu Glu Glu
                485                 490                 495
Glu Glu Pro Glu Gln Lys Pro Cys Leu Lys Pro Thr Leu Arg Pro Ile
            500                 505                 510
Ser Ser Ala Pro Ser Val Ser Ser Ala Ser Gly Asn Ala Thr Pro Asn
            515                 520                 525
Thr Pro Gly Asp Glu Ser Pro Cys Gly Ile Ile Ile Pro His Glu Asn
        530                 535                 540
Ser Pro Asp Gln Gln Gln Pro Glu Glu His Arg Pro Lys Ile Gly Leu
545                 550                 555                 560
Ser Leu Lys Leu Gly Ala Ser Asn Ser Pro Gly Gln Pro Asn Ser Val
                565                 570                 575
Lys Arg Lys Lys Leu Pro Val Asp Ser Val Phe Asn Lys Phe Glu Asp
            580                 585                 590
Glu Asp Ser Asp Asp Val Pro Arg Lys Arg Lys Leu Val Pro Leu Asp
        595                 600                 605
Tyr Gly Glu Asp Lys Asn Ala Thr Lys Gly Thr Val Asn Thr Glu
    610                 615                 620
Glu Lys Arg Lys His Ile Lys Ser Leu Ile Glu Lys Ile Pro Thr Ala
625                 630                 635                 640
Lys Pro Glu Leu Phe Ala Tyr Pro Leu Asp Trp Ser Ile Val Asp Ser
                645                 650                 655
Ile Leu Met Glu Arg Arg Ile Arg Pro Trp Ile Asn Lys Lys Ile Ile
            660                 665                 670
Glu Tyr Ile Gly Glu Glu Glu Ala Thr Leu Val Asp Phe Val Cys Ser
        675                 680                 685
Lys Val Met Ala His Ser Ser Pro Gln Ser Ile Leu Asp Asp Val Ala
    690                 695                 700
Met Val Leu Asp Glu Glu Ala Glu Val Phe Ile Val Lys Met Trp Arg
705                 710                 715                 720
Leu Leu Ile Tyr Glu Thr Glu Ala Lys Lys Ile Gly Leu Val Lys
                725                 730                 735
```

REGULATED ANGIOGENESIS GENES AND POLYPEPTIDES

DESCRIPTION OF THE DRAWINGS

FIG. 1 is the amino acid comparison between XM$_{13}$087061 (SEQ ID NO 59) and ANH0009 (SEQ ID NO 2).

FIG. 2 (A–B) is the amino acid comparison between X68560 (SEQ ID NO 60), ANH0024A (SEQ ID NO 4), ANH0024B (SEQ ID NO 6), ANH0024C (SEQ ID NO 8), and ANH0024D (SEQ ID NO 10).

FIG. 3 is the amino acid comparison between XM_045848 (SEQ ID NO 61) and ANH0039 (SEQ ID NO 12).

FIG. 4 is the amino acid comparison between XM_55371 (SEQ ID NO 62) and ANH0068 (SEQ ID NO 14).

FIG. 5 is the amino acid comparison between XM_076374 (SEQ ID NO 63) and ANH0114 (SEQ ID NO 16).

FIG. 6 (A–B is the amino acid comparison between AL133047 (SEQ ID NO 64), ANH0144A (SEQ ID NO 18), ANH0144B (SEQ ID NO 20), and ANH0144C (SEQ ID NO 22).

FIG. 7 (A–B) is the amino acid comparison between XM_086643 (SEQ ID NO 65) and ANH0241 (SEQ ID NO 24).

FIG. 8 is the amino acid comparison between AK027731 (SEQ ID NO 66) and ANH0245 (SEQ ID NO 26).

FIG. 9 (A–B) is the amino acid comparison between AK000913 (SEQ ID NO 67), NM_004713 (SEQ ID NO 68), and ANH0296 (SEQ ID NO 28).

FIG. 10 is the amino acid comparison between XM_053487 (SEQ ID NO 69) and ANH0423 (SEQ ID NO 30).

FIG. 11 is the amino acid comparison between NM_000366 (SEQ ID NO 70), ANH0459B (SEQ ID NO 32), ANH0459C (SEQ ID NO 34), and ANH0459D (SEQ ID NO 36).

FIG. 12 is the amino acid comparison between AL133087 (SEQ ID NO 71) and ANH0769 (SEQ ID NO 38).

FIG. 13 is the amino acid comparison between NM_014882 (SEQ ID NO 73) and ANH0658 (SEQ ID NO 40).

FIG. 14 is the amino acid comparison between XM_015539 (SEQ ID NO 74) and ANH0668 (SEQ ID NO 42).

FIG. 15 is the amino acid comparison between XM_087631 (SEQ ID NO 75) and ANH0757 (SEQ ID NO 44).

FIG. 16 (A–B) is the amino acid comparison between XM_048092 (SEQ ID NO 76), ANH0687A (SEQ ID NO 46), and ANH0687B (SEQ ID NO 48).

FIG. 17 is the amino acid comparison between NM_052877 (SEQ ID NO 77) and ANH0693 (SEQ ID NO 50).

FIG. 18 (A–B) is the amino acid comparison between AAF19255 (SEQ ID NO 79), AAC97961 (SEQ ID NO 80), ANH0122A (SEQ ID NO 54), and ANH0122B (SEQ ID NO 56).

FIG. 19 (A–B) is the amino acid comparison between XM_001738 (SEQ ID NO 78) and ANH0316 (SEQ ID NO 58).

DESCRIPTION OF THE INVENTION

The present invention relates to all facets of novel polynucleotides, the polypeptides they encode, antibodies and specific binding partners thereto, and their applications to research, diagnosis, drug discovery, therapy, clinical medicine, forensic science and medicine, etc. The polynucleotides are expressed in angiogenesis and are therefore useful in variety of ways, including, but not limited to, as molecular markers for blood vessels and blood vessel formation, as drug targets, and for detecting, diagnosing, staging, monitoring, prognosticating, preventing, treating, and/or determining predisposition to diseases and conditions of the vascular system. The identification of specific genes, and groups of genes, expressed in pathways physiologically relevant to angiogenesis permits the definition of functional and disease pathways, and the delineation of targets in these pathways which are useful in diagnostic, therapeutic, and clinical applications. The present invention also relates to methods of using the polynucleotides and related products (proteins, antibodies, etc.) in business and computer-related methods, e.g., advertising, displaying, offering, selling, etc., such products for sale, commercial use, licensing, etc.

Angiogenesis, the process of blood vessel formation, is a key event in many physiological processes that underlie normal and diseased tissue function. During ontogeny, angiogenesis is necessary to establish to the network of blood vessels required for normal cell, tissue and organ development and maintenance. In the adult organism, the production of new blood vessels is needed for organ homeostasis, e.g., in the cycling of the female endometrium, for blood vessel maturation during wound healing, and other processes involved in the maintenance of organism integrity. It also is important in regenerative medicine, including, e.g., in promoting tissue repair, tissue engineering, and the growth of new tissues, inside and outside the body.

Not all angiogenesis is beneficial. Inappropriate and ectopic expression of angiogenesis can be deleterious to an organism. A number of pathological conditions are associated with the growth of extraneous blood vessels. These include, e.g., diabetic retinopathy, neovascular glaucoma, psoriasis, retrolental fibroplasias, angiofibroma, inflammation, etc. In addition, the increased blood supply associated with cancerous and neoplastic tissue, encourages growth, leading to rapid tumor enlargement and metastasis.

Because of the importance of angiogenesis in many physiological processes, its regulation has application in a vast arena of technologies and treatments. For instance, induction of neoangiogenesis has been used for the treatment of ischemic myocardial diseases, and other conditions (e.g., ischemic limb, stroke) produced by the lack of adequate blood supply. See, e.g., Rosengart et al., *Circulation*, 100(5):468–74, 1999. In growth new tissues from progenitor and stem cells, angiogenesis is one of the key processes necessary. Where vascularization is undesirable, such as for cancer and the mentioned pathological conditions, inhibition of angiogenesis has been used as a treatment therapy. See, e.g., U.S. Pat. No. 6,024,688 for treating neoplasms using angiogenesis inhibitors.

A number of different factors have been identified which stimulate angiogenesis, e.g., by activating normally quiescent endothelial cells, by acting as a chemoattractant to developing capillaries, by stimulating gene expression, etc. These factors include, e.g. fibroblast growth factors, such as FGF-1 and FGF-2, vascular endothelial growth factor (VEGF), platelet-derived endothelial cell growth factor (PD-ECGF), etc. Inhibition of angiogenesis has been achieved using drugs, such as TNP-470, monoclonal antibodies, antisense nucleic acids and proteins, such as angiostatin and endostatin. See, e.g., Battegay, *J. Mol. Med.*, 73, 333–346 (1995); Hanahan et al., *Cell*, 86, 353–364 (1996); Folkman, N. *Engl. J. Med.*, 333, 1757–1763 (1995).

Activity of a polynucleotide or gene in modulating or regulating angiogenesis can be determined according to any effective in vivo or in vitro methods. One useful model to study angiogenesis is based on the observation that, when a reconstituted basement membrane matrix, such as Matrigel®, supplemented with growth factor (e.g., FGF-1), is injected subcutaneously into a host animal, endothelial cells are recruited into the matrix, forming new blood vessels over a period of several days. See, e.g., Passaniti et al., *Lab. Invest.*, 67:519–528, 1992. By sampling the extract at different times, angiogenesis can be temporally dissected, permitting the identification of genes involved in all stages of angiogenesis, including, e.g., migration of endothelial cells into the matrix, commitment of endothelial cells to angiogenesis pathway, cell elongation and formation of sac-like spaces, and establishment of functional capillaries comprising connected, and linear structures containing red blood cells. To stabilize the growth factor and/or slow its release from the matrix, the growth factor can be bound to heparin or another stabilizing agent. The matrix can also be periodically re-infused with growth factor to enhance and extend the angiogenic process.

Other useful systems for studying angiogenesis, include, e.g., neovascularization of tumor explants (e.g., U.S. Pat. Nos. 5,192,744; 6,024,688), chicken chorioallantoic membrane (CAM) assay (e.g., Taylor and Folkman, *Nature*, 297:307–312, 1982; Eliceiri et al., *J. Cell Biol.*, 140, 1255–1263, 1998), bovine capillary endothelial (BCE) cell assay (e.g., U.S. Pat. No. 6,024,688; Polverini, P. J. et al., *Methods Enzymol.*, 198:440–450, 1991), migration assays, HUVEC (human umbilical cord vascular endothelial cell) growth inhibition assay (e.g., U.S. Pat. No. 6,060,449).

The present invention relates to polynucleotides, and the polypeptides they encode, which are related to angiogenesis and the vascular system. These polynucleotides were identified using a model system for angiogenesis. In this system, a Matrigel™ plug implant comprising FGF-1 is implanted subcutaneously into a host mouse. The initial bolus of FGF attracts endothelial cells into the implant, but does not result in new blood vessel formation. After about 10–15 days, the implant is re-infused with FGF-1. The FGF-1 stimulates the endothelial cells already present in the implant, initiating the process of angiogenesis. Tissue samples, removed at different intervals, can be analyzed to determine their gene expression patterns.

In results reported here, samples of the Matrigel™ plug were harvested immediately prior to the re-injection with FGF-1, and then 1, 8, and 24 hours later. These samples were analyzed for gene expression, and differentially-expressed genes were identified by several methods. At least eight different expression patterns were observed. These were classified according to whether the genes were up- (U) or down- (D) regulated, and whether the expression of the differentially-regulated gene was transient (T) or sustained (S). The term "transient" indicates that the gene expression levels changed temporarily, and then returned to the basal level. "Sustained" indicates that the expression levels changed, and then remained relatively stable. The sample removed prior to the FGF-1 re-infusion was used to establish the basal levels of gene expression, prior to angiogenesis. "L" indicates that expression levels were low; "H" indicates that expression levels were high. The following patterns were observed:

U1S: Gene up-regulated at 1-hour, and remained up in the 8- and 24-hour assays.

U8S: Gene up-regulated at 8-hours, and remained up in 24-hour assay.

U1T: Gene up-regulated at 1-hour, but returned to basal level in the 8- and 24-hour assays.

U8T: Gene up-regulated at 8-hours, but returned to basal level in the 24-hour assay.

D1S: Gene down-regulated at 1-hour, and remained down in the 8- and 24-hour assays.

D8S: Gene down-regulated at 8-hours, and remained down in the 24-hour assay.

D1T: Gene down-regulated at 1-hour, but returned to basal level in the 8- and 24-assays.

D8T: Gene down-regulated at 8-hours, but returned to basal level in 24-hour assay.

D24: Gene down-regulated in the 24-hour assay.

At the first time point ("0"), endothelial and other cells are present in the Matrigel™ plug, but angiogenesis has not begun. After 1 hour, the endothelial cells have been stimulated by FGF, and genes involved in angiogenesis have been activated. By 8 hours, the endothelial cells have organized into a rudimentary tubes, but are not yet functional. At the end of 24 hours, the tubes have become functional, and are filled with blood cells. SEQ ID NOS 1–58 represent the human homologs of polynucleotides identified in this assay system. It should be recognized that the specific expression patterns summarized Table 3 reflect the kinetics and particularities of this system.

In accordance with the present invention, genes have been identified which are differentially expressed in angiogenesis. By the phrase "differential expression," it is meant that the levels of expression of a gene, as measured by its transcription or translation product, are different depending upon the time point (see below) in development when the cells are assayed. There are no absolute amounts by which the gene expression levels must vary, as long as the differences are measurable.

The phrase "up-regulated" indicates that an mRNA transcript or other nucleic acid corresponding to a polynucleotide of the present invention is expressed in larger amounts at a given developmental stage as compared to another at a given developmental stage as compared to another. The phrase "down-regulated" indicates that an mRNA transcript or other nucleic acid corresponding to a polynucleotide of the present invention is expressed in lower amounts at a given developmental stage as compared to another.

Not all subjects in an animal population will display the same gene expression profile, even when they express same or similar phenotypes. For instance, a group of patients may all have a cancer in which angiogenesis has been initiated, but they may not have 100% identical patterns of angiogenic gene expression. There are a number of reasons for such differences, including, e.g., variability among patient genetic backgrounds, differences in their exposure to environmental and other exogenous factors that influence gene expression, drug histories, cancer type, stage, and grade, allelic variations in the angiogenic genes, etc. For these reasons, there can be circumstances where one gene is inadequate as a general tool to assess and treat angiogenesis. As a result, it may be desirable to use the genes in combination, rather than one at a time, to increase the diagnostic and therapeutic efficacy. While one particular gene may not be fully penetrant in all individuals exhibiting angiogenesis, using a set of genes enhances the probability of identifying angiogenesis is a broad population sample.

Table 1 is a list of differentially regulated genes in angiogenesis, and their corresponding functional and structural polypeptide domains. Table 3 summarizes the expression profile of these genes.

The polynucleotide and polypeptide sequences are shown in FIGS. 1–19 and SEQ ID NOS 1–58. Membrane (i.e., cell-surface) proteins coded for by regulated genes (e.g., ANH0668 and ANH0095) are useful targets for antibodies and other binding partners (e.g., ligands, aptamers, small peptides, etc.) to selectively target agents to angiogenic tissue for any purpose, included, but not limited to, imaging, therapeutic, diagnostic, drug delivery, gene therapy, etc. For example, binding partners, such as antibodies, can be used to block angiogenesis, e.g., in cancer. Membrane (e.g., when shed into the blood and other fluid) and other differentially expressed proteins can also be used as markers to determine in a cancer patient whether angiogenesis in the cancer is progressing. Especially useful proteins are those which are not expressed in peripheral blood, such as ANH0144, ANH0459, ANH0687, and ANH0316.

Polynucleotides of the present invention have been mapped to specific chromosomal bands. Different human disorders are associated with these chromosome locations. See, Table 2. The polynucleotides and polypeptides they encode can be used as linkage markers, diagnostic targets, therapeutic targets, for any of the mentioned disorders, as well as any disorders or genes mapping in proximity to them.

The present invention relates to the complete polynucleotide and polypeptide sequences disclosed herein, as well as fragments thereof. Useful fragments include those which are unique and which do not overlap any known gene, which overlap with a known sequence, which span alternative splice junctions, which are unique to a public sequence as indicated in the figures, which span an alternative splice junction of a public sequence, etc. Unique sequences can also be described as being specific for a gene because they are characteristic of the gene, but not related genes. The unique or specific sequences included polypeptide sequences, coding nucleotide sequences (e.g., as illustrated in the figures), and non-coding nucleotide sequences.

Below, for illustration, are some examples of polypeptides (included are the polynucleotides which encode them); however, the present invention includes all fragments, especially of the categories mentioned above are exemplified below.

ANH009 (SEQ ID NO 2): polypeptides comprising, consisting of, or consisting essentially of about amino acids 1–247, 248–378, polypeptide fragments thereof, and polynucleotides encoding said polypeptides;

ANH0024A (SEQ ID NO 4): polypeptides comprising, consisting of, or consisting essentially of about amino acids 1–93, 94–285, 286–781, 285–286, polypeptide fragments thereof, and polynucleotides encoding said polypeptides;

ANH0024B (SEQ ID NO 6): polypeptides comprising, consisting of, or consisting essentially of about amino acids 1–52, 52–53, polypeptide fragments thereof, and polynucleotides encoding said polypeptides;

ANH0024C (SEQ ID NO 8): polypeptides comprising, consisting of, or consisting essentially of about amino acids 1–496, polypeptide fragments thereof, and polynucleotides encoding said polypeptides;

ANH0024D (SEQ ID NO 10): polypeptides comprising, consisting of, or consisting essentially of about amino acids 1–26, polypeptide fragments thereof, and polynucleotides encoding said polypeptides;

ANH0039 (SEQ ID NO 12): polypeptides comprising, consisting of, or consisting essentially of about amino acids 75–137, polypeptide fragments thereof, and polynucleotides encoding said polypeptides;

ANH0068 (SEQ ID NO 14): polypeptides comprising, consisting of, or consisting essentially of about amino acids 1–11, 11–12, 12–297, polypeptide fragments thereof, and polynucleotides encoding said polypeptides;

ANH0114 (SEQ ID NO 16): polypeptides comprising, consisting of, or consisting essentially of about amino acids 345, 444–621, 444–472, 473–621, polypeptide fragments thereof, and polynucleotides encoding said polypeptides;

ANH144A (SEQ ID NO 18): polypeptides comprising, consisting of, or consisting essentially of about amino acids 1–693, 176, 176–177, 610–611, 695–717, 611–693, 938–1070, polypeptide fragments thereof, and polynucleotides encoding said polypeptides;

ANH144B (SEQ ID NO 20): polypeptides comprising, consisting of, or consisting essentially of about amino acids 611–718, 802–803, 1001–1023, polypeptide fragments thereof, and polynucleotides encoding said polypeptides;

ANH144C (SEQ ID NO 22): polypeptides comprising, consisting of, or consisting essentially of about amino acids 177–179, polypeptide fragments thereof, and polynucleotides encoding said polypeptides;

ANH0241 (SEQ ID NO 24): polypeptides comprising, consisting of, or consisting essentially of about amino acids 1–933, 934–1214, polypeptide fragments thereof, and polynucleotides encoding said polypeptides;

ANH0245 (SEQ ID NO 26): polypeptides comprising, consisting of, or consisting essentially of about amino acids 1–18, 18–359, polypeptide fragments thereof, and polynucleotides encoding said polypeptides;

ANH0296 (SEQ ID NO 28): polypeptides comprising, consisting of, or consisting essentially of about amino acids 1–518, 518–519, 519–720, 721–1082, polypeptide fragments thereof, and polynucleotides encoding said polypeptides;

ANH0423 (SEQ ID NO 30): polypeptides comprising, consisting of, or consisting essentially of about amino acids 596–725, polypeptide fragments thereof, and polynucleotides encoding said polypeptides;

ANH0459B (SEQ ID NO 32): polypeptides comprising, consisting of, or consisting essentially of about amino acids 41–80, polypeptide fragments thereof, and polynucleotides encoding said polypeptides;

ANH0459C (SEQ ID NO 34): polypeptides comprising, consisting of, or consisting essentially of about amino acids 1–44, 153–176, 222–245, polypeptide fragments thereof, and polynucleotides encoding said polypeptides;

ANH0769 (SEQ ID NO 38): polypeptides comprising, consisting of, or consisting essentially of about amino acids 1–311, polypeptide fragments thereof, and polynucleotides encoding said polypeptides;

ANH0658 (SEQ ID NO 40): polypeptides comprising, consisting of, or consisting essentially of about amino acids 4–19, polypeptide fragments thereof, and polynucleotides encoding said polypeptides;

ANH0668 (SEQ ID NO 42): polypeptides comprising, consisting of, or consisting essentially of about amino acids 129–130, polypeptide fragments thereof, and polynucleotides encoding said polypeptides;

ANH0757 (SEQ ID NO 44): polypeptides comprising, consisting of, or consisting essentially of about amino acids 1–448, 448–449, 532–639, polypeptide fragments thereof, and polynucleotides encoding said polypeptides;

ANH0687A (SEQ ID NO 46): polypeptides comprising, consisting of, or consisting essentially of about amino acids 99–100, 283–314, polypeptide fragments thereof, and polynucleotides encoding said polypeptides;

ANH0687B (SEQ ID NO 48): polypeptides comprising, consisting of, or consisting essentially of about amino acids 490–491, polypeptide fragments thereof, and polynucleotides encoding said polypeptides;

ANH0693 (SEQ ID NO 50): polypeptides comprising, consisting of, or consisting essentially of about amino acids 1–91, 92–268, polypeptide fragments thereof, and polynucleotides encoding said polypeptides;

ANH0316 (SEQ ID NO 58): polypeptides comprising, consisting of, or consisting essentially of about amino acids 1–25, 25–26, 115–116, 1–116, polypeptide fragments thereof, and polynucleotides encoding said polypeptides.

Nucleic Acids

A mammalian polynucleotide, or fragment thereof, of the present invention is a polynucleotide having a nucleotide sequence obtainable from a natural source. When the species name is used, e.g., human ANH0316, it indicates that the polynucleotide or polypeptide is obtainable from a natural source. It therefore includes naturally-occurring normal, naturally-occurring mutant, and naturally-occurring polymorphic alleles (e.g., SNPs), differentially-spliced transcripts, splice-variants, etc. By the term "naturally-occurring," it is meant that the polynucleotide is obtainable from a natural source, e.g., animal tissue and cells, body fluids, tissue culture cells, forensic samples. Natural sources include, e.g., living cells obtained from tissues and whole organisms, tumors, cultured cell lines, including primary and immortalized cell lines. Naturally-occurring mutations can include deletions (e.g., a truncated amino- or carboxy-terminus), substitutions, inversions, or additions of nucleotide sequence. These genes can be detected and isolated by polynucleotide hybridization according to methods which one skilled in the art would know, e.g., as discussed below.

A polynucleotide according to the present invention can be obtained from a variety of different sources. It can be obtained from DNA or RNA, such as polyadenylated mRNA or total RNA, e.g., isolated from tissues, cells, or whole organism. The polynucleotide can be obtained directly from DNA or RNA, from a cDNA library, from a genomic library, etc. The polynucleotide can be obtained from a cell or tissue (e.g., from an embryonic or adult tissues) at a particular stage of development, having a desired genotype, phenotype, disease status, etc. A polynucleotide which "codes without interruption" refers to a polynucleotide having a continuous open reading frame ("ORF") as compared to an ORF which is interrupted by introns or other noncoding sequences.

Polynucleotides and polypeptides (including any part of the polynucleotides listed in Tables 1–3) can be excluded as compositions from the present invention if, e.g., listed in a publicly available databases on the day this application was filed and/or disclosed in a patent application having an earlier filing or priority date than this application and/or conceived and/or reduced to practice earlier than a polynucleotide in this application.

As described herein, the phrase "an isolated polynucleotide which is SEQ ID NO," or "an isolated polynucleotide which is selected from SEQ ID NO," refers to an isolated nucleic acid molecule from which the recited sequence was derived (e.g., a cDNA derived from mRNA; cDNA derived from genomic DNA). Because of sequencing errors, typographical errors; etc., the actual naturally-occurring sequence may differ from a SEQ ID listed herein. Thus, the phrase indicates the specific molecule from which the sequence was derived, rather than a molecule having that exact recited nucleotide sequence, analogously to how a culture depository number refers to a specific cloned fragment in a cryotube.

As explained in more detail below, a polynucleotide sequence of the invention can contain the complete sequence as shown in SEQ ID NO 1–58, degenerate sequences thereof, anti-sense, muteins thereof, genes comprising said sequences, full-length cDNAs comprising said sequences, complete genomic sequences, fragments thereof, homologs, primers, nucleic acid molecules which hybridize thereto, derivatives thereof, etc.

Genomic

The present invention also relates genomic DNA from which the polynucleotides of the present invention can be derived. A genomic DNA coding for a human, mouse, or other mammalian polynucleotide, can be obtained routinely, for example, by screening a genomic library (e.g., a YAC library) with a polynucleotide of the present invention, or by searching nucleotide databases, such as GenBank and EMBL, for matches. Promoter and other regulatory regions (including both 5' and 3' regions, as well introns) can be identified upstream of coding and expressed RNAs, and assayed routinely for activity, e.g., by joining to a reporter gene (e.g., CAT, GFP, alkaline phosphatase, luciferase, galatosidase). A promoter obtained from a polynucleotide of the present invention can be used, e.g., in gene therapy to obtain tissue-specific expression of a heterologous gene (e.g., coding for a therapeutic product or cytotoxin). 5' and/or 3' sequences can also be used to modulate stability of a nucleic acid, regulate its translation and/or transcription, etc.

Constructs

A polynucleotide of the present invention can comprise additional polynucleotide sequences, e.g., sequences to enhance expression, detection, uptake, cataloging, tagging, etc. A polynucleotide can include only coding sequence; a coding sequence and additional non-naturally occurring or heterologous coding sequence (e.g., sequences coding for leader, signal, secretory, targeting, enzymatic, fluorescent, antibiotic resistance, and other functional or diagnostic peptides); coding sequences and non-coding sequences, e.g., untranslated sequences at either a 5' or 3' end, or dispersed in the coding sequence, e.g., introns.

A polynucleotide according to the present invention also can comprise an expression control sequence operably linked to a polynucleotide as described above. The phrase "expression control sequence" means a polynucleotide sequence that regulates expression of a polypeptide coded for by a polynucleotide to which it is functionally ("operably") linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can include an initiation codon and additional nucleotides to place a partial nucleotide sequence of the present invention in-frame in order to produce a polypeptide (e.g., pET vectors from Promega have been designed to permit a molecule to be inserted into all three reading frames to identify the one that results in polypeptide expression). Expression control sequences can be heterologous or endogenous to the normal gene.

A polynucleotide of the present invention can also comprise nucleic acid vector sequences, e.g., for cloning, expression, amplification, selection, etc. Any effective vector can be used. A vector is, e.g., a polynucleotide molecule which can replicate autonomously in a host cell, e.g., containing an origin of replication. Vectors can be useful to perform manipulations, to propagate, and/or obtain large quantities of the recombinant molecule in a desired host. A skilled worker can select a vector depending on the purpose desired, e.g., to propagate the recombinant molecule in bacteria, yeast, insect, or mammalian cells. The following vectors are provided by way of example. Bacterial: pQE70, pQE60, pQE-9 (Qiagen), pBS, pD10, Phagescript, phiX174, pBK Phagemid, pNH8A, pNH16a, pNH18Z, pNH46A (Stratagene); Bluescript KS+II (Stratagene); ptrc99a, pKK223-3, pKK233-3, pDR540, pRIT5 (Pharmacia). Eukaryotic: PWLNEO, pSV2CAT, pOG44, pXT1, pSG (Stratagene), pSVK3, PBPV, PMSG, pSVL (Pharmacia), pCR2.1/TOPO, pCRII/TOPO, pCR4/TOPO, pTrcHisB, pCMV6-XL4, etc. However, any other vector, e.g., plasmids, viruses, or parts thereof, may be used as long as they are replicable and viable in the desired host. The vector can also comprise sequences which enable it to replicate in the host whose genome is to be modified.

Hybridization

Polynucleotide hybridization, as discussed in more detail below, is useful in a variety of applications, including, in gene detection methods, for identifying mutations, for making mutations, to identify homologs in the same and different species, to identify related members of the same gene family, in diagnostic and prognostic assays, in therapeutic applications (e.g., where an antisense polynucleotide is used to inhibit expression), etc.

The ability of two single-stranded polynucleotide preparations to hybridize together is a measure of their nucleotide sequence complementarity, e.g., base-pairing between nucleotides, such as A-T, G-C, etc. The invention thus also relates to polynucleotides, and their complements, which hybridize to a polynucleotide comprising a nucleotide sequence as set forth in SEQ ID NO 1–58 and genomic sequences thereof. A nucleotide sequence hybridizing to the latter sequence will have a complementary polynucleotide strand, or act as a template for one in the presence of a polymerase (i.e., an appropriate polynucleotide synthesizing enzyme). The present invention includes both strands of polynucleotide, e.g., a sense strand and an anti-sense strand.

Hybridization conditions can be chosen to select polynucleotides which have a desired amount of nucleotide complementarity with the nucleotide sequences set forth in SEQ ID NO 1–58 and genomic sequences thereof. A polynucleotide capable of hybridizing to such sequence, preferably, possesses, e.g., about 70%, 75%, 80%, 85%, 87%, 90%, 92%, 95%, 97%, 99%, or 100% complementarity, between the sequences. The present invention particularly relates to polynucleotide sequences which hybridize to the nucleotide sequences set forth in SEQ ID NO 1–58 or genomic sequences thereof, under low or high stringency conditions. These conditions can be used, e.g., to select corresponding homologs in non-human species.

Polynucleotides which hybridize to polynucleotides of the present invention can be selected in various ways. Filter-type blots (i.e., matrices containing polynucleotide, such as nitrocellulose), glass chips, and other matrices and substrates comprising polynucleotides (short or long) of interest, can be incubated in a prehybridization solution (e.g., 6×SSC, 0.5% SDS, 100 μg/ml denatured salmon sperm DNA, 5×Denhardt's solution, and 50% formamide), at 22–68° C., overnight, and then hybridized with a detectable polynucleotide probe under conditions appropriate to achieve the desired stringency. In general, when high homology or sequence identity is desired, a high temperature can be used (e.g., 65° C.). As the homology drops, lower washing temperatures are used. For salt concentrations, the lower the salt concentration, the higher the stringency. The length of the probe is another consideration. Very short probes (e.g., less than 100 base pairs) are washed at lower temperatures, even if the homology is high. With short probes, formamide can be omitted. See, e.g., *Current Protocols in Molecular Biology,* Chapter 6, Screening of Recombinant Libraries; Sambrook et al., *Molecular Cloning,* 1989, Chapter 9.

For instance, high stringency conditions can be achieved by incubating the blot overnight (e.g., at least 12 hours) with a long polynucleotide probe in a hybridization solution containing, e.g., about 5×SSC, 0.5% SDS, 100 μg/ml denatured salmon sperm DNA and 50% formamide, at 42° C. Blots can be washed at high stringency conditions that allow, e.g., for less than 5% bp mismatch (e.g., wash twice in 0.1% SSC and 0.1% SDS for 30 min at 65° C.), i.e., selecting sequences having 95% or greater sequence identity.

Other non-limiting examples of high stringency conditions includes a final wash at 65° C. in aqueous buffer containing 30 mM NaCl and 0.5% SDS. Another example of high stringent conditions is hybridization in 7% SDS, 0.5 M NaPO$_4$, pH 7, 1 mM EDTA at 50° C., e.g., overnight, followed by one or more washes with a 1% SDS solution at 42° C. Whereas high stringency washes can allow for less than 5% mismatch, reduced or low stringency conditions can permit up to 20% nucleotide mismatch. Hybridization at low stringency can be accomplished as above, but using lower formamide conditions, lower temperatures and/or lower salt concentrations, as well as longer periods of incubation time.

Hybridization can also be based on a calculation of melting temperature (Tm) of the hybrid formed between the probe and its target, as described in Sambrook et al. Generally, the temperature Tm at which a short oligonucleotide (containing 18 nucleotides or fewer) will melt from its target sequence is given by the following equation: Tm=(number of A's and T's)×2° C.+(number of C's and G's)×4° C. For longer molecules, Tm=81.5+16.6 log$_{10}$[Na$^{30}$]+0.41 (%GC)−600/N where [Na$^+$] is the molar concentration of sodium ions, %GC is the percentage of GC base pairs in the probe, and N is the length. Hybridization can be carried out at several degrees below this temperature to ensure that the probe and target can hybridize. Mismatches can be allowed for by lowering the temperature even further.

Stringent conditions can be selected to isolate sequences, and their complements, which have, e.g., at least about 90%, 95%, or 97%, nucleotide complementarity between the probe (e.g., a short polynucleotide of SEQ ID NO 1–58 or genomic sequences thereof) and a target polynucleotide.

Other homologs of polynucleotides of the present invention can be obtained from mammalian and non-mammalian sources according to various methods. For example, hybridization with a polynucleotide can be employed to select homologs, e.g., as described in Sambrook et al., *Molecular Cloning,* Chapter 11, 1989. Such homologs can have varying amounts of nucleotide and amino acid sequence identity and similarity to such polynucleotides of the present invention. Mammalian organisms include, e.g., mice, rats, monkeys, pigs, cows, etc. Non-mammalian organisms include, e.g., vertebrates, invertebrates, zebra fish, chicken, Drosophila, *C. elegans,* Xenopus, yeast such as *S. pombe, S. cerevisiae,* roundworms, prokaryotes, plants, Arabidopsis, artemia, viruses, etc.

Alignment

Alignments can be accomplished by using any effective algorithm. For pairwise alignments of DNA sequences, the methods described by Wilbur-Lipman (e.g., Wilbur and Lipman, *Proc. Natl. Acad. Sci.*, 80:726–730, 1983) or Martinez/Needleman-Wunsch (e.g., Martinez, *Nucleic Acid Res.*, 11:4629–4634, 1983) can be used. For instance, if the Martinez/Needleman-Wunsch DNA alignment is applied, the minimum match can be set at 9, gap penalty at 1.10, and gap length penalty at 0.33. The results can be calculated as a similarity index, equal to the sum of the matching residues divided by the sum of all residues and gap characters, and then multiplied by 100 to express as a percent. Similarity index for related genes at the nucleotide level in accordance with the present invention can be greater than 70%, 80%, 85%, 90%, 95%, 99%, or more. Pairs of protein sequences can be aligned by the Lipman-Pearson method (e.g., Lipman and Pearson, *Science*, 227:1435–1441, 1985) with k-tuple set at 2, gap penalty set at 4, and gap length penalty set at 12. Results can be expressed as percent similarity index, where related genes at the amino acid level in accordance with the present invention can be greater than 65%, 70%, 75%, 80%, 85%, 90%, 95%, 99%, or more. Various commercial and free sources of alignment programs are available, e.g., MegAlign by DNA Star, BLAST (National Center for Biotechnology Information), BCM (Baylor College of Medicine) Launcher, etc. BLAST can be used to calculate amino acid sequence identity, amino acid sequence homology, and nucleotide sequence identity. These calculations can be made along the entire length of each of the target sequences which are to be compared.

After two sequences have been aligned, a "percent sequence identity" can be determined. For these purposes, it is convenient to refer to a Reference Sequence and a Compared Sequence, where the Compared Sequence is compared to the Reference Sequence. Percent sequence identity can be determined according to the following formula: Percent Identity=$100[1-(C/R)]$, wherein C is the number of differences between the Reference Sequence and the Compared Sequence over the length of alignment between the Reference Sequence and the Compared Sequence where (i) each base or amino acid in the Reference Sequence that does not have a corresponding aligned base or amino acid in the Compared Sequence, (ii) each gap in the Reference Sequence, (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

Percent sequence identity can also be determined by other conventional methods, e.g., as described in Altschul et al., *Bull. Math. Bio.* 48:603–616, 1986 and Henikoff and Henikoff, *Proc. Natl. Acad. Sci. USA* 89:10915–10919, 1992.

Specific Polynucleotide Probes

A polynucleotide of the present invention can comprise any continuous nucleotide sequence of SEQ ID NO 1–58, sequences which share sequence identity thereto, or complements thereof The term "probe" refers to any substance that can be used to detect, identify, isolate, etc., another substance. A polynucleotide probe is comprised of nucleic acid can be used to detect, identify, etc., other nucleic acids, such as DNA and RNA.

These polynucleotides can be of any desired size that is effective to achieve the specificity desired. For example, a probe can be from about 7 or 8 nucleotides to several thousand nucleotides, depending upon its use and purpose. For instance, a probe used as a primer PCR can be shorter than a probe used in an ordered array of polynucleotide probes. Probe sizes vary, and the invention is not limited in any way by their size, e.g., probes can be from about 7–2000 nucleotides, 7–1000, 8–700, 8–600, 8–500, 8–400, 8–300, 8–150, 8–100, 8–75, 7–50, 10–25, 14–16, at least about 8, at least about 10, at least about 15, at least about 25, etc. The polynucleotides can have non-naturally-occurring nucleotides, e.g., inosine, AZT, 3TC, etc. The polynucleotides can have 100% sequence identity or complementarity to a sequence of SEQ ID NO 1–58, or it can have mismatches or nucleotide substitutions, e.g., 1, 2, 3, 4, or 5 substitutions. The probes can be single-stranded or double-stranded.

In accordance with the present invention, a polynucleotide can be present in a kit, where the kit includes, e.g., one or more polynucleotides, a desired buffer (e.g., phosphate, tris, etc.), detection compositions, RNA or cDNA from different tissues to be used as controls, libraries, etc. The polynucleotide can be labeled or unlabeled, with radioactive or non-radioactive labels as known in the art. Kits can comprise one or more pairs of polynucleotides for amplifying nucleic acids specific for angiogenesis genes of the present invention, e.g., comprising a forward and reverse primer effective in PCR. These include both sense and anti-sense orientations. For instance, in PCR-based methods (such as RT-PCR), a pair of primers are typically used, one having a sense sequence and the other having an antisense sequence.

Another aspect of the present invention is a nucleotide sequence that is specific to, or for, a selective polynucleotide. The phrases "specific for" or "specific to" a polynucleotide have a functional meaning that the polynucleotide can be used to identify the presence of one or more target genes in a sample and distinguish them from non-target genes. It is specific in the sense that it can be used to detect polynucleotides above background noise ("non-specific binding"). A specific sequence is a defined order of nucleotides (or amino acid sequences, if it is a polypeptide sequence) which occurs in the polynucleotide, e.g., in the nucleotide sequences of SEQ ID NO 1–58, and which is characteristic of that target sequence, and substantially no non-target sequences. A probe or mixture of probes can comprise a sequence or sequences that are specific to a plurality of target sequences, e.g., where the sequence is a consensus sequence, a functional domain, etc., e.g., capable of recognizing a family of related genes. Such sequences can be used as probes in any of the methods described herein or incorporated by reference. Both sense and antisense nucleotide sequences are included. A specific polynucleotide according to the present invention can be determined routinely.

A polynucleotide comprising a specific sequence can be used as a hybridization probe to identify the presence of, e.g., human or mouse polynucleotide, in a sample comprising a mixture of polynucleotides, e.g., on a Northern blot. Hybridization can be performed under high stringent conditions (see, above) to select polynucleotides (and their complements which can contain the coding sequence) having at least 90%, 95%, 99%, etc., identity (i.e., complementarity) to the probe, but less stringent conditions can also be used. A specific polynucleotide sequence can also be fused in-frame, at either its 5' or 3' end, to various nucleotide sequences as mentioned throughout the patent, including coding sequences for enzymes, detectable markers, GFP, etc, expression control sequences, etc.

A polynucleotide probe, especially one that is specific to a polynucleotide of the present invention, can be used in gene detection and hybridization methods as already described. In one embodiment, a specific polynucleotide probe can be used to detect whether a particular tissue or cell-type is present in a target sample. To carry out such a method, a selective polynucleotide can be chosen which is characteristic of the desired target tissue. Such polynucleotide is preferably chosen so that it is expressed or displayed in the target tissue, but not in other tissues which are present in the sample. For instance, if detection of vascular is desired, it may not matter whether the selective polynucleotide is expressed in other tissues, as long as it is not expressed in cells normally present in blood, e.g., peripheral blood mononuclear cells. Starting from the selective polynucleotide, a specific polynucleotide probe can be designed which hybridizes (if hybridization is the basis of the assay) under the hybridization conditions to the selective polynucleotide, whereby the presence of the selective polynucleotide can be determined.

Probes which are specific for polynucleotides of the present invention can also be prepared using involve transcription-based systems, e.g., incorporating an RNA polymerase promoter into a selective polynucleotide of the present invention, and then transcribing anti-sense RNA using the polynucleotide as a template. See, e.g., U.S. Pat. No. 5,545,522.

Polynucleotide Composition

A polynucleotide according to the present invention can comprise, e.g., DNA, RNA, synthetic polynucleotide, peptide polynucleotide, modified nucleotides, dsDNA, ssDNA, ssRNA, dsRNA, and mixtures thereof. A polynucleotide can be single- or double-stranded, triplex, DNA:RNA, duplexes, comprise hairpins, and other secondary structures, etc. Nucleotides comprising a polynucleotide can be joined via various known linkages, e.g., ester, sulfamate, sulfamide, phosphorothioate, phosphoramidate, methylphosphonate, carbamate, etc., depending on the desired purpose, e.g., resistance to nucleases, such as RNAse H, improved in vivo stability, etc. See, e.g., U.S. Pat. No. 5,378,825. Any desired nucleotide or nucleotide analog can be incorporated, e.g., 6-mercaptoguanine, 8-oxo-guanine, etc.

Various modifications can be made to the polynucleotides, such as attaching detectable markers (avidin, biotin, radioactive elements, fluorescent tags and dyes, energy transfer labels, energy-emitting labels, binding partners, etc.) or moieties which improve hybridization, detection, and/or stability. The polynucleotides can also be attached to solid supports, e.g., nitrocellulose, magnetic or paramagnetic microspheres (e.g., as described in U.S. Pat. Nos. 5,411,863; 5,543,289; for instance, comprising ferromagnetic, supermagnetic, paramagnetic, superparamagnetic, iron oxide and polysaccharide), nylon, agarose, diazotized cellulose, latex solid microspheres, polyacrylamides, etc., according to a desired method. See, e.g., U.S. Pat. Nos. 5,470,967, 5,476,925, and 5,478,893.

Polynucleotide according to the present invention can be labeled according to any desired method. The polynucleotide can be labeled using radioactive tracers such as $^{32}$P, $^{35}$S, $^{3}$H, or $^{14}$C, to mention some commonly used tracers. The radioactive labeling can be carried out according to any method, such as, for example, terminal labeling at the 3' or 5' end using a radiolabeled nucleotide, polynucleotide kinase (with or without dephosphorylation with a phosphatase) or a ligase (depending on the end to be labeled). A non-radioactive labeling can also be used, combining a polynucleotide of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

Nucleic Acid Detection Methods

Another aspect of the present invention relates to methods and processes for detecting angiogenesis genes of the present invention. Detection methods have a variety of applications, including for diagnostic, prognostic, forensic, and research applications. To accomplish gene detection, a polynucleotide in accordance with the present invention can be used as a "probe." The term "probe" or "polynucleotide probe" has its customary meaning in the art, e.g., a polynucleotide which is effective to identify (e.g., by hybridization), when used in an appropriate process, the presence of a target polynucleotide to which it is designed. Identification can involve simply determining presence or absence, or it can be quantitative, e.g., in assessing amounts of a gene or gene transcript present in a sample. Probes can be useful in a variety of ways, such as for diagnostic purposes, to identify homologs, and to detect, quantitate, or isolate a polynucleotide of the present invention in a test sample.

Assays can be utilized which permit quantification and/or presence/absence detection of a target nucleic acid in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g., Saiki et al., *Science,* 241:53, 1988; U.S. Pat. Nos. 4,683,195, 4,683,202, and 6,040,166; *PCR Protocols: A Guide to Methods and Applications,* Innis et al., eds., Academic Press, New York, 1990), reverse transcriptase polymerase chain reaction ("RT-PCR"), anchored PCR, rapid amplification of cDNA ends ("RACE") (e.g., Schaefer in *Gene Cloning and Analysis: Current Innovations,* Pages 99–115, 1997), ligase chain reaction ("LCR") (EP 320 308), one-sided PCR (Ohara et al., *Proc. Natl. Acad. Sci.,* 86:5673–5677, 1989), indexing methods (e.g., U.S. Pat. No. 5,508,169), in situ hybridization, differential display (e.g., Liang et al., *Nucl. Acid. Res.,* 21:3269–3275, 1993; U.S. Pat. Nos. 5,262,311, 5,599,672 and 5,965,409; WO097/18454; Prashar and Weissman, *Proc. Natl. Acad. Sci.,* 93:659–663, and U.S. Pat. Nos. 6,010,850 and 5,712,126; Welsh et al., *Nucleic Acid Res.,* 20:4965–4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO 88/10315), polynucleotide arrays (e.g., U.S. Pat. Nos. 5,143,854, 5,424,186; 5,700,637, 5,874,219, and 6,054,270; PCT WO 92/10092; PCT WO 90/15070), Qbeta Replicase (PCT/US87/00880), Strand Displacement Amplification ("SDA"), Repair Chain Reaction ("RCR"), nuclease protection assays, subtraction-based methods, Rapid-Scan™, etc. Additional useful methods include, but are not limited to, e.g., template-based amplification methods, competitive PCR (e.g., U.S. Pat. No. 5,747,251), redox-based assays (e.g., U.S. Pat. No. 5,871, 918), Taqman-based assays (e.g., Holland et al., *Proc. Natl. Acad, Sci.,* 88:7276–7280, 1991; U.S. Pat. Nos. 5,210,015 and 5,994,063), real-time fluorescence-based monitoring (e.g., U.S. Pat. 5,928,907), molecular energy transfer labels (e.g., U.S. Pat. Nos. 5,348,853, 5,532,129, 5,565,322, 6,030, 787, and 6,117,635; Tyagi and Kramer, *Nature Biotech.,*

14:303–309, 1996). Any method suitable for single cell analysis of gene or protein expression can be used, including in situ hybridization, immunocytochemistry, MACS, FACS, flow cytometry, etc. For single cell assays, expression products can be measured using antibodies, PCR, or other types of nucleic acid amplification (e.g., Brady et al., *Methods Mol. & Cell. Biol.* 2, 17–25, 25, 1990; Eberwine et al., 1992, *Proc. Natl. Acad. Sci.,* 89, 3010–3014, 1992; U.S. Pat. No. 5,723,290). These and other methods can be carried out conventionally, e.g., as described in the mentioned publications.

Many of such methods may require that the polynucleotide is labeled, or comprises a particular nucleotide type useful for detection. The present invention includes such modified polynucleotides that are necessary to carry out such methods. Thus, polynucleotides can be DNA, RNA, DNA:RNA hybrids, PNA, etc., and can comprise any modification or substituent which is effective to achieve detection.

Detection can be desirable for a variety of different purposes, including research, diagnostic, prognostic, and forensic. For diagnostic purposes, it may be desirable to identify the presence or quantity of a polynucleotide sequence in a sample, where the sample is obtained from tissue, cells, body fluids, etc. In a preferred method as described in more detail below, the present invention relates to a method of detecting a polynucleotide comprising, contacting a target polynucleotide in a test sample with a polynucleotide probe under conditions effective to achieve hybridization between the target and probe; and detecting hybridization.

Any test sample in which it is desired to identify a polynucleotide or polypeptide thereof can be used, including, e.g., blood, urine, saliva, stool (for extracting nucleic acid, see, e.g., U.S. Pat. No. 6,177,251), swabs comprising tissue, biopsied tissue, tissue sections, cultured cells, etc.

Detection can be accomplished in combination with polynucleotide probes for other genes, e.g., genes which are expressed in other disease states, tissues, cells, such as brain, heart, kidney, spleen, thymus, liver, stomach, small intestine, colon, muscle, lung, testis, placenta, pituitary, thyroid, skin, adrenal gland, pancreas, salivary gland, uterus, ovary, prostate gland, peripheral blood cells (T-cells, lymphocytes, etc.), embryo, normal breast fat, adult and embryonic stem cells, specific cell-types, such as endothelial, epithelial, myocytes, adipose, luminal epithelial, basoepithelial, myoepithelial, stromal cells, etc.

Polynucleotides can be used in wide range of methods and compositions, including for detecting, diagnosing, staging, grading, assessing, prognosticating, etc. diseases and disorders associated with angiogenesis genes and polypeptides of the present invention, for monitoring or assessing therapeutic and/or preventative measures, in ordered arrays, etc. Any method of detecting genes and polynucleotides represented by SEQ ID NO 1–58, and variations thereof, can be used; certainly, the present invention is not to be limited how such methods are implemented.

Along these lines, the present invention relates to methods of detecting angiogenesis genes of the present invention in a sample comprising nucleic acid. Such methods can comprise one or more the following steps in any effective order, e.g., contacting said sample with a polynucleotide probe under conditions effective for said probe to hybridize specifically to nucleic acid in said sample, and detecting the presence or absence of probe hybridized to nucleic acid in said sample, wherein said probe can be a polynucleotide selected from SEQ ID NO 1–58, a polynucleotide having, e.g., about 70%, 80%, 85%, 90%, 95%, 99%, or more sequence identity thereto, effective or specific fragments thereof, or complements thereto. The detection method can be applied to any sample, e.g., cultured primary, secondary, or established cell lines, tissue biopsy, blood, urine, stool, cerebral spinal fluid, and other bodily fluids, for any purpose.

Contacting the sample with probe can be carried out by any effective means in any effective environment. It can be accomplished in a solid, liquid, frozen, gaseous, amorphous, solidified, coagulated, colloid, etc., mixtures thereof, matrix. For instance, a probe in an aqueous medium can be contacted with a sample which is also in an aqueous medium, or which is affixed to a solid matrix, or vice-versa.

Generally, as used throughout the specification, the term "effective conditions" means, e.g., the particular milieu in which the desired effect is achieved. Such a milieu, includes, e.g., appropriate buffers, oxidizing agents, reducing agents, pH, co-factors, temperature, ion concentrations, suitable age and/or stage of cell (such as, in particular part of the cell cycle, or at a particular stage where particular genes are being expressed) where cells are being used, culture conditions (including substrate, oxygen, carbon dioxide, etc.). When hybridization is the chosen means of achieving detection, the probe and sample can be combined such that the resulting conditions are functional for said probe to hybridize specifically to nucleic acid in said sample.

The phrase "hybridize specifically" indicates that the hybridization between single-stranded polynucleotides is based on nucleotide sequence complementarity. The effective conditions are selected such that the probe hybridizes to a preselected and/or definite target nucleic acid in the sample. For instance, if detection of a polynucleotide set forth in SEQ ID NO 1–58, or a polymorphism thereof, is desired, a probe can be selected which can hybridize to such target gene under high stringent conditions, without significant hybridization to other genes in the sample. To detect homologs of a polynucleotide set forth in SEQ ID NO 1–58, the effective hybridization conditions can be less stringent, and/or the probe can comprise codon degeneracy, such that a homolog is detected in the sample.

As already mentioned, the methods can be carried out by any effective process, e.g., by Northern blot analysis, polymerase chain reaction (PCR), reverse transcriptase PCR, RACE PCR, in situ hybridization, etc., as indicated above. When PCR based techniques are used, two or more probes are generally used. One probe can be specific for a defined sequence which is characteristic of a selective polynucleotide, but the other probe can be specific for the selective polynucleotide, or specific for a more general sequence, e.g., a sequence such as polyA which is characteristic of mRNA, a sequence which is specific for a promoter, ribosome binding site, or other transcriptional features, a consensus sequence (e.g., representing a functional domain). For the former aspects, 5' and 3' probes (e.g., polyA, Kozak, etc.) are preferred which are capable of specifically hybridizing to the ends of transcripts. When PCR is utilized, the probes can also be referred to as "primers" in that they can prime a DNA polymerase reaction.

In addition to testing for the presence or absence of polynucleotides, the present invention also relates to determining the amounts at which polynucleotides of the present invention are expressed in sample and determining the differential expression of such polynucleotides in samples. Such methods can involve substantially the same steps as described above for presence/absence detection, e.g., contacting with probe, hybridizing, and detecting hybridized probe, but using more quantitative methods and/or comparisons to standards.

The amount of hybridization between the probe and target can be determined by any suitable methods, e.g., PCR, RT-PCR, RACE PCR, Northern blot, polynucleotide microarrays, Rapid-Scan, etc., and includes both quantitative and qualitative measurements. For further details, see the hybridization methods described above and below. Determining by such hybridization whether the target is differentially expressed (e.g., up-regulated or down-regulated) in the sample can also be accomplished by any effective means. For instance, the target's expression pattern in the sample can be compared to its pattern in a known standard, such as in a normal tissue, or it can be compared to another gene in the same sample. When a second sample is utilized for the comparison, it can be a sample of normal tissue that is known not to contain diseased cells. The comparison can be performed on samples which contain the same amount of RNA (such as polyadenylated RNA or total RNA), or, on RNA extracted from the same amounts of starting tissue. Such a second sample can also be referred to as a control or standard. Hybridization can also be compared to a second target in the same tissue sample. Experiments can be performed that determine a ratio between the target nucleic acid and a second nucleic acid (a standard or control), e.g., in a normal tissue. When the ratio between the target and control are substantially the same in a normal and sample, the sample is determined or diagnosed not to contain cells. However, if the ratio is different between the normal and sample tissues, the sample is determined to contain cancer cells. The approaches can be combined, and one or more second samples, or second targets can be used. Any second target nucleic acid can be used as a comparison, including "housekeeping" genes, such as beta-actin, alcohol dehydrogenase, or any other gene whose expression does not vary depending upon the disease status of the cell.

Methods of Identifying Polymorphisms, Mutations, etc., of Angiogenesis Genes of the Present Invention Polynucleotides of the present invention can also be utilized to identify mutant alleles, SNPs, gene rearrangements and modifications, and other polymorphisms of the wild-type gene. Mutant alleles, polymorphisms, SNPs, etc., can be identified and isolated from cancers that are known, or suspected to have, a genetic component. Identification of such genes can be carried out routinely (see, above for more guidance), e.g., using PCR, hybridization techniques, direct sequencing, mismatch reactions (see, e.g., above), RFLP analysis, SSCP (e.g., Orita et al., *Proc. Natl. Acad. Sci.,* 86:2766, 1992), etc., where a polynucleotide having a sequence selected from SEQ ID NO 1–58, and variations thereof, are used as a probe. The selected mutant alleles, SNPs, polymorphisms, etc., can be used diagnostically to determine whether a subject has, or is susceptible to a disorder associated with a gene of the present invention, as well as to design therapies and predict the outcome of the disorder. Methods involve, e.g., diagnosing a disorder associated with an angiogenesis polynucleotide or polypeptide, or determining susceptibility to a disorder, comprising, detecting the presence of a mutation in a gene represented by a polynucleotide selected from SEQ ID NO 1–58, and variations thereof. The detecting can be carried out by any effective method, e.g., obtaining cells from a subject, determining the gene sequence or structure of a target gene (using, e.g., mRNA, cDNA, genomic DNA, etc), comparing the sequence or structure of the target gene to the structure of the normal gene, whereby a difference in sequence or structure indicates a mutation in the gene in the subject. Polynucleotides can also be used to test for mutations, SNPs, polymorphisms, etc., e.g., using mismatch DNA repair technology as described in U.S. Pat. No. 5,683,877; U.S. Pat. No. 5,656,430; Wu et al., *Proc. Natl. Acad. Sci.,* 89:8779–8783, 1992.

The present invention also relates to methods of detecting polymorphisms in angiogenesis genes of the present invention, comprising, e.g., comparing the structure of: genomic DNA comprising all or part of an angiogenesis gene of the present invention, mRNA comprising all or part of an angiogenesis gene of the present invention, cDNA comprising all or part of an angiogenesis gene of the present invention, or a polypeptide comprising all or part of an angiogenesis gene of the present invention, with the structure of an angiogenesis gene of the present invention, e.g., as set forth in SEQ ID NO 1–58. The methods can be carried out on a sample from any source, e.g., cells, tissues, body fluids, blood, urine, stool, hair, egg, sperm, etc.

These methods can be implemented in many different ways. For example, "comparing the structure" steps include, but are not limited to, comparing restriction maps, nucleotide sequences, amino acid sequences, RFLPs, DNase sites, DNA methylation fingerprints (e.g., U.S. Pat. No. 6,214,556), protein cleavage sites, molecular weights, electrophoretic mobilities, charges, ion mobility, etc., between a standard gene (e.g., SEQ ID NO 1–58) and a polymorphism. The term "structure" can refer to any physical characteristics or configurations which can be used to distinguish between nucleic acids and polypeptides. The methods and instruments used to accomplish the comparing step depends upon the physical characteristics which are to be compared. Thus, various techniques are contemplated, including, e.g., sequencing machines (both amino acid and polynucleotide), electrophoresis, mass spectrometer (U.S. Pat. Nos. 6,093,541, 6,002,127), liquid chromatography, HPLC, etc.

To carry out such methods, "all or part" of the gene or polypeptide can be compared. For example, if nucleotide sequencing is utilized, the entire gene can be sequenced, including promoter, introns, and exons, or only parts of it can be sequenced and compared, e.g., exon 1, exon 2, etc.

Mutagenesis

Mutated polynucleotide sequences of the present invention are useful for various purposes, e.g., to create mutations of the polypeptides they encode, to identify functional regions of genomic DNA, to produce probes for screening libraries, etc. Mutagenesis can be carried out routinely according to any effective method, e.g., oligonucleotide-directed (Smith, M., *Ann. Rev. Genet.* 19:423–463, 1985), degenerate oligonucleotide-directed (Hill et al., *Method Enzymology,* 155:558–568, 1987), region-specific (Myers et al., *Science,* 229:242–246, 1985; Derbyshire et al., *Gene,* 46:145, 1986; Ner et al., *DNA,* 7:127, 1988), linker-scanning (McKnight and Kingsbury, *Science,* 217:316–324, 1982), directed using PCR, recursive ensemble mutagenesis (Arkin and Yourvan, *Proc. Natl. Acad. Sci.,* 89:7811–7815, 1992), random mutagenesis (e.g., U.S. Pat. Nos. 5,096,815; 5,198,346; and 5,223,409), site-directed mutagenesis (e.g., Walder et al., *Gene,* 42:133, 1986; Bauer et al., *Gene,* 37:73, 1985; Craik, *Bio Techniques,* Jan. 12–19, 1985, Smith et al., *Genetic Engineering: Principles and Methods,* Plenum Press, 1981), phage display (e.g., Lowman et al., *Biochem.* 30:10832–10837, 1991; Ladner et al., U.S. Pat. No. 5,223,409; Huse, WIPO Publication WO 92/06204), etc. Desired sequences can also be produced by the assembly of target sequences using mutually priming oligonucleotides (Uhlmann, *Gene,* 71:29–40, 1988). For directed mutagenesis methods, analysis of the three-dimensional structure of a polypeptide can be used to guide and facilitate making mutants which effect polypeptide activity. Sites of substrate-enzyme interaction or other biological activities can also be determined by analysis of crystal structure as determined by such techniques as nuclear magnetic resonance, crystallography or photoaffinity labeling. See, for example, de Vos et al., Science 255:306–312, 1992; Smith et al., J. Mol. Biol. 224:899–904, 1992; Wlodaver et al., FEBS Lett. 309:59–64, 1992.

In addition, libraries of angiogenesis genes and fragments thereof can be used for screening and selection of variants. For instance, a library of coding sequences can be generated by treating a double-stranded DNA with a nuclease under conditions where the nicking occurs, e.g., only once per molecule, denaturing the double-stranded DNA, renaturing it to for double-stranded DNA that can include sense/antisense pairs from different nicked products, removing single-stranded portions from reformed duplexes by treatment with S1 nuclease, and ligating the resulting DNAs into an expression vecore. By this method, expression libraries can be made comprising a "mutagenized" gene. The entire coding sequence or parts thereof can be used.

Polynucleotide Expression, Polypeptides Produced Thereby, and Specific-binding Partners Thereto.

A polynucleotide according to the present invention can be expressed in a variety of different systems, in vitro and in vivo, according to the desired purpose. For example, a polynucleotide can be inserted into an expression vector, introduced into a desired host, and cultured under conditions effective to achieve expression of a polypeptide coded for by the polynucleotide, to search for specific binding partners. Effective conditions include any culture conditions which are suitable for achieving production of the polypeptide by the host cell, including effective temperatures, pH, medium, additives to the media in which the host cell is cultured (e.g., additives which amplify or induce expression such as butyrate, or methotrexate if the coding polynucleotide is adjacent to a dhfr gene), cycloheximide, cell densities, culture dishes, etc. A polynucleotide can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which a polynucleotide of the present invention has been introduced is a transformed host cell. The polynucleotide can be extrachromosomal or integrated into a chromosome(s) of the host cell. It can be stable or transient. An expression vector is selected for its compatibility with the host cell. Host cells include, mammalian cells, e.g., COS, CV1, BHK, CHO, HeLa, LTK, NIH 3T3, 293, endothelial, epithelial, muscle, embryonic and adult stem cells, ectodermal, mesenchymal, endodermal, neoplastic, blood, bovine CPAE (CCL-209), bovine FBHE (CRL-1395), human HUV-EC-C (CRL-1730), mouse SVEC4-10EHR1 (CRL-2161), mouse MS1 (CRL-2279), mouse MS1 VEGF (CRL-2460), insect cells, such as Sf9 (*S. frugipeda*) and Drosophila, bacteria, such as *E. coli,* Streptococcus, bacillus, yeast, such as Sacharomyces, *S. cerevisiae,* fungal cells, plant cells, embryonic or adult stem cells (e.g., mammalian, such as mouse or human).

Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, MMTV, SV40, trp, lac, tac, or T7 promoters for bacterial hosts; or alpha factor, alcohol oxidase, or PGH promoters for yeast. RNA promoters can be used to produced RNA transcripts, such as T7 or SP6. See, e.g., Melton et al., *Polynucleotide Res.,* 12(18):7035–7056, 1984; Dunn and Studier. *J. Mol. Bio.,* 166:477–435, 1984; U.S. Pat. No. 5,891,636; Studier et al., *Gene Expression Technology, Methods in Enzymology,* 85:60–89, 1987. In addition, as discussed above, translational signals (including in-frame insertions) can be included.

When a polynucleotide is expressed as a heterologous gene in a transfected cell line, the gene is introduced into a cell as described above, under effective conditions in which the gene is expressed. The term "heterologous" means that the gene has been introduced into the cell line by the "hand-of-man." Introduction of a gene into a cell line is discussed above. The transfected (or transformed) cell expressing the gene can be lysed or the cell line can be used intact.

For expression and other purposes, a polynucleotide can contain codons found in a naturally-occurring gene, transcript, or cDNA, for example, e.g., as set forth in SEQ ID NO 1–58, or it can contain degenerate codons coding for the same amino acid sequences. For instance, it may be desirable to change the codons in the sequence to optimize the sequence for expression in a desired host. See, e.g., U.S. Pat. Nos. 5,567,600 and 5,567,862.

A polypeptide according to the present invention can be recovered from natural sources, transformed host cells (culture medium or cells) according to the usual methods, including, detergent extraction (e.g., non-ionic detergent, Triton X-100, CHAPS, octylglucoside, Igepal CA-630), ammonium sulfate or ethanol precipitation, acid extraction, anion or cation exchange chromatography, phosphocellulose chromatography, hydrophobic interaction chromatography, hydroxyapatite chromatography, lectin chromatography, gel electrophoresis. Protein refolding steps can be used, as necessary, in completing the configuration of the mature protein. Finally, high performance liquid chromatography (HPLC) can be employed for purification steps. Another approach is express the polypeptide recombinantly with an affinity tag (Flag epitope, HA epitope, myc epitope, 6×His, maltose binding protein, chitinase, etc) and then purify by anti-tag antibody-conjugated affinity chromatography.

The present invention also relates to polypeptides of angiogenesis genes of the present invention, e.g., an isolated human polypeptide comprising or having the amino acid sequence set forth in SEQ ID NO 1–58, an isolated polypeptide comprising an amino acid sequence having at least about 98%, 99%, or more amino acid sequence identity to the amino acid sequence set forth in SEQ ID NO 1–58, and optionally having one or more of its activities.

Fragments specific to these polypeptides can also used, e.g., to produce antibodies or other immune responses, as well as competitors, agonists, antagonists, and ligands. These fragments can be referred to as being "specific for" the targeted gene. The latter phrase, as already defined, indicates that the peptides are characteristic of the targeted gene, and that the defined sequences are substantially absent from all other protein types. Such polypeptides can be of any size which is necessary to confer specificity, e.g., 5, 8, 10, 12, 15, 20, etc.

The present invention also relates to antibodies, and other specific-binding partners, which are specific for polypeptides encoded by polynucleotides of the present invention. Antibodies, e.g., polyclonal, monoclonal, recombinant, chimeric, humanized, single-chain, Fab, and fragments thereof, can be prepared according to any desired method. See, also, screening recombinant immunoglobulin libraries (e.g., Orlandi et al., Proc. Natl. Acad. Sci., 86:3833–3837, 1989; Huse et al., Science, 256:1275–1281, 1989); in vitro stimulation of lymphocyte populations; Winter and Milstein, Nature, 349: 293–299, 1991. The antibodies can be IgM, IgG, subtypes, IgG2a, IgG1, etc. Antibodies, and immune responses, can also be generated by administering naked DNA See, e.g., U.S. Pat. Nos. 5,703,055; 5,589,466; 5,580, 859. Antibodies can be used from any source, including, goat, rabbit, mouse, chicken (e.g., IgY; see, Duan, W0/029444 for methods of making antibodies in avian hosts, and harvesting the antibodies from the eggs). An antibody specific for a polypeptide means that the antibody recognizes a defined sequence of amino acids within or including the polypeptide. Other specific binding partners include, e.g., aptamers and PNA. Antibodies can be prepared against specific epitopes or domains, e.g., as identified above.

The preparation of polyclonal antibodies is well-known to those skilled in the art. See, for example, Green et al., Production of Polyclonal Antisera, in IMMUNOCHEMICAL PROTOCOLS (Manson, ed.), pages 1–5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992). The preparation of monoclonal antibodies likewise is conventional. See, for example, Kohler & Milstein, Nature 256:495 (1975); Coligan et al., sections 2.5.1–2.6.7; and Harlow et al., ANTIBODIES: A LABORATORY MANUAL, page 726 (Cold Spring Harbor Pub. 1988).

Antibodies can also be humanized, e.g., where they are to be used therapeutically. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat Acad. Sci. USA 86:3833 (1989), which is hereby incorporated in its entirety by reference. Techniques for producing humanized monoclonal antibodies are described, for example, in U.S. Pat. No. 6,054,297, Jones et al., Nature 321: 522 (1986); Riechmann et al., Nature 332: 323 (1988); Verhoeyen et al., Science 239: 1534 (1988); Carter et al., Proc. Nat'l Acad. Sci. USA 89: 4285 (1992); Sandhu, Crit. Rev. Biotech. 12: 437 (1992); and Singer et al., J. Immunol. 150: 2844 (1993).

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., Ann. Rev. Immunol. 12: 433 (1994). Cloning and expression vectors that are useful for producing a human immunoglobulin phage library can be obtained commercially, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described, e.g., in Green et al., Nature Genet. 7:13 (1994); Lonberg et al., Nature 368:856 (1994); and Taylor et al., Int. Immunol. 6:579 (1994).

Antibody fragments of the present invention can be prepared by proteolytic hydrolysis of the antibody or by expression in $E.$ $coli$ of nucleic acid encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab').sub.2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and No. 4,331,647, and references contained therein. These patents are hereby incorporated in their entireties by reference. See also Nisoiihoff et al., Arch. Biochem. Biophys. 89:230 (1960); Porter, Biochem. J. 73:119 (1959); Edelman etal, METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques can also be used. For example, Fv fragments comprise an association of V.sub.H and V.sub.L chains. This association may be noncovalent, as described in Inbar et al., Proc. Nat'l Acad. Sci. USA 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise V.sub.H and V.sub.L chains connected by a peptide linker. These single-chain antigen binding proteins (sFv) are prepared by constructing a structural gene comprising nucleic acid sequences encoding the V.sub.H and V.sub.L domains connected by an oligonucleotide. The structural gene is inserted into an expression vector, which is subsequently introduced into a host cell such as $E.$ $coli$. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird etal., Science 242:423–426 (1988); Ladneret al., U.S. Pat. No. 4,946,778; Pack et al., Bio/Technology 11: 1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

The term "antibody" as used herein includes intact molecules as well as fragments thereof, such as Fab, F(ab')2, and Fv which are capable of binding to an epitopic determinant present in Bin1 polypeptide. Such antibody fragments retain some ability to selectively bind with its antigen or receptor. The term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics. Antibodies can be prepared against specific epitopes or polypeptide domains.

Antibodies which bind to polypeptides of the present invention can be prepared using an intact polypeptide or fragments containing small peptides of interest as the immunizing antigen. The polypeptide or peptide used to immunize an animal can be conjugated to a carrier protein, if desired. Such commonly used carriers which are chemically coupled to the immunizing peptide include keyhole limpet hemocyanin (KLH), thyroglobulin, bovine serum albumin (BSA), and tetanus toxoid.

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

Anti-idiotype technology can also be used to produce invention monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Methods of Detecting Polypeptides

Polypeptides coded for genes of the present invention can be detected, visualized, determined, quantitated, etc. according to any effective method useful methods include, e.g., but are not limited to, immunoassays, RIA (radioimmunassay), ELISA, (enzyme-linked-immunosorbent assay), immunoflourescence, flow cytometry, histology, electron microscopy, light microscopy, in situ assays, immunoprecipitation, Western blot, etc.

Immunoassays may be carried in liquid or on biological support. For instance, a sample (e.g., blood, stool, urine, cells, tissue, body fluids, etc.) can be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled gene specific antibody. The solid phase support can then be washed with a buffer a second time to remove unbound antibody. The amount of bound label on solid support may then be detected by conventional means.

A "solid phase support or carrier" includes any support capable of binding an antigen, antibody, or other specific binding partner. Supports or carriers include glass, polystyrene, polypropylene, polyethylene, dextran, nylon, amylases, natural and modified celluloses, polyacrylamides, and magnetite. A support material can have any structural or physical configuration. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads One of the many ways in which gene peptide-specific antibody can be detectably labeled is by linking it to an enzyme and using it in an enzyme immunoassay (EIA). See, e.g., Voller, A., "The Enzyme Linked Immunosorbent Assay (ELISA)," 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla. The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, .alpha.-glycerophosphate, dehydrogenase, triose phosphate isomerase, horseradish peroxidase, alkaline phosphatase, asparaginase, glucose oxidase, .beta.-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect peptides through the use of a radioimmunoassay (RIA). See, e.g., Weintraub, B., Principles of Radioimmunoassays, Seventh Training Course on Radioligand Assay Techniques, The Endocrine Society, March, 1986. The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as those in the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.
Diagnostic The present invention also relates to methods and compositions for diagnosing a vascular disorder, or determining susceptibility to a disorder, using polynucleotides, polypeptides, and specific-binding partners of the present invention to detect, assess, determine, etc., genes of the present invention. In such methods, the gene can serve as a marker for the disorder, e.g., where the gene, when mutant, is a direct cause of the disorder; where the gene is affected by another gene(s) which is directly responsible for the disorder, e.g., when the gene is part of the same signaling pathway as the directly responsible gene; and, where the gene is chromosomally linked to the gene(s) directly responsible for the disorder, and segregates with it. Many other situations are possible. To detect, assess, determine, etc., a probe specific for the gene can be employed as described above and below. Any method of detecting and/or assessing the gene can be used, including detecting expression of the gene using polynucleotides, antibodies, or other specific-binding partners.

The present invention relates to methods of diagnosing a vascular disorder or a disorder associated with a gene of the present invention or determining a subject's susceptibility to such disorder, comprising, e.g., assessing the expression of said gene (or polypeptide encoded thereby) in a tissue sample comprising tissue or cells suspected of having the disorder (e.g., where the sample comprises vascular tissue). The phrase "diagnosing" indicates that it is determined whether the sample has the disorder. A "disorder" means, e.g., any abnormal condition as in a disease or malady. "Determining a subject's susceptibility to a disease or disorder" indicates that the subject is assessed for whether she is predisposed to get such a disease or disorder, where the predisposition is indicated by abnormal expression of the gene (e.g., gene mutation, gene expression pattern is not normal, etc.). Predisposition or susceptibility to a disease may result when a such disease is influenced by epigenetic, environmental, etc., factors. This includes prenatal screening where samples from the fetus or embryo (e.g., via amniocentesis or CV sampling) are analyzed for the expression of the gene. Such diseases include, e.g., inflammatory diseases, such as rheumatoid arthritis, osteoarthritis, asthma, pulmonary fibrosis, age-related macular degeneration (ARMD), diabetic retinopathy, macular degeneration, and retinopathy of prematurity (ROP), endometriosis, cancer, Coats' disease, peripheral retinal neovascularization, neovascular glaucoma, psoriasis, retrolental fibroplasias, angiofibroma, inflammation, etc. Examples of other diseases associated with genes of the present invention as shown in Table 2.

By the phrase "assessing expression of said gene," it is meant that the functional status of the gene is evaluated. This includes, but is not limited to, measuring expression levels of said gene, determining the genomic structure of said gene, determining the mRNA structure of transcripts from said gene, or measuring the expression levels of polypeptide coded for by said gene. Thus, the term "assessing expression" includes evaluating the all aspects of the transcriptional and translational machinery of the gene. For instance, if a promoter defect causes, or is suspected of causing, the disorder, then a sample can be evaluated (i.e., "assessed") by looking (e.g., sequencing or restriction mapping) at the promoter sequence in the gene, by detecting transcription products (e.g., RNA), by detecting translation product (e.g., polypeptide). Any measure of whether the gene is functional can be used, including, polypeptide, polynucleotide, and functional assays for the gene's biological activity.

In making the assessment, it can be useful to compare the results to a normal gene, e.g., a gene which is not associated with the disorder. The nature of the comparison can be determined routinely, depending upon how the assessing is accomplished. If, for example, the mRNA levels of a sample is detected, then the mRNA levels of a normal can serve as a comparison, or a gene which is known not to be affected by the disorder. Methods of detecting mRNA are well known, and discussed above, e.g., but not limited to, Northern blot analysis, polymerase chain reaction (PCR), reverse transcriptase PCR, RACE PCR, etc. Similarly, if polypeptide production is used to evaluate the gene, then the polypeptide in a normal tissue sample can be used as a comparison, or, polypeptide from a different gene whose expression is known not to be affected by the disorder. These are only examples of how such a method could be carried out.

Assessing the effects of therapeutic and preventative interventions (e.g., administration of a drug, chemotherapy, radiation, etc.) on vascular disorders or conditions is a major effort in drug discovery, clinical medicine, and pharmacogenomics. The evaluation of therapeutic and preventative measures, whether experimental or already in clinical use, has broad applicability, e.g., in clinical trials, for monitoring the status of a patient, for analyzing and assessing animal models, and in any scenario involving cancer treatment and prevention. Analyzing the expression profiles of polynucleotides of the present invention can be utilized as a parameter by which interventions are judged and measured. Treatment of a disorder can change the expression profile in some manner which is prognostic or indicative of the drug's effect on it. Changes in the profile can indicate, e.g., drug toxicity, return to a normal level, etc. Accordingly, the present invention also relates to methods of monitoring or assessing a therapeutic or preventative measure (e.g., chemotherapy, radiation, anti-neoplastic drugs, antibodies, etc.) in a subject having a condition or disorder associated with angiogenesis, comprising, e.g., detecting the expression levels of a gene or polypeptide of the present invention. A subject can be a cell-based assay system, non-human animal model, human patient, etc. Detecting can be accomplished as described for the methods above and below. By "therapeutic or preventative intervention," it is meant, e.g., a drug administered to a patient, surgery, radiation, chemotherapy, and other measures taken to prevent, treat, or diagnose a disorder.

Methods of Detecting Angiogenesis

The present invention also relates to detecting the presence and/or extent of blood vessels in a sample. The detected blood vessels can be established or pre-existing vessels, newly formed vessels, vessels in the process of forming, or combinations thereof. A blood vessel includes any biological structure that conducts blood, including arteries, veins, capillaries, microvessels, vessel lumen, endothelial-lined sinuses, etc. These methods are useful for a variety of purposes. In cancer, for instance, the extent of vascularization can be an important factor in determining the clinical behavior of neoplastic cells. See, e.g., Weidner et al., *N. Engl. J. Med.,* 324:1–8, 1991. Thus, the presence and extent of blood vessels, including the angiogenic process itself, can be useful for the diagnosis, prognosis, treatment, etc., of cancer and other neoplasms. Detection of vessels can also be utilized for the diagnosis, prognosis, treatment, of any diseases or conditions associated with vessel growth and production, to assess agents which modulate angiogenesis, to assess angiogenic gene therapy, etc.

An example of a method of detecting the presence or extent of blood vessels in a sample is determining an angiogenic index of a tissue or cell sample comprising, e.g., assessing in a sample, the expression levels of a nucleic acid or polypeptide of the present invention, whereby said levels are indicative of the angiogenic index. By the phrase "angiogenic index," it is meant the extent or degree of vascularity of the tissue, e.g., the number or amount of blood vessels in the sample of interest. Amounts of nucleic acid or polypeptide can be assessed (e.g., determined, detected, etc.) by any suitable method. There is no limitation on how detection is performed.

For instance, if nucleic acid is to be assessed, e.g., an mRNA corresponding to a differentially-expressed gene, the methods for detecting it, assessing its presence and/or amount, can be determined by any the methods mentioned above, e.g., nucleic acid based detection methods, such as Northern blot analysis, RT-PCR, RACE, differential display, NASBA and other transcription based amplification systems, polynucleotide arrays, etc. If RT-PCR is employed, cDNA can be prepared from the mRNA extracted from a sample of interest. Once the cDNA is obtained, PCR can be employed using oligonucleotide primer pairs that are specific for a differentially-expressed gene. The specific probes can be of a single sequence, or they can be a combination of different sequences. A polynucleotide array can also be used to assess nucleic, e.g., where the RNA of the sample of interest is labeled (e.g., using a transcription based amplification method, such as U.S. Pat. No. 5,716,785) and then hybridized to probe fixed to a solid substrate.

Polypeptide detection can also be carried out by any available method, e.g., by Western blots, ELISA, dot blot, immunoprecipitation, RIA, immunohistochemistry, etc. For instance, a tissue section can be prepared and labeled with a specific antibody (indirect or direct), visualized with a microscope, and then the number of vessels in a particular field of view counted, where staining with antibody is used to identify and count the vessels. Amount of a polypeptide can be quantitated without visualization, e.g., by preparing a lysate of a sample of interest, and then determining by ELISA or Western the amount of polypeptide per quantity of tissue. Again, there is no limitation on how detection is performed.

In addition to assessing the angiogenic index using an antibody or polynucleotide, other methods of determining tissue vascularity can be applied. Tissue vascularity is typically determined by assessing the number and density of vesssels present in a given sample. For example, microvessel density (MVD) can be estimated by counting the number of endothelial clusters in a high-power microscopic field, or detecting a marker specific for microvascular endothelium or other markers of growing or established blood vessels, such as CD31 (also known as platelet-endothelial cell adhesion molecule or PECAM). A CD31 antibody can be employed in conventional immunohistological methods to immunostain tissue sections as described by, e.g., Penfold et al., *Br. J. Oral and Maxill. Surg.,* 34: 37–41; U.S. Pat. No. 6,017,949; Dellas et al., *Gyn. Oncol.,* 67:27–33, 1997; and others.

In addition to the angiogenesis genes and polypeptides of the present invention, other genes and their corresponding products can be detected. For instance, it may be desired to detect a gene which is expressed ubiquitously in the sample. A ubiquitously expressed gene, or product thereof, is present in all cell types, e.g., in about the same amount, e.g., beta-actin. Similarly, a gene or polypeptide that is expressed selectively in the tissue or cell of interest can be detected. A selective gene or polypeptide is characteristic of the tissue or cell-type in which it is made. This can mean that it is expressed only in the tissue or cell, and in no other tissue- or cell-type, or it can mean that it is expressed preferentially, differentially, and more abundantly (e.g., at least 5-fold, 10-fold, etc., or more) when compared to other types. The expression of the ubiquitous or selective gene or gene product can be used as a control or reference marker to compare to the expression of differentially-expression genes. Typically, expression of the gene can be assessed by detecting mRNA produced from it. Other markers for blood vessels and angiogenesis can also be detected, such as angiogenesis-related genes or polypeptides. By the phrase "angiogenesis-related," it is meant that it is associated with blood vessels and therefore indicative of their presence. There are a number of different genes and gene products that are angiogenesis-related, e.g., Vezfl (e.g., Xiang et al., Dev. Bio., 206:123–141, 1999), VEGF, VEGF receptors (such as KDR/Flk-1), angiopoietin, Tie-1 and Tie-2 (e.g., Sato et al., Nature, 376:70–74, 1995), PECAM-1 or CD31 (e.g., DAKO, Glostrup. Denmark), CD34, factor VIII-related antigen (e.g., Brustmann et al., Gyn. Oncol., 67:20–26, 1997).

Identifying Agent Methods

The present invention also relates to methods of identifying agents, and the agents themselves, which modulate angiogenesis genes and the polypeptides which encode them. These agents can be used to modulate the biological activity of the polypeptide encoded for the gene, or the gene, itself. Agents which regulate the gene or its product are useful in variety of different environments, including as medicinal agents to treat or prevent disorders associated with said genes, such as neovascularization in cancer, and as research reagents to modify the function of tissues and cell. In addition, the polypeptides these genes encode can interact with other proteins and binding partners (such as nucleic acids) which are present naturally in a cell, e.g., to form multi-subunit functional assemblies and other complexes, that perform specific physiological functions in a cell.

Methods of identifying agents generally comprise steps in which an agent is placed in contact with the gene, transcription product, translation product, or other target, and then a determination is performed to assess whether the agent "modulates" the target. The specific method utilized will depend upon a number of factors, including, e.g., the target (i.e., is it the gene or polypeptide encoded by it), the environment (e.g., in vitro or in vivo), the composition of the agent, etc.

For modulating the expression of a gene, a method can comprise, in any effective order, one or more of the following steps, e.g., contacting a gene (e.g., in a cell population) with a test agent under conditions effective for said test agent to modulate the expression of said gene, and determining whether said test agent modulates said gene. An agent can modulate expression of the gene at any level, including transcription, translation, and/or perdurance of the nucleic acid (e.g., degradation, stability, etc.) in the cell. For modulating the biological activity of polypeptides, a method can comprise, in any effective order, one or more of the following steps, e.g., contacting a polypeptide (e.g., in a cell, lysate, or isolated) with a test agent under conditions effective for said test agent to modulate the biological activity of said polypeptide, and determining whether said test agent modulates said biological activity.

Contacting the gene or polypeptide with the test agent can be accomplished by any suitable method and/or means that places the agent in a position to functionally control expression or biological activity. Functional control indicates that the agent can exert its physiological effect through whatever mechanism it works. The choice of the method and/or means can depend upon the nature of the agent and the condition and type of environment in which the gene or polypeptide is presented, e.g., lysate, isolated, or in a cell population (such as, in vivo, in vitro, organ explants, etc.). For instance, if the cell population is an in vitro cell culture, the agent can be contacted with the cells by adding it directly into the culture medium. If the agent cannot dissolve readily in an aqueous medium, it can be incorporated into liposomes, or another lipophilic carrier, and then administered to the cell culture. Contact can also be facilitated by incorporation of agent with carriers and delivery molecules and complexes, by injection, by infusion, etc.

After the agent has been administered in such a way that it can gain access to the gene or polypeptide, it can be determined whether the test agent modulates its expression or biological activity. Modulation can be of any type, quality, or quantity, e.g., increase, facilitate, enhance, up-regulate, stimulate, activate, amplify, augment, induce, decrease, down-regulate, diminish, lessen, reduce, etc. The modulatory quantity can also encompass any value, e.g., 1%, 5%, 10%, 50%, 75%, 1-fold, 2-fold, 5-fold, 10-fold, 100-fold,etc. To modulate gene expression means, e.g., that the test agent has an effect on its expression, e.g., to effect the amount of transcription, to effect RNA splicing, to effect translation of the RNA into polypeptide, to effect RNA or polypeptide stability, to effect polyadenylation or other processing of the RNA, to effect post-transcriptional or post-translational processing, etc. To modulate biological activity means, e.g., that a functional activity of the polypeptide is changed in comparison to its normal activity in the absence of the agent. This effect includes, increase, decrease, block, inhibit, enhance, etc.

A test agent can be of any molecular composition, e.g., chemical compounds, biomolecules, such as polypeptides, lipids, nucleic acids (e.g., antisense to a polynucleotide sequence selected from SEQ ID NO 1–58), carbohydrates, antibodies, ribozymes, double-stranded RNA, aptamers, etc. For example, polypeptide fragments can be used to competitively inhibit polypeptides from binding to protein or DNA or from forming dimers. Antibodies can also be used to modulate the biological activity a polypeptide in a lysate or other cell-free form. Antisense can also be used as test agents to modulate gene expression.

The present invention also relates to methods of identifying modulators of the genes and polypeptides of the present invention in a cell population capable of forming blood vessels, comprising, one or more of the following steps in any effective order, e.g., contacting the cell population with a test agent under conditions effective for said test agent to modulate its expression or biological activity. These methods are useful, e.g., for drug discovery in identifying and confirming the angiogenic activity of agents, for identifying molecules in the normal pathway of angiogenesis, etc.

Any cell population capable of forming blood vessels can be utilized. Useful models, included those mentioned above, e.g., in vivo Matrigel-type assays, tumor neovascularization assays, CAM assays, BCE assays, migration assays, HUVEC growth inhibition assays, animal models (e.g., tumor growth in athymic mice), models involving hybrid cell and electronic-based components, etc. Cells can include, e.g., endothelial, epithelial, muscle, embryonic and adult stem cells, ectodermal, mesenchymal, endodermal, neoplastic, blood, bovine CPAE (CCL-209), bovine FBHE (CRL-1395), human HUV-EC-C (CRL-1730), mouse SVEC4-10EHR1 (CRL-2161), mouse MS1 (CRL-2279), mouse MS1 VEGF (CRL-2460), stem cells, etc. The phrase "capable of forming blood vessels" does not indicate a particular cell-type, but simply that the cells in the population are able under appropriate conditions to form blood vessels. In some circumstances, the population may be heterogeneous, comprising more than one cell-type, only some which actually differentiate into blood vessels, but others which are necessary to initiate, maintain, etc., the process of vessel formation.

The cell population can be contacted with the test agent in any manner and under any conditions suitable for it to exert an effect on the cells, and to modulate the differentially-expressed gene or polypeptide. The means by which the test agent is delivered to the cells may depend upon the type of test agent, e.g., its chemical nature, and the nature of the cell population. Generally, a test agent must have access to the cell population, so it must be delivered in a form (or pro-form) that the population can experience physiologically, i.e., to put in contact with the cells. For instance, if the intent is for the agent to enter the cell, if necessary, it can be associated with any means that facilitate or enhance cell penetrance, e.g., associated with antibodies or other reagents specific for cell-surface antigens, liposomes, lipids, chelating agents, targeting moieties, etc. Cells can also be treated, manipulated, etc., to enhance delivery, e.g., by electroporation, pressure variation, etc.

A purpose of administering or delivering the test agents to cells capable of forming blood vessels is to determine whether they modulate the gene or polypeptide. By the phrase "modulate," it is meant that the gene or polypeptide affects the polypeptide or gene in some way. Modulation includes effects on transcription, RNA splicing, RNA editing, transcript stability and turnover, translation, polypeptide activity, and, in general, any process involved in the expression and production of the gene and gene product. The modulatory activity can be in any direction, and in any amount, including, up, down, enhance, increase, stimulate, activate, induce, turn on, turn off, decrease, block, inhibit, suppress, prevent, etc.

Any type of test agent can be used, comprising any material, such as chemical compounds, biomolecules, such as polypeptides (including polypeptide fragments and mimics), lipids, nucleic acids, carbohydrates, antibodies, small molecules, fusion proteins, etc. Test agents include, e.g., protamine (Taylor et al., *Nature*, 297:307, 1982), heparins, steroids, such as tetrahydrocortisol, which lack gluco- and mineral-corticoid activity (e.g., Folkman et al., *Science*, 221:719, 1983 and U.S. Pat. Nos. 5,001,116 and 4,994,443), angiostatins (e.g., WO 95/292420), triazines (e.g., U.S. Pat. No. 6,150,362), thrombospondins, endostatins, platelet factor 4, fumagillin-derivate AGH 1470, alpha-interfon, quinazolinones (e.g., U.S. Pat. No. 6,090,814), substituted dibenzothiophenes (e.g., U.S. Pat. No. 6,022,307), deoxytetracyclines, cytokines, chemokines, FGFs, etc.

Whether the test agent modulates a gene or polypeptide can be determined by any suitable method. These methods include, detecting gene transcription, detecting mRNA, detecting polypeptide and activity thereof. The detection methods includes those mentioned herein, e.g., PCR, RT-PCR, Northern blot, ELISA, Western, RIA, yeast two-hybrid system (e.g., for identifying natural and synthetic nucleic acids and their products). In addition, further downstream targets can be used to assess the effects of modulators, including, the presence or absence of neoangiogenesis (e.g., using any of the mentioned test systems, such as CAM, BCE, in vivo Matrigel-type assays) as modulated by a test agent.

The present invention also relates to methods of regulating angiogenesis in a system comprising cells, comprising administering to the system an effective amount of a modulator of a differentially-expressed gene or polypeptide under conditions effective for the modulator to modulate the gene or polypeptide, whereby angiogenesis is regulated. A system comprising cells can be an in vivo system, such as a heart or limb present in a patient (e.g., angiogenic therapy to treat myocardial infarction), isolated organs, tissues, or cells, in vitro assays systems (CAM, BCE, etc), animal models (e.g., in vivo, subcutaneous, chronically ischemic lower limb in a rabbit model, cancer models), hosts in need of treatment (e.g., hosts suffering from angiogenesis related diseases, such as cancer, ischemic syndromes, arterial obstructive disease, to promote collateral circulation, to promote vessel growth into bioengineered tissues, etc.

A modulator useful in such method are those mentioned already, e.g., nucleic acid (such as an anti-sense to a gene to disrupt transcription or translation of the gene), antibodies (e.g., to inhibit a cell-surface protein, such as an antibody specific-for the extracellular domain). Antibodies and other agents which target a polypeptide can be conjugated to a cytotoxic or cytostatic agent, such as those mentioned already. A modulator can also be a differentially-expressed gene, itself, e.g., when it is desired to deliver the polypeptide to cells analogously to gene therapy methods. A complete gene, or a coding sequence operably linked to an expression control sequence (i.e., an expressible gene) can be used to produce polypeptide in the target cells.

By the phrase "regulating angiogenesis," it is meant that angiogenesis is effected in a desired way by the modulator. This includes, inhibiting, blocking, reducing, stimulating, inducing, etc., the formation of blood vessels. For instance, in cancer, where the growth of new blood vessels is undesirable, modulators of a differentially-expressed can be used to inhibit their formation, thereby treating the cancer. Such inhibitory modulators include, e.g., antibodies to the extracellular regions of a differentially-expressed polypeptide, and, antisense RNA to inhibit translation of a differentially-expressed mRNA into polypeptide (for guidance on administering and designing anti-sense, see, e.g., U.S. Pat. Nos. 6,153,595, 6,133,246, 6,117,847, 6,096,722, 6,087,343, 6,040,296, 6,005,095, 5,998,383, 5,994,230, 5,891,725, 5,885,970, and 5,840,708). On the other hand, angiogenesis can be stimulated to treat ischemic syndromes and arterial obstructive disease, to promote collateral circulation, and to promote vessel growth into bioengineered tissues, etc., by administering the a differentially-expressed gene or polypeptide to a target cell population.

Markers

The polynucleotides of the present invention can be used with other markers, especially angiogenesis markers, to identity, detect, stage, diagnosis, determine, prognosticate, treat, etc., tissue, diseases and conditions, etc, of the vascular tissue. Markers can be polynucleotides, polypeptides, antibodies, ligands, specific binding partners, etc. The targets for such markers include, but are not limited genes and polypeptides that are selective for angiogenesis and vascular tissues.

Therapeutics

Selective polynucleotides, polypeptides, and specific-binding partners thereto, can be utilized in therapeutic applications, especially to treat diseases and conditions of vascular tissue, including angiogenesis. Useful methods include, but are not limited to, immunotherapy (e.g., using specific-binding partners to polypeptides), vaccination (e.g., using a selective polypeptide or a naked DNA encoding such polypeptide), protein or polypeptide replacement therapy, gene therapy (e.g., germ-line correction, antisense), etc.

Various immunotherapeutic approaches can be used. For instance, unlabeled antibody that specifically recognizes a tissue-specific antigen can be used to stimulate the body to destroy or attack the cancer, to cause down-regulation, to produce complement-mediated lysis, to inhibit cell growth, etc., of target cells which display the antigen, e.g., analogously to how c-erbB-2 antibodies are used to treat breast cancer. In addition, antibody can be labeled or conjugated to enhance its deleterious effect, e.g., with radionuclides and other energy emitting entitities, toxins, such as ricin, exotoxin A (ETA), and diphtheria, cytotoxic or cytostatic agents, immunomodulators, chemotherapeutic agents, etc. See, e.g., U.S. Pat. No. 6,107,090.

An antibody or other specific-binding partner can be conjugated to a second molecule, such as a cytotoxic agent, and used for targeting the second molecule to a tissue-antigen positive cell (Vitetta, E. S. et al., 1993, Immunotoxin therapy, in DeVita, Jr., V. T. et al., eds, Cancer: Principles and Practice of Oncology, 4th ed., J. B. Lippincott Co., Philadelphia, 2624–2636). Examples of cytotoxic agents include, but are not limited to, antimetabolites, alkylating agents, anthracyclines, antibiotics, anti-mitotic agents, radioisotopes and chemotherapeutic agents. Further examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, 1-dehydrotestosterone, diptheria toxin, Pseudomonas exotoxin (PE) A, PE40, abrin, elongation factor-2 and glucocorticoid. Techniques for conjugating therapeutic agents to antibodies are well.

In addition to immunotherapy, polynucleotides and polypeptides can be used as targets for non-immunotherapeutic applications, e.g., using compounds which interfere with function, expression (e.g., antisense as a therapeutic agent), assembly, etc. RNA interference can be used in vitro and in vivo to silence a gene when its expression contributes to a disease (but also for other purposes, e.g., to identify the gene's function to change a developmental pathway of a cell, etc.). See, e.g., Sharp and Zamore, *Science*, 287:2431–2433, 2001; Grishok et al., *Science*, 287:2494, 2001.

Delivery of therapeutic agents can be achieved according to any effective method, including, liposomes, viruses, plasmid vectors, bacterial delivery systems, orally, systemically, etc. Therapeutic agents of the present invention can be administered in any form by any effective route, including, e.g., oral, parenteral, enteral, intraperitoneal, topical, transdermal (e.g., using any standard patch), ophthalmic, nasally, local, non-oral, such as aerosol, inhalation, subcutaneous, intramuscular, buccal, sublingual, rectal, vaginal, intra-arterial, and intrathecal, etc. They can be administered alone, or in combination with any ingredient(s), active or inactive.

In addition to therapeutics, per se, the present invention also relates to methods of treating a diseases and conditions of the vascular tissues, comprising, e.g., administering to a subject in need thereof a therapeutic agent which is effective for regulating a gene or polypeptide and/or which is effective in treating said disease or condition. The term "treating" is used conventionally, e.g., the management or care of a subject for the purpose of combating, alleviating, reducing, relieving, improving the condition of, etc., of a disease or disorder. Diseases or disorders which can be treated in accordance with the present invention include, but are not limited to inflammatory diseases, such as rheumatoid arthritis, osteoarthritis, asthma, pulmonary fibrosis, age-related macular degeneration (ARMD), diabetic retinopathy, macular degeneration, and retinopathy of prematurity (ROP), endometriosis, cancer, Coat' disease, peripheral retinal neovascularization, neovascular glaucoma, psoriasis, retrolental fibroplasias, angiofibroma, inflammation, and any of the disorders listed in Table 2, etc.

By the phrase "altered expression," it is meant that the disease is associated with a mutation in the gene, or any modification to the gene (or corresponding product) which affects its normal function. Thus, expression of a gene refers to, e.g., transcription, translation, splicing, stability of the mRNA or protein product, activity of the gene product, differential expression, etc.

Any agent which "treats" the disease can be used. Such an agent can be one which regulates its expression. Expression refers to the same acts already mentioned, e.g. transcription, translation, splicing, stability of the mRNA or protein product, activity of the gene product, differential expression, etc. For instance, if the condition was a result of a complete deficiency of the gene product, administration of gene product to a patient would be said to treat the disease and regulate the gene's expression. Many other possible situations are possible, e.g., where the gene is aberrantly expressed, and the therapeutic agent regulates the aberrant expression by restoring its normal expression pattern.

Antisense

Antisense polynucleotide (e.g., RNA) can also be prepared from a polynucleotide according to the present invention, preferably an anti-sense to a sequence of SEQ ID NO 1–58. Antisense polynucleotide can be used in various ways, such as to regulate or modulate expression of the polypeptides they encode, e.g., inhibit their expression, for in situ hybridization, for therapeutic purposes, for making targeted mutations (in vivo, triplex, etc.) etc. For guidance on administering and designing anti-sense, see, e.g., U.S. Pat. Nos. 6,200,960, 6,200,807, 6,197,584, 6,190,869, 6,190,661, 6,187,587, 6,168,950, 6,153,595, 6,150,162, 6,133,246, 6,117,847, 6,096,722, 6,087,343, 6,040,296, 6,005,095, 5,998,383, 5,994,230, 5,891,725, 5,885,970, and 5,840,708. An antisense polynucleotides can be operably linked to an expression control sequence. A total length of about 35 bp can be used in cell culture with cationic liposomes to facilitate cellular uptake, but for in vivo use, preferably shorter oligonucleotides are administered, e.g. 25 nucleotides.

Antisense polynucleotides can comprise modified, nonnaturally-occurring nucleotides and linkages between the nucleotides (e.g., modification of the phosphate-sugar backbone; methyl phosphonate, phosphorothioate, or phosphorodithioate linkages; and 2'-O-methyl ribose sugar units), e.g., to enhance in vivo or in vitro stability, to confer nuclease resistance, to modulate uptake, to modulate cellular distribution and compartmentalization, etc. Any effective nucleotide or modification can be used, including those already mentioned, as known in the art, etc., e.g., disclosed in U.S. Pat. Nos. 6,133,438; 6,127,533; 6,124,445; 6,121, 437; 5,218,103 (e.g., nucleoside thiophosphoramidites); 4,973,679; Sproat et al., "2'-O-Methyloligoribonucleotides: synthesis and applications," Oligonucleotides and Analogs A Practical Approach, Eckstein (ed.), IRL Press, Oxford, 1991, 49–86; Iribarren et al., "2'-O-Alkyl Oligoribonucleotides as Antisense Probes," Proc. Natl. Acad. Sci. USA, 1990, 87, 7747–7751; Cotton et al., "2'-O-methyl, 2'-O-ethyl oligoribonucleotides and phosphorothioate oligodeoxyribonucleotides as inhibitors of the in vitro U7 snRNP-dependent mRNA processing event," Nucl. Acids Res., 1991, 19, 2629–2635.

Arrays

The present invention also relates to an ordered array of polynucleotide probes and specific-binding partners (e.g., antibodies) for detecting the expression of a gene or polypeptide of the present invention in a sample, comprising, one or more polynucleotide probes or specific binding partners associated with a solid support, wherein each probe is specific for said gene or polypeptide, The probes can comprise a nucleotide sequence of SEQ ID NO 1–58 which is specific for said gene, a nucleotide sequence having sequence identity to SEQ ID NO 1–58 which is specific for said gene or polynucleotide, or complements thereto, or a specific-binding partner which is specific for said genes.

The phrase "ordered array" indicates that the probes are arranged in an identifiable or position-addressable pattern, e.g., such as the arrays disclosed in U.S. Pat. Nos. 6,156,501, 6,077,673, 6,054,270, 5,723,320, 5,700,637, WO09919711, WO00023803. The probes are associated with the solid support in any effective way. For instance, the probes can be bound to the solid support, either by polymerizing the probes on the substrate, or by attaching a probe to the substrate. Association can be, covalent, electrostatic, noncovalent, hydrophobic, hydrophilic, noncovalent, coordination, adsorbed, absorbed, polar, etc. When fibers or hollow filaments are utilized for the array, the probes can fill the hollow orifice, be absorbed into the solid filament, be attached to the surface of the orifice, etc. Probes can be of any effective size, sequence identity, composition, etc., as already discussed.

Ordered arrays can further comprise polynucleotide probes or specific-binding partners which are specific for other genes, including genes specific for angiogenesis or vascular tissues.

Transgenic Animals

The present invention also relates to transgenic animals comprising one or genes of the present invention. Such genes, as discussed in more detail below, include, but are not limited to, functionally-disrupted genes, mutated genes, ectopically or selectively-expressed genes, inducible or regulatable genes, etc. These transgenic animals can be produced according to any suitable technique or method, including homologous recombination, mutagenesis (e.g., ENU, Rathkolb et al., *Exp. Physiol.*, 85(6):635–644, 2000), and the tetracycline-regulated gene expression system (e.g., U.S. Pat. No. 6,242,667). The term "gene" as used herein includes any part of a gene, i.e., regulatory sequences, promoters, enhancers, exons, introns, coding sequences, etc. The nucleic acid present in the construct or transgene can be naturally-occurring wild-type, polymorphic, or mutated.

Along these lines, polynucleotides of the present invention can be used to create transgenic animals, e.g. a non-human animal, comprising at least one cell whose genome comprises a functional disruption of a gene of the present invention, e.g., represented by the genes set forth in Tables 1–3. By the phrases "functional disruption" or "functionally disrupted," it is meant that the gene does not express a biologically-active product. It can be substantially deficient in at least one functional activity coded for by the gene. Expression of a polypeptide can be substantially absent, i.e., essentially undetectable amounts are made. However, polypeptide can also be made, but which is deficient in activity, e.g., where only an amino-terminal portion of the gene product is produced. Such an animal can show aberrant or defective angiogenesis (e.g., angiogenesis is increased or decreased, such as excessive or extraneous angiogenesis, or insufficient angiogenesis or vascularization), leading to a host of effects on different organ systems.

The transgenic animal can comprise one or more cells. When substantially all its cells contain the engineered gene, it can be referred to as a transgenic animal "whose genome comprises" the engineered gene. This indicates that the endogenous gene loci of the animal has been modified and substantially all cells contain such modification.

Functional disruption of the gene can be accomplished in any effective way, including, e.g., introduction of a stop codon into any part of the coding sequence such that the resulting polypeptide is biologically inactive (e.g., because it lacks a catalytic domain, a ligand binding domain, etc.), introduction of a mutation into a promoter or other regulatory sequence that is effective to turn it off, or reduce transcription of the gene, insertion of an exogenous sequence into the gene which inactivates it (e.g., which disrupts the production of a biologically-active polypeptide or which disrupts the promoter or other transcriptional machinery), deletion of sequences from the gene, etc. Insertions can be made in the novel parts of the genes as shown in the attached figures. Examples of transgenic animals having functionally disrupted genes are well known, e.g., as described in U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824. A transgenic animal which comprises the functional disruption can also be referred to as a "knock-out" animal, since the biological activity of said gene has been "knocked-out." Knock-outs can be homozygous or heterozygous.

For creating functional disrupted genes, and other gene mutations, homologous recombination technology is of special interest since it allows specific regions of the genome to be targeted. Using homologous recombination methods, genes can be specifically-inactivated, specific mutations can be introduced, and exogenous sequences can be introduced at specific sites. These methods are well known in the art, e.g., as described in the patents above. See, also, Robertson, *Biol. Reproduc.*, 44(2):238–245, 1991. Generally, the genetic engineering is performed in an embryonic stem (ES) cell, or other pluripotent cell line (e.g., adult stem cells, EG cells), and that genetically-modified cell (or nucleus) is used to create a whole organism. Nuclear transfer can be used in combination with homologous recombination technologies.

For example, the endogenous locus can be disrupted in mouse ES cells using a positive-negative selection method (e.g., Mansour et al., *Nature*, 336:348–352, 1988). In this method, a targeting vector can be constructed which comprises a part of the gene to be targeted. A selectable marker, such as neomycin resistance genes, can be inserted into a an exon present in the targeting vector, disrupting it. When the vector recombines with the ES cell genome, it disrupts the function of the gene. The presence in the cell of the vector can be determined by expression of neomycin resistance. See, e.g., U.S. Pat. No. 6,239,326. Cells having at least one functionally disrupted gene can be used to make chimeric and germline animals, e.g., animals having somatic and/or germ cells comprising the engineered gene. Homozygous knock-out animals can be obtained from breeding heterozygous knock-out animals. See, e.g., U.S. Pat. No. 6,225,525.

A transgenic animal, or animal cell, lacking one or more functional activiteis can be used to decipher angiogenesis, or any of the utilities mentioned in any issued U.S. Patent on transgenic animals, including, U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824. For instance, deficient animal cells can be utilized to study angiogenesis. By knocking-out the genes which are involved in angiogenesis, e.g., one at a time, the physiological pathways can be dissected out and identified.

The present invention also relates to non-human, transgenic animal whose genome comprises a recombinant nucleic acid of the present invention (e.g., SEQ ID NOS 1–58) operatively linked to an expression control sequence effective to express said coding sequence, e.g., in vascular and endothelial tissues. Such a transgenic animal can also be referred to as a "knock-in" animal since an exogenous gene has been introduced, stably, into its genome. For instance, the endogenous locus can be knocked-out, and a polynucleotide of the present invention, e.g., SEQ ID NOS 1–58, can be inserted.

A recombinant nucleic acid refers to a gene which has been introduced into a target host cell and optionally modified, such as cells derived from animals, plants, bacteria, yeast, etc. A recombinant nucleic acid includes completely synthetic nucleic acid sequences, semi-synthetic nucleic acid sequences, sequences derived from natural sources, and chimeras thereof. "Operable linkage" has the meaning used through the specification, i.e., placed in a functional relationship with another nucleic acid. When a gene is operably linked to an expression control sequence, as explained above, it indicates that the gene (e.g., coding sequence) is joined to the expression control sequence (e.g., promoter) in such a way that facilitates transcription and translation of the coding sequence. As described above, the phrase "genome" indicates that the genome of the cell has been modified. In this case, the recombinant nucleic acid has been stably integrated into the genome of the animal. The nucleic acid in operable linkage with the expression control sequence can also be referred to as a construct or transgene.

Any expression control sequence can be used depending on the purpose. For instance, if selective expression is desired, then expression control sequences which limit its expression can be selected. These include, e.g., tissue or cell-specific promoters, introns, enhancers, etc. For various methods of cell and tissue-specific expression, see, e.g., U.S. Pat. Nos. 6,215,040, 6,210,736, and 6,153,427. These also include the endogenous promoter, i.e., the coding sequence can be operably linked to its own promoter. Inducible and regulatable promoters can also be utilized.

The present invention also relates to a transgenic animal which contains a functionally disrupted and a transgene stably integrated into the animals genome. Such an animal can be constructed using combinations any of the above- and below-mentioned methods. Such animals have any of the aforementioned uses, including permitting the knock-out of the normal gene and its replacement with a mutated gene. Such a transgene can be integrated at the endogenous gene locus so that the functional disruption and "knock-in" are carried out in the same step.

In addition to the methods mentioned above, transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology, cloning methods, nuclear transfer methods. See, also, e.g., U.S. Patent Nos. 4,736,866; 4,873,191; 4,873,316; 5,082,779;

5,304,489; 5,174,986; 5,175,384; 5,175,385; 5,221,778; Gordon et al., Proc. Natl. Acad. Sci., 77:7380–7384, 1980; Palmiter et al., Cell, 41:343–345, 1985; Palmiter et al., Ann. Rev. Genet., 20:465–499, 1986; Askew et al., Mol. Cell. Bio., 13:4115–4124, 1993; Games et al. Nature, 373:523–527, 1995; Valancius and Smithies, Mol. Cell. Bio., 11:1402–1408, 1991; Stacey et al., Mol. Cell. Bio., 14:1009–1016, 1994; Hasty et al., Nature, 350:243–246, 1995; Rubinstein et al., Nucl. Acid Res., 21:2613–2617, 1993; Cibelli et al., Science, 280:1256–1258, 1998. For guidance on recombinase excision systems, see, e.g., U.S. Pat. Nos. 5,626,159, 5,527,695, and 5,434,066. See also, Orban, P. C., et al., "Tissue- and Site-Specific DNA Recombination in Transgenic Mice," Proc. Natl. Acad. Sci. USA, 89:6861–6865 (1992); O'Gorman, S., et al., "Recombinase-Mediated Gene Activation and Site-Specific Integration in Mammalian Cells," Science, 251:1351–1355 (1991); Sauer, B., et al., "Cre-stimulated recombination at loxP-Containing DNA sequences placed into the mammalian genome," Polynucleotides Research, 17(1):147–161 (1989); Gagneten, S. et al. (1997) Nucl. Acids Res. 25:3326–3331; Xiao and Weaver (1997) Nucl. Acids Res. 25:2985–2991; Agah, R. et al. (1997) J. Clin. Invest. 100:169–179; Barlow, C. et al. (1997) Nucl. Acids Res. 25:2543–2545; Araki, K. et al. (1997) Nucl. Acids Res. 25:868–872; Mortensen, R. N. et al. (1992) Mol. Cell. Biol. 12:2391–2395 (G418 escalation method); Lakhlani, P. P. et al. (1997) Proc. Natl. Acad. Sci. USA 94:9950–9955 ("hit and run"); Westphal and Leder (1997) Curr. Biol. 7:530–533 (transposon-generated "knock-out" and "knock-in"); Templeton, N. S. et al. (1997) Gene Ther. 4:700–709 (methods for efficient gene targeting, allowing for a high frequency of homologous recombination events, e.g., without selectable markers); PCT International Publication WO 93/22443 (functionally-disrupted).

A polynucleotide according to the present invention can be introduced into any non-human animal, including a non-human mammal, mouse (Hogan et al., *Manipulating the Mouse Embryo: A Laboratory Manual, Cold Spring Harbor Laboratory,* Cold Spring Harbor, New York, 1986), pig (Hammer et al., Nature, 315:343–345, 1985), sheep (Hammer et al., Nature, 315:343–345, 1985), cattle, rat, or primate. See also, e.g., Church, 1987, Trends in Biotech. 5:13–19; Clark et al., Trends in Biotech. 5:20–24, 1987); and DePamphilis et al., BioTechniques, 6:662–680, 1988. Transgenic animals can be produced by the methods described in U.S. Pat. No. 5,994,618, and utilized for any of the utilities described therein.

Database

The present invention also relates to electronic forms of polynucleotides, polypeptides, etc., of the present invention, including computer-readable medium (e.g., magnetic, optical, etc., stored in any suitable format, such as flat files or hierarchical files) which comprise such sequences, or fragments thereof, e-commerce-related means, etc. Along these lines, the present invention relates to methods of retrieving gene sequences from a computer-readable medium, comprising, one or more of the following steps in any effective order, e.g., selecting a cell or gene expression profile, e.g., a profile that specifies that said gene is expressed in blood vessels, and retrieving said gene sequence, where the gene sequence is represented by SEQ ID NOS 1–58.

A "gene expression profile" means the list of tissues, cells, etc., in which a defined gene is expressed (i.e, transcribed and/or translated). A "cell expression profile" means the genes which are expressed in the particular cell type. The profile can be a list of the tissues in which the gene is expressed, but can include additional information as well, including level of expression (e.g., a quantity as compared or normalized to a control gene), and information on temporal (e.g., at what point in the cell-cycle or developmental program) and spatial expression. By the phrase "selecting a gene or cell expression profile," it is meant that a user decides what type of gene or cell expression pattern he is interested in retrieving, e.g., he may require that the gene is differentially expressed in a tissue, or he may require that the gene is not expressed in heart, but must be expressed in cells capable of forming blood vessels. Any pattern of expression preferences may be selected. The selecting can be performed by any effective method. In general, "selecting" refers to the process in which a user forms a query that is used to search a database of gene expression profiles. The step of retrieving involves searching for results in a database that correspond to the query set forth in the selecting step. Any suitable algorithm can be utilized to perform the search query, including algorithms that look for matches, or that perform optimization between query and data. The database is information that has been stored in an appropriate storage medium, having a suitable computer-readable format. Once results are retrieved, they can be displayed in any suitable format, such as HTML.

For instance, the user may be interested in identifying genes that are expressed in a vascular tissue. He may not care whether small amounts of expression occur in other tissues, as long as such genes are not expressed in peripheral blood lymphocytes. A query is formed by the user to retrieve the set of genes from the database having the desired gene or cell expression profile. Once the query is inputted into the system, a search algorithm is used to interrogate the database, and retrieve results.

The present invention also relates to methods of selecting a gene expressed in vascular tissue (e.g., during angiogenesis) from a database comprising polynucleotide sequences, comprising displaying, in a computer-readable medium, a polynucleotide sequence or polypeptide sequence for SEQ ID NOS 1–58, or complements to the polynucleotide sequence, wherein said displayed sequences have been retrieved from said database upon selection by a user. The phrase "upon selection by a user" indicates that a user of the database has specified or directed a search or other retrieval feature that results in the retrieval and display of the target sequences. For example, the user could ask the database to display polynucleotides or polypeptides expressed during angiogenesis by inputting an appropriate inquiry. The user could also input sequence information, and request the display of any sequences in the database that match the inputted sequence information. One or more sequences can be displayed at a time in response to any user inquiry.

Advertising, Licensing, etc., Methods

The present invention also relates to methods of advertising, licensing, selling, purchasing, brokering, etc., genes, polynucleotides, specific-binding partners, antibodies, etc., of the present invention. Methods can comprises, e.g., displaying a gene, polypeptide, or antibody specific thereto in a printed or computer-readable medium (e.g., on the Web or Internet), accepting an offer to purchase said gene, polypeptide, or antibody.

Other

A polynucleotide, probe, polypeptide, antibody, specific-binding partner, etc., according to the present invention can be isolated. The term "isolated" means that the material is in a form in which it is not found in its original environment or in nature, e.g., more concentrated, more purified, separated from component, etc. An isolated polynucleotide includes, e.g., a polynucleotide having the sequenced separated from the chromosomal DNA found in a living animal, e.g., as the complete gene, a transcript, or a cDNA. This polynucleotide can be part of a vector or inserted into a chromosome (by specific gene-targeting or by random integration at a position other than its normal position) and still be isolated in that it is not in a form that is found in its natural environment. A polynucleotide, polypeptide, etc., of the present invention can also be substantially purified. By substantially purified, it is meant that polynucleotide or polypeptide is separated and is essentially free from other polynucleotides or polypeptides, i.e., the polynucleotide or polypeptide is the primary and active constituent. A polynucleotide can also be a recombinant molecule. By "recombinant," it is meant that the polynucleotide is an arrangement or form which does not occur in nature. For instance, a recombinant molecule comprising a promoter sequence would not encompass the naturally-occurring gene, but would include the promoter operably linked to a coding sequence not associated with it in nature, e.g., a reporter gene, or a truncation of the normal coding sequence.

The term "marker" is used herein to indicate a means for detecting or labeling a target. A marker can be a polynucleotide (usually referred to as a "probe"), polypeptide (e.g., an antibody conjugated to a detectable label), PNA, or any effective material.

The topic headings set forth above are meant as guidance where certain information can be found in the application, but are not intended to be the only source in the application where information on such topic can be found. Reference materials For other aspects of the polynucleotides, reference is made to standard textbooks of molecular biology. See, e.g., Hames et al., *Polynucleotide Hybridization,* IL Press, 1985; Davis et al., *Basic Methods in Molecular Biology,* Elsevir Sciences Publishing, Inc., New York, 1986; Sambrook et al., *Molecular Cloning,* CSH Press, 1989; Howe, *Gene Cloning and Manipulation,* Cambridge University Press, 1995; Ausubel et al., *Current Protocols in Molecular Biology,* John Wiley & Sons, Inc., 1994–1998.

The preceding description, utilize the present invention to its fullest extent. The preceding preferred specific embodiments are, therefore, to be construed as merely illustrative, and not limiting the remainder of the disclosure in any way whatsoever. The entire disclosure of all applications, patents and publications, cited above and in the figures are hereby incorporated by reference in their entirety.

TABLE 1

| Name | Ref Seq | Domain | Domain description | Begin | End |
|---|---|---|---|---|---|
| ANH0009 | XM_087061: similar to heterogeneous nuclear ribonucleoprotein A3 | rrm | RNA recognition motif | 37 | 198 |
| ANH0024A | X68560: SPR2 transcription factor | zf-C2H2 | Zinc finger, C2H2 type | 621 | 703 |
| ANH0024A | | Autotransporter | Autotransporter beta-domain | 197 | 463 |
| ANH0024B | | zf-C2H2 | Zinc finger, C2H2 type | 580 | 662 |
| ANH0024B | | Autotransporter | Autotransporter beta-domain | 156 | 422 |
| ANH0024C | | zf-C2H2 | Zinc finger, C2H2 type | 336 | 418 |
| ANH0024D | | zf-C2H2 | Zinc finger, C2H2 type | 595 | 677 |
| ANH0024D | | Autotransporter | Autotransporter beta-domain | 171 | 437 |
| ANH0039 | XM_045848: calumenin | efhand | EF hand | 72 | 297 |
| ANH0068 | XM_055371: uridine 5' monophosphate hydrolase 1 (UMPH1) | | No domain found | | |
| ANH0114 | XM_076374: similar to Kelch-related protein 1 | Kelch | Kelch motif (4) | 348 | 600 |
| ANH0114 | | BTB | BTB/POZ domain | 23 | 128 |
| ANH0144A | XM_098238; AL133047: similar to SH3 domain protein D19 | SH3 | SH3 domain | 778 | 1067 |
| ANH0144A | | Tymo_45kd_70kd | Tymovirus 45/70Kd protein | 261 | 624 |
| ANH0144B | | SH3 | SH3 domain | 863 | 993 |
| ANH0144B | | Atrophin-1 | Atrophin-1 family | 10 | 787 |
| ANH0144C | | SH3 | SH3 domain | 781 | 1070 |
| ANH0144C | | Tymo_45kd_70kd | Tymovirus45/70Kd protein | 264 | 627 |
| ANH0241 | XM_086643 | PHD | PHD-finger | 90 | 133 |
| ANH0241 | | bromodomain | Bromodomain | 154 | 240 |
| ANH0241 | | zf-MYND | MYND finger | 1028 | 1062 |
| ANH0241 | | PWWP | PWWP domain | 274 | 345 |
| ANH0241 | | Parathyroid | Parathyroid hormone family | 517 | 638 |
| ANH0241 | | Granin | Granin (chromogranin or secretogranin | 410 | 989 |
| ANH0241 | | zf-B_box | B-box zinc finger | 1023 | 1067 |
| ANH0245 | NM_032847; AK027731 | | No domain found | | |
| ANH0296 | AK000913; NM_004713 | Ribosomal_L22 | Ribosomal protein L22p/L17e | 328 | 412 |
| ANH0296 | | Caulimo_VI | Caulimovirus viroplasmin | 386 | 795 |
| ANH0296 | | Peripla_BP_2 | Periplasmic binding protein | 223 | 465 |
| ANH0296 | | SART-1 | SART-1 family | 385 | 930 |
| ANH0423 | XM_053487: FGD1 family member | RhoGEF | Guanine exchange factor for Rho-like GTPases | 161 | 340 |
| | | PH | Pleckstrin homology domain | 371 | 471 |
| | | FYVE | Protein present in Fab1, YOTB, Vac1, and EEA1 | 524 | 589 |
| | | PH | Pleckstrin homology domain | 605 | 705 |

TABLE 1-continued

| Name | Ref Seq | Domain | Domain description | Begin | End |
|---|---|---|---|---|---|
| ANH0459B | NM_000366: tropomyosin 1 (TPM1) | Tropomyosin | Tropomyosin | 48 | 284 |
| ANH0459C | | Tropomyosin | Tropomyosin | 12 | 244 |
| ANH0459C | | spectrin | Spectrin repeat | 145 | 244 |
| ANH0459D | | Tropomyosin | Tropomyosin | 1 | 158 |
| ANH0769 | XM_038985; AL133087 | ank | Ankyrin repeat | 7 | 991 |
| ANH0769 | | Avirulence | Xanthomonas avirulence protein, Avr/P | 205 | 664 |
| ANH0658 | NM_014882 | RhoGAP | RhoGAP domain | 177 | 331 |
| ANH0658 | | PH | PH domain | 47 | 151 |
| ANH0658 | | Peptidase_S9_N | Prolyl oligopeptidase, N-terminal bet | 16 | 355 |
| ANH0668 | XM_015539 | TM | Transmembrane domain | 65 | 87 |
| | | TM | Transmembrane domain | 97 | 119 |
| ANH0757 | XM_087631 | bZIP | bZIP transcription factor | 519 | 583 |
| ANH0687A | XM_048092 | WH1 | WH1 domain | 1 | 101 |
| ANH0687A | | Ran_BP1 | RanBP1 domain | 5 | 101 |
| ANH0687B | | WH1 | WH1 domain | 1 | 101 |
| ANH0687B | | Ran_BP1 | RanBP1 domain | 5 | 103 |
| ANH0687B | | Armadillo_seg | Armadillo/beta-catenin-like repeat | 352 | 392 |
| ANR0693 | NM_052877 | | No domain found | | |
| ANH0095 | AK023027 | TM | Transmembrane | 40 | 62 |
| ANH0122A | | RRM | RNA recognition motif | 88 | 160 |
| | | | Coiled coil | 271 | 352 |
| | | | Coiled coil | 385 | 554 |
| | | PW1 | PW1, domain in splicing factor | 763 | 836 |
| ANH0122B | | RRM | RNA recognition motif | 88 | 160 |
| | | | Coiled coil | 271 | 490 |
| | | PW1 | PW1, domain in splicing factor | 699 | 772 |
| ANH0316 | NM_005807; XM_001738: proteoglycan 4 | Somatomedin_B | Somatomedin B domain | 25 | 68 |
| ANH0316 | | hemopexin | Hemopexin | 1067 | 1157 |
| ANH0316 | | GASA | Gibberellin regulated protein | 4 | 72 |
| ANH0316 | | wap | WAP-type (Whey Acidic Protein) | 29 | 66 |

TABLE 2

| Clone ID | Locus | Associated Diseases |
|---|---|---|
| ANH0009 | 2q31.2 | Erythermalgia, Familial Primary; Cancer; Primary Pulmonary Hypertension locus |
| ANH0024A | 2q37 | Early pregnancy loss and stillborns; |
| ANH0024B | | Autism; |
| ANH0024C | | Cancer, including oral squamous cell carcinomas; |
| ANH0024D | | Brachydactyly, Type E (Bde); Systemic Lupus Etythematosus, Susceptibility To, 2 (Sleb2); Brachydactyly-Mental Retardation Syndrome; Holoprosencephaly 6 |
| ANH0039 | 7q36 | Cancer; Holoprosencephaly (HPE) Polydactyly, Preaxial Ii (Ppd2); Acropectoral Syndrome |
| ANH0068 | 7p15.3 | Deafness, Autosomal Dominant Nonsyndromic Sensorineural 5 (Dfna5); Retinitis Pigmentosa 9 (Rp9); *Stroke And Cerebral Cavernous Malformations 2 (Ccm2) |
| ANH0114 | 3p21 | Cancer; Moditier of Hirschsprung disease (HSCR), Aicardi-Goutieres Syndrome 1 (Ags1); Spinocerebellar Ataxia 7 (Sca7); Larsen Syndrome, Autosomal Dominant (Lrs1); *Vasculopathy, Retinal, With Cerebral Leukodystrophy |
| ANH0144A | 4q31 | Deafness, Autosomal Recessive 26 (Dfnb26); |
| ANH0144B | | Cancer; |
| ANH0144C | | Schizophrenia susceptibility locus |
| ANH0241 | 20q13.3 | Complex Obesity Trait |
| ANH0245 | 8q24.13 | Spastic Paraplegia 8, Autosomal Dominant (Spg8); Childhood Absence Epilepsy (Cae); Epilepsy, Myoclonic, Benign Adult Familial; *Epidermolysis Bullosa Simplex, Ogna Type; Macular Dystrophy, Atypical Vitelliform (Vmd1); Tibial Hemimelia |

TABLE 2-continued

| Clone ID | Locus | Associated Diseases |
|---|---|---|
| ANH0296 | 14q21 | Deafness, Autosomal Dominant Nonsyndromic Sensorineural 23 (DFNA23) |
| ANH0423 | 9q22 | Cataract, Autosomal Recessive, Early-Onset, Pulverulent; Hemophagocytic Lymphohistiocytosis, Familial, 1; Amyotrophic Lateral Sclerosis With Frontotemporal Dementia; Nephronophthisis 2 (NPHP2) |
| ANH0459B ANH0459C ANH0459D | 15q22.1 | Type 3 Familial Hypertrophic Cardiomyopathy (mutations in tropomyosin gene associated with disease, e.g., Thierfelder et al., Cell, 77: 701–712, 1994) |
| ANH0769 | 2q33.1 | Paroxysmal Nonkinesigenic Dyskinesia (Pnkd); Ichthyosis, Lamellar, 2 (Li2) |
| ANH0658 | 2p13.1 | Spastic Paraplegia 17 |
| ANH0668 | 11q12 | Hereditary Spastic Paraplegia; Psoriasis; Breast Carcinoma and other cancers; Osteoporosis-pseudoglioma syndrome |
| ANH0757 | 5q35.2 | Congenital development disorder (Zhu et al., Am. J. Med. Genet., 98:317–9, 2001) |
| ANH0687A | 2p16.1 | Cancer; |
| ANH0687B | | Carney Complex |
| ANH0693 | 1p34.1 | Ptosis, Hereditary Congenital 1 (PTOS1) |
| ANH0095 | 14q32.33 | Immunoglobulin Heavy Chain Regulator, Included (1GHR) |
| ANH122 | 14q24.3 | Leber congenital amaurosis type III; Familial arrhythmogenic right ventricular dysplasia-1 (ARVD1) |
| ANH0316 | 1q25-q31 | Febrile Convulsions And Temporal Lobe Epilepsy |

TABLE 3

| Clone ID | Protein-Length (amino acids) | SEQ ID NO | Expression |
|---|---|---|---|
| ANH0009 | 358 | 1, 2 | D24 L |
| ANH0024A | 781 | 3, 4 | U8S L |
| ANH0024B | 740 | 5, 6 | |
| ANH0024C | 496 | 7, 8 | |
| ANH0024D | 755 | 9, 10 | |
| ANH0039 | 315 | 11, 12 | D8S L |
| ANH0068 | 297 | 13, 14 | U1S L |
| ANH0114 | 621 | 15, 16 | U8T H |
| ANH0144A | 1070 | 17, 18 | D8S L |
| ANH0144B | 1023 | 19, 20 | |
| ANH0144C | 1073 | 21, 22 | |
| ANH0241 | 1214 | 23, 24 | D1T L |
| ANH0245 | 359 | 25, 26 | D1T L |
| ANH0296 | 1082 | 27, 28 | U1S H |
| ANH0423 | 725 | 29, 30 | U1T L |
| ANH0459B | 284 | 31, 32 | D1S L |
| ANH0459C | 245 | 33, 34 | |
| ANH0459D | 158 | 35, 36 | |
| ANH0769 | 994 | 37, 38 | U1S L |
| ANH0658 | 645 | 39, 40 | U1T L |
| ANH0668 | 186 | 41, 42 | D1T L |
| ANH0757 | 639 | 43, 44 | U1S H |
| ANH0687A | 641 | 45, 46 | D1T L |
| ANH0687B | 817 | 47, 48 | |
| ANH0693 | 268 | 49, 50 | D8S L |
| ANH0095 | 65 | 51, 52 | U1S H |
| ANH122A | 843 | 53, 54 | U1S L |
| ANH122B | 779 | 55, 56 | |
| ANH0316 | 1320 | 57, 58 | U8T L |

What is claimed is:

1. An isolated polynucleotide comprising, a polynucleotide sequence which codes without interruption for human ANH0769 comprising the amino acid sequence set forth in SEQ ID NO 38, or a complement thereto.

2. An isolated polynucleotide of claim 1, comprising the polynucleotide sequence set forth in nucleotide positions 174–3155 of SEQ ID NO 37, or a complement thereto.

3. An isolated polynucleotide of claim 1, wherein said polynucleotide sequence is operably linked to a promoter sequence.

* * * * *